US009221886B2

(12) United States Patent
Liu et al.

(10) Patent No.: US 9,221,886 B2
(45) Date of Patent: Dec. 29, 2015

(54) SUPERCHARGED PROTEINS FOR CELL PENETRATION

(75) Inventors: David R. Liu, Lexington, MA (US); Brian R. McNaughton, Cambridge, MA (US); James Joseph Cronican, Somerville, MA (US); David B. Thompson, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 125 days.

(21) Appl. No.: 13/318,032

(22) PCT Filed: Apr. 28, 2010

(86) PCT No.: PCT/US2010/001250
§ 371 (c)(1),
(2), (4) Date: Jan. 9, 2012

(87) PCT Pub. No.: WO2010/129023
PCT Pub. Date: Nov. 11, 2010

(65) Prior Publication Data
US 2012/0100569 A1 Apr. 26, 2012

Related U.S. Application Data

(60) Provisional application No. 61/173,430, filed on Apr. 28, 2009, provisional application No. 61/321,428, filed on Apr. 6, 2010.

(51) Int. Cl.
| | |
|---|---|
| *C12N 15/09* | (2006.01) |
| *C12N 9/96* | (2006.01) |
| *C12N 5/00* | (2006.01) |
| *A61K 38/43* | (2006.01) |
| *C07H 21/04* | (2006.01) |
| *C07K 1/00* | (2006.01) |
| *C07K 14/435* | (2006.01) |
| *C07K 7/06* | (2006.01) |
| *C07K 7/08* | (2006.01) |
| *C07K 14/00* | (2006.01) |

(52) U.S. Cl.
CPC ............. *C07K 14/43595* (2013.01); *C07K 7/06* (2013.01); *C07K 7/08* (2013.01); *C07K 14/001* (2013.01); *C07K 2319/01* (2013.01); *C12N 2740/13043* (2013.01)

(58) Field of Classification Search
CPC ...... C07K 7/06; C07K 7/08; C07K 14/43595; C07K 2319/01; C07K 14/001; C12N 2740/13043
USPC ................. 435/69.7, 188, 375, 377; 424/94.1; 536/23.4; 530/350
See application file for complete search history.

(56) References Cited

U.S. PATENT DOCUMENTS

| | | | |
|---|---|---|---|
| 4,270,537 A | 6/1981 | Romaine | |
| 4,596,556 A | 6/1986 | Morrow et al. | |
| 4,790,824 A | 12/1988 | Morrow et al. | |
| 4,886,499 A | 12/1989 | Cirelli et al. | |
| 4,940,460 A | 7/1990 | Casey et al. | |
| 4,941,880 A | 7/1990 | Burns | |
| 5,015,235 A | 5/1991 | Crossman | |
| 5,064,413 A | 11/1991 | McKinnon et al. | |
| 5,141,496 A | 8/1992 | Dalto et al. | |
| 5,190,521 A | 3/1993 | Hubbard et al. | |
| 5,258,453 A * | 11/1993 | Kopecek et al. | 525/54.1 |
| 5,312,335 A | 5/1994 | McKinnon et al. | |
| 5,328,483 A | 7/1994 | Jacoby | |
| 5,334,144 A | 8/1994 | Alchas et al. | |
| 5,339,163 A | 8/1994 | Homma et al. | |
| 5,383,851 A | 1/1995 | McKinnon, Jr. et al. | |
| 5,417,662 A | 5/1995 | Hjertman et al. | |

(Continued)

FOREIGN PATENT DOCUMENTS

| | | |
|---|---|---|
| WO | WO 91/00345 A | 1/1991 |
| WO | WO 97/13537 A1 | 4/1997 |

(Continued)

OTHER PUBLICATIONS

Chica et al., Semi-rational approaches to engineering enzyme activity: combining the benefits of directed evolution and rational design. Curr. Opi. Biotechnol., 2005, vol. 16: 378-384.*
Devos et al., Practical limits of function prediction. Proteins: Structure, Function, and Genetics. 2000, vol. 41: 98-107.*
Haupt et al., Stage-specific conditional mutagenesis in mouse embryonic stem cell-derived neural cells and postmitotic neurons by direct delivery of biologically active Cre recombinase. Stem Cells., 2007, vol. 25: 181-188.*
Peitz et al., Enhanced purification of cell-permeant Cre and germline transmission after transduction into mouse embryonic stem cells. Genesis., 2007, vol. 45: 508-517.*
Seffernick et al., Melamine deaminase and Atrazine chlorohydrolase: 98 percent identical but functionally different. J. Bacteriol., 2001, vol. 183 (8): 2405-2410.*
Sen et al., Developments in directed evolution for improving enzyme functions. Appl. Biochem. Biotechnol., 2007, vol. 143: 212-223.*
Whisstock et al., Prediction of protein function from protein sequence. Q. Rev. Biophysics., 2003, vol. 36 (3): 307-340.*
Witkowski et al., Conversion of b-ketoacyl synthase to a Malonyl Decarboxylase by replacement of the active cysteine with glutamine. Biochemistry, 1999, vol. 38: 11643-11650.*

(Continued)

*Primary Examiner* — Ganapathirama Raghu
(74) *Attorney, Agent, or Firm* — Wolf, Greenfield & Sacks, P.C.

(57) ABSTRACT

Compositions, preparations, systems, and related methods for delivering a supercharged protein, or a complex of a supercharged protein and an agent (e.g., nucleic acids, peptides, proteins, small molecules) to cells are provided. Such systems and methods include the use of supercharged proteins. For example, superpositively charged proteins may be associated with nucleic acids (which typically have a net negative charge) via electrostatic interactions. In some embodiments, such systems and methods involve altering the primary sequence of a protein in order to "supercharge" the protein (e.g., to generate a superpositively-charged protein). In some embodiments, complexes comprising supercharged proteins and one or more agents to be delivered are useful as therapeutic agents. In some embodiments, complexes and/or pharmaceutical compositions thereof are administered to a subject in need thereof. The inventive complexes or pharmaceutical compositions thereof may be used to treat proliferative diseases, infectious diseases, cardiovascular diseases, inborn errors in metabolism, genetic diseases, etc.

25 Claims, 69 Drawing Sheets

(56) References Cited

U.S. PATENT DOCUMENTS

| | | | |
|---|---|---|---|
| 5,466,220 A | 11/1995 | Brenneman | |
| 5,480,381 A | 1/1996 | Weston | |
| 5,503,627 A | 4/1996 | McKinnon et al. | |
| 5,520,639 A | 5/1996 | Peterson et al. | |
| 5,527,288 A | 6/1996 | Gross et al. | |
| 5,569,189 A | 10/1996 | Parsons | |
| 5,574,142 A * | 11/1996 | Meyer et al. ............... | 536/23.1 |
| 5,599,302 A | 2/1997 | Lilley et al. | |
| 5,649,912 A | 7/1997 | Peterson | |
| 5,704,911 A | 1/1998 | Parsons | |
| 5,893,397 A | 4/1999 | Peterson et al. | |
| 5,977,089 A | 11/1999 | Arimilli et al. | |
| 5,993,412 A | 11/1999 | Deily et al. | |
| 6,005,087 A | 12/1999 | Cook et al. | |
| 6,031,086 A | 2/2000 | Switzer | |
| 6,127,533 A | 10/2000 | Cook et al. | |
| 6,225,460 B1 | 5/2001 | Bischofberger et al. | |
| 6,399,754 B1 | 6/2002 | Cook | |
| 6,403,779 B1 | 6/2002 | Kawasaki et al. | |
| 7,241,869 B2 | 7/2007 | Springer et al. | |
| 7,252,960 B2 | 8/2007 | Yamada et al. | |
| 7,271,241 B2 | 9/2007 | Waldo | |
| 7,306,937 B2 | 12/2007 | Poulose et al. | |
| 7,417,131 B2 | 8/2008 | Lukyanov | |
| 8,450,279 B2 * | 5/2013 | Jo et al. ............... | 514/19.8 |
| 2003/0134352 A1 | 7/2003 | Freimuth et al. | |
| 2003/0175950 A1 | 9/2003 | McSwiggen | |
| 2003/0236214 A1 | 12/2003 | Wolff et al. | |
| 2004/0092470 A1 | 5/2004 | Leonard et al. | |
| 2004/0102606 A1 | 5/2004 | Balicki et al. | |
| 2004/0110928 A1 | 6/2004 | Crisanti et al. | |
| 2004/0162235 A1 | 8/2004 | Trubetskoy et al. | |
| 2004/0176282 A1 | 9/2004 | Dalby et al. | |
| 2004/0192626 A1 | 9/2004 | McSwiggen et al. | |
| 2004/0215400 A1 | 10/2004 | Slovic et al. | |
| 2005/0020525 A1 | 1/2005 | McSwiggen et al. | |
| 2005/0032733 A1 | 2/2005 | McSwiggen et al. | |
| 2005/0059005 A1 | 3/2005 | Tuschl et al. | |
| 2005/0119181 A1 | 6/2005 | Pepinsky et al. | |
| 2005/0260192 A1 | 11/2005 | Springer et al. | |
| 2007/0105182 A1 | 5/2007 | Raines et al. | |
| 2009/0142820 A1 | 6/2009 | Bradbury et al. | |
| 2010/0209994 A1 | 8/2010 | Liu et al. | |
| 2011/0112040 A1 | 5/2011 | Liu et al. | |
| 2012/0129759 A1 | 5/2012 | Liu et al. | |

FOREIGN PATENT DOCUMENTS

| | | |
|---|---|---|
| WO | WO 97/37705 A1 | 10/1997 |
| WO | WO 99/34850 A1 | 7/1999 |
| WO | WO 02/18583 A2 | 3/2002 |
| WO | WO 2005/000097 A2 | 1/2005 |
| WO | WO 2005/035559 A1 | 4/2005 |
| WO | WO 2005/078074 A2 | 8/2005 |
| WO | WO 2007/143574 A1 | 12/2007 |
| WO | WO 2009/116984 A2 | 9/2009 |
| WO | WO 2009/134808 A2 | 11/2009 |

OTHER PUBLICATIONS

Supplementary European Search Report for 07784283.9 mailed Oct. 12, 2009.
U.S. Appl. No. 61/507,897, filed Jul. 14, 2011, Liu.
International Search Report and Written Opinion for PCT/US2007/070254 mailed Nov. 8, 2007.
International Preliminary Report on Patentability for PCT/US2007/070254 mailed Dec. 18, 2008.
Invitation to Pay Additional Fees for PCT/US2009/041984 mailed Jan. 27, 2010.
International Search Report and Written Opinion for PCT/US2009/041984 mailed Apr. 20, 2010.
International Preliminary Report on Patentability for PCT/US2009/041984 mailed Nov. 11, 2010.
International Search Report and Written Opinion for PCT/US2010/001250 mailed Apr. 12, 2011.
International Preliminary Report on Patentability for PCT/US2010/001250 mailed Nov. 10, 2011.
GenBank Submission; NIH/NCBI, Accession No. P42212, Prasher et al.; Mar. 21, 2006.
UniProtKB/Swiss-Prot O75683: Magoulas et al.: Sep. 21, 2011.
UniProtKB/Swiss-Prot O75925: Liu et al.: Dec. 14, 2011.
UniProtKB/Swiss-Prot P05412: Hattori et al.: Dec. 14, 2011.
UniProtKB/Swiss-Prot P09429: Wen et al.: Dec. 14, 2011.
UniProtKB/Swiss-Prot P12034: Haub et al.: Dec. 14, 2011.
UniProtKB/Swiss-Prot P12956: Chan et al.: Dec. 14, 2011.
UniProtKB/Swiss-Prot P14210: Miyazawa et al.: Dec. 14, 2011.
UniProtKB/Swiss-Prot P16401: Albig et al.: Dec. 14, 2011.
UniProtKB/Swiss-Prot P18509: Ohkubo et al.: Dec. 14, 2011.
UniProtKB/Swiss-Prot P21741: Tsutsui et al.: Dec. 14, 2011.
UniProtKB/Swiss-Prot P35659: von Lindern et al.: Dec. 14, 2011.
UniProtKB/Swiss-Prot P36578: Bagni et al.: Dec. 14, 2011.
UniProtKB/Swiss-Prot P41218: Briggs et al.: Dec. 14, 2011.
UniProtKB/Swiss-Prot P54274: Chong et al.: Dec. 14, 2011.
UniProtKB/Swiss-Prot P62805: Sierra et al.: Dec. 14, 2011.
UniProtKB/Swiss-Prot P81534: Harder et al.: Sep. 21, 2011.
UniProtKB/Swiss-Prot P83369: Ota et al.: Dec. 14, 2011.
UniProtKB/Swiss-Prot Q03164: Tkachuk et al.: Dec. 14, 2011.
UniProtKB/Swiss-Prot Q12796: Chen et al.: Dec. 14, 2011.
UniProtKB/Swiss-Prot Q13601: Gerhard et al.: Dec. 14, 2011.
UniProtKB/Swiss-Prot Q15287: Badolato et al.: Dec. 14, 2011.
UniProtKB/Swiss-Prot Q66PJ3: Mural et al.: Dec. 14, 2011.
UniProtKB/Swiss-Prot Q7L7L0: Marzluff et al.: Dec. 14, 2011.
UniProtKB/Swiss-Prot Q8N5F7: Chen et al.: Dec. 14, 2011.
UniProtKB/Swiss-Prot Q8N726: Stone et al.: Dec. 14, 2011.
UniProtKB/Swiss-Prot Q8N9Q2: Ota et al.: Dec. 14, 2011.
UniProtKB/Swiss-Prot Q8TDN6: Kaser et al.: Dec. 14, 2011.
UniProtKB/Swiss-Prot Q8WVK2: Nakamura et al.: Dec. 14, 2011.
UniProtKB/Swiss-Prot Q96FI4: Takao et al.: Dec. 14, 2011.
UniProtKB/Swiss-Prot Q9NWT8: Ota et al.: Dec. 14, 2011.
UniProtKB/Swiss-Prot Q99075: Higashiyama et al.: Dec. 14, 2011.
UniProtKB/Swiss-Prot Q99848: Shire et al.: Dec. 14, 2011.
UniProtKB/Swiss-Prot Q9H6F5: Hoshino et al.: Jan. 19, 2010.
UniProtKB/Swiss-Prot Q9HC23: Li et al.: Dec. 14, 2011.
UniProtKB/Swiss-Prot Q9UK58: Dickinson et al.: Dec. 14, 2011.
UniProtKB/Swiss-Prot Q9Y258: Guo et al.: Dec. 14, 2011.
Abremski et al., Studies on the properties of P1 site-specific recombination: evidence for topologically unlinked products following recombination. Cell. Apr. 1983;32(4):1301-11.
Akinc et al., A combinatorial library of lipid-like materials for delivery of RNAi therapeutics. Nat Biotechnol. May 2008;26(5):561-9. Epub Apr. 27, 2008.
Ali-Osman et al., Molecular cloning, characterization, and expression in *Escherichia coli* of full-length cDNAs of three human glutathione S-transferase Pi gene variants. Evidence for differential catalytic activity of the encoded proteins. J Biol Chem. Apr. 11, 1997;272(15):10004-12.
Altschul et al., Basic local alignment search tool. J Mol Biol. Oct. 5, 1990;215(3):403-10.
Anastassiadis et al., Dre recombinase, like Cre, is a highly efficient site-specific recombinase in *E. coli*, mammalian cells and mice. Dis Model Mech. Sep.-Oct. 2009;2(9-10):508-15. Epub Aug. 19, 2009.
Andrews et al., The rough energy landscape of superfolder GFP is linked to the chromophore. J Mol Biol. Oct. 19, 2007;373(2):476-90. Epub Aug. 15, 2007.
Apple et al., Cationization of protein antigens. IV. Increased antigen uptake by antigen-presenting cells. J Immunol. May 15, 1988;140(10):3290-5.
Atkinson et al., Delivering the goods: viral and non-viral gene therapy systems and the inherent limits on cargo DNA and internal sequences. Genetica. May 2010;138(5):485-98. Epub Jan. 19, 2010.
Atwell et al., Structural plasticity in a remodeled protein-protein interface. Science. Nov. 7, 1997;278(5340):1125-8.
Bae et al., Protective anti-tumour immune responses by murine dendritic cells pulsed with recombinant Tat-carcinoembryonic antigen derived from *Escherichia coli*. Clin Exp Immunol. Jul. 2009;157(1):128-38.

(56) References Cited

OTHER PUBLICATIONS

Baeuerle et al., Chlorate—a potent inhibitor of protein sulfation in intact cells. Biochem Biophys Res Commun. Dec. 15, 1986;141(2):870-7.
Baker et al., Electrostatics of nanosystems: application to microtubules and the ribosome. Proc Natl Acad Sci U S A. Aug. 28, 2001;98(18):10037-41. Epub Aug. 21, 2001.
Bartel, MicroRNAs: genomics, biogenesis, mechanism, and function. Cell. Jan. 23, 2004;116(2):281-97.
Beard et al., Efficient method to generate single-copy transgenic mice by site-specific integration in embryonic stem cells. Genesis. Jan. 2006;44(1):23-8.
Borodovsky et al., A novel active site-directed probe specific for deubiquitylating enzymes reveals proteasome association of USP14. EMBO J. Sep. 17, 2001;20(18):5187-96.
Boussif et al., A versatile vector for gene and oligonucleotide transfer into cells in culture and in vivo: polyethylenimine. Proc Natl Acad Sci U S A. Aug. 1, 1995;92(16):7297-301.
Brambrink et al., Sequential expression of pluripotency markers during direct reprogramming of mouse somatic cells. Cell Stem Cell. Feb. 7, 2008;2(2):151-9.
Brummelkamp et al., Stable suppression of tumorigenicity by virus-mediated RNA interference. Cancer Cell. Sep. 2002;2(3):243-7.
Brunet et al., The transcription factor Engrailed-2 guides retinal axons. Nature. Nov. 3, 2005;438(7064):94-8.
Bumcrot et al., RNAi therapeutics: a potential new class of pharmaceutical drugs. Nat Chem Biol. Dec. 2006;2(12):711-9.
Buskirk et al., Creating small-molecule-dependent switches to modulate biological functions. Chem Biol. Feb. 2005;12(2):151-61.
Buskirk et al., Directed evolution of ligand dependence: small-molecule-activated protein splicing. Proc Natl Acad Sci U S A. Jul. 20, 2004;101(29):10505-10. Epub Jul. 9, 2004.
Bystroff et al., Crystal structure of unliganded *Escherichia coli* dihydrofolate reductase. Ligand-induced conformational changes and cooperativity in binding. Biochemistry. Feb. 26, 1991;30(8):2227-39.
Cabantous et al., In vivo and in vitro protein solubility assays using split GFP. Nat Methods. Oct. 2006;3(10):845-54.
Cabantous et al., New molecular reporters for rapid protein folding assays. PLoS One. Jun. 11, 2008;3(6):e2387.
Cabantous et al., Protein tagging and detection with engineered self-assembling fragments of green fluorescent protein. Nat Biotechnol. Jan. 2005;23(1):102-7. Epub Dec. 5, 2004.
Cabantous et al., Recent advances in GFP folding reporter and split-GFP solubility reporter technologies. Application to improving the folding and solubility of recalcitrant proteins from *Mycobacterium tuberculosis*. J Struct Funct Genomics. 2005;6(2-3):113-9.
Cardoso et al., siRNA delivery by a transferrin-associated lipid-based vector: a non-viral strategy to mediate gene silencing. J Gene Med. Mar. 2007;9(3):170-83.
Carillo et al., The Multiple Sequence Alignment Problem in Biology. SIAM J Applied Math. 1988;48(5):1073-82.
Carlotti et al., Lentiviral vectors efficiently transduce quiescent mature 3T3-L1 adipocytes. Mol Ther. Feb. 2004;9(2):209-17.
Caron et al., Intracellular delivery of a Tat-eGFP fusion protein into muscle cells. Mol Ther. Mar. 2001;3(3):310-8.
Carroll, Zinc-finger nucleases as gene therapy agents. Gene Ther. Nov. 2008;15(22):1463-8. Epub Sep. 11, 2008.
Cava et al., Expression and use of superfolder green fluorescent protein at high temperatures in vivo: a tool to study extreme thermophile biology. Environ Microbiol. Mar. 2008;10(3):605-13. Epub Jan. 7, 2008.
Chakraborty, Potentiality of small interfering RNAs (siRNA) as recent therapeutic targets for gene-silencing. Curr Drug Targets. Mar. 2007;8(3):469-82.
Chandler et al., Targeting tumor cells via EGF receptors: selective toxicity of an HBEGF-toxin fusion protein. Int J Cancer. Sep. 25, 1998;78(1):106-11.
Charton et al., The structural dependence of amino acid hydrophobicity parameters. J Theor Biol. Dec. 21, 1982;99(4):629-44.

Chen et al., A general strategy for the evolution of bond-forming enzymes using yeast display. Proc Natl Acad Sci U S A. Jul. 12, 2011;108(28):11399-404. Epub Jun. 22, 2011.
Chen et al., HDAC4 regulates neuronal survival in normal and diseased retinas. Science. Jan. 9, 2009;323(5911):256-9.
Chiti et al., Protein misfolding, functional amyloid, and human disease. Annu Rev Biochem. 2006;75:333-66.
Chiti et al., Rationalization of the effects of mutations on peptide and protein aggregation rates. Nature. Aug. 14, 2003;424(6950):805-8.
Chiti et al., Studies of the aggregation of mutant proteins in vitro provide insights into the genetics of amyloid diseases. Proc Natl Acad Sci U S A. Dec. 10, 2002;99 Suppl 4:16419-26. Epub Oct. 8, 2002.
Chun et al., Split GFP complementation assay: a novel approach to quantitatively measure aggregation of tau in situ: effects of GSK3beta activation and caspase 3 cleavage. J Neurochem. Dec. 2007;103(6):2529-39. Epub Oct. 1, 2007.
Cioce et al., Hepatocyte growth factor (HGF)/NK1 is a naturally occurring HGF/scatter factor variant with partial agonist/antagonist activity. J Biol Chem. May 31, 1996;271(22):13110-5.
Clackson et al., A hot spot of binding energy in a hormone-receptor interface. Science. Jan. 20, 1995;267(5196):383-6.
Cohen et al., Therapeutic approaches to protein-misfolding diseases. Nature. Dec. 18, 2003;426(6968):905-9.
Cornette et al., Hydrophobicity scales and computational techniques for detecting amphipathic structures in proteins. J Mol Biol. Jun. 5, 1987;195(3):659-85.
Crameri et al., Improved green fluorescent protein by molecular evolution using DNA shuffling. Nat Biotechnol. Mar. 1996;14(3):315-9.
Cronican et al., A class of human proteins that deliver functional proteins into mammalian cells in vitro and in vivo. Chem Biol. Jul. 29, 2011;18(7):833-8.
Cronican et al., Potent delivery of functional proteins into Mammalian cells in vitro and in vivo using a supercharged protein. ACS Chem Biol. Aug. 20, 2010;5(8):747-52.
Czerwinski et al., Cytotoxic agents directed to peptide hormone receptors: defining the requirements for a successful drug. Proc Natl Acad Sci U S A. Sep. 29, 1998;95(20):11520-5.
Daniels et al., Intrinsically cell-permeable miniature proteins based on a minimal cationic PPII motif. J Am Chem Soc. Nov. 28, 2007;129(47):14578-9. Epub Nov. 6, 2007.
Darimont et al., Structure and specificity of nuclear receptor-coactivator interactions. Genes Dev. Nov. 1, 1998;12(21):3343-56.
Deshayes et al., Cell-penetrating peptides: tools for intracellular delivery of therapeutics. Cell Mol Life Sci. Aug. 2005;62(16):1839-49.
Deshayes et al., Chapter 11. Peptide-mediated delivery of nucleic acids into mammalian cells. Methods Mol Biol. 2007;386:299-308.
Devereux et al., A comprehensive set of sequence analysis programs for the VAX. Nucleic Acids Res. Jan. 11, 1984;12(1 Pt 1):387-95.
Dirr et al., Refined crystal structure of porcine class Pi glutathione S-transferase (pGST P1-1) at 2.1 A resolution. J Mol Biol. Oct. 14, 1994;243(1):72-92.
Domen et al., Cationization of protein antigens. III. Abrogation of oral tolerance. J Immunol. Nov. 15, 1987;139(10):3195-8.
Dorsett et al., siRNAs: applications in functional genomics and potential as therapeutics. Nat Rev Drug Discov. Apr. 2004;3(4):318-29.
Doudna et al., The chemical repertoire of natural ribozymes. Nature. Jul. 11, 2002;418(6894):222-8.
Dubowchik et al., Cathepsin B-labile dipeptide linkers for lysosomal release of doxorubicin from internalizing immunoconjugates: model studies of enzymatic drug release and antigen-specific in vitro anti-cancer activity. Bioconjug Chem. Jul.-Aug. 2002;13(4):855-69.
Duncan et al., Degradation of side-chains of N-(2-hydroxypropyl)methacrylamide copolymers by lysosomal thiol-proteinases. Biosci Rep. Dec. 1982;2(12):1041-6.
Dykxhoorn et al., Killing the messenger: short RNAs that silence gene expression. Nat Rev Mol Cell Biol. Jun. 2003;4(6):457-67.
Elbashir et al., Duplexes of 21-nucleotide RNAs mediate RNA interference in cultured mammalian cells. Nature. May 24, 2001;411(6836):494-8.

(56) References Cited

OTHER PUBLICATIONS

Elbashir et al., Functional anatomy of siRNAs for mediating efficient RNAi in *Drosophila melanogaster* embryo lysate. EMBO J. Dec. 3, 2001;20(23):6877-88.
Elbashir et al., RNA interference is mediated by 21- and 22-nucleotide RNAs. Genes Dev. Jan. 15, 2001;15(2):188-200.
Elenius et al., Activation of HER4 by heparin-binding EGF-like growth factor stimulates chemotaxis but not proliferation. EMBO J. Mar. 17, 1997;16(6):1268-78.
Erbacher et al., Putative role of chloroquine in gene transfer into a human hepatoma cell line by DNA/lactosylated polylysine complexes. Exp Cell Res. May 25, 1996;225(1):186-94.
Fire et al., Potent and specific genetic interference by double-stranded RNA in Caenorhabditis elegans. Nature. Feb. 19, 1998;391(6669):806-11.
Fisher et al., Evaluating the specificity of antisense oligonucleotide conjugates. A DNA array analysis. J Biol Chem. Jun. 21, 2002;277(25):22980-4. Epub Apr. 10, 2002.
Fowler et al., Rational design of aggregation-resistant bioactive peptides: reengineering human calcitonin. Proc Natl Acad Sci U S A. Jul. 19, 2005;102(29):10105-10. Epub Jul. 8, 2005.
Frankel et al., Cellular uptake of the tat protein from human immunodeficiency virus. Cell. Dec. 23, 1988;55(6):1189-93.
Frokjaer et al., Protein drug stability: a formulation challenge. Nat Rev Drug Discov. Apr. 2005;4(4):298-306.
Fuchs et al., Arginine grafting to endow cell permeability. ACS Chem Biol. Mar. 20, 2007;2(3):167-70. Epub Feb. 23, 2007.
Fuchs et al., Increasing the potency of a cytotoxin with an arginine graft. Protein Eng Des Sel. Oct. 2007;20(10):505-9. Epub Oct. 22, 2007.
Fuchs et al., Pathway for polyarginine entry into mammalian cells. Biochemistry. Mar. 9, 2004;43(9):2438-44.
Futaki et al., Arginine-rich peptides. An abundant source of membrane-permeable peptides having potential as carriers for intracellular protein delivery. J Biol Chem. Feb. 23, 2001;276(8):5836-40. Epub Nov. 17, 2000.
Futaki et al., Structural variety of membrane permeable peptides. Curr Protein Pept Sci. Apr. 2003;4(2):87-96.
Futami et al., Preparation of potent cytotoxic ribonucleases by cationization: enhanced cellular uptake and decreased interaction with ribonuclease inhibitor by chemical modification of carboxyl groups. Biochemistry. Jun. 26, 2001;40(25):7518-24.
Gabel et al., Mannose 6-phosphate receptor-mediated endocytosis of acid hydrolases: internalization of beta-glucuronidase is accompanied by a limited dephosphorylation. J Cell Biol. Nov. 1986;103(5):1817-27.
Gampe et al., Asymmetry in the PPARgamma/RXRalpha crystal structure reveals the molecular basis of heterodimerization among nuclear receptors. Mol Cell. Mar. 2000;5(3):545-55.
Giepmans et al., The fluorescent toolbox for assessing protein location and function. Science. Apr. 14, 2006;312(5771):217-24.
Gitlin et al., Why are proteins charged? Networks of charge-charge interactions in proteins measured by charge ladders and capillary electrophoresis. Angew Chem Int Ed Engl. May 5, 2006;45(19):3022-60.
Glover et al., Crystal structure of the heterodimeric bZIP transcription factor c-Fos-c-Jun bound to DNA. Nature. Jan. 19, 1995;373(6511):257-61.
Goodchild, Hammerhead ribozymes: biochemical and chemical considerations. Curr Opin Mol Ther. Jun. 2000;2(3):272-81.
Green et al., Autonomous functional domains of chemically synthesized human immunodeficiency virus tat trans-activator protein. Cell. Dec. 23, 1988;55(6):1179-88.
Gregory et al., Chapter 3. MicroRNA biogenesis: isolation and characterization of the microprocessor complex. Methods Mol Biol. 2006;342:33-47.
Gudiksen et al., Eliminating positively charged lysine epsilon-NH3+ groups on the surface of carbonic anhydrase has no significant influence on its folding from sodium dodecyl sulfate. J Am Chem Soc. Apr. 6, 2005;127(13):4707-14.
Guo et al., Structure of Cre recombinase complexed with DNA in a site-specific recombination synapse. Nature. Sep. 4, 1997;389(6646):40-6.
Hamelryck et al., An amino acid has two sides: a new 2D measure provides a different view of solvent exposure. Proteins. Apr. 1, 2005;59(1):38-48.
Hammond et al., An RNA-directed nuclease mediates post-transcriptional gene silencing in *Drosophila* cells. Nature. Mar. 16, 2000;404(6775):293-6.
Hanna et al., Direct reprogramming of terminally differentiated mature B lymphocytes to pluripotency. Cell. Apr. 18, 2008;133(2):250-64.
Hansen et al., Predicting cell-penetrating peptides. Adv Drug Deliv Rev. Mar. 1, 2008;60(4-5):572-9. Epub Oct. 22, 2007.
Harder et al., Isolation and characterization of human beta-defensin-3, a novel human inducible peptide antibiotic. J Biol Chem. Feb. 23, 2001;276(8):5707-13. Epub Nov. 20, 2000.
Hasadsri et al., Functional protein delivery into neurons using polymeric nanoparticles. J Biol Chem. Mar. 13, 2009;284(11):6972-81. Epub Jan. 7, 2009.
Helene, The anti-gene strategy: control of gene expression by triplex-forming-oligonucleotides. Anticancer Drug Des. Dec. 1991;6(6):569-84.
Helene et al., Control of gene expression by triple helix-forming oligonucleotides. The antigene strategy. Ann N Y Acad Sci. Oct. 28, 1992;660:27-36.
Hockemeyer et al., Efficient targeting of expressed and silent genes in human ESCs and iPSCs using zinc-finger nucleases. Nat Biotechnol. Sep. 2009;27(9):851-7. Epub Aug. 13, 2009.
Hollenback et al., Daxx and histone deacetylase II associate with chromatin through an interaction with core histones and the chromatin-associated protein Dek. J Cell Sci. Aug. 15, 2002;115(Pt 16):3319-30.
Hopkins et al., Internalization and processing of 9yclone9ring and the 9yclone9ring receptor in human carcinoma A431 cells. J Cell Biol. Aug. 1983;97(2):508-21.
Hoshino et al., Redundant promoter elements mediate IL-3-induced expression of a novel cytokine-inducible gene, cyclon. FEBS Lett. Mar. 6, 2007;581(5):975-80. Epub Feb 7, 2007.
Iannone et al., Multiplexed molecular interactions of nuclear receptors using fluorescent microspheres. Cytometry. Aug. 1, 2001;44(4):326-37.
Janin, Surface and inside volumes in globular proteins. Nature. Feb. 8, 1979;277(5696):491-2.
Jantsch et al., Small interfering RNA (siRNA) delivery into murine bone marrow-derived dendritic cells by electroporation. J Immunol Methods. Aug. 20, 2008;337(1):71-7. Epub Apr. 28, 2008.
Jarver et al., In vivo biodistribution and efficacy of peptide mediated delivery. Trends Pharmacol Sci. Nov. 2010;31(11):528-35. Epub Sep. 7, 2010.
Jia et al., Demonstration of two novel methods for predicting functional siRNA efficiency. BMC Bioinformatics. May 29, 2006;7:271. 10 pages.
Joliot et al., Antennapedia homeobox peptide regulates neural morphogenesis. Proc Natl Acad Sci U S A. Mar. 1, 1991;88(5):1864-8.
Kada et al., Rapid estimation of avidin and streptavidin by fluorescence quenching or fluorescence polarization. Biochim Biophys Acta. Mar. 14, 1999;1427(1):44-8.
Kandavelou et al., Targeted manipulation of mammalian genomes using designed zinc finger nucleases. Biochem Biophys Res Commun. Oct. 9, 2009;388(1):56-61. Epub Jul. 25, 2009.
Kaouass et al., Histonefection: Novel and potent non-viral gene delivery. J Control Release. Jul. 20, 2006;113(3):245-54. Epub Jun. 27, 2006.
Kim et al., Generation of human induced pluripotent stem cells by direct delivery of reprogramming proteins. Cell Stem Cell. Jun. 5, 2009;4(6):472-6. Epub May 28, 2009.
Kim et al., miTarget: microRNA target gene prediction using a support vector machine. BMC Bioinformatics. Sep. 18, 2006;7:411. 12 pages.

(56) References Cited

OTHER PUBLICATIONS

Kim et al., Targeted genome editing in human cells with zinc finger nucleases constructed via modular assembly. Genome Res. Jul. 2009;19(7):1279-88. Epub May 21, 2009.
Knight et al., Global analysis of predicted proteomes: functional adaptation of physical properties. Proc Natl Acad Sci U S A. Jun. 1, 2004;101(22):8390-5. Epub May 18, 2004.
Krek et al., Combinatorial microRNA target predictions. Nat Genet. May 2005;37(5):495-500. Epub Apr. 3, 2005.
Krutzfeldt et al., Silencing of microRNAs in vivo with 'antagomirs'. Nature. Dec. 1, 2005;438(7068):685-9. Epub Oct. 30, 2005.
Kuhlman et al., Design of a novel globular protein fold with atomic-level accuracy. Science. Nov. 21, 2003;302(5649):1364-8.
Kumar et al., Transvascular delivery of small interfering RNA to the central nervous system. Nature. Jul. 5, 2007;448(7149):39-43. Epub Jun. 17, 2007.
Kunkel et al., Efficient site-directed mutagenesis using uracil-containing DNA. Methods Enzymol. 1991;204:125-39.
Kurreck, Antisense technologies. Improvement through novel chemical modifications. Eur J Biochem. Apr. 2003;270(8):1628-44.
Kyte et al., A simple method for displaying the hydropathic character of a protein. J Mol Biol. May 5, 1982;157(1):105-32.
Lai et al., Vault nanoparticles containing an adenovirus-derived membrane lytic protein facilitate toxin and gene transfer. ACS Nano. Mar. 24, 2009;3(3):691-9.
Lawrence et al., Supercharging proteins can impart unusual resilience. J Am Chem Soc. Aug. 22, 2007;129(33):10110-2. Epub Aug. 1, 2007.
Lee et al., The interpretation of protein structures: estimation of static accessibility. J Mol Biol. Feb. 14, 1971;55(3):379-400.
Lewis et al., Methotrexate-resistant variants of human dihydrofolate reductase with substitutions of leucine 22. Kinetics, crystallography, and potential as selectable markers. J Biol Chem. Mar. 10, 1995;270(10):5057-64.
Lewis et al., Prediction of mammalian microRNA targets. Cell. Dec. 26, 2003; 115(7):787-98.
Li et al., Defining the optimal parameters for hairpin-based knockdown constructs. RNA. Oct. 2007;13(10):1765-74. Epub Aug. 13, 2007.
Liu et al., siRNA delivery into human T cells and primary cells with carbon-nanotube transporters. Angew Chem Int Ed Engl. 2007;46(12):2023-7.
Loeb, Chemical and Physical Behavior of Casein Solutions. J Gen Physiol. Mar. 20, 1921;3(4):547-555.
Löfgren et al., Antiprion properties of prion protein-derived cell-penetrating peptides. FASEB J. Jul. 2008;22(7):2177-84. Epub Feb. 22, 2008.
Loison et al., A ubiquitin-based assay for the cytosolic uptake of protein transduction domains. Mol Ther. Feb. 2005;11(2):205-14.
Loladze et al., Removal of surface charge-charge interactions from ubiquitin leaves the protein folded and very stable. Protein Sci. Jan. 2002;11(1):174-7.
Lombardo et al., Gene editing in human stem cells using zinc finger nucleases and integrase-defective lentiviral vector delivery. Nat Biotechnol. Nov. 2007;25(11):1298-306. Epub Oct. 28, 2007.
Lundberg et al., Delivery of short interfering RNA using endosomolytic cell-penetrating peptides. FASEB J. Sep. 2007;21(11):2664-71. Epub Apr. 26, 2007.
Ma et al., Non-classical nuclear localization signal peptides for high efficiency lipofection of primary neurons and neuronal cell lines. Neuroscience. 2002;112(1):1-5.
Magliery et al., Combinatorial approaches to protein stability and structure. Eur J Biochem. May 2004;271(9):1595-608.
Maher, DNA triple-helix formation: an approach to artificial gene repressors? Bioessays. Dec. 1992;14(12):807-15.
Mallery et al., Antibodies mediate intracellular immunity through tripartite motif-containing 21 (TRIM21). Proc Natl Acad Sci U S A. Nov. 16, 2010;107(46):19985-90. Epub Nov. 2, 2010.

Mani et al., Design, engineering, and characterization of zinc finger nucleases. Biochem Biophys Res Commun. Sep. 23, 2005;335(2):447-57.
Matsuda et al., Controlled expression of transgenes introduced by in vivo electroporation. Proc Natl Acad Sci U S A. Jan. 16, 2007;104(3):1027-32. Epub Jan. 5, 2007.
McInerney et al., Determinants of coactivator LXXLL motif specificity in nuclear receptor transcriptional activation. Genes Dev. Nov. 1, 1998;12(21):3357-68.
McManus et al., Small interfering RNA-mediated gene silencing in T lymphocytes. J Immunol. Nov. 15, 2002;169(10):5754-60.
McNaughton et al., Mammalian cell penetration, siRNA transfection, and DNA transfection by supercharged proteins. Proc Natl Acad Sci U S A. Apr. 14, 2009;106(15):6111-6. Epub Mar. 23, 2009.
Meade et al., Enhancing the cellular uptake of siRNA duplexes following noncovalent packaging with protein transduction domain peptides. Adv Drug Deliv Rev. Mar. 1, 2008;60(4-5):530-6. Epub Oct. 22, 2007.
Meyer et al., Breathing life into polycations: functionalization with pH-responsive endosomolytic peptides and polyethylene glycol enables siRNA delivery. J Am Chem Soc. Mar. 19, 2008;130(11):3272-3. Epub Feb. 21, 2008.
Michienzi et al., Intracellular applications of ribozymes. Methods Enzymol. 2001;341:581-96.
Mitchell et al., Polyarginine enters cells more efficiently than other polycationic homopolymers. J Pept Res. Nov. 2000;56(5):318-25.
Mootz et al., Protein splicing triggered by a small molecule. J Am Chem Soc. Aug. 7, 2002;124(31):9044-5.
Mor-Vaknin et al., The DEK nuclear autoantigen is a secreted chemotactic factor. Mol Cell Biol. Dec. 2006;26(24):9484-96. Epub Oct. 9, 2006.
Morris et al., Lentiviral-mediated delivery of siRNAs for antiviral therapy. Gene Ther. Mar. 2006;13(6):553-8.
Muckerheide et al., Cationization of protein antigens. I. Alteration of immunogenic properties. J Immunol. Feb. 1, 1987;138(3):833-7.
Muckerheide et al., Cationization of protein antigens. II. Alteration of regulatory properties. J Immunol. May 1, 1987;138(9):2800-4.
Myers et al., Optimal alignments in linear space. CABIOS. 1989;4(1):11-17.
Myou et al., Blockade of focal clustering and active conformation in beta 2-integrin-mediated adhesion of eosinophils to intercellular adhesion molecule-1 caused by transduction of HIV TAT-dominant negative Ras. J Immunol. Sep. 1, 2002;169(5):2670-6.
Naito et al., siVirus: web-based antiviral siRNA design software for highly divergent viral sequences. Nucleic Acids Res. Jul. 1, 2006;34(Web Server issue): W448-50.
Nakamura et al., ALL-1 is a histone methyltransferase that assembles a supercomplex of proteins involved in transcriptional regulation. Mol Cell. Nov. 2002;10(5):1119-28.
Nakase et al., Methodological and cellular aspects that govern the internalization mechanisms of arginine-rich cell-penetrating peptides. Adv Drug Deliv Rev. Mar. 1, 2008;60(4-5):598-607. Epub Oct. 22, 2007.
Nolden et al., Stem cell engineering using transducible Cre recombinase. Methods Mol Med. 2007;140:17-32.
Novina et al., The RNAi revolution. Nature. Jul. 8, 2004;430(6996):161-4.
Okita et al., Generation of germline-competent induced pluripotent stem cells. Nature. Jul. 19, 2007;448(7151):313-7. Epub Jun. 6, 2007.
Pakula et al., Genetic analysis of protein stability and function. Annu Rev Genet. 1989;23:289-310.
Pan et al., Reprogramming human fibroblasts using HIV-1 TAT recombinant proteins OCT4, SOX2, KLF4 and c-MYC. Mol Biol Rep. Apr. 2010;37(4):2117-24. Epub Aug. 9, 2009.
Pardridge et al., Enhanced endocytosis and anti-human immunodeficiency virus type 1 activity of anti-rev antibodies after cationization. J Infect Dis. Jan. 1994;169(1):55-61.
Pawar et al., Prediction of "aggregation-prone" and "aggregation-susceptible" regions in proteins associated with neurodegenerative diseases. J Mol Biol. Jul. 8, 2005;350(2):379-92.

(56) References Cited

OTHER PUBLICATIONS

Payne et al., Internalization and trafficking of cell surface proteoglycans and proteoglycan-binding ligands. Traffic. Apr. 2007;8(4):389-401.

Pédelacq et al., Engineering and characterization of a superfolder green fluorescent protein. Nat Biotechnol. Jan. 2006;24(1):79-88. Epub Dec. 20, 2005.

Pédelacq et al., Engineering soluble proteins for structural genomics. Nat Biotechnol. Sep. 2002;20(9):927-32. Epub Aug. 19, 2002.

Pelletier et al., An in vivo library-versus-library selection of optimized protein-protein interactions. Nat Biotechnol. Jul. 1999;17(7):683-90.

Pelletier et al., Oligomerization domain-directed reassembly of active dihydrofolate reductase from rationally designed fragments. Proc Natl Acad Sci U S A. Oct. 13, 1998;95(21):12141-6.

Perez et al., Establishment of HIV-1 resistance in CD4+ T cells by genome editing using zinc-finger nucleases. Nat Biotechnol. Jul. 2008;26(7):808-16. Epub Jun. 29, 2008.

Phillips et al., Binding and stability determinants of the PPARgamma nuclear receptor-coactivator interface as revealed by shotgun alanine scanning and in vivo selection. J Am Chem Soc. Aug. 30, 2006;128(34):11298-306.

Picard et al., SRC-1 and TIF2 control energy balance between white and brown adipose tissues. Cell. Dec. 27, 2002;111(7):931-41.

Proft, Sortase-mediated protein ligation: an emerging biotechnology tool for protein modification and immobilization. Biotechnol Lett. Jan. 2010;32(1):1-10. Epub Sep 1, 2009.

Rehmsmeier et al., Fast and effective prediction of microRNA/target duplexes. RNA. Oct. 2004;10(10):1507-17.

Reynolds et al., Rational siRNA design for RNA interference. Nat Biotechnol. Mar. 2004;22(3):326-30. Epub Feb. 1, 2004.

Richmond, Solvent accessible surface area and excluded volume in proteins. Analytical equations for overlapping spheres and implications for the hydrophobic effect. J Mol Biol. Sep. 5, 1984;178(1):63-89.

Rizk et al., An engineered substance P variant for receptor-mediated delivery of synthetic antibodies into tumor cells. Proc Natl Acad Sci U S A. Jul. 7, 2009;106(27):11011-5. Epub Jun. 22, 2009.

Rose et al., Hydrophobicity of amino acid residues in globular proteins. Science. Aug. 30, 1985;229(4716):834-8.

Rosenbluh et al., Translocation of histone proteins across lipid bilayers and Mycoplasma membranes. J Mol Biol. Jan. 14, 2005;345(2):387-400.

Rosi et al., Oligonucleotide-modified gold nanoparticles for intracellular gene regulation. Science. May 19, 2006;312(5776):1027-30.

Rozema et al., Dynamic PolyConjugates for targeted in vivo delivery of siRNA to hepatocytes. Proc Natl Acad Sci U S A. Aug. 7, 2007;104(32):12982-7. Epub Jul. 24, 2007.

Ruzza et al., Tat cell-penetrating peptide has the characteristics of a poly(proline) II helix in aqueous solution and in SDS micelles. J Pept Sci. Jul. 2004;10(7):423-6.

Ryu et al., Enhanced uptake of a heterologous protein with an HIV-1 Tat protein transduction domains (PTD) at both termini. Mol Cells. Dec. 31, 2003;16(3):385-91.

Sacchetti et al., Green fluorescent protein variants fold differentially in prokaryotic and eukaryotic cells. J Cell Biochem Suppl. 2001;Suppl 36:117-28.

Santoro et al., Unfolding free energy changes determined by the linear extrapolation method. 1. Unfolding of phenylmethanesulfonyl alpha-chymotrypsin using different denaturants. Biochemistry. Oct. 18, 1988;27(21):8063-8.

Sawano et al., Directed evolution of green fluorescent protein by a new versatile PCR strategy for site-directed and semi-random mutagenesis. Nucleic Acids Res. Aug. 15, 2000;28(16):E78.

Schlesinger et al., Molecular conservation of 74 amino acid sequence of ubiquitin between cattle and man. Nature. May 29, 1975;255(5507):423-4.

Schmid et al., Albumin-binding prodrugs of camptothecin and doxorubicin with an Ala-Leu-Ala-Leu-linker that are cleaved by cathepsin B: synthesis and antitumor efficacy. Bioconjug Chem. May-Jun. 2007;18(3):702-16. Epub Mar. 23, 2007.

Schueler-Furman et al., Conserved residue clustering and protein structure prediction. Proteins. Aug. 1, 2003;52(2):225-35.

Schwarze et al., In vivo protein transduction: delivery of a biologically active protein into the mouse. Science. Sep. 3, 1999;285(5433):1569-72.

Seale et al., Transcriptional control of brown fat determination by PRDM16. Cell Metab. Jul. 2007;6(1):38-54.

Segura et al., Synthesis and in vitro characterization of an ABC triblock copolymer for siRNA delivery. Bioconjug Chem. May-Jun. 2007;18(3):736-45. Epub Mar. 15, 2007.

Shaner et al., A guide to choosing fluorescent proteins. Nat Methods. Dec. 2005;2(12):905-9.

Shaner et al., Improved monomeric red, orange and yellow fluorescent proteins derived from *Discosoma* sp. red fluorescent protein. Nat Biotechnol. Dec. 2004;22(12):1567-72. Epub Nov. 21, 2004.

Shaw et al., Lysine acetylation can generate highly charged enzymes with increased resistance toward irreversible inactivation. Protein Sci. Aug. 2008;17(8):1446-55. Epub May 1, 2008.

Shinkai et al., A novel human CC chemokine, eotaxin-3, which is expressed in IL-4-stimulated vascular endothelial cells, exhibits potent activity toward eosinophils. J Immunol. Aug. 1, 1999;163(3):1602-10.

Smith et al., Coregulator function: a key to understanding tissue specificity of selective receptor modulators. Endocr Rev. Feb. 2004;25(1):45-71.

Smith et al., Minimally cationic cell-permeable miniature proteins via alpha-helical arginine display. J Am Chem Soc. Mar. 12, 2008;130(10):2948-9. Epub Feb. 14, 2008.

Sokolova et al., Inorganic nanoparticles as carriers of nucleic acids into cells. Angew Chem Int Ed Engl. 2008;47(8):1382-95.

Sonawane et al., Chloride accumulation and swelling in endosomes enhances DNA transfer by polyamine-DNA polyplexes. J Biol Chem. Nov. 7, 2003;278(45):44826-31. Epub Aug. 27, 2003.

Song et al., Antibody mediated in vivo delivery of small interfering RNAs via cell-surface receptors. Nat Biotechnol. Jun. 2005;23(6):709-17. Epub May 22, 2005.

Soutschek et al., Therapeutic silencing of an endogenous gene by systemic administration of modified siRNAs. Nature. Nov. 11, 2004;432(7014):173-8.

Stemmer et al., Single-step assembly of a gene and entire plasmid from large numbers of oligodeoxyribonucleotides. Gene. Oct. 16, 1995;164(1):49-53.

Stewart et al., Lentivirus-delivered stable gene silencing by RNAi in primary cells. RNA. Apr. 2003;9(4):493-501.

Stradtfeld et al., Defining molecular cornerstones during fibroblast to iPS cell reprogramming in mouse. Cell Stem Cell. Mar. 6, 2008;2(3):230-40. Epub Feb. 14, 2008.

Strait et al, Calcium regulation of endothelin-1 synthesis in rat inner medullary collecting duct. Am J Physiol Renal Physiol. Aug. 2007;293(2):F601-6. Epub Jun. 6, 2007.

Strickler et al., Protein stability and surface electrostatics: a charged relationship. Biochemistry. Mar. 7, 2006;45(9):2761-6.

Sun et al., Catalytic nucleic acids: from lab to applications. Pharmacol Rev. Sep. 2000;52(3):325-47.

Tabara et al., The rde-1 gene, RNA interference, and transposon silencing in C. elegans. Cell. Oct. 15, 1999;99(2):123-32.

Takahashi et al., Induction of pluripotent stem cells from adult human fibroblasts by defined factors. Cell. Nov. 30, 2007;131(5):861-72.

Takahashi et al., Induction of pluripotent stem cells from fibroblast cultures. Nat Protoc. 2007;2(12):3081-9.

Takahashi et al., Induction of pluripotent stem cells from mouse embryonic and adult fibroblast cultures by defined factors. Cell. Aug. 25, 2006;126(4):663-76. Epub Aug. 10, 2006.

Takeuchi et al., Direct and rapid cytosolic delivery using cell-penetrating peptides mediated by pyrenebutyrate. ACS Chem Biol. Jun. 20, 2006;1(5):299-303.

Tang et al., Structural diversity of self-cleaving ribozymes. Proc Natl Acad Sci U S A. May 23, 2000;97(11):5784-9.

Thillet et al., Site-directed mutagenesis of mouse dihydrofolate reductase. Mutants with increased resistance to methotrexate and trimethoprim. J Biol Chem. Sep. 5, 1988;263(25):12500-8.

(56) References Cited

OTHER PUBLICATIONS

Thompson et al., Construction and expression of a synthetic streptavidin-encoding gene in *Escherichia coli*. Gene. Dec. 22, 1993;136(1-2):243-6.

Thorén et al., The antennapedia peptide penetratin translocates across lipid bilayers—the first direct observation. FEBS Lett. Oct. 6, 2000;482(3):265-8.

Triguero et al., Blood-brain barrier transport of cationized immunoglobulin G: enhanced delivery compared to native protein. Proc Natl Acad Sci U S A. Jun. 1989;86(12):4761-5.

Trouet et al., A covalent linkage between daunorubicin and proteins that is stable in serum and reversible by lysosomal hydrolases, as required for a lysosomotropic drug-carrier conjugate: in vitro and in vivo studies. Proc Natl Acad Sci U S A. Jan. 1982;79(2):626-9.

Urnov et al., Highly efficient endogenous human gene correction using designed zinc-finger nucleases. Nature. Jun. 2, 2005;435(7042):646-51. Epub Apr. 3, 2005.

Vajdos et al., Comprehensive functional maps of the antigen-binding site of an anti-ErbB2 antibody obtained with shotgun scanning mutagenesis. J Mol Biol. Jul. 5, 2002;320(2):415-28.

Vasey et al., Phase I clinical and pharmacokinetic study of PK1 [N-(2-hydroxypropyl)methacrylamide copolymer doxorubicin]: first member of a new class of chemotherapeutic agents-drug-polymer conjugates. Cancer Research Campaign Phase I/II Committee. Clin Cancer Res. Jan. 1999;5(1):83-94.

Veldhoen et al., Cellular delivery of small interfering RNA by a non-covalently attached cell-penetrating peptide: quantitative analysis of uptake and biological effect. Nucleic Acids Res. 2006;34(22):6561-73. Epub Nov. 28, 2006.

Wadia et al., Modulation of cellular function by TAT mediated transduction of full length proteins. Curr Protein Pept Sci. Apr. 2003;4(2):97-104.

Wadia et al., Transducible TAT-HA fusogenic peptide enhances escape of TAT-fusion proteins after lipid raft macropinocytosis. Nat Med. Mar. 2004;10(3):310-5. Epub Feb. 8, 2004.

Waldo, Genetic screens and directed evolution for protein solubility. Curr Opin Chem Biol. Feb. 2003;7(1):33-8.

Waldo et al., Rapid protein-folding assay using green fluorescent protein. Nat Biotechnol. Jul. 1999;17(7):691-5.

Wang et al., Neutralizing antibodies to therapeutic enzymes: considerations for testing, prevention and treatment. Nat Biotechnol. Aug. 2008;26(8):901-8.

Wang et al., The functions of microRNAs in plants. Front Biosci. May 1, 2007;12:3975-82.

Weber et al., Structural origins of high-affinity biotin binding to streptavidin. Science. Jan. 6, 1989;243(4887):85-8.

Weiss et al., Rapid mapping of protein functional epitopes by combinatorial alanine scanning. Proc Natl Acad Sci U S A. Aug. 1, 2000;97(16):8950-4.

Wernig et al., In vitro reprogramming of fibroblasts into a pluripotent ES-cell-like state. Nature. Jul. 19, 2007;448(7151):318-24. Epub Jun. 6, 2007.

Wolfenden et al., Affinities of amino acid side chains for solvent water. Biochemistry. Feb. 17, 1981;20(4):849-55.

Wu et al., Ligand and coactivator identity determines the requirement of the charge clamp for coactivation of the peroxisome proliferator-activated receptor gamma. J Biol Chem. Mar. 7, 2003;278(10):8637-44. Epub Dec. 26, 2002.

Yang et al., Directed evolution approach to a structural genomics project: Rv2002 from *Mycobacterium tuberculosis*. Proc Natl Acad Sci U S A. Jan. 21, 2003;100(2):455-60. Epub Jan. 10, 2003.

Yin et al., Cell-penetrating peptide-conjugated antisense oligonucleotides restore systemic muscle and cardiac dystrophin expression and function. Hum Mol Genet. Dec. 15, 2008;17(24):3909-18. Epub Sep. 10, 2008.

Yiu et al., Filtering of ineffective siRNAs and improved siRNA design tool. Bioinformatics. Jan. 15, 2005;21(2):144-51. Epub Aug. 27, 2004.

Yu et al., Induced pluripotent stem cell lines derived from human somatic cells. Science. Dec. 21, 2007;318(5858):1917-20. Epub Nov. 20, 2007.

Yuen et al., Control of transcription factor activity and osteoblast differentiation in mammalian cells using an evolved small-molecule-dependent intein. J Am Chem Soc. Jul. 12, 2006;128(27):8939-46.

Zaccolo et al., An approach to random mutagenesis of DNA using mixtures of triphosphate derivatives of nucleoside analogues. J Mol Biol. Feb. 2, 1996;255(4):589-603.

Zamore et al., RNAi: double-stranded RNA directs the ATP-dependent cleavage of mRNA at 21 to 23 nucleotide intervals. Cell. Mar. 31, 2000;101(1):25-33.

Zelphati et al., Intracellular delivery of proteins with a new lipid-mediated delivery system. J Biol Chem. Sep. 14, 2001;276(37):35103-10. Epub Jul. 10, 2001.

Zhao et al., A developmental view of microRNA function. Trends Biochem Sci. Apr. 2007;32(4):189-97. Epub Mar. 9, 2007.

Zhou et al., Extreme makeover: converting one cell into another. Cell Stem Cell. Oct. 9, 2008;3(4):382-8.

Zhou et al., Generation of induced pluripotent stem cells using recombinant proteins. Cell Stem Cell. May 8, 2009;4(5):381-4. Epub Apr. 23, 2009.

Zhou et al., In vivo reprogramming of adult pancreatic exocrine cells to beta-cells. Nature. Oct. 2, 2008;455(7213):627-32. Epub Aug. 27, 2008.

Extended European Search Report for EP 12155208.7, mailed Jul. 30, 2012.

Extended European Search Report for EP 09739610.5, mailed Jul. 16, 2012.

Extended European Search Report for EP 10772365.2, mailed Dec. 5, 2012.

Office Communication, mailed Nov. 26, 2012, for U.S. Appl. No. 12/303,047.

Office Communication, mailed Jan. 16, 2013, for U.S. Appl. No. 13/341,231.

Mae et al., Cell-penetrating peptides as vectors for peptide, protein and oligonucleotide delivery. Curr Opin Pharmacology. 2006;6(5):509-14.

Pace et al., Charge-charge interactions influence the denatured state ensemble and contribute to protein stability. Protein Sci. Jul. 2000;9(7):1395-8.

Sanchez-Ruiz et al., To charge or not to charge? Trends Biotechnol. Apr. 2001;19(4):132-5.

Simeonov et al., Surface supercharged human enteropeptidase light chain shows improved solubility and refolding yield. Protein Eng Des Sel. Mar. 2011;24(3):261-8. doi: 10.1093/protein/gzq104. Epub Nov. 16, 2010.

Thompson et al., Cellular uptake mechanisms and endosomal trafficking of supercharged proteins. Chem Biol. Jul. 27, 2012;19(7):831-43. doi: 10.1016/j.chembiol.2012.06.014.

Thompson et al., Engineering and identifying supercharged proteins for macromolecule delivery into mammalian cells. Methods Enzymol. 2012;503:293-319. doi: 10.1016/B978-0-12-396962-0.00012-4.

Office Communication, mailed Mar. 26, 2013, for U.S. Appl. No. 12/989,829.

Boswell et al., Effects of charge on antibody tissue distribution and pharmacokinetics. Bioconjug Chem. Dec. 15, 2010;21(12):2153-63. doi: 10.1021/bc100261d. Epub Nov. 5, 2010.

Kwon et al., Antitumor effect of a transducible fusogenic peptide releasing multiple proapoptotic peptides by caspase-3. Mol Cancer Ther. Jun. 2008;7(6):1514-22. doi: 10.1158/1535-7163.MCT-07-2009.

Orange et al., Cell penetrating peptide inhibitors of nuclear factor-kappa B. Cell Mol Life Sci. Nov. 2008;65(22):3564-91. doi: 10.1007/s00018-008-8222-z.

Rittner et al., New basic membrane-destabilizing peptides for plasmid-based gene delivery in vitro and in vivo. Mol Ther. Feb. 2002;5(2):104-14.

(56) References Cited

OTHER PUBLICATIONS

Kueltzo et al., Conformational lability of herpesvirus protein VP22. *J Biol Chem.* Oct. 27, 2000;275(43):33213-21.
Lundberg et al., Positively charged DNA-binding proteins cause apparent cell membrane translocation. *Biochem Biophys Res Commun.* Feb. 22, 2002;291(2):367-71.
Mouzakitis et al., Characterization of VP22 in herpes simplex virus-infected cells. *J Virol.* Oct. 2005;79(19):12185-98.
Selzer et al., Rational design of faster associating and tighter binding protein complexes. Nat Struct Biol. Jul. 2000;7(7):537-41.
[No Author Listed] Database UniProt, Accession: P02258, URL<http://www.uniprot.org/uniprot/P02258>, [Jul. 21, 1986 uploaded].
[No Author Listed] Database UniProt, Accession: P08814, URL<http://www.uniprot.org/uniprot/P08814>, [Jan. 11, 1988 uploaded].
Genbank Submission; NIH/NCBI, Accession No. M60748.1, Albig et al., Mar. 7, 1995, last accessed Sep. 3, 2014.
[No Author Listed] Innovage, Protein Calculator, Histone H1, accessed on Sep. 3, 2014.
Calloni et al., Investigating the effects of mutations on protein aggregation in the cell. J Biol Chem. Mar. 18, 2005;280(11):10607-13. Epub Dec. 16, 2004.
Wyman et al., Design, synthesis, and characterization of a cationic peptide that binds to nucleic acids and permeabilizes bilayers. Biochemistry. Mar. 11, 1997;36(10):3008-17.

\* cited by examiner

FIGURE 14B
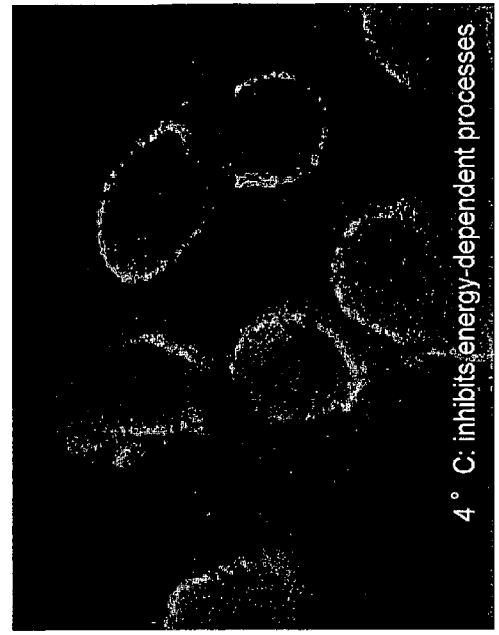
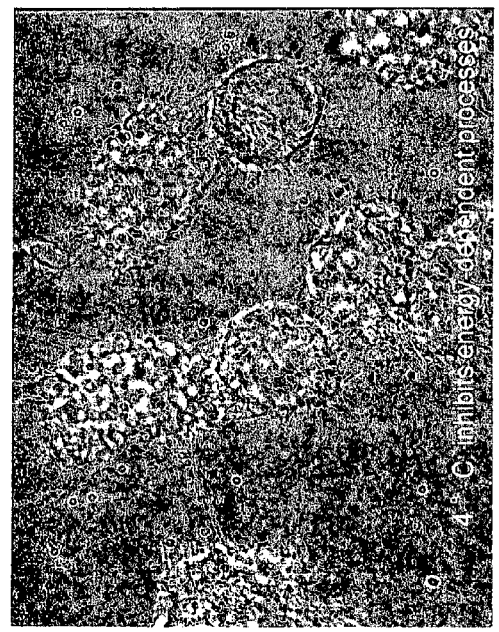

SUPERCHARGED PROTEINS FOR CELL PENETRATION

RELATED APPLICATIONS

The present application is a national stage filing under 35 U.S.C. §371 of international PCT application, PCT/US2010/001250, filed Apr. 28, 2010, which claims priority under 35 U.S.C. §119(e) to U.S. provisional patent applications, U.S. Ser. No. 61/173,430, filed Apr. 28, 2009, and U.S. Ser. No. 61/321,428, filed Apr. 6, 2010, each of which is incorporated herein by reference.

GOVERNMENT SUPPORT

This invention was made with U.S. Government support under contract number R01 GM 065400 awarded by the National Institutes of Health/NIGMS. The U.S. Government has certain rights in the invention.

BACKGROUND OF THE INVENTION

The effectiveness of an agent intended for use as a therapeutic, diagnostic, or other application is often highly dependent on its ability to penetrate cellular membranes or tissue to induce a desired change in biological activity. Although many therapeutic drugs, diagnostic or other product candidates, whether protein, nucleic acid, organic small molecule, or inorganic small molecule, show promising biological activity in vitro, many fail to reach or penetrate target cells to achieve the desired effect, often due to physiochemical properties that result in inadequate biodistribution in vivo.

In particular, nucleic acids have great potential as effective therapeutic agents and as research tools. The generality and sequence-specificity of siRNA-mediated gene regulation has raised the possibility of using siRNAs as gene-specific therapeutic agents (Bumcrot et al., 2006, *Nat. Chem. Biol.*, 2:711-19; incorporated herein by reference). The suppression of gene expression by short interfering RNA (siRNA) has also emerged as a valuable tool for studying gene and protein function (Dorsett et al., 2004, *Nat. Rev. Drug Discov.*, 3:318-29; Dykxhoorn et al., 2003, *Nat. Rev. Mol. Cell. Biol.*, 4:457-67; Elbashir et al., 2001, *Nature*, 411:494-98; each of which is incorporated herein by reference). However, the delivery of nucleic acids such as siRNAs to cells has been found to be unpredictable and is typically inefficient. One obstacle to effective delivery of nucleic acids to cells is inducing cells to take up the nucleic acid. Much work has been done to identify agents that can aid in the delivery of nucleic acids to cells. Commercially available cationic lipid reagents are typically used to transfect siRNA in cell culture. The effectiveness of cationic lipid-based siRNA delivery, however, varies greatly by cell type. Also, a number of cell lines including some primary neuron, T-cell, fibroblast, and epithelial cell lines have demonstrated resistance to common cationic lipid transfection techniques (Carlotti et at, 2004, *Mol. Ther.*, 9:209-17; Ma et al., 2002, *Neuroscience*, 112:1-5; McManus et al., 2002, *J. Immunol.*, 169:5754-60; Strait et al., 2007, *Am. J. Physiol. Renal Physiol.*, 293:F601-06; each of which is incorporated herein by reference). Alternative transfection approaches including electroporation (Jantsch et al., 2008, *J. Immunol. Methods*, 337:71-77; incorporated herein by reference) and virus-mediated siRNA delivery (Brummelkamp et al., 2002, *Cancer Cell*, 2:243-47; Stewart et al., 2003, *RNA*, 9:493-501; each of which is incorporated herein by reference) have also been used; however, these methods can be cytotoxic or perturb cellular function in unpredictable ways and have limited value for the delivery of nucleic acids (e.g., siRNA) as therapeutic agents in a subject.

Recent efforts to address the challenges of nucleic acid delivery have resulted in a variety of new nucleic acid delivery platforms. These methods include lipidoids (Akinc et al., 2008, *Nat. Biotechnol.*, 26:561-69; incorporated herein by reference), cationic polymers (Segura and Hubbell, 2007, *Bioconjug. Chem.*, 18:736-45; incorporated herein by reference), inorganic nanoparticles (Sokolova and Epple, *Angew Chem. Int. Ed. Engl.*, 47:1382-95; incorporated herein by reference), carbon nanotubes (Liu et al., 2007, *Angew Chem. Int. Ed. Engl.*, 46:2023-27; incorporated herein by reference), cell-penetrating peptides (Deshayes et al., 2005, *Cell Mol. Life. Sci.*, 62:1839-49; and Meade and Dowdy, 2008, *Adv. Drug Deliv. Rev.*, 60: 530-36; both of which are incorporated herein by reference), and chemically modified siRNA (Krutzfeldt et al., 2005, *Nature* 438: 685-89; incorporated herein by reference). Each of these delivery systems offers benefits for particular applications; in most cases, however, questions regarding cytotoxicity, ease of preparation, stability, or generality remain. Easily prepared reagents capable of effectively delivering nucleic acids (e.g., siRNA) to a variety of cell lines without significant cytotoxicity therefore remain of considerable interest.

Given the current interest in RNAi therapies and other nucleic acid-based therapies, there remains a need in the art for reagents and systems that can be used to deliver nucleic acids as well as other agents (e.g., peptides, proteins, small molecules) to a wide variety of cell types predictably and efficiently.

Similarly, the inability of most proteins to spontaneously enter mammalian cells limits their usefulness as research tools and their potential as therapeutic agents. Proteins have demonstrated great potential as research tools (including hormones, cytokines, and antibodies) and as human therapeutics (including erythropoietin, insulin, and interferons). Due to the inability of most proteins to spontaneously enter cells, however, exogenous proteins are largely restricted to interacting with extracellular targets. Over the past decade, techniques for the delivery of proteins into mammalian cells have been developed to address intracellular targets. These techniques include lipid-based reagents (Zelphati et al., *J. Biol. Chem.* 276, 35103-35110, 2001), nanoparticles (Hasadsri et al., *J. Biol. Chem.*, 2009), vault ribonucleoprotein particles (Lai et al., *ACS Nano* 3, 691-699, 2009), and genetic or chemical fusion to receptor ligands (Gabel et al., *J. Cell Biol.* 103, 1817-1827, 1986; Rizk et al., *Proc. Natl. Acad. Sci. U.S.A.* 106, 11011-11015, 2009) or cell-penetrating peptides (Wadia et al., *Curr. Protein Pept. Sci.* 4, 97-104, 2003; Zhou et al., *Cell Stem Cell* 4, 381-384, 2009). Perhaps the most common method for protein delivery is genetic fusion to protein transduction domains (PTDs) including the HIV-1 transactivator of transcription (Tat) peptide and polyarginine peptides. These cationic PTDs promote association with negatively charged cell-surface structures and subsequent endocytosis of exogenous proteins. Both Tat and polyarginine have been used to deliver a variety of macromolecules into cells both in vitro and in vivo (Wadia et al., *Curr. Protein Pept. Sci.* 4, 97-104, 2003; Zhou et al., *Cell Stem Cell* 4, 381-384, 2009; Myou et al., *J. Immunol.* 169, 2670-2676, 2002; Bae et al., *Clin. Exp. Immunol.* 157, 128-138, 2009; Schwarze et al., *Science* 285, 1569-1572, 1999). Despite these advances, intracellular targets in many cases remain difficult to perturb using exogenous proteins; even modest success can require high concentrations of exogenous protein due to the low efficiency with which proteins are functionally delivered into cells (Zhou et al., *Cell Stem Cell* 4, 381-384, 2009; Wang et al., *Nat. Biotechnol.* 26, 901-908, 2008).

SUMMARY OF THE INVENTION

The present invention provides novel systems, compositions, preparations, and related methods for delivering nucleic acids and other agents (e.g., peptides, proteins, small molecules) into cells using a protein that has been modified to result in an increase or decrease in the overall surface charge on the protein, referred to henceforth as "supercharging." Thus, supercharging can be used to promote the entry into a cell in vivo or in vitro of a supercharged protein, or agent(s) associated with the supercharged protein that together form a complex. Such systems and methods may comprise the use of proteins that have been engineered to be supercharged and include all such modifications, including but not limited to, those involving changes in amino acid sequence as well as the attachment of charged moieties to the protein. Examples of engineered supercharged proteins are described in international PCT patent application, PCT/US07/70254, filed Jun. 1, 2007, published as WO 2007/143574 on Dec. 13, 2007; and in U.S. provisional patent applications, U.S. Ser. No. 60/810, 364, filed Jun. 2, 2006, and U.S. Ser. No. 60/836,607, filed Aug. 9, 2006; each of which is entitled "Protein Surface Remodeling," and each of which is incorporated herein by reference. Further examples of supercharged proteins useful in drug delivery are also described herein. The present invention also contemplates the use of naturally occurring supercharged proteins to enhance cell penetration of associated agents that together form a complex or to enhance the cell penetration of the naturally occurring supercharged protein itself. Typically, the supercharged protein, engineered or naturally occurring, is positively charged. In certain embodiments, superpositively charged proteins may be associated with nucleic acids (which typically have a net negative charge) via electrostatic interactions, thereby aiding in the delivery of the nucleic acid to a cell. Superpositively charged proteins may also be associated covalently or non-covalently with the nucleic acid to be delivered in other ways. Other agents such as peptides or small molecules may also be delivered to cells using supercharged proteins that are covalently bound or otherwise associated (e.g., electrostatic interactions) with the agent to be delivered. In certain embodiments, the supercharged protein is fused with a second protein sequence. For example, in certain embodiments, the agent to be delivered and the superpositively charged protein are expressed together in a single polypeptide chain as a fusion protein. In certain embodiments, the fusion protein has a linker, e.g., a cleavable linker between the supercharged protein and the other protein component. In certain embodiments, the agent to be delivered and the supercharged protein, e.g., a superpositively charged protein, are associated with each other via a cleavable linker (e.g., a linker cleavable by a protease or esterase, disulfide bond). The supercharged protein, e.g., a superpositively charged protein, useful in the present invention is typically non-antigenic, biodegradable, and/or biocompatible. In certain embodiments, the superpositively charged protein does not have biological activity or any deleterious biological activity. In certain embodiments the supercharged protein has a mutation or other alteration (e.g., a post-translational modification such as a cleavage or other covalent modification) which decreases or abolishes a biological activity exhibited by the protein prior to supercharging. This may be of particular interest when the supercharged protein is of interest not because of its own biological activity but for use in delivering an agent to a cell. Without wishing to be bound by a particular theory, anionic cell-surface proteoglycans are thought to serve as a receptor for the actin-dependent endocytosis of the superpositively charged protein bound to its payload. The inventive supercharged proteins or delivery system using supercharged, e.g., superpositively charged proteins, may include the use of other pharmaceutically acceptable excipients such as polymers, lipids, carbohydrates, small molecules, targeting moieties, endosomolytic agents, proteins, peptides, etc. For example, a supercharged protein or complex of a supercharged protein, e.g., a superpositively charged protein, and agent to be delivered may be contained within or be associated with a microparticle, nanoparticle, picoparticle, micelle, liposome, or other drug delivery system. In other embodiments, only the agent to be delivered and the supercharged protein are used to deliver the agent to a cell. In certain embodiments, the supercharged protein is chosen to deliver itself or an associated agent to a particular cell or tissue type. In certain embodiments, the supercharged, e.g., superpositively charged, protein or agent to be delivered and the supercharged protein are combined with an agent that disrupts endosomolytic vesicles or enhances the degradation of endosomes (e.g., chloroquine, pyrene butyric acid, fusogenic peptides, polyethyleneimine, hemagglutinin 2 (HA2) peptide, melittin peptide). Thus, escape of the agent to be delivered from the endosome into the cytosol is enhanced.

In some embodiments, the inventive systems and methods involve altering the primary sequence of a protein in order to "supercharge" the protein. In other embodiments, the inventive systems and methods involve the attachment of charged moieties to the protein in order to "supercharge" the protein. That is, the overall net charge on the modified protein is increased (either more positive charge or more negative charge) compared to the unmodified protein. In certain embodiments, the protein is supercharged, e.g., superpositively charged, to enable the delivery of nucleic acids or other agents to a cell. Any protein may be "supercharged". Typically, the protein is non-immunogenic and either naturally or upon supercharging has the ability to transfect or deliver itself or an associated agent into a cell. In certain embodiments, the activity of the supercharged protein is approximately or substantially the same as the protein without modification. In other embodiments, the activity of the supercharged protein is substantially decreased as compared to the protein without modification. Such activity may not be relevant to the delivery of itself or an associated agent, e.g., nucleic acids, to cells as described herein. In some embodiments, supercharging a protein results in increasing the protein's resistance to aggregation, solubility, ability to refold, and/or general stability under a wide range of conditions as well as increasing the protein's ability to deliver itself or an associated agent, e.g., nucleic acids, to a cell. In certain embodiments, the supercharged protein helps to target itself or an associated agent to be delivered to a particular cell type, tissue, or organ. In certain embodiments, supercharging a protein includes the steps of: (a) identifying surface residues of a protein of interest; (b) optionally, identifying the particular surface residues that are not highly conserved among other proteins related to the protein of interest (i.e., determining which amino acids are not essential for the activity or function of the protein); (c) determining the hydrophilicity of the identified surface residues; and (d) replacing an one or more of the identified charged or polar, solvent-exposed residues with an amino acid that is charged at physiological pH. See published international PCT patent application, PCT/US07/70254, filed Jun. 1, 2007, published as WO 2007/143574 on Dec. 13, 2007; and U.S. Provisional patent applications, U.S. Ser. No. 60/810, 364, filed Jun. 2, 2006, and U.S. Ser. No. 60/836,607, filed Aug. 9, 2006; each of which is entitled "Protein Surface Remodeling"; and each of which is incorporated herein by reference. Exemplary methods of preparing supercharged proteins and exemplary protein sequences illustrating the use of method are described herein. In certain embodiments, to make a positively charged "supercharged" protein, the residues identified for modification are mutated either to lysine (Lys) or arginine (Arg) residues (i.e., amino acids that are positively charged at physiological pH). In certain embodiments, to make a negatively charged "supercharged" protein, the residues identified for modification are mutated either to aspartate (Asp) or glutamate (Glu) residues (i.e., amino acids that are negatively charged at physiological pH). Each of the above steps may be carried out using any technique, computer software, algorithm, methodology, paradigm, etc. known in the art. After the modified protein is created, it may be tested for its activity and/or the desired property being sought (e.g., the ability to delivery a nucleic acid or other agent into a cell). In certain embodiments, the supercharged protein is less susceptible to aggregation. In certain embodiments, a positively charged "supercharged" protein (e.g., superpositively charged green fluorescent protein (GFP) such +36 GFP) is useful in delivering a nucleic acid (e.g., an siRNA agent) to a cell (e.g., a mammalian cell, a human cell). In certain embodiments, the inventive system allows for the delivery of nucleic acids into cells normally resistant to transfection (e.g., neuronal cells, T-cells, fibroblasts, and epithelial cells). In certain embodiments, rather than engineering a supercharged protein, a naturally occurring supercharged protein is identified and used in the inventive drug delivery system. Examples of naturally occurring supercharged proteins include, but are not limited to, cyclon (ID No.: Q9H6F5), PNRC1 (ID No.: Q12796), RNPS1 (ID No.: Q15287), SURF6 (ID No.: O75683), AR6P (ID No.: Q66PJ3), NKAP (ID No.: Q8N5F7), EBP2 (ID No.: Q99848), LSM11 (ID No.: P83369), RL4 (ID No.: P36578), KRR1 (ID No.: Q13601), RY-1 (ID No.: Q8WVK2), BriX (ID No.: Q8TDN6), MNDA (ID No.: P41218), H1b (ID No.: P16401), cyclin (ID No.: Q9UK58), MDK (ID No.: P21741), Midkine (ID No.: P21741), PROK (ID No.: Q9HC23), FGF5 (ID No.: P12034), SFRS (ID No.: Q8N9Q2), AKIP (ID No.: Q9NWT8), CDK (ID No.: Q8N726), beta-defensin (ID No.: P81534), Defensin 3 (ID No.: P81534); PAVAC (ID No.: P18509), PACAP (ID No.: P18509), eotaxin-3 (ID No.: Q9Y258), histone H2A (ID No.: Q7L7L0), HMGB1 (ID No.: P09429), C-Jun (ID No.: P05412), TERF 1 (ID No.: P54274), N-DEK (ID No.: P35659), PIAS 1 (ID No.: O75925), Ku70 (ID No.: P12956), HBEGF (ID No.: Q99075), and HGF (ID No.: P14210), HRX (ID No.: Q03164), histone 4 (ID No.: P62805).

In certain embodiments, once a supercharged protein has been obtained, systems and methods in accordance with the invention involve associating one or more nucleic acids or other agents with the supercharged protein and contacting the resulting complex with a cell under suitable conditions for the cell to take up the payload. The nucleic acid may be a DNA, RNA, and/or hybrid or derivative thereof. In certain embodiments, the nucleic acid is an RNAi agent, RNAi-inducing agent, short interfering RNA (siRNA), short hairpin RNA (shRNA), micro RNA (miRNA), antisense RNA, ribozyme, catalytic DNA, RNA that induces triple helix formation, aptamer, vector, plasmid, viral genome, artificial chromosome, etc. In some embodiments, the nucleic acid is single-stranded. In other embodiments, the nucleic acid is double-stranded. In some embodiments, a nucleic acid may comprise one or more detectable labels (e.g., fluorescent tags and/or radioactive atoms). In certain embodiments, the nucleic acid is modified or derivatized (e.g., to be less susceptible to degradation, to improve transfection efficiency). In certain embodiments, the modification of the nucleic acid prevents the degradation of the nucleic acid. In certain embodiments, the modification of the nucleic acid aids in the delivery of the nucleic acid to a cell. Other agents that may be delivered using a supercharged protein include small molecules, peptides, and proteins. The resulting complex may then be combined or associated with other pharmaceutically acceptable excipient(s) to form a composition suitable for delivering the agent to a cell, tissue, organ, or subject.

Supercharged proteins may be associated with nucleic acids (or other agents) via non-covalent interactions to form a complex. Although covalent association of the supercharged protein with a nucleic acid is possible, it is typically not necessary to achieve delivery of the nucleic acid. In some embodiments, supercharged proteins are associated with nucleic acids via electrostatic interactions. Supercharged proteins may be associated with nucleic acids through other non-covalent interactions or covalent interactions. The supercharged proteins may have a net positive charge of at least +5, +10, +15, +20, +25, +30, +35, +40, or +50. In some embodiments, superpositively charged proteins are associated with nucleic acids that have an overall net negative charge. The resulting complex may have a net negative or positive charge. In certain embodiments, the complex has a net positive charge. For example, +36 GFP may be associated with a negatively charged siRNA.

Supercharged proteins may be associated with other agents besides nucleic acids via non-covalent or covalent interactions. For example, a negatively charged protein may be associated with a superpositively charged protein through electrostatic interactions. For agents that are not charged or do not have sufficient charge, the agent may be covalently associated with the supercharged protein to effect delivery of the agent to a cell. For example, a peptide therapeutic may be fused to the supercharged protein in order to deliver the peptide therapeutic to a cell. In certain embodiments, the supercharged protein and the peptide may be joined via a cleavable linker. To give but another example, a small molecule may be conjugated to a supercharged protein for delivery to a cell. The agent may also be associated with the supercharged protein through non-covalent interactions (e.g., ligand-receptor interaction, dipole-dipole interaction, etc.).

The present invention provides complexes comprising supercharged proteins and one or more molecules of the agent to be delivered. In some embodiments, such complexes comprise multiple agent molecules per supercharged protein molecule. In some embodiments, such complexes comprise 1, 2, 3, 4, 5, 6, 7, 8, 9, 10, 20, or more agent (e.g., nucleic acids) molecules per supercharged protein molecule. In certain particular embodiments, a complex comprises approximately 1-2 nucleic acid molecules (e.g., siRNA) to approximately 1 supercharged protein molecule. In other embodiments, such complexes comprise multiple protein molecules per agent molecule. In some embodiments, such complexes comprise 1, 2, 3, 4, 5, 6, 7, 8, 9, 10, 20, or more protein molecules per agent molecule. In certain embodiments, such complexes comprise approximately one agent molecule and approximately one superpositively charged protein molecule. In certain embodiments, the overall net charge on the agent/supercharged protein complex is negative. In certain embodiments, the overall net charge on the agent/supercharged protein complex is positive. In certain embodiments, the overall net charge on the agent/supercharged protein complex is neutral. In certain particular embodiments, the overall net charge on the nucleic acid/supercharged protein complex is positive.

In another aspect, the present invention provides pharmaceutical compositions comprising: a) one or more supercharged proteins; b) one or more complexes of supercharged protein and an agent to be delivered; or c) one or more of a) or one or more of b), in accordance with the invention and at least one pharmaceutically acceptable excipient. The amount of the complex in the composition may be the amount useful to induce a desired biological response in the cell, for example, increase or decrease the expression of a particular gene in the cell. In certain embodiments, the complex is associated with a targeting moiety (e.g., small molecule, protein, peptide, carbohydrate, etc.) used to direct the delivery of the agent to a particular cell, type of cell, tissue, or organ.

In some embodiments, a supercharged protein or complexes comprising supercharged proteins, engineered or naturally occurring, and one or more nucleic acids (and/or pharmaceutical compositions thereof) are useful as therapeutic agents. In some embodiments, a nucleic acid and/or supercharged protein may be therapeutically active. In certain embodiments, the nucleic acid is therapeutically active. For example, some conditions (e.g., cancer, inflammatory diseases) are associated with the expression of certain mRNAs and/or proteins. Supercharged proteins associated with RNAi agents targeting an expressed mRNA may be useful for treating such conditions. Alternatively, some conditions are associated with underexpression of certain mRNAs and/or proteins (e.g., cancer, inborn errors in metabolism). Supercharged proteins associated with vectors that drive expression of the deficient mRNA and/or protein may be useful for treating such conditions.

The present invention also provides kits useful for producing the inventive supercharged protein or supercharged protein/agent complexes or compositions thereof, and/or using such complexes to transfect or deliver the supercharged protein or an agent into a cell. The inventive kits may also include instructions for administering or using the inventive supercharged proteins or complexes, or a pharmaceutical composition thereof. For example, the kit may include instructions for prescribing the pharmaceutical composition to a subject. The kit may include enough materials for multiple unit doses of the agent. The kit may be designed for therapeutic or research purposes. The kit may optionally include the agent (e.g. siRNA, peptide, drug) to be delivered, or the agent may be provided by the end user.

The present invention also provides a method of introducing a supercharged protein or an agent associated with a supercharged protein, or both, into a cell. The inventive method comprises contacting the supercharged protein, or a supercharged protein and an agent associated with the supercharged protein with the cell, e.g., under conditions sufficient to allow penetration of said supercharged protein, or an agent associated with a supercharged protein, into the cell, thereby introducing a supercharged protein, or an agent associated with a supercharged protein, or both, into a cell. In certain embodiments, sufficient supercharged protein or agent enters the cell to allow for one or more of detection of the supercharged protein or agent in the cell; a change in a biological property of the cell, e.g., growth rate, pattern of gene expression, or viability, of the cell; or detection of a biological effect of the supercharged protein or agent. In certain embodiments, the contact is performed in vitro. In certain embodiments, the contact is performed in vivo, e.g., in the body of a subject, e.g., a human or other animal. In one in vivo embodiment, sufficient supercharged protein, agent, or both is present in the cell to provide a detectable effect in the subject, e.g., a therapeutic effect. In one in vivo embodiment, sufficient supercharged protein, agent, or both is present in the cell to allow imaging of one or more penetrated cells or tissues. In certain embodiments, the observed or detectable effect arises from cell penetration.

The present invention also provides a method of evaluating a supercharged protein for cell penetration comprising: optionally, selecting a supercharged protein; providing said supercharged protein; and contacting said supercharged protein with a cell and determining if the supercharged protein penetrates the cell, thereby providing an evaluation of a supercharged protein for cell penetration.

The present invention also provides a method of evaluating a supercharged protein for cell penetration comprising: selecting a protein to be supercharged; obtaining a set of one or a plurality of residues to be varied to produce a supercharged protein, wherein the set was generated by a method described herein (obtaining includes generating the set or receiving the identity of one or more members of the set from another party); providing (e.g., by making or receiving it from another party) a supercharged protein having said set of varied residues; and contacting said supercharged protein with a cell and determining if the supercharged protein penetrates the cell, thereby of evaluating a supercharged protein for cell penetration. The method can allow for a party to develop supercharged proteins or to collaborate with others to do so.

In some embodiments, the present invention provides a supercharged protein associated with a functional peptide or protein able to penetrate a cell and deliver the functional peptide or protein into the cell. The functional peptide or protein may be delivered through the plasma membrane, into cytoplasm, through the nuclear membrane, and/or into the nucleus. The functional protein or peptide is associated with the supercharged protein for delivery. In some embodiments, the supercharged protein is covalently bound to the functional peptide or protein. In some embodiments, the supercharged protein is bound to the functional protein or peptide via a peptide (amide) bond, in some cases forming a fusion protein. In some embodiments, the supercharged protein and the functional protein or peptide are associated through a linker connecting the supercharged protein to the functional peptide or protein. The linker may be cleavable or uncleavable. In some embodiments, the linker comprises an amide, ester, ether, carbon-carbon, or disulfide bond although any covalent bond in the chemical art may be used. In some embodiments, the linker comprises a labile bond, cleavage of which results in separation of the supercharged protein from the peptide or protein to be delivered. In some embodiments, the supercharged protein or linker is cleaved under conditions found in the cell (e.g., a reductive environment). In some embodiments, the supercharged protein or the linker is cleaved by a cellular enzyme. In some embodiments, the cellular enzyme is a cellular protease or a cellular esterase. In some embodiments, the cellular protease is an endosomal protease or an endosomal esterase. In some embodiments, the cellular enzyme is specifically expressed in a target cell or cell type, resulting in preferential or specific endosomal release of the functional protein or peptide in the target cell or cell type. The target sequence of the protease may be engineered into the linker between the functional protein or peptide to be delivered and the supercharged protein. In some embodiments, the target cell or cell type is a cancer cell or cancer cell type, a cell or cell type of the immune system, or a pathologic or diseased cell or cell type. In some embodiments, the supercharged protein or the linker comprises an amino acid sequence chosen from the group including X-AGVF-X (SEQ ID NO: 11), X-GFLG-X (SEQ ID NO: 12), X-FK-X (SEQ ID NO: 13), X-AL-X (SEQ ID NO: 14), X-ALAL-X (SEQ ID NO: 15), or X-ALALA-X (SEQ ID NO: 16), wherein X denotes the supercharged protein or the functional peptide or protein.

In some embodiments, the functional protein or peptide to be delivered into a cell is a transcription factor, a tumor suppressor, a developmental regulator, a growth factor, a metastasis suppressor, a pro-apoptotic protein, a zinc finger nuclease, or a recombinase. In some embodiments, the functional protein is p53, Rb (retinoblastoma protein), BRCA1, BRCA2, PTEN, APC, CD95, ST7, ST14, a BCL-2 family protein, a caspase; BRMS1, CRSP3, DRG1, KAI1, KISS1, NM23, a TIMP-family protein, a BMP-family growth factor, EGF, EPO, FGF, G-CSF, GM-CSF, a GDF-family growth factor, HGF, HDGF, IGF, PDGF, TPO, TGF-α, TGF-β, VEGF; a zinc finger nuclease targeting a site within the human CCR5 gene, Cre, Dre, or FLP recombinase.

In certain embodiments, the invention provides methods of delivering a peptide or protein to a cell. In some embodiments, the method includes a step of contacting the cell with a supercharged protein associated with the peptide or the protein to be delivered, under conditions sufficient for the peptide or protein to enter the cell. In some embodiments, the supercharged protein associated with the peptide or the protein is a supercharged protein associated with a functional peptide or protein.

In some embodiments, the peptide or protein to be delivered is a nuclear peptide or protein and the method results in delivery of the protein or peptide to the nucleus of the cell. In some embodiments, the protein delivered to the cell is a transcription factor. In some embodiments, the protein delivered to the cell is a reprogramming factor. In some embodiments, the cell is a somatic cell from a subject diagnosed with a disease. In certain embodiments, the cell is a mammalian cell (e.g., a human cell). In some embodiments, the cell is contacted with a supercharged protein associated with a reprogramming factor in an amount, for a time, and under conditions sufficient to induce reprogramming of the cell to a pluripotent state or less differentiated state. In some embodiments, the method further includes a step of isolating a pluripotent cell generated from a somatic cell. In some embodiments, the method further comprises a step of differentiating the isolated pluripotent cell, or progeny thereof, into a differentiated cell type. In some embodiments, the method further comprises a step of using the pluripotent cell, or differentiated progeny thereof, in a cell replacement therapeutic approach.

In some embodiments, the cell is a cell carrying an undesired genomic allele and the supercharged protein is associated with a nuclease specifically targeting the allele. In some embodiments, the undesired allele is associated with a disease, and the nuclease induces a mutation in the allele. In some embodiments, the cell is contacted ex vivo and then reintroduced into the subject after successful targeting of the undesired allele by the nuclease. In some embodiments, the nuclease is a zinc finger nuclease. In some embodiments, the nuclease targets the human CCR5 gene. In some embodiments, the subject is a subject diagnosed with HIV/AIDS, and the cell is a T-lymphocyte.

In some embodiments, the protein is a recombinase, and the cell's genome comprises a recombination site recognized by the recombinase. In some embodiments, the cell comprises a plurality of recombination sites recognized by the recombinase, and recombinase-mediated recombination of the plurality of recombination sites results in deletion of a region of the genome (e.g., a diseased gene).

In some embodiments, the cell is a tumor cell, and the protein is a tumor suppressor protein, a metastasis suppressor protein, a cytostatic or a cytotoxic protein.

These and other aspects and embodiments of the invention, as well as various advantages and utilities will be more apparent with respect to the drawings and detailed description of the invention.

DEFINITIONS

Agent to be delivered: As used herein, the phrase "agent to be delivered" refers to any substance that can be delivered to a subject, organ, tissue, cell, subcellular locale, and/or extracellular matrix locale. In some embodiments, the agent to be delivered is a biologically active agent, i.e., it has activity in a biological system and/or organism. For instance, a substance that, when administered to an organism, has a biological effect on that organism, is considered to be biologically active. In particular embodiments, where an agent to be delivered is a biologically active agent, a portion of that agent that shares at least one biological activity of the agent as a whole is typically referred to as a "biologically active" portion. In some embodiments, an agent to be delivered is a therapeutic agent. As used herein, the term "therapeutic agent" refers to any agent that, when administered to a subject, has a beneficial effect. The term "therapeutic agent" refers to any agent that, when administered to a subject, has a therapeutic, diagnostic, and/or prophylactic effect and/or elicits a desired biological and/or pharmacological effect. As used herein, the term "therapeutic agent" may be a nucleic acid that is delivered to a cell by via its association with a supercharged protein. In certain embodiments, the agent to be delivered is a nucleic acid. In certain embodiments, the agent to be delivered is DNA. In certain embodiments, the agent to be delivered is RNA. In certain embodiments, the agent to be delivered is a peptide or protein. In certain embodiments, the agent to be delivered is a small molecule. In some embodiments, the agent to be delivered is useful as an in vivo or in vitro imaging agent. In some of these embodiments, it is, and in others it is not, biologically active.

Animal: As used herein, the term "animal" refers to any member of the animal kingdom. In some embodiments, "animal" refers to humans at any stage of development. In some embodiments, "animal" refers to non-human animals at any stage of development. In certain embodiments, the non-human animal is a mammal (e.g., a rodent, a mouse, a rat, a rabbit, a monkey, a dog, a cat, a sheep, cattle, a primate, or a pig). In some embodiments, animals include, but are not limited to, mammals, birds, reptiles, amphibians, fish, and worms. In some embodiments, the animal is a transgenic animal, genetically-engineered animal, or a clone.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Associated with: As used herein, the terms "associated with," "conjugated," "linked," "attached," and "tethered," when used with respect to two or more moieties, means that the moieties are physically associated or connected with one another, either directly or via one or more additional moieties that serves as a linking agent, to form a structure that is sufficiently stable so that the moieties remain physically associated under the conditions in which the structure is used, e.g., physiological conditions. A supercharged protein is typically associated with a nucleic acid by a mechanism that involves non-covalent binding (e.g., electrostatic interactions). In certain embodiments, a positively charged, supercharged protein is associated with a nucleic acid through electrostatic interactions to form a complex. In some embodiments, a sufficient number of weaker interactions can provide sufficient stability for moieties to remain physically associated under a variety of different conditions. In certain embodiments, the agent to be delivered is covalently bound to the supercharged protein. In some embodiments, a peptide or protein is associated with a supercharged protein by a covalent bond (e.g., an amide bond). In some embodiments, a peptide or protein is associated with a supercharged protein directly by a peptide bond, or indirectly via a linker.

Biocompatible: As used herein, the term "biocompatible" refers to substances that are not toxic to cells. In some embodiments, a substance is considered to be "biocompatible" if its addition to cells in vivo does not induce inflammation and/or other adverse effects in vivo. In some embodiments, a substance is considered to be "biocompatible" if its addition to cells in vitro or in vivo results in less than or equal to about 50%, about 45%, about 40%, about 35%, about 30%, about 25%, about 20%, about 15%, about 10%, about 5%, or less than about 5% cell death.

Biodegradable: As used herein, the term "biodegradable" refers to substances that are degraded under physiological conditions. In some embodiments, a biodegradable substance is a substance that is broken down by cellular machinery. In some embodiments, a biodegradable substance is a substance that is broken down by chemical processes.

Biologically active: As used herein, the phrase "biologically active" refers to a characteristic of any substance that has activity in a biological system and/or organism. For instance, a substance that, when administered to an organism, has a biological effect on that organism, is considered to be biologically active. In particular embodiments, where a nucleic acid is biologically active, a portion of that nucleic acid that shares at least one biological activity of the whole nucleic acid is typically referred to as a "biologically active" portion.

Carbohydrate: The term "carbohydrate" refers to a sugar or polymer of sugars. The terms "saccharide," "polysaccharide," "carbohydrate," and "oligosaccharide" may be used interchangeably. Most carbohydrates are aldehydes or ketones with many hydroxyl groups, usually one on each carbon atom of the molecule. Carbohydrates generally have the molecular formula $C_nH_{2n}O_n$. A carbohydrate may be a monosaccharide, a disaccharide, trisaccharide, oligosaccharide, or polysaccharide. The most basic carbohydrate is a monosaccharide, such as glucose, sucrose, galactose, mannose, ribose, arabinose, xylose, and fructose. Disaccharides are two joined monosaccharides. Exemplary disaccharides include sucrose, maltose, cellobiose, and lactose. Typically, an oligosaccharide includes between three and six monosaccharide units (e.g., raffinose, stachyose), and polysaccharides include six or more monosaccharide units. Exemplary polysaccharides include starch, glycogen, and cellulose. Carbohydrates may contain modified saccharide units such as 2'-deoxyribose wherein a hydroxyl group is removed, 2'-fluororibose wherein a hydroxyl group is replace with a fluorine, or N-acetylglucosamine, a nitrogen-containing form of glucose (e.g., 2'-fluororibose, deoxyribose, and hexose). Carbohydrates may exist in many different forms, for example, conformers, cyclic forms, acyclic forms, stereoisomers, tautomers, anomers, and isomers.

Characteristic portion: As used herein, the term a "characteristic portion" of a substance, in the broadest sense, is one that shares some degree of sequence and/or structural identity and/or at least one functional characteristic with the relevant intact substance. For example, a "characteristic portion" of a protein or polypeptide is one that contains a continuous stretch of amino acids, or a collection of continuous stretches of amino acids, that together are characteristic of a protein or polypeptide. In some embodiments, each such continuous stretch generally will contain at least 2, at least 5, at least 10, at least 15, at least 20; at least 50, or more amino acids. A "characteristic portion" of a nucleic acid is one that contains a continuous stretch of nucleotides, or a collection of continuous stretches of nucleotides, that together are characteristic of a nucleic acid. In some embodiments, each such continuous stretch generally will contain at least 2, at least 5, at least 10, at least 15, at least 20, at least 50, or more nucleotides. In some embodiments, a characteristic portion is biologically active.

Conserved: As used herein, the term "conserved" refers to nucleotides or amino acid residues of a polynucleotide sequence or amino acid sequence, respectively, that are those that occur unaltered in the same position of two or more related sequences being compared. Nucleotides or amino acids that are relatively conserved are those that are conserved amongst more related sequences than nucleotides or amino acids appearing elsewhere in the sequences. In some embodiments, two or more sequences are said to be "completely conserved" if they are 100% identical to one another. In some embodiments, two or more sequences are said to be "highly conserved" if they are at least 70% identical, at least 80% identical, at least 90% identical, or at least 95% identical to one another. In some embodiments, two or more sequences are said to be "highly conserved" if they are about 70% identical, about 80% identical, about 90% identical, about 95%, about 98%, or about 99% identical to one another. In some embodiments, two or more sequences are said to be "conserved" if they are at least 30% identical, at least 40% identical, at least 50% identical, at least 60% identical, at least 70% identical, at least 80% identical, at least 90% identical, or at least 95% identical to one another. In some embodiments, two or more sequences are said to be "conserved" if they are about 30% identical, about 40% identical, about 50% identical, about 60% identical, about 70% identical, about 80% identical, about 90% identical, about 95% identical, about 98% identical, or about 99% identical to one another.

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end processing); (3) translation of an RNA into a polypeptide or protein; and (4) post-translational modification of a polypeptide or protein.

Functional: As used herein, a "functional" biological molecule is a biological molecule in a form in which it exhibits a property and/or activity by which it is characterized.

Fusion protein: As used herein, a "fusion protein" includes a first protein moiety, e.g., a supercharged protein, having a peptide linkage with a second protein moiety. In certain embodiments, the fusion protein is encoded by a single fusion gene.

Gene: As used herein, the term "gene" has its meaning as understood in the art. It will be appreciated by those of ordinary skill in the art that the term "gene" may include gene regulatory sequences (e.g., promoters, enhancers, etc.) and/or intron sequences. It will further be appreciated that definitions of gene include references to nucleic acids that do not encode proteins but rather encode functional RNA molecules such as RNAi agents, ribozymes, tRNAs, etc. For the purpose of clarity it should be noted that, as used in the present application, the term "gene" generally refers to a portion of a nucleic acid that encodes a protein; the term may optionally encompass regulatory sequences, as will be clear from context to those of ordinary skill in the art. This definition is not intended to exclude application of the term "gene" to non-protein-coding expression units but rather to clarify that, in most cases, the term as used in this document refers to a protein-coding nucleic acid.

Gene product or expression product: As used herein, the term "gene product" or "expression product" generally refers to an RNA transcribed from the gene (pre- and/or post-processing) or a polypeptide (pre- and/or post-modification) encoded by an RNA transcribed from the gene.

Green fluorescent protein: As used herein, the term "green fluorescent protein" (GFP) refers to a protein originally isolated from the jellyfish *Aequorea victoria* that fluoresces green when exposed to blue light or a derivative of such a protein (e.g., a supercharged version of the protein). The amino acid sequence of wild type GFP is as follows:

```
                                          (SEQ ID NO: 17)
MSKGEELFTG  VVPILVELDG  DVNGHKFSVS  GEGEGDATYG

KLTLKFICTT  GKLPVPWPTL  VTTFSYGVQC  FSRYPDHMKQ

HDFFKSAMPE  GYVQERTIFF  KDDGNYKTRA  EVKFEGDTLV

NRIELKGIDF  KEDGNILGHK  LEYNYNSHNV  YIMADKQKNG

IKVNFKIRHN  IEDGSVQLAD  HYQQNTPIGD  GPVLLPDNHY

LSTQSALSKD  PNEKRDHMVL  LEFVTAAGIT  HGMDELYK.
```

Proteins that are at least 70%, at least 75%, at least 80%, at least 85%, at least 90%, at least 95%, at least 98%, or at least 99% homologous are also considered to be green fluorescent proteins. In certain embodiments, the green fluorescent protein is supercharged. In certain embodiments, the green fluorescent protein is superpositively charged (e.g., +15 GFP, +25 GFP, and +36 GFP as described herein). In certain embodiments, the GFP may be modified to include a polyhistidine tag for ease in purification of the protein. In certain embodiments, the GFP may be fused with another protein or peptide (e.g., hemagglutinin 2 (HA2) peptide). In certain embodiments, the GFP may be further modified biologically or chemically (e.g., post-translational modifications, proteolysis, etc.).

Homology: As used herein, the term "homology" refers to the overall relatedness between polymeric molecules, e.g. between nucleic acid molecules (e.g. DNA molecules and/or RNA molecules) and/or between polypeptide molecules. In some embodiments, polymeric molecules are considered to be "homologous" to one another if their sequences are at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% identical. In some embodiments, polymeric molecules are considered to be "homologous" to one another if their sequences are at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% similar. The term "homologous" necessarily refers to a comparison between at least two sequences (nucleotides sequences or amino acid sequences). In accordance with the invention, two nucleotide sequences are considered to be homologous if the polypeptides they encode are at least about 50% identical, at least about 60% identical, at least about 70% identical, at least about 80% identical, or at least about 90% identical for at least one stretch of at least about 20 amino acids. In some embodiments, homologous nucleotide sequences are characterized by the ability to encode a stretch of at least 4-5 uniquely specified amino acids. Both the identity and the approximate spacing of these amino acids relative to one another must be considered for nucleotide sequences to be considered homologous. For nucleotide sequences less than 60 nucleotides in length, homology is determined by the ability to encode a stretch of at least 4-5 uniquely specified amino acids. In accordance with the invention, two protein sequences are considered to be homologous if the proteins are at least about 50% identical, at least about 60% identical, at least about 70% identical, at least about 80% identical, or at least about 90% identical for at least one stretch of at least about 20 amino acids.

Hydrophilic: As used herein, a "hydrophilic" substance is a substance that may be soluble in polar dispersion media. In some embodiments, a hydrophilic substance can transiently bond with polar dispersion media. In some embodiments, a hydrophilic substance transiently bonds with polar dispersion media through hydrogen bonding. In some embodiments, the polar dispersion medium is water. In some embodiments, a hydrophilic substance may be ionic. In some embodiments, a hydrophilic substance may be non-ionic. In some embodiments, a substance is hydrophilic relative to another substance because it is more soluble in water, polar dispersion media, or hydrophilic dispersion media than is the other substance. In some embodiments, a substance is hydrophilic relative to another substance because it is less soluble in oil, non-polar dispersion media, or hydrophobic dispersion media than is the other substance.

Hydrophobic: As used herein, a "hydrophobic" substance is a substance that may be soluble in non-polar dispersion media. In some embodiments, a hydrophobic substance is repelled from polar dispersion media. In some embodiments, the polar dispersion medium is water. In some embodiments, hydrophobic substances are non-polar. In some embodiments, a substance is hydrophobic relative to another substance because it is more soluble in oil, non-polar dispersion media, or hydrophobic dispersion media than is the other substance. In some embodiments, a substance is hydrophobic relative to another substance because it is less soluble in water, polar dispersion media, or hydrophilic dispersion media than is the other substance.

Identity: As used herein, the term "identity" refers to the overall relatedness between polymeric molecules, e.g., between nucleic acid molecules (e.g. DNA molecules and/or RNA molecules) and/or between polypeptide molecules. Calculation of the percent identity of two nucleic acid sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using methods such as those described in Computational Molecular Biology, Lesk, A. M., ed., Oxford University Press, New York, 1988; Biocomputing: Informatics and Genome Projects, Smith, D. W., ed., Academic Press, New York, 1993; Sequence Analysis in Molecular Biology, von Heinje, G., Academic Press, 1987; Computer Analysis of Sequence Data, Part I, Griffin, A. M., and Griffin, H. G., eds., Humana Press, New Jersey, 1994; and Sequence Analysis Primer, Gribskov, M. and Devereux, J., eds., M Stockton Press, New York, 1991; each of which is incorporated herein by reference. For example, the percent identity between two nucleotide sequences can be determined using the algorithm of Meyers and Miller (CABIOS, 1989, 4:11-17), which has been incorporated into the ALIGN program (version 2.0) using a PAM120 weight residue table, a gap length penalty of 12 and a gap penalty of 4. The percent identity between two nucleotide sequences can, alternatively, be determined using the GAP program in the GCG software package using an NWSgapdna.CMP matrix. Methods commonly employed to determine percent identity between sequences include, but are not limited to those disclosed in Carillo, H., and Lipman, D., SIAM J Applied Math.; 48:1073 (1988); incorporated herein by reference. Techniques for determining identity are codified in publicly available computer programs. Exemplary computer software to determine homology between two sequences include, but are not limited to, GCG program package, Devereux, J., et al., *Nucleic Acids Research,* 12(1), 387 (1984)), BLASTP, BLASTN, and FASTA Atschul, S. F. et al., *J. Molec. Biol.,* 215, 403 (1990)).

Inhibit expression of a gene: As used herein, the phrase "inhibit expression of a gene" means to cause a reduction in the amount of an expression product of the gene. The expression product can be an RNA transcribed from the gene (e.g., an mRNA) or a polypeptide translated from an mRNA transcribed from the gene. Typically a reduction in the level of an mRNA results in a reduction in the level of a polypeptide translated therefrom. The level of expression may be determined using standard techniques for measuring mRNA or protein.

In vitro: As used herein, the term "in vitro" refers to events that occur in an artificial environment, e.g., in a test tube or reaction vessel, in cell culture, in a Petri dish, etc., rather than within an organism (e.g., animal, plant, or microbe).

In vivo: As used herein, the term "in vivo" refers to events that occur within an organism (e.g., animal, plant, or microbe).

Isolated: As used herein, the term "isolated" refers to a substance or entity that has been (1) separated from at least some of the components with which it was associated when initially produced (whether in nature or in an experimental setting), and/or (2) produced, prepared, and/or manufactured by the hand of man. Isolated substances and/or entities may be separated from at least about 10%, about 20%, about 30%, about 40%, about 50%, about 60%, about 70%, about 80%, about 90%, or more of the other components with which they were initially associated. In some embodiments, isolated agents are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components.

microRNA (miRNA): As used herein, the term "microRNA" or "miRNA" refers to an RNAi agent that is approximately 21 nucleotides (nt)-23 nt in length. miRNAs can range between 18 nt-26 nt in length. Typically, miRNAs are single-stranded. However, in some embodiments, miRNAs may be at least partially double-stranded. In certain embodiments, miRNAs may comprise an RNA duplex (referred to herein as a "duplex region") and may optionally further comprises one to three single-stranded overhangs. In some embodiments, an RNAi agent comprises a duplex region ranging from 15 bp to 29 bp in length and optionally further comprising one or two single-stranded overhangs. An miRNA may be formed from two RNA molecules that hybridize together, or may alternatively be generated from a single RNA molecule that includes a self-hybridizing portion. In general, free 5' ends of miRNA molecules have phosphate groups, and free 3' ends have hydroxyl groups. The duplex portion of an miRNA usually, but does not necessarily, comprise one or more bulges consisting of one or more unpaired nucleotides. One strand of an miRNA includes a portion that hybridizes with a target RNA. In certain embodiments, one strand of the miRNA is not precisely complementary with a region of the target RNA, meaning that the miRNA hybridizes to the target RNA with one or more mismatches. In some embodiments, one strand of the miRNA is precisely complementary with a region of the target RNA, meaning that the miRNA hybridizes to the target RNA with no mismatches. Typically, miRNAs are thought to mediate inhibition of gene expression by inhibiting translation of target transcripts. However, in some embodiments, miRNAs may mediate inhibition of gene expression by causing degradation of target transcripts.

Nucleic acid: As used herein, the term "nucleic acid," in its broadest sense, refers to any compound and/or substance that is or can be incorporated into an oligonucleotide chain. In some embodiments, a nucleic acid is a compound and/or substance that is or can be incorporated into an oligonucleotide chain via a phosphodiester linkage. In some embodiments, "nucleic acid" refers to individual nucleic acid residues (e.g. nucleotides and/or nucleosides). In some embodiments, "nucleic acid" refers to an oligonucleotide chain comprising individual nucleic acid residues. As used herein, the terms "oligonucleotide" and "polynucleotide" can be used interchangeably to refer to a polymer of nucleotides (e.g., a string of at least two nucleotides). In some embodiments, "nucleic acid" encompasses RNA as well as single and/or double-stranded DNA and/or cDNA. Furthermore, the terms "nucleic acid," "DNA," "RNA," and/or similar terms include nucleic acid analogs, i.e. analogs having other than a phosphodiester backbone. For example, the so-called "peptide nucleic acids," which are known in the art and have peptide bonds instead of phosphodiester bonds in the backbone, are considered within the scope of the present invention. The term "nucleotide sequence encoding an amino acid sequence" includes all nucleotide sequences that are degenerate versions of each other and/or encode the same amino acid sequence. Nucleotide sequences that encode proteins and/or RNA may include introns. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, backbone modifications, etc. A nucleic acid sequence is presented in the 5' to 3' direction unless otherwise indicated. The term "nucleic acid segment" is used herein to refer to a nucleic acid sequence that is a portion of a longer nucleic acid sequence. In many embodiments, a nucleic acid segment comprises at least 3, at least 4, at least 5, at least 6, at least 7, at least 8, at least 9, at least 10, or more residues. In some embodiments, a nucleic acid is or comprises natural nucleosides (e.g. adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolopyrimidine, 3-methyl adenosine, 5-methylcytidine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages). In some embodiments, the present invention is specifically directed to "unmodified nucleic acids," meaning nucleic acids (e.g. polynucleotides and residues, including nucleotides and/or nucleosides) that have not been chemically modified in order to facilitate or achieve delivery.

Polymer: As used herein, the term "polymer" refers to any substance comprising at least two repeating structural units (i.e., "monomers") which are associated with one another. In some embodiments, monomers are covalently associated with one another. In some embodiments, monomers are non-covalently associated with one another. Polymers may be homopolymers or copolymers comprising two or more monomers. In terms of sequence, copolymers may be random, block, graft, or comprise a combination of random, block, and/or graft sequences. In some embodiments, block copolymers are diblock copolymers. In some embodiments, block copolymers are triblock copolymers. In some embodiments, polymers can be linear or branched polymers. In some embodiments, polymers in accordance with the invention comprise blends, mixtures, and/or adducts of any of the polymers described herein. Typically, polymers in accordance with the present invention are organic polymers. In some embodiments, polymers are hydrophilic. In some embodiments, polymers are hydrophobic. In some embodiments, polymers modified with one or more moieties and/or functional groups.

Protein: As used herein, the term "protein" refers to a polypeptide (i.e., a string of at least two amino acids linked to one another by peptide bonds). Proteins may include moieties other than amino acids (e.g., may be glycoproteins) and/or may be otherwise processed or modified. Those of ordinary skill in the art will appreciate that a "protein" can be a complete polypeptide chain as produced by a cell (with or without a signal sequence), or can be a functional portion thereof. Those of ordinary skill will further appreciate that a protein can sometimes include more than one polypeptide chain, for example linked by one or more disulfide bonds or associated by other means. Polypeptides may contain L-amino acids, D-amino acids, or both and may contain any of a variety of amino acid modifications or analogs known in the art. Useful modifications include, e.g., addition of a chemical entity such as a carbohydrate group, a phosphate group, a farnesyl group, an isofarnesyl group, a fatty acid group, an amide group, a terminal acetyl group, a linker for conjugation, functionalization, or other modification (e.g., alpha amidation), etc. In a preferred embodiment, the modifications of the peptide lead to a more stable peptide (e.g., greater half-life in vivo). These modifications may include cyclization of the peptide, the incorporation of D-amino acids, etc. None of the modifications should substantially interfere with the desired biological activity of the peptide. In certain embodiments, the modifications of the peptide lead to a more biologically active peptide. In some embodiments, polypeptides may comprise natural amino acids, non-natural amino acids, synthetic amino acids, amino acid analogs, and combinations thereof. The term "peptide" is typically used to refer to a polypeptide having a length of less than about 100 amino acids.

Reprogramming factor: As used herein, the term "reprogramming factor" refers to a factor that, alone or in combination with other factors, can change the state of a cell from a somatic, differentiated state into a pluripotent stem cell state. Non limiting examples of reprogramming factors include a protein, e.g., a transcription factor, a peptide, a nucleic acid, or a small molecule.

RNA interference (RNAi): As used herein, the term "RNA interference" or "RNAi" refers to sequence-specific inhibition of gene expression and/or reduction in target RNA levels mediated by an RNA, which RNA comprises a portion that is substantially complementary to a target RNA. Typically, at least part of the substantially complementary portion is within the double stranded region of the RNA. In some embodiments, RNAi can occur via selective intracellular degradation of RNA. In some embodiments, RNAi can occur by translational repression.

RNAi agent: As used herein, the term "RNAi agent" or "RNAi" refers to an RNA, optionally including one or more nucleotide analogs or modifications, having a structure characteristic of molecules that can mediate inhibition of gene expression through an RNAi mechanism. In some embodiments, RNAi agents mediate inhibition of gene expression by causing degradation of target transcripts. In some embodiments, RNAi agents mediate inhibition of gene expression by inhibiting translation of target transcripts. Generally, an RNAi agent includes a portion that is substantially complementary to a target RNA. In some embodiments, RNAi agents are at least partly double-stranded. In some embodiments, RNAi agents are single-stranded. In some embodiments, exemplary RNAi agents can include siRNA, shRNA, and/or miRNA. In some embodiments, RNAi agents may be composed entirely of natural RNA nucleotides (i.e., adenine, guanine, cytosine, and uracil). In some embodiments, RNAi agents may include one or more non-natural RNA nucleotides (e.g., nucleotide analogs, DNA nucleotides, etc.). Inclusion of non-natural RNA nucleic acid residues may be used to make the RNAi agent more resistant to cellular degradation than RNA. In some embodiments, the term "RNAi agent" may refer to any RNA, RNA derivative, and/or nucleic acid encoding an RNA that induces an RNAi effect (e.g., degradation of target RNA and/or inhibition of translation). In some embodiments, an RNAi agent may comprise a blunt-ended (i.e., without overhangs) dsRNA that can act as a Dicer substrate. For example, such an RNAi agent may comprise a blunt-ended dsRNA which is ≥25 base pairs length, which may optionally be chemically modified to abrogate an immune response.

RNAi-inducing agent: As used herein, the term "RNAi-inducing agent" encompasses any entity that delivers, regulates, and/or modifies the activity of an RNAi agent. In some embodiments, RNAi-inducing agents may include vectors (other than naturally occurring molecules not modified by the hand of man) whose presence within a cell results in RNAi and leads to reduced expression of a transcript to which the RNAi-inducing agent is targeted. In some embodiments, RNAi-inducing agents are RNAi-inducing vectors. In some embodiments, RNAi-inducing agents are compositions comprising RNAi agents and one or more pharmaceutically acceptable excipients and/or carriers. In some embodiments, an RNAi-inducing agent is an "RNAi-inducing vector," which refers to a vector whose presence within a cell results in production of one or more RNAs that self-hybridize or hybridize to each other to form an RNAi agent (e.g. siRNA, shRNA, and/or miRNA). In various embodiments, this term encompasses plasmids, e.g., DNA vectors (whose sequence may comprise sequence elements derived from a virus), or viruses (other than naturally occurring viruses or plasmids that have not been modified by the hand of man), whose presence within a cell results in production of one or more RNAs that self-hybridize or hybridize to each other to form an RNAi agent. In general, the vector comprises a nucleic acid operably linked to expression signal(s) so that one or more RNAs that hybridize or self-hybridize to form an RNAi agent are transcribed when the vector is present within a cell. Thus the vector provides a template for intracellular synthesis of the RNA or RNAs or precursors thereof. For purposes of inducing RNAi, presence of a viral genome in a cell (e.g., following fusion of the viral envelope with the cell membrane) is considered sufficient to constitute presence of the virus within the cell. In addition, for purposes of inducing RNAi, a vector is considered to be present within a cell if it is introduced into the cell, enters the cell, or is inherited from a parental cell, regardless of whether it is subsequently modified or processed within the cell. An RNAi-inducing vector is considered to be targeted to a transcript if presence of the vector within a cell results in production of one or more RNAs that hybridize to each other or self-hybridize to form an RNAi agent that is targeted to the transcript, i.e., if presence of the vector within a cell results in production of one or more RNAi agents targeted to the transcript.

Short, interfering RNA (siRNA): As used herein, the term "short, interfering RNA" or "siRNA" refers to an RNAi agent comprising an RNA duplex (referred to herein as a "duplex region") that is approximately 19 base pairs (bp) in length and optionally further comprises one to three single-stranded overhangs. In some embodiments, an RNAi agent comprises a duplex region ranging from 15 bp to 29 bp in length and optionally further comprising one or two single-stranded overhangs. An siRNA may be formed from two RNA molecules that hybridize together, or may alternatively be generated from a single RNA molecule that includes a self-hybridizing portion. In general, free 5' ends of siRNA molecules have phosphate groups, and free 3' ends have hydroxyl groups. The duplex portion of an siRNA may, but typically does not, comprise one or more bulges consisting of one or more unpaired nucleotides. One strand of an siRNA includes a portion that hybridizes with a target transcript. In certain embodiments, one strand of the siRNA is precisely complementary with a region of the target transcript, meaning that the siRNA hybridizes to the target transcript without a single mismatch. In some embodiments, one or more mismatches between the siRNA and the targeted portion of the target transcript may exist. In some embodiments in which perfect complementarity is not achieved, any mismatches are generally located at or near the siRNA termini. In some embodiments, siRNAs mediate inhibition of gene expression by causing degradation of target transcripts.

Short hairpin RNA (shRNA): As used herein, the term "short hairpin RNA" or "shRNA" refers to an RNAi agent comprising an RNA having at least two complementary portions hybridized or capable of hybridizing to form a double-stranded (duplex) structure sufficiently long to mediate RNAi (typically at least approximately 19 bp in length), and at least one single-stranded portion, typically ranging between approximately 1 nucleotide (nt) and approximately 10 nt in length that forms a loop. In some embodiments, an shRNA comprises a duplex portion ranging from 15 bp to 29 bp in length and at least one single-stranded portion, typically ranging between approximately 1 nt and approximately 10 nt in length that forms a loop. The duplex portion may, but typically does not, comprise one or more bulges consisting of one or more unpaired nucleotides. In some embodiments, siRNAs mediate inhibition of gene expression by causing degradation of target transcripts. shRNAs are thought to be processed into siRNAs by the conserved cellular RNAi machinery. Thus shRNAs may be precursors of siRNAs. Regardless, siRNAs in general are capable of inhibiting expression of a target RNA, similar to siRNAs.

Small molecule: In general, a "small molecule" refers to a substantially non-peptidic, non-oligomeric organic compound either prepared in the laboratory or found in nature. Small molecules, as used herein, can refer to compounds that are "natural product-like," however, the term "small molecule" is not limited to "natural product-like" compounds. Rather, a small molecule is typically characterized in that it contains several carbon-carbon bonds, and has a molecular weight of less than 1500 g/mol, less than 1250 g/mol, less than 1000 g/mol, less than 750 g/mol, less than 500 g/mol, or less than 250 g/mol, although this characterization is not intended to be limiting for the purposes of the present invention. In certain other embodiments, natural-product-like small molecules are utilized.

Similarity: As used herein, the term "similarity" refers to the overall relatedness between polymeric molecules, e.g. between nucleic acid molecules (e.g. DNA molecules and/or RNA molecules) and/or between polypeptide molecules. Calculation of percent similarity of polymeric molecules to one another can be performed in the same manner as a calculation of percent identity, except that calculation of percent similarity takes into account conservative substitutions as is understood in the art.

Stable: As used herein, the term "stable" as applied to a protein refers to any aspect of protein stability. The stable modified protein as compared to the original unmodified protein possesses any one or more of the following characteristics: more soluble, more resistant to aggregation, more resistant to denaturation, more resistant to unfolding, more resistant to improper or undesired folding, greater ability to renature, increased thermal stability, increased stability in a variety of environments (e.g., pH, salt concentration, presence of detergents, presence of denaturing agents, etc.), and increased stability in non-aqueous environments. In certain embodiments, the stable modified protein exhibits at least two of the above characteristics. In certain embodiments, the stable modified protein exhibits at least three of the above characteristics. Such characteristics may allow the active protein to be produced at higher levels. For example, the modified protein can be overexpressed at a higher level without aggregation than the unmodified version of the protein. Such characteristics may also allow the protein to be used as a therapeutic agent or a research tool.

Subject: As used herein, the term "subject" or "patient" refers to any organism to which a composition in accordance with the invention may be administered, e.g., for experimental, diagnostic, prophylactic, and/or therapeutic purposes. Typical subjects include animals (e.g., mammals such as mice, rats, rabbits, non-human primates, and humans) and/or plants.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Suffering from: An individual who is "suffering from" a disease, disorder, and/or condition has been diagnosed with or displays one or more symptoms of a disease, disorder, and/or condition.

Supercharge: As used herein, the term "supercharge" refers to any modification of a protein that results in the increase or decrease of the overall net charge of the protein. Modifications include, but are not limited to, alterations in amino acid sequence or addition of charged moieties (e.g., carboxylic acid groups, phosphate groups, sulfate groups, amino groups). Supercharging also refers to the association of an agent with a charged protein, naturally occurring or modified, to form a complex with increased or decreased charge relative to the agent alone.

Supercharged complex: As defined herein, a "supercharged complex" refers to the combination of one or more agents associated with a supercharged protein, engineered or naturally occurring, that collectively has an increased or decreased charge relative to the agent alone.

Susceptible to: An individual who is "susceptible to" a disease, disorder, and/or condition has not been diagnosed with and/or may not exhibit symptoms of the disease, disorder, and/or condition. In some embodiments, an individual who is susceptible to a disease, disorder, and/or condition (for example, cancer) may be characterized by one or more of the following: (1) a genetic mutation associated with development of the disease, disorder, and/or condition; (2) a genetic polymorphism associated with development of the disease, disorder, and/or condition; (3) increased and/or decreased expression and/or activity of a protein and/or nucleic acid associated with the disease, disorder, and/or condition; (4) habits and/or lifestyles associated with development of the disease, disorder, and/or condition; (5) a family history of the disease, disorder, and/or condition; and (6) exposure to and/or infection with a microbe associated with development of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Targeting agent or targeting moiety: As used herein, the term "targeting agent" or "targeting moiety" refers to any substance that binds to a component associated with a cell, tissue, and/or organ. Such a component is referred to as a "target" or a "marker." A targeting agent or targeting moiety may be a polypeptide, glycoprotein, nucleic acid, small molecule, carbohydrate, lipid, etc. In some embodiments, a targeting agent or targeting moiety is an antibody or characteristic portion thereof. In some embodiments, a targeting agent or targeting moiety is a receptor or characteristic portion thereof. In some embodiments, a targeting agent or targeting moiety is a ligand or characteristic portion thereof. In some embodiments, a targeting agent or targeting moiety is a nucleic acid targeting agent (e.g. an aptamer) that binds to a cell type specific marker. In some embodiments, a targeting agent or targeting moiety is an organic small molecule. In some embodiments, a targeting agent or targeting moiety is an inorganic small molecule.

Target gene: As used herein, the term "target gene" refers to any gene whose expression is altered by an RNAi or other agent.

Target transcript: As used herein, the term "target transcript" refers to any mRNA transcribed from a target gene.

Therapeutically effective amount: As used herein, the term "therapeutically effective amount" means an amount of an agent to be delivered (e.g., nucleic acid, drug, therapeutic agent, diagnostic agent, prophylactic agent, etc.) that is sufficient, when administered to a subject suffering from or susceptible to a disease, disorder, and/or condition, to treat, improve symptoms of, diagnose, prevent, and/or delay the onset of the disease, disorder, and/or condition.

Transcription factor: As used herein, the term "transcription factor" refers to a DNA-binding protein that regulates transcription of DNA into RNA, for example, by activation or repression of transcription. Some transcription factors effect regulation of transcription alone, while others act in concert with other proteins. Some transcription factor can both activate and repress transcription under certain conditions. In general, transcription factors bind a specific target sequence or sequences highly similar to a specific consensus sequence in a regulatory region of a target gene. Transcription factors may regulate transcription of a target gene alone or in a complex with other molecules.

Treating: As used herein, the term "treating" refers to partially or completely alleviating, ameliorating, improving, relieving, delaying onset of, inhibiting progression of, reducing severity of, and/or reducing incidence of one or more symptoms or features of a particular disease, disorder, and/or condition. For example, "treating" cancer may refer to inhibiting survival, growth, and/or spread of a tumor. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition. In some embodiments, treatment comprises delivery of a supercharged protein associated with a therapeutically active nucleic acid to a subject in need thereof.

Unmodified: As used herein, "unmodified" refers to the protein or agent prior to being supercharged or associated in a complex with a supercharged protein, engineered or naturally occurring.

Vector: As used herein, "vector" refers to a nucleic acid molecule which can transport another nucleic acid to which it has been linked. In some embodiment, vectors can achieve extra-chromosomal replication and/or expression of nucleic acids to which they are linked in a host cell such as a eukaryotic and/or prokaryotic cell. Vectors capable of directing the expression of operatively linked genes are referred to herein as "expression vectors."

DETAILED DESCRIPTION OF CERTAIN EMBODIMENTS OF THE INVENTION

Figure 1A:
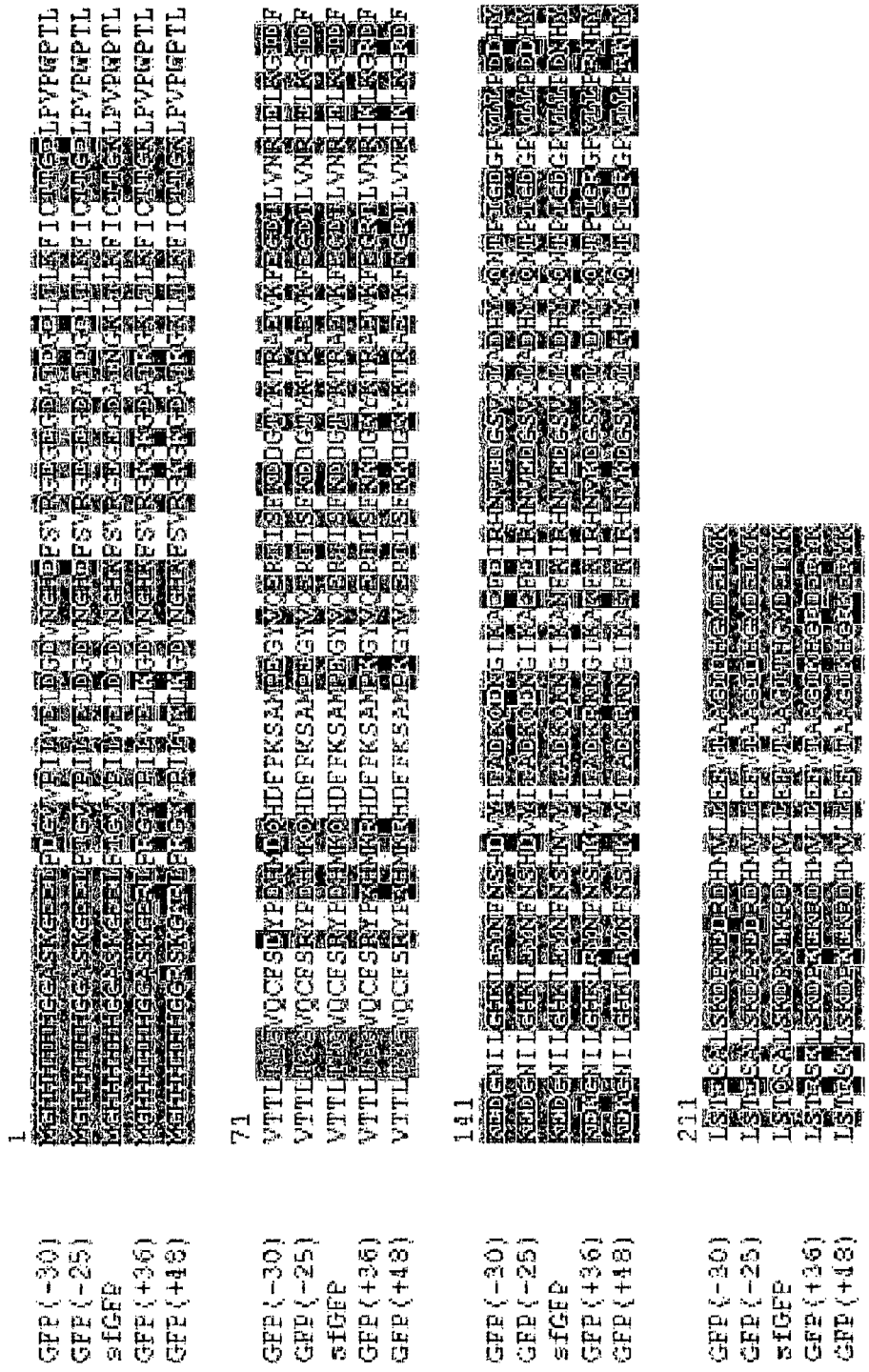
FIG. 1 Supercharged green fluorescent proteins (GFPs). (A) Protein sequences of GFP variants, with fluorophore-forming residues highlighted, negatively charged residues highlighted, and positively charged residues highlighted. (B-D) Electrostatic surface potentials of sfGFP(B), GFP(+36) (C), and GFP(−30) (D), colored from −25 kT/e to +25 kT/e. Sequences correspond, from top to bottom, to SEQ ID NO: 5, SEQ ID NO: 3, SEQ ID NO: 110, SEQ ID NO: 7, and SEQ ID NO: 9, respectively.

The present invention provides compositions, preparations, systems, and related methods for enhancing delivery of a protein or other agent to cells by supercharging the protein itself or by associating the protein or other agent (e.g., peptides, proteins, small molecules) with a supercharged protein. Such systems and methods generally comprise the use of supercharged proteins. In some embodiments, the supercharged protein itself is delivered to the interior of a cell, e.g., to cause a biological effect on the cell into which it penetrates for therapeutic benefit. Supercharged proteins can also be used to deliver other agents. For example, superpositively charged proteins may be associated with agents having a negative charge, e.g., nucleic acids (which typically have a net negative charge) or negatively charged peptides or proteins via electrostatic interactions to form complexes. Supernegatively charged proteins may be associated with agents having a positive charge. Agents to be delivered may also be associated with the supercharged protein through covalent linkages or other non-covalent interactions. In some embodiments, such compositions, preparations, systems, and methods involve altering the primary sequence of a protein in order to "supercharge" the protein (e.g., to generate a super-positively-charged protein). In certain embodiments, the inventive system uses a naturally occurring protein to form a complex. In certain embodiments, the inventive complex comprises a supercharged protein and one or more agents to be delivered (e.g., nucleic acid, protein, peptide, small molecule). In one example of cellular uptake, supercharged proteins have been found to be endocytosed by cells. The supercharged protein, or the supercharged protein mixed with an agent to be delivered to form a protein/agent complex, is effectively transfected into the cell. Mechanistic studies indicate the endocytosis of these complexes involves sulfated cell surface proteoglycans but does not involve clathrin or caveolin. In some embodiments, supercharged protein or complexes comprising supercharged proteins and one or more agents to be delivered are useful as therapeutic agents, diagnostic agents, or research tools. In some embodiments, an agent and/or supercharged protein may be therapeutically active. In some embodiments, a supercharged protein or complex is used to modulate the expression of a gene in a cell. In some embodiments, a supercharged protein or complex is used to modulate a biological pathway (e.g., a signaling pathway, a metabolic pathway) in a cell. In some embodiments, a supercharged protein or complex is used to inhibit the activity of an enzyme in a cell. In some embodiments, inventive supercharged proteins or complexes and/or pharmaceutical compositions thereof are administered to a subject in need thereof. In some embodiments, inventive supercharged proteins or complexes and/or compositions thereof are contacted with a cell under conditions effective to transfect the agent into a cell (e.g., human cells, mammalian cells, T-cells, neurons, stem cells, progenitor cells, blood cells, fibroblasts, epithelial cells, etc.). In some embodiments, delivery of a supercharged protein or complex to cells involves administering a supercharged protein or a complex comprising supercharged proteins associated with therapeutic agents to a subject in need thereof.

Supercharged Proteins

Supercharged proteins can be produced by changing non-conserved amino acids on the surface of a protein to more polar or charged amino acid residues. The amino acid residues to be modified may be hydrophobic, hydrophilic, charged, or a combination thereof. Supercharged proteins can also be produced by the attachment of charged moieties to the protein in order to supercharge the protein. Supercharged proteins frequently are resistant to aggregation, have an increased ability to refold, resist improper folding, have improved solubility, and are generally more stable under a wide range of conditions, including denaturing conditions such as heat or the presence of a detergent.

Any protein may be modified using the inventive system to produce a supercharged protein. Natural as well as unnatural proteins (e.g., engineered proteins) may be modified. Example of proteins that may be modified include receptors, membrane bound proteins, transmembrane proteins, enzymes, transcription factors, extracellular proteins, therapeutic proteins, cytokines, messenger proteins, DNA-binding proteins, RNA-binding proteins, proteins involved in signal transduction, structural proteins, cytoplasmic proteins, nuclear proteins, hydrophobic proteins, hydrophilic proteins, etc. A protein to be modified may be derived from any species of plant, animal, and/or microorganism. In certain embodiments, the protein is a mammalian protein. In certain embodiments, the protein is a human protein. In certain embodiments, the protein is derived from an organism typically used in research. For example, the protein to be modified may be from a primate (e.g., ape, monkey), rodent (e.g., rabbit, hamster, gerbil), pig, dog, cat, fish (e.g., *Danio rerio*), nematode (e.g., *C. elegans*), yeast (e.g., *Saccharomyces cervisiae*), or bacteria (e.g., *E. coli*). In certain embodiments, the protein is non-immunogenic. In certain embodiments, the protein is non-antigenic. In certain embodiments, the protein does not have inherent biological activity or has been modified to have no biological activity. In certain embodiments, the protein is chosen based on its targeting ability. In certain embodiments, the protein is green fluorescent protein.

In some embodiments, the protein to be modified is one whose structure has been characterized, for example, by NMR or X-ray crystallography. In some embodiments, the protein to be modified is one whose structure has been correlated and/or related to biochemical activity (e.g., enzymatic activity, protein-protein interactions, etc.). In some embodiments, such information provides guidance for selection of amino acid residues to be modified or not modified (e.g., so that biological function is maintained or so that biological activity can be reduced or eliminated). In certain embodiments, the inherent biological activity of the protein is reduced or eliminated to reduce the risk of deleterious and/or undesired effects.

In some embodiments, the protein to be modified is one that is useful in the delivery of a nucleic acid or other agent to a cell. In some embodiments, the protein to be modified is an imaging, labeling, diagnostic, prophylactic, or therapeutic agent. In some embodiments, the protein to be modified is one that is useful for delivering an agent, e.g., a nucleic acid, to a particular cell. In some embodiments, the protein to be modified is one that has desired biological activity. In some embodiments, the protein to be modified is one that has desired targeting activity. In some embodiments, non-conserved surface residues of a protein of interest are identified and at least some of them replaced with a residue that is hydrophilic, polar, and/or charged at physiological pH. In some embodiments, non-conserved surface residues of a protein of interest are identified and at least some of them replaced with a residue that is positively charged at physiological pH.

The surface residues of the protein to be modified are identified using any method(s) known in the art. In certain embodiments, surface residues are identified by computer modeling of the protein. In certain embodiments, the three-dimensional structure of the protein is known and/or determined, and surface residues are identified by visualizing the structure of the protein. In some embodiments, surface residues are predicted using computer software. In certain particular embodiments, an Average Neighbor Atoms per Sidechain Atom (AvNAPSA) value is used to predict surface exposure. AvNAPSA is an automated measure of surface exposure which has been implemented as a computer program. A low AvNAPSA value indicates a surface exposed residue, whereas a high value indicates a residue in the interior of the protein. In certain embodiments, the software is used to predict the secondary structure and/or tertiary structure of a protein, and surface residues are identified based on this prediction. In some embodiments, the prediction of surface residues is based on hydrophobicity and hydrophilicity of the residues and their clustering in the primary sequence of the protein. Besides in silico methods, surface residues of the protein may also be identified using various biochemical techniques, for example, protease cleavage, surface modification, etc.

Optionally, of the surface residues, it is then determined which are conserved or important to the functioning of the protein. The step of determining which residues are conserved is optional when it is not necessary to preserve the underlying biological activity of the protein. Identification of conserved residues can be determined using any method known in the art. In certain embodiments, conserved residues are identified by aligning the primary sequence of the protein of interest with related proteins. These related proteins may be from the same family of proteins. For example, if the protein is an immunoglobulin, other immunoglobulin sequences may be used. Related proteins may also be the same protein from a different species. For example, conserved residues may be identified by aligning the sequences of the same protein from different species. To give but another example, proteins of similar function or biological activity may be aligned. Preferably, 2, 3, 4, 5, 6, 7, 8, 9, or 10 different sequences are used to determine the conserved amino acids in the protein. In certain embodiments, a residue is considered conserved if over 50%, over 60%, over 70%, over 75%, over 80%, over 90%, or over 95% of the sequences have the same amino acid in a particular position. In other embodiments, the residue is considered conserved if over 50%, over 60%, over 70%, over 75%, over 80%, over 90%, or over 95% of the sequences have the same or a similar (e.g., valine, leucine, and isoleucine; glycine and alanine; glutamine and asparagine; or aspartate and glutamate) amino acid in a particular position. Many software packages are available for aligning and comparing protein sequences as described herein. As would be appreciated by one of skill in the art, either the conserved residues may be determined first or the surface residues may be determined first. The order does not matter. In certain embodiments, a computer software package may determine surface residues and conserved residues simultaneously. Important residues in the protein may also be identified by mutagenesis of the protein. For example, alanine scanning of the protein can be used to determine the important amino acid residues in the protein. In some embodiments, site-directed mutagenesis may be used. In certain embodiments, conserving the original biological activity of the protein is not important, and therefore, the steps of identifying the conserved residues and preserving them in the supercharged protein are not performed.

Each of the surface residues is identified as hydrophobic or hydrophilic. In certain embodiments, residues are assigned a hydrophobicity score. For example, each surface residue may be assigned an octanol/water log P value. Other hydrophobicity parameters may also be used. Such scales for amino acids have been discussed in: Janin, 1979, *Nature*, 277:491; Wolfenden et al., 1981, *Biochemistry*, 20:849; Kyte et al., 1982, *J. Mol. Biol.*, 157:105; Rose et al., 1985, *Science*, 229:834; Cornette et al., 1987, *J. Mol. Biol.*, 195:659; Charton and Charton, 1982, *J. Theor. Biol.*, 99:629; each of which is incorporated by reference. Any of these hydrophobicity parameters may be used in the inventive method to determine which residues to modify. In certain embodiments, hydrophilic or charged residues are identified for modification.

At least one identified surface residue is then chosen for modification. In certain embodiments, hydrophobic residue(s) are chosen for modification. In other embodiments, hydrophilic and/or charged residue(s) are chosen for modification. In certain embodiments, more than one residue is chosen for modification. In certain embodiments, 1, 2, 3, 4, 5, 6, 7, 8, 9, or 10 of the identified residues are chosen for modification. In certain embodiments, over 10, over 15, over 20, or over 25 residues are chosen for modification. As would be appreciated by one of skill in the art, the larger the protein, the more residues that will need to be modified. Also, the more hydrophobic or susceptible to aggregation or precipitation the protein is, the more residues may need to be modified. In certain embodiments, multiple variants of a protein, each with different modifications, are produced and tested to determine the best variant in terms of delivery of a nucleic acid to a cell, stability, biocompatibility, and/or biological activity.

In certain embodiments, residues chosen for modification are mutated into more hydrophilic residues (including charged residues). Typically, residues are mutated into more hydrophilic natural amino acids. In certain embodiments, residues are mutated into amino acids that are charged at physiological pH. For example, a residue may be changed to an arginine, aspartate, glutamate, histidine, or lysine. In certain embodiments, all the residues to be modified are changed into the same different residue. For example, all the chosen residues are changed to a lysine residue. In other embodiments, the chosen residues are changed into different residues; however, all the final residues may be either positively charged or negatively charged at physiological pH. In certain embodiments, to create a negatively charged protein, all the residues to be mutated are converted to glutamate and/or aspartate residues. In certain embodiments, to create a positively charged protein, all the residues to be mutated are converted to lysine residues. For example, all the chosen residues for modification are asparagine, glutamine, lysine, and/or arginine, and these residues are mutated into aspartate or glutamate residues. To give but another example, all the chosen residues for modification are aspartate, glutamate, asparagine, and/or glutamine, and these residues are mutated into lysine. This approach allows for modifying the net charge on the protein to the greatest extent.

In some embodiments, a protein may be modified to keep the net charge on the modified protein the same as on the unmodified protein. In some embodiments, a protein may be modified to decrease the overall net charge on the protein while increasing the total number of charged residues on the surface. In certain embodiments, the theoretical net charge is increased by at least +1, at least +2, at least +3, at least +4, at least +5, at least +10, at least +15, at least +20, at least +25, at least +30, at least +35, or at least +40. In certain embodiments, the theoretical net charge is decreased by at least −1, at least −2, at least −3, at least −4, at least −5, at least −10, at least −15, at least −20, at least −25, at least −30, at least −35, or at least −40. In certain embodiments, the chosen amino acids are changed into non-ionic, polar residues (e.g., cysteine, serine, threonine, tyrosine, glutamine, asparagine).

In certain embodiments, the amino acid residues mutated to charged amino acids residues are separated from each other by at least 1, at least 2, at least 3, at least 4, at least 5, at least 6, at least 7, at least 8, at least 9, at least 10, at least 15, at least 20, or at least 25 amino acid residues. In certain embodiments, the amino acid residues mutated to positively charged amino acids residues (e.g., lysine) are separated from each other by at least 1, at least 2, at least 3, at least 4, at least 5, at least 6, at least 7, at least 8, at least 9, at least 10, at least 15, at least 20, or at least 25 amino acid residues. Typically, these intervening sequence are based on the primary amino acid of the protein being supercharged. In certain embodiments, only two charged amino acids are allowed to be in a row in a supercharged protein. In certain embodiments, only three or fewer charged amino acids are allowed to be in a row in a supercharged protein. In certain embodiments, only four or fewer charged amino acids are allowed to be in a row in a supercharged protein. In certain embodiments, only five or fewer charged amino acids are allowed to be in a row in a supercharged protein.

In certain embodiments, a surface exposed loop, helix, turn, or other secondary structure may contain only 1, 2, 3, 4, 5, 6, 7, 8, 9, or 10 charged residues. Distributing the charged residues over the protein typically is thought to allow for more stable proteins. In certain embodiments, only 1, 2, 3, 4, or 5 residues per 15-20 amino acids of the primary sequence are mutated to charged amino acids (e.g., lysine). In certain embodiments, on average only 1, 2, 3, 4, or 5 residues per 10 amino acids of the primary sequence are mutated to charged amino acids (e.g., lysine). In certain embodiments, on average only 1, 2, 3, 4, or 5 residues per 15 amino acids of the primary sequence are mutated to charged amino acids (e.g., lysine). In certain embodiments, on average only 1, 2, 3, 4, or 5 residues per 20 amino acids of the primary sequence are mutated to charged amino acids (e.g., lysine). In certain embodiments, on average only 1, 2, 3, 4, or 5 residues per 25 amino acids of the primary sequence are mutated to charged amino acids (e.g., lysine). In certain embodiments, on average only 1, 2, 3, 4, or 5 residues per 30 amino acids of the primary sequence are mutated to charged amino acids (e.g., lysine).

In certain embodiments, at least 50%, at least 60%, at least 70%, at least 80%, or at least 90% of the mutated charged amino acid residues of the supercharged protein are solvent exposed. In certain embodiments, at least 50%, at least 60%, at least 70%, at least 80%, or at least 90% of the mutated charged amino acids residues of the supercharged protein are on the surface of the protein. In certain embodiments, less than 5%, less than 10%, less than 20%, less than 30%, less than 40%, less than 50% of the mutated charged amino acid residues are not solvent exposed. In certain embodiments, less than 5%, less than 10%, less than 20%, less than 30%, less than 40%, less than 50% of the mutated charged amino acid residues are internal amino acid residues.

In some embodiments, amino acids are selected for modification using one or more predetermined criteria. For example, to generate a superpositively charged protein, AvNAPSA values may be used to identify aspartic acid, glutamic acid, asparagine, and/or glutamine residues with AvNAPSA values below a certain threshold value, and one or more (e.g., all) of these residues may be changed to lysines. In some embodiments, to generate a superpositively charged protein, AvNAPSA is used to identify aspartic acid, glutamic acid, asparagine, and/or glutamine residues with AvNAPSA below a certain threshold value, and one or more (e.g., all) of these are changed to arginines. In some embodiments, to generate a supernegative protein, AvNAPSA is used to identify asparagine, glutamine, lysine, and/or arginine residues with AvNAPSA values below a certain threshold value, and one or more (e.g., all) of these are changed to aspartic acid residues. In some embodiments, to generate a supernegatively charged protein, AvNAPSA is used to identify asparagine, glutamine, lysine, and/or arginine residues with AvNAPSA values below a certain threshold value, and one or more (e.g., all) of these are changed to glutamic acid residues. In some embodiments, the certain threshold value is 40 or below. In some embodiments, the certain threshold value is 35 or below. In some embodiments, the certain threshold value is 30 or below. In some embodiments, the certain threshold value is 25 or below. In some embodiments, the certain threshold value is 20 or below. In some embodiments, the certain threshold value is 19 or below, 18 or below, 17 or below, 16 or below, 15 or below, 14 or below, 13 or below, 12 or below, 11 or below, 10 or below, 9 or below, 8 or below, 7 or below, 6 or below, 5 or below, 4 or below, 3 or below, 2 or below, or 1 or below. In some embodiments, the certain threshold value is 0.

In some embodiments, solvent-exposed residues are identified by the number of neighbors. In general, residues that have more neighbors are less solvent-exposed than residues that have fewer neighbors. In some embodiments, solvent-exposed residues are identified by half sphere exposure, which accounts for the direction of the amino acid side chain (Hamelryck, 2005, *Proteins*, 59:8-48; incorporated herein by reference). In some embodiments, solvent-exposed residues are identified by computing the solvent exposed surface area, accessible surface area, and/or solvent excluded surface of each residue. See, e.g., Lee et al., *J. Mol. Biol.* 55(3):379-400, 1971; Richmond, *J. Mol. Biol.* 178:63-89, 1984; each of which is incorporated herein by reference.

The desired modifications or mutations in the protein may be accomplished using any techniques known in the art. Recombinant DNA techniques for introducing such changes in a protein sequence are well known in the art. In certain embodiments, the modifications are, made by site-directed mutagenesis of the polynucleotide encoding the protein. Other techniques for introducing mutations are discussed in *Molecular Cloning: A Laboratory Manual*, 2nd Ed., ed. by Sambrook, Fritsch, and Maniatis (Cold Spring Harbor Laboratory Press: 1989); the treatise, *Methods in Enzymology* (Academic Press, Inc., N.Y.); Ausubel et al. *Current Protocols in Molecular Biology* (John Wiley & Sons, Inc., New York, 1999); each of which is incorporated herein by reference. The modified protein is expressed and tested. In certain embodiments, a series of variants is prepared, and each variant is tested to determine its biological activity and its stability. The variant chosen for subsequent use may be the most stable one, the most active one, or the one with the greatest overall combination of activity and stability. After a first set of variants is prepared an additional set of variants may be prepared based on what is learned from the first set. Variants are typically created and overexpressed using recombinant techniques known in the art.

Supercharged proteins may be further modified. Proteins including supercharged proteins can be modified using techniques known to those of skill in the art. For example, supercharged proteins may be modified chemically or biologically. One or more amino acids may be added, deleted, or changed from the primary sequence. For example, a polyhistidine tag or other tag may be added to the supercharged protein to aid in the purification of the protein. Other peptides or proteins may be added onto the supercharged protein to alter the biological, biochemical, and/or biophysical properties of the protein. For example, an endosomolytic peptide may be added to the primary sequence of the supercharged protein, or a targeting peptide may be added to the primary sequence of the supercharged protein. Other modifications of the supercharged protein include, but are not limited to, post-translational modifications (e.g., glycosylation, phosphorylation, acylation, lipidation, farnesylation, acetylation, proteolysis, etc.). In certain embodiments, the supercharged protein may be modified to reduce its immunogenicity. In certain embodiments, the supercharged protein may be modified to enhance its ability to delivery a nucleic acid to a cell. In certain embodiments, the supercharged protein may be conjugated to a polymer. For example, the protein may be PEGylated by conjugating the protein to a polyethylene glycol (PEG) polymer. One of skill in the art can envision a multitude of ways of modifying the supercharged protein without departing from the scope of the present invention. Methods described herein allow supercharging proteins by imposing changes in the protein sequence of the protein to be supercharged. Other methods can be used to produce supercharged proteins without modification of the protein sequence. For example, moieties that alter charge can be attached to proteins (e.g., by chemical or enzymatic reactions) to provide surface charge to achieve supercharging. In certain embodiments, the method of modifying proteins described in Shaw et al., *Protein Science* 17:1446, 2008 is used to supercharge a protein.

The international PCT patent application (PCT/US07/70254, filed Jun. 1, 2007, published as WO 2007/143574 on Dec. 13, 2007, entitled "Protein Surface Remodeling;" incorporated herein by reference) and U.S. provisional patent applications (U.S. Ser. No. 60/810,364, filed Jun. 2, 2006, and U.S. Ser. No. 60/836,607, filed Aug. 9, 2006; both of which are entitled "Protein Surface Remodeling"; and both of which are incorporated herein by reference) describe the design and creation of variants of several different proteins. These variants have been shown to be more stable and to retain their fluorescence. For example, a green fluorescent protein (GFP) from *Aequorea victoria* is described in GenBank Accession Number P42212, incorporated herein by reference. The amino acid sequence of this wild type GFP is as follows:

```
                                          (SEQ ID NO: 1)
MSKGEELFTGVVPILVELDGDVNGHKFSVSGEGEGDATYGKLTL

KFICTTGKLPVPWPTLVTTFSYGVQCFSRYPDHMKQHDFFKSAMP

EGYVQERTIFFKDDGNYKTRAEVKFEGDTLVNRIELKGIDFKEDG

NILGHKLEYNYNSHNVYIMADKQKNGIKVNFKIRHNIEDGSVQL

ADHYQQNTPIGDGPVLLPDNHYLSTQSALSKDPNEKRDHMVLLE

FVTAAGITHGMDELYK
```

Wild type GFP has a theoretical net charge of −7. Variants with a theoretical net charge of −29, −30, −25, +15, +25, +36, +48, and +49 have been created. Even after heating the +36 GFP to 95° C., 100% of the variant protein is soluble and the protein retains ≥70% of its fluorescence. +15, +25, and +36 GFP have been found to be particularly useful in transfecting nucleic acids into cells. In particular, +36 GFP has been found to be highly cell permeable and capable of efficiently delivering nucleic acids into a variety of mammalian cells, including cell lines resistant to transfection using other transfection methods. Therefore, GFP or other proteins with a net charge of at least +25, at least +30, at least +35, or at least +40 are thought to be particularly useful in transfecting nucleic acids into a cell.

The capacity of supercharged GFPs to penetrate mammalian cells increases as a function of theoretical net charge even at charges as high as +25 and +36. U.S. provisional patent applications, U.S. Ser. No. 61/173,430 and 61/105,287, and PCT application, PCT/US2009/041984, each of which is incorporated herein by reference. This property contrasts with peptidic protein transduction domains (PTDs) such as arginine oligomers, which have been observed to lose mammalian cell penetration ability when their net theoretical charge exceeds +15 (Mitchell et al., *J. Pept. Res.* 56, 318-325, 2000). The cell penetration potency of +36 GFP may therefore be due in part to charge distribution over a comparatively large area, which may provide a more stable and extended cationic surface that interacts more effectively with cells (e.g., mammalian cells).

The significantly greater potency of +36 GFP mediated protein delivery compared with that of Tat and Arg$_9$ may also be a consequence of its structure. Unlike the globular β-barrel of GFP, the nine-residue Tat peptide and Arg$_9$ peptides are unlikely to be well-folded, although the former has been observed to adopt a structure similar to a poly(proline) II helix (Ruzza et al., *J. Pept. Sci.* 10, 423-426, 2004).

Accordingly, in some embodiments, particularly useful supercharged proteins are proteins that allow for a charge distribution or a surface charge density similar to that of +36 GFP. Further, in some embodiments, particularly useful supercharged proteins are proteins exhibiting a stable folded structure not easily perturbed by supercharging, thus allowing the supercharged protein to be well folded. In some embodiments, particularly useful supercharged proteins are proteins sharing a structural feature with a supercharged protein described herein, for example, a globular structure, or a β-barrel structure. Protein folding, protein fold structure stability and perturbation of protein folding by substitution of specific amino acids with differently charged amino acids, charge distribution, and surface charge density can be modeled in silico by methods and algorithms provided herein and others known to those of skill in the art. Accordingly, it will be apparent to those of skill in the art from no more than routine experimentation, whether a supercharged protein in question will be well folded. Thus, those of skill in the art will be able to identify from a given amino acid sequence whether a given supercharged protein will be useful for a system for cell delivery or methods as described herein.

The amino acid sequences of the variants of GFP that have been created include:

```
GFP-NEG7
                                          (SEQ ID NO: 2)
MGHHHHHHGGASKGEELFTGVVPILVELDGDVNGHKFSVRGEGEGD
ATNGKLTLKFICTTGKLPVPWPTLVTTLTYGVQCFSRYPDHMKQHD
FFKSAMPEGYVQERTISFKDDGTYKTRAEVKFEGDTLVNRIELKGI
DFKEDGNILGHKLEYNFNSHNVYITADKQKNGIKANFKIRHNVEDG
SVQLADHYQQNTPIGDGPVLLPDNHYLSTQSALSKDPNEKRDHMVL
LEFVTAAGITHGMDELYK

GFP-NEG25
                                          (SEQ ID NO: 3)
MGHHHHHHGGASKGEELFTGVVPILVELDGDVNGHEFSVRGEGEGD
ATEGELTLKFICTTGELPVPWPTLVTTLTYGVQCFSRYPDHMKQHD
FFKSAMPEGYVQERTISFKDDGTYKTRAEVKFEGDTLVNRIELKGI
DFKEDGNILGHKLEYNFNSHDVYITADKQENGIKAEFEIRHNVEDG
SVQLADHYQQNTPIGDGPVLLPDDHYLSTESALSKDPNEDRDHMVL
LEFVTAAGIDHGMDELYK

GFP-NEG29
                                          (SEQ ID NO: 4)
MGHHHHHHGGASKGEELFDGEVPILVELDGDVNGHEFSVRGEGEGD
ATEGELTLKFICTTGELPVPWPTLVTTLTYGVQCFSRYPDHMDQHD
FFKSAMPEGYVQERTISFKDDGTYKTRAEVKFEGDTLVNRIELKGI
DFKEDGNILGHKLEYNFNSHDVYITADKQENGIKAEFEIRHNVEDG
SVQLADHYQQNTPIGDGPVLLPDDHYLSTESALSKDPNEDRDHMVL
LEFVTAAGIDHGMDELYK

GFP-NEG30
                                          (SEQ ID NO: 5)
MGHHHHHHGGASKGEELFDGVVPILVELDGDVNGHEFSVRGEGEGD
ATEGELTLKFICTTGELPVPWPTLVTTLTYGVQCFSDYPDHMDQHD
FFKSAMPEGYVQERTISFKDDGTYKTRAEVKFEGDTLVNRIELKGI
DFKEDGNILGHKLEYNFNSHDVYITADKQENGIKAEFEIRHNVEDG
SVQLADHYQQNTPIGDGPVLLPDDHYLSTESALSKDPNEDRDHMVL
LEFVTAAGIDHGMDELYK

GFP-POS15
                                          (SEQ ID NO: 6)
MGHHHHHHGGASKGERLFTGVVPILVELDGDVNGHKFSVRGEGEGD
ATRGKLTLKFICTTGKLPVPWPTLVTTLTYGVQCFSRYPKHMKRHD
FFKSAMPEGYVQERTISFKKDGTYKTRAEVKFEGRTLVNRIELKGR
DFKEKGNILGHKLEYNFNSHNVYITADKRKNGIKANFKIRHNVKDG
SVQLADHYQQNTPIGRGPVLLPRNHYLSTRSALSKDPKEKRDHMVL
LEFVTAAGITHGMDELYK

GFP-POS25
                                         (SEQ ID NO: 18)
MGHHHHHFIGGASKGERLFTGVVPILVELDGDVNGHKFSVRGKGKGD
DATRGKLTLKFICTTGKLPVPWPTLVTTLTYGVQCFSRYPKHMKRH
DFFKSAMPKGYVQERTISFKKDGTYKTRAEVKFEGRTLVNRIKLKG
RDFKEKGNILGHKLRYNFNSHNVYITADKRKNGIKANFKIRHNVKD
GSVQLADHYQQNTPIGRGPVLLPRNHYLSTRSALSKDPKEKRDHMV
LLEFVTAAGITHGMDELYK

GFP-POS36
                                          (SEQ ID NO: 7)
MGHHHHHHGGASKGERLFRGKVPILVELKGDVNGHKFSVRGKGKGD
ATRGKLTLKFICTTGKLPVPWPTLVTTLTYGVQCFSRYPKHMKRHD
FFKSAMPKGYVQERTISFKKDGKYKTRAEVKFEGRTLVNRIKLKGR
DFKEKGNILGHKLRYNFNSHKVYITADKRKNGIKAKFKIRHNVKDG
SVQLADHYQQNTPIGRGPVLLPRNHYLSTRSKLSKDPKEKRDHMVL
LEFVTAAG1KHGRDERYK

GFP-POS42
                                          (SEQ ID NO: 8)
MGHHHHHHGGRSKGKRLFRGKVPILVELKGDVNGHKFSVRGKGKGD
ATRGKLTLKFICTTGKLPVPWPTLVTTLTYGVQCFSRYPKHMKRHD
FFKSAMPKGYVQERTISFKKDGKYKTRAEVKFEGRTLVNRIKLKGR
DFKEKGNILGHKLRYNFNSHKVYITADKRKNGIKAKFKIRHNVKDG
SVQLADHYQQNTPIGRGPVLLPRKHYLSTRSKLSKDPKEKRDHMVL
LEFVTAAGIKHGRKERYK

GFP-POS48
                                          (SEQ ID NO: 9)
MGHHHHHHGGRSKGKRLFRGKVPILVKLKGDVNGHKFSVRGKGKGD
ATRGKLTLKFICTTGKLPVPWPTLVTTLTYGVQCFSRYPKHMKRHD
FFKSAMPKGYVQERTISFKKDGKYKTRAEVKFKGRTLVNRIKLKGR
DFKEKGNILGHKLRYNFNSHKVYITADKRKNGIKAKFKIRHNVKDG
SVQLAKHYQQNTPIGRGPVLLPRKHYLSTRSKLSKDPKEKRDHMVL
LEFVTAAGIKHGRKERYK

GFP-POS49
                                         (SEQ ID NO: 10)
MGHHHHHHGGRSKGKRLFRGKVPILVKLKGDVNGHKFSVRGKGKGD
ATRGKLTLKFICTTGKLPVPWPTLVTTLTYGVQCFSRYPKHMKRHD
FFKSAMPKGYVQERTISFKKDGKYKTRAEVKFKGRTLVNRIKLKGR
DFKEKGNILGHKLRYNFNSHKVYITADKRKNGIKAKFKIRHNVKDG
SVQLAKHYQQNTPIGRGPVLLPRKHYLSTRSKLSKDPKEKRDHMVL
KEFVTAAGIKHGRKERYK
```

In order to promote the escape of the supercharged protein, or delivered agent, e.g., nucleic acid, from the endosomes, a supercharged protein may be fused to or associated with a protein, peptide, or other entity known to enhance endosome degradation or lysis of the endosome. In certain embodiments, the peptide is hemagglutinin 2 (HA2) peptide which is know to enhance endosome degradation. In certain particular embodiments, HA2 peptide is fused to supercharged GFP (e.g., +36 GFP). In certain particular embodiments, the fused protein is of the sequence:

```
+36 GFP-HA2
                                         (SEQ ID NO: 19)
MGHHHHHHGGASKGERLFRGKVPILVELKGDVNGHKFSVRGKGKGD

ATRGKLTLKFICTTGKLPVPWPTLVTTLTYGVQCFSRYPKHMKRHD

FFKSAMPKGYVQERTISFKKDGKYKTRAEVKFEGRTLVNRIKLKGR

DFKEKGNILGHKLRYNFNSHKVYITADKRKNGIKAKFKIRHNVKDG

SVQLADHYQQNTPIGRGPVLLPRNHYLSTRSKLSKDPKEKRDHMVL

LEFVTAAGIKHGRDERYKGSAGSAAGSGEFGLFGAIAGFIENGWEG

MIDG
```

In certain embodiments, the endosomolytic peptide is melittin peptide (GIGAVLKVLTTGLPALISWIKRKRQQ, SEQ ID NO: 20) (Meyer et al. *JACS* 130(11): 3272-3273, 2008; which is incorporated herein by reference). In certain embodiments, the melittin peptide is modified by one, two, three, four, or five amino acid substitutions, deletions, and/or additions. In certain embodiments, the melittin peptide is of the sequence: CIGAVLKVLTTGLPALISWIKRKRQQ (SEQ ID NO: 21). In certain particular embodiments, the melittin peptide is fused to supercharged GFP (e.g., +36 GFP).

In certain embodiments, the endosomolytic peptide is penetratin peptide (RQIKIWFQNRRMKWKK-amide, SEQ ID NO: 22), bovine PrP (1-30) peptide (MVKSKIGSWILVLF-VAMWSDVGLCKKRPKP-amide, SEQ ID NO: 23), MPGΔ$^{NLS}$ peptide (which lacks a functional nuclear localization sequence because of a K→S substitution) (GALFLG-WLGAAGSTMGAPKSKRKV, SEQ ID NO: 24), TP-10 peptide (AGYLLGKINLKALAALAKKIL-amide, SEQ ID NO: 25), and/or EB1 peptide (LIRLWSHLIHIWFQNRRLK-WKKK-amide, SEQ ID NO: 26) (Lundberg et al. 2007, *FASEB J.* 21:2664; incorporated herein by reference). In certain embodiments, the penetratin, PrP (1-30), MPG, TP-10, and/or EB1 peptide is modified by one, two, three, four, or five amino acid substitutions, deletions, and/or additions. In certain particular embodiments, the PrP (1-30), MPG, TP-10, and/or EB1 peptide is fused to supercharged GFP (e.g., +36 GFP).

Other peptides or proteins may also be fused to the supercharged protein. For example, a targeting peptide may be fused to the supercharged protein in order to selectively deliver the supercharged protein, or associated agent, e.g., nucleic acid, to a particular cell type. Peptides or proteins that enhance the transfection of the nucleic acid may also be used. In certain embodiments, the peptide fused to the supercharged protein is a peptide hormone. In certain embodiments, the peptide fused to the supercharged protein is a peptide ligand.

As would be appreciated by one of skill in the art, homologous proteins are also considered to be within the scope of this invention. For example, any protein that includes a stretch of about 20, about 30, about 40, about 50, or about 100 amino acids which are about 40%, about 50%, about 60%, about 70%, about 80%, about 90%, about 95%, or about 100% identical to any of the above sequences can be utilized in accordance with the invention. Alternatively or additionally, addition and deletion variants can be utilized in accordance with the invention. In certain embodiments, any GFP with a mutated residue as shown in any of the above sequences can be utilized in accordance with the invention. In certain embodiments, a protein sequence to be utilized in accordance with the invention includes 2, 3, 4, 5, 6, 7, 8, 9, 10, or more mutations as shown in any of the sequences above.

Other proteins that may be supercharged and used, e.g., in the delivery of agents, e.g., nucleic acids, include other GFP-style fluorescent proteins. In certain embodiments, the supercharged protein is a supercharged version of blue fluorescent protein. In certain embodiments, the supercharged protein is a supercharged version of cyan fluorescent protein. In certain embodiments, the supercharged protein is a supercharged version of yellow fluorescent protein. Exemplary fluorescent proteins include, but are not limited to, enhanced green fluorescent protein (EGFP), AcGFP, TurboGFP, Emerald, Azami Green, ZsGreen, EBFP, Sapphire, T-Sapphire, ECFP, mCFP, Cerulean, CyPet, AmCyan1, Midori-Ishi Cyan, mTFP1 (Teal), enhanced yellow fluorescent protein (EYFP), Topaz, Venus, mCitrine, YPet, PhiYFP, ZsYellow1, mBanana, Kusabira Orange, mOrange, dTomato, dTomato-Tandem, DsRed, DsRed2, DsRed-Express (T1), DsRed-Monomer, mTangerine, mStrawberry, AsRed2, mRFP1, JRed, mCherry, HcRed1, mRaspberry, HcRed1, HcRed-Tandem, mPlum, and AQ143.

Yet other proteins that may be supercharged and used, e.g., in the delivery of an agent, e.g., nucleic acids, include histone components or histone-like proteins. In certain embodiments, the histone component is histone linker H1. In certain embodiments, the histone component is core histone H2A. In certain embodiments, the histone component is core histone H2B. In certain embodiments, the histone component is core histone H3. In certain embodiments, the histone component is core histone H4. In certain embodiments, the protein is the archael histone-like protein, HPhA. In certain embodiments, the protein is the bacterial histone-like protein, TmHU.

Other proteins that may be supercharged and used, e.g., in the delivery of an agent, e.g., nucleic acids, include high-mobility-group proteins (HMGs). In certain embodiments, the protein is HMG1. In certain embodiments, the protein is HMG17. In certain embodiments, the protein is HMG1-2.

Other proteins that may be supercharged and used, e.g., in the delivery of an agent, e.g., nucleic acids, include anti-cancer agents, such as anti-apoptotic agents, cell cycle regulators, etc.

Other proteins that may be supercharged and used, e.g., in the delivery of an agent, e.g., nucleic acids, are enzymes, including, but not limited to, amylases, pectinases, hydrolases, proteases, glucose isomerase, lipases, phytases, etc. In some embodiments, proteins that may be supercharged and used, e.g., in the delivery of an agent, e.g., nucleic acids, are lysosomal enzymes, including, but not limited to, alglucerase, imiglucerase, agalsidase beta, α-1-iduronidase, acid α-glucosidase, iduronate-2-sulfatase, N-acetylgalactosamine-4-sulfatase, etc. (Wang et al., 2008, *NBT,* 26:901-08; incorporated herein by reference).

Other proteins that may be supercharged and used, e.g., in the delivery of an agent, e.g., nucleic acids, are presented in Table 1. Some of the proteins listed in Table 1 include a listing of residues that may be modified in order to supercharge those proteins. The identity of the residues was identified computationally by downloading a PDB file of the protein of interest. The residues of the pdb file were sorted by ascending avNapsa values, and the first 15 ASP, GLU, ASN or GLN residues were proposed for mutation to LYS.

PDB files, by convention, number amino acids by their order in the wild type protein. The PDB file, however, may not contain the full length wildtype protein. The input protein sequence is the sequence of the amino acids that are included in the PDB. The proposed mutations provide the number of the amino acid in the full length wildtype protein and also the number in the input protein sequence. The proposed mutations are provided in the following format: Wildtype residue_Chain:Residue Number in Wildtype Protein Chain (Residue Number in Input Chain)_Proposed Residue. Wildtype residue refers to the identity of the amino acid in the wild type protein. Chain refers to the designation of the peptide chain of the specified mutation. Residue number in wildtype protein refers to the number of the amino acid in the designated protein chain of the specified mutation in the full length wild type protein. Residue number in input chain refers to the number of the amino acid in the designated protein chain that was included in the analyzed PDB.

TABLE 1

Exemplary Proteins that can be Supercharged

| PROTEIN TYPE<br>Protein Subtype<br>Protein (PDB #) | Input Protein Sequence | 15 Possible Mutations to Generate Positively Supercharged Protein<br>Wildtype residue_Chain: Residue Number in Wildtype Protein Chain (Residue Number in InputChain)_Proposed Residue |
|---|---|---|
| MEMBRANE PROTEINS | | |
| Cystic fibrosis transmembrane conductance regulator(CFTR) (2bbs) | Chain A:<br>STTEVVMENVTAFWEEGFGELFE KAKGTPVLKDINFKIERGQLLAV AGSTGAGKTSLLMMIMGELEPSE GKIKHSGRISFCSQNSWIMPGTI KENIIGVSYDEYRYRSVIKACQL EEDISKFAEKDNIVLITLSGGQR ARISLARAVYKDADLYLLDSPFG YLDVLTEKEIFESCVCKLMANKT RILVTSKMEHLKKADKILILHEG SSYFYGTFSELQNLRPDFSSKLM SFDQFSAERRNSILTETLHRFSL (SEQ ID NO: 27) | ASP_A: 513(102)_LYS, GLU_A: 514(103)_LYS, GLU_A: 656(238)_LYS, GLU_A: 474(64)_LYS, GLU_A: 528(117)_LYS, GLU_A: 535(124)_LYS, ASN_A: 635(220)_LYS, ASN_A: 494(84)_LYS, ASP_A: 579(164)_LYS, ASP_A: 639(224)_LYS, GLN_A: 652(234)_LYS, GLU_A: 402(15)_LYS, ASP_A: 565(150)_LYS, GLU_A: 664(246)_LYS, GLU_A: 403(16)_LYS, |
| RECEPTORS | | |
| Cytokine Receptors | | |
| Type I | | |
| EPO receptor (1eer) | Chain B:<br>DPKFESKAALLAARGPEELLCFT ERLEDLVCFWEEAASAGVGPGQY SFSYQLEDEPWKLCRLHQAPTAR GAVRFWCSLPTADTSSFVPLELR VTAASGAPRYHRVIHINEVVLLD APVGLVARLADESGHVVLRWLPP PETPMTSHIRYEVDVSAGQGAGS VQRVEILEGRTECVLSNLRGRTR YTFAVRARMAEPSFGGFWSEWSE PVSL (SEQ ID NO: 28) | ASP_B: 8(1)_LYS, ASP_B: 133(126)_LYS, ASP_B: 61(54)_LYS, GLU_B: 134(127)_LYS, GLU_B: 147(140)_LYS, ASN_B: 185(178)_LYS, GLU_B: 12(5)_LYS, GLU_B: 62(55)_LYS, GLU_B: 24(17)_LYS, GLN_B: 164(157)_LYS, GLN_B: 170(163)_LYS, GLU_B: 60(53)_LYS, GLU_B: 25(18)_LYS, GLN_B: 52(45)_LYS, GLU_B: 173(166)_LYS |
| GM-CSF receptor | | |
| G-CSF receptor (2d9q) | Chain B:<br>CGHISVSAPIVHLGDPITASCII KQNCSHLDPEPQILWRLGAELQP GGRQQRLSDGTQESIITLPHLNH TQAFLSCSLNWGNSLQILDQVEL RAGYPPAIPHNLSCLMNLTTSSL ICQWEPGPETHLPTSFTLKSFKS RGNCQTQGDSILDCVPKDGQSHC SIPRKHLLLYQNMGIWVQAENAL GTSMSPQLCLDPMDVVKLEPPML RTMDPQAGCLQLSWEPWQPGLHI NQKCELRHKPQRGEASWALVGPL PLEALQYELCGLLPATAYTLQIR CIRWPLPGHWSDWSPSLELRTTE (SEQ ID NO: 29) | ASN_B: 84(82)_LYS, ASP_B: 57(55)_LYS, ASP_B: 213(211)_LYS, ASP_B: 158(156)_LYS, GLN_B: 222(213)_LYS, GLU_B: 253(244)_LYS, ASP_B: 149(147)_LYS, GLN_B: 234(225)_LYS, GLN_B: 160(158)_LYS, GLU_B: 270(261)_LYS, GLU_B: 45(43)_LYS, GLN_B: 145(143)_LYS, GLU_B: 308(299)_LYS, ASN_B: 28(26)_LYS, GLU_B: 93(91)_LYS |
| Growth hormone receptor(1axi) | Chain B:<br>EPKFTKCRSPERETFSCHWTDEG PIQLFYTRRNEWKECPDYVSAGE NSCYFNSSFTSIAIPYCIKLTSN GGTVDEKCFSVDEIVQPDPPIAL NWTLLNVSLTGIHADIQVRWEAP | ASN_B: 72(33)_LYS, GLN_B: 166(121)_LYS, GLU_B: 183(138)_LYS, ASP_B: 190(145)_LYS, GLU_B: 79(34)_LYS, GLU_B: 32(1)_LYS, ASP_B: 52(21)_LYS, GLU_B: 61(22)_LYS, ASN_B: 182(137)_LYS, ASN_B: 114(69)_LYS, |

TABLE 1-continued

Exemplary Proteins that can be Supercharged

| PROTEIN TYPE<br>Protein Subtype<br>Protein (PDB #) | Input Protein Sequence | 15 Possible Mutations to Generate<br>Positively Supercharged Protein<br>Wildtype residue_Chain: Residue Number in<br>Wildtype Protein Chain (Residue<br>Number in InputChain)_Proposed Residue |
|---|---|---|
| | RNADIQKGWMVLEYELQYKEVNE<br>TKWKMMDPILTTSVPVYSLKVDK<br>EYEVRVRSKQRNSGNYGEFSEVL<br>YVTLPQM<br>(SEQ ID NO: 30) | ASN_B: 218(173)_LYS, GLU_B: 91(46)_LYS,<br>ASN_B: 162(117)_LYS, ASN_B: 97(52)_LYS,<br>ASN_B: 143(98)_LYS |
| Type II | | |
| Interferon receptors | | |
| Immunoglobulin<br>superfamily receptors | | |
| IL-1 receptor | Chain B:<br>CKEREEKIILVSSANEIDVRPCP<br>LNPNEHKGTITWYKDDSKTPVST<br>EQASRIHQHKEKLWFVPAKVEDS<br>GHYYCVVRNSSYCLRIKISAKFV<br>ENEPNLCYNAQAIFKQKLPVAGD<br>GGLVCPYMEFFKNENNELPKLQW<br>YKDCKPLLLDNIHFSGVKDRLIV<br>MNVAEKHRGNYTCHASYTYLGKQ<br>YPITRVIEFITLEENKPTRPVIV<br>SPANETMEVDLGSQTQLICNVTG<br>QLSDIAYWKWNGSVIDEDDPYLG<br>EDYYSVENPANICRRSTLITVLN<br>ISEIESRFYKHPFTCFAKINITH<br>GIDAAYIQLIYPVT<br>(SE9 ID NO: 31) | ASN_B: 30(25)_LYS, ASN_B: 32(27)_LYS,<br>ASN_B: 102(97)_LYS, ASN_B: 135(130)_LYS,<br>ASP_B: 253(248)_LYS, ASP_B: 254(249)_LYS,<br>ASP_B: 153(148)_LYS, GLU_B: 252(247)_LYS,<br>GLU_B: 8(3)_LYS, ASP_B: 44(39)_LYS,<br>GLU_B: 72(67)_LYS, ASN_B: 136(131)_LYS,<br>GLU_B: 137(132)_LYS, ASN_B: 204(199)_LYS,<br>ASN_B: 269(264)_LYS |
| C-kit receptor | | |
| TNF receptor family | | |
| TNF alpha receptor<br>(CD120) (1ext) | Chain A:<br>(SEQ ID NO: 153)<br>SVCPQGKYIHPPQNNSICCTKCHKG<br>TYLYNDCPGPGQDTDCRECESGS<br>FTASENHLRHCLSCSKCRKEMGQ<br>VEISSCTVDRDTVCGCRICNQYRH<br>YWSENLFQCFNCSLCLNGTVHLS<br>CQEKQNTVCTCHAGFFLRENECV<br>SCSNCKKSLECTICLCLPQIEN<br>Chain B:<br>MDSVCPQGKYIHPQNNSICCTKC<br>HKGTYLYNDCPGPGQDTDCRECE<br>SGSFTASENHLRHCLSCSKCRKE<br>MGQVEISSCTVDRDTVCGCRKNQ<br>YRHYWSENLFQCFNCSLCLNGTV<br>HLSCQEKQNTVCTCHAGFFLREN<br>ECVSCSNCKKSLECTKLCLP<br>(SEQ ID NO: 32) | GLU_A: 171(159)_LYS, ASN_A: 172(160)_LYS,<br>GLN_B: 24(14)_LYS, GLN_B: 24(12)_LYS,<br>GLU_A: 109(97)_LYS, ASN_A: 25(13)_LYS,<br>GLN_A: 169(157)_LYS, ASN_A: 23(15)_LYS,<br>GLU_B: 109(99)_LYS, ASN_A: 110(98)_LYS,<br>GLN_B: 48(38)_LYS, GLN_A: 17(5)_LYS,<br>ASN_A: 26(14)_LYS, GLN_A: 48(36)_LYS,<br>GLN_B: 17(7)_LYS |
| Lymphotoxin β<br>receptor(1rf3) | Chain A:<br>NTGLLESQLSRHDQMLSVHDIRL<br>ADMDLRFQVLETASYNGVLIWKI<br>RDYICRRKQEAVMGKTLSLYSQP<br>FYTGYFGYKMCARVYLNGDGMGK<br>GTHLSLFFVIMRGEYDALLPWPF<br>KQKVTLMLMDQGSSRRHLGDAFK<br>PDPNSSSFKICPTGEMNIASGCP<br>VFVAQTYLENGTYIKDDTIFIKV<br>IVDTSDLPDP<br>(SEQ ID NO: 33) | ASN_A: 313(1)_LYS, ASP_A: 487(175)_LYS,<br>ASN_A: 453(141)_LYS, GLU_A: 463(151)_LYS,<br>ASP_A: 500(188)_LYS, GLU_A: 318(6)_LYS,<br>GLN_A: 320(8)_LYS, ASP_A: 325(12)_LYS,<br>GLU_A: 346(34)_LYS, GLU_A: 417(105)_LYS,<br>ASN_A: 481(169)_LYS, ASP_A: 503(191)_LYS,<br>GLN_A: 326(14)_LYS, ASP_A: 337(25)_LYS,<br>ASP_A: 339(27)_LYS |
| CD40L(1aly) | Chain A:<br>GDQNPQIAAHVISEASSKTTSVL<br>QWAEKGYYTMSNNLVTLENGKQL<br>TVKRQGLYYIYAQVITCSNREAS<br>SQAPPIASLCLKSPGRFERILLR<br>AANTHSSAICPCGQQSIHLGGVF | ASP_A: 117(2)_LYS, GLN_A: 118(3)_LYS,<br>ASN_A : 119(4)_LYS, ASN_A: 151(36)_LYS,<br>ASN_A: 157(42)_LYS, GLN_A: 166(51)_LYS,<br>GLN_A: 186(71)_LYS, GLU_A: 202(87)_LYS,<br>GLU_A: 230(115)_LYS, GLN_A: 121(6)_LYS, |

TABLE 1-continued

Exemplary Proteins that can be Supercharged

| PROTEIN TYPE<br>Protein Subtype<br>Protein (PDB #) | Input Protein Sequence | 15 Possible Mutations to Generate<br>Positively Supercharged Protein<br>Wildtype residue_Chain: Residue Number in<br>Wildtype Protein Chain (Residue<br>Number in InputChain)_Proposed Residue |
|---|---|---|
| | ELQPGASVFVNVIDPSQVSHGTG<br>FTSFGLLKL<br>(SEQ ID NO: 34) | ASN_A: 150(35)_LYS, GLU_A: 156(41)_LYS,<br>ASN_A: 210(95)_LYS, GLN_A: 220(105)_LYS,<br>GLU_A: 182(67)_LYS |
| Chemokine receptors | | |
| IL-8 receptor | | |
| CCR1 | | |
| CXCR4 | | |
| TGF beta receptors | | |
| TGF beta receptors 1,<br>2, 3 (1vjy) | Chain A:<br>IARTIVLQESIGKGRFGEVWRGK<br>WRGEEVAVKIFSSREERSWFREA<br>EIYQTVMLRHENILGFIAADNKD<br>NGTWTQLWLVSDYHEHGSLFDYL<br>NRYTVTVEGMIKLALSTASGLAH<br>LHMEIVGTQGKPAIAHRDLKSKN<br>ILVKKNGTCCIADLGLAVRHDSA<br>TDTIDIRVGTKRYMAPEVLDDSI<br>MKHFESFKRADIYAMGLVFWEIA<br>RRCSIGGIHEDYQLPYYDLVPSD<br>PSVEEMRKVVCEQKLRFNIPNRW<br>QSCEALRVMAKIMRECWYANGAA<br>RLTALRIKKTLSQLSQQEGIKM<br>(SEQ ID NO: 35) | ASN_A: 344(144)_LYS, ASN_A: 456(252)_LYS,<br>ASN_A: 270(70)_LYS, GLN_A: 324(124)_LYS,<br>GLN_A: 448(244)_LYS, GLU_A: 227(27)_LYS,<br>ASP_A: 366(166)_LYS, ASP_A: 430(226)_LYS,<br>ASP_A: 435(231)_LYS, GLN_A: 498(294)_LYS,<br>GLN_A: 208(8)_LYS, ASP_A: 269(69)_LYS,<br>GLU_A: 447(243)_LYS, ASN_A: 453(249)_LYS,<br>GLN_A: 494(290)_LYS |
| TRANSCRIPTION<br>FACTORS | | |
| p53 (2vuk) | Chain A:<br>SVPSQKTYQGSYGFRLGFLHSGT<br>AKSVTCTYSPALNKLFCQLAKTC<br>PVQLWVDSTPPPGTRVRAMAIYK<br>QSQHMTEVVRRCPHHERCSDSDG<br>LAPPQHLIRVEGNLRAEYLDDRN<br>TFRHSVVVPCEPPEVGSDCTTIH<br>YNYMCYSSCMGGMNRRPILTIIT<br>LEDSSGNLLGRDSFEVRVCACPG<br>RDRRTEEENLR<br>(SEQ ID NO: 36)<br>Chain B:<br>SSVPSQKTYQGSYGFRLGFLHSG<br>TAKSVTCTYSPALNKLFCQLAKT<br>CPVQLWVDSTPPPGTRVRAMAIY<br>KQSQHMTEVVRRCPHHERCSDSD<br>GLAPPQHLIRVEGNLRAEYLDDR<br>NTFRHSVVVPCEPPEVGSDCTTI<br>HYNYMCYSSCMGGMNRRPILTII<br>TLEDSSGNLLGRDSFEVRVCACP<br>GRDRRTEEENLR<br>(SEQ ID NO: 37) | ASN_A: 210(115)_LYS, ASN_A: 288(193)_LYS,<br>GLN_B: 167(73)_LYS, ASN_B: 210(116)_LYS,<br>ASN_B: 288(194)_LYS, GLU_B: 287(192)_LYS,<br>GLU_B: 287(193)_LYS, ASP_A: 208(113)_LYS,<br>GLU_A: 224(129)_LYS, ASP_B: 208(114)_LYS,<br>GLU_B: 224(130)_LYS, ASP_A: 148(53)_LYS,<br>ASP_A: 186(91)_LYS, ASP_B: 148(54)_LYS,<br>ASN_A: 131(36)_LYS |
| NF-kappaB(2o61) | Chain B:<br>MDGPYLQILEQPKQRGFRFRYVC<br>EGPSHGGLPGASSEKNKKSYPQV<br>KICNYVGPAKVIVQLVTNGKNIH<br>LHAHSLVGKHCEDGICTVTAGPK<br>DMVVGFANLGILHVTKKKVFETL<br>EARMTEACIRGYNPGLLVHPDLA<br>YLQAEGGGDRQLGDREKELIRQA<br>ALQQTKEMDLSVVRLMFTAFLPD<br>STGSFTRRLEPVVSDAIYDSKAP<br>NASNLKIVRMDRTAGCVTGGEEI<br>YLLCDKVQKDDIQIRFYEEEENG | ASP_B: 38(2)_LYS, ASN_B: 75(39)_LYS,<br>ASN_B: 288(252)_LYS, GLU_B: 287(251)_LYS,<br>ASP_B: 188(152)_LYS, GLU_B: 286(250)_LYS,<br>ASP_B: 318(282)_LYS, GLU_B: 60(24)_LYS,<br>GLU_B: 73(37)_LYS, GLN_B: 185(149)_LYS,<br>ASP_B: 220(184)_LYS, ASP_B: 336(300)_LYS,<br>ASP_B: 172(136)_LYS, ASP_B: 179(143)_LYS,<br>GLU_B: 192(156)_LYS |

TABLE 1-continued

Exemplary Proteins that can be Supercharged

| PROTEIN TYPE<br>Protein Subtype<br>Protein (PDB #) | Input Protein Sequence | 15 Possible Mutations to Generate Positively Supercharged Protein<br>Wildtype residue_Chain: Residue Number in Wildtype Protein Chain (Residue Number in InputChain)_Proposed Residue |
|---|---|---|
| | GVWEGFGDFSPTDVHRQFAIVFK<br>TPKYKDINITKPASVFVQLRRKS<br>DLETSEPKPFLYYPE<br>(SEQ ID NO: 38) | |
| Additional exemplary transcript. factors can be found in Table 2 | | |
| ENZYMES | | |
| Misc enzymes | | |
| Tissue plasminogen activator(1rtf) | Chain A:<br>TTCCGLRQY<br>(SEQ ID NO: 39)<br>Chain B:<br>IKGGLFADIASHPWQAAIFAKHH<br>RRGGERFLCGGILISSCWILSAA<br>HCFQQQQQEEEEERRRRRFFFFF<br>PPPPPPHHLTVILGRTYRVVPGE<br>EEQKFEVEKYIVHKEFDDDTYDN<br>DIALLQLKSSSSSDDDDDSSSSS<br>SSSSSRRRRRCAQESSVVRTVCL<br>PPADLQLPDWTECELSGYGKHEA<br>LSPFYSERLKEAHVRLYPSSRCT<br>TTSSSQQQHLLNRTVTDNMLCAG<br>DTTTRRRSSSNNNLHDACQGDSG<br>GPLVCLNDGRMTLVGIISWGLGC<br>GGQQKDVPGVYTKVTNYLDWIRD<br>NMRP<br>(SEQ ID NO: 40) | ASP_B: 110(102)_LYS, GLN_B: 60(47)_LYS,<br>GLU_B: 60(48)_LYS, ASP_B: 110(102)_LYS,<br>ASP_B: 204(204)_LYS, ASP_B: 97(88)_LYS,<br>ASP_B: 127(122)_LYS, ASN_B: 186(186)_LYS,<br>GLN_B: 60(47)_LYS, GLU_B: 60(48)_LYS,<br>ASN_B: 173(170)_LYS, ASP_B: 240(240)_LYS,<br>GLN_B: 60(47)_LYS, GLU_B: 60(48)_LYS,<br>GLU_B: 78(69)_LYS |
| Factor IX | Chain A:<br>VVGGEDAKPGQFPWQVVLNGKVD<br>AFCGGSIVNEKWIVTAAHCVEET<br>TGVKITVVAGEHNIEETEHTEQK<br>RNVIRIIPHHNYNNNAAAAAAIN<br>KYNHDIALLELDEPLVLNSYVTP<br>ICIADKEYTTTNNNIIIFLKFGS<br>GYVSGWGRVFHKGRSALVLQYLR<br>VPLVDRATCLRSTKFTIYNNMFC<br>AGGFFHEGGGRRDSCQGDSGGPH<br>VTEVEGTSFLTGIISWGEECAAM<br>KGKYGIYTKVSRYVNWIKEKTK<br>LT<br>(SEQ ID NO: 41)<br>Chain B:<br>MTCNIKNGRCEQFCKNSADNKVV<br>CSCTEGYRLAENQKSCEPAVPFP<br>CGRVSVSQTSK<br>(SEQ ID NO: 42) | ASN_A: 95(80)_LYS, ASP_B: 104(19)_LYS,<br>GLU_A: 60(44)_LYS, GLU_A: 204(194)_LYS,<br>GLU_A: 240(230)_LYS, GLU_B: 119(34)_LYS,<br>ASN_B: 120(35)_LYS, GLU_A: 74(59)_LYS,<br>GLU_A: 75(60)_LYS, ASN_A: 93(78)_LYS,<br>ASN_A: 97(84)_LYS, GLU_A: 127(114)_LYS,<br>GLU_A: 186(175)_LYS, ASN_B: 105(20)_LYS,<br>GLU_A: 60(44)_LYS |
| deoxyribonuclease I (rhDNase) | | |
| Enzyme Replacement | | |
| glucocerebrosidase | Chain A:<br>EFARPCIPKSFGYSSVVCVCNAT<br>YCDSFDPPALGTFSRYESTRSGR<br>RMELSMGPIQANHTGTGLLLTLQ<br>PEQKFQKVKGFGGAMTDAAALNI<br>LALSPPAQNLLLKSYFSEEGIGY<br>NIIRVPMASCDFSIRTYTYADTP<br>DDFQLHNFSLPEEDTKLKIPLIH<br>RALQLAQRPVSLLASPWTSPTWL<br>KTNGAVNGKGSLKGQPGDIYHQT<br>WARYFVKFLDAYAEHKLQFWAVT<br>AENEPSAGLLSGYPFQCLGFTPE<br>HQRDFIARDLGPTLANSTHHNVR<br>LLMLDDQRLLLPHWAKVVLTDPE<br>AAKYVHGIAVHWYLDFLAPAKAT | GLU_A: -1(1)_LYS, GLU_A: 72(71)_LYS,<br>GLN_A: 497(496)_LYS, ASP_A: 27(29)_LYS,<br>ASN_A: 59(58)_LYS, GLN_A: 73(72)_LYS,<br>GLN_A: 143(142)_LYS, GLU_A: 151(150)_LYS,<br>GLU_A: 222(221)_LYS, ASN_A: 270(269)_LYS,<br>GLN_A: 440(439)_LYS, ASP_A: 453(452)_LYS,<br>ASN_A: 333(332)_LYS, ASN_A: 275(274)_LYS,<br>ASN_A: 442(441)_LYS |

TABLE 1-continued

Exemplary Proteins that can be Supercharged

| PROTEIN TYPE<br>Protein Subtype<br>Protein (PDB #) | Input Protein Sequence | 15 Possible Mutations to Generate Positively Supercharged Protein<br>Wildtype residue_Chain: Residue Number in Wildtype Protein Chain (Residue Number in InputChain)_Proposed Residue |
|---|---|---|
| | LGETHRLFPNTMLFASEACVGSK<br>FWEQSVRLGSWDRGMQYSHSIIT<br>NLLYHVVGWTDWNLALNPEGGPN<br>WVRNFVDSPIIVDITKDTFYKQP<br>MFYHLGHFSKFIPEGSQRVGLVA<br>SQKNDLDAVALMHPDGSAVVVVL<br>NRSSKDVPLTIKDPAVGFLETIS<br>PGYSIHTYLWHRQ<br>(SEQ ID NO: 43) | |
| alpha galactosidase A | Chain A:<br>LDNGLARTPTMGWLHWERFMCNL<br>DCQEEPDSCISEKLFMEMAELMV<br>SEGWKDAGYEYLCIDDCWMAPQR<br>DSEGRLQADPQRFPHGIRQLANY<br>VHSKGLKLGIYADVGNKTCAGFP<br>GSFGYYDIDAQTFADWGVDLLKF<br>DGCYCDSLENLADGYKHMSLALN<br>RTGRSIVYSCEWPLYMWPFQKPN<br>YTEIRQYCNHWRNFADIDDSWKS<br>IKSILDWTSFNQERIVDVAGPGG<br>WNDPDMLVIGNFGLSWNQQVTQM<br>ALWAIMAAPLFMSNDLRHISPQA<br>KALLQDKDVIAINQDPLGKQGYQ<br>LRQGDNFEVWERPLSGLAWAVAM<br>INRQEIGGPRSYTIAVASLGKGV<br>ACNPACFITQLLPVKRKLGFYEW<br>TSRLRSHINPTGTVLLQLENTM<br>(SEQ ID NO: 44) | GLU_A: 103(72)_LYS, GLN_A: 57(26)_LYS,<br>GLU_A: 58(27)_LYS, GLU_A: 178(147)_LYS,<br>ASP_A: 101(70)_LYS, ASP_A: 175(144)_LYS,<br>GLN_A: 212(181)_LYS, GLN_A: 306(275)_LYS,<br>GLN_A: 333(302)_LYS, ASP_A: 335(304)_LYS,<br>GLU_A: 59(28)_LYS, GLN_A: 111(80)_LYS,<br>ASN_A: 215(184)_LYS, GLU_A: 251(220)_LYS,<br>GLU_A: 358(327)_LYS |
| arylsulfatase-A<br>(iduronidase, α-L-) | Chain A:<br>RPPNIVLIFADDLGYGDLGCYGH<br>PSSTTPNLDQLAAGGLRFTDFYV<br>PVSLPSRAALLTGRLPVRMGMYP<br>GVLVPSSRGGLPLEEVTVAEVLA<br>ARGYLTGMAGKWHLGVGPEGAFL<br>PPHQGFHRFLGIPYSHDQGPCQN<br>LTCFPPATPCDGGCDQGLVPIPL<br>LANLSVEAQPPWLPGLEARYMAF<br>AHDLMADAQRQDRPFFLYYASHH<br>THYPQFSGQSFAERSGRGPFGDS<br>LMELDAAVGTLMTAIGDLGLLEE<br>TLVIFTADNGPETMRMSRGGCSG<br>LLRCGKGTTYEGGVREPALAFWP<br>GHIAPGVTHELASSLDLLPTLAA<br>LAGAPLPNVTLDGFDLSPLLLGT<br>GKSPRQSLFFYPSYPDEVRGVFA<br>VRTGKYKAHFFTQGSAHSDTTAD<br>PACHASSSLTAHEPPLLYDLSKD<br>PGENYNLLGATPEVLQALKQLQL<br>LKAQLDAAVTFGPSQVARGEDPA<br>LQICCHPGCTPRPACCHCP<br>(SEQ ID NO: 45) | ASN_A: 350(331)_LYS, GLU_A: 103(84)_LYS,<br>GLU_A: 451(428)_LYS, GLN_A: 215(196)_LYS,<br>ASP_A: 216(197)_LYS, GLU_A: 424(405)_LYS,<br>ASP_A: 267(248)_LYS, GLU_A: 131(112)_LYS,<br>ASP_A: 411(392)_LYS, GLN_A: 454(431)_LYS,<br>GLN_A: 465(442)_LYS, GLN_A: 51(33)_LYS,<br>ASN_A: 158(139)_LYS, ASP_A: 207(188)_LYS,<br>GLN_A: 371(352)_LYS |
| arylsulfatase B(N-<br>acetylgalactos-amine-<br>4-sulfatase)(1fsu) | Chain A:<br>SRPPHLVFLLADDLGWNDVGFHG<br>SRIRTPHLDALAAGGVLLDNYYT<br>QPLTPSRSQLLTGRYQIRTGLQH<br>QIIWPCQPSCVPLDEKLLPQLLK<br>EAGYTTHMVGKWHLGMYRKECLP<br>TRRGFDTYFGYLLGSEDYYSHER<br>CTLIDALNVTRCALDFRDGEEVA<br>TGYKNMYSTNIFTKRAIALITNH<br>PPEKPLFLYLALQSVHEPLQVPE<br>EYLKPYDFIQDKNRHHYAGMVSL<br>MDEAVGNVTAALKSSGLWNNTVF<br>IFSTDNGGQTLAGGNNWPLRGRK<br>WSLWEGGVRGVGFVASPLLKQKG<br>VKNRELIHISDWLPTLVKLARGH<br>TNGTKPLDGFDVWKTISEGSPSP<br>RIELLHNIDPNFVDSSPCSAFNT<br>SVHAAIRHGNWKLLTGYPGCGYW | GLU_A: 229(187)_LYS, ASN_A: 188(146)_LYS,<br>GLU_A: 249(207)_LYS, GLU_A: 250(208)_LYS,<br>ASN_A: 366(324)_LYS, ASN_A: 456(397)_LYS,<br>ASN_A: 458(399)_LYS, ASP_A: 125(83)_LYS,<br>ASN_A: 225(183)_LYS, ASP_A: 256(214)_LYS,<br>GLU_A: 490(431)_LYS, GLU_A: 201(159)_LYS,<br>ASN_A: 208(166)_LYS, GLN_A: 259(217)_LYS,<br>ASN_A: 398(356)_LYS |

TABLE 1-continued

Exemplary Proteins that can be Supercharged

| PROTEIN TYPE<br>Protein Subtype<br>Protein (PDB #) | Input Protein Sequence | 15 Possible Mutations to Generate<br>Positively Supercharged Protein<br>Wildtype residue_Chain: Residue Number in<br>Wildtype Protein Chain (Residue<br>Number in InputChain)_Proposed Residue |
|---|---|---|
| | FPPPSQYNVSEIPSSDPPTKTLW<br>LFDIDRDPEERHDLSREYPHIVT<br>KLLSRLQFYHKHSVPVYFPAQDP<br>RCDPKATGVWGPWM<br>(SEQ ID NO: 46) | |
| galactosylcera-<br>midase | | |
| beta-galactosidase | | |
| beta-hexosaminidase<br>A (2gix) | Chain A:<br>LWPWPQNFQTSDQRYVLYPNNFQ<br>FQYDVSSAAQPGCSVLDEAFQRY<br>RDLLFGTLEKNVLVVSVVTPGCN<br>QLPTLESVENYTLTINDDQCLLL<br>SETVWGALRGLETFSQLVWKSAE<br>GTFFINKTEIEDFPRFPHRGLLL<br>DTSRHYLPLSSILDTLDVMAYNK<br>LNVFHWHLVDDPSFPYESFTFPE<br>LMRKGSYNPVTHIYTAQDVKEVI<br>EYARLRGIRVLAEFDTPGHTLSW<br>GPGIPGLLTPCYSGSEPSGTFGP<br>VNPSLNNTYEFMSTFFLEVSSVF<br>PDFYLHLGGDEVDFTCWKSNPEI<br>QDFMRKKGFGEDFKQLESFYIQT<br>LLDIVSSYGKGYVVWQEVFDNKV<br>KIQPDTIIQVWREDIPVNYMKEL<br>ELVTKAGFRALLSAPWYLNRISY<br>GPDWKDFYVVEPLAFEGTPEQKA<br>LVIGGEACMWGEYVDNTNLVPRL<br>WPRAGAVAERLWSNKLTSDLTFA<br>YERLSHFRCELLRRGVQAQPLNV<br>GFCEQEFEQ<br>(SEQ ID NO: 47) | GLN_A: 528(492)_LYS, GLU_A: 151(115)_LYS,<br>ASP_A: 123(87)_LYS, GLU_A: 523(487)_LYS,<br>GLU_A: 527(491)_LYS, GLU_A: 111(75)_LYS,<br>GLN_A: 237(201)_LYS, ASP_A: 34(12)_LYS,<br>ASN_A: 43(21)_LYS, ASN_A: 42(20)_LYS,<br>GLN_A: 106(70)_LYS, ASN_A: 295(259)_LYS,<br>GLU_A: 447(411)_LYS, ASP_A: 492(456)_LYS,<br>ASN_A: 518(482)_LYS |
| Hexosaminidase A<br>and B(2gjx) | Chain A:<br>LWPWPQNFQTSDQRYVLYPNNFQ<br>FQYDVSSAAQPGCSVLDEAFQRY<br>RDLLFGTLEKNVLVVSVVTPGCN<br>QLPTLESVENYTLTINDDQCLLL<br>SETVWGALRGLETFSQLVWKSAE<br>GTFFINKTEIEDFPRFPHRGLLL<br>DTSRHYLPLSSILDTLDVMAYNK<br>LNVFHWHLVDDPSFPYESFTFPE<br>LMRKGSYNPVTHIYTAQDVKEVI<br>EYARLRGIRVLAEFDTPGHTLSW<br>GPGIPGLLTPCYSGSEPSGTFGP<br>VNPSLNNTYEFMSTFFLEVSSVF<br>PDFYLHLGGDEVDFTCWKSNPEI<br>QDFMRKKGFGEDFKQLESFYIQT<br>LLDIVSSYGKGYVVWQEVFDNKV<br>KIQPDTIIQVWREDIPVNYMKEL<br>ELVTKAGFRALLSAPWYLNRISY<br>GPDWKDFYVVEPLAFEGTPEQKA<br>LVIGGEACMWGEYVDNTNLVPRL<br>WPRAGAVAERLWSNKLTSDLTFA<br>YERLSHFRCELLRRGVQAQPLNV<br>GFCEQEFEQ<br>(SEQ ID NO: 48)<br>Chain B:<br>PALWPLPLSVKMTPNLLHLAPEN<br>FYISHSPNSTAGPSCTLLEEAFR<br>RYHGYIFGTQVQQLLVSITLQSE<br>CDAFPNISSDESYTLLVKEPVAV<br>LKANRVWGALRGLETFSQLVYQD<br>SYGTFTINESTIIDSPRFSHRGI<br>LIDTSRHYLPVKIILKTLDAMAF<br>NKFNVLHWHIVDDQSFPYQSITF<br>PELSNKGSYSLSHVYTPNDVRMV<br>IEYARLRGIRVLPEFDTPGHTLS<br>WGKGQKDLLTPCYSDSFGPINPT | ASP_B: 317(245)_LYS, ASP_A: 123(87)_LYS,<br>ASP_B: 518(446)_LYS, ASP_C: 317(246)_LYS,<br>GLN_C: 475(404)_LYS, GLU_A: 111(75)_LYS,<br>GLN_B: 475(403)_LYS, ASP_C: 518(447)_LYS,<br>GLU_D: 111(75)_LYS, GLN_D: 528(492)_LYS,<br>ASP_A: 34(12)_LYS, GLN_A: 528(492)_LYS,<br>ASN_B: 327(255)_LYS, GLN_B: 373(301)_LYS,<br>ASP_B: 523(451)_LYS |

TABLE 1-continued

Exemplary Proteins that can be Supercharged

| PROTEIN TYPE<br>Protein Subtype<br>Protein (PDB #) | Input Protein Sequence | 15 Possible Mutations to Generate Positively Supercharged Protein<br>Wildtype residue_Chain: Residue Number in Wildtype Protein Chain (Residue Number in InputChain)_Proposed Residue |
|---|---|---|
| | LNTTYSFLTTFFKEISEVFPDQF<br>IHLGGDEVEFKCWESNPKIQDFM<br>RQKGFGTDFKKLESFYIQKVLDI<br>IATINKGSIVWQEVFDDKAKLAP<br>GTIVEVWKDSAYPEELSRVTASG<br>FPVILSAPWYLDLISYGQDWRKY<br>YKVEPLDFGGTQKQKLFIGGEA<br>CLWGEYVDATNLTPRLWPRASAV<br>GERLWSSKDVRDMDDAYDRLTRH<br>RCRMVERGIAAQPLYAGYCN<br>(SEQ ID NO: 49)<br>Chain C:<br>PALWPLPLSVKMTPNLLHLAPEN<br>FYISHSPNSTAGPSCTLLEEAFR<br>RYHGYIFGTQVQQLLVSITLQSE<br>CDAFPNISSDESYTLLVKEPVAV<br>LKANRVWGALRGLETFSQLVYQD<br>SYGTFTINESTIIDSPRFSHRGI<br>LIDTSRHYLPVKIILKTLDAMAF<br>NKFNVLHWHIVDDQSFPYQSITF<br>PELSNKGSYSLSHVYTPNDVRMV<br>IEYARLRGIRVLPEFDTPGHTLS<br>WGKGQKDLLTPCYSLDSFGPINP<br>TLNTTYSFLTTFFKEISEVFPDQ<br>FIHLGGDEVEFKCWESNPKIQDF<br>MRQKGFGTDFKKLESFYIQKVLD<br>IIATINKGSIVWQEVFDDKAKLA<br>PGTIVEVWKDSAYPEELSRVTAS<br>GFPVILSAPWYLDLISYGQDWRK<br>YYKVEPLDFGGTQKQKLFIGGE<br>ACLWGEYVDATNLTPRLWPRASA<br>VGERLWSSKDVRDMDDAYDRLTR<br>HRCRMVERGIAAQPLYAGYCN<br>(SEQ ID NO: 50)<br>Chain D:<br>LWPWPQNFQTSDQRYVLYPNNFQ<br>FQYDVSSAAQPGCSVLDEAFQRY<br>RDLLFGTLEKNVLVVSVVTPGCN<br>QLPTLESVENYTLTINDDQCLLL<br>SETVWGALRGLETFSQLVWKSAE<br>GTFFINKTEIEDFPRFPHRGLLL<br>DTSRHYLPLSSILDTLDVMAYNK<br>LNVFHWHLVDDPSFPYESFTFPE<br>LMRKGSYNPVTHIYTAQDVKEVI<br>EYARLRGIRVLAEFDTPGHTLSW<br>GPGIPGLLTPCYSGSEPSGTFGP<br>VNPSLNNTYEFMSTFFLEVSSVF<br>PDFYLHLGGDEVDFTCWKSNPEI<br>QDFMFGEDFKQLESFYIQTLLDI<br>VSSYGKGYVVWQEVFDNKVKIQP<br>DTIIQVWREDIPVNYMKELELVT<br>KAGFRALLSAPWYLNRISYGPDW<br>KDFYVVEPLAFEGTPEQKALVIG<br>GEACMWGEYVDNTNLVPRLWPRA<br>GAVAERLWSNKLTSDLTFAYERL<br>SHFRCELLRRGVQAQPLNVGFCE<br>QEFEQ<br>(SEQ ID NO: 51) | |
| SMPD1 gene product | | |
| NPC1 and NPC2 (transmembrane proteins) | | |

TABLE 1-continued

Exemplary Proteins that can be Supercharged

| PROTEIN TYPE<br>Protein Subtype<br>Protein (PDB #) | Input Protein Sequence | 15 Possible Mutations to Generate Positively Supercharged Protein<br>Wildtype residue_Chain: Residue Number in Wildtype Protein Chain (Residue Number in InputChain)_Proposed Residue |
|---|---|---|
| ASAH1 (N-acylsphingosine amidohydrolase (acid ceramidase) 1) | | |
| alpha-glucosidase | | |
| phenylalanine hydroxylase (PAH) (1j8u) | Chain A:<br>VPWFPRTIQELDRFANQILSYGA<br>ELDADHPGFKDPVYRARRKQFAD<br>IAYNYRHGQPIPRVEYMEEEKKT<br>WGTVFKTLKSLYKTHACYEYNHI<br>FPLLEKYCGFHEDNIPQLEDVSQ<br>FLQTCGFRLRPVAGLLSSRDFL<br>GGLAFRVFHCTQYIRHGSKPMYT<br>PEPDICHELLGHVPLFSDRSFAQ<br>FSQEIGLASLGAPDEYIEKLATI<br>YWFTVEFGLCKQGDSIKAYGAGL<br>LSSFGELQYCLSEKPKLLPLELE<br>KTAIQNYTVTEFQPLYYVAESFN<br>DAKEKVRNFAATIPRPFSVRYDP<br>YTQRIEVL<br>(SEQ ID NO: 52) | ASP_A: 338(221)_LYS, GLU_A: 360(243)_LYS,<br>ASN_A: 376(259)_LYS, GUT_A: 381(264)_LYS,<br>GLN_A: 172(55)_LYS, GLU_A: 316(199)_LYS,<br>ASN_A: 133(16)_LY S, ASP_A: 151(34)_LYS,<br>ASN_A: 167(50)_LYS, GLU_A: 178(61)_LYS,<br>ASP_A: 145(28)_LYS, GLU_A: 181(64)_LYS,<br>GLN_A: 134(17)_LYS, ASP_A: 143(26)_LYS,<br>GLU_A: 182(65)_LYS |
| Cathepsin A | Chain A:<br>APDQDEIQRLPGLAKQPSFRQYS<br>GYLKSSGSKHLHYWFVESQKDPE<br>NSPVVLWLNGGPGCSSLDGLLTE<br>HGPFLVQPDGVTLEYNPYSWNLI<br>ANVLYLESPAGVGFSYSDDKFYA<br>TNDTEVAQSNFEALQDFFRLFPE<br>YKNNKLFLTGESYAGIYIPTLAV<br>LVMQDPSMNLQGLAVGNGLSSYE<br>QNDNSLVYFAYYHGLLGNRLWSS<br>LQTHCCSQNKCNFYDNKDLECVT<br>NLQEVARIVGNSGLNIYNLYAPC<br>AGGVPSHFRYEKDTVVVQDLGNI<br>FTRLPLKRMWHQALLRSGDKVRM<br>DPPCTNTTAASTYLNNPYVRKAL<br>NIPEQLPQWDMCNFLVNLQYRRL<br>YRSMNSQYLKLLSSQKYQILLYN<br>GDVDMACNFMGDEWFVDSLNQKM<br>EVQRRPWLVKYGDSGEQIAGFVK<br>EFSHIAFLTIKGAGHMVPTDKPL<br>AAFTMFSRFLNKQPY<br>(SEQ ID NO: 53) | GLN_A: 215(215)_LYS, ASN_A: 216(216)_LYS,<br>GLN_A: 327(327)_LYS, ASP_A: 404(404)_LYS,<br>ASP_A: 3(3)_LYS, ASP_A: 111(111)_LYS,<br>GLN_A: 394(394)_LYS, GLN_A: 450(450)_LYS,<br>ASP_A: 110(110)_LYS, GLN_A: 165(165)_LYS,<br>ASP_A: 266(266)_LYS, GLN_A: 288(288)_LYS,<br>GLU_A: 326(326)_LYS, ASN_A: 388(388)_LYS,<br>ASN_A: 448(448)_LYS |
| STRUCTURAL PROTEINS | | |
| Collagen | | |
| Elastin | | |
| Actin (1lot) | Chain B:<br>DETTALVCDNGSGLVKAGFAGDD<br>APRAVFPSIVGRPRDSYVGDEAQ<br>SKRGILTLKYPIEGIITNWDDME<br>KIWHHTFYNELRVAPEEHPTLLT<br>EAPLNPKANREKMTQIMFETFNV<br>PAMYVAIQAVLSLYASGRTTGIV<br>LDSGDGVTHNVPIYEGYALPHAI<br>MRLDLAGRDLTDYLMKILTERGY<br>SFVTTAEREIVRDIKEKLCYVAL<br>DFENEMATAASSSSLEKSYELPD<br>GQVITIGNERFRCPETLFQPSFI<br>GMESAGIHETTYNSIMKCDIDIR<br>KDLYANNVMSGGTTMYPGIADRM<br>QKEITALAPSTMKIKIIAPPERK | ASP_B: 3(1)_LYS, GLU_B: 4(2)_LYS,<br>ASP_B: 244(230)_LYS, ASP_B: 51(38)_LYS,<br>ASP_B: 288(274)_LYS, GLN_B: 246(232)_LYS,<br>GLU_B: 167(153)_LYS, ASP_B: 286(272)_LYS,<br>GLN_B: 354(340)_LYS, ASP_B: 80(66)_LYS,<br>ASP_B: 222(208)_LYS, GLU_B: 224(210)_LYS,<br>GLU_B: 270(256)_LYS, GLU_B: 364(350)_LYS,<br>GLU_B: 195(181)_LYS |

TABLE 1-continued

Exemplary Proteins that can be Supercharged

| PROTEIN TYPE<br>Protein Subtype<br>Protein (PDB #) | Input Protein Sequence | 15 Possible Mutations to Generate Positively Supercharged Protein<br>Wildtype residue_Chain: Residue Number in Wildtype Protein Chain (Residue Number in InputChain)_Proposed Residue |
|---|---|---|
| | YSVWIGGSILASLSTFQQMWITK<br>QEYDEAGPSIVHRK<br>(SEQ ID NO: 54) | |
| Tubilin (3cb2) | Chain A:<br>PREIITLQLGQCGNQIGFEFWKQ<br>LCAEHGISPEAIVEEFATEGTDR<br>KDVFFYQADDEHYIPRAVLLDLE<br>PRVIHSILNSPYAKLYNPENIYL<br>SEHGGGAGNNWASGFSQGEKIHE<br>DIFDIIDREADGSDSLEGFVLCH<br>SIAGGTGSGLGSYLLERLNDRYP<br>KKLVQTYSVFPNQDEMSDVVVQP<br>YNSLLTLKRLTQNADCLVVLDNT<br>ALNRIATDRLHIQNPSFSQINQL<br>VSTIMSASTTTLRYPGYMNNDLI<br>GLIASLIPTPRLHFLMTGYTPLT<br>SVRKTTVLDVMRRLLQPKNVMVS<br>TGRDTNHCYIAILNIIQGEVDPT<br>QVHKSLQRIRERKLANFIPWGPA<br>SIQVALSRKSPYRVSGLMMANHT<br>SISSLFERTCRQYDKLRKREAFL<br>EQFRKEDMFKDNFDEMDTSREIV<br>QQLIDEYHAATRPDYISW<br>(SEQ ID NO: 55)<br>Chain B:<br>REIITLQLGQCGNQIGFEFWKQL<br>CAEHGISPEAIVEEFATEGTDRK<br>DVFFYQADDEHYIPRAVLLDLEP<br>RVIHSILNSPYAKLYNPENIYLS<br>EHGAGNNWASGFSQGEKIHEDIF<br>DIIDREADGSDSLEGFVLCHSIA<br>GGTGSGLGSYLLERLNDRYPKKL<br>VQTYSVFPNQDEMSDVVVQPYNS<br>LLTLKRLTQNADCLVVLDNTALN<br>RIATDRLHIQNPSFSQINQLVST<br>IMSASTTTLRYPGYMNNDLIGLI<br>ASLIPTPRLHFLMTGYTPLTKTT<br>VLDVMRRLLQPKNVMVSTTNHCY<br>IAILNIIQGEVDPTQVHKSLQRI<br>RERLANFIPWGPASIQVALSRKS<br>PYLPRVSGLMMANHTSISSLFER<br>TCRQYDKLRKREAFLEQFRKEDM<br>FKDNFDEMDTSREIVQQLIDEYH<br>AATRPDYISW<br>(SEQ ID NO: 56) | ASP_A: 310(303)_LYS, GLU_A: 43(42)_LYS,<br>ASP_A: 56(55)_LYS, ASP_A: 57(56)_LYS,<br>GLU_A: 39(38)_LYS, GLU_A: 177(176)_LYS,<br>ASP_A: 180(179)_LYS, GLU_B: 95(93)_LYS,<br>ASP_B: 57(55)_LYS, ASP_B: 130(126)_LYS,<br>ASP_B: 176(172)_LYS, ASN_A: 79(78)_LYS,<br>ASP_A: 127(126)_LYS, ASP_A: 130(129)_LYS,<br>ASP_A: 216(215)_LYS |
| Keratin | | |
| Myosin (2fxo) | Chain A:<br>GSSPLLKSAEREKEMASMKEEFT<br>RLKEALEKSEARRKELEEKMVSL<br>LQEKNDLQLQVQAEQDNLADAEE<br>RCDQLIKNKIQLEAKVKEMNKRL<br>EDEEEMNAELTAKKRKLEDECSE<br>LKRDIDDLELTLAK<br>(SEQ ID NO: 57)<br>Chain B:<br>SPLLKSAEREKEMASMKEEFTRL<br>KEALEKSEARRKELEEKMVSLLQ<br>EKNDLQLQVQAEQDNLADAEERC<br>DQLIKNKIQLEAKVKEMNKRLED<br>EEEMNAELTAKKRKLEDECSELK<br>RDIDDLELTL<br>(SEQ ID NO: 58)<br>Chain C:<br>SSPLLKSAEREKEMASMKEEFTR<br>LKEALEKSEARRKELEEKMVSLL<br>QEKNDLQLQVQAEQDNLADAEER<br>CDQLIKNKIQLEAKVKEMNKRLE<br>DEEEMNAELTAKKRKLEDECSEL<br>KRDIDDLELTLA | GLU_A: 844(10)_LYS, GLU_A: 854(20)_LYS,<br>GLU_B: 854(18)_LYS, GLN_B: 882(46)_LYS,<br>ASP_B: 956(120)_LYS, GLN_D: 882(46)_LYS,<br>GLU_A: 848(14)_LYS, GLU_A: 875(41)_LYS,<br>GLN_A: 882(48)_LYS, GLN_B: 914(80)_LYS,<br>GLU_A: 921(87)_LYS, ASP_A: 956(122)_LYS,<br>GLU_B: 848(12)_LYS, GLU_B: 864(28)_LYS,<br>GLU_B: 875(39)_LYS |

TABLE 1-continued

Exemplary Proteins that can be Supercharged

| PROTEIN TYPE<br>Protein Subtype<br>Protein (PDB #) | Input Protein Sequence | 15 Possible Mutations to Generate Positively Supercharged Protein<br>Wildtype residue_Chain: Residue Number in Wildtype Protein Chain (Residue Number in InputChain)_Proposed Residue |
|---|---|---|
| | (SEQ ID NO: 59)<br>Chain D:<br>SPLLKSAEREKEMASMKEEFTRL<br>KEALEKSEARRKELEEKMVSLLQ<br>EKNDLQLQVQAEQDNLADAEERC<br>DQLIKNKIQLEAKVKEMNKRLED<br>EEEMNAELTAKKRKLEDECSELK<br>RDIDDLELTLAK<br>(SEQ ID NO: 60) | |
| EXTRACELLUL. PROTEINS | | |
| Cytokines | | |
| Colony Stimulating Factors | | |
| G-CSF | Chain A:<br>LPQSFLLKCLEQVRKIQGDGAAL<br>QEKLCATYKLCHPEELVLLGHSL<br>GIPWAPLLAGCLSQLHSGLFLYQ<br>GLLQALEGISPELGPTLDTLQLD<br>VADFATTIWQQMEELGMMPAFAS<br>AFQRRAGGVLVASHLQSFLEVSY<br>RVLRHLA<br>(SEQ ID NO: 61) | GLU_A: 123(106)_LYS, GLU_A: 122(105)_LYS,<br>GLN_A: 11(3)_LYS, GLU_A: 45(37)_LYS,<br>GLU_A: 46(38)_LYS, GLU_A: 98(81)_LYS,<br>GLU_A: 19(11)_LYS, GLN_A: 119(102)_LYS,<br>ASP_A: 112(95)_LYS, GLN_A: 77(60)_LYS,<br>GLU_A: 33(25)_LYS, GLN_A: 90(73)_LYS,<br>GLU_A: 93(76)_LYS, ASP_A: 104(87)_LYS.<br>GLU_A: 162(135)_LYS |
| GM-CSF | Chain B:<br>EHVNAIQEARRLLNLSRDTAAEM<br>NETVEVISEMFDLQEPTCLQTRL<br>ELYKQGLRGSLTKLKGPLTMMAS<br>HYKQHCPPTPETSCATQIITFES<br>FKENLKDFLLVIP<br>(SEQ ID NO: 62) | GLN_B: 50(37)_LYS, GLU_B: 14(1)_LYS,<br>GLU_B: 51(38)_LYS, GLN_B: 86(73)_LYS,<br>ASN_B: 27(14)_LYS, ASP_B: 48(35)_LYS,<br>ASN_B: 17(4)_LYS, ASP_B: 31(18)_LYS,<br>GLU_B: 93(80)_LYS, GLN_B: 99(86)_LYS,<br>GLU_B: 21(8)_LYS, ASN_B: 37(24)_LYS,<br>GLU_B: 45(32)_LYS, GLN_B: 64(51)_LYS,<br>GLU_B: 108(95)_LYS |
| Interferons<br>Interferon alfa-2 | Chain B:<br>CDLPQTHSLGSRRTLMLLAQMRK<br>ISLFSCLKDRHDFGFPQEEFGNQ<br>FQKAETIPVLHEMIQQIFNLFST<br>KDSSAAWDETLLDKFYTELYQQL<br>NDLEACVIQGVGVTETPLMKEDS<br>ILAVRKYFQRITLYLKEKKYSPC<br>AWEVVRAEIMRSFSLSTNLQESL<br>RSKE<br>(SEQ ID NO: 63) | LU_B: 165(165)_LYS, GLN_B: 5(5)_LYS,<br>GLU_B: 107(107)_LYS, GLN_B: 46(46)_LYS,<br>GLN_B: 101(101)_LYS, ASN_B: 45(45)_LYS,<br>ASN_B: 65(65)_LYS, GLU_B: 132(132)_LYS,<br>GLU_B: 159(159)_LYS, GLU_B: 41(41)_LYS,<br>ASP_B: 82(82)_LYS, ASP_B: 2(2)_LYS,<br>GLN_B: 20(20)_LYS, ASP_B: 35(35)_LYS,<br>ASP_B: 71(71)_LYS |
| Interferon beta-1 | Chain A:<br>MSYNLLGFLQRSSNFQCQKLLWQ<br>LNGRLEYCLKDRMNFDIPEEIKQ<br>LQQFQKEDAALTIYEMLQNIFAI<br>FRQDSSSTGWNETIVENLLANVY<br>HQINHLKTVLEEKLEKEDFTRGK<br>LMSSLHLKRYYGRILHYLKAKEY<br>SHCAWTIVRVEILRNFYFINRLT<br>GYLRN<br>(SEQ ID NO: 64) | ASP_A: 110(110)_LYS, GLU_A: 29(29)_LYS,<br>ASN_A: 37(37)_LYS, GLU_A: 42(42)_LYS,<br>GLU_A: 109(109)_LYS, GLU_A: 46(46)_LYS,<br>GLN_A: 48(48)_LYS, GLN_A: 49(49)_LYS,<br>GLU_A: 103(103)_LYS, GLU_A: 107(107)_LYS,<br>ASP_A: 39(39)_LYS, GLN_A: 51(51)_LYS,<br>GLU_A: 104(104)_LYS, ASN_A: 166(166)_LYS,<br>GLN_A: 23(23)_LYS |
| Interferon gamma-1b | Chain A:<br>MQDPYVKEAENLKKYFNAGHSDV<br>ADNGTLFLGILKNWKEESDRKIM<br>QSQIVSFYFKLFKNFKDDQSIQK<br>SVETIKEDMNVKFFNSNKKKRDD<br>FEKLTNYSVTDLNVQRKAIDELI<br>QVMAELGANVSGEFVKEAENLKK<br>YFNDNGTLFLGILKNWKEESDRK<br>IMQSQIVSFYFKLFKNFKDDQSI | ASN_A: 225(143)_LYS, ASP_A: 224(142)_LYS,<br>GLN_A: 1(2)_LYS, ASP_A: 2(3)_LYS,<br>GLN_A: 64(65)_LYS, GLU_A: 238(156)_LYS,<br>GLN_A: 264(182)_LYS, ASP_A: 24(25)_LYS,<br>ASN_A: 25(26)_LYS, ASP_A: 102(103)_LYS,<br>ASN_A: 297(215)_LYS, ASP_A: 302(220)_LYS,<br>GLU_A: 38(39)_LYS, ASN_A: 59(60)_LYS,<br>ASP_A: 63(64)_LYS |

TABLE 1-continued

Exemplary Proteins that can be Supercharged

| PROTEIN TYPE<br>Protein Subtype<br>Protein (PDB #) | Input Protein Sequence | 15 Possible Mutations to Generate Positively Supercharged Protein<br>Wildtype residue_Chain: Residue Number in Wildtype Protein Chain (Residue Number in InputChain)_Proposed Residue |
|---|---|---|
| | QKSVETIKEDMNVKFFNSNKKKR<br>DDFEKLTNYSVTDLNVQRKAIHE<br>LIQVMAELSPAA<br>(SEQ ID NO: 65) | |
| Interleukins | | |
| IL-2 (1M47) | Chain A:<br>STKKTQLQLEHLLLDLQMILNGI<br>NNYKNPKLTRMLTFKFYMPKKAT<br>ELKHLQCLEEELKPLEEVLNLAQ<br>NFHLRPRDLISNINVIVLELKGF<br>MCEYADETATIVEFLNRWITFCQ<br>SIISTLT<br>(SEQ ID NO: 66) | ASN_A: 77(70)_LYS, ASN_A: 33(28)_LYS, ASP_A: 109(98)_LYS, GLN_A: 74(69)_LYS, ASP_A: 84(77)_LYS, GLU_A: 95(88)_LYS, GLU_A: 110(99)_LYS, ASN_A: 26(21)_LYS, ASN_A: 29(24)_LYS, ASN_A: 30(25)_LYS, GLU_A: 52(47)_LYS, GLU_A: 68(63)_LYS, ASN_A: 71(66)_LYS, GLU_A: 61(56)_LYS, GLU_A: 62(57)_LYS |
| IL-1 receptor antagonist (1irb) | Chain A:<br>ALWQFNGMIKCKIPSSEPLLDFN<br>NYGCYCGLGGSGTPVDDLDRCCQ<br>THDNCYKQAKKLDSCKVLVDNPY<br>TNNYSYSCSNNEITCSSENNACE<br>AFICNCDRNAAICFSKVPYNKEH<br>KNLDAANC<br>(SEQ ID NO: 67) | ASN_A: 79(79)_LYS, GLU_A: 114(114)_LYS, ASP_A: 59(59)_LYS, GLU_A: 87(87)_LYS, ASP_A: 21(21)_LYS, ASN_A: 50(50)_LYS, ASP_A: 66(66)_LYS, GLU_A: 81(81)_LYS, ASP_A: 119(119)_LYS, ASN_A: 122(122)_LYS, ASN_A: 80(80)_LYS, ASN_A: 89(89)_LYS, ASN_A: 112(112)_LYS, GLU_A: 17(17)_LYS, GLN_A: 54(54)_LYS |
| IL-1 (2nvh) | Chain A:<br>APVRSLNCTLRDSQQKSLVMSGP<br>YELKALHLQGQDMEQQVVFSMSF<br>VQGEESNDKIPVALGLKEKNLYL<br>SCVLKDDKPTLQLESVDPKNYPK<br>KKMEKRFVFNKIEINNKLEFESA<br>QFPNWYISTSQAENMPVFLGGTK<br>GGQDITDFTMQFVS<br>(SEQ ID NO: 68) | GLN_A: 34(34)_LYS, ASN_A: 53(53)_LYS, ASP_A: 75(75)_LYS, ASP_A: 76(76)_LYS, ASN_A: 107(107)_LYS, ASN_A: 89(89)_LYS, ASN_A: 108(108)_LYS, ASP_A: 35(35)_LYS, ASP_A: 86(86)_LYS, GLU_A: 50(50)_LYS, GLN_A: 141(141)_LYS, GLN_A: 32(32)_LYS, GLU_A: 37(37)_LYS, ASP_A: 54(54)_LYS, GLU_A: 64(64)_LYS |
| Ciliary neurotrophic factor (CNTF) (1cnt) | Chain 1:<br>PHRRDLCSRSIWLARKIRSDLTA<br>LTESYVKHQGLWSELTEAERLQE<br>NLQAYRTFHVLLARLLEDQQVHF<br>TPTEGDFHQAIHTLLLQVAAFAY<br>QIEELMILLEYKIPRNEADGMLF<br>EKKLWGLKVLQELSQWTVRSIHD<br>LRFISSHQTGIP<br>(SEQ ID NO: 69)<br>Chain 4:<br>HRRDLCSRSIWLARKIRSDLTAL<br>TESYVKHQGLELTEAERLQENLQ<br>AYRTFHVLLARLLEDQQEGDFHQ<br>AIHTLLLQVAAFAYQIEELMILL<br>EYKIPRNKKLWGLKVLQELSQWT<br>VRSIHDLRFIS<br>(SEQ ID NO: 70) | GLU_4: 66(34)_LYS, GLU_1: 66(37)_LYS, GLU_1: 153(116)_LYS, ASN_4: 137(99)_LYS, ASP_1: 104(75)_LYS, GLU_1: 131(102)_LYS, GLU_1: 138(109)_LYS, GLU_4: 71(39)_LYS, ASP_1: 140(111)_LYS, GLU_1: 164(127)_LYS, GLN_1: 167(130)_LYS, GLU_4: 131(93)_LYS, ASP_1: 15(5)_LYS, GLU_1: 36(26)_LYS, ASN_1: 137(108)_LYS |
| TNFs | | |
| TNF-alpha (4tsv) | Chain A:<br>DKPVAHVVANPQAEGQLQWSNRR<br>ANALLANGVELRDNQLVVPIEGL<br>FLIYSQVLFKGQGCPSTHVLLTH<br>TISRIAVSYQTKVNLLSAIKSPC<br>QRETPEGAEAKPWYEPIYLGGVF<br>QLEKGDRLSAEINRPDYLDFAES<br>GQVYFGIIAL<br>(SEQ ID NO: 71) | ASP_A: 10(1)_LYS, GLU_A: 107(98)_LYS, GLN_A: 21(12)_LYS, GLN_A: 102(93)_LYS, GLU_A: 146(137)_LYS, ASN_A: 34(25)_LYS, GLU_A: 23(14)_LYS, ASP_A: 45(36)_LYS, GLN_A: 88(79)_LYS, GLN_A: 125(116)_LYS, ASN_A: 39(30)_LYS, GLN_A: 67(58)_LYS, GLU_A: 110(101)_LYS, GLU_A: 53(44)_LYS, ASN_A: 92(83)_LYS |
| TNF-beta (lymphotoxin) (1tnr) | Chain A:<br>KPAAHLIGDPSKQNSLLWRANTD<br>RAFLQDGFSLSNNSLLVPTSGIY<br>FVYSQVVFSGKAYSPKATSSPLY<br>LAHEVQLFSSQYPFHVPLLSSQK<br>MVYPGLQEPWLHSMYHGAAFQLT | GLN_A: 107(80)_LYS, ASP_A: 50(23)_LYS, ASN_A: 62(35)_LYS, GLU_A: 127(100)_LYS, GLN_A: 140(113)_LYS, ASN_A: 41(14)_LYS, ASP_A: 56(29)_LYS, ASN_A: 48(21)_LYS, GLN_A: 55(28)_LYS, GLN_A: 118(91)_LYS, |

TABLE 1-continued

Exemplary Proteins that can be Supercharged

| PROTEIN TYPE<br>Protein Subtype<br>Protein (PDB #) | Input Protein Sequence | 15 Possible Mutations to Generate Positively Supercharged Protein<br>Wildtype residue_Chain: Residue Number in Wildtype Protein Chain (Residue Number in InputChain)_Proposed Residue |
|---|---|---|
| | QGDQLSTHTDGIPHLVLSPSTVF<br>FGAFAL<br>(SEQ ID NO: 72) | GLN_A: 40(13)_LYS, GLN_A: 143(116)_LYS,<br>GLN_A: 126(99)_LYS, ASP_A: 152(125)_LYS,<br>ASN_A: 63(36)_LYS |
| Peptide Hormones | | |
| Erythropoietin | Chain A:<br>APPRLICDSRVLERYLLEAKEAE<br>KITTGCAEHCSLNEKITVPDTKV<br>NFYAWKRMEVGQQAVEVWQGLAL<br>LSEAVLRGQALLVKSSQPWEPLQ<br>LHVDKAVSGLRSLTTLLRALGAQ<br>KEAISNSDAASAAPLRTITADTF<br>RKLFRVYSNFLRGKLKLYTGEAC<br>RTGDR<br>(SEQ ID NO: 73) | ASP_A: 165(165)_LYS, GLU_A: 89(89)_LYS,<br>GLU_A: 31(31)_LYS, ASP_A: 123(123)_LYS,<br>ASN_A: 47(47)_LYS, GLU_A: 55(55)_LYS,<br>GLN_A: 86(86)_LYS, ASN_A: 36(36)_LYS,<br>GLU_A: 37(37)_LYS, GLU_A: 159(159)_LYS,<br>ASP_A: 8(8)_LYS, GLN_A: 92(92)_LYS,<br>ASP_A: 96(96)_LYS, GLU_A: 13(13)_LYS,<br>GLU_A: 21(21)_LYS |
| Insulin | Chain A:<br>GIVEQCCTSICSLYQLENYCN<br>(SEQ ID NO: 74)<br>Chain B:<br>FVNQHLCGSHLVEALYLVCGERG<br>FFYTPK<br>(SEQ ID NO: 75) | ASN_B: 3(3)_LYS, GLU_B: 13(13)_LYS,<br>GLU_B: 21(21)_LYS, GLU_A: 4(4)_LYS,<br>GLN_A: 5(5)_LYS, ASN_A: 21(21)_LYS,<br>GLN_A: 15(15)_LYS, ASN_A: 18(18)_LYS,<br>GLN_B: 4(4)_LYS, GLU_A: 17(17)_LYS |
| Growth hormone<br>(GH) (Somatotropin)<br>(1huw) | Chain A:<br>FPTIPLSRLADNAWLRADRLNQL<br>AFDTYQEFEEAYIPKEQIHSFWW<br>NPQTSLCPSESIPTPSNKEETQQ<br>KSNLELLRISLLLIQSWLEPVQF<br>LRSVFANSLVYGASDSNVYDLLK<br>DLEEGIQTLMGRLEALLKNYGLL<br>YCFNKDMSKVSTYLRTVQCRSVE<br>GSCGF<br>(SEQ ID NO: 76) | GLU_A: 129(129)_LYS, GLU_A: 39(39)_LYS,<br>ASN_A: 47(47)_LYS, ASN_A: 63(63)_LYS,<br>GLU_A: 65(65)_LYS, GLU_A: 66(66)_LYS,<br>GLU_A: 88(88)_LYS, GLN_A: 40(40)_LYS,<br>GLN_A: 69(69)_LYS, ASP_A: 107(107)_LYS,<br>ASP_A: 112(112)_LYS, GLU_A: 33(33)_LYS,<br>GLN_A: 91(91)_LYS, ASN_A: 99(99)_LYS,<br>ASP_A: 116(116)_LYS |
| Follicle-stimulating<br>hormone (FSH) | Chain C:<br>CHHRICHCSNRVFLCQESKVTEI<br>PSDLPRNAIELRFVLTKLRVIQK<br>GAFSGFGDLEKIEISQNDVLEVI<br>EADVFSNLPKLHEIRIEKANNLL<br>YINPEAFQNLPNLQYLLISNTGI<br>KHLPDVHKIHSLQKVLLDIQDNI<br>NIHTIERNSFVGLSFESVILWLN<br>KNGIQEIHNCAFNGTQLDELNLS<br>DNNNLEELPNDVFHGASGPVILD<br>ISRTRIHSLPSYGLENLKKLRAR<br>STYNLKKLPTLE<br>(SEQ ID NO: 77) | ASP_C: 43(26)_LYS, ASN_C: 27(10)_LYS,<br>ASN_C: 47(30)_LYS, ASN_C: 112(95)_LYS,<br>ASN_C: 251(234)_LYS, GLU_C: 259(242)_LYS,<br>GLU_C: 34(17)_LYS, GLU_C: 239(222)_LYS,<br>ASN_C: 240(223)_LYS, GLU_C: 39(22)_LYS,<br>ASP_C: 71(54)_LYS, ASN_C: 205(188)_LYS,<br>GLU_C: 207(190)_LYS, ASN_C: 211(194)_LYS,<br>GLU_C: 76(59)_LYS |
| Gonadotropin-<br>releasing hormone<br>(GnRH) | | |
| Thyrotropin-releasing<br>hormone(TRH) | | |
| somatostatin(growth-<br>hormone-inhibiting<br>hormone | | |
| Leptin(1ax8) | Chain A:<br>IQKVQDDTKTLIKTIVTRINDIL<br>DFIPGLHPILTLSKMDQTLAVYQ<br>QILTSMPSRNVIQISNDLENLRD<br>LLHVLAFSKSCHLPEASGLETLD | GLN_A: 4(2)_LYS, ASP_A: 23(21)_LYS,<br>ASP_A: 40(24)_LYS, GLU_A: 105(89)_LYS,<br>ASP_A: 108(92)_LYS, GLU_A: 100(84)_LYS,<br>ASP_A: 8(6)_LYS, ASN_A: 22(20)_LYS, |

TABLE 1-continued

Exemplary Proteins that can be Supercharged

| PROTEIN TYPE<br>Protein Subtype<br>Protein (PDB #) | Input Protein Sequence | 15 Possible Mutations to Generate Positively Supercharged Protein<br>Wildtype residue_Chain: Residue Number in Wildtype Protein Chain (Residue Number in InputChain)_Proposed Residue |
|---|---|---|
| | SLGGVLEASGYSTEVVALSRLQG<br>SLQDMLWQLDLSPGC<br>(SEQ ID NO: 78) | ASP_A: 141(125)_LYS, ASN_A: 78(62)_LYS,<br>ASP_A: 9(7)_LYS, GLN_A: 73(59)_LYS,<br>ASP_A: 85(69)_LYS, ASN_A: 72(56)_LYS,<br>GLU_A: 81(65)_LYS |
| Growth-hormone-releasing hormone (GHRH) | | |
| Insulin-like growth factor (or somatomedin) (1wqi) | Chain 1:<br>PETLCGAELVDALQFVCGDRGFY<br>FNKPTGYGSSSRRAPQTGIVDEC<br>CFRSCDLRRLEMYCAP<br>(SEQ ID NO: 79) | GLU_I: 3(2)_LYS, ASP_I: 20(19)_LYS,<br>GLU_I: 9(8)_LYS, ASP_I: 12(11)_LYS,<br>ASN_I: 26(25)_LYS, GLN_I: 40(39)_LYS,<br>ASP_I: 153(52)_LYS, ASP_I: 45(44)_LYS,<br>GLU_I: 58(57)_LYS, GLN_I: 15(14)_LYS,<br>GLU_I: 46(45)_LYS |
| Antimullerian hormone (or mullerian inhibiting factor or hormone) | | |
| Adiponectin (1c28) | Chain A:<br>MYRSAFSVGLETRVTVPNVPIRF<br>TKIFYNQQNHYDGSTGKFYCNIP<br>GLYYFSYHITVYMKDVKVSLFKK<br>DKAVLFTYDYQENVDQASGSVL<br>LHLEVGDQVWLQVYYADNVNDST<br>FTGFLLYHDT<br>(SEQ ID NO: 80)<br>Chain B:<br>MYRSAFSVGLPNVPIRFTKIFYN<br>QQNHYDGSTGKFYCNIPGLYYFS<br>YHITVYMKDVKVSLFKKDKVLFT<br>YDQYQEKVDQASGSVLLHLEVGD<br>QVWLQVYDSTFTGFLLYHD<br>(SEQ ID NO: 81)<br>Chain C:<br>MYRSAFSVGLETRVTVPIRFTKI<br>FYNQQNHYDGSTGKFYCNIPGLY<br>YFSYHITVDVKVSLFKKDKAVLF<br>TQASGSVLLHLEVGDQVWLQNDS<br>TFTGFLLYHD<br>(SEQ ID NO: 82) | ASP_C: 173(55)_LYS, GLN_B: 191(72)_LYS,<br>GLU_A: 194(82)_LYS, ASP_A: 182(70)_LYS,<br>GLN_B: 193(74)_LYS, GLN_A: 143(31)_LYS,<br>ASN_B: 130(12)_LYS, GLN_B: 143(25)_LYS,<br>ASP_B: 182(64)_LYS, ASP_B: 190(71)_LYS,<br>GLN_C: 143(28)_LYS, ASP_C: 182(64)_LYS,<br>ASP_B: 173(55)_LYS, ASP_B: 245(111)_LYS,<br>ASN_A: I44(32)_LYS |
| Adrenocorticotropic hormone (or corticotropin) | | |
| Angiotensinogen and angiotensin | | |
| Antidiuretic hormone (or vasopressin, arginine vasopressin) | | |
| Atrial-natriuretic peptide (or atriopeptin) | | |
| B-type natriuretic peptide (BNP) | | |
| Calcitonin | | |
| Cholecystokinin | | |
| Corticotropin-releasing hormone | | |

TABLE 1-continued

Exemplary Proteins that can be Supercharged

| PROTEIN TYPE<br>Protein Subtype<br>Protein (PDB #) | Input Protein Sequence | 15 Possible Mutations to Generate Positively Supercharged Protein<br>Wildtype residue_Chain: Residue Number in Wildtype Protein Chain (Residue Number in InputChain)_Proposed Residue |
|---|---|---|
| Gastrin | | |
| Luteinizing hormone (LH) | | |
| Coagulation Factors | | |
| Factor VIII (aka antihemophilic factor) (2r7e) | Chain A:<br>ATRRYYLGAVELSWDYMQSDLGE<br>LPVDARFPPRVPKSFPFNTSVVY<br>KKTLFVEFTDHLFNIAKPRPPWM<br>GLLGPTIQAEVYDTVVITLKNMA<br>SHPVSLHAVGVSYWKASEGAEYD<br>DQTSQREKEDDKVFPGGSHTYVW<br>QVLKENGPMASDPLCLTYSYLSH<br>VDLVKDLNSGLIGALLVCREGSL<br>AKEKTQTLHKFILLFAVFDEGKS<br>WHSETKNAASARAWPKMHTVNGY<br>VNRSLPGLIGCHRKSVYWHVIGM<br>GTTPEVHSIFLEGHTFLVRNHRQ<br>ASLEISPITFLTAQTLLMDLGQF<br>LLFCHISSHQHDGMEAYVKVDSC<br>PEEPQFDDDNSPSFIQIRSVAKK<br>HPKTWVHYIAAEEEDWDYAPLVL<br>APDDRSYKSQYLNNGPQRIGRKY<br>KKVRFMAYTDETFKTREAIQHES<br>GILGPLLYGEVGDTLLIIFKNQA<br>SRPYNIYPHGITDVRPLYSRRLP<br>KGVKHLKDFPILPGEIFKYKWTV<br>TVEDGPTKSDPRCLTRYYSSFVN<br>MERDLASGLIGPLLICYKESVDQ<br>RGNQIMSDKRNVILFSVFDENRS<br>WYLTENIQRFLPNPAGVQLEDPE<br>FQASNIMHSINGYVFDSLQLSVC<br>LHEVAYWYILSIGAQTDFLSVFF<br>SGYTFKHKMVYEDTLTLFPFSGE<br>TVFMSMENPGLWILGCHNSDFRN<br>RGMTALLKVSSCDKNTGDYYEDS<br>YED<br>(SEQ ID NO: 83)<br>Chain B:<br>RSFQKKTRHYFIAAVERLWDYGM<br>SSSPHVLRNRAQSGSVPQFKKVV<br>FQEFTDGSFTQPLYRGELNEHLG<br>LLGPYIRAEVEDNIMVTFRNQAS<br>RPYSFYSSLISYEEDQRQGAEPR<br>KNFVKPNETKTYFWKVQHHMAPT<br>KDEFDCKAWAYSSDVDLEKDVHS<br>GLIGPLLVCHTNTLNPAHGRQVT<br>VQEFALFFTIFDETKSWYFTENM<br>ERNCRAPCNIQMEDPTFKENYRF<br>HAINGYIMDTLPGLVMAQDQRIR<br>WYLLSMGSNENIHSIHFSGHVFT<br>VRKKEEYKMALYNLYPGVFETVE<br>MLPSKAGIWRVECLIGEHLHAGM<br>STLFLVYSNKCQTPLGMASGHIR<br>DFQITASGQYGQWAPKLARLHYS<br>GSINAWSTKEPFSWIKVDLLAPM<br>IIHGIKTQGARQKFSSLYISQFI<br>IMYSLDGKKWQTYRGNSTGTLMV<br>FFGNVDSSGIKHNIFNPPIIARY<br>IRLHPTHYSIRSTLRMELMGCDL<br>NSCSMPLGMESKAISDAQITASS<br>YFTNMFATWSPSKARLHLQGRSN<br>AWRPQVNNPKEWLQVDFQKTMKV<br>TGVTTQGVKSLLTSMYVKEFLIS<br>SSQDGHQWTLFFQNGKVKVFQGN | GLN_A: 334(327)_LYS, ASN_A: 214(214)_LYS,<br>ASP_A: 361(329)_LYS, ASP_A: 27(27)_LYS,<br>GLU_A: 211(211)_LYS, GLU_A: 331(324)_LYS,<br>GLU_A: 332(325)_LYS, ASP_A: 363(331)_LYS,<br>ASN_A: 714(682)_LYS, ASN_A: 41(41)_LYS,<br>ASP_A: 362(330)_LYS, ASN_A: 364(332)_LYS,<br>GLU_A: 720(688)_LYS, GLN_B: 1692(4)_LYS,<br>ASP_A: 403(371)_LYS |

TABLE 1-continued

Exemplary Proteins that can be Supercharged

| PROTEIN TYPE<br>Protein Subtype<br>Protein (PDB #) | Input Protein Sequence | 15 Possible Mutations to Generate Positively Supercharged Protein<br>Wildtype residue_Chain: Residue Number in Wildtype Protein Chain (Residue Number in InputChain)_Proposed Residue |
|---|---|---|
| | QDSFTPVVNSLDPPLLTRYLRIH<br>PQSWVHQIALRMEVLGCEAQDLY<br>(SEQ ID NO: 84) | |
| Other | | |
| Human serum albumin (1ao6) | Chain A:<br>SEVAHRFKDLGEENFKALVLIAF<br>AQYLQQCPFEDHVKLVNEVTEFA<br>KTCVADESAENCDKSLHTLFGDK<br>LCTVATLRETYGEMADCCAKQEP<br>ERNECFLQHKDDNPNLPRLVRPE<br>VDVMCTAFHDNEETFLKKYLYEI<br>ARRHPYFYAPELLFFAKRYKAAF<br>TECCQAADKAACLLPKLDELRDE<br>GKASSAKQRLKCASLQKFGERAF<br>KAWAVARLSQRFPKAEFAEVSKL<br>VTDLTKVHTECCHGDLLECADDR<br>ADLAKYICENQDSISSKLKECCE<br>KPLLEKSHCIAEVENDEMPADLP<br>SLAADFVESKDVCKNYAEAKDVF<br>LGMFLYEYARRHPDYSVVLLLRL<br>AKTYETTLEKCCAAADPHECYAK<br>VFDEFKPLVEEPQNLIKQNCELF<br>EQLGEYKFQNALLVRYTKKVPQV<br>STPTLVEVSRNLGKVGSKCCKHP<br>EAKRMPCAEDYLSVVLNQLCVLH<br>EKTPVSDRVTKCCTESLVNRRPC<br>FSALEVDETYVPKEFNAETFTFH<br>ADICTLSEKERQIKKQTALVELV<br>KHKPKATKEQLKAVMDDFAAFVE<br>KCCKADDKETCFAEEGKKLVAAS<br>QAA<br>(SEQ ID NO: 85)<br>Chain B:<br>SEVAHRFKDLGEENFKALVLIAF<br>AQYLQQCPFEDHVKLVNEVTEFA<br>KTCVADESAENCDKSLHTLFGDK<br>LCTVATLRETYGEMADCCAKQEP<br>ERNECFLQHKDDNPNLPRLVRPE<br>VDVMCTAFHDNEETFLKKYLYEI<br>ARRHPYFYAPELLFFAKRYKAAF<br>TECCQAADKAACLLPKLDELRDE<br>GKASSAKQRLKCASLQKFGERAF<br>KAWAVARLSQRFPKAEFAEVSKL<br>VTDLTKVHTECCHGDLLECADDR<br>ADLAKYICENQDSISSKLKECCE<br>KPLLEKSHCIAEVENDEMPADLP<br>SLAADFVESKDVCKNYAEAKDVF<br>LGMFLYEYARRHPDYSVVLLLRL<br>AKTYETTLEKCCAAADPHECYAK<br>VFDEFKPLVEEPQNLIKQNCELF<br>EQLGEYKFQNALLVRYTKKVPQV<br>STPTLVEVSRNLGKVGSKCCKHP<br>EAKRMPCAEDYLSVVLNQLCVLH<br>EKTPVSDRVTKCCTESLVNRRPC<br>FSALEVDETYVPKEFNAETFTFH<br>ADICTLSEKERQIKKQTALVELV<br>KHKPKATKEQLKAVMDDFAAFVE<br>KCCKADDKETCFAEEGKKLVAAS<br>QAA<br>(SEQ ID NO: 86) | ASP_B: 301(297)_LYS, ASP_A: 301(297)_LYS,<br>GLU_A: 505(501)_LYS, GLU_B: 505(501)_LYS,<br>GLU_A: 82(78)_LYS, GLU_A: 542(538)_LYS,<br>GLU_B: 82(78)_LYS, GLU_B: 542(538)_LYS,<br>GLU_A: 17(13)_LYS, GLU_A: 37(33)_LYS,<br>ASP_A: 562(558)_LYS, GLU_B: 17(13)_LYS,<br>GLU_B: 37(33)_LYS, ASP_B: 375(371)_LYS,<br>ASP_B: 562(558)_LYS |
| Alpha 1-Antitrypsin | Chain A:<br>HPTFNKITPNLAEFAFSLYRQLA<br>HQSNSTNIFFSPVSIAAAFAMLS<br>LGAKGDTHDEILEGLNFNLTEIP<br>EAQIHEGFQELLRTLNQPDSQLQ<br>LTTGNGLFLSEGLKLVDKFLEDV<br>KKLYHSEAFTVNFGDTEEAKKQI<br>NDYVEKGTQGKIVDLVKELDRDT<br>VFALVNYIFFKGKWERPFEVKDT | GLN_A: 212(193)_LYS, GLU_A: 86(67)_LYS,<br>GLU_A: 175(156)_LYS, ASN_A: 278(259)_LYS,<br>ASP_A: 280(261)_LYS, ASN_A: 46(27)_LYS,<br>GLU_A: 257(238)_LYS, GLU_A: 279(260)_LYS,<br>GLN_A: 44(25)_LYS, ASP_A: 270(251)_LYS,<br>GLU_A: 277(258)_LYS, GLN_A: 305(286)_LYS,<br>ASN_A: 314(295)_LYS, GLU_A: 346(327)_LYS,<br>GLN_A: 91(72)_LYS |

TABLE 1-continued

Exemplary Proteins that can be Supercharged

| PROTEIN TYPE<br>Protein Subtype<br>Protein (PDB #) | Input Protein Sequence | 15 Possible Mutations to Generate Positively Supercharged Protein<br>Wildtype residue_Chain: Residue Number in Wildtype Protein Chain (Residue Number in InputChain)_Proposed Residue |
|---|---|---|
| | EEEDFHVDQVTTVKVPMMKRLGM<br>FNIQHCKKLSSWVLLMKYLGNAT<br>AIFFLPDEGKLQHLENELTHDII<br>TKFLENEDRRSASLHLPKLSITG<br>TYDLKSVLGQLGITKVFSNGADL<br>SGVTEEAPLKLSKAVHKAVLTID<br>EKGTEAAGAMFLEAIPMSIPPEV<br>KFNKPFVFLMIEQNTKSPLFMGK<br>VVNPTQK<br>(SEQ ID NO: 87) | |
| Hemoglobin(1bz0) | Chain A:<br>VLSPADKTNVKAAWGKVGAHAGE<br>YGAEALERMFLSFPTTKTYFPHF<br>DLSHGSAQVKGHGKKVADALTNA<br>VAHVDDMPNALSALSDLHAHKLR<br>VDPVNFKLLSHCLLVTLAAHLPA<br>EFTPAVHASLDKFLASVSTVLTS<br>KYR<br>(SEQ ID NO: 88)<br>Chain B:<br>VHLTPEEKSAVTALWGKVNVDEV<br>GGEALGRLLVVYPWTQRFFESFG<br>DLSTPDAVMGNPKVKAHGKKVLG<br>AFSDGLAHLDNLKGTFATLSELH<br>CDKLHVDPENFRLLGNVLVCVLA<br>HHFGKEFTPPVQAAYQKVVAGVA<br>NALAHKYH<br>(SEQ ID NO: 89) | GLU_B: 43(43)_LYS, ASN_B: 19(19)_LYS,<br>ASP_A: 75(75)_LYS, GLU_B: 6(6)_LYS,<br>ASP_B: 73(73)_LYS, ASP_A: 47(47)_LYS,<br>GLU_B: 101(101)_LYS, ASN_A: 68(68)_LYS,<br>ASP_A: 74(74)_LYS, ASN_A: 78(78)_LYS,<br>ASP_A: 94(94)_LYS, ASP_B: 79(79)_LYS,<br>ASP_B: 94(94)_LYS, ASP_B: 99(99)_LYS,<br>GLU_B: 121(121)_LYS |

TABLE 2

Exemplary Transcription Factors that can be Supercharged

Classified according to their regulatory function:

I. constitutively-active - present in all cells at all times - general transcription factors, Sp1, NF1, CCAAT
II. conditionally-active - requires activation
    II.A developmental (cell specific) - expression is tightly controlled, but, once expressed, require no additional activation - GATA, HNF, PIT-1, MyoD, Myf5, Hox, Winged Helix
    II.B signal-dependent - requires external signal for activation
        II.B.1 extracellular ligand-dependent - nuclear receptors
        II.B.2 intracellular ligand-dependent - activated by small intracellular molecules - SREBP, p53, orphan nuclear receptors
        II.B.3 cell membrane receptor-dependent - second messenger signaling cascades resulting in the phosphorylation of the transcription factor
            II.B.3.a resident nuclear factors - reside in the nucleus regardless of activation state - CREB, AP-1, Mef2
            II.B.3.b latent cytoplasmic factors - inactive form reside in the cytoplasm, but, when activated, are translocated into the nucleus - STAT, R-SMAD, NF-kB, Notch, TUBBY, NFAT Classified based on sequence similarity and hence the tertiary structure of their DNA binding domains:

1 Superclass: Basic Domains (Basic-helix-loop-helix)
  1.1 Class: Leucine zipper factors (bZIP)
    1.1.1 Family: AP-1(-like) components; includes (c-Fos/c-Jun)
    1.1.2 Family: CREB
    1.1.3 Family: C/EBP-like factors
    1.1.4 Family: bZIP/PAR
    1.1.5 Family: Plant G-box binding factors
    1.1.6 Family: ZIP only
  1.2 Class: Helix-loop-helix factors (bHLH)
    1.2.1 Family: Ubiquitous (class A) factors
    1.2.2 Family: Myogenic transcription factors (MyoD)
    1.2.3 Family: Achaete-Scute
    1.2.4 Family: Tal/Twist/Atonal/Hen
  1.3 Class: Helix-loop-helix/leucine zipper factors (bHLH-ZIP)
    1.3.1 Family: Ubiquitous bHLH-ZIP factors; includes USF (USF1, USF2); SREBP (SREBP)
    1.3.2 Family: Cell-cycle controlling factors; includes c-Myc
  1.4 Class: NF-1
    1.4.1 Family: NF-1 (A, B, C, X)
  1.5 Class: RF-X
    1.5.1 Family: RF-X (1, 2, 3, 4, 5, ANK)
  1.6 Class: bHSH
2 Superclass: Zinc-coordinating DNA-binding domains
  2.1 Class: Cys4 zinc finger of nuclear receptor type
    2.1.1 Family: Steroid hormone receptors
    2.1.2 Family: Thyroid hormone receptor-like factors
  2.2 Class: diverse Cys4 zinc fingers
    2.2.1 Family: GATA-Factors
  2.3 Class: Cys2His2 zinc finger domain
    2.3.1 Family: Ubiquitous factors, includes TFIIIA, Sp1
    2.3.2 Family: Developmental/cell cycle regulators; includes Kruppel
    2.3.4 Family: Large factors with NF-6B-like binding properties
  2.4 Class: Cys6 cysteine-zinc cluster
  2.5 Class: Zinc fingers of alternating composition
3 Superclass: Helix-turn-helix
  3.1 Class: Homeo domain
    3.1.1 Family: Homeo domain only; includes Ubx
    3.1.2 Family: POU domain factors; includes Oct
    3.1.3 Family: Homeo domain with LIM region
    3.1.4 Family: homeo domain plus zinc finger motifs
  3.2 Class: Paired box
    3.2.1 Family: Paired plus homeo domain
    3.2.2 Family: Paired domain only
  3.3 Class: Fork head/winged helix
    3.3.1 Family: Developmental regulators; includes forkhead
    3.3.2 Family: Tissue-specific regulators

TABLE 2-continued

Exemplary Transcription Factors that can be Supercharged 3.3.3 Family: Cell-cycle controlling factors
3.3.0 Family: Other regulators
3.4 Class: Heat Shock Factors
    3.4.1 Family: HSF
3.5 Class: Tryptophan clusters
    3.5.1 Family: Myb
    3.5.2 Family: Ets-type
    3.5.3 Family: Interferon regulatory factors
3.6 Class: TEA (transcriptional enhancer factor) domain
    3.6.1 Family: TEA (TEAD1, TEAD2, TEAD3, TEAD4)
4 Superclass: beta-Scaffold Factors with Minor Groove Contacts
    4.1 Class: RHR (Rel homology region)
        4.1.1 Family: Rel/ankyrin; NF-kappaB
        4.1.2 Family: ankyrin only
        4.1.3 Family: NFAT (Nuclear Factor of Activated T-cells) (NFATC1, NFATC2, NFATC3)
    4.2 Class: STAT
        4.2.1 Family: STAT
    4.3 Class: p53
        4.3.1 Family: p53
    4.4 Class: MADS box
        4.4.1 Family: Regulators of differentiation; includes (Mef2)
        4.4.2 Family: Responders to external signals, SRF (serum response factor) (SRF)
    4.5 Class: beta-Barrel alpha-helix transcription factors
    4.6 Class: TATA binding proteins
        4.6.1 Family: TBP
        4.7.1 Family: SOX genes, SRY
        4.7.2 Family: TCF-1 (TCF1)
        4.7.3 Family: HMG2-related, SSRP1
        4.7.5 Family: MATA
    4.8 Class: Heteromeric CCAAT factors
        4.8.1 Family: Heteromeric CCAAT factors
    4.9 Class: Grainyhead
        4.9.1 Family: Grainyhead
    4.10 Class: Cold-shock domain factors
        4.10.1 Family: csd
    4.11 Class: Runt
        4.11.1 Family: Runt
0 Superclass: Other Transcription Factors
    0.1 Class: Copper fist proteins
    0.2 Class: HMGI(Y) (HMGA1)
        0.2.1 Family: HMGI(Y)
    0.3 Class: Pocket domain
    0.4 Class: E1A-like factors
    0.5 Class: AP2/EREBP-related factors
        0.5.1 Family: AP2
        0.5.2 Family: EREBP
        0.5.3 Superfamily: AP2/B3
            0.5.3.1 Family: ARF
            0.5.3.2 Family: ABI
            0.5.3.3 Family: RAV In certain embodiments, a subset of the mutation proposed in Table 1 for a particular protein are made to create the supercharged protein. In certain embodiments, at least two mutations are made. In certain embodiments, at least three mutations are made. In certain embodiments, at least four mutations are made. In certain embodiments, at least five mutations are made. In certain embodiments, at least ten mutations are made. In certain embodiments, at least fifteen mutations are made. In certain embodiments, at least twenty mutations are made. In certain embodiments, all the proposed mutations are made to create the superpositively charged protein. In certain embodiments, none of the proposed mutations are made but rather one or more charged moieties are added to the protein to create the superpositively charged protein.

In certain embodiments, the supercharged protein is a naturally occurring supercharged protein. In certain embodiments, the theoretical net charge on the naturally occurring supercharged protein is at least +1, at least +2, at least +3, at least +4, at least +5, at least +10, at least +15, at least +20, at least +25, at least +30, at least +35, or at least +40. In certain embodiments, the supercharged protein has a charge:molecular weight ratio of at least approximately 0.8. In certain embodiments, the supercharged protein has a charge:molecular weight ratio of at least approximately 1.0. In certain embodiments, the supercharged protein has a charge:molecular weight ratio of at least approximately 1.2. In certain embodiments, the supercharged protein has a charge:molecular weight ratio of at least approximately 1.4. In certain embodiments, the supercharged protein has a charge:molecular weight ratio of at least approximately 1.5. In certain embodiments, the supercharged protein has a charge:molecular weight ratio of at least approximately 1.6. In certain embodiments, the supercharged protein has a charge:molecular weight ratio of at least approximately 1.7. In certain embodiments, the supercharged protein has a charge:molecular weight ratio of at least approximately 1.8. In certain embodiments, the supercharged protein has a charge:molecular weight ratio of at least approximately 1.9. In certain embodiments, the supercharged protein has a charge:molecular weight ratio of at least approximately 2.0. In certain embodiments, the supercharged protein has a charge:molecular weight ratio of at least approximately 2.5. In certain embodiments, the supercharged protein has a charge:molecular weight ratio of at least approximately 3.0. In certain embodiments, the molecular weight of the protein ranges from approximately 4 kDa to approximately 100 kDa. In certain embodiments, the molecular weight of the protein ranges from approximately 10 kDa to approximately 45 kDa. In certain embodiments, the molecular weight of the protein ranges from approximately 5 kDa to approximately 50 kDa. In certain embodiments, the molecular weight of the protein ranges from approximately 10 kDa to approximately 60 kDa. In certain embodiments, the naturally occurring supercharged protein is histone related. In certain embodiments, the naturally occurring supercharged protein is ribosome related. Examples of naturally occurring supercharged proteins include, but are not limited to, cyclon (ID No.: Q9H6F5); PNRC1 (ID No.: Q12796); RNPS1 (ID No.: Q15287); SURF6 (ID No.: O75683); AR6P (ID No.: Q66PJ3); NKAP (ID No.: Q8N5F7); EBP2 (ID No.: Q99848); LSM11 (ID No.: P83369); RL4 (ID No.: P36578); KRR1 (ID No.: Q13601); RY-1 (ID No.: Q8WVK2); BriX (ID No.: Q8TDN6); MNDA (ID No.: P41218); H1b (ID No.: P16401); cyclin (ID No.: Q9UK58); MDK (ID No.: P21741); Midkine (ID No.: P21741); PROK (ID No.: Q9HC23); FGF5 (ID No.: P12034); SFRS (ID No.: Q8N9Q2); AKIP (ID No.: Q9NWT8); CDK (ID No.: Q8N726); beta-defensin (ID No.: P81534); Defensin 3 (ID No.: P81534); PAVAC (ID No.: P18509); PACAP (ID No.: P18509); eotaxin-3 (ID No.: Q9Y258); histone H2A (ID No.: Q7L7L0); HMGB1 (ID No.: P09429); C-Jun (ID No.: P05412); TERF 1 (ID No.: P54274); N-DEK (ID No.: P35659); PIAS 1 (ID No.: O75925); Ku70 (ID No.: P12956); HBEGF (ID No.: Q99075); and HGF (ID No.: P14210). In certain embodiments, the supercharged protein utilized in the invention is U4/U6.U5 tri-snRNP-associated protein 3 (ID No.: Q8WVK2); beta-defensin (ID No.: P81534); Protein SFRS121P1 (ID No.: Q8N9Q2); midkine (ID No.: P21741); C-C motif chemokine 26 (ID No.: Q9Y258); surfeit locus protein 6 (ID No.: O75683); Aurora kinase A-interacting protein (ID No.: Q9NWT8); NF-kappa-B-activating protein (ID No.: Q8N5F7); histone H1.5 (ID No.: P16401); histone H2A type 3 (ID No.: Q7L7L0); 60S ribosomal protein L4 (ID No.: P36578); isoform 1 of RNA-binding protein with serine-rich domain 1 (ID No.: Q15287-1); isoform 4 of cyclin-dependent kinase inhibitor 2A (ID No.: Q8N726-1); isoform 1 of prokineticin-2 (ID No.:

Q9HC23-1); isoform 1 of ADP-ribosylation factor-like protein 6-interacting protein 4 (ID No.: Q66PJ3-1); isoform long of fibroblast growth factor 5 (ID No.: P12034-1); or isoform 1 of cyclin-L1 (ID No.: Q9UK58-1). Other possible naturally occurring supercharged proteins from the human proteome that may be utilized in the present invention are included in the list below. The proteins listed have a charge:molecular weight ratio of greater than 0.8.

| Ratio | Charge | Name | aa | MW |
|---|---|---|---|---|
| Cationic Proteins | | | | |

['3.49', 23, 'sp|P04553|HSP1_HUMAN Sperm protamine-P1 OS = *Homo sapiens* GN = PRM1', 51, 6822]
['3.00', 19, 'sp|P09430|STP1_HUMAN Spermatid nuclear transition protein 1 OS = *Homo sapiens* GN = TNP1', 55, 6424]
['2.19', 23, 'sp|Q9UNZ5|L10K_HUMAN Leydig cell tumor 10 kDa protein homolog OS = *Homo sapiens* GN = C19orf53', 99, 10576]
['2.07', 27, 'sp|P04554|PRM2_HUMAN Protamine-2 OS = *Homo sapiens* GN = PRM2', 102, 13050]
['1.80', 18, 'sp|Q5EE01|CUG2_HUMAN Cancer-up-regulated gene 2 protein OS = *Homo sapiens* GN = C6orf173', 88, 10061]
['1.78', 17, 'sp|O00479|HMGN4_HUMAN High mobility group nucleosome-binding domain-containing protein 4 OS = *Homo sapiens* GN = HMGN4', 90, 9538]
['1.65', 25, 'sp|Q9BRT6|CL031_HUMAN UPF0446 protein C12orf31 OS = *Homo sapiens* GN = C12orf31', 129, 15225]
['1.62', 80, 'sp|Q8IV32|CCD71_HUMAN Coiled-coil domain-containing protein 71 OS = *Homo sapiens* GN = CCDC71', 467, 49618]
['1.59', 24, 'sp|Q05952|STP2_HUMAN Nuclear transition protein 2 OS = *Homo sapiens* GN = TNP2', 138, 15640]
['1.57', 22, 'sp|Q07325|CXCL9_HUMAN C—X—C motif chemokine 9 OS = *Homo sapiens* GN = CXCL9', 125, 14018]
['1.56', 11, 'sp|Q9Y2S6|CCD72_HUMAN Coiled-coil domain-containing protein 72 OS = *Homo sapiens* GN = CCDC72', 64, 7066]
['1.55', 29, 'sp|Q8WVK2|SNUT3_HUMAN U4/U6.U5 tri-snRNP-associated protein 3 OS = *Homo sapiens*', 155, 18860]
['1.55', 11, 'sp|P81534|D103A_HUMAN Beta-defensin 103 OS = *Homo sapiens* GN = DEFB103A', 67, 7697]
['1.54', 8, 'sp|Q5VTU8|AT5EL_HUMAN ATP synthase subunit epsilon-like protein, mitochondrial OS = *Homo sapiens* GN = ATP5EP2', 51, 5806]
['1.45', 10, 'sp|P84101|SERF2_HUMAN Small EDRK-rich factor 2 OS = *Homo sapiens* GN = SERF2', 59, 6899]
['1.40', 102, 'sp|A6NNA2|SRR2L_HUMAN SRRM2-like protein OS = *Homo sapiens*', 665, 72877]
['1.39', 40, 'sp|Q8N9E0|F133A_HUMAN Protein FAM133A OS = *Homo sapiens* GN = FAM133A', 248, 28940]
['1.38', 35, 'sp|A6NF02|NPPL2_HUMAN NPIP-like protein ENSP00000346774 OS = *Homo sapiens*', 221, 26005]
['1.37', 11, 'sp|Q7Z4L0|COX83_HUMAN Cytochrome c oxidase polypeptide 8C, mitochondrial OS = *Homo sapiens* GN = COX8C', 72, 8128]
['1.35', 34, 'sp|O75200|NPPL1_HUMAN NPIP-like protein LOC440350 OS = *Homo sapiens*', 221, 25868]
['1.32', 18, 'sp|Q6UXB2|VCC1_HUMAN VEGF co-regulated chemokine 1 OS = *Homo sapiens* GN = CXCL17', 119, 13819]
['1.32', 10, 'sp|Q8N688|DB123_HUMAN Beta-defensin 123 OS = *Homo sapiens* GN = DEFB123', 67, 8104]
['1.31', 36, 'sp|Q5U4N7|GDF5O_HUMAN Protein GDF5OS, mitochondrial OS = *Homo sapiens* GN = GDF5OS', 250, 28153]
['1.31', 12, 'sp|O00198|HRK_HUMAN Activator of apoptosis harakiri OS = *Homo sapiens* GN = HRK', 91, 9883]
['1.30', 29, 'sp|Q8WW32|HMGB4_HUMAN High mobility group protein B4 OS = *Homo sapiens* GN = HMGB4', 186, 22404]
['1.28', 23, 'sp|Q8N9Q2|S12IP_HUMAN Protein SFRS12IP1 OS = *Homo sapiens* GN = SFRS12IP1', 155, 18176]
['1.26', 19, 'sp|P21741|MK_HUMAN Midkine OS = *Homo sapiens* GN = MDK', 143, 15585]
['1.26', 16, 'sp|Q08E93|F27E3_HUMAN Protein FAM27E3 OS = *Homo sapiens* GN = FAM27E3', 113, 13507]
['1.23', 44, 'sp|Q96QD9|FYTD1_HUMAN Forty-two-three domain-containing protein 1 OS = *Homo sapiens* GN = FYTTD1', 318, 35799]
['1.23', 16, 'sp|P62314|SMD1_HUMAN Small nuclear ribonucleoprotein Sm D1 OS = *Homo sapiens* GN = SNRPD1', 119, 13281]
['1.23', 13, 'sp|Q9Y258|CCL26_HUMAN C-C motif chemokine 26 OS = *Homo sapiens* GN = CCL26', 94, 10647]
['1.22', 10, 'sp|Q96PI1|SPRR4_HUMAN Small proline-rich protein 4 OS = *Homo sapiens* GN = SPRR4', 79, 8793]
['1.21', 24, 'sp|B2CW77|KILIN_HUMAN Killin OS = *Homo sapiens*', 178, 19957]
['1.20', 10, 'sp|Q9Y5V0|ZN706_HUMAN Zinc finger protein 706 OS = *Homo sapiens* GN = ZNF706', 76, 8497]
['1.20', 6, 'sp|P56381|ATP5E_HUMAN ATP synthase subunit epsilon, mitochondrial OS = *Homo sapiens* GN = ATP5E', 51, 5779]
['1.19', 61, 'sp|Q9HAH1|ZN556_HUMAN Zinc finger protein 556 OS = *Homo sapiens* GN = ZNF556', 456, 51581]
['1.19', 30, 'sp|P17026|ZNF22_HUMAN Zinc finger protein 22 OS = *Homo sapiens* GN = ZNF22', 224, 25915]
['1.18', 16, 'sp|Q9NRJ3|CCL28_HUMAN C-C motif chemokine 28 OS = *Homo sapiens* GN = CCL28', 127, 14279]
['1.16', 11, 'sp|O43262|LEU2_HUMAN Leukemia-associated protein 2 OS = *Homo sapiens* GN = DLEU2', 84, 10196]
['1.15', 38, 'sp|Q6PK04|CC137_HUMAN Coiled-coil domain-containing protein 137 OS = *Homo sapiens* GN = CCDC137', 289, 33231]
['1.15', 18, 'sp|A8MYZ5|YC026_HUMAN IQ domain-containing protein ENSP00000381760 OS = *Homo sapiens*', 130, 15797]
['1.15', 16, 'sp|Q5T7N7|F27E1_HUMAN Protein FAM27E1 OS = *Homo sapiens* GN = FAM27E1', 126, 14751]
['1.15', 16, 'sp|Q5SNX5|F27E2_HUMAN Protein FAM27E2 OS = *Homo sapiens* GN = FAM27E2', 125, 14710]
['1.15', 16, 'sp|O00585|CCL21_HUMAN C-C motif chemokine 21 OS = *Homo sapiens* GN = CCL21', 134, 14646]
['1.15', 6, 'sp|Q13794|APR_HUMAN Phorbol-12-myristate-13-acetate-induced protein 1 OS = *Homo sapiens* GN = PMAIP1', 54, 6030]
['1.14', 13, 'sp|P19875|MIP2A_HUMAN Macrophage inflammatory protein 2-alpha OS = *Homo sapiens* GN = CXCL2', 107, 11388]
['1.14', 12, 'sp|Q9P021|CRIPT_HUMAN Cysteine-rich PDZ-binding protein OS = *Homo sapiens* GN = CRIPT', 101, 11215]
['1.14', 11, 'sp|O14625|CXL11_HUMAN C—X—C motif chemokine 11 OS = *Homo sapiens* GN = CXCL11', 94, 10364]
['1.13', 10, 'sp|P61580|NP10_HUMAN HERV-K_5q33.3 provirus Np9 protein OS = *Homo sapiens*', 75, 8892]
['1.12', 46, 'sp|O75683|SURF6_HUMAN Surfeit locus protein 6 OS = *Homo sapiens* GN = SURF6', 361, 41450]
['1.12', 15, 'sp|P0C7P0|CISD3_HUMAN CDGSH iron sulfur domain-containing protein 3, mitochondrial OS = *Homo sapiens* GN = CISD3', 127, 14215]
['1.10', 37, 'sp|Q9Y2B4|T53G5_HUMAN TP53-target gene 5 protein OS = *Homo sapiens* GN = TP53TG5', 290, 34019]
['1.10', 33, 'sp|Q9Y3A2|UTP11_HUMAN Probable U3 small nucleolar RNA-associated protein 11 OS = *Homo sapiens* GN = UTP11L', 253, 30446]
['1.10', 21, 'sp|Q9HCT0|FGF22_HUMAN Fibroblast growth factor 22 OS = *Homo sapiens* GN = FGF22', 170, 19662]
['1.10', 11, 'sp|P51671|CCL11_HUMAN Eotaxin OS = *Homo sapiens* GN = CCL11', 97, 10731]
['1.09', 14, 'sp|Q9Y421|FA32A_HUMAN Protein FAM32A OS = *Homo sapiens* GN = FAM32A', 112, 13178]
['1.09', 12, 'sp|Q2M2W7|CQ058_HUMAN UPF0450 protein C17orf58 OS = *Homo sapiens* GN = C17orf58', 97, 11205]
['1.09', 11, 'sp|Q99616|CCL13_HUMAN C-C motif chemokine 13 OS = *Homo sapiens* GN = CCL13', 98, 10986]
['1.09', 11, 'sp|P0C665|PRAC2_HUMAN Small nuclear protein PRAC2 OS = *Homo sapiens* GN = PRAC2', 90, 10483]
['1.09', 11, 'sp|P0C0P6|NPS_HUMAN Neuropeptide S OS = *Homo sapiens* GN = NPS', 89, 10103]
['1.08', 21, 'sp|Q8IXL9|IQCF2_HUMAN IQ domain-containing protein F2 OS = *Homo sapiens* GN = IQCF2', 164, 19627]
['1.08', 8, 'sp|Q13891|BT3L2_HUMAN Transcription factor BTF3 homolog 2 OS = *Homo sapiens* GN = BTF3L2', 67, 7605]
['1.08', 7, 'sp|P56378|68MP_HUMAN 6.8 kDa mitochondrial proteolipid OS = *Homo sapiens* GN = MP68', 58, 6662]
['1.08', 6, 'sp|P15516|HIS3_HUMAN Histatin-3 OS = *Homo sapiens* GN = HTN3', 51, 6149]
['1.07', 26, 'sp|Q5T7N8|F27D1_HUMAN Protein FAM27D1 OS = *Homo sapiens* GN = FAM27D1', 215, 24905]
['1.07', 24, 'sp|Q9NWT8|AKIP_HUMAN Aurora kinase A-interacting protein OS = *Homo sapiens* GN = AURKAIP1', 199, 22354]
['1.07', 16, 'sp|A8MQ11|PM2L5_HUMAN Postmeiotic segregation increased 2-like protein 5 OS = *Homo sapiens* GN = PMS2L5', 134, 15169]
['1.07', 15, 'sp|Q6UXT8|F150A_HUMAN Protein FAM150A OS = *Homo sapiens* GN = FAM150A', 129, 14268]
['1.06', 61, 'sp|Q14593|ZN273_HUMAN Zinc finger protein 273 OS = *Homo sapiens* GN = ZNF273', 504, 58045]

-continued

| Ratio | Charge | Name | aa | MW |
|---|---|---|---|---|

['1.06', 9, 'sp|Q9ULZ1|APEL_HUMAN Apelin OS = Homo sapiens GN = APLN', 77, 8569]
['1.05', 10, 'sp|Q9UGL9|CRCT1_HUMAN Cysteine-rich C-terminal protein 1 OS = Homo sapiens GN = CRCT1', 99, 9735]
['1.05', 10, 'sp|P81277|PRRP_HUMAN Prolactin-releasing peptide OS = Homo sapiens GN = PRLH', 87, 9639]
['1.04', 31, 'sp|P52744|ZN138_HUMAN Zinc finger protein 138 OS = Homo sapiens GN = ZNF138', 262, 30591]
['1.04', 11, 'sp|Q6IPR1|LYRM5_HUMAN LYR motif-containing protein 5 OS = Homo sapiens GN = LYRM5', 88, 10604]
['1.04', 9, 'sp|P09669|COX6C_HUMAN Cytochrome c oxidase polypeptide VIc OS = Homo sapiens GN = COX6C', 75, 8781]
['1.04', 7, 'sp|Q9NRQ5|CK075_HUMAN UPF0443 protein C11orf75 OS = Homo sapiens GN = C11orf75', 59, 6738]
['1.03', 23, 'sp|Q8NHZ7|MB3L2_HUMAN Methyl-CpG-binding domain protein 3-like 2 OS = Homo sapiens GN = MBD3L2', 204, 22695]
['1.03', 11, 'sp|Q9HD34|LYRM4_HUMAN LYR motif-containing protein 4 OS = Homo sapiens GN = LYRM4', 91, 10758]
['1.03', 10, 'sp|Q06250|WIT1_HUMAN Wilms tumor-associated protein OS = Homo sapiens GN = WIT1', 92, 10038]
['1.02', 40, 'sp|Q9NP08|HMX1_HUMAN Homeobox protein HMX1 OS = Homo sapiens GN = HMX1', 373, 39225]
['1.02', 15, 'sp|Q9H963|ZN702_HUMAN Zinc finger protein 702 OS = Homo sapiens GN = ZNF702', 129, 15053]
['1.02', 14, 'sp|P37108|SRP14_HUMAN Signal recognition particle 14 kDa protein OS = Homo sapiens GN = SRP14', 136, 14569]
['1.02', 12, 'sp|P52926|HMGA2_HUMAN High mobility group protein HMGI-C OS = Homo sapiens GN = HMGA2', 109, 11832]
['1.02', 7, 'sp|P58511|F165B_HUMAN UPF0601 protein FAM165B OS = Homo sapiens GN = FAM165B', 58, 6886]
['1.01', 24, 'sp|P52743|ZN137_HUMAN Zinc finger protein 137 OS = Homo sapiens GN = ZNF137', 207, 24114]
['1.01', 18, 'sp|Q8N912|CN180_HUMAN Transmembrane protein C14orf180 OS = Homo sapiens GN = C14orf180', 160, 18051]
['1.01', 14, 'sp|Q8N8V8|TM105_HUMAN Transmembrane protein 105 OS = Homo sapiens GN = TMEM105', 129, 13990]
['1.01', 14, 'sp|Q5TZK3|F74A4_HUMAN Protein FAM74A4 OS = Homo sapiens GN = FAM74A4', 123, 14772]
['1.01', 14, 'sp|P42127|ASIP_HUMAN Agouti-signaling protein OS = Homo sapiens GN = ASIP', 132, 14515]
['1.01', 10, 'sp|P60468|SC61B_HUMAN Protein transport protein Sec61 subunit beta OS = Homo sapiens GN = SEC61B', 96, 9974]
['1.01', 9, 'sp|P61581|NP11_HUMAN HERV-K_22q11.21 provirus Np9 protein OS = Homo sapiens', 75, 8893]
['1.00', 72, 'sp|Q6ZQV5|ZN788_HUMAN Zinc finger protein 788 OS = Homo sapiens GN = ZNF788', 615, 71992]
['1.00', 70, 'sp|Q5HYK9|ZN667_HUMAN Zinc finger protein 667 OS = Homo sapiens GN = ZNF667', 610, 70157]
['1.00', 26, 'sp|Q9H0W7|THAP2_HUMAN THAP domain-containing protein 2 OS = Homo sapiens GN = THAP2', 228, 26259]
['0.99', 20, 'sp|P35318|ADML_HUMAN ADM OS = Homo sapiens GN = ADM', 185, 20420]
['0.99', 18, 'sp|P21246|PTN_HUMAN Pleiotrophin OS = Homo sapiens GN = PTN', 168, 18942]
['0.99', 13, 'sp|P23582|ANFC_HUMAN C-type natriuretic peptide OS = Homo sapiens GN = NPPC', 126, 13246]
['0.99', 10, 'sp|P02778|CXL10_HUMAN C—X—C motif chemokine 10 OS = Homo sapiens GN = CXCL10', 98, 10881]
['0.98', 15, 'sp|P14555|PA2GA_HUMAN Phospholipase A2, membrane associated OS = Homo sapiens GN = PLA2G2A', 144, 16082]
['0.98', 12, 'sp|Q8NDT4|ZN663_HUMAN Zinc finger protein 663 OS = Homo sapiens GN = ZNF663', 106, 12434]
['0.98', 12, 'sp|O00175|CCL24_HUMAN C-C motif chemokine 24 OS = Homo sapiens GN = CCL24', 119, 13133]
['0.97', 17, 'sp|Q5T6X4|F162B_HUMAN UPF0389 protein FAM162B OS = Homo sapiens GN = FAM162B', 162, 17684]
['0.97', 15, 'sp|Q7Z4H4|ADM2_HUMAN ADM2 OS = Homo sapiens GN = ADM2', 148, 15865]
['0.97', 11, 'sp|P09341|GROA_HUMAN Growth-regulated alpha protein OS = Homo sapiens GN = CXCL1', 107, 11301]
['0.97', 6, 'sp|O15263|BD02_HUMAN Beta-defensin 2 OS = Homo sapiens GN = DEFB4', 64, 7037]
['0.96', 40, 'sp|Q96N58|ZN578_HUMAN Zinc finger protein 578 OS = Homo sapiens GN = ZNF578', 365, 42596]
['0.96', 19, 'sp|Q9NPH9|IL26_HUMAN Interleukin-26 OS = Homo sapiens GN = IL26', 171, 19842]
['0.96', 19, 'sp|Q8NHX4|SPTA3_HUMAN Spermatogenesis-associated protein 3 OS = Homo sapiens GN = SPATA3', 183, 19948]
['0.96', 16, 'sp|P59020|DSCR9_HUMAN Down syndrome critical region protein 9 OS = Homo sapiens GN = DSCR9', 149, 16743]
['0.96', 8, 'sp|Q3LI70|KR196_HUMAN Keratin-associated protein 19-6 OS = Homo sapiens GN = KRTAP19-6', 84, 9125]
['0.96', 7, 'sp|Q9Y6X1|SERP1_HUMAN Stress-associated endoplasmic reticulum protein 1 OS = Homo sapiens GN = SERP1', 66, 7373]
['0.96', 4, 'sp|Q9P0U5|INGX_HUMAN Inhibitor of growth protein, X-linked OS = Homo sapiens GN = INGX', 42, 5076]
['0.95', 7, 'sp|Q8N6R1|SERP2_HUMAN Stress-associated endoplasmic reticulum protein 2 OS = Homo sapiens GN = SERP2', 65, 7430]
['0.94', 33, 'sp|Q9H7B2|BXDC1_HUMAN Brix domain-containing protein 1 OS = Homo sapiens GN = BXDC1', 306, 35582]
['0.94', 17, 'sp|Q96MF4|CC140_HUMAN Coiled-coil domain-containing protein 140 OS = Homo sapiens GN = CCDC140', 163, 18252]
['0.94', 16, 'sp|Q8WW36|ZCH13_HUMAN Zinc finger CCHC domain-containing protein 13 OS = Homo sapiens GN = ZCCHC13', 166, 18005]
['0.94', 12, 'sp|O60519|CRBL2_HUMAN cAMP-responsive element-binding protein-like 2 OS = Homo sapiens GN = CREBL2', 120, 13783]
['0.93', 16, 'sp|Q9H1E1|RNAS7_HUMAN Ribonuclease 7 OS = Homo sapiens GN = RNASE7', 156, 17471]
['0.93', 16, 'sp|Q14236|EPAG_HUMAN Early lymphoid activation gene protein OS = Homo sapiens GN = EPAG', 149, 17843]
['0.93', 16, 'sp|P0C7M6|IQCF3_HUMAN IQ domain-containing protein F3 OS = Homo sapiens GN = IQCF3', 154, 18250]
['0.93', 11, 'sp|O43927|CXL13_HUMAN C—X—C motif chemokine 13 OS = Homo sapiens GN = CXCL13', 109, 12664]
['0.93', 9, 'sp|Q9Y6G1|TM14A_HUMAN Transmembrane protein 14A OS = Homo sapiens GN = TMEM14A', 99, 10712]
['0.93', 9, 'sp|Q7Z7B7|DB132_HUMAN Beta-defensin 132 OS = Homo sapiens GN = DEFB132', 95, 10610]
['0.93', 8, 'sp|Q5T5B0|LCE3E_HUMAN Late cornified envelope protein 3E OS = Homo sapiens GN = LCE3E', 92, 9506]
['0.93', 7, 'sp|Q9NPE3|NOLA3_HUMAN H/ACA ribonucleoprotein complex subunit 3 OS = Homo sapiens GN = NOLA3', 64, 7705]
['0.92', 23, 'sp|Q95707|RPP29_HUMAN Ribonuclease P protein subunit p29 OS = Homo sapiens GN = POP4', 25, 25424]
['0.92', 14, 'sp|Q9NPJ4|PNRC2_HUMAN Proline-rich nuclear receptor coactivator 2 OS = Homo sapiens GN = PNRC2', 139, 15590]
['0.92', 11, 'sp|O14599|VCY2_HUMAN Testis-specific basic protein Y 2 OS = Homo sapiens GN = BPY2', 106, 12035]
['0.92', 8, 'sp|Q8WVI0|U640_HUMAN UPF0640 protein OS = Homo sapiens', 70, 8696]
['0.92', 5, 'sp|Q96IX5|USMG5_HUMAN Up-regulated during skeletal muscle growth protein 5 OS = Homo sapiens GN = USMG5', 58, 6457]
['0.91', 8, 'sp|P61582|NP12_HUMAN HERV-K_1q22 provirus Np9 protein OS = Homo sapiens', 75, 8820]
['0.90', 81, 'sp|Q08AN1|ZN616_HUMAN Zinc finger protein 616 OS = Homo sapiens GN = ZNF616', 781, 90263]
['0.90', 42, 'sp|Q8N5F7|NKAP_HUMAN NF-kappa-B-activating protein OS = Homo sapiens GN = NKAP', 415, 47138]
['0.90', 41, 'sp|A6NM28|ZFP92_HUMAN Zinc finger protein 92 homolog OS = Homo sapiens GN = ZFP92', 416, 45791]
['0.90', 35, 'sp|Q14093|CYLC2_HUMAN Cylicin-2 OS = Homo sapiens GN = CYLC2', 348, 39078]
['0.90', 18, 'sp|Q6ZT77|ZN826_HUMAN Zinc finger protein 826 OS = Homo sapiens GN = ZNF826', 177, 20579]
['0.90', 10, 'sp|Q5T751|LCE1C_HUMAN Late cornified envelope protein 1C OS = Homo sapiens GN = LCE1C', 118, 11543]
['0.90', 8, 'sp|P61583|NP8_HUMAN HERV-K_3q12.3 provirus Np9 protein OS = Homo sapiens GN = ERVK5', 75, 8907]
['0.90', 7, 'sp|Q30KQ2|DB130_HUMAN Beta-defensin 130 OS = Homo sapiens GN = DEFB130', 79, 8735]
['0.89', 35, 'sp|O75698|HUG1_HUMAN Protein HUG-1 OS = Homo sapiens GN = HUG1', 362, 39386]
['0.89', 22, 'sp|Q8N7Y1|PRR10_HUMAN Proline-rich protein 10 OS = Homo sapiens GN = PRR10', 241, 25772]
['0.89', 22, 'sp|Q5TFG8|F164B_HUMAN UPF0418 protein FAM164B OS = Homo sapiens GN = FAM164B', 222, 24665]
['0.89', 18, 'sp|Q7RTS1|BHLH8_HUMAN Class B basic helix-loop-helix protein 8 OS = Homo sapiens GN = BHLHB8', 189, 20818]
['0.89', 10, 'sp|Q5T7P3|LCE1B_HUMAN Late cornified envelope protein 1B OS = Homo sapiens GN = LCE1B', 118, 11626]
['0.89', 10, 'sp|Q5T754|LCE1F_HUMAN Late cornified envelope protein 1F OS = Homo sapiens GN = LCE1F', 118, 11654]
['0.89', 10, 'sp|P19876|MIP2B_HUMAN Macrophage inflammatory protein 2-beta OS = Homo sapiens GN = CXCL3', 107, 11342]

-continued

| Ratio | Charge | Name | aa | MW |
|---|---|---|---|---|

['0.89', 9, 'sp|P80098|CCL7_HUMAN C-C motif chemokine 7 OS = *Homo sapiens* GN = CCL7', 99, 11200]
['0.89', 7, 'sp|Q969E1|LEAP2_HUMAN Liver-expressed antimicrobial peptide 2 OS = *Homo sapiens* GN = LEAP2', 77, 8813]
['0.89', 7, 'sp|Q30KP9|DB135_HUMAN Beta-defensin 135 OS = *Homo sapiens* GN = DEFB135', 77, 8753]
['0.88', 50, 'sp|Q96CS4|ZN689_HUMAN Zinc finger protein 689 OS = *Homo sapiens* GN = ZNF689', 500, 56906]
['0.88', 24, 'sp|Q5EBM4|ZN542_HUMAN Zinc finger protein 542 OS = *Homo sapiens* GN = ZNF542', 241, 27663]
['0.88', 11, 'sp|Q96BP2|CHCH1_HUMAN Coiled-coil-helix-coiled-coil-helix domain-containing protein 1 OS = *Homo sapiens* GN = CHCHD1', 118, 13474]
['0.88', 9, 'sp|Q6UX46|F150B_HUMAN Protein FAM150B OS = *Homo sapiens* GN = FAM150B', 91, 10541]
['0.87', 65, 'sp|Q6ZR52|ZN493_HUMAN Zinc finger protein 493 OS = *Homo sapiens* GN = ZNF493', 646, 75341]
['0.87', 30, 'sp|Q99848|EBP2_HUMAN Probable rRNA-processing protein EBP2 OS = *Homo sapiens* GN = EBNA1BP2', 306, 34851]
['0.87', 12, 'sp|P62318|SMD3_HUMAN Small nuclear ribonucleoprotein Sm D3 OS = *Homo sapiens* GN = SNRPD3', 126, 13916]
['0.87', 10, 'sp|A0PJW8|DAPL1_HUMAN Death-associated protein-like 1 OS = *Homo sapiens* GN = DAPL1', 107, 11879]
['0.87', 9, 'sp|Q5T7P2|LCE1A_HUMAN Late cornified envelope protein 1A OS = *Homo sapiens* GN = LCE1A', 110, 10982]
['0.87', 5, 'sp|Q96KF2|PRAC_HUMAN Small nuclear protein PRAC OS = *Homo sapiens* GN = PRAC', 57, 5958]
['0.86', 59, 'sp|Q03923|ZNF85_HUMAN Zinc finger protein 85 OS = *Homo sapiens* GN = ZNF85', 595, 68718]
['0.86', 54, 'sp|Q6N045|ZNP12_HUMAN Zinc finger protein ZnFP12 OS = *Homo sapiens*', 540, 62759]
['0.86', 43, 'sp|Q8IZC7|ZN101_HUMAN Zinc finger protein 101 OS = *Homo sapiens* GN = ZNF101', 436, 50339]
['0.86', 41, 'sp|P42696|RBM34_HUMAN RNA-binding protein 34 OS = *Homo sapiens* GN = RBM34', 430, 48564]
['0.86', 20, 'sp|Q9Y324|FCF1_HUMAN rRNA-processing protein FCF1 homolog OS = *Homo sapiens* GN = FCF1', 198, 23369]
['0.86', 15, 'sp|Q969E3|UCN3_HUMAN Urocortin-3 OS = *Homo sapiens* GN = UCN3', 161, 17861]
['0.86', 13, 'sp|P09132|SRP19_HUMAN Signal recognition particle 19 kDa protein OS = *Homo sapiens* GN = SRP19', 144, 16155]
['0.85', 54, 'sp|Q9BWE0|REPI1_HUMAN Replication initiator 1 OS = *Homo sapiens* GN = REPIN1', 567, 63574]
['0.85', 42, 'sp|Q8NCK3|ZN485_HUMAN Zinc finger protein 485 OS = *Homo sapiens* GN = ZNF485', 441, 50280]
['0.85', 22, 'sp|P11487|FGF3_HUMAN INT-2 proto-oncogene protein OS = *Homo sapiens* GN = FGF3', 239, 26886]
['0.85', 19, 'sp|Q99748|NRTN_HUMAN Neurturin OS = *Homo sapiens* GN = NRTN', 197, 22405]
['0.85', 6, 'sp|P15954|COX7C_HUMAN Cytochrome c oxidase subunit 7C, mitochondrial OS = *Homo sapiens* GN = COX7C', 63, 7245]
['0.84', 42, 'sp|Q8N8L2|ZN491_HUMAN Zinc finger protein 491 OS = *Homo sapiens* GN = ZNF491', 437, 50949]
['0.84', 22, 'sp|Q86XF7|ZN575_HUMAN Zinc finger protein 575 OS = *Homo sapiens* GN = ZNF575', 245, 26763]
['0.84', 9, 'sp|Q5T752|LCE1D_HUMAN Late cornified envelope protein 1D OS = *Homo sapiens* GN = LCE1D', 114, 11229]
['0.84', 6, 'sp|Q9NRX6|T167B_HUMAN Transmembrane protein 167B OS = *Homo sapiens* GN = TMEM167B', 74, 8294]
['0.84', 5, 'sp|P80294|MT1H_HUMAN Metallothionein-1H OS = *Homo sapiens* GN = MT1H', 61, 6039]
['0.83', 50, 'sp|Q9P255|ZN492_HUMAN Zinc finger protein 492 OS = *Homo sapiens* GN = ZNF492', 531, 61158]
['0.83', 50, 'sp|A6NK75|ZNF98_HUMAN Zinc finger protein 98 OS = *Homo sapiens* GN = ZNF98', 531, 61144]
['0.83', 32, 'sp|O15480|MAGB3_HUMAN Melanoma-associated antigen B3 OS = *Homo sapiens* GN = MAGEB3', 346, 39179]
['0.83', 29, 'sp|Q96GY0|F164A_HUMAN UPF0418 protein FAM164A OS = *Homo sapiens* GN = FAM164A', 325, 35062]
['0.83', 26, 'sp|Q96PP4|TSG13_HUMAN Testis-specific gene 13 protein OS = *Homo sapiens* GN = TSGA13', 275, 31777]
['0.83', 17, 'sp|O15499|GSC2_HUMAN Homeobox protein goosecoid-2 OS = *Homo sapiens* GN = GSC2', 205, 21544]
['0.83', 10, 'sp|P56847|TNG2_HUMAN Protein TNG2 OS = *Homo sapiens* GN = TNG2', 110, 12856]
['0.83', 7, 'sp|Q9BYE3|LCE3D_HUMAN Late cornified envelope protein 3D OS = *Homo sapiens* GN = LCE3D', 92, 9443]
['0.83', 5, 'sp|P07438|MT1B_HUMAN Metallothionein-1B OS = *Homo sapiens* GN = MT1B', 61, 6115]
['0.82', 31, 'sp|Q6AZW8|ZN660_HUMAN Zinc finger protein 660 OS = *Homo sapiens* GN = ZNF660', 331, 38270]
['0.82', 11, 'sp|O43612|OREX_HUMAN Orexin OS = *Homo sapiens* GN = HCRT', 131, 13362]
['0.82', 10, 'sp|Q96DA6|TIM14_HUMAN Mitochondrial import inner membrane translocase subunit TIM14 OS = *Homo sapiens* GN = DNAJC19', 116, 12498]
['0.82', 9, 'sp|Q96A98|TIP39_HUMAN Tuberoinfundibular peptide of 39 residues OS = *Homo sapiens* GN = PTH2', 100, 11202]
['0.82', 9, 'sp|P80162|CXCL6_HUMAN C—X—C motif chemokine 6 OS = *Homo sapiens* GN = CXCL6', 114, 11897]
['0.81', 23, 'sp|Q9P031|TAP26_HUMAN Thyroid transcription factor 1-associated protein 26 OS = *Homo sapiens* GN = CCDC59', 241, 28669]
['0.81', 11, 'sp|Q6ZST2|ZCH23_HUMAN Zinc finger CCHC domain-containing protein 23 OS = *Homo sapiens* GN = ZCCHC23', 131, 14409]
['0.81', 11, 'sp|P62316|SMD2_HUMAN Small nuclear ribonucleoprotein Sm D2 OS = *Homo sapiens* GN = SNRPD2', 118, 13526]
['0.81', 10, 'sp|O95182|NDUA7_HUMAN NADH dehydrogenase [ubiquinone] 1 alpha subcomplex subunit 7 OS = *Homo sapiens* GN = NDUFA7', 113, 12551]
['0.81', 10, 'sp|A6NFY7|LYRM8_HUMAN LYR motif-containing protein ENSP00000368165 OS = *Homo sapiens*', 115, 12806]
['0.81', 7, 'sp|Q7Z3B0|CE043_HUMAN UPF0542 protein C5orf43 OS = *Homo sapiens* GN = C5orf43', 74, 8625]
['0.80', 72, 'sp|Q9UII5|ZN107_HUMAN Zinc finger protein 107 OS = *Homo sapiens* GN = ZNF107', 783, 90672]
['0.80', 69, 'sp|Q9Y3M9|ZN337_HUMAN Zinc finger protein 337 OS = *Homo sapiens* GN = ZNF337', 751, 86874]
['0.80', 49, 'sp|Q5SXM1|ZN678_HUMAN Zinc finger protein 678 OS = *Homo sapiens* GN = ZNF678', 525, 61411]
['0.80', 47, 'sp|Q96BV0|ZN775_HUMAN Zinc finger protein 775 OS = *Homo sapiens* GN = ZNF775', 537, 59751]
['0.80', 40, 'sp|P51522|ZNF83_HUMAN Zinc finger protein 83 OS = *Homo sapiens* GN = ZNF83', 428, 49778]
['0.80', 19, 'sp|Q9UGY1|NOL12_HUMAN Nucleolar protein 12 OS = *Homo sapiens* GN = NOL12', 213, 24662]
['0.80', 19, 'sp|O76093|FGF18_HUMAN Fibroblast growth factor 18 OS = *Homo sapiens* GN = FGF18', 207, 23988]
['0.80', 16, 'sp|P20800|EDN2_HUMAN Endothelin-2 OS = *Homo sapiens* GN = EDN2', 178, 19959]
['0.80', 8, 'sp|Q9NRX3|NUA4L_HUMAN NADH dehydrogenase [ubiquinone] 1 alpha subcomplex subunit 4-like 2 OS = *Homo sapiens* GN = NDUFA4L2', 87, 9965]
['0.80', 8, 'sp|Q02221|CX6A2_HUMAN Cytochrome c oxidase polypeptide 6A2, mitochondrial OS = *Homo sapiens* GN = COX6A2', 97, 10815]
['0.80', 5, 'sp|Q9P0U1|TOM7_HUMAN Mitochondrial import receptor subunit TOM7 homolog OS = *Homo sapiens* GN = TOMM7', 55, 6248]
Histones

['2.70', 59, 'sp|P10412|H14_HUMAN Histone H1.4 OS = *Homo sapiens* GN = HIST1H1E', 219, 21865]
['2.66', 60, 'sp|P16401|H15_HUMAN Histone H1.5 OS = *Homo sapiens* GN = HIST1H1B', 226, 22580]
['2.60', 58, 'sp|P16402|H13_HUMAN Histone H1.3 OS = *Homo sapiens* GN = HIST1H1D', 221, 22349]
['2.57', 55, 'sp|P16403|H12_HUMAN Histone H1.2 OS = *Homo sapiens* GN = HIST1H1C', 213, 21364]
['2.55', 53, 'sp|P07305|H10_HUMAN Histone H1.0 OS = *Homo sapiens* GN = H1F0', 194, 20862]
['2.47', 54, 'sp|Q02539|H11_HUMAN Histone H1.1 OS = *Homo sapiens* GN = HIST1H1A', 215, 21842]
['2.10', 46, 'sp|P22492|H1T_HUMAN Histone H1t OS = *Homo sapiens* GN = HIST1H1T', 207, 22018]
['1.79', 40, 'sp|Q92522|H1X_HUMAN Histone H1x OS = *Homo sapiens* GN = H1FX', 213, 22487]
['1.63', 42, 'sp|Q75WM6|H1FNT_HUMAN Testis-specific H1 histone OS = *Homo sapiens* GN = H1FNT', 234, 25888]
['1.60', 18, 'sp|P62805|H4_HUMAN Histone H4 OS = *Homo sapiens* GN = HIST1H4A', 103, 11367]

-continued

| Ratio | Charge | Name | aa | MW |
|---|---|---|---|---|

['1.56', 17, 'sp|Q99525|H4G_HUMAN Histone H4-like protein type G OS = *Homo sapiens* GN = HIST1H4G', 98, 11009]
['1.39', 35, 'sp|P60008|HILS1_HUMAN Spermatid-specific linker histone H1-like protein OS = *Homo sapiens* GN = HILS1', 231, 25631]
['1.32', 18, 'sp|Q93079|H2B1H_HUMAN Histone H2B type 1-H OS = *Homo sapiens* GN = HIST1H2BH', 126, 13892]
['1.32', 18, 'sp|O60814|H2B1K_HUMAN Histone H2B type 1-K OS = *Homo sapiens* GN = HIST1H2BK', 126, 13890]
['1.31', 20, 'sp|Q71DI3|H32_HUMAN Histone H3.2 OS = *Homo sapiens* GN = HIST2H3A', 136, 15388]
['1.31', 20, 'sp|P84243|H33_HUMAN Histone H3.3 OS = *Homo sapiens* GN = H3F3A', 136, 15327]
['1.31', 20, 'sp|P68431|H31_HUMAN Histone H3.1 OS = *Homo sapiens* GN = HIST1H3A', 136, 15404]
['1.31', 18, 'sp|Q99880|H2B1L_HUMAN Histone H2B type 1-L OS = *Homo sapiens* GN = HIST1H2BL', 126, 13952]
['1.31', 18, 'sp|Q99879|H2B1M_HUMAN Histone H2B type 1-M OS = *Homo sapiens* GN = HIST1H2BM', 126, 13989]
['1.31', 18, 'sp|Q99877|H2B1N_HUMAN Histone H2B type 1-N OS = *Homo sapiens* GN = HIST1H2BN', 126, 13922]
['1.31', 18, 'sp|Q8N257|H2B3B_HUMAN Histone H2B type 3-B OS = *Homo sapiens* GN = HIST3H2BB', 126, 13908]
['1.31', 18, 'sp|Q5QNW6|H2B2F_HUMAN Histone H2B type 2-F OS = *Homo sapiens* GN = HIST2H2BF', 126, 13920]
['1.31', 18, 'sp|Q16778|H2B2E_HUMAN Histone H2B type 2-E OS = *Homo sapiens* GN = HIST2H2BE', 126, 13920]
['1.31', 18, 'sp|P58876|H2B1D_HUMAN Histone H2B type 1-D OS = *Homo sapiens* GN = HIST1H2BD', 126, 13936]
['1.31', 18, 'sp|P57053|H2BFS_HUMAN Histone H2B type F-S OS = *Homo sapiens* GN = H2BFS', 126, 13944]
['1.31', 18, 'sp|P33778|H2B1B_HUMAN Histone H2B type 1-B OS = *Homo sapiens* GN = HIST1H2BB', 126, 13950]
['1.31', 18, 'sp|P23527|H2B1O_HUMAN Histone H2B type 1-O OS = *Homo sapiens* GN = HIST1H2BO', 126, 13906]
['1.31', 18, 'sp|P06899|H2B1J_HUMAN Histone H2B type 1-J OS = *Homo sapiens* GN = HIST1H2BJ', 126, 13904]
['1.30', 20, 'sp|Q16695|H31T_HUMAN Histone H3.1t OS = *Homo sapiens* GN = HIST3H3', 136, 15508]
['1.29', 18, 'sp|Q96A08|H2B1A_HUMAN Histone H2B type 1-A OS = *Homo sapiens* GN = HIST1H2BA', 127, 14167]
['1.28', 12, 'sp|P05204|HMGN2_HUMAN Non-histone chromosomal protein HMG-17 OS = *Homo sapiens* GN = HMGN2', 90, 9392]
['1.24', 17, 'sp|Q16777|H2A2C_HUMAN Histone H2A type 2-C OS = *Homo sapiens* GN = HIST2H2AC', 129, 13988]
['1.23', 17, 'sp|Q93077|H2A1C_HUMAN Histone H2A type 1-C OS = *Homo sapiens* GN = HIST1H2AC', 130, 14105]
['1.23', 17, 'sp|Q7L7L0|H2A3_HUMAN Histone H2A type 3 OS = *Homo sapiens* GN = HIST3H2A', 130, 14121]
['1.23', 17, 'sp|Q6FI13|H2A2A_HUMAN Histone H2A type 2-A OS = *Homo sapiens* GN = HIST2H2AA3', 130, 14095]
['1.23', 17, 'sp|P20671|H2A1D_HUMAN Histone H2A type 1-D OS = *Homo sapiens* GN = HIST1H2AD', 130, 14107]
['1.23', 17, 'sp|P0C0S8|H2A1_HUMAN Histone H17/2A type 1 OS = *Homo sapiens* GN = HIST1H2AG', 130, 14091]
['1.23', 17, 'sp|P04908|H2A1B_HUMAN Histone H2A type 1-B/E OS = *Homo sapiens* GN = HIST1H2AB', 130, 14135]
['1.19', 18, 'sp|Q6NXT2|H3L_HUMAN Histone H3-like OS = *Homo sapiens*', 135, 15213]
['1.18', 16, 'sp|Q96KK5|H2A1H_HUMAN Histone H2A type 1-H OS = *Homo sapiens* GN = HIST1H2AH', 128, 13906]
['1.17', 16, 'sp|Q99878|H2A1J_HUMAN Histone H2A type 1-J OS = *Homo sapiens* GN = HIST1H2AJ', 128, 13936]
['1.16', 16, 'sp|Q8IUE6|H2A2B_HUMAN Histone H2A type 2-B OS = *Homo sapiens* GN = HIST2H2AB', 130, 13995]
['1.09', 15, 'sp|Q96QV6|H2A1A_HUMAN Histone H2A type 1-A OS = *Homo sapiens* GN = HIST1H2AA', 131, 14233]
['1.08', 16, 'sp|P16104|H2AX_HUMAN Histone H2A.x OS = *Homo sapiens* GN = H2AFX', 143, 15144]
['1.08', 14, 'sp|Q71UI9|H2AV_HUMAN Histone H2A.V OS = *Homo sapiens* GN = H2AFV', 128, 13508]
['1.07', 14, 'sp|P0C0S5|H2AZ_HUMAN Histone H2A.Z OS = *Homo sapiens* GN = H2AFZ', 128, 13552]

Ribosome

['2.87', 19, 'sp|P62861|RS30_HUMAN 40S ribosomal protein S30 OS = *Homo sapiens* GN = FAU', 59, 6647]
['2.84', 18, 'sp|P62891|RL39_HUMAN 60S ribosomal protein L39 OS = *Homo sapiens* GN = RPL39', 51, 6406]
['2.57', 16, 'sp|Q96EH5|RL39L_HUMAN 60S ribosomal protein L39-like OS = *Homo sapiens* GN = RPL39L', 51, 6292]
['2.54', 28, 'sp|P61927|RL37_HUMAN 60S ribosomal protein L37 OS = *Homo sapiens* GN = RPL37', 97, 11077]
['2.28', 40, 'sp|P47914|RL29_HUMAN 60S ribosomal protein L29 OS = *Homo sapiens* GN = RPL29', 159, 17752]
['2.17', 28, 'sp|P49207|RL34_HUMAN 60S ribosomal protein L34 OS = *Homo sapiens* GN = RPL34', 117, 13292]
['2.17', 27, 'sp|Q969Q0|RL36L_HUMAN 60S ribosomal protein L36a-like OS = *Homo sapiens* GN = RPL36AL', 106, 12468]
['2.17', 27, 'sp|P83881|RL36A_HUMAN 60S ribosomal protein L36a OS = *Homo sapiens* GN = RPL36A', 106, 12440]
['2.07', 30, 'sp|P42766|RL35_HUMAN 60S ribosomal protein L35 OS = *Homo sapiens* GN = RPL35', 123, 14551]
['2.07', 25, 'sp|Q9Y3U8|RL36_HUMAN 60S ribosomal protein L36 OS = *Homo sapiens* GN = RPL36', 105, 12253]
['1.97', 35, 'sp|P83731|RL24_HUMAN 60S ribosomal protein L24 OS = *Homo sapiens* GN = RPL24', 157, 17778]
['1.92', 30, 'sp|P46779|RL28_HUMAN 60S ribosomal protein L28 OS = *Homo sapiens* GN = RPL28', 137, 15747]
['1.90', 44, 'sp|P84098|RL19_HUMAN 60S ribosomal protein L19 OS = *Homo sapiens* GN = RPL19', 196, 23465]
['1.85', 19, 'sp|P61513|RL37A_HUMAN 60S ribosomal protein L37a OS = *Homo sapiens* GN = RPL37A', 92, 10275]
['1.72', 37, 'sp|Q07020|RL18_HUMAN 60S ribosomal protein L18 OS = *Homo sapiens* GN = RPL18', 188, 21634]
['1.69', 22, 'sp|P62854|RS26_HUMAN 40S ribosomal protein S26 OS = *Homo sapiens* GN = RPS26', 115, 13015]
['1.68', 39, 'sp|P50914|RL14_HUMAN 60S ribosomal protein L14 OS = *Homo sapiens* GN = RPL14', 213, 23289]
['1.66', 26, 'sp|P62910|RL32_HUMAN 60S ribosomal protein L32 OS = *Homo sapiens* GN = RPL32', 135, 15859]
['1.65', 39, 'sp|P61313|RL15_HUMAN 60S ribosomal protein L15 OS = *Homo sapiens* GN = RPL15', 204, 24146]
['1.63', 26, 'sp|P46776|RL27A_HUMAN 60S ribosomal protein L27a OS = *Homo sapiens* GN = RPL27A', 148, 16561]
['1.63', 19, 'sp|Q9P0J6|RM36_HUMAN 39S ribosomal protein L36, mitochondrial OS = *Homo sapiens* GN = MRPL36', 103, 11784]
['1.62', 39, 'sp|P26373|RL13_HUMAN 60S ribosomal protein L13 OS = *Homo sapiens* GN = RPL13', 211, 24261]
['1.61', 52, 'sp|Q02878|RL6_HUMAN 60S ribosomal protein L6 OS = *Homo sapiens* GN = RPL6', 288, 32727]
['1.59', 25, 'sp|P61353|RL27_HUMAN 60S ribosomal protein L27 OS = *Homo sapiens* GN = RPL27', 136, 15797]
['1.55', 36, 'sp|P40429|RL13A_HUMAN 60S ribosomal protein L13a OS = *Homo sapiens* GN = RPL13A', 203, 23577]
['1.55', 27, 'sp|P62750|RL23A_HUMAN 60S ribosomal protein L23a OS = *Homo sapiens* GN = RPL23A', 156, 17695]
['1.54', 33, 'sp|Q9NZE8|RM35_HUMAN 39S ribosomal protein L35, mitochondrial OS = *Homo sapiens* GN = MRPL35', 188, 21514]
['1.53', 19, 'sp|P18077|RL35A_HUMAN 60S ribosomal protein L35a OS = *Homo sapiens* GN = RPL35A', 110, 12537]
['1.50', 71, 'sp|P36578|RL4_HUMAN 60S ribosomal protein L4 OS = *Homo sapiens* GN = RPL4', 427, 47697]
['1.49', 15, 'sp|Q9BQ48|RM34_HUMAN 39S ribosomal protein L34, mitochondrial OS = *Homo sapiens* GN = MRPL34', 92, 10164]
['1.48', 25, 'sp|Q9UNX3|RL26L_HUMAN 60S ribosomal protein L26-like 1 OS = *Homo sapiens* GN = RPL26L1', 145, 17256]
['1.48', 25, 'sp|P61254|RL26_HUMAN 60S ribosomal protein L26 OS = *Homo sapiens* GN = RPL26', 145, 17258]
['1.47', 42, 'sp|P62753|RS6_HUMAN 40S ribosomal protein S6 OS = *Homo sapiens* GN = RPS6', 249, 28680]
['1.46', 11, 'sp|P63173|RL38_HUMAN 60S ribosomal protein L38 OS = *Homo sapiens* GN = RPL38', 70, 8217]
['1.45', 11, 'sp|O75394|RM33_HUMAN 39S ribosomal protein L33, mitochondrial OS = *Homo sapiens* GN = MRPL33', 65, 7619]
['1.41', 34, 'sp|P62241|RS8_HUMAN 40S ribosomal protein S8 OS = *Homo sapiens* GN = RPS8', 208, 24205]
['1.39', 19, 'sp|P62851|RS25_HUMAN 40S ribosomal protein S25 OS = *Homo sapiens* GN = RPS25', 125, 13742]
['1.38', 41, 'sp|P62424|RL7A_HUMAN 60S ribosomal protein L7a OS = *Homo sapiens* GN = RPL7A', 266, 29995]
['1.38', 40, 'sp|P18124|RL7_HUMAN 60S ribosomal protein L7 OS = *Homo sapiens* GN = RPL7', 248, 29225]

| Ratio | Charge | Name | aa | MW |
|---|---|---|---|---|

['1.38', 25, 'sp|P46778|RL21_HUMAN 60S ribosomal protein L21 OS = *Homo sapiens* GN = RPL21', 160, 18564]
['1.37', 28, 'sp|Q02543|RL18A_HUMAN 60S ribosomal protein L18a OS = *Homo sapiens* GN = RPL18A', 176, 20762]
['1.36', 9, 'sp|P62273|RS29_HUMAN 40S ribosomal protein S29 OS = *Homo sapiens* GN = RPS29', 56, 6676]
['1.35', 37, 'sp|P62917|RL8_HUMAN 60S ribosomal protein L8 OS = *Homo sapiens* GN = RPL8', 257, 28024]
['1.35', 21, 'sp|P62266|RS23_HUMAN 40S ribosomal protein S23 OS = *Homo sapiens* GN = RPS23', 143, 15807]
['1.32', 39, 'sp|O95478|NSA2_HUMAN Ribosome biogenesis protein NSA2 homolog OS = *Homo sapiens* GN = TINP1', 260, 30065]
['1.30', 20, 'sp|Q86WX3|S19BP_HUMAN 40S ribosomal protein S19-binding protein 1 OS = *Homo sapiens* GN = RPS19BP1', 136, 15433]
['1.28', 22, 'sp|Q9BYC9|RM20_HUMAN 39S ribosomal protein L20, mitochondrial OS = *Homo sapiens* GN = MRPL20', 149, 17442]
['1.26', 23, 'sp|P62280|RS11_HUMAN 40S ribosomal protein S11 OS = *Homo sapiens* GN = RPS11', 158, 18430]
['1.21', 18, 'sp|Q4U2R6|RM51_HUMAN 39S ribosomal protein L51, mitochondrial OS = *Homo sapiens* GN = MRPL51', 128, 15094]
['1.19', 20, 'sp|P62277|RS13_HUMAN 40S ribosomal protein S13 OS = *Homo sapiens* GN = RPS13', 151, 17222]
['1.19', 17, 'sp|P62899|RL31_HUMAN 60S ribosomal protein L31 OS = *Homo sapiens* GN = RPL31', 125, 14462]
['1.16', 20, 'sp|P62269|RS18_HUMAN 40S ribosomal protein S18 OS = *Homo sapiens* GN = RPS18', 152, 17718]
['1.14', 17, 'sp|P62829|RL23_HUMAN 60S ribosomal protein L23 OS = *Homo sapiens* GN = RPL23', 140, 14865]
['1.12', 33, 'sp|P82914|RT15_HUMAN 28S ribosomal protein S15, mitochondrial OS = *Homo sapiens* GN = MRPS15', 257, 29842]
['1.10', 51, 'sp|Q92901|RL3L_HUMAN 60S ribosomal protein L3-like OS = *Homo sapiens* GN = RPL3L', 407, 46295]
['1.10', 18, 'sp|P62249|RS16_HUMAN 40S ribosomal protein S16 OS = *Homo sapiens* GN = RPS16', 146, 16445]
['1.09', 23, 'sp|P18621|RL17_HUMAN 60S ribosomal protein L17 OS = *Homo sapiens* GN = RPL17', 184, 21397]
['1.07', 21, 'sp|Q9UHA3|RLP24_HUMAN Probable ribosome biogenesis protein RLP24 OS = *Homo sapiens* GN = C15orf15', 163, 19621]
['1.07', 16, 'sp|O60783|RT14_HUMAN 28S ribosomal protein S14, mitochondrial OS = *Homo sapiens* GN = MRPS14', 128, 15138]
['1.06', 16, 'sp|O15235|RT12_HUMAN 28S ribosomal protein S12, mitochondrial OS = *Homo sapiens* GN = MRPS12', 138, 15172]
['1.05', 48, 'sp|P39023|RL3_HUMAN 60S ribosomal protein L3 OS = *Homo sapiens* GN = RPL3', 403, 46108]
['1.03', 25, 'sp|P27635|RL10_HUMAN 60S ribosomal protein L10 OS = *Homo sapiens* GN = RPL10', 214, 24603]
['1.03', 16, 'sp|Q9P0M9|RM27_HUMAN 39S ribosomal protein L27, mitochondrial OS = *Homo sapiens* GN = MRPL27', 148, 16072]
['1.03', 11, 'sp|P82921|RT21_HUMAN 28S ribosomal protein S21, mitochondrial OS = *Homo sapiens* GN = MRPS21', 87, 10741]
['1.02', 12, 'sp|Q9BQC6|RT63_HUMAN Ribosomal protein 63, mitochondrial OS = *Homo sapiens* GN = MRP63', 102, 12266]
['1.00', 28, 'sp|Q6DKI1|RL7L_HUMAN 60S ribosomal protein L7-like 1 OS = *Homo sapiens* GN = RPL7L1', 246, 28660]
['0.99', 22, 'sp|P46781|RS9_HUMAN 40S ribosomal protein S9 OS = *Homo sapiens* GN = RPS9', 194, 22591]
['0.98', 53, 'sp|O76021|RL1D1_HUMAN Ribosomal L1 domain-containing protein 1 OS = *Homo sapiens* GN = RSL1D1', 490, 54972]
['0.97', 32, 'sp|Q5T653|RM02_HUMAN 39S ribosomal protein L2, mitochondrial OS = *Homo sapiens* GN = MRPL2', 305, 33300]
['0.96', 23, 'sp|Q96L21|RL10L_HUMAN 60S ribosomal protein L10-like OS = *Homo sapiens* GN = RPL10L', 214, 24518]
['0.96', 21, 'sp|Q9NVS2|RT18A_HUMAN 28S ribosomal protein S18a, mitochondrial OS = *Homo sapiens* GN = MRPS18A', 196, 22183]
['0.96', 9, 'sp|Q71UM5|RS27L_HUMAN 40S ribosomal protein S27-like protein OS = *Homo sapiens* GN = RPS27L', 84, 9477]
['0.96', 9, 'sp|P42677|RS27_HUMAN 40S ribosomal protein S27 OS = *Homo sapiens* GN = RPS27', 84, 9461]
['0.93', 38, 'sp|Q15050|RRS1_HUMAN Ribosome biogenesis regulatory protein homolog OS = *Homo sapiens* GN = RRS1', 365, 41193]
['0.90', 14, 'sp|Q6P1L8|RM14_HUMAN 39S ribosomal protein L14, mitochondrial OS = *Homo sapiens* GN = MRPL14', 145, 15947]
['0.90', 14, 'sp|P39019|RS19_HUMAN 40S ribosomal protein S19 OS = *Homo sapiens* GN = RPS19', 145, 16060]
['0.87', 25, 'sp|Q9HD33|RM47_HUMAN 39S ribosomal protein L47, mitochondrial OS = *Homo sapiens* GN = MRPL47', 252, 29577]
['0.86', 21, 'sp|P62906|RL10A_HUMAN 60S ribosomal protein L10a OS = *Homo sapiens* GN = RPL10A', 217, 24831]
['0.84', 26, 'sp|P15880|RS2_HUMAN 40S ribosomal protein S2 OS = *Homo sapiens* GN = RPS2', 293, 31324]
['0.83', 13, 'sp|Q9Y3D5|RT18C_HUMAN 28S ribosomal protein S18c, mitochondrial OS = *Homo sapiens* GN = MRPS18C', 142, 15849]
RS Domain

['1.74', 44, 'sp|Q01130|SFRS2_HUMAN Splicing factor, arginine/serine-rich 2 OS = *Homo sapiens* GN = SFRS2', 221, 25476]
['1.66', 93, 'sp|Q08170|SFRS4_HUMAN Splicing factor, arginine/serine-rich 4 OS = *Homo sapiens* GN = SFRS4', 494, 56678]
['1.35', 26, 'sp|P84103|SFRS3_HUMAN Splicing factor, arginine/serine-rich 3 OS = *Homo sapiens* GN = SFRS3', 164, 19329]
['0.91', 48, 'sp|P05519|SFR11_HUMAN Splicing factor arginine/serine-rich 11 OS = *Homo sapiens* GN = SFRS11', 484, 53542]
Isoforms

['2.10', 36, 'sp|Q8N2M8-2|SFR16_HUMAN Isoform 2 of Splicing factor, arginine/serine-rich 16 OS = *Homo sapiens* GN = SFRS16', 159, 17218]
['1.96', 41, 'sp|Q8IZA3-2|H1FOO_HUMAN Isoform 2 of Histone H1oo OS = *Homo sapiens* GN = H1FOO', 207, 21010]
['1.93', 51, 'sp|Q9BUV0-3|CA063_HUMAN Isoform 3 of UPF0471 protein C1orf63 OS = *Homo sapiens* GN = C1orf63', 226, 26604]
['1.93', 10, 'sp|Q9Y5P2-3|CSAG2_HUMAN Isoform 3 of Chondrosarcoma-associated gene 2/3A protein OS = *Homo sapiens* GN = CSAG2', 48, 5216]
['1.87', 28, 'sp|Q8NAV1-2|PR38A_HUMAN Isoform 2 of Pre-mRNA-splicing factor 38A OS = *Homo sapiens* GN = PRPF38A', 125, 15462]
['1.83', 10, 'sp|Q32NB8-4|PGPS1_HUMAN Isoform 4 of CDP-diacylglycerol--glycerol-3-phosphate 3-phosphatidyltransferase, mitochondrial OS = *Homo sapiens* GN = PGS1', 50, 5463]
['1.77', 50, 'sp|Q9BUV0-2|CA063_HUMAN Isoform 2 of UPF0471 protein C1orf63 OS = *Homo sapiens* GN = C1orf63', 242, 28363]
['1.74', 30, 'sp|P49760-2|CLK2_HUMAN Isoform Short of Dual specificity protein kinase CLK2 OS = *Homo sapiens* GN = CLK2', 139, 17569]
['1.68', 46, 'sp|Q16629-1|SFRS7_HUMAN Isoform 1 of Splicing factor, arginine/serine-rich 7 OS = *Homo sapiens* GN = SFRS7', 238, 27366]
['1.68', 25, 'sp|P62847-2|RS24_HUMAN Isoform 2 of 40S ribosomal protein S24 OS = *Homo sapiens* GN = RPS24', 130, 15068]
['1.66', 59, 'sp|Q8IZA3-1|H1FOO_HUMAN Isoform 1 of Histone H1oo OS = *Homo sapiens* GN = H1FOO', 346, 35813]
['1.66', 53, 'sp|Q9BRL6-1|SFR2B_HUMAN Isoform 1 of Splicing factor, arginine/serine-rich 2B OS = *Homo sapiens* GN = SFRS2B', 282, 32287]
['1.65', 25, 'sp|P62847-1|RS24_HUMAN Isoform 1 of 40S ribosomal protein S24 OS = *Homo sapiens* GN = RPS24', 133, 15423]
['1.61', 54, 'sp|Q9BUV0-1|CA063_HUMAN Isoform 1 of UPF0471 protein C1orf63 OS = *Homo sapiens* GN = C1orf63', 290, 33613]
['1.61', 50, 'sp|Q9BRL6-2|SFR2B_HUMAN Isoform 2 of Splicing factor, arginine/serine-rich 2B OS = *Homo sapiens* GN = SFRS2B', 275, 31424]
['1.61', 6, 'sp|Q92876-3|KLK6_HUMAN Isoform 3 of Kallikrein-6 OS = *Homo sapiens* GN = KLK6', 40, 4333]
['1.60', 54, 'sp|Q15287-1|RNPS1_HUMAN Isoform 1 of RNA-binding protein with serine-rich domain 1 OS = *Homo sapiens* GN = RNPS1', 305, 34208]
['1.58', 32, 'sp|Q13875-2|MOBP_HUMAN Isoform 2 of Myelin-associated oligodendrocyte basic protein OS = *Homo sapiens* GN = MOBP', 182, 20772]
['1.57', 49, 'sp|Q15287-2|RNPS1_HUMAN Isoform 2 of RNA-binding protein with serine-rich domain 1 OS = *Homo sapiens* GN = RNPS1', 282, 31709]
['1.57', 32, 'sp|Q13875-1|MOBP_HUMAN Isoform 1 of Myelin-associated oligodendrocyte basic protein OS = *Homo sapiens* GN = MOBP', 183, 20959]
['1.56', 50, 'sp|Q66PJ3-5|AR6P4_HUMAN Isoform 5 of ADP-ribosylation factor-like protein 6-interacting protein 4 OS = *Homo sapiens* GN = ARL6IP4', 304, 32178]

-continued

| Ratio | Charge | Name | aa | MW |
|---|---|---|---|---|

['1.55', 44, 'sp|Q9HB58-4|SP110_HUMAN Isoform 4 of Sp110 nuclear body protein OS = *Homo sapiens* GN = SP110', 248, 28609]
['1.54', 33, 'sp|Q66PJ3-6|AR6P4_HUMAN Isoform 6 of ADP-ribosylation factor-like protein 6-interacting protein 4 OS = *Homo sapiens* GN = ARL6IP4', 215, 22007]
['1.51', 28, 'sp|P49761-2|CLK3_HUMAN Isoform 2 of Dual specificity protein kinase CLK3 OS = *Homo sapiens* GN = CLK3', 152, 18971]
['1.44', 18, 'sp|Q14CB8-4|RHG19_HUMAN Isoform 4 of Rho GTPase-activating protein 19 OS = *Homo sapiens* GN = ARHGAP19', 112, 12547]
['1.44', 13, 'sp|Q13875-3|MOBP_HUMAN Isoform 3 of Myelin-associated oligodendrocyte basic protein OS = *Homo sapiens* GN = MOBP', 81, 9614]
['1.43', 44, 'sp|O75494-2|FUSIP_HUMAN Isoform 2 of FUS-interacting serine-arginine-rich protein 1 OS = *Homo sapiens* GN = FUSIP1', 261, 31213]
['1.43', 12, 'sp|Q15651-2|HMGN3_HUMAN Isoform 2 of High mobility group nucleosome-binding domain-containing protein 3 OS = *Homo sapiens* GN = HMGN3', 77, 8377]
['1.42', 56, 'sp|Q13247-1|SFRS6_HUMAN Isoform SRP55-1 of Splicing factor, arginine/serine-rich 6 OS = *Homo sapiens* GN = SFRS6', 344, 39586]
['1.42', 44, 'sp|O75494-1|FUSIP_HUMAN Isoform 1 of FUS-interacting serine-arginine-rich protein 1 OS = *Homo sapiens* GN = FUSIP1', 262, 31300]
['1.42', 8, 'sp|Q70YC5-5|ZN365_HUMAN Isoform 6 of Protein ZNF365 OS = *Homo sapiens* GN = ZNF365', 51, 5653]
['1.41', 48, 'sp|Q9UK58-3|CCNL1_HUMAN Isoform 3 of Cyclin-L1 OS = *Homo sapiens* GN = CCNL1', 299, 34688]
['1.41', 9, 'sp|Q2NKX9-2|CB068_HUMAN Isoform 2 of UPF0561 protein C2orf68 OS = *Homo sapiens* GN = C2orf68', 58, 6747]
['1.39', 25, 'sp|Q66K41-2|Z385C_HUMAN Isoform 2 of Zinc finger protein 385C OS = *Homo sapiens* GN = ZNF385C', 174, 18242]
['1.38', 10, 'sp|Q9UQ07-3|MOK_HUMAN Isoform 3 of MAPK/MAK/MRK overlapping kinase OS = *Homo sapiens* GN = RAGE', 73, 7879]
['1.37', 42, 'sp|Q13243-3|SFRS5_HUMAN Isoform SRP40-4 of Splicing factor, arginine/serine-rich 5 OS = *Homo sapiens* GN = SFRS5', 269, 30858]
['1.36', 23, 'sp|Q6PGN9-4|PSRC1_HUMAN Isoform D of Proline/serine-rich coiled-coil protein 1 OS = *Homo sapiens* GN = PSRC1', 163, 16980]
['1.36', 15, 'sp|Q6P1Q0-6|LTMD1_HUMAN Isoform 6 of LETM1 domain-containing protein 1 OS = *Homo sapiens* GN = LETMD1', 99, 11221]
['1.36', 10, 'sp|O75920-2|SERF1_HUMAN Isoform Short of Small EDRK-rich factor 1 OS = *Homo sapiens* GN = SERF1A', 62, 7336]
['1.35', 68, 'sp|Q7L4I2-1|RSRC2_HUMAN Isoform 1 of Arginine/serine-rich coiled-coil protein 2 OS = *Homo sapiens* GN = RSRC2', 434, 50559]
['1.35', 31, 'sp|Q96HZ4-2|HES6_HUMAN Isoform 2 of Transcription cofactor HES-6 OS = *Homo sapiens* GN = HES6', 214, 23483]
['1.35', 24, 'sp|Q8N726-1|CD2A2_HUMAN Isoform 4 of Cyclin-dependent kinase inhibitor 2A, isoform 4 OS = *Homo sapiens* GN = CDKN2A', 173, 18005]
['1.35', 11, 'sp|Q5JUX0-2|SPIN3_HUMAN Isoform 2 of Spindlin-3 OS = *Homo sapiens* GN = SPIN3', 77, 8415]
['1.34', 17, 'sp|P49450-2|CENPA_HUMAN Isoform 2 of Histone H3-like centromeric protein A OS = *Homo sapiens* GN = CENPA', 114, 13001]
['1.31', 58, 'sp|Q7L4I2-2|RSRC2_HUMAN Isoform 2 of Arginine/serine-rich coiled-coil protein 2 OS = *Homo sapiens* GN = RSRC2', 386, 44878]
['1.29', 40, 'sp|Q13243-1|SFRS5_HUMAN Isoform SRP40-1 of Splicing factor, arginine/serine-rich 5 OS = *Homo sapiens* GN = SFRS5', 272, 31263]
['1.28', 47, 'sp|Q9UK58-2|CCNL1_HUMAN Isoform 2 of Cyclin-L1 OS = *Homo sapiens* GN = CCNL1', 320, 37273]
['1.28', 15, 'sp|Q66K41-3|Z385C_HUMAN Isoform 3 of Zinc finger protein 385C OS = *Homo sapiens* GN = ZNF385C', 114, 11856]
['1.25', 35, 'sp|Q5BKY9-1|F133B_HUMAN Isoform 1 of Protein FAM133B OS = *Homo sapiens* GN = FAM133B', 247, 28385]
['1.25', 9, 'sp|Q86SI9-3|CEI_HUMAN Isoform 3 of Protein CEI OS = *Homo sapiens* GN = C5orf38', 70, 7333]
['1.24', 47, 'sp|Q96IZ7-1|RSRC1_HUMAN Isoform 1 of Arginine/serine-rich coiled-coil protein 1 OS = *Homo sapiens* GN = RSRC1', 334, 38677]
['1.24', 41, 'sp|P62995-1|TRA2B_HUMAN Isoform 1 of Splicing factor, arginine/serine-rich 10 OS = *Homo sapiens* GN = SFRS10', 288, 33665]
['1.24', 30, 'sp|Q86SI9-2|CEI_HUMAN Isoform 2 of Protein CEI OS = *Homo sapiens* GN = C5orf38', 226, 24375]
['1.24', 17, 'sp|Q9HC23-1|PROK2_HUMAN Isoform 1 of Prokineticin-2 OS = *Homo sapiens* GN = PROK2', 129, 14314]
['1.23', 41, 'sp|Q96S94-3|CCNL2_HUMAN Isoform 3 of Cyclin-L2 OS = *Homo sapiens* GN = CCNL2', 298, 33839]
['1.23', 33, 'sp|Q5BKY9-2|F133B_HUMAN Isoform 2 of Protein FAM133B OS = *Homo sapiens* GN = FAM133B', 237, 27193]
['1.23', 17, 'sp|Q9BTM1-1|H2AJ_HUMAN Isoform 1 of Histone H2A.J OS = *Homo sapiens* GN = H2AFJ', 129, 14019]
['1.22', 44, 'sp|Q66PJ3-4|AR6P4_HUMAN Isoform 4 of ADP-ribosylation factor-like protein 6-interacting protein 4 OS = *Homo sapiens* GN = ARL6IP4', 338, 36210]
['1.22', 11, 'sp|Q8TEW8-4|PAR3L_HUMAN Isoform 4 of Partitioning-defective 3 homolog B OS = *Homo sapiens* GN = PARD3B', 79, 9007]
['1.21', 46, 'sp|Q13247-3|SFRS6_HUMAN Isoform SRP55-3 of Splicing factor, arginine/serine-rich 6 OS = *Homo sapiens* GN = SFRS6', 335, 38418]
['1.21', 44, 'sp|Q66PJ3-3|AR6P4_HUMAN Isoform 3 of ADP-ribosylation factor-like protein 6-interacting protein 4 OS = *Homo sapiens* GN = ARL6IP4', 341, 36612]
['1.20', 45, 'sp|Q66PJ3-2|AR6P4_HUMAN Isoform 2 of ADP-ribosylation factor-like protein 6-interacting protein 4 OS = *Homo sapiens* GN = ARL6IP4', 352, 37638]
['1.20', 12, 'sp|Q8N6C7-2|PGSF1_HUMAN Isoform 2 of Pituitary gland-specific factor 1 OS = *Homo sapiens* GN = PGSF1', 91, 10048]
['1.19', 38, 'sp|Q13595-1|TRA2A_HUMAN Isoform Long of Transformer-2 protein homolog OS = *Homo sapiens* GN = TRA2A', 282, 32688]
['1.17', 45, 'sp|Q66PJ3-1|AR6P4_HUMAN Isoform 1 of ADP-ribosylation factor-like protein 6-interacting protein 4 OS = *Homo sapiens* GN = ARL6IP4', 360, 38395]
['1.17', 12, 'sp|O75365-3|TP4A3_HUMAN Isoform 3 of Protein tyrosine phosphatase type IVA 3 OS = *Homo sapiens* GN = PTP4A3', 87, 10494]
['1.16', 24, 'sp|P02686-3|MBP_HUMAN Isoform 3 of Myelin basic protein OS = *Homo sapiens* GN = MBP', 197, 21493]
['1.15', 22, 'sp|P17096-3|HMGA1_HUMAN Isoform HMG-R of High mobility group protein HMG-I/HMG-Y OS = *Homo sapiens* GN = HMGA1', 179, 19694]
['1.15', 7, 'sp|Q8IU53-2|CASC2_HUMAN Isoform 2 of Protein CASC2, isoforms 1/2 OS = *Homo sapiens* GN = CASC2', 55, 6154]
['1.14', 13, 'sp|P31260-2|HXA10_HUMAN Isoform 2 of Homeobox protein Hox-A10 OS = *Homo sapiens* GN = HOXA10', 94, 11452]
['1.14', 12, 'sp|Q9NZQ0-2|RABJ_HUMAN Isoform 2 of Rab and DnaJ domain-containing protein OS = *Homo sapiens* GN = RBJ', 90, 10621]
['1.14', 10, 'sp|Q8IVJ8-2|APRG1_HUMAN Isoform 2 of AP20 region protein 1 OS = *Homo sapiens* GN = APRG1', 78, 8910]
['1.14', 9, 'sp|Q6QHF9-10|PAOX_HUMAN Isoform 12 of Peroxisomal N(1)-acetyl-spermine/spermidine oxidase OS = *Homo sapiens* GN = PAOX', 83, 8694]
['1.14', 9, 'sp|P02686-7|MBP_HUMAN Isoform 7 of Myelin basic protein OS = *Homo sapiens* GN = MBP', 74, 8265]
['1.13', 38, 'sp|Q9UQ35-3|SRRM2_HUMAN Isoform 3 of Serine/arginine repetitive matrix protein 2 OS = *Homo sapiens* GN = SRRM2', 311, 34212]
['1.13', 22, 'sp|P02686-4|MBP_HUMAN Isoform 4 of Myelin basic protein OS = *Homo sapiens* GN = MBP', 186, 20245]
['1.13', 20, 'sp|P02686-5|MBP_HUMAN Isoform 5 of Myelin basic protein OS = *Homo sapiens* GN = MBP', 171, 18590]
['1.13', 12, 'sp|P17096-2|HMGA1_HUMAN Isoform HMG-Y of High mobility group protein HMG-I/HMG-Y OS = *Homo sapiens* GN = HMGA1', 96, 10678]
['1.12', 24, 'sp|Q5HYI7-3|MTX3_HUMAN Isoform 3 of Metaxin-3 OS = *Homo sapiens* GN = MTX3', 201, 22355]
['1.11', 31, 'sp|Q9GZR2-2|REXO4_HUMAN Isoform 2 of RNA exonuclease 4 OS = *Homo sapiens* GN = REXO4', 250, 28390]
['1.11', 8, 'sp|Q6H9L7-4|TAIL1_HUMAN Isoform 4 of Thrombospondin and AMOP domain-containing isthmin-like protein 1 OS = *Homo sapiens* GN = THSD3', 76, 7995]
['1.10', 20, 'sp|Q15170-1|TCAL1_HUMAN Isoform 1 of Transcription elongation factor A protein-like 1 OS = *Homo sapiens* GN = TCEAL1', 157, 18354]
['1.10', 11, 'sp|Q6ZUS6-3|CC149_HUMAN Isoform 3 of Coiled-coil domain-containing protein 149 OS = *Homo sapiens* GN = CCDC149', 86, 10164]
['1.10', 7, 'sp|Q70UQ0-3|IKIP_HUMAN Isoform 3 of Inhibitor of nuclear factor kappa-B kinase-interacting protein OS = *Homo sapiens* GN = IKIP', -continued

| Ratio | Charge | Name | aa | MW |
|---|---|---|---|---|

70, 7141]
['1.09', 18, 'sp|P02686-6|MBP_HUMAN Isoform 6 of Myelin basic protein OS = *Homo sapiens* GN = MBP', 160, 17343]
['1.09', 17, 'sp|P49450-1|CENPA_HUMAN Isoform 1 of Histone H3-like centromeric protein A OS = *Homo sapiens* GN = CENPA', 140, 15990]
['1.08', 13, 'sp|Q8WWL7-3|CCNB3_HUMAN Isoform 3 of G2/mitotic-specific cyclin-B3 OS = *Homo sapiens* GN = CCNB3', 111, 12195]
['1.07', 15, 'sp|Q2NKX9-3|CB068_HUMAN Isoform 3 of UPF0561 protein C2orf68 OS = *Homo sapiens* GN = C2orf68', 127, 14480]
['1.07', 10, 'sp|Q8IUX4-2|ABC3F_HUMAN Isoform 2 of DNA dC->dU-editing enzyme APOBEC-3F OS = *Homo sapiens* GN = APOBEC3F', 79, 9444]
['1.06', 9, 'sp|Q8IU53-1|CASC2_HUMAN Isoform 1 of Protein CASC2, isoforms 1/2 OS = *Homo sapiens* GN = CASC2', 76, 8607]
['1.06', 8, 'sp|Q9UBR5-3|CKLF_HUMAN Isoform CKLF3 of Chemokine-like factor OS = *Homo sapiens* GN = CKLF', 67, 7652]
['1.05', 20, 'sp|Q2I0M5-2|RSPO4_HUMAN Isoform 2 of R-spondin-4 OS = *Homo sapiens* GN = RSPO4', 172, 19606]
['1.05', 8, 'sp|Q9NPS7-2|F41CL_HUMAN Isoform 2 of Protein FAM41C-like OS = *Homo sapiens*', 63, 7681]
['1.05', 6, 'sp|O75460-2|ERN1_HUMAN Isoform 2 of Serine/threonine-protein kinase/endoribonuclease IRE1 OS = *Homo sapiens* GN = ERN1', 70, 6648]
['1.04', 46, 'sp|Q5SSJ5-3|HP1B3_HUMAN Isoform 3 of Heterochromatin protein 1-binding protein 3 OS = *Homo sapiens* GN = HP1BP3', 401, 44434]
['1.04', 18, 'sp|Q15973-2|ZN124_HUMAN Isoform 4 of Zinc finger protein 124 OS = *Homo sapiens* GN = ZNF124', 156, 17830]
['1.04', 8, 'sp|Q9NPS7-1|F41CL_HUMAN Isoform 1 of Protein FAM41C-like OS = *Homo sapiens* GN = ', 64, 7809]
['1.03', 90, 'sp|Q13427-1|PPIG_HUMAN Isoform 1 of Peptidyl-prolyl cis-trans isomerase G OS = *Homo sapiens* GN = PPIG', 754, 88618]
['1.03', 29, 'sp|Q9BRU9-1|UTP23_HUMAN Isoform 1 of rRNA-processing protein UTP23 homolog OS = *Homo sapiens* GN = UTP23', 249, 28430]
['1.03', 18, 'sp|Q6PH81-1|CP087_HUMAN Isoform 1 of UPF0547 protein C16orf87 OS = *Homo sapiens* GN = C16orf87', 154, 17799]
['1.03', 17, 'sp|Q7Z6I8-2|CE024_HUMAN Isoform 2 of UPF0461 protein C5orf24 OS = *Homo sapiens* GN = C5orf24', 155, 16724]
['1.03', 17, 'sp|P49759-2|CLK1_HUMAN Isoform Short of Dual specificity protein kinase CLK1 OS = *Homo sapiens* GN = CLK1', 136, 16570]
['1.03', 13, 'sp|Q8NG50-4|RDM1_HUMAN Isoform 4 of RAD52 motif-containing protein 1 OS = *Homo sapiens* GN = RDM1', 116, 13173]
['1.03', 12, 'sp|P17096-1|HMGA1_HUMAN Isoform HMG-I of High mobility group protein HMG-I/HMG-Y OS = *Homo sapiens* GN = HMGA1', 107, 11676]
['1.03', 10, 'sp|P48061-1|SDF1_HUMAN Isoform Beta of Stromal cell-derived factor 1 OS = *Homo sapiens* GN = CXCL12', 93, 10665]
['1.02', 17, 'sp|P82912-3|RT11_HUMAN Isoform 3 of 28S ribosomal protein S11, mitochondrial OS = *Homo sapiens* GN = MRPS11', 161, 16903]
['1.02', 15, 'sp|Q8N1T3-2|MYO1H_HUMAN Isoform 2 of Myosin-Ih OS = *Homo sapiens* GN = MYO1H', 127, 14805]
['1.02', 10, 'sp|Q9NZ81-2|PRR13_HUMAN Isoform 2 of Proline-rich protein 13 OS = *Homo sapiens* GN = PRR13', 98, 10531]
['1.02', 7, 'sp|Q9Y2A0-3|TPAP1_HUMAN Isoform 3 of p53-activated protein 1 OS = *Homo sapiens* GN = TP53AP1', 60, 6937]
['1.01', 32, 'sp|Q9UBB5-3|MBD2_HUMAN Isoform 3 of Methyl-CpG-binding domain protein 2 OS = *Homo sapiens* GN = MBD2', 302, 31744]
['1.01', 19, 'sp|Q9NWS8-4|RMND1_HUMAN Isoform 4 of Required for meiotic nuclear division protein 1 homolog OS = *Homo sapiens* GN = RMND1', 170, 19360]
['1.01', 17, 'sp|Q9H2U2-5|IPYR2_HUMAN Isoform 5 of Inorganic pyrophosphatase 2, mitochondrial OS = *Homo sapiens* GN = PPA2', 157, 16961]
['1.01', 13, 'sp|P08949-1|NMB_HUMAN Isoform 1 of Neuromedin-B OS = *Homo sapiens* GN = NMB', 121, 13255]
['1.00', 37, 'sp|Q09FC8-3|ZN415_HUMAN Isoform 3 of Zinc finger protein 415 OS = *Homo sapiens* GN = ZNF415', 325, 37237]
['1.00', 35, 'sp|Q6ZN11-2|ZN793_HUMAN Isoform 2 of Zinc finger protein 793 OS = *Homo sapiens* GN = ZNF793', 312, 35909]
['1.00', 31, 'sp|Q96IZ7-2|RSRC1_HUMAN Isoform 2 of Arginine/serine-rich coiled-coil protein 1 OS = *Homo sapiens* GN = RSRC1', 276, 31528]
['1.00', 8, 'sp|Q7Z4H3-3|HDDC2_HUMAN Isoform 3 of HD domain-containing protein 2 OS = *Homo sapiens* GN = HDDC2', 71, 8163]
['0.99', 10, 'sp|P56134-2|ATPK_HUMAN Isoform 2 of ATP synthase subunit f, mitochondrial OS = *Homo sapiens* GN = ATP5J2', 88, 10363]
['0.98', 50, 'sp|Q3SXZ3-2|ZN718_HUMAN Isoform 2 of Zinc finger protein 718 OS = *Homo sapiens* GN = ZNF718', 446, 51561]
['0.98', 35, 'sp|Q8IXZ2-2|ZC3H3_HUMAN Isoform 2 of Zinc finger CCCH domain-containing protein 3 OS = *Homo sapiens* GN = ZC3H3', 335, 35929]
['0.98', 24, 'sp|Q9NP64-2|NO40_HUMAN Isoform 2 of Nucleolar protein of 40 kDa OS = *Homo sapiens* GN = ZCCHC17', 217, 24918]
['0.97', 48, 'sp|Q499Z4-1|ZN672_HUMAN Isoform 1 of Zinc finger protein 672 OS = *Homo sapiens* GN = ZNF672', 452, 50224]
['0.97', 11, 'sp|P10747-2|CD28_HUMAN Isoform 2 of T-cell-specific surface glycoprotein CD28 OS = *Homo sapiens* GN = CD28', 101, 11527]
['0.97', 9, 'sp|Q9HC16-3|ABC3G_HUMAN Isoform 3 of DNA dC->dU-editing enzyme APOBEC-3G OS = *Homo sapiens* GN = APOBEC3G', 79, 9385]
['0.97', 5, 'sp|Q16517-2|NNAT_HUMAN Isoform Beta of Neuronatin OS = *Homo sapiens* GN = NNAT', 54, 6153]
['0.97', 4, 'sp|Q96T75-4|DSCR8_HUMAN Isoform 4 of Down syndrome critical region protein 8 OS = *Homo sapiens* GN = DSCR8', 37, 4295]
['0.96', 61, 'sp|Q5VTL8-1|PR38B_HUMAN Isoform 1 of Pre-mRNA-splicing factor 38B OS = *Homo sapiens* GN = PRPF38B', 546, 64467]
['0.96', 14, 'sp|Q8TCC3-3|RM30_HUMAN Isoform 3 of 39S ribosomal protein L30, mitochondrial OS = *Homo sapiens* GN = MRPL30', 131, 15190]
['0.95', 21, 'sp|Q9NY12-1|NOLA1_HUMAN Isoform 1 of H/ACA ribonucleoprotein complex subunit 1 OS = *Homo sapiens* GN = NOLA1', 217, 22347]
['0.95', 14, 'sp|Q7Z7F7-1|RM55_HUMAN Isoform 1 of 39S ribosomal protein L55, mitochondrial OS = *Homo sapiens* GN = MRPL55', 128, 15128]
['0.95', 14, 'sp|Q7Z422-4|CA144_HUMAN Isoform 4 of UPF0485 protein C1orf144 OS = *Homo sapiens* GN = C1orf144', 133, 14760]
['0.95', 11, 'sp|Q2T9K0-3|TMM44_HUMAN Isoform 3 of Transmembrane protein 44 OS = *Homo sapiens* GN = TMEM44', 113, 12491]
['0.94', 70, 'sp|Q8NDQ6-4|ZN540_HUMAN Isoform 4 of Zinc finger protein 540 OS = *Homo sapiens* GN = ZNF540', 637, 74992]
['0.94', 56, 'sp|Q8WXA9-1|SFR12_HUMAN Isoform 1 of Splicing factor, arginine/serine-rich 12 OS = *Homo sapiens* GN = SFRS12', 508, 59380]
['0.94', 43, 'sp|Q3MIS6-2|ZN528_HUMAN Isoform 2 of Zinc finger protein 528 OS = *Homo sapiens* GN = ZNF528', 395, 45715]
['0.94', 22, 'sp|O60258-2|FGF17_HUMAN Isoform 2 of Fibroblast growth factor 17 OS = *Homo sapiens* GN = FGF17', 205, 23669]
['0.94', 10, 'sp|Q9BU19-4|ZN692_HUMAN Isoform 4 of Zinc finger protein 692 OS = *Homo sapiens* GN = ZNF692', 96, 10818]
['0.93', 27, 'sp|Q6P1L5-2|AL2SC_HUMAN Isoform 2 of Amyotrophic lateral sclerosis 2 chromosomal region candidate gene 13 protein OS = *Homo sapiens* GN = ALS2CR13', 289, 29427]
['0.93', 27, 'sp|P12034-1|FGF5_HUMAN Isoform Long of Fibroblast growth factor 5 OS = *Homo sapiens* GN = FGF5', 268, 29550]
['0.92', 89, 'sp|Q9N4W9-2|ZN808_HUMAN Isoform 2 of Zinc finger protein 808 OS = *Homo sapiens* GN = ZNF808', 834, 96803]
['0.92', 20, 'sp|Q5T4W7-1|ARTN_HUMAN Isoform 1 of Artemin OS = *Homo sapiens* GN = ARTN', 220, 22878]
['0.92', 15, 'sp|O15444-1|CCL25_HUMAN Isoform 1 of C-C motif chemokine 25 OS = *Homo sapiens* GN = CCL25', 150, 16609]
['0.92', 12, 'sp|Q8IVJ8-3|APRG1_HUMAN Isoform 3 of AP20 region protein 1 OS = *Homo sapiens* GN = APRG1', 119, 13172]
['0.91', 67, 'sp|Q8NDQ6-2|ZN540_HUMAN Isoform 2 of Zinc finger protein 540 OS = *Homo sapiens* GN = ZNF540', 628, 73708]
['0.91', 19, 'sp|P05019-1|IGF1B_HUMAN Isoform IGF-IB of Insulin-like growth factor IB OS = *Homo sapiens* GN = IGF1', 195, 21841]

-continued

| Ratio | Charge | Name | aa | MW |
|---|---|---|---|---|

['0.91', 14, 'sp|O60565-2|GREM1_HUMAN Isoform 2 of Gremlin-1 OS = *Homo sapiens* GN = GREM1', 143, 16292]
['0.91', 12, 'sp|Q96A00-2|PP14A_HUMAN Isoform 2 of Protein phosphatase 1 regulatory subunit 14A OS = *Homo sapiens* GN = PPP1R14A', 120, 13479]
['0.91', 8, 'sp|P08118-2|MSMB_HUMAN Isoform PSP57 of Beta-microseminoprotein OS = *Homo sapiens* GN = MSMB', 77, 8778]
['0.90', 53, 'sp|Q9UK58-1|CCNL1_HUMAN Isoform 1 of Cyclin-L1 OS = *Homo sapiens* GN = CCNL1', 526, 59633]
['0.90', 40, 'sp|Q03924-1|ZN117_HUMAN Isoform 1 of Zinc finger protein 117 OS = *Homo sapiens* GN = ZNF117', 383, 45066]
['0.90', 27, 'sp|Q9BXY4-1|RSPO3_HUMAN Isoform 1 of R-spondin-3 OS = *Homo sapiens* GN = RSPO3', 272, 30928]
['0.90', 16, 'sp|Q86SG4-3|DPCA2_HUMAN Isoform 3 of Dresden prostate carcinoma protein 2 OS = *Homo sapiens* GN = C15orf21', 150, 17975]
['0.90', 13, 'sp|P47902-2|CDX1_HUMAN Isoform 2 of Homeobox protein CDX-1 OS = *Homo sapiens* GN = CDX1', 130, 14660]
['0.89', 44, 'sp|Q9NXE8-1|CCD49_HUMAN Isoform 1 of Coiled-coil domain-containing protein 49 OS = *Homo sapiens* GN = CCDC49', 425, 49647]
['0.89', 44, 'sp|Q03924-2|ZN117_HUMAN Isoform 2 of Zinc finger protein 117 OS = *Homo sapiens* GN = ZNF117', 427, 50051]
['0.89', 40, 'sp|Q147U1-2|ZN846_HUMAN Isoform 2 of Zinc finger protein 846 OS = *Homo sapiens* GN = ZNF846', 404, 45838]
['0.89', 29, 'sp|Q9BXY4-2|RSPO3_HUMAN Isoform 2 of R-spondin-3 OS = *Homo sapiens* GN = RSPO3', 292, 33233]
['0.89', 20, 'sp|Q5T4W7-3|ARTN_HUMAN Isoform 3 of Artemin OS = *Homo sapiens* GN = ARTN', 228, 23616]
['0.89', 18, 'sp|Q6UXX9-3|RSPO2_HUMAN Isoform 3 of R-spondin-2 OS = *Homo sapiens* GN = RSPO2', 179, 20972]
['0.89', 13, 'sp|Q7Z422-2|CA144_HUMAN Isoform 2 of UPF0485 protein C1orf144 OS = *Homo sapiens* GN = C1orf144', 132, 14604]
['0.89', 9, 'sp|Q8NFV4-3|ABHDB_HUMAN Isoform 3 of Abhydrolase domain-containing protein 11 OS = *Homo sapiens* GN = ABHD11', 97, 10361]
['0.89', 8, 'sp|P48061-2|SDF1_HUMAN Isoform Alpha of Stromal cell-derived factor 1 OS = *Homo sapiens* GN = CXCL12', 89, 10103]
['0.88', 15, 'sp|Q92466-3|DDB2_HUMAN Isoform D2 of DNA damage-binding protein 2 OS = *Homo sapiens* GN = DDB2', 156, 17434]
['0.88', 8, 'sp|Q9HD64-2|GAGD2_HUMAN Isoform B of G antigen family D member 2 OS = *Homo sapiens* GN = XAGE1', 81, 9077]
['0.88', 7, 'sp|Q9BZJ0-5|CRNL1_HUMAN Isoform 5 of Crooked neck-like protein 1 OS = *Homo sapiens* GN = CRNKL1', 74, 7946]
['0.88', 6, 'sp|Q8TC05-3|MDM1_HUMAN Isoform 3 of Nuclear protein MDM1 OS = *Homo sapiens* GN = MDM1', 69, 7926]
['0.87', 74, 'sp|Q9NYF8-4|BCLF1_HUMAN Isoform 4 of Bcl-2-associated transcription factor 1 OS = *Homo sapiens* GN = BCLAF1', 747, 85937]
['0.87', 67, 'sp|Q8NDQ6-1|ZN540_HUMAN Isoform 1 of Zinc finger protein 540 OS = *Homo sapiens* GN = ZNF540', 660, 77093]
['0.87', 52, 'sp|Q03936-2|ZNF92_HUMAN Isoform 2 of Zinc finger protein 92 OS = *Homo sapiens* GN = ZNF92', 517, 60209]
['0.87', 44, 'sp|Q8NEP9-3|ZN555_HUMAN Isoform 3 of Zinc finger protein 555 OS = *Homo sapiens* GN = ZNF555', 440, 51594]
['0.87', 25, 'sp|P22090|RS4Y1_HUMAN 40S ribosomal protein S4, Y isoform 1 OS = *Homo sapiens* GN = RPS4Y1', 263, 29455]
['0.87', 20, 'sp|P55075-2|FGF8_HUMAN Isoform FGF-8A of Fibroblast growth factor 8 OS = *Homo sapiens* GN = FGF8', 204, 23522]
['0.87', 20, 'sp|P12272-3|PTHR_HUMAN Isoform 3 of Parathyroid hormone-related protein OS = *Homo sapiens* GN = PTHLH', 209, 23942]
['0.87', 16, 'sp|Q7Z7F7-2|RM55_HUMAN Isoform 2 of 39S ribosomal protein L55, mitochondrial OS = *Homo sapiens* GN = MRPL55', 164, 18902]
['0.87', 12, 'sp|P10747-4|CD28_HUMAN Isoform 4 of T-cell-specific surface glycoprotein CD28 OS = *Homo sapiens* GN = CD28', 123, 14013]
['0.86', 33, 'sp|Q8N8C0-2|ZN781_HUMAN Isoform 2 of Zinc finger protein 781 OS = *Homo sapiens* GN = ZNF781', 327, 38274]
['0.86', 29, 'sp|Q15973-1|ZN124_HUMAN Isoform 3 of Zinc finger protein 124 OS = *Homo sapiens* GN = ZNF124', 296, 33852]
['0.86', 23, 'sp|Q9H0A6-4|RNF32_HUMAN Isoform 4 of RING finger protein 32 OS = *Homo sapiens* GN = RNF32', 235, 27130]
['0.86', 21, 'sp|Q8IWN7-2|RP1L1_HUMAN Isoform 2 of Retinitis pigmentosa 1-like 1 protein OS = *Homo sapiens* GN = RP1L1', 222, 24854]
['0.86', 20, 'sp|Q6PI47-3|KCD18_HUMAN Isoform 3 of BTB/POZ domain-containing protein KCTD18 OS = *Homo sapiens* GN = KCTD18', 221, 23414]
['0.86', 18, 'sp|O75494-4|FUSIP_HUMAN Isoform 4 of FUS-interacting serine-arginine-rich protein 1 OS = *Homo sapiens* GN = FUSIP1', 173, 21000]
['0.86', 13, 'sp|P10747-3|CD28_HUMAN Isoform 3 of T-cell-specific surface glycoprotein CD28 OS = *Homo sapiens* GN = CD28', 136, 15369]
['0.86', 7, 'sp|P16157-20|ANK1_HUMAN Isoform Mu20 of Ankyrin-1 OS = *Homo sapiens* GN = ANK1', 74, 8374]
['0.85', 45, 'sp|Q68DY1-2|ZN626_HUMAN Isoform 2 of Zinc finger protein 626 OS = *Homo sapiens* GN = ZNF626', 464, 53889]
['0.85', 21, 'sp|O60258-1|FGF17_HUMAN Isoform 1 of Fibroblast growth factor 17 OS = *Homo sapiens* GN = FGF17', 216, 24891]
['0.85', 17, 'sp|P82912-1|RT11_HUMAN Isoform 1 of 28S ribosomal protein S11, mitochondrial OS = *Homo sapiens* GN = MRPS11', 194, 20615]
['0.85', 13, 'sp|Q9BWV2-3|SPAT9_HUMAN Isoform 3 of Spermatogenesis-associated protein 9 OS = *Homo sapiens* GN = SPATA9', 135, 15275]
['0.85', 12, 'sp|Q9Y5P2-1|CSAG2_HUMAN Isoform 1 of Chondrosarcoma-associated gene 2/3A protein OS = *Homo sapiens* GN = CSAG2', 127, 14429]
['0.85', 10, 'sp|Q6RVD6-1|SPAT8_HUMAN Isoform 1 of Spermatogenesis-associated protein 8 OS = *Homo sapiens* GN = SPATA8', 105, 11727]
['0.84', 46, 'sp|Q3SXZ3-1|ZN718_HUMAN Isoform 1 of Zinc finger protein 718 OS = *Homo sapiens* GN = ZNF718', 478, 55404]
['0.84', 36, 'sp|Q3SY52-3|ZIK1_HUMAN Isoform 3 of Zinc finger protein interacting with ribonucleoprotein K OS = *Homo sapiens* GN = ZIK1', 384, 43717]
['0.84', 24, 'sp|Q9BU76-1|MMTA2_HUMAN Isoform 1 of Multiple myeloma tumor-associated protein 2 OS = *Homo sapiens* GN = MMTAG2', 263, 29411]
['0.84', 24, 'sp|Q8TD47|RS4Y2_HUMAN 40S ribosomal protein S4, Y isoform 2 OS = *Homo sapiens* GN = RPS4Y2', 263, 29295]
['0.84', 20, 'sp|Q96CX3-2|ZN501_HUMAN Isoform 2 of Zinc finger protein 501 OS = *Homo sapiens* GN = ZNF501', 215, 24880]
['0.84', 20, 'sp|Q147U1-3|ZN846_HUMAN Isoform 3 of Zinc finger protein 846 OS = *Homo sapiens* GN = ZNF846', 210, 24075]
['0.84', 9, 'sp|P56134-1|ATPK_HUMAN Isoform 1 of ATP synthase subunit f, mitochondrial OS = *Homo sapiens* GN = ATP5J2', 94, 10917]
['0.83', 48, 'sp|Q96S94-1|CCNL2_HUMAN Isoform 1 of Cyclin-L2 OS = *Homo sapiens* GN = CCNL2', 520, 58147]
['0.83', 27, 'sp|Q9NWB6-2|ARGL1_HUMAN Isoform 2 of Arginine and glutamate-rich protein 1 OS = *Homo sapiens* GN = ARGLU1', 273, 32885]
['0.83', 24, 'sp|P62701|RS4X_HUMAN 40S ribosomal protein S4, X isoform OS = *Homo sapiens* GN = RPS4X', 263, 29597]
['0.83', 23, 'sp|Q6UXX9-1|RSPO2_HUMAN Isoform 1 of R-spondin-2 OS = *Homo sapiens* GN = RSPO2', 243, 28314]
['0.83', 20, 'sp|P55075-3|FGF8_HUMAN Isoform FGF-8B of Fibroblast growth factor 8 OS = *Homo sapiens* GN = FGF8', 215, 24711]
['0.83', 12, 'sp|Q8N3H0-1|F19A2_HUMAN Isoform 1 of Protein FAM19A2 OS = *Homo sapiens* GN = FAM19A2', 131, 14620]
['0.83', 12, 'sp|Q6N063-3|OGFD2_HUMAN Isoform 3 of 2-oxoglutarate and iron-dependent oxygenase domain-containing protein 2 OS = *Homo sapiens* GN = OGFOD2', 129, 14734]

| Ratio | Charge | Name | aa | MW |
|---|---|---|---|---|
| ['0.83', | 9, | 'sp|Q56VL3-2|OCAD2_HUMAN Isoform 2 of OCIA domain-containing protein 2 OS = *Homo sapiens* GN = OCIAD2', | 99, | 11029] |
| ['0.82', | 34, | 'sp|Q8N8C0-1|ZN781_HUMAN Isoform 1 of Zinc finger protein 781 OS = *Homo sapiens* GN = ZNF781', | 355, | 41526] |
| ['0.82', | 20, | 'sp|Q5T4W7-2|ARTN_HUMAN Isoform 2 of Artemin OS = *Homo sapiens* GN = ARTN', | 237, | 24471] |
| ['0.82', | 17, | 'sp|Q9NY12-2|NOLA1_HUMAN Isoform 2 of H/ACA ribonucleoprotein complex subunit 1 OS = *Homo sapiens* GN = NOLA1', | 199, | 20834] |
| ['0.81', | 37, | 'sp|Q96SQ7-2|ATOH8_HUMAN Isoform 2 of Protein atonal homolog 8 OS = *Homo sapiens* GN = ATOH8', | 416, | 45785] |
| ['0.81', | 22, | 'sp|Q9NP64-1|NO40_HUMAN Isoform 1 of Nucleolar protein of 40 kDa OS = *Homo sapiens* GN = ZCCHC17', | 241, | 27569] |
| ['0.81', | 22, | 'sp|Q92913-1|FGF13_HUMAN Isoform 1A of Fibroblast growth factor 13 OS = *Homo sapiens* GN = FGF13', | 245, | 27563] |
| ['0.81', | 21, | 'sp|P55075-1|FGF8_HUMAN Isoform FGF-8E of Fibroblast growth factor 8 OS = *Homo sapiens* GN = FGF8', | 233, | 26525] |
| ['0.81', | 18, | 'sp|O75494-3|FUSIP_HUMAN Isoform 3 of FUS-interacting serine-arginine-rich protein 1 OS = *Homo sapiens* GN = FUSIP1', | 183, | 22222] |
| ['0.81', | 9, | 'sp|Q7L592-3|CB056_HUMAN Isoform 3 of UPF0511 protein C2orf56, mitochondrial OS = *Homo sapiens* GN = C2orf56', | 99, | 11289] |
| ['0.81', | 7, | 'sp|Q6PDA7-3|SG11A_HUMAN Isoform 3 of Sperm-associated antigen 11A OS = *Homo sapiens* GN = SPAG11A', | 82, | 9075] |
| ['0.80', | 72, | 'sp|O14746-2|TERT_HUMAN Isoform 2 of Telomerase reverse transcriptase OS = *Homo sapiens* GN = TERT', | 807, | 90225] |
| ['0.80', | 54, | 'sp|Q86YE8-4|ZN573_HUMAN Isoform 4 of Zinc finger protein 573 OS = *Homo sapiens* GN = ZNF573', | 578, | 67865] |
| ['0.80', | 30, | 'sp|O95218-1|ZRAB2_HUMAN Isoform 1 of Zinc finger Ran-binding domain-containing protein 2 OS = *Homo sapiens* GN = ZRANB2', | 330, | 37404] |
| ['0.80', | 24, | 'sp|Q96CX3-1|ZN501_HUMAN Isoform 1 of Zinc finger protein 501 OS = *Homo sapiens* GN = ZNF501', | 271, | 31178] |
| ['0.80', | 22, | 'sp|Q92915-1|FGF14_HUMAN Isoform 1 of Fibroblast growth factor 14 OS = *Homo sapiens* GN = FGF14', | 247, | 27701] |
| ['0.80', | 16, | 'sp|P82912-2|RT11_HUMAN Isoform 2 of 28S ribosomal protein S11, mitochondrial OS = *Homo sapiens* GN = MRPS11', | 193, | 20459] |

Nucleic Acids

The present invention provides systems and methods for delivery of nucleic acids to cells in vivo or in vitro. Such systems and methods typically involve association of one or more nucleic acids with supercharged proteins to form a complex, and delivery of the complex to one or more cells. In some embodiments, the nucleic acid may have therapeutic activity. In some embodiments, delivery of the complex to cells involves administering a complex comprising supercharged proteins associated with a nucleic acid to a subject in need thereof. In some embodiments, a nucleic acid by itself may not be able to enter the interior of a cell, but is able to enter the interior of a cell when complexed with a supercharged protein. In some embodiments, a supercharged protein is utilized to allow a nucleic acid to enter a cell. Nucleic acids in accordance with the invention may themselves have therapeutic activity or may direct expression of an RNA and/or protein that has therapeutic activity. Therapeutic activities of nucleic acids are discussed in further detail below.

The term "nucleic acid," in its broadest sense, includes any compound and/or substance that is or can be incorporated into an oligonucleotide chain. Exemplary nucleic acids for use in accordance with the present invention include, but are not limited to, one or more of DNA, RNA, hybrids thereof, RNAi-inducing agents, RNAi agents, siRNAs, shRNAs, miRNAs, antisense RNAs, ribozymes, catalytic DNA, RNAs that induce triple helix formation, aptamers, vectors, etc., described in further detail below.

Nucleic acids for use in accordance with the invention may be prepared according to any available technique including, but not limited to chemical synthesis, enzymatic synthesis, enzymatic or chemical cleavage of a longer precursor, etc. Methods of synthesizing RNAs are known in the art (see, e.g., Gait, M. J. (ed.) *Oligonucleotide synthesis: a practical approach*, Oxford [Oxfordshire], Washington, D.C.: IRL Press, 1984; and Herdewijn, P. (ed.) *Oligonucleotide synthesis: methods and applications*, Methods in Molecular Biology, v. 288 (Clifton, N.J.) Totowa, N.J.: Humana Press, 2005; both of which are incorporated herein by reference).

Nucleic acids may comprise naturally occurring nucleosides, modified nucleosides, naturally occurring nucleosides with hydrocarbon linkers (e.g., an alkylene) or a polyether linker (e.g., a PEG linker) inserted between one or more nucleosides, modified nucleosides with hydrocarbon or PEG linkers inserted between one or more nucleosides, or a combination of thereof. In some embodiments, nucleotides or modified nucleotides can be replaced with a hydrocarbon linker or a polyether linker provided that the function of the nucleic acid is not substantially reduced by the substitution.

It will be appreciated by those of ordinary skill in the art that nucleic acids in accordance with the present invention may comprise nucleotides entirely of the types found in naturally occurring nucleic acids, or may instead include one or more nucleotide analogs or have a structure that otherwise differs from that of a naturally occurring nucleic acid. U.S. Pat. Nos. 6,403,779; 6,399,754; 6,225,460; 6,127,533; 6,031,086; 6,005,087; 5,977,089 (each of which is incorporated herein by reference); and references therein disclose a wide variety of specific nucleotide analogs and modifications that may be used. See Crooke, S. (ed.) *Antisense Drug Technology: Principles, Strategies, and Applications* (1$^{st}$ ed), Marcel Dekker; ISBN: 0824705661; 1st edition (2001; incorporated herein by reference) and references therein. For example, 2'-modifications include halo, alkoxy and allyloxy groups. In some embodiments, the 2'-OH group is replaced by a group selected from H, OR, R, halo, SH, SR, $NH_2$, NHR, $NR_2$ or CN, wherein R is $C_1$-$C_6$ alkyl, alkenyl, or alkynyl, and halo is F, Cl, Br, or I. Examples of modified linkages include phosphorothioate and 5'-N-phosphoramidite linkages.

Nucleic acids comprising a variety of different nucleotide analogs, modified backbones, or non-naturally occurring internucleoside linkages can be utilized in accordance with the present invention. Nucleic acids of the present invention may include natural nucleosides (i.e., adenosine, thymidine, guanosine, cytidine, uridine, deoxyadenosine, deoxythymidine, deoxyguanosine, and deoxycytidine) or modified nucleosides. Examples of modified nucleotides include base modified nucleoside (e.g., aracytidine, inosine, isoguanosine, nebularine, pseudouridine, 2,6-diaminopurine, 2-aminopurine, 2-thiothymidine, 3-deaza-5-azacytidine, 2'-deoxyuridine, 3-nitorpyrrole, 4-methylindole, 4-thiouridine, 4-thiothymidine, 2-aminoadenosine, 2-thiothymidine, 2-thiouridine, 5-bromocytidine, 5-iodouridine, inosine, 6-azauridine, 6-chloropurine, 7-deazaadenosine, 7-deazaguanosine, 8-azaadenosine, 8-azidoadenosine, benzimidazole, M1-methyladenosine, pyrrolo-pyrimidine, 2-amino-6-chloropurine, 3-methyl adenosine, 5-propynylcytidine, 5-propynyluridine, 5-bromouridine, 5-fluorouridine, 5-methylcytidine, 7-deazaadenosine, 7-deazaguanosine, 8-oxoadenosine, 8-oxoguanosine, O(6)-methylguanine, and 2-thiocytidine), chemically or biologically modified bases (e.g., methylated bases), modified sugars (e.g., 2'-fluororibose, 2'-aminoribose, 2'-azidoribose, 2'-O-methylribose, L-enantiomeric nucleosides arabinose, and hexose), modified phosphate groups (e.g., phosphorothioates and 5'-N-phosphoramidite linkages), and combinations thereof. Natural and modified nucleotide monomers for the chemical synthesis of nucleic acids are readily available. In some cases, nucleic acids comprising such modifications display improved properties relative to nucleic acids consisting only of naturally occurring nucleotides. In some embodiments, nucleic acid modifications described herein are utilized to reduce and/or prevent digestion by nucleases (e.g. exonucleases, endonucleases, etc.). For example, the structure of a nucleic acid may be stabilized by including nucleotide analogs at the 3' end of one or both strands order to reduce digestion.

Modified nucleic acids need not be uniformly modified along the entire length of the molecule. Different nucleotide modifications and/or backbone structures may exist at various positions in the nucleic acid. One of ordinary skill in the art will appreciate that the nucleotide analogs or other modification(s) may be located at any position(s) of a nucleic acid such that the function of the nucleic acid is not substantially affected. To give but one example, modifications may be located at any position of a nucleic acid targeting moiety such that the ability of the nucleic acid targeting moiety to specifically bind to the target is not substantially affected. The modified region may be at the 5'-end and/or the 3'-end of one or both strands. For example, modified nucleic acid targeting moieties in which approximately 1 to approximately 5 residues at the 5' and/or 3' end of either of both strands are nucleotide analogs and/or have a backbone modification have been employed. A modification may be a 5' or 3' terminal modification. One or both nucleic acid strands may comprise at least 50% unmodified nucleotides, at least 80% unmodified nucleotides, at least 90% unmodified nucleotides, or 100% unmodified nucleotides.

Nucleic acids in accordance with the present invention may, for example, comprise a modification to a sugar, nucleoside, or internucleoside linkage such as those described in U.S. Patent Publications 2003/0175950, 2004/0192626, 2004/0092470, 2005/0020525, and 2005/0032733; each of which is incorporated herein by reference. The present invention encompasses the use of any nucleic acid having any one or more of the modification described therein. For example, a number of terminal conjugates, e.g., lipids such as cholesterol, lithocholic acid, aluric acid, or long alkyl branched chains have been reported to improve cellular uptake. Analogs and modifications may be tested using, e.g., using any appropriate assay known in the art, for example, to select those that result in improved target gene silencing by an RNAi agent, etc. In some embodiments, nucleic acids in accordance with the present invention may comprise one or more non-natural nucleoside linkages. In some embodiments, one or more internal nucleotides at the 3'-end, 5'-end, or both 3'- and 5'-ends of the nucleic acid targeting moiety are inverted to yield a linkage such as a 3'-3' linkage or a 5'-5' linkage.

In some embodiments, nucleic acids in accordance with the present invention are not synthetic, but are naturally-occurring entities that have been isolated from their natural environments.

RNAi Agents
RNA Interference

In some embodiments, nucleic acids that can be associated with supercharged proteins include agents that mediate RNA interference (RNAi). RNAi is a mechanism that inhibits expression of specific genes. RNAi typically inhibits gene expression at the level of translation, but can function by inhibiting gene expression at the level of transcription. RNAi targets include any RNA that might be present in cells, including but not limited to, cellular transcripts, pathogen transcripts (e.g., from viruses, bacteria, fungi, etc.), transposons, vectors, etc.

The RNAi pathway is initiated by the enzyme dicer, which cleaves long, double-stranded RNA (dsRNA) molecules into short fragments of 20-25 base pairs, optionally with a few unpaired overhang bases on one or both ends. One of the two strands of each fragment, known as the guide strand, is then incorporated into the RNA-induced silencing complex (RISC) and pairs with complementary sequences. The other strand is degraded during RISC activation. The most well-studied outcome of this recognition event is post-transcriptional gene silencing. This occurs when the guide strand specifically pairs with a target transcript and induces degradation of the target transcript by argonaute, the catalytic component of the RISC complex. Another outcome is epigenetic changes to a gene (e.g., histone modification and DNA methylation) affecting the degree to which the gene is transcribed.

Introduction of long double-stranded RNA (e.g., greater than 30 bp) into mammalian cells results in systemic, non-specific inhibition of translation due to activation of the interferon response. A breakthrough occurred when it was found that this obstacle could be overcome by the use of synthetic short RNAs (e.g., 19-25 bp) that can be either delivered exogenously (Elbashir et al., 2001, *Nature*, 411:494; incorporated herein by reference) or expressed endogenously from RNA polymerase II or III promoters.

The phenomenon of RNAi is discussed in greater detail, for example, in the following references, each of which is incorporated herein by reference: Elbashir et al., 2001, *Genes Dev.*, 15:188; Fire et al., 1998, *Nature*, 391:806; Tabara et al., 1999, *Cell*, 99:123; Hammond et al., *Nature*, 2000, 404:293; Zamore et al., 2000, *Cell*, 101:25; Chakraborty, 2007, *Curr. Drug Targets*, 8:469; and Morris and Rossi, 2006, *Gene Ther.*, 13:553.

As used herein, the term "RNAi agent" refers to an RNA, optionally including one or more nucleotide analogs or modifications, having a structure characteristic of molecules that can mediate inhibition of gene expression through an RNAi mechanism. Generally, an RNAi agent includes a portion that is substantially complementary to a target RNA. In some embodiments, RNAi agents are at least partly double-stranded. In some embodiments, RNAi agents are single-stranded. In some embodiments, exemplary RNAi agents can include short interfering RNA (siRNA), short hairpin RNA (shRNA), and/or micro RNA (miRNA). In some embodiments, the term "RNAi agent" may refer to any RNA, RNA derivative, and/or nucleic acid encoding an RNA that induces an RNAi effect (e.g., degradation of target RNA and/or inhibition of translation).

As used herein, the term "RNAi-inducing agent" encompasses any entity that delivers, regulates, and/or modifies the activity of an RNAi agent. In some embodiments, RNAi-inducing agents may include vectors (other than naturally occurring molecules not modified by the hand of man) whose presence within a cell results in RNAi and leads to reduced expression of a transcript to which the RNAi-inducing agent is targeted. In some embodiments, an RNAi-inducing agent is an "RNAi-inducing vector," which refers to a vector whose presence within a cell results in production of one or more RNAs that self-hybridize or hybridize to each other to form an RNAi agent (e.g. siRNA, shRNA, and/or miRNA). In various embodiments, this term encompasses plasmids, e.g., DNA vectors (whose sequence may comprise sequence elements derived from a virus), or viruses (other than naturally occurring viruses or plasmids that have not been modified by the hand of man), whose presence within a cell results in production of one or more RNAs that self-hybridize or hybridize to each other to form an RNAi agent. In general, the vector comprises a nucleic acid operably linked to expression signal(s) so that one or more RNAs that hybridize or self-hybridize to form an RNAi agent are transcribed when the vector is present within a cell. Thus the vector provides a template for intracellular synthesis of the RNA or RNAs or precursors thereof. In some embodiments, RNAi-inducing agents are compositions comprising RNAi agents and one or more pharmaceutically acceptable excipients and/or carriers. For the purposes of the present invention, any partly or fully double-stranded short RNA as described herein, one strand of which binds to a target transcript and reduces its expression (i.e., reduces the level of the transcript and/or reduces synthesis of the polypeptide encoded by the transcript) is considered to be an RNAi-inducing agent, regardless of whether it acts by triggering degradation, inhibiting translation, or by other means. In addition any precursor RNA structure that may be processed in vivo (i.e., within a cell or organism) to generate such an RNAi-inducing agent is useful in the present invention.

RNAi agents in accordance with the invention may target any portion of a transcript. In some embodiments, a target transcript is located within a coding sequence of a gene. In some embodiments, a target transcript is located within non-coding sequence. In some embodiments, a target transcript is located within an exon. In some embodiments, a target transcript is located within an intron. In some embodiments, a target transcript is located within a 5' untranslated region (UTR) or 3' UTR of a gene. In some embodiments, a target transcript is located within an enhancer region. In some embodiments, a target transcript is located within a promoter.

For any particular gene target, design of RNAi agents and/or RNAi-inducing agents typically follows certain guidelines. In general, it is desirable to avoid sections of target transcript that may be shared with other transcripts whose degradation is not desired. In some embodiments, RNAi agents and/or RNAi-inducing entities target transcripts and/or portions thereof that are highly conserved. In some embodiments, RNAi agents and/or RNAi-inducing entities target transcripts and/or portions thereof that are not highly conserved.

siRNAs and shRNAs

As used herein, an "siRNA" refers to an RNAi agent comprising an RNA duplex (referred to herein as a "duplex region") that is approximately 19 base pairs (bp) in length and optionally further comprises one or two single-stranded overhangs. In some embodiments, an siRNA comprises a duplex region ranging from 15 bp to 29 bp in length and optionally further comprising one or two single-stranded overhangs. An siRNA is typically formed from two RNA molecules (i.e., two strands) that hybridize together. One strand of an siRNA includes a portion that hybridizes with a target transcript. In some embodiments, siRNAs mediate inhibition of gene expression by causing degradation of target transcripts.

As used herein, an "shRNA" refers to an RNAi agent comprising an RNA having at least two complementary portions hybridized or capable of hybridizing to form a double-stranded (duplex) structure sufficiently long to mediate RNAi (typically at least approximately 19 bp in length), and at least one single-stranded portion, typically ranging between approximately 1 nucleotide (nt) and approximately 10 nt in length that forms a loop. In some embodiments, an shRNA comprises a duplex portion ranging from 15 bp to 29 bp in length and at least one single-stranded portion, typically ranging between approximately 1 nt and approximately 10 nt in length that forms a loop. In some embodiments, the single-stranded portion is approximately 1 nt, approximately 2 nt, approximately 3 nt, approximately 4 nt, approximately 5 nt, approximately 6 nt, approximately 7 nt, approximately 8 nt, approximately 9 nt, or approximately 10 nt in length. In some embodiments, shRNAs are processed into siRNAs by cellular RNAi machinery (e.g., by Dicer). Thus, in some embodiments, shRNAs may be precursors of siRNAs. Regardless, siRNAs in general are capable of inhibiting expression of a target RNA, similar to siRNAs. As used herein, the term "short RNAi agent" is used to refer to siRNAs and shRNAs, collectively.

As mentioned above, short RNAi agents typically include a base-paired region ("duplex region") between approximately 15 nt and approximately 29 nt long, e.g., approximately 19 nt long, and may optionally have one or more free or looped ends. In some embodiments, short RNAi agents have a duplex region of about 15 nt, about 16 nt, about 17 nt, about 18 nt, about 19 nt, about 20 nt, about 21 nt, about 22 nt, about 23 nt, about 24 nt, about 25 nt, about 26 nt, about 27 nt, about 28 nt, or about 29 nt in length. However, it is not required that the administered agent have this structure. For example, RNAi-inducing agents may comprise any structure capable of being processed in vivo to the structure of a short RNAi agent. In some embodiments, an RNAi-inducing agent is delivered to a cell, where it undergoes one or more processing steps before becoming a functional short RNAi agent. In such cases, those of ordinary skill in the art will appreciate that it is desirable for the RNAi-inducing agent to include sequences that may be necessary and/or helpful for its processing.

In describing RNAi-inducing agents and/or short RNAi agents, it is convenient to refer to an agent as having two strands. In general, the sequence of the duplex portion of one strand of an RNAi-inducing agent and/or short RNAi agent is substantially complementary to the target transcript in this region. The sequence of the duplex portion of the other strand of the RNAi-inducing agent and/or short RNAi agent is typically substantially identical to the targeted portion of the target transcript. The strand comprising the portion complementary to the target is referred to as the "antisense strand," while the other strand is often referred to as the "sense strand." The portion of the antisense strand that is complementary to the target may be referred to as the "inhibitory region."

RNAi-inducing agents and/or short RNAi agents typically include a region (the "duplex region"), one strand of which contains an inhibitory region between 15 nt to 29 nt in length that is sufficiently complementary to a portion of the target transcript (the "target portion"), so that a hybrid (the "core region") can form in vivo between this strand and the target transcript. The core region is understood not to include overhangs.

In some embodiments, short RNAi agents have an inhibitory region of about 15 nt, about 16 nt, about 17 nt, about 18 nt, about 19 nt, about 20 nt, about 21 nt, about 22 nt, about 23 nt, about 24 nt, about 25 nt, about 26 nt, about 27 nt, about 28 nt, or about 29 nt in length. In some embodiments, short RNAi agents have an inhibitory region of about 19 nt in length. In some embodiments, hybridization of one strand of a short RNAi agent to its target transcript yields a core region of about 15 nt, about 16 nt, about 17 nt, about 18 nt, about 19 nt, about 20 nt, about 21 nt, about 22 nt, about 23 nt, about 24 nt, about 25 nt, about 26 nt, about 27 nt, about 28 nt, or about 29 nt in length. In some embodiments, hybridization of one strand of a short RNAi agent to its target transcript yields a core region of about 19 nt in length.

Target transcripts are often cleaved near the center of the duplex region. In some embodiments, target transcripts are cleaved at 11 nt or 12 nt downstream of the first base pair of the duplex that forms between the siRNA and target transcript (see, e.g., Elbashir et al., 2001, *Genes Dev.*, 15:188; incorporated herein by reference).

In some embodiments, siRNAs comprise 3'-overhangs at one or both ends of the duplex region. In some embodiments, an shRNA comprises a 3' overhang at its free end. In some embodiments, siRNAs comprise a single nucleotide 3'-overhang. In some embodiments, siRNAs comprise a 3'-overhang of 2 nt. In some embodiments, siRNAs comprise a 3'-overhang of 1 nt. Overhangs, if present, may, but need not be, complementary to the target transcript. siRNAs with 2 nt-3 nt overhangs on their 3'-ends are frequently efficient in reducing target transcript levels than siRNAs with blunt ends.

Any desired sequence (e.g., UU) may simply be appended to the 3' ends of antisense and/or sense core regions to generate 3'-overhangs. In general, overhangs containing one or more pyrimidines, usually U, T, or dT, are employed. When synthesizing RNAi-inducing agents, it may be more convenient to use T rather than U in the overhang(s). Use of dT rather than T may confer increased stability.

In some embodiments, the inhibitory region of a short RNAi agent is 100% complementary to a region of a target transcript. However, in some embodiments, the inhibitory region of a short RNAi agent is less than 100% complementary to a region of a target transcript. The inhibitory region need only be sufficiently complementary to a target transcript such that hybridization can occur, e.g., under physiological conditions in a cell and/or in an in vitro system that supports RNAi (e.g., a *Drosophila* extract system).

One of ordinary skill in the art will appreciate that short RNAi agent duplexes may tolerate mismatches and/or bulges, particularly mismatches within the central region of the duplex, while still leading to effective silencing. One of skill in the art will also recognize that it may be desirable to avoid mismatches in the central portion of the short RNAi agent/target transcript core region (see, e.g., Elbashir et al., *EMBO J.* 20:6877, 2001). For example, the 3' nucleotides of the antisense strand of the siRNA often do not contribute significantly to specificity of the target recognition and may be less critical for target cleavage.

In some embodiments, short RNAi agents having duplex regions that exhibit one or more mismatches typically have no more than 6 total mismatches. In some embodiments, short RNAi agents have 1, 2, 3, 4, 5, or 6 total mismatches in their duplex regions. In some embodiments, the duplex regions have stretches of perfect complementarity that are at least 5 nt in length (e.g., 6, 7, or more nt). In some embodiments, no more than 20% of the nucleotides within a duplex region are mismatched. In some embodiments, no more than 15% of the nucleotides within a duplex region are mismatched. In some embodiments, no more than 10% of the nucleotides within a duplex region are mismatched. In some embodiments, no more than 5% of the nucleotides within a duplex region are mismatched. In some embodiments, none of the nucleotides within a duplex region are mismatched. Duplex regions may include two stretches of perfect complementarity separated by a region of mismatch. In some embodiments, there are multiple areas of mismatch.

In some embodiments, core regions (e.g., formed by hybridization of one strand of a short RNAi agent with a target transcript), which exhibit one or more mismatches typically, have no more than 6 total mismatches. In some embodiments, core regions have 1, 2, 3, 4, 5, or 6 total mismatches. In some embodiments, core regions comprise stretches of perfect complementarity that are at least 5 nt in length (e.g., 6, 7, or more nt). In some embodiments, no more than 20% of the nucleotides within a core region are mismatched. In some embodiments, no more than 15% of the nucleotides within a core region are mismatched. In some embodiments, no more than 10% of the nucleotides within a core region are mismatched. In some embodiments, no more than 5% of the nucleotides within a core region are mismatched. In some embodiments, none of the nucleotides within a core region are mismatched. Core regions may include two stretches of perfect complementarity separated by a region of mismatch. In some embodiments, there are multiple areas of mismatch.

In some embodiments, one or both strands of a short RNAi agent may include one or more "extra" nucleotides that form a "bulge." One or more bulges (e.g., 5 nt-10 nt long) may be present.

In some embodiments, short RNAi agents can be designed and/or predicted using one or more of a large number of available algorithms. To give but a few examples, the following resources can be utilized to design and/or predict RNAi agents: algorithms found at Alnylum Online, Dharmacon Online, OligoEngine Online, Molecula Online, Ambion Online, BioPredsi Online, RNAi Web Online, Chang Bioscience Online, Invitrogen Online, LentiWeb Online GenScript Online, Protocol Online; Reynolds et al., 2004, *Nat. Biotechnol.*, 22:326; Naito et al., 2006, *Nucleic Acids Res.*, 34:W448; Li et al., 2007, *RNA*, 13:1765; Yiu et al., 2005, *Bioinformatics*, 21:144; and Jia et al., 2006, *BMC Bioinformatics*, 7: 271; each of which is incorporated herein by reference).

micro RNAs micro RNAs (miRNAs) are genomically encoded non-coding RNAs of about 21-23 nucleotides in length that help regulate gene expression, particularly during development (see, e.g., Bartel, 2004, *Cell*, 116:281; Novina and Sharp, 2004, *Nature*, 430:161; and U.S. Patent Publication 2005/0059005; also reviewed in Wang and Li, 2007, *Front. Biosci.*, 12:3975; and Zhao, 2007, *Trends Biochem. Sci.*, 32:189; each of which are incorporated herein by reference). The phenomenon of RNA interference, broadly defined, includes the endogenously induced gene silencing effects of miRNAs as well as silencing triggered by foreign dsRNA. Mature miRNAs are structurally similar to siRNAs produced from exogenous dsRNA, but before reaching maturity, miRNAs first undergo extensive post-transcriptional modification. An miRNA is typically expressed from a much longer RNA-coding gene as a primary transcript known as a pri-miRNA, which is processed in the cell nucleus to a 70-nucleotide stem-loop structure called a pre-miRNA by the microprocessor complex. This complex consists of an RNase III enzyme called Drosha and a dsRNA-binding protein Pasha. The dsRNA portion of this pre-miRNA is bound and cleaved by dicer to produce the mature miRNA molecule that can be integrated into the RISC complex; thus, miRNA and siRNA share the same cellular machinery downstream of their initial processing (Gregory et al., 2006, *Meth. Mol. Biol.,* 342:33; incorporated herein by reference). In general, miRNAs are not perfectly complementary to their target transcripts.

In some embodiments, miRNAs can range between 18 nt-26 nt in length. Typically, miRNAs are single-stranded. However, in some embodiments, miRNAs may be at least partially double-stranded. In certain embodiments, miRNAs may comprise an RNA duplex (referred to herein as a "duplex region") and may optionally further comprises one or two single-stranded overhangs. In some embodiments, an RNAi agent comprises a duplex region ranging from 15 bp to 29 bp in length and optionally further comprising one to three single-stranded overhangs. An miRNA may be formed from two RNA molecules that hybridize together, or may alternatively be generated from a single RNA molecule that includes a self-hybridizing portion. The duplex portion of an miRNA usually, but does not necessarily, comprise one or more bulges consisting of one or more unpaired nucleotides. One strand of an miRNA includes a portion that hybridizes with a target RNA. In certain embodiments, one strand of the miRNA is not precisely complementary with a region of the target RNA, meaning that the miRNA hybridizes to the target RNA with one or more mismatches. In some embodiments, one strand of the miRNA is precisely complementary with a region of the target RNA, meaning that the miRNA hybridizes to the target RNA with no mismatches. Typically, miRNAs are thought to mediate inhibition of gene expression by inhibiting translation of target transcripts. However, in some embodiments, miRNAs may mediate inhibition of gene expression by causing degradation of target transcripts.

In some embodiments, miRNAs have a duplex region of about 15 nt, about 16 nt, about 17 nt, about 18 nt, about 19 nt, about 20 nt, about 21 nt, about 22 nt, about 23 nt, about 24 nt, about 25 nt, about 26 nt, about 27 nt, about 28 nt, or about 29 nt in length. In some embodiments, miRNAs have an inhibitory region of about 15 nt, about 16 nt, about 17 nt, about 18 nt, about 19 nt, about 20 nt, about 21 nt, about 22 nt, about 23 nt, about 24 nt, about 25 nt, about 26 nt, about 27 nt, about 28 nt, or about 29 nt in length.

In some embodiments, miRNAs have duplex regions that exhibit one or more mismatches in their duplex regions. In some embodiments, miRNAs have duplex regions that exhibit 1, 2, 3, 4, 5, 6, 7, 8, or 9 total mismatches in their duplex regions. In some embodiments, the duplex regions have stretches of perfect complementarity that are 1, 2, 3, 4, 5, 6, 7, 8, or 9 nt in length. Duplex regions may include two stretches of perfect complementarity separated by a region of mismatch. In some embodiments, there are multiple areas of mismatch. In some embodiments, about 50% of the nucleotides within a duplex region are mismatched. In some embodiments, about 40% of the nucleotides within a duplex region are mismatched. In some embodiments, about 30% of the nucleotides within a duplex region are mismatched. In some embodiments, about 20% of the nucleotides within a duplex region are mismatched. In some embodiments, about 10% of the nucleotides within a duplex region are mismatched. In some embodiments, about 5% of the nucleotides within a duplex region are mismatched.

In some embodiments, core regions (e.g., formed by hybridization of one strand of an miRNA with a target transcript) have 1, 2, 3, 4, 5, 6, 7, 8, or 9 total mismatches. In some embodiments, core regions comprise stretches of perfect complementarity that are 1, 2, 3, 4, 5, 6, 7, 8, or 9 nt in length. Core regions may include two stretches of perfect complementarity separated by a region of mismatch. In some embodiments, there are multiple areas of mismatch. In some embodiments, there are multiple areas of mismatch. In some embodiments, about 50% of the nucleotides within a core region are mismatched. In some embodiments, about 40% of the nucleotides within a core region are mismatched. In some embodiments, about 30% of the nucleotides within a core region are mismatched. In some embodiments, about 20% of the nucleotides within a core region are mismatched. In some embodiments, about 10% of the nucleotides within a core region are mismatched. In some embodiments, about 5% of the nucleotides within a core region are mismatched.

In some embodiments, one or both strands of an miRNA may include one or more "extra" nucleotides that form a "bulge." One or more bulges (e.g., 5 nt-10 nt long) may be present.

In some embodiments, short RNAi agents can be designed and/or predicted using one or more of a large number of available algorithms. To give but a few examples, the following resources can be utilized to design and/or predict RNAi agents: algorithms at PicTar Online, Protocol Online, EMBL Online; Rehmsmeier et al., 2004, *RNA,* 10:1507; Kim et al., 2006, *BMC Bioinformatics,* 7:411; Lewis et al., 2003, *Cell,* 115:787; and Krek et al., 2005, *Nat. Genet.,* 37:495; each of which is incorporated herein by reference.

Antisense RNAs

In some embodiments, nucleic acids that can be associated with supercharged proteins include antisense RNAs. Antisense RNAs are typically RNA strands of various lengths that bind to target transcripts and block their translation (e.g., either through degradation of mRNA and/or by sterically blocking critical steps of the translation process).

Antisense RNAs exhibit many of the same characteristics of RNAi agents described above. For example, antisense RNAs exhibit sufficient complementarity to a target transcript to allow hybridization of the antisense RNA to the target transcript. Mismatches are tolerated, as described above for RNAi agents, as long as hybridization to the target can still occur. In general, antisense RNAs are longer than short RNAi agents, and can be of any length, as long as hybridization can still occur. In some embodiments, antisense RNAs are about 20 nt, about 30 nt, about 40 nt, about 50 nt, about 75 nt, about 100 nt, about 150 nt, about 200 nt, about 250 nt, about 500 nt, or longer. In some embodiments, antisense RNAs comprise an inhibitory region that hybridizes with a target transcript of about 20 nt, about 30 nt, about 40 nt, about 50 nt, about 75 nt, about 100 nt, about 150 nt, about 200 nt, about 250 nt, about 500 nt, or longer.

Ribozymes

In some embodiments, nucleic acids that can be associated with supercharged proteins include ribozymes. A ribozyme (from ribonucleic acid enzyme; also called RNA enzyme or catalytic RNA) is an RNA molecule that catalyzes a chemical reaction. Many natural ribozymes catalyze either the hydrolysis of one of their own phosphodiester bonds, or the hydrolysis of bonds in other RNAs, but they have also been found to catalyze the aminotransferase activity of the ribosome.

In some embodiments, ribozymes used for gene-knockdown applications have a catalytic domain that is flanked by sequences complementary to a target transcript. The mechanism of gene silencing generally involves binding of a ribozyme to a target transcript via Watson-Crick base pairing, followed by cleavage of the phosphodiester backbone of the target transcript by transesterification (Kurreck, 2003, *Eur. J. Biochem.,* 270:1628; Sun et al., 2000, *Pharmacol. Rev.,* 52:325; Doudna and Cech, 2002, *Nature,* 418:222; Goodchild, 2000, *Curr. Opin. Mol. Ther.,* 2:272; Michienzi and Rossi, 2001, *Methods Enzymol.,* 341:581; each of which is incorporated herein by reference). Once the target transcript is destroyed, ribozymes dissociate and subsequently can repeat cleavage on additional substrates. In some embodiments, a ribozyme to be associated with a supercharged protein is a hammerhead ribozyme. Hammerhead ribozymes were first isolated from viroid RNAs that undergo site-specific self-cleavage as part of their replication process.

In some embodiments, ribozymes are naturally-occurring ribozymes, including but not limited to, peptidyl transferase 23S rRNA, RNase P, Group I and Group II introns, GIR1 branching ribozyme, leadzyme, hairpin ribozyme, hammerhead ribozyme, HDV ribozyme, mammalian CPEB3 ribozyme, VS ribozyme, glmS ribozyme, and CoTC ribozyme.

In some embodiments, ribozymes are artificial ribozymes. For example, artificially-produced self-cleaving RNAs that have good enzymatic activity have been produced. Tang and Breaker (1997, *Proc. Natl. Acad. Sci.*, 97:5784; incorporated herein by reference) isolated self-cleaving RNAs by in vitro selection of RNAs originating from random-sequence RNAs. Some of the synthetic ribozymes that were produced had novel structures, while some were similar to the naturally occurring hammerhead ribozyme.

In some embodiments, techniques used to discover artificial ribozymes involve Darwinian evolution. This approach takes advantage of RNA's dual nature as both a catalyst and an informational polymer, thereby allowing an investigator to produce vast populations of RNA catalysts using polymerase enzymes. Ribozymes are mutated by reverse transcribing them with reverse transcriptase into various cDNA and amplified with mutagenic PCR. The selection parameters in these experiments often differ. To give but one example, an approach for selecting a ligase ribozyme might involve using biotin tags, which are covalently linked to a substrate. If a candidate ribozyme possesses the desired ligase activity, a streptavidin matrix can be used to recover the active molecules.

Deoxyribozymes

In some embodiments, nucleic acids that can be associated with supercharged proteins include catalytic DNAs ("deoxyribozymes"). Deoxyribozymes bind to RNA substrates, typically via Watson-Crick base pairing, and site-specifically cleave target transcripts, similarly to ribozymes. Deoxyribozymes molecules have been produced by in vitro evolution since no natural examples of DNA enzymes are known. Two different catalytic motifs, with different cleavage site specificities, have been identified. Deoxyribozymes have been produced with different cleavage specificities, allowing researchers to target all possible dinucleotide sequences.

Aptamers

In some embodiments, nucleic acids that can be associated with supercharged proteins include aptamers. Aptamers are oligonucleic acid molecules that bind specific target molecules. Aptamers may be engineered through repeated rounds of in vitro selection (e.g., via systematic evolution of ligands by exponential enrichment, "SELEX") to bind to various molecular targets such as small molecules, proteins, nucleic acids, cells, tissues, and/or organisms. Aptamers typically bind to their targets due to the three-dimensional structure of the aptamer. Aptamers generally do not bind to their targets via traditional Watson-Crick base pairing.

The first aptamer-based drug approved by the U.S. Food and Drug Administration (FDA) in treatment for age-related macular degeneration (AMD), called MACUGEN® (OSI Pharmaceuticals). In addition, ARC1779 (Archemix, Cambridge, Mass.) is a potent, selective, first-in-class antagonist of von Willebrand Factor (vWF) and is being evaluated in patients diagnosed with acute coronary syndrome (ACS) who are undergoing percutaneous coronary intervention (PCI).

In general, unmodified aptamers are usually cleared rapidly from the bloodstream, with a half-life of minutes to hours. This is presumably due to nuclease degradation and clearance from the body by the kidneys, which occur because aptamers tend to have low molecular weights. Unmodified aptamers may be particularly suited for treating transient conditions (e.g., blood clotting), and/or for treating organs where local delivery is possible (e.g., the eye, skin, etc.). Rapid clearance can be desirable in applications such as in vivo diagnostic imaging. For example, a tenascin-binding aptamer (Schering AG) can be utilized for cancer imaging. In some embodiments, aptamers with increased half-lives are desirable. Certain modifications (e.g., 2'-fluorine-substituted pyrimidines, polyethylene glycol (PEG) linkage, etc.) may increase the half-life of aptamers.

RNA that Induce Triple Helix Formation

In some embodiments, nucleic acids that can be associated with supercharged proteins include RNAs that induce triple helix formation. In some embodiments, endogenous target gene expression may be reduced by targeting deoxyribonucleotide sequences complementary to the regulatory region of the target gene (i.e., the target gene's promoter and/or enhancers) to form triple helical structures that prevent transcription of the target gene in target muscle cells in the body (see generally, Helene, 1991, *Anticancer Drug Des.* 6:569; Helene et al., 1992, *Ann, N.Y. Acad. Sci.* 660:27; and Maher, 1992, *Bioassays* 14:807).

Vectors

In some embodiments, nucleic acids that can be associated with supercharged proteins include vectors. As used herein, "vector" refers to a nucleic acid molecule which can transport another nucleic acid to which it has been linked. In some embodiment, vectors can achieve extra-chromosomal replication and/or expression of nucleic acids to which they are linked in a host cell such as a eukaryotic and/or prokaryotic cell. Exemplary vectors include plasmids, cosmids, viruses, viral genomes, artificial chromosomes, bacterial artificial chromosomes, and/or yeast artificial chromosomes. In certain embodiments, vectors include elements such as promoters, enhancers, ribosomal binding sites, etc.

In some embodiments, vectors are capable of directing the expression of operatively linked genes ("expression vectors"). In some embodiments, expression of the operatively linked gene may result in production of a functional nucleic acid (e.g., RNAi agent, antisense RNA, aptamer, ribozyme, etc.). In some embodiments, expression of the operatively linked gene may result in production of a protein (e.g., a therapeutic, diagnostic, and/or prophylactic protein). In some embodiments, a therapeutic protein is a protein-based drug (e.g., an antibody-based drug, a peptide-based drug, etc.). In some embodiments, a prophylactic protein may be a protein antigen and/or antibody. In some embodiments, a diagnostic protein may be one that exhibits certain characteristics before delivery to a cell by a supercharged protein, but exhibits detectably different characteristics after delivery.

In some embodiments, a vector is a viral vector. In some embodiments, a vector is of bacterial origin. In some embodiments, a vector is of fungal origin. In some embodiments, a vector is of eukaryotic origin. In some embodiments, a vector is of prokaryotic origin. In some embodiments, a vector may be delivered to a cell via a supercharged protein, where it subsequently replicates in vivo. In some embodiments, a vector may be delivered to a cell via a supercharged protein, where it is subsequently transcribed in vivo.

Labeled Nucleic Acids

In some embodiments, nucleic acids in accordance with the invention are tagged with a detectable label. Suitable labels that can be used in accordance with the invention include, but are not limited to, fluorescent, chemiluminescent, phosphorescent, and/or radioactive labels. In some embodiments, nucleic acids comprise at least one nucleotide that is attached to at least one fluorescent moiety (e.g., fluorescein, rhodamine, coumarin, cyanine-3, cyanine-5, Alexa Fluor, and DyLight Fluor, etc.). Any fluorescent moiety that can be associated with a nucleic acid can be utilized in accordance with the invention. In some embodiments, nucleic acids comprise at least one radioactive nucleotide (e.g., a nucleotide containing $^{32}P$ or $^{35}S$). In some embodiments, nucleic acids comprise at least one nucleotide that is attached to at least one radioactive moiety.

Cellular Nucleic Acids Targeted by Delivered Nucleic Acids

In some embodiments, nucleic acids (e.g., siRNAs, shRNAs, miRNAs, antisense RNAs, ribozymes, etc.) to be delivered to cells using supercharged proteins are useful for targeting cellular nucleic acids for degradation. Any cellular nucleic acid can be targeted for degradation. Exemplary cellular nucleic acids that can be targeted for degradation include, but are not limited to, GAPDH, β-actin, β-tubulin, and c-myc.

Peptides and Proteins

The present invention provides systems and methods for delivery of proteins or peptides to cells in vivo, ex vivo, or in vitro. Such systems and methods typically involve association of a peptide or protein with supercharged proteins to form a complex, and delivery of the complex to a cell. In some embodiments, the protein or peptide to be delivered by the supercharged protein has therapeutic activity. In some embodiments, delivery of the complex to a cell involves administering a complex comprising a supercharged protein associated with a peptide or protein to a subject in need thereof.

In some embodiments, a peptide or protein by itself may not be able to enter a cell, but is able to enter a cell when associated with a supercharged protein, for example, via a covalent bond or a non-covalent interaction. In some embodiments, the complex includes a peptide or protein that is covalently bound to a supercharged protein. In some embodiments, the complex includes a peptide or protein fused to a supercharged protein via a peptide bond, for example, via direct fusion or via a peptide linker as provided herein. In some embodiments, the complex includes a peptide or protein that is bound to a supercharged protein by non-covalent interaction. In some embodiments, a supercharged protein is utilized to allow a peptide or protein to enter a cell. In some embodiments, the peptide or protein delivered to the cell in a complex with a supercharged protein is separated from the supercharged protein after delivery to the cell, for example by cleavage of a linker peptide by a cellular protease (e.g., an endosomal protease) or by dissociation of a peptide or protein from a supercharged protein in a specific cellular microenvironment, for example the endosome. In some embodiments, peptides or proteins delivered to a cell by a system or method provided by this invention have therapeutic activity.

In some embodiments, a functional protein is delivered to a cell in vivo, ex vivo, or in vitro by a system or method provided herein. In some embodiments, a functional protein is a protein able to carry out a biological function within the target cell, for example, an enzyme able to catalyze an enzymatic reaction in the target cell, a transcription factor able to interact with the genome of a target cell and to activate or inhibit transcription of a target gene in the cell, a recombinase able to interact with the genome of a target cell and to recombine its target sites, a nuclease able to bind and cut a nucleic acid molecule within a target cell, a binding partner of a cellular molecule able to bind that molecule in the target cell, or a substrate of an enzyme of the target cell able to interact with that enzyme in the target cell.

In some embodiments, a functional protein is associated with a supercharged protein and subsequently delivered to a cell in vivo, ex vivo, or in vitro. A functional protein can be associated with a supercharged protein via a covalent bond, for example, a peptide bond, a carbon-carbon bond, or a disulfide bond, or via non-covalent interaction. In some embodiments, a functional protein is produced that is fused to a supercharged protein via a peptide bond, for example, directly or via a peptide linker as described herein. Methods for the generation and isolation of fusion proteins are well known to those of skill in the art.

In some embodiments, a method for generating a fusion of a functional protein and a supercharged protein includes the generation of an expression nucleic acid construct containing the coding sequences of the functional protein and the supercharged protein, as well as, optionally, a peptide linker, in frame, the expression of such a recombinant fusion protein in a prokaryotic or eukaryotic cell in culture, the extraction and purification of the fusion protein of the fusion protein. In some embodiments, a nucleic acid construct is generated in the form of an expression vector, for example, a vector suitable for propagation in a bacterial host and for expression in a prokaryotic or eukaryotic cell.

In some embodiments, a vector suitable for fusion protein expression is generated by cloning of a nucleotide sequence coding for a functional protein to be delivered into a cloning vector including a nucleotide sequence coding for a supercharged protein under the control of a eukaryotic and/or a prokaryotic promoter, by a cloning approach that results in both coding sequences being in frame with each other. In some embodiments, the cloning vector includes a nucleotide sequence coding for a peptide linker between a nucleotide sequence coding for a supercharged protein and a restriction site useful for inserting a nucleotide sequence coding for a protein in frame with the linker and the supercharged protein. In some embodiments, the cloning vector further includes an additional sequence enhancing expression of a fusion protein in a prokaryotic or eukaryotic cell or facilitating purification of expressed fusion proteins from such cells, for example, a sequence stabilizing a transcript encoding the fusion protein, such as a poly-A signal, a spliceable intron, a sequence encoding an in-frame peptide or protein domain tag (e.g., an Arg-tag, calmodulin-binding peptide tag, cellulose-binding domain tag, DsbA tag, c-myc-tag, glutathione S-transferase tag, FLAG-tag, HAT-tag, His-tag, maltose-binding protein tag, NusA tag, S-tag, SBP-tag, Strep-tag, or thioredoxin tag), or a selection marker or reporter cassette allowing for identification of cells harboring and expressing the expression construct and/or quantifying the level of expression in such cells. Methods for cloning and expressing fusion proteins are well known to those in the art, see, for example Sambrook et al, Molecular Cloning: a laboratory manual, Volume 1-3, CSHL Press (1989); Gellissen et al., Production of recombinant proteins, Wiley-VCH, 2005.

In some embodiments, the protein is associated with a supercharged GFP, for example +36 GFP, for delivery to a target cell. While +36 GFP is capable of delivering exogenous protein into a very high fraction of treated cells, it is likely that only a portion of the delivered protein can reach a given subcellular location. The importance of endosomal disruption in the delivery of macromolecules has been previously demonstrated (Wadia et al., Nat. Med. 10, 310-315, 2004) and in some embodiments, additional steps to effect enhanced endosomal escape, as provided herein or known in the art, are performed. Highly efficient protein internalization, when coupled with effective endosomal release, has the potential to minimize the requisite doses of exogenous protein agents, enhancing their potential as research tools and leads for therapeutic development.

The widespread use of GFP fusion proteins in biological research suggests that fusions with +36 GFP may represent a fairly general approach to constructing cell-permeable protein reagents. The high solubility and aggregation resistance of supercharged GFP (Lawrence et al., JACS 129, 10110-10112, 2007) may also facilitate the isolation of such fusions. Based on the rapid and potent protein delivery properties of superpositively charged proteins as provided herein, for example of +36 GFP, and on the widespread use of PTDs such as Tat and polyarginine, our results collectively suggest the potential of superpositively charged proteins as a new platform for the growing number of protein delivery applications.

In some embodiments, a fusion protein including a peptide or protein and a supercharged protein are administered to a target cell after isolation and/or purification. In some embodiments, cells expressing such a fusion protein are collected, lysed, and the soluble fraction of the cell lysate is administered to a target cell after removal of the insoluble fraction by centrifugation or filtration. In some embodiments, cells expressing a fusion protein including a peptide or protein and a supercharged protein are collected, lysed and the fusion protein is isolated from the lysate, for example from the soluble fraction of the lysate. Protein isolation methods and technologies are well known to those of skill in the art and include, for example, affinity chromatography or immunoprecipitation. The methods suitable for isolating and/or purifying a specific fusion protein will depend on the nature of the fusion protein. For example, a His-tagged fusion protein can readily be isolated and purified via Ni or Co ion chromatography, while fusion proteins tagged with other peptides or domains or untagged fusion proteins can be purified by other well established methods.

Proteins suitable for delivery to a target cell in vivo, ex vivo, or in vitro, by a system or method provided herein will be apparent to those of skill in the art and include, for example, DNA-binding proteins, such as transcription factors, histones, zinc-finger proteins, including zinc-finger nucleases, cytoskeletal proteins, receptor proteins, chaperone proteins, intracellular ligands, epigenetic perturbators, such as histone acetyltransferase or deacetylases, DNA methyltransferases, modulators of cellular signaling pathways, such as kinases and phosphatases, proteases targeting a specific cellular protein and, for example, disrupting or activating a signaling pathway, and other enzymes, such as oxidoreductases, transferases, hydrolases, lyases, isomerases, or ligases.

In some embodiments, a method or system provided herein is used to deliver a therapeutic protein to a cell. Examples of therapeutic proteins include, but are not limited to, a protein preventing or inhibiting the proliferation of a cell or cell population, such as a tumor suppressor protein (e.g., p53, retinoblastoma protein, BRCA1, BRCA2, PTEN, APC, CD95, ST7, or ST14); a protein inducing cell death in a cell or cell population (e.g., p53, a proapoptotic member of the BCL-2 family of proteins, or a caspase); a protein preventing or inhibiting metastasis formation, such as a metastasis suppressor protein (e.g., BRMS1, CRSP3, DRG1, KAI1, KISS1, NM23, or a TIMP-family protein); a protein inducing proliferation of a cell or cell population, such as a growth factor (e.g., a BMP-family growth factor, EGF, EPO, FGF, G-CSF, GM-CSF, a GDF-family growth factor, HGF, HDGF, IGF, PDGF, TPO, TGF-α, TGF-β, or VEGF); or a zinc finger nuclease targeting a specific site within the genome of a cell.

Transcription Factors

In some embodiments, a transcription factor is delivered to a cell by a system or method provided by aspects of this invention. In some embodiments, a transcription factor is delivered to a cell in an amount sufficient to activate or inhibit transcription of a target gene of the transcription factor within the cell. In some embodiments, a transcription factor is delivered in an amount and over a time period sufficient to effect a change in the phenotype of a target cell, for example, a change in cellular function, or a change in developmental potential.

In some embodiments, the transcription factor delivered to a cell by a system or method of this invention is a basic-helix-loop-helix factor, for example, a leucine zipper factor (ZIP, e.g., an AP-1(-like) component, for example, c-Fos or c-Jun, a CREB or C/EBP-like factor, a bZIP/PAR factor, a G-box binding factor, a ZIP factor); a helix-loop-helix factor (bHLH, e.g., a ubiquitous (class A) factor, a myogenic transcription factor (e.g., MyoD), an achaete-scute factor, a Tal/Twist/Atonal/Hen factor); a helix-loop-helix/leucine zipper factor (bHLH-ZIP, e.g., a ubiquitous bHLH-ZIP factor, such as a USF or SREBP factor, a cell-cycle controlling factor, e.g. c-Myc); a NF-1 factor (e.g., NF-1A, NF-1B, NF-1C, NF-1X); or a RF-X factor (e.g. RF-X1, RF-X2, RF-X3, RF-X4, RF-X5, ANK).

In some embodiments, the transcription factor delivered to a cell by a system or method of this invention is a zinc-coordinating DNA-binding domain containing transcription factor, for example, a Cys4 zinc finger nuclear receptor type factor (e.g., a steroid hormone receptor, a thyroid hormone receptor-like factor); a Cys4 zinc finger factor (e.g., a GATA-factor); a Cys2His2 zinc finger domain factor (e.g., a ubiquitous factor including, for example, TFIIIA and Sp1, a developmental/cell cycle regulator, including, for example Krüppel and Krüppel-like factors (e.g., Klf2, Klf4); a factor with NF-6B-like binding properties; a Cys6 cysteine-zinc cluster factor; or a zinc finger factors of alternating composition.

In some embodiments, the transcription factor delivered to a cell by a system or method of this invention is a helix-turn-helix transcription factor, for example, a homeo domain factor (e.g., a homeo domain only factor, including, for example, Ubx, a POU domain factor, for example; POU5F1 or other Oct-family transcription factor, a homeo domain with LIM region factor, a homeo domain plus zinc finger motif factor); a paired box transcription factor (e.g., a paired plus homeo domain factor, or a paired domain only factor); a forkhead/winged helix factor (e.g., a developmental regulator, for example FOXD3, a tissue-specific regulator, a cell-cycle controlling factor); a heat shock factor; a tryptophan cluster factor (e.g., a Myb factor, an Ets-type factor, an interferon regulatory factor); a transcriptional enhancer domain factor (e.g. a TEA factor, for example, TEAD1, TEAD2, TEAD3, or TEAD4).

In some embodiments, the transcription factor delivered to a cell by a system or method of this invention is a beta-scaffold factor with minor groove contacts, for example, a Rel-homology region factor (e.g. a Rel/ankyrin factor, a NF-kappaB factor, an ankyrin only factor, a Nuclear Factor of Activated T-cells, for example NFATC1, NFATC2, or NFATC3); a STAT factor (e.g. a STAT family factor, for example, STAT3); a p53 factor; a MADS box factor (e.g. a regulator of differentiation, for example, Mef2, a responders to external signals, for example, SRF serum response factor (SRF)); a beta-barrel alpha-helix transcription factor (e.g., a TATA binding protein, a sry-box only factor, for example, Sox2, a TCF factor, for example, TCF1, a HMG2-related factor, for example, SSRP1, a MATA factor); a heteromeric CCAAT factor; a grainyhead factor; a cold-shock domain factor; a runt factor.

In some embodiments, the transcription factor delivered to a cell by a system or method of this invention is a copper fist protein transcription factor, a HMG factor (e.g., a HMGI-Y or HMGA1), a pocket domain transcription factor, a E1A-like factor, a AP2/EREBP-related factor, an ARF factor, an ABI factor, or a RAV factor.

Other transcription factors suitable for delivery to a cell by systems or methods provided herein will be apparent to those of skill in the art.

In some embodiments, a transcription factor or other protein specific for a pluripotent cell type is delivered to a somatic cell by a system or method provided herein. In some embodiments, a transcription factor or other protein specific for embryonic stem cells (ES cells) is delivered to a somatic cell by a system or method provided herein. Transcription factors and other proteins specific for a pluripotent cell type and/or ES cells are well known to those of skill in the art, and include Oct4, Sox2, Klf4, Nanog, Lin-28, and c-Myc (see, for example, Takahashi et al., Cell 126(4):663-76; Takahashi et al., Cell 131(5):861-72, 2007, Yu et al., Science 318(5858): 1917-20, 2007).

In some embodiments, a reprogramming factor or a combination of reprogramming factors is delivered to a somatic cell in an amount and for a time period sufficient to reprogram the somatic cell to a pluripotent state. Reprogramming factors are well known in the art and include transcription factors and other proteins specific for a pluripotent cell type, for example, ES cells, as described herein, including, but not limited to Oct4 (POU5F1), Sox2, Klf4, and c-myc, as well as Nanog and Lin-28. Combinations of transcription factors sufficient for reprogramming are well known in the art and include, for example, the following combinations: Oct4, Sox2, Klf4, and c-Myc; Oct4, Sox2, Nanog, and Lin-28; Oct4, Klf4, and c-Myc; Oct4 and Sox2; Oct4 and Klf4. It is well established in the art that expression of reprogramming factors, or of combinations of reprogramming factors, in somatic cells, for example, in primary fibroblast cells or terminally differentiated lymphocyte cells of an adult subject, results in the reprogramming of some of these cells to a pluripotent state. See, for example, Takahashi et al., Cell, 2007, Yu et al., Science 2007, Okita et al., Nature 448(7151):313-7, 2007, Takahashi et al., Nature Protocols 2(12):3081-9; 2007, Wernig et al., Nature 448(7151):318-24, 2007, and Hanna et al., Cell, 133(2):250-64, 2008). Initially, reprogramming technology relied on expression of reprogramming factors in target cells from viral vectors. In some embodiments of this invention, the drawback of viral integration and, thus, undesired modification of the cell genome is overcome by delivering a suitable combination of reprogramming factors to a target cell. Methods for direct delivery of reprogramming factors associated with protein transduction domains (e.g. TAT and Arg$_9$) to somatic cells are known to those in the art (Pan et al., Molecular Biology Reports, PMID 19669668, 2009, Zhou et al., Cell Stem Cell 4:381-84, 2009, and Kim et al., Cell stem Cell 4:472-76, 2009). However, such methods are either very inefficient or rely on additional administration of a compound perturbing the epigenetic state of the target cell.

In contrast to methods employing conventional protein transduction domains, some systems or methods for the delivery of functional proteins to a cell as provided herein are highly efficient allowing to effect a higher end-concentration of a functional protein in a target cell while reducing or eliminating toxicity and cell viability problems often accompanying and limiting systems employing conventional protein transduction domains (see Example 7).

In some embodiments, a target cell, for example, a somatic cell, is contacted with a reprogramming factor or a combination of reprogramming factors associated with a supercharged protein provided herein. In some embodiments, a target cell is contacted with a combination including 2-5 reprogramming factors associated with a supercharged protein provided herein. In some embodiments, a target cell is contacted with a combination including 2, 3, 4, 5, 6, 7, 8, 9, 10, or more reprogramming factors associated with a supercharged protein provided herein. In some embodiments the target cell is a primary somatic cell and is contacted in vitro or ex vivo with a reprogramming factor.

In some embodiments, a target cell is contacted, or repeatedly contacted, with a combination of reprogramming factors associated with a supercharged protein as provided herein until the formation of a pluripotent cell is detected. Methods for detecting pluripotent cells are well known to those in the art and include, for example, morphological analysis, and detection of pluripotency-associated marker expression (e.g., SSEA1, SSEA4, Oct4, Sox2, and Nanog) by well established methods such as immunohistochemistry, fluorescence activated cell sorting (FACS), or fluorescent microscopy. In some embodiments, a target cell is contacted with a combination of reprogramming factors associated with a supercharged protein as provided herein for a period of at least about 10-12 days, at least about 12-15 days, at least about 15-20 days, at least about 20-25 days, at least about 25-30 days, at least about 30-40 days, at least about 40-50 days, at least about 50-60 days, at least about 60-70, at least about 70-100 days.

In some embodiments, a reprogramming factor or a combination of reprogramming factors is delivered to a somatic cell by a method or system as provided herein in an amount and for a time period effective to reprogram the cell to a pluripotent state. As will be apparent to those of skill in the art, the amount necessary to reprogram a cell is dependent on various factors, for example, on the cell type and the treatment schedule. For example, it has been reported that primary fibroblast cells need a minimal time of 10-16 days of exposure to virally expressed reprogramming factors in order to subsequently establish a state of pluripotency (Brambrink et al., Cell Stem Cell 2(2):151-59, 2008; Stadtfeld et al., Cell Stem Cell 2(3):230-40, 2008). It has been demonstrated that fibroblast cells can be reprogrammed by contacting the cells with a combination of reprogramming factors associated with a conventional protein transduction domain for a period of time followed by an incubation period in media not containing reprogramming factors and repeating this cycle several times until reprogrammed cells are detectable. For example, human fibroblast cells can be reprogrammed with a combination of Oct4, Sox2, Klf4, and c-Myc fused to a Arg9 protein transduction domain by incubation with whole cell extracts from cells expressing the reprogramming factors for 16 h, subsequent washing and incubation in ES cell media for several days, and repetition of this cycle for 4-6 times (Kim et al., Cell 2009). In general, delivery of reprogramming factors to a target somatic cell by a system or method provided herein will be at a concentration below a concentration at which significant toxicity can be observed. The critical concentration will depend, for example, on the reprogramming factor, the supercharged protein it is associated with, the type of association, and the type of cell being treated.

A useful concentration of a transcription factor associated with a supercharged protein for delivery of the transcription factor to a specific cell type can be established by those of skill in the art by routine experimentation. In some embodiments a target cell is contacted in vitro or ex vivo with a reprogramming factor at a concentration of about 1 pM to about 1 µM. In some embodiments, a target cell is contacted in vitro or ex vivo with a reprogramming factor at a concentration of about 1 pM, about 2.5 pM, about 5 pM, about 7.5 pM, about 10 pM, about 20 pM, about 25 pM, about 30 pM, about 40 pM, about 50 pM, about 60 pM, about 70 pM, about 75 pM, about 80 pM, about 90 pM, about 100 pM, about 200 pM, about 250 pM, about 300 pM, about 400 pM, about 500 pM, about 600 pM, about 700 pM, about 750 pM, about 800 pM, about 900 pM, about 1 nM, about 2 nM, about 3 nM, about 4 nM, about 5 nM, about 6 nM, about 7 nM, about 8 nM, about 9 nM, about 10 nM, about 20 nM, about 25 nM, about 30 nM, about 40 nM, about 50 nM, about 60 nm, about 70 nM, about 75 nM, about 80 nM, about 90 nM, about 100 nM, about 200 nM, about 250 nM, about 300 nM, about 400 nM, about 500 nM, about 600 nM, about 700 nM, about 750 nM, about 800 nM, about 900 nM, or about 1 µM. A useful time of reprogramming factor administration, and, if necessary, incubation after administration in the absence of reprogramming factors, as well as a number of administration/incubation cycles useful to achieve reprogramming of a cell of a given cell type can also be established by those of skill in the art by routine experimentation.

In some embodiments, the target cell for delivery of a reprogramming factor or a combination of reprogramming factors by a system or method provided herein, is a primary cell obtained by a biopsy from a subject. In some embodiments, the subject is diagnosed to have a disease. In some embodiments the disease is a degenerative disease characterized by diminished function of a specific cell type, for example, a neural cell. In some embodiments, a somatic cell obtained from a subject is reprogrammed to a pluripotent state by delivery of a reprogramming factor or a combination of reprogramming factors associated with a supercharged protein as provided herein. In some embodiments, a pluripotent cell is isolated after reprogramming of a somatic cell from a subject by transcription factors delivered by a system or method provided herein. In some embodiments, a pluripotent cell obtained after reprogramming of a somatic cell from a subject or differentiated progeny of such a pluripotent cell is used in a cell-replacement therapeutic approach. In some embodiments, cells of a cell type that is defective or exhibits diminished function in the subject are differentiated from a reprogrammed, pluripotent cell isolated from a somatic cell population obtained from the subject after reprogramming by methods or systems provided herein. In some embodiments the reprogrammed cells or their differentiated progeny are administered to the subject from which the somatic cell was obtained in an autologous cell replacement therapeutic approach.

Methods for the culture and selection of reprogrammed, pluripotent cells are well known to those in the art. Methods for differentiation of such cells into functional differentiated cell types are also well known for many cell types of therapeutic interest and will be apparent to those of skill in the art. In general, a method useful for the differentiation of embryonic stem cells will be applicable to the differentiation of reprogrammed, pluripotent cells.

In some embodiments, a transcription factor able to convert a cell from one differentiated state into another is delivered to a target cell in vitro or in vivo by a system or method provided herein. Transcription factors that effect transdifferentiation are known in the art (see, e.g., Zhou et al., *Nature* 455:627-33, 2008). In some embodiments, a combination of the transcription factors Ngn3, Pdx1, and Mafa are delivered to a differentiated pancreatic exocrine cell by a system or method as provided by this invention. It is known in the art that expression of a combination of these transcription factors results in the reprogramming of differentiated pancreatic exocrine cells to insulin-producing β-cells (Zhou et al., Nature 455:627-33, 2008). In some embodiments, a reprogrammed insulin-producing β-cells is derived from a subject having a deficiency in insulin-producing β-cells and is used in a cell-replacement therapeutic approach involving the subject.

Nucleases

In some embodiments, a nuclease is delivered to a target cell by a system or method provided herein. In some embodiments, a zinc-finger nuclease is delivered to a target cell by a system or method provided herein.

Zinc finger nucleases are a class of artificial nucleases that comprise a DNA cleavage domain and a zinc finger DNA binding domain. In some embodiments, the DNA cleavage domain is a non-specific DNA cleavage domain of a restriction endonuclease, for example, of FokI. In some embodiments, the DNA cleavage domain is a domain that only cleaves double-stranded DNA when dimerized with a second DNA cleavage domain of the same type. In some embodiments, the DNA cleavage domain is fused to the C-terminus of the zinc finger domain via a linker, for example, a peptide linker. In some embodiments, the zinc finger domain comprises between about 3 and about 6 zinc fingers and specifically recognizes and binds a target sequence of about 9-20 nucleotides in length. In some embodiments, a plurality of zinc finger nuclease molecules is delivered to a target cell by a system or method provided by this invention, with the zinc finger domain of one zinc finger nuclease molecule binding a target sequence in close proximity of the target sequence of a second zinc finger nuclease molecule. In some embodiments, the zinc finger domains of the zinc finger nuclease molecules binding target sequences in close proximity to each other are different. In some embodiments, a zinc finger nuclease molecule delivered to a cell by a system or method provided herein binds a target nucleic acid sequence in close proximity to the target sequence of another zinc finger nuclease molecule, so that the DNA cleavage domains of the molecules dimerize and cleave a DNA molecule at a site between the two target sequences.

In some embodiments, the genome of the target cell is edited by a zinc-finger nuclease or a plurality of zinc finger nucleases targeting a specific sequence of the genome after delivery. In some embodiments, a double-strand break is introduced at a specific site within the genome of a target cell by a zinc finger nuclease or a plurality of zinc finger nucleases, resulting in a disruption of the targeted genomic sequence. In some embodiments, the targeted genomic sequence is a nucleic acid sequence within the coding region of a gene. In some embodiments, the double-strand break introduced by the zinc finger nuclease or the plurality of zinc finger nucleases leads to a mutation within the target gene that impairs the expression of the respective gene product.

In some embodiments, the delivery of a zinc finger nuclease to a target cell results in a clinically or therapeutically beneficial disruption of the function of a specific gene. For example, in some embodiments, a zinc-finger nuclease targeting a nucleic acid sequence within the human CCR5 gene is delivered to T-cells of a human subject, for example, a subject diagnosed with an HIV infection/AIDS, by systems or methods provided herein, and zinc-finger-mediated editing of the CCR5 gene in the target T-cells leads to a loss-of function CCR5 gene mutation associated with resistance to HIV infection. In some embodiments, the mutation effected in the target T-cells by the zinc finger nuclease mimics the naturally occurring CCR5Δ32 mutation (Kim et al., Genome Research, 19:1279-88, 2009).

In some embodiments, cells from a subject are obtained and a zinc finger nuclease is delivered to the cells by a system or method provided herein ex vivo. In some embodiments, the treated cells are selected for those cells in which a desired zinc-finger nuclease-mediated genomic editing event has been effected. In some embodiments, treated cells carrying a desired genomic mutation or alteration are returned to the subject they were obtained from. For example, in some embodiments, CD4$^+$ T-lymphocytes are obtained from a subject diagnosed with HIV/AIDS and a zinc finger nuclease targeting a specific site within the CCR5 gene is delivered to the cells ex vivo. In some embodiments, CD4$^+$ T-lymphocytes with the desired CCR5 mutation, for example, a mutation mimicking the naturally occurring CCR5Δ32 mutation, are selected and isolated by methods well known to those of skill in the art. In some embodiments, the cells are returned to the subject they were obtained from after the desired zinc-finger nuclease-mediated CCR5 mutation has been achieved.

Methods for engineering, generation, and isolation of zinc-finger nucleases targeting specific sequences and editing cellular genomes at specific target sequences, including at sequences within the human CCR5 gene, are well known in the art (see, e.g., Mani et al., Biochemical and Biophysical Research Communications 335:447-457, 2005; Perez et al., Nature Biotechnology 26:808-16, 2008; Kim et al., Genome Research, 19:1279-88, 2009; Urnov et al., Nature 435:646-51, 2005; Carroll et al., Gene Therapy 15:1463-68, 2005; Lombardo et al., Nature Biotechnology 25:1298-306, 2007; Kandavelou et al., Biochemical and Biophysical Research Communications 388:56-61, 2009; and Hockemeyer et al., Nature Biotechnology 27(9):851-59, 2009).

Recombinases

In some embodiments, a recombinase is delivered to a target cell by a system or method as provided herein. In some embodiments, the genome of the target cell comprises a nucleotide sequence recognized by the recombinase to be delivered. In some embodiments, the recombinase is Cre recombinase and the genome of the target cell comprises a loxP site. In some embodiments, the recombinase is FLP recombinase and the target cell comprises a flp recombination site. In some embodiments, the recombinase is Dre recombinase and the genome of the target cell comprises a rox recombination site. In some embodiments, the recombinase is delivered to a target cell comprising a reporter gene flanked by two recombination sites to loop out the reporter gene. In some embodiments, the recombinase is delivered to a target cell comprising a recombination site recognized by the recombinase in its genome in temporal proximity with the delivery of a nucleic acid construct comprising a recombination site recognized by the recombinase to insert part of the nucleic acid into the target cell genome by recombinase-mediated recombination. Methods for recombinase-mediated excision of reporter genes and the recombinase-mediated insertion of nucleic acid constructs are well known in the art (see, e.g., Beard et al., Genesis 44(1):23-28), Nolden et al., Methods in Molecular Medicine 140:17-32, 2007, Anastassiadis et al., Disease Models and Mechanisms 2(9-10):508-15, 2009).

In some embodiments, a target cell comprises a recombination site, for example, a loxP site or a flp site, and a recombinase recognizing the recombination site, for example Cre or FLP recombinase, is delivered to the target cell by a system or method provided herein. In some embodiments, the target cell comprises two recombination sites, for example, two loxP or flp sites flanking a gene of interest, or a part of a gene of interest, for example an exon or a promoter region, or a reporter cassette previously introduced into the cell. In some embodiments, delivery of a recombinase effects recombinase-mediated excision, also referred to as loopout, of a nucleic acid sequence flanked by recombination sites in the target cell. In some embodiments, the delivery of a recombinase to a target cell by a system or method provided by this invention effects the excision of a nucleic acid sequence of about 500b, about 1 kb, about 2 kb, about 2-5 kb, about 5-10 kb, about 10-20 kb, about 20-50 kb, about 50-100 kb, about 100-200 kb, or more than about 200 kb.

Small Molecules

The present invention provides systems and methods for delivery of small molecules to cells in vivo or in vitro. Such systems and methods typically involve association of one or more small molecules with supercharged proteins to form a complex, and delivery of the complex to one or more cells. In some embodiments, the small molecule may have therapeutic activity. Preferably, though not necessarily, the drug is one that has already been deemed safe and effective for use in humans or animals by the appropriate governmental agency or regulatory body. In certain embodiments, the small molecule is a drug approved by the U.S. Food and Drug Administration for use in humans or other animals. For example, drugs approved for human use are listed by the FDA under 21 C.F.R. §§330.5, 331 through 361, and 440 through 460, incorporated herein by reference; drugs for veterinary use are listed by the FDA under 21 C.F.R. §§500 through 589, incorporated herein by reference. All listed drugs are considered acceptable for use in accordance with the present invention. In some embodiments, delivery of the complex to cells involves administering a complex comprising supercharged proteins associated with a small molecule to a subject in need thereof. In some embodiments, a small molecule by itself may not be able to enter the interior of a cell, but is able to enter the interior of a cell when complexed with a supercharged protein. In some embodiments, a supercharged protein is utilized to allow a small molecule to enter a cell.

Formation of Complexes

The present invention provides complexes comprising supercharged proteins associated with one or more agents to be delivered. In some embodiments, supercharged proteins are associated with one or more agents to be delivered by non-covalent interactions. In some embodiments, supercharged proteins are associated with one or more nucleic acids by electrostatic interactions. In certain embodiments, supercharged proteins have an overall net positive charge, and the agent to be delivered such as nucleic acids have an overall net negative charge.

In certain embodiments, supercharged proteins are associated with one or more agents to be delivered by covalent interactions. For example, a supercharged protein may be fused to a peptide or protein to be delivered. Covalent interaction may be direct or indirect. In some embodiments, such covalent interactions are mediated by one or more linkers. In some embodiments, the linker is a cleavable linker. In certain embodiments, the cleavable linker comprises an amide, ester, or disulfide bond. For example, the linker may be an amino acid sequence that is cleavable by a cellular enzyme. In certain embodiments, the enzyme is a protease. In other embodiments, the enzyme is an esterase. In some embodiments, the enzyme is one that is more highly expressed in certain cell types than in other cell types. For example, the enzyme may be one that is more highly expressed in tumor cells than in non-tumor cells. Exemplary linkers and enzymes that cleave those linkers are presented in Table 3.

TABLE 3

Cleavable Linkers

| Linker Sequence | Enzyme(s) Targeting Linker |
|---|---|
| $X^1$-AGVF-X (SEQ ID NO: 90) | lysosomal thiol proteinases (see, e,g., Duncan et al., 1982, *Biosci, Rep.*, 2: 1041-46; incorporated herein by reference) |
| X-GFLG-X (SEQ ID NO: 91) | lysosomal cysteine proteinases (see, e.g., Vasey et al., *Clin. Canc. Res.*, 1999, 5: 83-94; incorporated herein by reference) |
| X-FK-X (SEQ ID NO: 92) | Cathepsin B - ubiquitous, overexpressed in many solid tumors, such as breast cancer (see, e.g., Dubowchik et al., 2002, *Bioconjugate Chem.*, 13: 855-69; incorporated herein by reference) |
| X-A*L-X (SEQ ID NO: 93) | Cathepsin B - ubiquitous, overexpressed in many solid tumors, such as breast cancer (see, e.g., Trouet et al., 1982, *Proc. Natl. Acad Sci.*, USA, 79: 626-29; incorporated herein by reference) |
| X-A*LA*L-X (SEQ ID NO: 94) | Cathepsin B - ubiquitous, overexpressed in many solid tumors (see, e.g., Schmid et al., 2007, *Bioconjugate Chem*, 18: 702-16; incorporated herein by reference) |
| X-AL*AL*A-X (SEQ ID NO: 95) | Cathepsin D - ubiquitous (see, e,g., Czerwinski et al., 1998, *Proc. Natl. Acad Sci.*, USA, 95: 11520-25; incorporated herein by reference) |

$^1$X denotes a supercharged protein and/or agent to be delivered
*refers to observed cleavage site To give but one particular example, a +36 GFP may be associated with an agent to be delivered by a cleavable linker, such as ALAL (SEQ ID NO: 96), to generate +36 GFP-(GGS)$_4$-ALAL-(GGS)$_4$-X (SEQ ID NO: 154; where X is the agent to be delivered).

In certain embodiments, the agent to be delivered is a nucleic acid. In some embodiments, complexes are formed by incubating supercharged proteins with nucleic acids. In some embodiments, formation of complexes is carried out in a buffered solution. In some embodiments, formation of complexes is carried out at or around pH 7. In some embodiments, formation of complexes is carried out at about pH 5, about pH 6, about pH 7, about pH 8, or about pH 9. Formation of complexes is typically carried out at a pH that does not negatively affect the function of the supercharged protein and/or nucleic acid.

In some embodiments, formation of complexes is carried out at room temperature. In some embodiments, formation of complexes is carried out at or around 37° C. In some embodiments, formation of complexes is carried out below 4° C., at about 4° C., at about 10° C., at about 15° C., at about 20° C., at about 25° C., at about 30° C., at about 35° C., at about 37° C., at about 40° C., or higher than 40° C. Formation of complexes is typically carried out at a temperature that does not negatively affect the function of the supercharged protein and/or nucleic acid.

In some embodiments, formation of complexes is carried out in serum-free medium. In some embodiments, formation of complexes is carried out in the presence of $CO_2$ (e.g., about 1%, about 2%, about 3%, about 4%, about 5%, about 6%, or more).

In some embodiments, formation of complexes is carried out using concentrations of nucleic acid of about 100 nm. In some embodiments, formation of complexes is carried out using concentrations of nucleic acid of about 25 nM, about 50 nM, about 75 nM, about 90 nM, about 100 nM, about 110 nM, about 125 nM, about 150 nM, about 175 nM, or about 200 nM. In some embodiments, formation of complexes is carried out using concentrations of supercharged protein of about 40 nM. In some embodiments, formation of complexes is carried out using concentrations of supercharged protein of about 10 nM, about 20 nM, about 30 nM, about 40 nM, about 50 nM, about 60 nM, about 70 nM, about 80 nM, about 90 nM, or about 100 nM.

In some embodiments, formation of complexes is carried out under conditions of excess nucleic acid. In some embodiments, formation of complexes is carried out with ratios of nucleic acid:supercharged protein of about 20:1, about 10:1, about 9:1, about 8:1, about 7:1, about 6:1, about 5:1, about 4:1, about 3:1, about 2:1, or about 1:1. In some embodiments, formation of complexes is carried out with ratios of nucleic acid:supercharged protein of about 3:1. In some embodiments, formation of complexes is carried out with ratios of supercharged protein:nucleic acid of about 20:1, about 10:1, about 9:1, about 8:1, about 7:1, about 6:1, about 5:1, about 4:1, about 3:1, about 2:1, or about 1:1.

In some embodiments, formation of complexes is carried out by mixing supercharged protein with nucleic acid, and agitating the mixture (e.g., by inversion). In some embodiments, formation of complexes is carried out by mixing supercharged protein with nucleic acid, and allowing the mixture to sit still. In some embodiments, the formation of the complex is carried out in the presence of a pharmaceutically acceptable carrier or excipient. In some embodiments, the complex is further combined with a pharmaceutically acceptable carrier or excipient. Exemplary excipients or carriers include water, solvents, lipids, proteins, peptides, endosomolytic agents (e.g., chloroquine, pyrene butyric acid), small molecules, carbohydrates, buffers, natural polymers, synthetic polymers (e.g., PLGA, polyurethane, polyesters, polycaprolactone, polyphosphazenes), pharmaceutical agents, etc.

In some embodiments, complexes comprising supercharged protein and nucleic may migrate more slowly in gel electrophoresis assays than either the supercharged protein alone or the nucleic acid alone.

Applications

The present invention provides supercharged proteins or complexes comprising supercharged proteins, naturally occurring or engineered, associated with agents to be delivered, as well as methods for using such complexes. Any agent may be delivered using the inventive system. In the case of delivering nucleic acids, since nucleic acids generally have net negative charges, supercharged proteins that associate with nucleic acids are typically superpositively charged proteins. The inventive supercharged proteins or complexes may be used to treat or prevent any disease that can benefit, e.g., from the delivery of an agent to a cell. The inventive supercharged proteins or complexes may also be used to transfect or treat cells for research purposes.

In some embodiments, supercharged proteins or complexes in accordance with the invention may be used for research purposes, e.g., to efficiently deliver nucleic acids to cells in a research context. In some embodiments, supercharged proteins may be used as research tools to efficiently transform cells with nucleic acids. In some embodiments, supercharged proteins may be used as research tools to efficiently introduce RNAi agents into cells for purposes of studying RNAi mechanisms. In some embodiments, supercharged proteins may be used as research tools to silence genes in a cell. In certain embodiments, supercharged proteins may be used to deliver a peptide or protein into a cell for the purpose of studying the biological activity of the peptide or protein. In certain embodiments, supercharged proteins may be introduced into a cell for the purpose of studying the biological activity of the peptide or protein. In certain embodiments, supercharged proteins may be used to deliver a small molecule into a cell for the purpose of studying the biological activity of the small molecule.

In some embodiments, supercharged proteins or complexes in accordance with the present invention may be used for therapeutic purposes. In some embodiments, supercharged proteins or complexes in accordance with the present invention may be used for treatment of any of a variety of diseases, disorders, and/or conditions, including but not limited to one or more of the following: autoimmune disorders (e.g. diabetes, lupus, multiple sclerosis, psoriasis, rheumatoid arthritis); inflammatory disorders (e.g. arthritis, pelvic inflammatory disease); infectious diseases (e.g. viral infections (e.g., HIV, HCV, RSV), bacterial infections, fungal infections, sepsis); neurological disorders (e.g. Alzheimer's disease, Huntington's disease; autism; Duchenne muscular dystrophy); cardiovascular disorders (e.g. atherosclerosis, hypercholesterolemia, thrombosis, clotting disorders, angiogenic disorders such as macular degeneration); proliferative disorders (e.g. cancer, benign neoplasms); respiratory disorders (e.g. chronic obstructive pulmonary disease); digestive disorders (e.g. inflammatory bowel disease, ulcers); musculoskeletal disorders (e.g. fibromyalgia, arthritis); endocrine, metabolic, and nutritional disorders (e.g. diabetes, osteoporosis); urological disorders (e.g. renal disease); psychological disorders (e.g. depression, schizophrenia); skin disorders (e.g. wounds, eczema); blood and lymphatic disorders (e.g. anemia, hemophilia); etc.

Supercharged proteins or complexes of the invention may be used in a clinical setting. For example, a supercharged protein may be associated with a nucleic acid that can be used for therapeutic applications. Such nucleic acids may include functional RNAs that are used to reduce levels of one or more target transcripts (e.g., siRNAs, shRNAs, microRNAs, antisense RNAs, ribozymes, etc.). In some embodiments, a disease, disorder, and/or condition may be associated with abnormally high levels of one or more particular mRNAs and/or proteins. To give but one particular example, many forms of breast cancer are associated with increased expression of the epidermal growth factor receptor (EGFR). Supercharged proteins may be utilized to deliver an RNAi agent that targets EGFR mRNA to cells (e.g., breast cancer tumor cells). Supercharged proteins may be efficiently taken up by tumor cells, resulting in delivery of the RNAi agent. Upon delivery, the RNAi agent may be effective to reduce levels of EGFR mRNA, thereby reducing levels of EGFR protein. Such a method may be an effective treatment for breast cancers (e.g., breast cancers associated with elevated levels of EGFR). One of ordinary skill in the art will recognize that similar methods may be used to treat any disease, disorder, and/or condition that is associated with elevated levels of one or more particular mRNAs and/or proteins.

In some embodiments, a disease, disorder, and/or condition may be associated with abnormally low levels of one or more particular mRNAs and/or proteins. To give but one particular example, tyrosinemia is a disorder in which the body cannot effectively break down the amino acid tyrosine. There are three types of tyrosinemia, each caused by a deficiency in a different enzyme. Supercharged proteins may be used to treat tyrosinemia by delivering a vector that drives expression of the deficient enzyme. Upon delivery of the vector to cells, cellular machinery can direct expression of the deficient enzyme, thereby treating a patient's tyrosinemia. One of ordinary skill in the art will recognize that similar methods may be used to treat any disease, disorder, and/or condition that is associated with abnormally low levels of one or more particular mRNAs and/or proteins.

As demonstrated in Examples 2 and 3, supercharged protein-based nucleic acid delivery to cells is successful, even using cell lines that are resistant to nucleic acid transfection using conventional cationic lipid-based transfection methods. Thus, in some embodiments, supercharged proteins are utilized to deliver nucleic acids to cells which are resistant to other methods of nucleic acid delivery (e.g., cationic lipid-based transformation methods, such as use of lipofectamine). Furthermore, the present inventors have demonstrated that, surprisingly, superpositively charged proteins can be used at low nanomolar (nM) concentrations (e.g., 1 nm to 100 nm) to effectively deliver nucleic acids to cells. In some embodiments, supercharged proteins can be used at about 1 nm, about 5 nm, about 10 nm, about 25 nm, about 50 nm, about 75 nm, about 100 nm, or higher than about 100 nm to effectively deliver nucleic acids to cells.

In some embodiments, a supercharged protein may be a therapeutic agent. For example, a supercharged protein may be a supercharged variant of a protein drug (e.g., abatacept, adalimumab, alefacept, erythropoietin, etanercept, human growth hormone, infliximab, insulin, trastuzumab, interferons, etc.). In some embodiments, a supercharged protein may be a therapeutic agent, and an associated nucleic acid may be useful for targeting delivery of the therapeutic protein to a target site. For example, a supercharged protein may be a supercharged variant of a protein drug (e.g., abatacept, adalimumab, alefacept, erythropoietin, etanercept, human growth hormone, infliximab, insulin, trastuzumab, interferons, etc.), and an associated nucleic acid may be an aptamer that efficiently targets the therapeutic protein to a target organ, tissue, and/or cell. The supercharged protein can also be an imaging, diagnostic, or other detection agent.

In some embodiments, one or both of the supercharged protein and an agent to be delivered (if present) may have detectable qualities. For example, one or both of the supercharged protein and the agent may comprise at least one fluorescent moiety. In some embodiments, the supercharged protein has inherent fluorescent qualities (e.g., GFP). In some embodiments, one or both of the supercharged protein and the agent to be delivered may be associated with at least one fluorescent moiety (e.g., conjugated to a fluorophore, fluorescent dye, etc.). Alternatively or additionally, one or both of the supercharged protein and the agent to be delivered may comprise at least one radioactive moiety (e.g., protein may comprise $^{35}$S; nucleic acid may comprise $^{32}$P; etc.). Such detectable moieties may be useful for detecting and/or monitoring delivery of the supercharged proteins or complexes to target sites.

In some embodiments, the supercharged protein or an agent associated with a supercharged protein includes a detectable label. These molecules can be used in detection, imaging, disease staging, diagnosis, or patient selection. Suitable labels include fluorescent, chemiluminescent, enzymatic labels, colorimetric, phosphorescent, density-based labels, e.g., labels based on electron density, and in general contrast agents, and/or radioactive labels.

Pharmaceutical Compositions

The present invention provides supercharged proteins and complexes comprising supercharged proteins associated with at least one agent to be delivered. Thus, the present invention provides pharmaceutical compositions comprising one or more supercharged proteins or one or more such complexes, and one or more pharmaceutically acceptable excipients. Pharmaceutical compositions may optionally comprise one or more additional therapeutically active substances. In accordance with some embodiments, a method of administering pharmaceutical compositions comprising one or more supercharged proteins or one or more complexes comprising supercharged proteins associated with at least one agent to be delivered to a subject in need thereof is provided. In some embodiments, compositions are administered to humans. For the purposes of the present disclosure, the phrase "active ingredient" generally refers to a supercharged protein or complex comprising a supercharged protein and at least one agent to be delivered as described herein.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the pharmaceutical compositions is contemplated include, but are not limited to, humans and/or other primates; mammals, including commercially relevant mammals such as cattle, pigs, horses, sheep, cats, dogs, mice, and/or rats; and/or birds, including commercially relevant birds such as chickens, ducks, geese, and/or turkeys.

Formulations of the pharmaceutical compositions described herein may be prepared by any method known or hereafter developed in the art of pharmacology. In general, such preparatory methods include the step of bringing the active ingredient into association with an excipient and/or one or more other accessory ingredients, and then, if necessary and/or desirable, shaping and/or packaging the product into a desired single- or multi-dose unit.

A pharmaceutical composition in accordance with the invention may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition in accordance with the invention will vary, depending upon the identity, size, and/or condition of the subject treated and further depending upon the route by which the composition is to be administered. By way of example, the composition may comprise between 0.1% and 100% (w/w) active ingredient.

Pharmaceutical formulations may additionally comprise a pharmaceutically acceptable excipient, which, as used herein, includes any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's *The Science and Practice of Pharmacy*, 21$^{st}$ Edition, A. R. Gennaro (Lippincott, Williams & Wilkins, Baltimore, Md., 2006; incorporated herein by reference) discloses various excipients used in formulating pharmaceutical compositions and known techniques for the preparation thereof. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this invention.

In some embodiments, a pharmaceutically acceptable excipient is at least 95%, at least 96%, at least 97%, at least 98%, at least 99%, or 100% pure. In some embodiments, an excipient is approved for use in humans and for veterinary use. In some embodiments, an excipient is approved by United States Food and Drug Administration. In some embodiments, an excipient is pharmaceutical grade. In some embodiments, an excipient meets the standards of the United States Pharmacopoeia (USP), the European Pharmacopoeia (EP), the British Pharmacopoeia, and/or the International Pharmacopoeia.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients may optionally be included in pharmaceutical formulations. Excipients such as cocoa butter and suppository waxes, coloring agents, coating agents, sweetening, flavoring, and/or perfuming agents can be present in the composition, according to the judgment of the formulator.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and/or combinations thereof.

Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and/or combinations thereof.

Exemplary surface active agents and/or emulsifiers include, but are not limited to, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum® [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween®20], polyoxyethylene sorbitan [Tween®60], polyoxyethylene sorbitan monooleate [Tween®80], sorbitan monopalmitate [Span®40], sorbitan monostearate [Span®60], sorbitan tristearate [Span®65], glyceryl monooleate, sorbitan monooleate [Span®80]), polyoxyethylene esters (e.g. polyoxyethylene monostearate [Myrj®45], polyoxyethylene hydrogenated castor oil, polyethoxylated castor oil, polyoxymethylene stearate, and Solutol®), sucrose fatty acid esters, polyethylene glycol fatty acid esters (e.g. Cremophor®), polyoxyethylene ethers, (e.g. polyoxyethylene lauryl ether [Brij®30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic®F 68, Poloxamer®188, cetrimonium bromide, cetylpyridinium chloride, benzalkonium chloride, docusate sodium, etc. and/or combinations thereof.

Exemplary binding agents include, but are not limited to, starch (e.g. cornstarch and starch paste); gelatin; sugars (e.g. sucrose, glucose, dextrose, dextrin, molasses, lactose, lactitol, mannitol); natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan); alginates; polyethylene oxide; polyethylene glycol; inorganic calcium salts; silicic acid; polymethacrylates; waxes; water; alcohol; etc.; and combinations thereof.

Exemplary preservatives may include, but are not limited to, antioxidants, chelating agents, antimicrobial preservatives, antifungal preservatives, alcohol preservatives, acidic preservatives, and/or other preservatives. Exemplary antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and/or sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and/or trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and/or thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and/or sorbic acid. Exemplary alcohol preservatives include, but are not limited to, ethanol, polyethylene glycol, phenol, phenolic compounds, bisphenol, chlorobutanol, hydroxybenzoate, and/or phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and/or phytic acid. Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus®, Phenonip®, methylparaben, Germall®115, Germaben®II, Neolone™, Kathon™, and/or Euxyl®.

Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and/or combinations thereof.

Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary oils include, but are not limited to, almond, apricot kernel, avocado, babassu, bergamot, black current seed, borage, cade, chamomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and/or combinations thereof.

Liquid dosage forms for oral and parenteral administration include, but are not limited to, pharmaceutically acceptable emulsions, microemulsions, solutions, suspensions, syrups, and/or elixirs. In addition to active ingredients, liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, oral compositions can include adjuvants such as wetting agents, emulsifying and suspending agents, sweetening, flavoring, and/or perfuming agents. In certain embodiments for parenteral administration, compositions are mixed with solubilizing agents such as Cremophor®, alcohols, oils, modified oils, glycols, polysorbates, cyclodextrins, polymers, and/or combinations thereof.

Injectable preparations, for example, sterile injectable aqueous or oleaginous suspensions may be formulated according to the known art using suitable dispersing agents, wetting agents, and/or suspending agents. Sterile injectable preparations may be sterile injectable solutions, suspensions, and/or emulsions in nontoxic parenterally acceptable diluents and/or solvents, for example, as a solution in 1,3-butanediol. Among the acceptable vehicles and solvents that may be employed are water, Ringer's solution, U.S.P., and isotonic sodium chloride solution. Sterile, fixed oils are conventionally employed as a solvent or suspending medium. For this purpose any bland fixed oil can be employed including synthetic mono- or diglycerides. Fatty acids such as oleic acid can be used in the preparation of injectables.

Injectable formulations can be sterilized, for example, by filtration through a bacterial-retaining filter, and/or by incorporating sterilizing agents in the form of sterile solid compositions which can be dissolved or dispersed in sterile water or other sterile injectable medium prior to use.

In order to prolong the effect of an active ingredient, it is often desirable to slow the absorption of the active ingredient from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are prepared by entrapping the drug in liposomes or microemulsions which are compatible with body tissues.

Compositions for rectal or vaginal administration are typically suppositories which can be prepared by mixing compositions with suitable non-irritating excipients such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, an active ingredient is mixed with at least one inert, pharmaceutically acceptable excipient such as sodium citrate or dicalcium phosphate and/or fillers or extenders (e.g. starches, lactose, sucrose, glucose, mannitol, and silicic acid), binders (e.g. carboxymethylcellulose, alginates, gelatin, polyvinylpyrrolidinone, sucrose, and acacia), humectants (e.g. glycerol), disintegrating agents (e.g. agar, calcium carbonate, potato or tapioca starch, alginic acid, certain silicates, and sodium carbonate), solution retarding agents (e.g. paraffin), absorption accelerators (e.g. quaternary ammonium compounds), wetting agents (e.g. cetyl alcohol and glycerol monostearate), absorbents (e.g. kaolin and bentonite clay), and lubricants (e.g. talc, calcium stearate, magnesium stearate, solid polyethylene glycols, sodium lauryl sulfate), and mixtures thereof. In the case of capsules, tablets and pills, the dosage form may comprise buffering agents.

Solid compositions of a similar type may be employed as fillers in soft and hard-filled gelatin capsules using such excipients as lactose or milk sugar as well as high molecular weight polyethylene glycols and the like. Solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type may be employed as fillers in soft and hard-filled gelatin capsules using such excipients as lactose or milk sugar as well as high molecular weight polyethylene glycols and the like.

Dosage forms for topical and/or transdermal administration of a composition may include ointments, pastes, creams, lotions, gels, powders, solutions, sprays, inhalants and/or patches. Generally, an active ingredient is admixed under sterile conditions with a pharmaceutically acceptable excipient and/or any needed preservatives and/or buffers as may be required. Additionally, the present invention contemplates the use of transdermal patches, which often have the added advantage of providing controlled delivery of a compound to the body. Such dosage forms may be prepared, for example, by dissolving and/or dispensing the compound in the proper medium. Alternatively or additionally, rate may be controlled by either providing a rate controlling membrane and/or by dispersing the compound in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions may be administered by devices which limit the effective penetration length of a needle into the skin, such as those described in PCT publication WO 99/34850 and functional equivalents thereof. Jet injection devices which deliver liquid compositions to the dermis via a liquid jet injector and/or via a needle which pierces the stratum corneum and produces a jet which reaches the dermis are suitable. Jet injection devices are described, for example, in U.S. Pat. Nos. 5,480,381; 5,599, 302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824;

4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes may be used in the classical mantoux method of intradermal administration.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (w/w) active ingredient, although the concentration of active ingredient may be as high as the solubility limit of the active ingredient in the solvent. Formulations for topical administration may further comprise one or more of the additional ingredients described herein.

A pharmaceutical composition may be prepared, packaged, and/or sold in a formulation suitable for pulmonary administration via the buccal cavity. Such a formulation may comprise dry particles which comprise the active ingredient and which have a diameter in the range from about 0.5 nm to about 7 nm or from about 1 nm to about 6 nm. Such compositions are conveniently in the form of dry powders for administration using a device comprising a dry powder reservoir to which a stream of propellant may be directed to disperse the powder and/or using a self propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nm and at least 95% of the particles by number have a diameter less than 7 nm. Alternatively, at least 95% of the particles by weight have a diameter greater than 1 nm and at least 90% of the particles by number have a diameter less than 6 nm. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50% to 99.9% (w/w) of the composition, and active ingredient may constitute 0.1% to 20% (w/w) of the composition. A propellant may further comprise additional ingredients such as a liquid non-ionic and/or solid anionic surfactant and/or a solid diluent (which may have a particle size of the same order as particles comprising the active ingredient).

Pharmaceutical compositions formulated for pulmonary delivery may provide an active ingredient in the form of droplets of a solution and/or suspension. Such formulations may be prepared, packaged, and/or sold as aqueous and/or dilute alcoholic solutions and/or suspensions, optionally sterile, comprising active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. Droplets provided by this route of administration may have an average diameter in the range from about 0.1 nm to about 200 nm.

Formulations described herein as being useful for pulmonary delivery are useful for intranasal delivery of a pharmaceutical composition. Another formulation suitable for intranasal administration is a coarse powder comprising the active ingredient and having an average particle from about 0.2 μm to 500 μm. Such a formulation is administered in the manner in which snuff is taken, i.e. by rapid inhalation through the nasal passage from a container of the powder held close to the nose.

Formulations suitable for nasal administration may, for example, comprise from about as little as 0.1% (w/w) and as much as 100% (w/w) of active ingredient, and may comprise one or more of the additional ingredients described herein. A pharmaceutical composition may be prepared, packaged, and/or sold in a formulation suitable for buccal administration. Such formulations may, for example, be in the form of tablets and/or lozenges made using conventional methods, and may, for example, 0.1% to 20% (w/w) active ingredient, the balance comprising an orally dissolvable and/or degradable composition and, optionally, one or more of the additional ingredients described herein. Alternately, formulations suitable for buccal administration may comprise a powder and/or an aerosolized and/or atomized solution and/or suspension comprising active ingredient. Such powdered, aerosolized, and/or aerosolized formulations, when dispersed, may have an average particle and/or droplet size in the range from about 0.1 nm to about 200 nm, and may further comprise one or more of any additional ingredients described herein.

A pharmaceutical composition may be prepared, packaged, and/or sold in a formulation suitable for ophthalmic administration. Such formulations may, for example, be in the form of eye drops including, for example, a 0.1/1.0% (w/w) solution and/or suspension of the active ingredient in an aqueous or oily liquid excipient. Such drops may further comprise buffering agents, salts, and/or one or more other of any additional ingredients described herein. Other opthalmically-administrable formulations which are useful include those which comprise the active ingredient in microcrystalline form and/or in a liposomal preparation. Ear drops and/or eye drops are contemplated as being within the scope of this invention.

General considerations in the formulation and/or manufacture of pharmaceutical agents may be found, for example, in *Remington: The Science and Practice of Pharmacy* 21$^{st}$ ed., Lippincott Williams & Wilkins, 2005 (incorporated herein by reference).

Administration

The present invention provides methods comprising administering supercharged proteins or complexes in accordance with the invention to a subject in need thereof. Supercharged proteins or complexes, or pharmaceutical, imaging, diagnostic, or prophylactic compositions thereof, may be administered to a subject using any amount and any route of administration effective for preventing, treating, diagnosing, or imaging a disease, disorder, and/or condition (e.g., a disease, disorder, and/or condition relating to working memory deficits). The exact amount required will vary from subject to subject, depending on the species, age, and general condition of the subject, the severity of the disease, the particular composition, its mode of administration, its mode of activity, and the like. Compositions in accordance with the invention are typically formulated in dosage unit form for ease of administration and uniformity of dosage. It will be understood, however, that the total daily usage of the compositions of the present invention will be decided by the attending physician within the scope of sound medical judgment. The specific therapeutically effective, prophylactically effective, or appropriate imaging dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

Supercharged proteins or complexes comprising supercharged proteins associated with at least one agent to be delivered and/or pharmaceutical, prophylactic, diagnostic, or imaging compositions thereof may be administered to animals, such as mammals (e.g., humans, domesticated animals, cats, dogs, mice, rats, etc.). In some embodiments, supercharged proteins or complexes and/or pharmaceutical, prophylactic, diagnostic, or imaging compositions thereof are administered to humans.

Supercharged proteins or complexes comprising supercharged proteins associated with at least one agent to be delivered and/or pharmaceutical, prophylactic, diagnostic, or imaging compositions thereof in accordance with the present invention may be administered by any route. In some embodiments, supercharged proteins or complexes, and/or pharmaceutical, prophylactic, diagnostic, or imaging compositions thereof, are administered by one or more of a variety of routes, including oral, intravenous, intramuscular, intraarterial, intramedullary, intrathecal, subcutaneous, intraventricular, transdermal, interdermal, rectal, intravaginal, intraperitoneal, topical (e.g. by powders, ointments, creams, gels, lotions, and/or drops), mucosal, nasal, buccal, enteral, vitreal, intratumoral, sublingual; by intratracheal instillation, bronchial instillation, and/or inhalation; as an oral spray, nasal spray, and/or aerosol, and/or through a portal vein catheter. In some embodiments, supercharged proteins or complexes, and/or pharmaceutical, prophylactic, diagnostic, or imaging compositions thereof, are administered by systemic intravenous injection. In specific embodiments, supercharged proteins or complexes and/or pharmaceutical, prophylactic, diagnostic, or imaging compositions thereof may be administered intravenously and/or orally. In specific embodiments, supercharged proteins or complexes, and/or pharmaceutical, prophylactic, diagnostic, or imaging compositions thereof, may be administered in a way which allows the supercharged protein or complex to cross the blood-brain barrier, vascular barrier, or other epithelial barrier.

However, the invention encompasses the delivery of supercharged proteins or complexes, and/or pharmaceutical, prophylactic, diagnostic, or imaging compositions thereof, by any appropriate route taking into consideration likely advances in the sciences of drug delivery.

In general the most appropriate route of administration will depend upon a variety of factors including the nature of the supercharged protein or complex comprising supercharged proteins associated with at least one agent to be delivered (e.g., its stability in the environment of the gastrointestinal tract, bloodstream, etc.), the condition of the patient (e.g., whether the patient is able to tolerate particular routes of administration), etc. The invention encompasses the delivery of the pharmaceutical, prophylactic, diagnostic, or imaging compositions by any appropriate route taking into consideration likely advances in the sciences of drug delivery.

In certain embodiments, compositions in accordance with the invention may be administered at dosage levels sufficient to deliver from about 0.0001 mg/kg to about 100 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day, to obtain the desired therapeutic, diagnostic, prophylactic, or imaging effect. The desired dosage may be delivered three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations).

Supercharged proteins or complexes comprising supercharged proteins associated with at least one agent to be delivered may be used in combination with one or more other therapeutic, prophylactic, diagnostic, or imaging agents. By "in combination with," it is not intended to imply that the agents must be administered at the same time and/or formulated for delivery together, although these methods of delivery are within the scope of the invention. Compositions can be administered concurrently with, prior to, or subsequent to, one or more other desired therapeutics or medical procedures. In general, each agent will be administered at a dose and/or on a time schedule determined for that agent. In some embodiments, the invention encompasses the delivery of pharmaceutical, prophylactic, diagnostic, or imaging compositions in combination with agents that may improve their bioavailability, reduce and/or modify their metabolism, inhibit their excretion, and/or modify their distribution within the body.

In will further be appreciated that therapeutically, prophylactically, diagnostically, or imaging active agents utilized in combination may be administered together in a single composition or administered separately in different compositions. In general, it is expected that agents utilized in combination with be utilized at levels that do not exceed the levels at which they are utilized individually. In some embodiments, the levels utilized in combination will be lower than those utilized individually.

The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, a composition useful for treating cancer in accordance with the invention may be administered concurrently with a chemotherapeutic agent), or they may achieve different effects (e.g., control of any adverse effects).

Kits

The invention provides a variety of kits for conveniently and/or effectively carrying out methods of the present invention. Typically kits will comprise sufficient amounts and/or numbers of components to allow a user to perform multiple treatments of a subject(s) and/or to perform multiple experiments.

In some embodiments, kits comprise one or more of (i) a supercharged protein, as described herein; (ii) an agent to be delivered; (iii) instructions for forming complexes comprising supercharged proteins associated with at least one agent.

In some embodiments, kits comprise one or more of (i) a supercharged protein, as described herein; (ii) a nucleic acid; (iii) instructions for forming complexes comprising supercharged proteins associated with at least one nucleic acid.

In some embodiments, kits comprise one or more of (i) a supercharged protein, as described herein; (ii) a peptide or protein; (iii) instructions for forming complexes comprising supercharged proteins associated with at least one peptide or protein to be delivered.

In some embodiments, kits comprise one or more of (i) a supercharged protein, as described herein; (ii) a small molecule; (iii) instructions for forming complexes comprising supercharged proteins associated with at least one small molecule.

In some embodiments, kits comprise one or more of (i) a supercharged protein or complex comprising supercharged proteins associated with at least one agent to be delivered, as described herein; (ii) at least one pharmaceutically acceptable excipient; (iii) a syringe, needle, applicator, etc. for administration of a pharmaceutical, prophylactic, diagnostic, or imaging composition to a subject; and (iv) instructions for preparing pharmaceutical composition and for administration of the composition to the subject.

In some embodiments, kits comprise one or more of (i) a pharmaceutical composition comprising a supercharged protein or complex comprising supercharged proteins associated with at least one agent to be delivered, as described herein; (ii) a syringe, needle, applicator, etc. for administration of the pharmaceutical, prophylactic, diagnostic, or imaging composition to a subject; and (iii) instructions for administration of the pharmaceutical, prophylactic, diagnostic, or imaging composition to the subject.

In some embodiments, kits comprise one or more components useful for modifying proteins of interest to produce supercharged proteins. These kits typically include all or most of the reagents needed create supercharged proteins. In certain embodiments, such a kit includes computer software to aid a researcher in designing a supercharged protein in accordance with the invention. In certain embodiments, such a kit includes reagents necessary for performing site-directed mutagenesis.

In some embodiments, kits may include additional components or reagents. For example, kits may comprise buffers, reagents, primers, oligonucleotides, nucleotides, enzymes, buffers, cells, media, plates, tubes, instructions, vectors, etc. In some embodiments, kits may comprise instructions for use.

In some embodiments, kits include a number of unit dosages of a pharmaceutical, prophylactic, diagnostic, or imaging composition comprising supercharged proteins or complexes comprising supercharged proteins and at least one agent to be delivered. A memory aid may be provided, for example in the form of numbers, letters, and/or other markings and/or with a calendar insert, designating the days/times in the treatment schedule in which dosages can be administered. Placebo dosages, and/or calcium dietary supplements, either in a form similar to or distinct from the dosages of the pharmaceutical, prophylactic, diagnostic, or imaging compositions, may be included to provide a kit in which a dosage is taken every day.

Kits may comprise one or more vessels or containers so that certain of the individual components or reagents may be separately housed. Kits may comprise a means for enclosing individual containers in relatively close confinement for commercial sale (e.g., a plastic box in which instructions, packaging materials such as styrofoam, etc., may be enclosed). Kit contents are typically packaged for convenience use in a laboratory.

These and other aspects of the present invention will be further appreciated upon consideration of the following Examples, which are intended to illustrate certain particular embodiments of the invention but are not intended to limit its scope, as defined by the claims.

EXAMPLES

Example 1

Supercharging Proteins can Impart Extraordinary Resilience

Figure 1B:
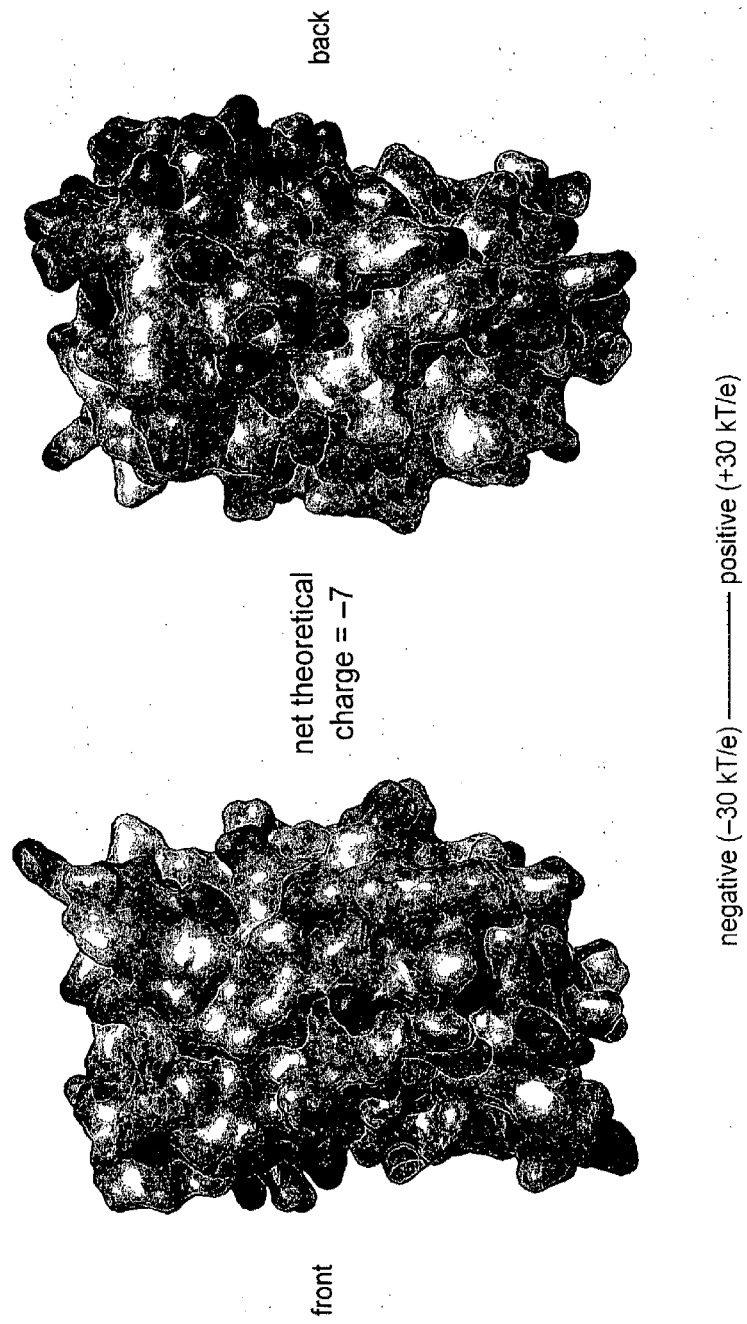
Figure 1C:
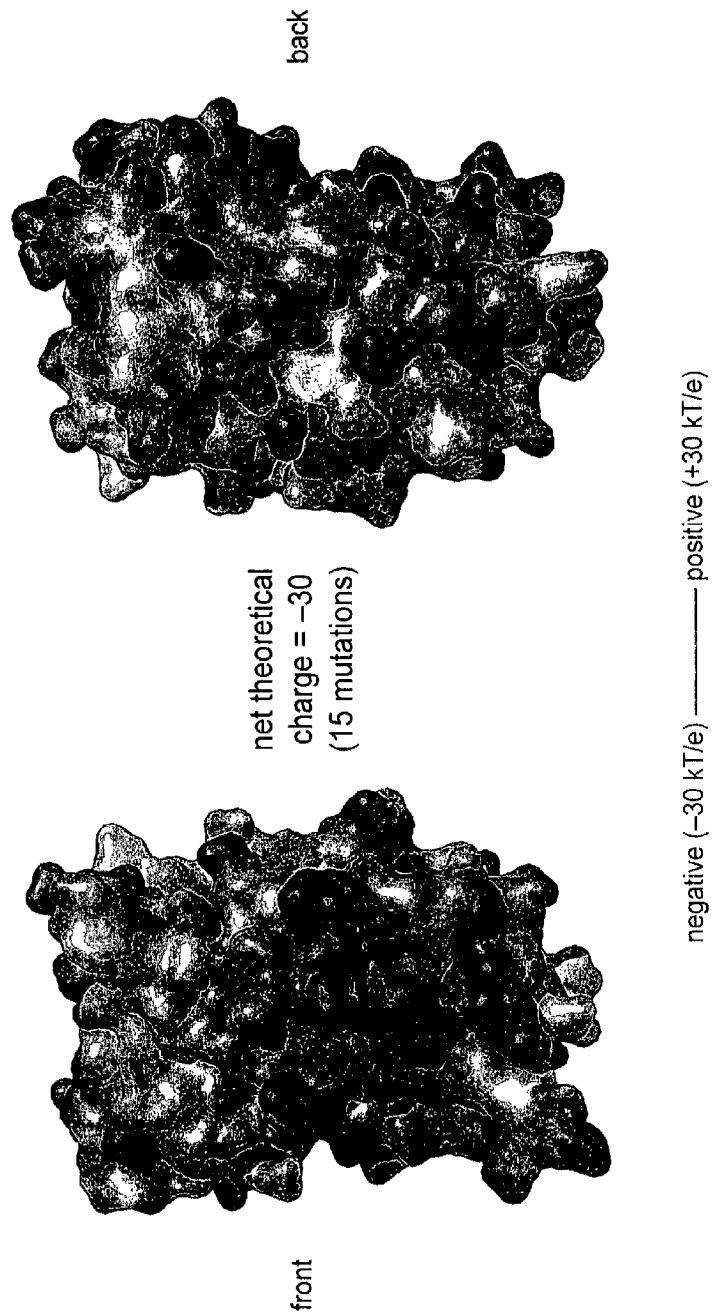
Figure 1D:
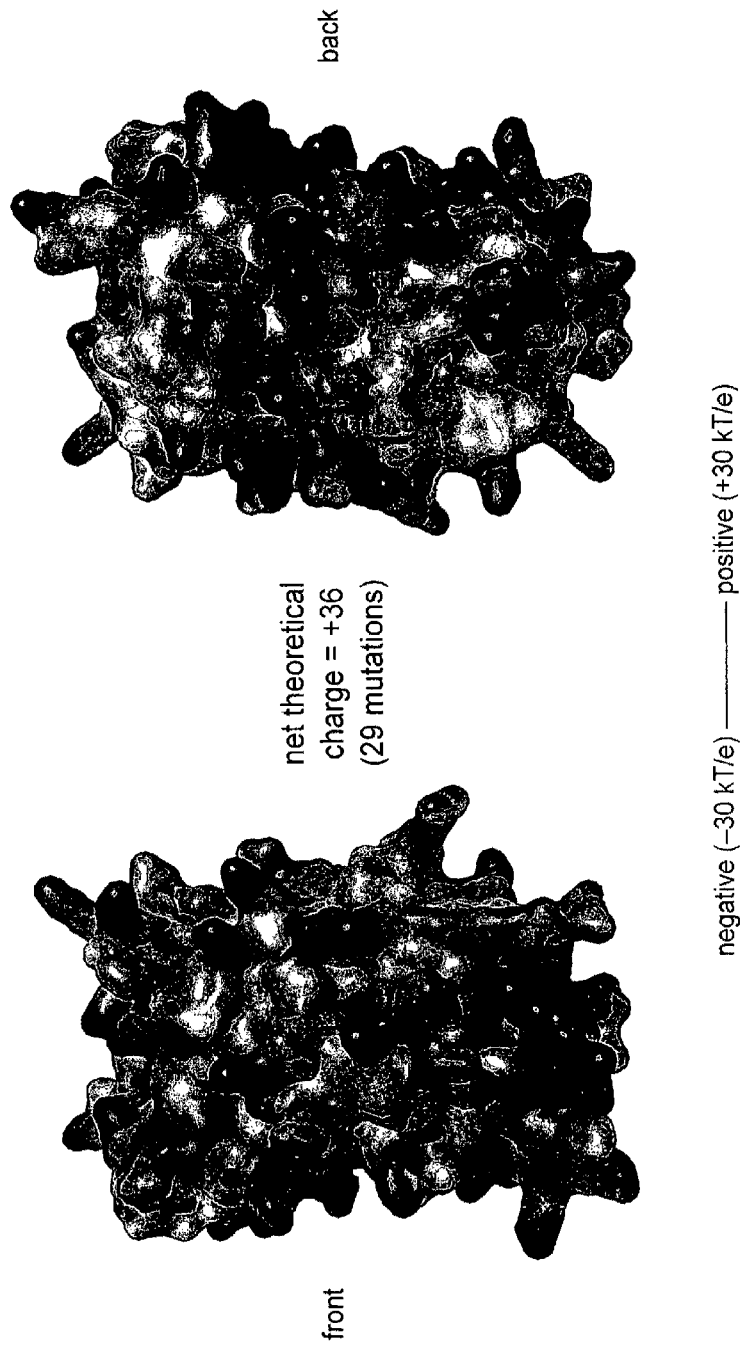

Materials and Methods
Design Procedure and Supercharged Protein Sequences
Solvent-exposed residues (shown in grey below) were identified from published structural data (Weber et al., 1989, *Science*, 243:85; Dirr et al., 1994, *J. Mol. Biol.*, 243:72; Pedelacq et al., 2006, *Nat. Biotechnol.*, 24:79; each of which is incorporated herein by reference) as those having AvNAPSA<150, where AvNAPSA is average neighbor atoms (within 10 Å) per sidechain atom. Charged or highly polar solvent-exposed residues (DERKNQ) were mutated either to Asp or Glu, for negative-supercharging; or to Lys or Arg, for positive-supercharging. Additional surface-exposed positions to mutate in green fluorescent protein (GFP) variants were chosen on the basis of sequence variability at these positions among GFP homologues.
Protein Expression and Purification
Synthetic genes optimized for *E. coli* codon usage were purchased from DNA 2.0, cloned into a pET expression vector (Novagen), and overexpressed in *E. coli* BL21(DE3) pLysS for 5-10 hours at 15° C. Cells were harvested by centrifugation and lysed by sonication. Proteins were purified by Ni-NTA agarose chromatography (Qiagen), buffer-exchanged into 100 mM NaCl, 50 mM potassium phosphate pH 7.5, and concentrated by ultrafiltration (Millipore). All GFP variants were purified under native conditions.
Electrostatic Surface Potential Calculations (FIG. 1B-D)
Models of −30 and +48 supercharged GFP variants were based on the crystal structure of superfolder GFP (Pedelacq et al., 2006, *Nat. Biotechnol.*, 24:79; incorporated herein by reference). Electrostatic potentials were calculated using APBS (Baker et al., 2001, *Proc. Natl. Acad. Sci., USA*, 98:10037; incorporated herein by reference) and rendered with PyMol (Delano, 2002, The PyMOL Molecular Graphics System, www.pymol.org; incorporated herein by reference) using a scale of −25 kT/e (red) to +25 kT/e (blue).
Protein Staining and UV-Induced Fluorescence (FIG. 2A)
0.2 µg of each GFP variant was analyzed by electrophoresis in a 10% denaturing polyacrylamide gel and stained with Coomassie brilliant blue dye. 0.2 µg of the same protein samples in 25 mM Tris pH 8.0 with 100 mM NaCl was placed in a 0.2 mL Eppendorf tube and photographed under UV light (360 nm).
Thermal Denaturation and Aggregation (FIG. 3A)
Purified GFP variants were diluted to 2 mg/mL in 25 mM Tris pH 8.0, 100 mM NaCl, and 10 mM beta-mercaptoethanol (BME), then photographed under UV illumination ("native"). The samples were heated to 100° C. for 1 minute, then photographed again under UV illumination ("boiled"). Finally, the samples were cooled 2 hours at room temperature and photographed again under UV illumination ("cooled").
Chemically Induced Aggregation (FIG. 3B)
2,2,2-trifluoroethanol (TFE) was added to produce solutions with 1.5 mg/mL protein, 25 mM Tris pH 7.0, 10 mM BME, and 40% TFE. Aggregation at 25° C. was monitored by right-angle light scattering.
Size-Exclusion Chromatography (Table 4)
The multimeric state of GFP variants was determined by analyzing 20-50 µg of protein on a Superdex 75 gel-filtration column. Buffer was 100 mM NaCl, 50 mM potassium phosphate pH 7.5. Molecular weights were determined by comparison with a set of monomeric protein standards of known molecular weights analyzed separately under identical conditions.

GFP(+36) similarly co-precipitated with high concentrations of RNA or DNA. Addition of NaCl was sufficient to dissolve these complexes, consistent with the electrostatic basis of

TABLE 4

Calculated and experimentally determined protein properties.

| name | MW (kD) | length (aa) | $n_{pos}$ | $n_{neg}$ | $n_{charged}$ | $Q_{net}$ | pI | ΔG (kcal/mol)$^a$ | native MW (kD)$^b$ | % soluble after boiling$^c$ |
|---|---|---|---|---|---|---|---|---|---|---|
| GFP (−30) | 27.8 | 248 | 19 | 49 | 68 | −30 | 4.8 | 10.2 | n.d. | 98 |
| GFP (−25) | 27.8 | 248 | 21 | 46 | 67 | −25 | 5.0 | n.d. | n.d. | n.d. |
| sfGFP | 27.8 | 248 | 27 | 34 | 61 | −7 | 6.6 | 11.2 | n.d. | 4 |
| GFP (+36) | 28.5 | 248 | 56 | 20 | 76 | +36 | 10.4 | 8.8 | n.d. | 97 |
| GFP (+48) | 28.6 | 248 | 63 | 15 | 78 | +48 | 10.8 | 7.1 | n.d. | n.d. |

Figure 2A:
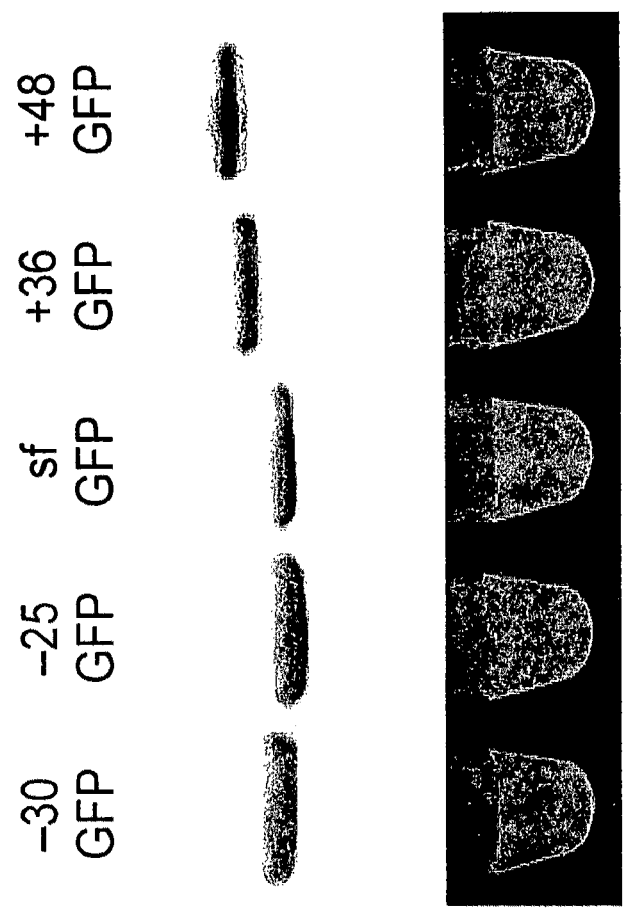
FIG. 2. Intramolecular properties of GFP variants. (A) Staining and UV fluorescence of purified GFP variants. Each lane and tube contains 0.2 µg of protein. (B) Circular dichroism spectra of GFP variants. (C) Thermodynamic stability of GFP variants, measured by guanidinium-induced unfolding.
Figure 2B:
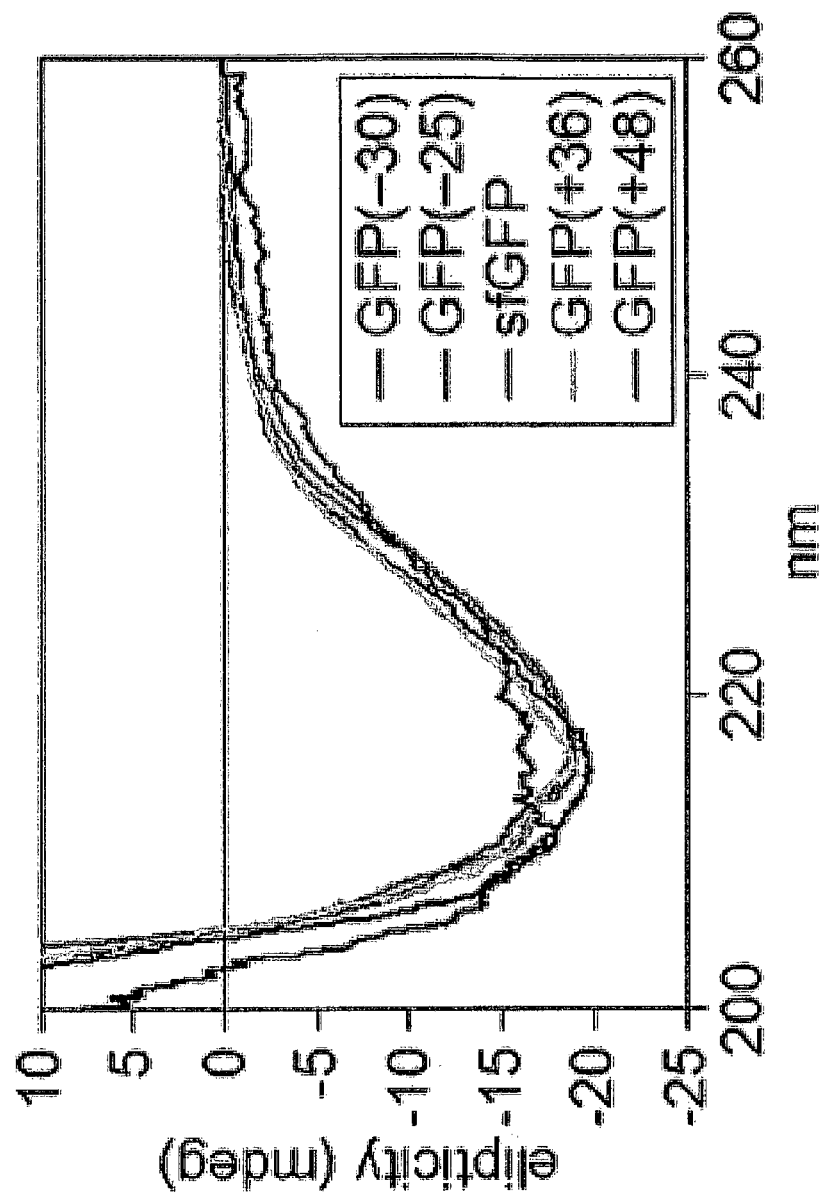
Figure 2C:
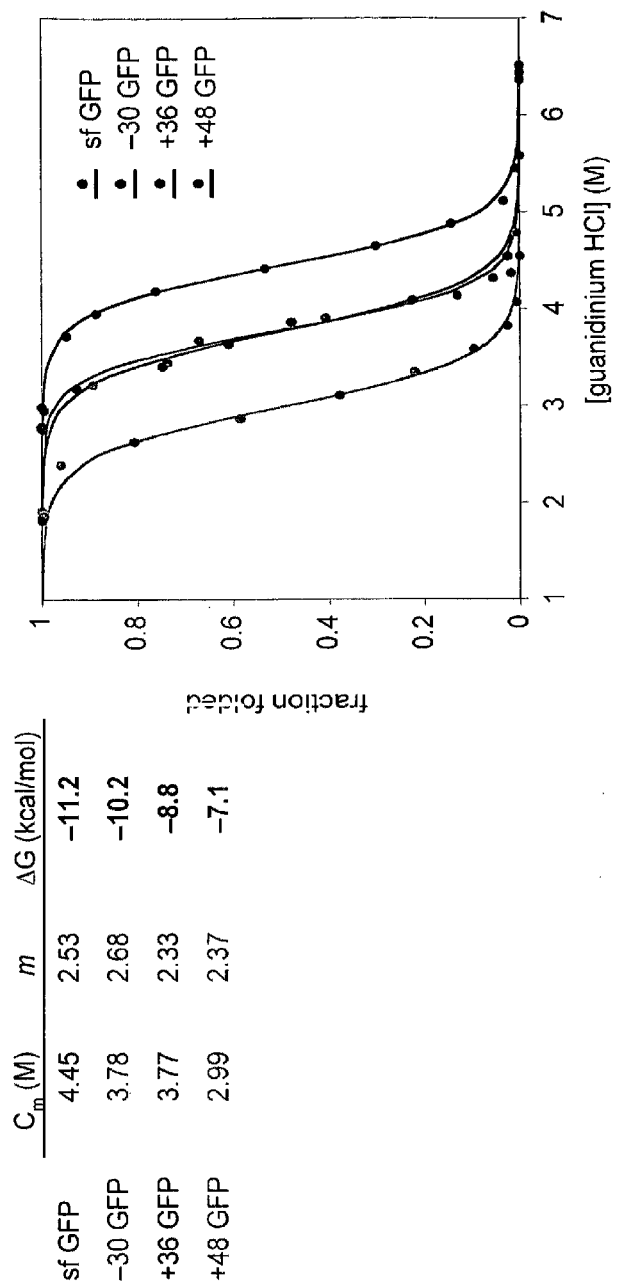

$n_{pos}$, number of positively charged amino acids (per monomer)
$n_{neg}$, number of negatively charged amino acids
$n_{charged}$, total number of charged amino acids
$Q_{net}$, theoretical net charge at neutral pH
pI, calculated isoelectric point
n.d., not determined
$^a$measured by guanidinium denaturation (FIG. 2C).
$^b$measured by size-exclusion chromatography.
$^c$percent protein remaining in supernatant after 5 min at 100° C., cooling to 25° C., and brief centrifugation.

Supercharged GFP

A variant of green fluorescent protein (GFP) called "superfolder GFP" (sfGFP) has been highly optimized for folding efficiency and resistance to denaturants (Pedelacq et al., 2006, Nat. Biotechnol., 24:79; incorporated herein by reference). Superfolder GFP has a net charge of −7, similar to that of wild-type GFP. Guided by a simple algorithm to calculate solvent exposure of amino acids (see Materials and Methods), a supercharged variant of GFP was designed. Supercharged GFP has a theoretical net charge of +36 and was created by mutating 29 of its most solvent-exposed residues to positively charged amino acids (FIG. 1). The expression of genes encoding either sfGFP or supercharged GFP ("GFP(+36)") yielded intensely green-fluorescent bacteria. Following protein purification, the fluorescence properties of GFP(+36) were measured and found to be very similar to those of sfGFP.

Additional supercharged GFPs having net charges of +48, −25, and −30 were designed and purified, all of which were also found to exhibit sfGFP-like fluorescence (FIG. 2A). All supercharged GFP variants showed circular dichroism spectra similar to that of sfGFP, indicating that the proteins have similar secondary structure content (FIG. 2B). The thermodynamic stabilities of the supercharged GFP variants were only modestly lower than that of sfGFP (1.0–4.1 kcal/mol, FIG. 2C and Table 4) despite the presence of as many as 36 mutations.

Figure 3A:
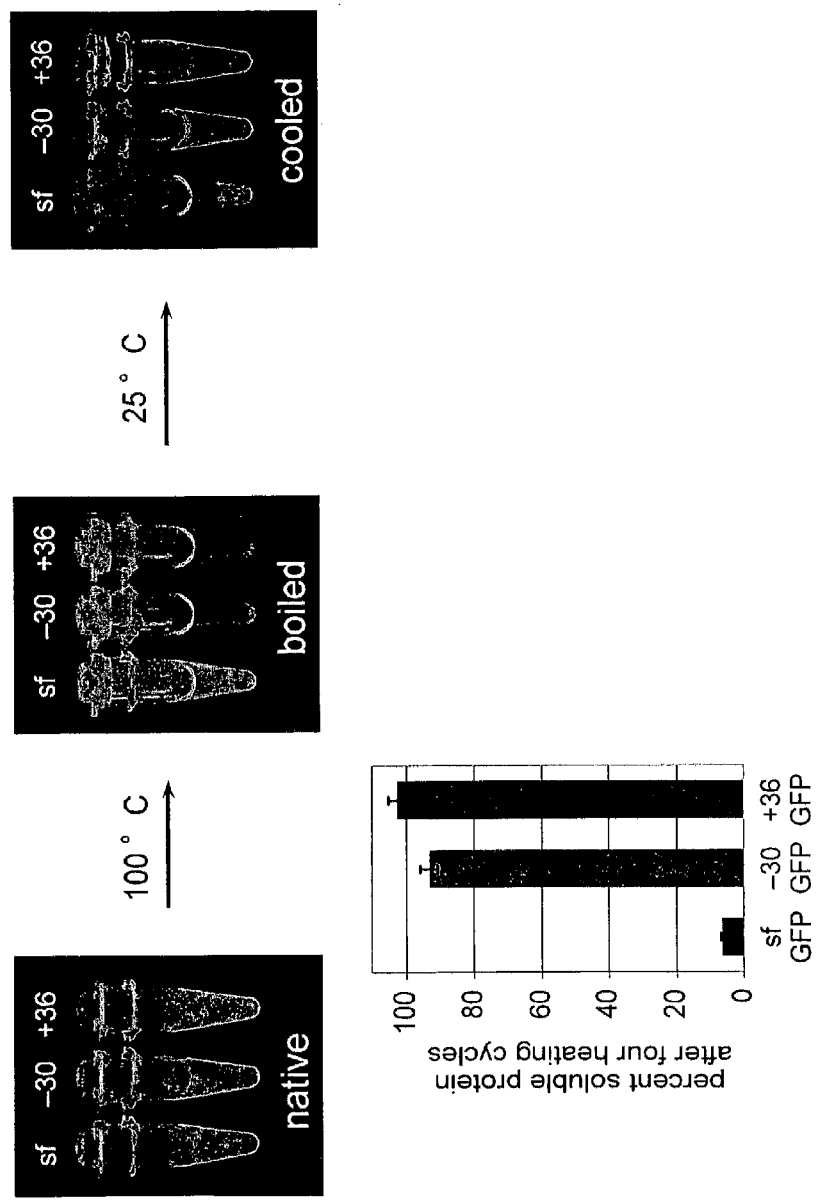
FIG. 3. Intermolecular properties of supercharged proteins. (A) UV-illuminated samples of purified GFP variants ("native"), those samples heated 1 minute at 100° C. ("boiled"), and those samples subsequently cooled for 2 hours at 25° C. ("cooled"). (B) Aggregation of GFP variants was induced with 40% TFE at 25° C. and monitored by right-angle light scattering. (C) Supercharged GFPs adhere reversibly to oppositely charged macromolecules. Sample 1: 6 µg of GFP(+36) in 30 µl of 25 mM Tris pH 7.0 and 100 mM NaCl. Sample 2: 6 µg of GFP(−30) added to sample 1. Sample 3: 30 µg of salmon sperm DNA added to sample 1. Sample 4: 20 µg of E. coli tRNA added to sample 1. Sample 5: Addition of 1 M NaCl to sample 4. Samples 6-8: identical to samples 1, 2, and 4, respectively, except using sfGFP instead of GFP(+36). All samples were spun briefly in a microcentrifuge and visualized under UV light.
Figure 3B:
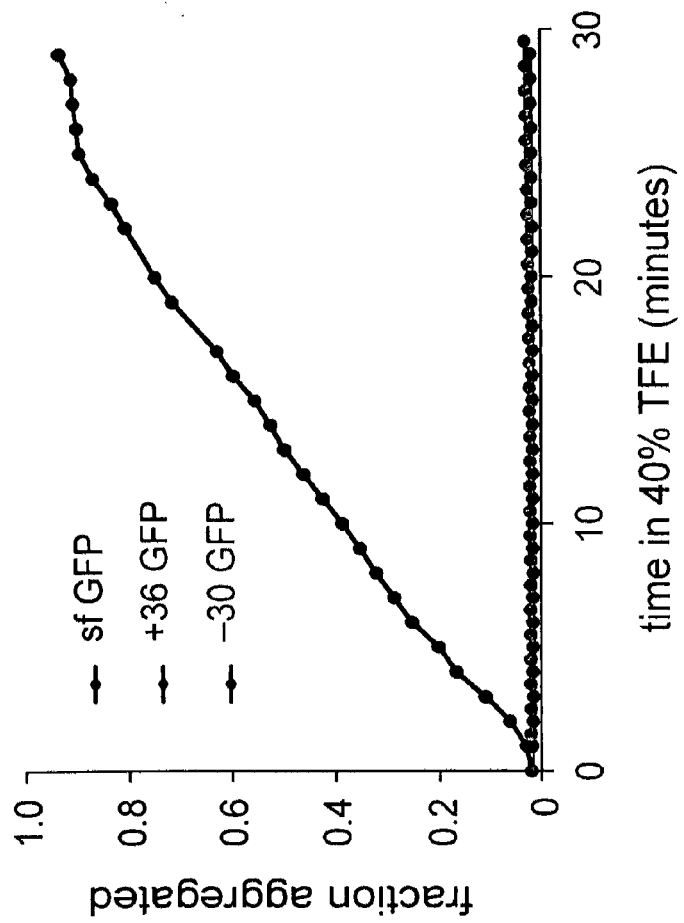

Although sfGFP is the product of a long history of GFP optimization (Giepmans et al., 2006, Science, 312:217; incorporated herein by reference), it remains susceptible to aggregation induced by thermal or chemical unfolding. Heating sfGFP to 100° C. induced its quantitative precipitation and the irreversible loss of fluorescence (FIG. 3A). In contrast, supercharged GFP(+36) and GFP(−30) remained soluble when heated to 100° C., and recovered significant fluorescence upon cooling (FIG. 3A). While 40% 2,2,2-trifluoroethanol (TFE) induced the complete aggregation of sfGFP at 25° C. within minutes, the +36 and −30 supercharged GFP variants suffered no significant aggregation or loss of fluorescence under the same conditions for hours (FIG. 3B).

Figure 3C:
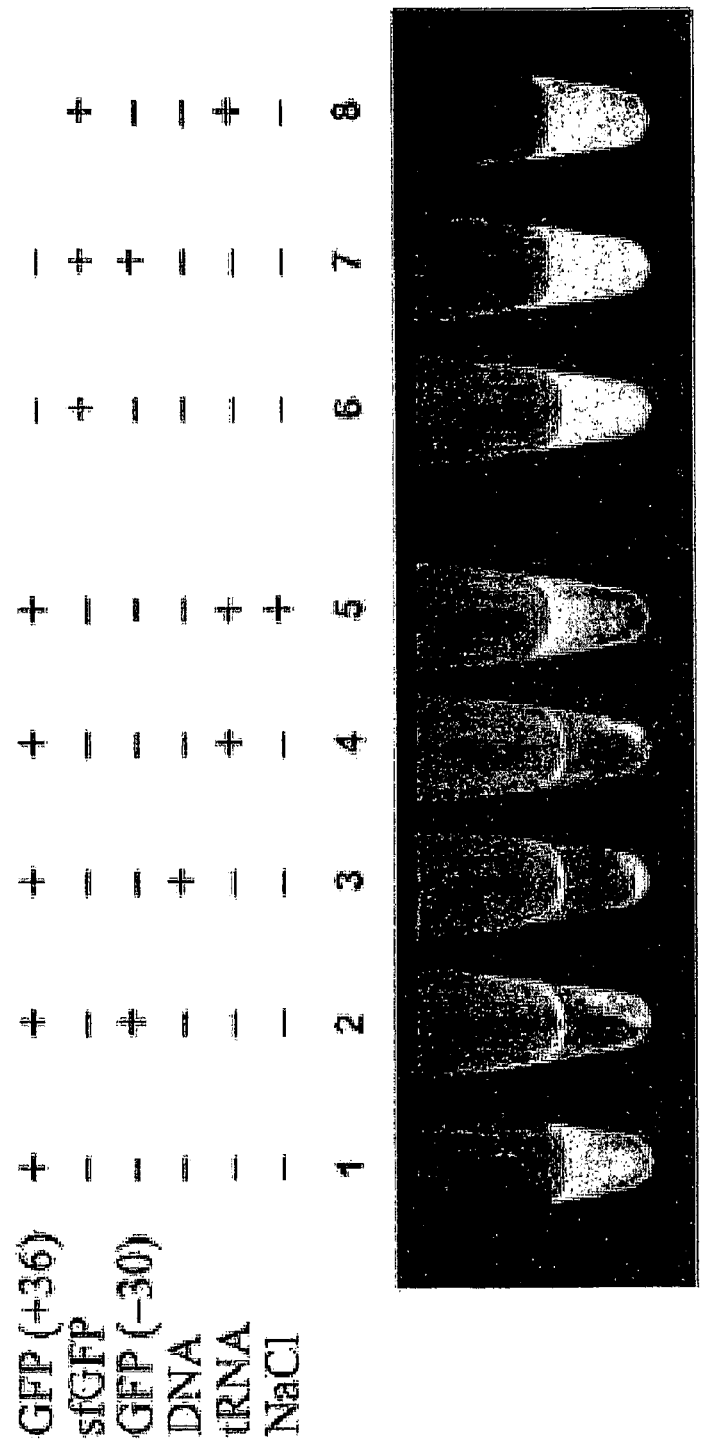
Figure 4A:
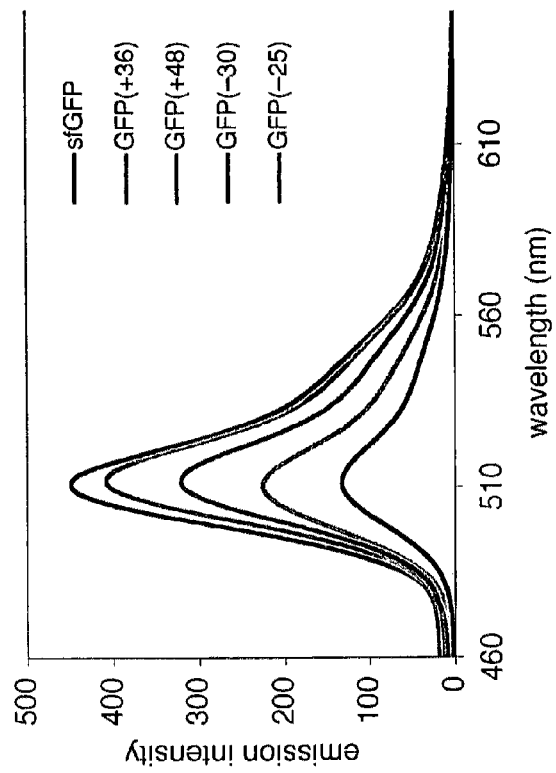
FIG. 4. (A) Excitation and (B) emission spectra of GFP variants. Each sample contained an equal amount of protein as quantitated by chromophore absorbance at 490 nm.
Figure 4B:
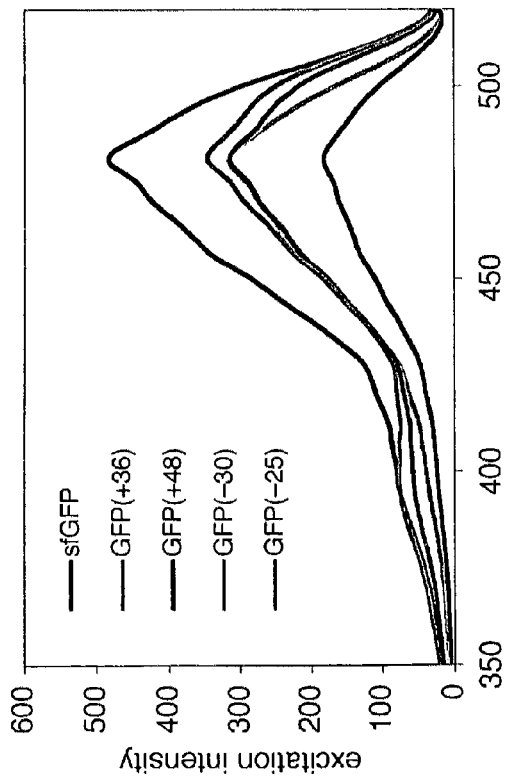

Supercharged GFP variants show a strong, reversible avidity for highly charged macromolecules of the opposite charge (FIG. 3C). When mixed together in 1:1 stoichiometry, GFP (+36) and GFP(−30) immediately formed a green fluorescent co-precipitate, indicating the association of folded proteins.

their formation. In contrast, sfGFP was unaffected by the addition of GFP(−30), RNA, or DNA (FIG. 3C).

Conclusion

In summary, monomeric and multimeric proteins of varying structures and functions can be "supercharged" by simply replacing their most solvent-exposed residues with like-charged amino acids. Supercharging profoundly alters the intermolecular properties of proteins, imparting remarkable aggregation resistance and the ability to associate in folded form with oppositely charged macromolecules like "molecular Velcro."

In contrast to these dramatic intermolecular effects, the intramolecular properties of the seven supercharged proteins studied here, including folding, fluorescence, ligand binding, and enzymatic catalysis, remained largely intact. Supercharging therefore may represent a useful approach for reducing the aggregation tendency and improving the solubility of proteins without abolishing their function. These principles may be particularly useful in de novo protein design efforts, where unpredictable protein handling properties including aggregation remain a significant challenge.

These observations may also illuminate the modest net-charge distribution of natural proteins (Knight et al., 2004, Proc. Natl. Acad. Sci., USA, 101:8390; Gitlin et al., 2006, Angew Chem Int Ed Engl, 45:3022; each of which is incorporated herein by reference): the net charge of 84% of Protein Data Bank (PDB) polypeptides, for example, falls within ±10. The results above argue against the hypothesis that high net charge creates sufficient electrostatic repulsion to force unfolding. Indeed, GFP(+48) has a higher positive net charge than any polypeptide currently in the PDB, yet retains the ability to fold and fluoresce. Instead, these findings suggest that nonspecific intermolecular adhesions may have disfavored the evolution of too many highly charged natural proteins. Almost all natural proteins with very high net charge, such as ribosomal proteins L3 (+36) and L15 (+44), which bind RNA, or calsequestrin (−80), which binds calcium cations, associate with oppositely charged species as part of their essential cellular functions.

Example 2

Supercharged Proteins can be Used to Efficiently Deliver Nucleic Acids to Cells

Figure 5:
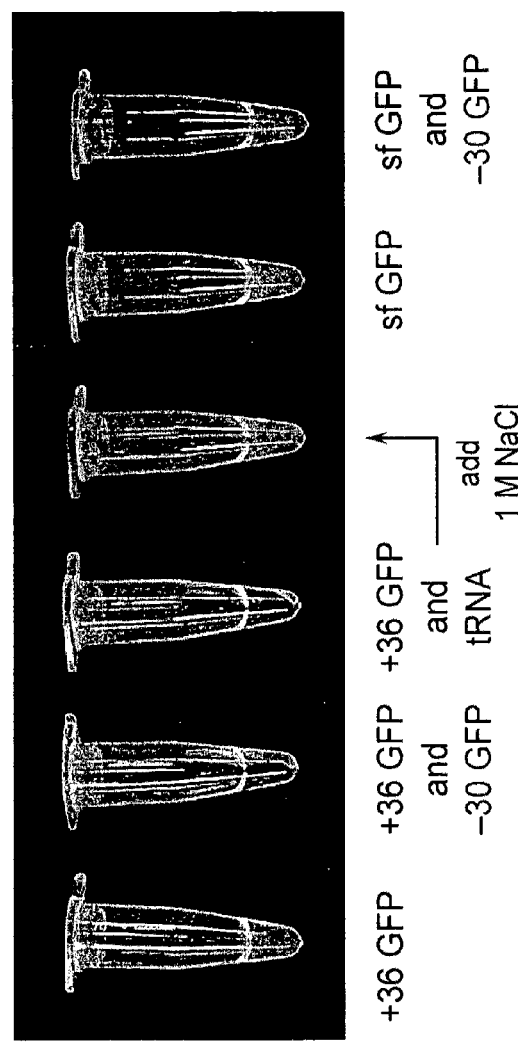
FIG. 5. Supercharged Surfaces Dominate Intermolecular Interactions. Supercharged GFPs adhere non-specifically and reversibly with oppositely charged macromolecules ("protein Velcro"). Such interactions can result in the formation of precipitates. Unlike aggregates of denatured proteins, these precipitates contain folded, fluorescent GFP and dissolve in 1 M salt. Shown here are: +36 GFP alone; +36 GFP mixed with −30 GFP; +36 GFP mixed with tRNA; +36 GFP mixed with tRNA in 1 M NaCl; sf GFP (−7); and sfGFP mixed with −30 GFP.

FIG. 5 demonstrates that supercharged GFPs associate non-specifically and reversibly with oppositely charged macromolecules ("protein Velcro"). Such interactions can result in the formation of precipitates. Unlike aggregates of denatured proteins, these precipitates contain folded, fluorescent GFP and dissolve in 1 M salt. Shown here are: +36 GFP alone; +36 GFP mixed with −30 GFP; +36 GFP mixed with tRNA; +36 GFP mixed with tRNA in 1 M NaCl; superfolder GFP ("sf GFP"; −7 GFP); and sfGFP mixed with −30 GFP.

Figure 6:
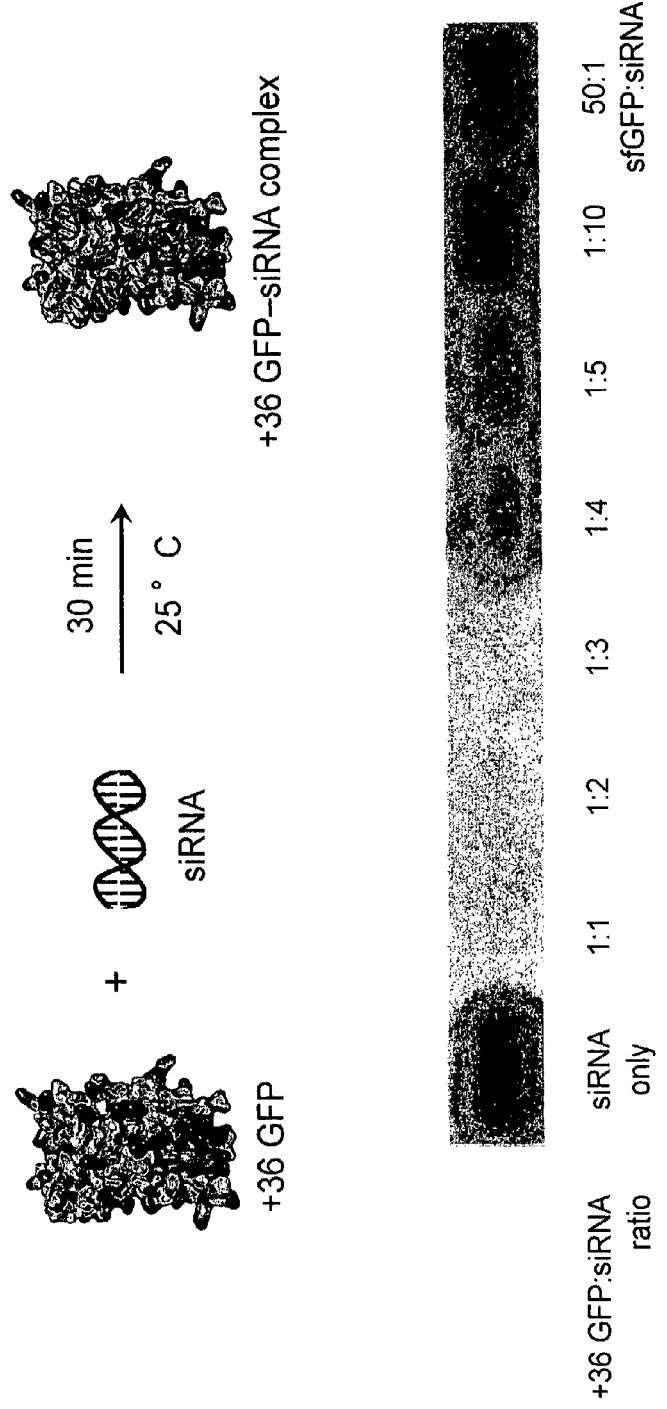
FIG. 6. Superpositive GFP Binds siRNA. GFP-siRNA complex does not co-migrate with siRNA in an agarose gel—+36 GFP was incubated with siRNA, and the resulting complexes were subjected to agarose gel electrophoresis. Various +36 GFP:siRNA ratios were tested in this assay: 0:1, 1:1, 1:2, 1:3, 1:4, 1:5, and 1:10. +36 GFP was shown to form a stable complex with siRNA in a ~1:3 stoichiometry. Non-superpositive proteins were shown not to bind siRNA. A 50:1 ratio of sfGFP:siRNA was tested, but, even at such high levels of excess, sfGFP did not associate with siRNA.

FIG. 6 demonstrates that superpositively charged GFP binds siRNA. The binding stoichiometry between +36 GFP and siRNA was determined by mixing various ratios of the two components (30 minutes at 25° C.) and running the mixture on a 3% agarose gel (Kumar et al., 2007, *Nature*, 449:39; incorporated herein by reference). Ratios of +36 GFP:siRNA tested were 0:1, 1:1, 1:2, 1:3, 1:4, 1:5, and 1:10. +36 GFP/siRNA complexes did not co-migrate with siRNA in an agarose gel. +36 GFP was shown to form a stable complex with siRNA in a ~1:3 stoichiometry, indicating that one supercharged GFP binds approximately three siRNA molecules. This property allows the application of low quantities of superpositively charged GFP to deliver siRNA effectively to cells. Moreover, because the delivery reagent is fluorescent, and therefore observable by fluorescence microscopy, siRNA delivery can be assessed using this spectroscopic technique. In contrast, non-superpositive proteins did not bind siRNA. A 50:1 ratio of sfGFP:siRNA was also tested, but, even at such high levels of excess, sfGFP did not associate with siRNA.

Figure 7:
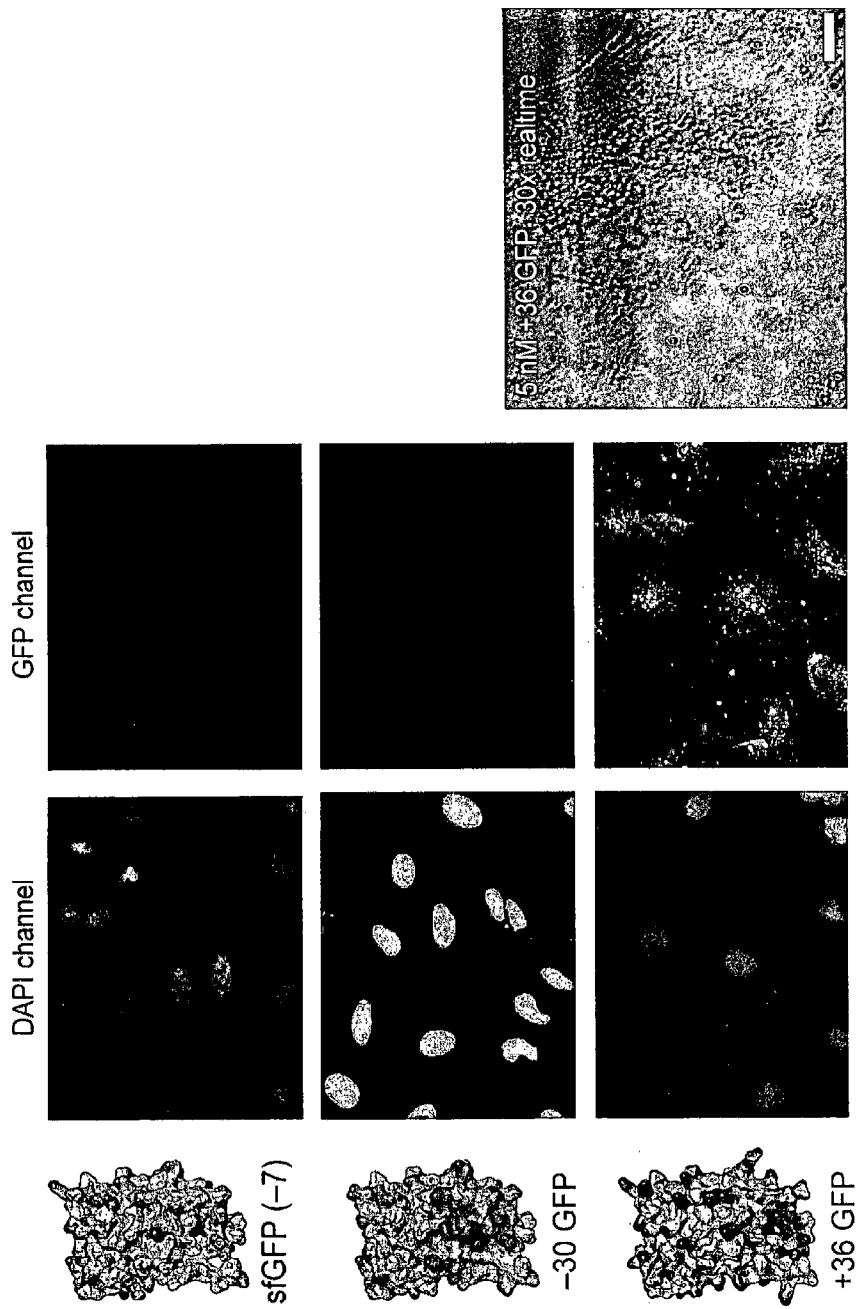
FIG. 7. Superpositive GFP Penetrates Cells. HeLa cells were incubated with GFP (either sf GFP (−7), −30 GFP, or +36 GFP), washed, fixed, and stained. +36 GFP, but not sfGFP or −30 GFP, potently penetrated HeLa cells. Left: DAPI staining of DNA to mark cells. Middle: GFP staining to mark where cellular uptake of GFP occurred. Right: movie showing +36 GFP localization as it occurs.

FIG. 7 demonstrates that superpositively charged GFP penetrates cells. HeLa cells were incubated with 1 nM GFP for 3 hours, washed, fixed, and stained. Three GFP variants were tested in this experiment: sfGFP (−7), −30 GFP, and +36 GFP. +36 GFP, but not sfGFP or −30 GFP, was shown to potently penetrate HeLa cells within minutes. Localization was shown to begin at the cell membrane, becoming punctate and intracellular thereafter. +36 GFP was shown to be stable in HeLa cells for ≥5 days. Results are shown in FIG. 7. On the left is DAPI staining of DNA to mark the position of cells. In the middle is GFP staining to show where cellular uptake of GFP occurred. On the right is a movie showing localization as it occurs.

In order to demonstrate the utility of superpositively charged GFP for siRNA delivery, siRNA transfection efficiency using Lipofectamine 2000™ (Invitrogen), a commonly used and commercially available cationic lipid transfection reagent, was compared to superpositively charged GFP-based siRNA transfection in HeLa cells.

Generally, for a cell culture condition with a total volume of 1 mL, cells are plated to ~80% confluency in 10% serum/media. The serum/media solution is removed, and cells are washed twice with PBS and 500 µL of serum-free media. In a separate vessel, 500 µL of serum free media is added, to which 1 µL of 50 µM siRNA solution (total concentration 100 nM) and 1.66 µL of 15 µM sc(+36)GFP (total concentration 40 nM) are added. The contents are mixed by inversion and allowed to incubate for 5 minutes. After such time, the mixture is added to the well containing 500 µL of serum-free media to give a final concentration of 50 nM siRNA and 20 nM scGFP. This solution is placed in a 37° C. incubator (5% CO$_2$) for 4 hours, removed, and washed twice with PBS. Cells are then treated with 1 mL 10% FBS/media. Cells were allowed to incubate for 4 days before being harvested to determine gene knockdown.

Figure 8:
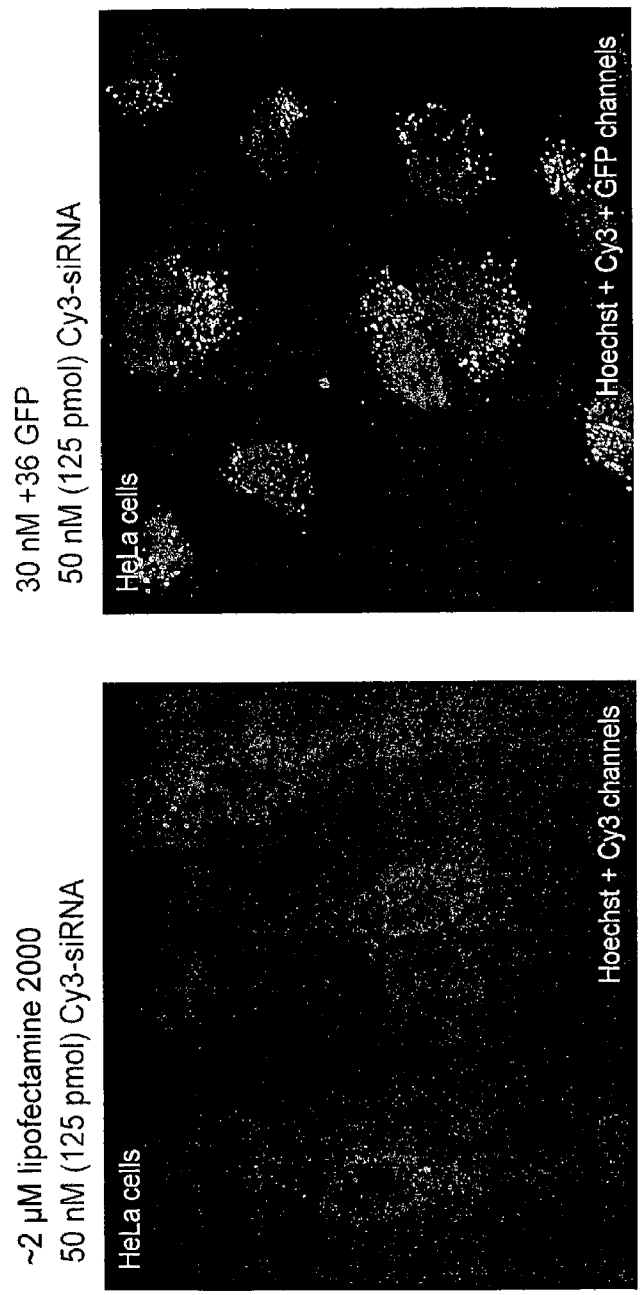
FIG. 8. Superpositive GFP Delivers siRNA into Human Cells. +36 GFP was shown to potently deliver siRNA into HeLa cells. Left: Lipofectamine 2000 and Cy3-siRNA; right: +36 GFP and Cy3-siRNA. +36 GFP was shown to potently deliver siRNA into HeLa cells. Hoechst channel was used to visualize DNA, thereby marking the position of cells; Cy3 channel was used to visualize Cy3-tagged siRNA; GFP channel was used to visualize GFP; Cy3/GFP channel overlap indicates sites of co-localization between siRNA and GFP.

FIG. 8 demonstrates that superpositively charged GFP is able to deliver siRNA into human cells. In particular, +36 GFP was shown to deliver siRNA into HeLa cells. +36 GFP delivered higher quantities of siRNA at a much higher transfection efficiency than Lipofectamine. HeLa cells were treated with either: ~2 µM lipofectamine 2000 and 50 nM (125 pmol) Cy3-siRNA (left); or 30 nM of +36 GFP and 50 nM (125 pmol) Cy3-siRNA (right). Unlike Lipofectamine, +36 GFP did not induce cytotoxicity, particularly upon addition of antibiotics such as penicillin and streptomycin.

Figure 9:
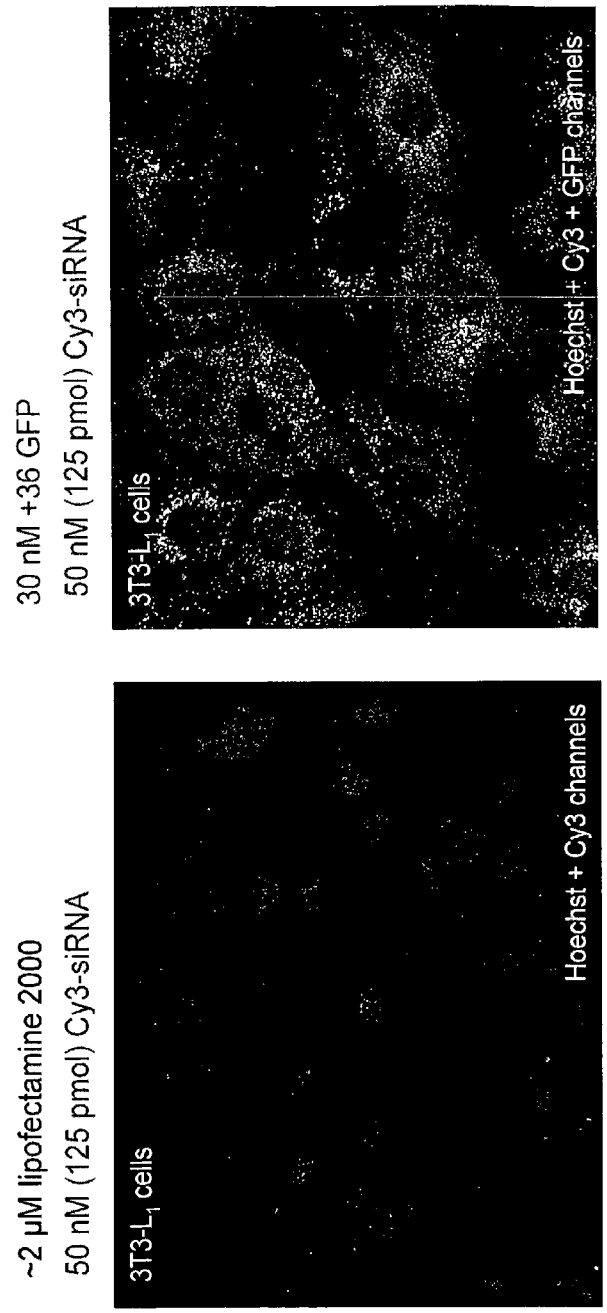
FIG. 9. Delivery of siRNA into Cell Lines Resistant to Traditional Transfection: murine 3T3-L$_1$ pre-adipocyte cells ("3T3L cells"). 3T3L cells were treated with either: lipofectamine 2000 and Cy3-siRNA (left); or +36 GFP and Cy3-siRNA (right). 3T3L cells were poorly transfected by Lipofectamine but were efficiently transfected by +36 GFP. Hoechst channel was used to visualize DNA, thereby marking the position of cells; Cy3 channel was used to visualize Cy3-tagged siRNA; GFP channel was used to visualize GFP. Cy3/GFP channel overlap indicates sites of co-localization between siRNA and GFP.
Figure 10:
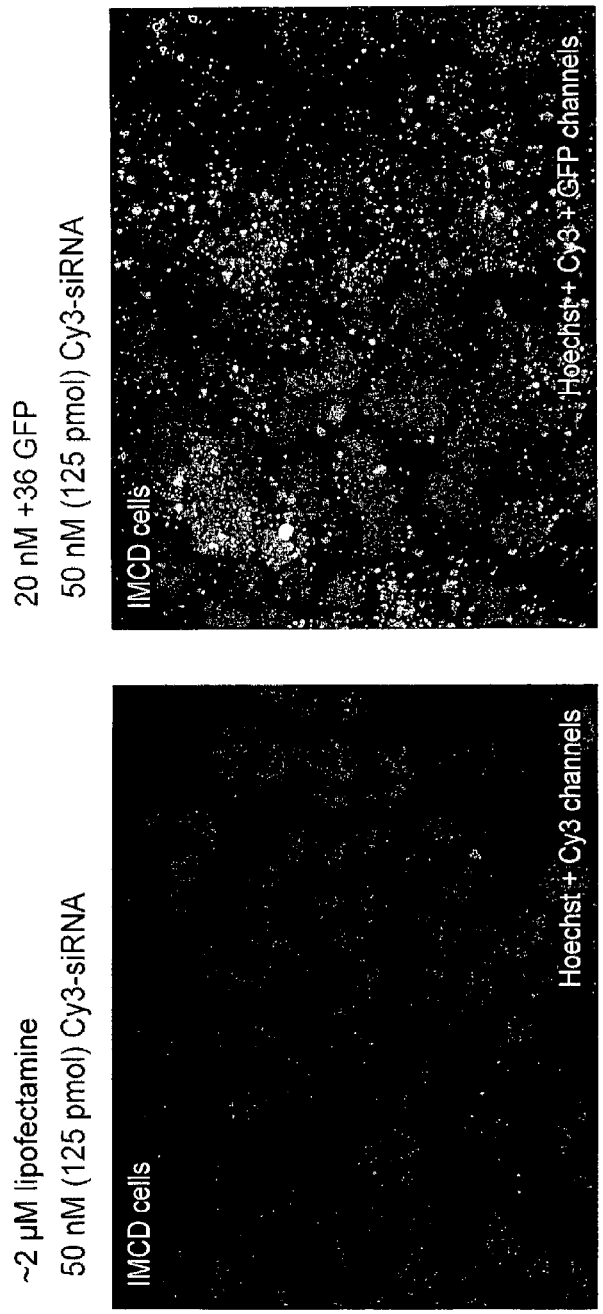
FIG. 10. Delivery of siRNA into Cell Lines Resistant to Traditional Transfection: rat IMCD cells. Rat IMCD cells were treated with either Lipofectamine 2000 and Cy3-siRNA (left); or +36 GFP and Cy3-siRNA (right). Rat IMCD cells were poorly transfected by Lipofectamine but were efficiently transfected by +36 GFP. Hoechst channel was used to visualize DNA, thereby marking the position of cells; Cy3 channel was used to visualize Cy3-tagged siRNA; GFP channel was used to visualize GFP. Cy3/GFP channel overlap indicates sites of co-localization between siRNA and GFP.
Figure 11:
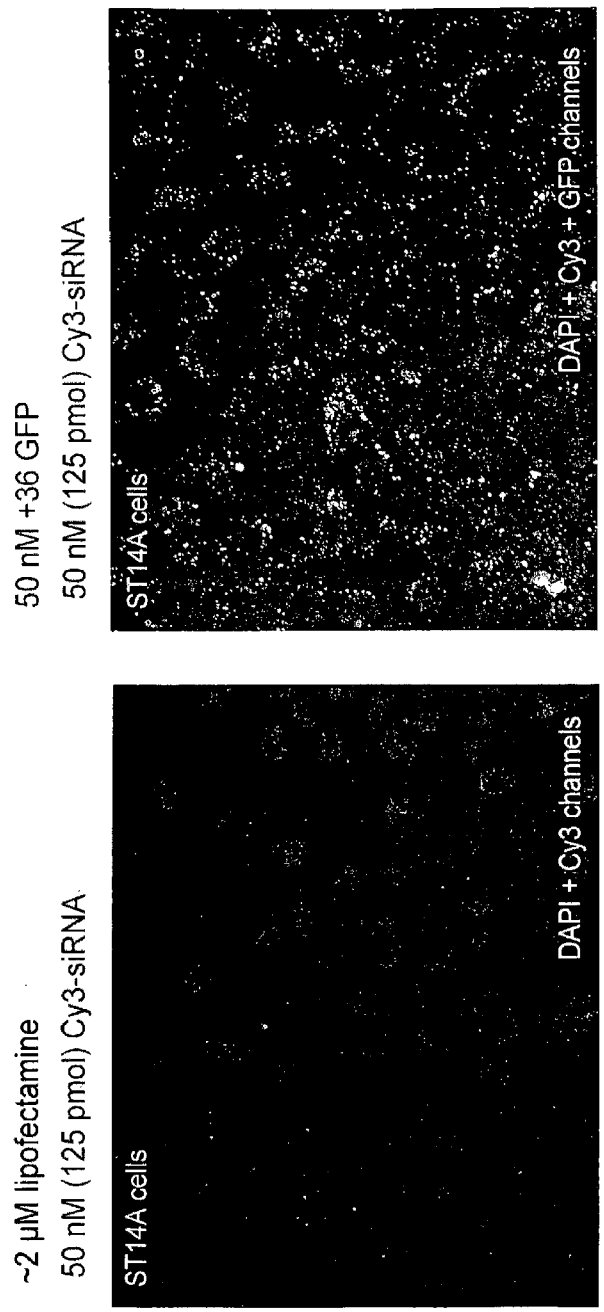
FIG. 11. Delivery of siRNA into Cell Lines Resistant to Traditional Transfection: human ST14A neurons. Human ST14A neurons were treated with either Lipofectamine 2000 and Cy3-siRNA (left); or +36 GFP and Cy3-siRNA (right). Human ST14A neurons were poorly transfected by Lipofectamine but were efficiently transfected by +36 GFP. DAPI channel was used to visualize DNA, thereby marking the position of cells; Cy3 channel was used to visualize Cy3-tagged siRNA; GFP channel was used to visualize GFP. Cy3/GFP channel overlap indicates sites of co-localization between siRNA and GFP.
Figure 12:
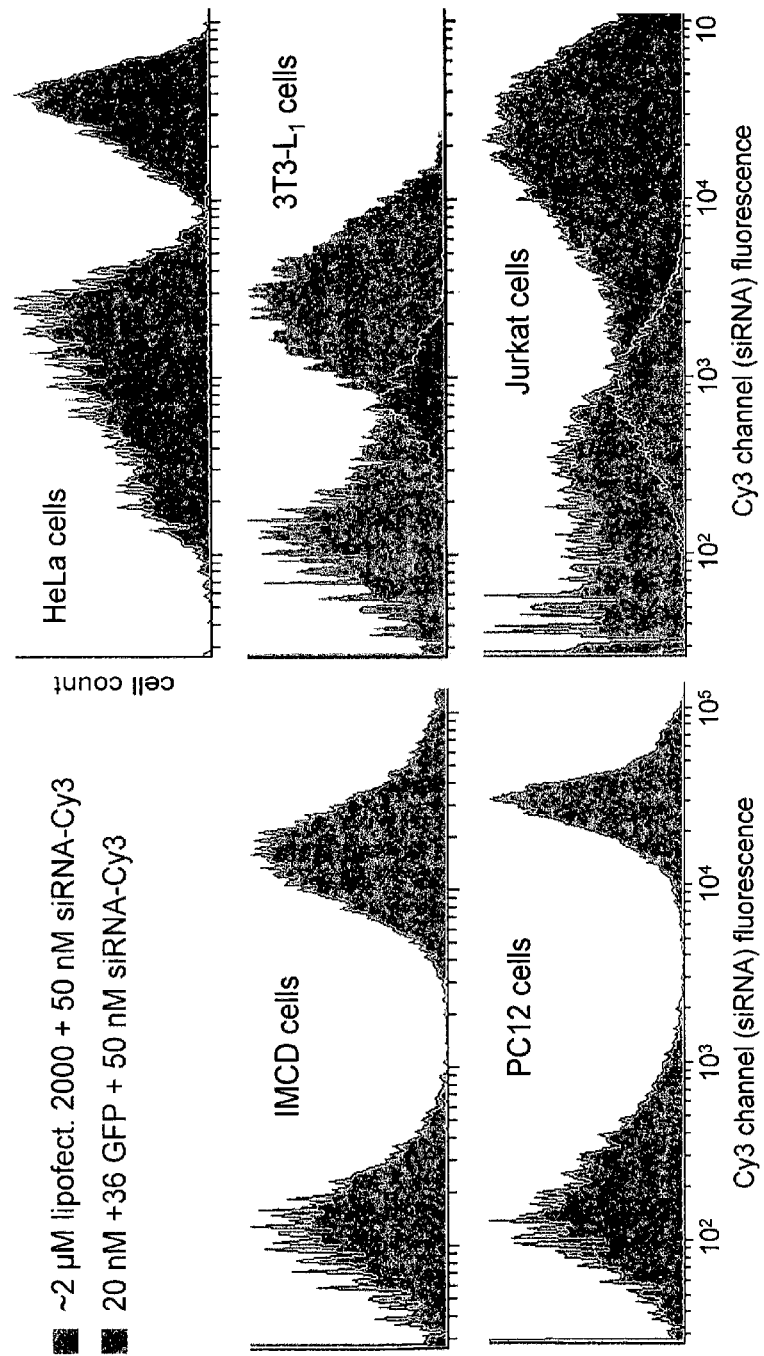
FIG. 12. Flow Cytometry Analysis of siRNA Transfection. LEFT: Lipofectamine. Each column corresponds to experiments performed with different transfection methods: lipofectamine; and 20 nM+36 GFP. Each chart corresponds to experiments performed with different cell types: IMCD cells, PC12 cells, HeLa cells, 3T3L cells, and Jurkat cells. The X-axis represents measurements obtained from the Cy3 channel, which is a readout of siRNA fluorescence. The Y-axis represents cell count in flow cytometry experiments. Flow cytometry data indicate that cells were more efficiently transfected with siRNA using +36 GFP than Lipofectamine.

In order to demonstrate the broad utility of supercharged proteins for nucleic acid delivery, this experiment has been repeated in a variety of cells, including cells that are resistant to cationic lipid-based siRNA transfection. FIGS. 9-11 demonstrate that superpositively charged GFP is able to deliver siRNA into cell lines that are resistant to traditional transfection methods. FIG. 9 demonstrates that superpositively charged GFP is able to deliver siRNA into 3T3-L$_1$ pre-adipocyte cells ("3T3L cells"). 3T3L cells were treated with either: ~2 µM Lipofectamine 2000 and 50 nM (125 pmol) Cy3-siRNA (left); or 30 nM+36 GFP and 50 nM (125 pmol) Cy3-siRNA (right). Murine 3T3-L$_1$ pre-adipocyte cells were poorly transfected by Lipofectamine but were efficiently transfected by +36 GFP. Hoechst channel, blue, was used to visualize DNA, thereby marking the position of cells; Cy3 channel, red, was used to visualize Cy3-tagged siRNA; GFP channel, green, was used to visualize GFP. Yellow indicates sites of co-localization between siRNA and GFP. Unlike Lipofectamine, +36 GFP did not induce cytotoxicity, particularly upon addition of antibiotics such as penicillin and streptomycin.

FIG. 10 demonstrates that superpositively charged GFP is able to deliver siRNA into rat IMCD cells. Rat IMCD cells were treated with either ~2 µM Lipofectamine 2000 and 50 nM (125 pmol) Cy3-siRNA (left); or 20 nM+36 GFP and 50 nM (125 pmol) Cy3-siRNA (right). Rat IMCD cells were poorly transfected by Lipofectamine but were efficiently transfected with +36 GFP. Hoechst channel, blue, was used to visualize DNA, thereby marking the position of cells; Cy3 channel, red, was used to visualize Cy3-tagged siRNA; GFP channel, green, was used to visualize GFP. Yellow indicates sites of co-localization between siRNA and GFP. Unlike Lipofectamine, +36 GFP did not induce cytotoxicity, particularly upon addition of antibiotics such as penicillin and streptomycin.

FIG. 11 demonstrates that superpositively charged GFP is able to deliver siRNA into human ST14A neurons. Human ST14A neurons were treated with either ~2 µM Lipofectamine 2000 and 50 nM (125 pmol) Cy3-siRNA; or 50 nM+36 GFP and 50 nM (125 pmol) Cy3-siRNA. Human ST14A neurons were weakly transfected by Lipofectamine but were efficiently transfected by +36 GFP. DAPI channel, blue, was used to visualize DNA, thereby marking the position of cells; Cy3 channel, red, was used to visualize Cy3-tagged siRNA; GFP channel, green, was used to visualize GFP. Yellow indicates sites of co-localization between siRNA and GFP. Results similar to those presented in FIGS. 9-11 were observed in two other cell types that are resistant to traditional transfection methods (i.e., Jurkat cells and PC12 cells). Unlike Lipofectamine, +36 GFP did not induce cytotoxicity, particularly upon addition of antibiotics such as penicillin and streptomycin.

Figure 13:
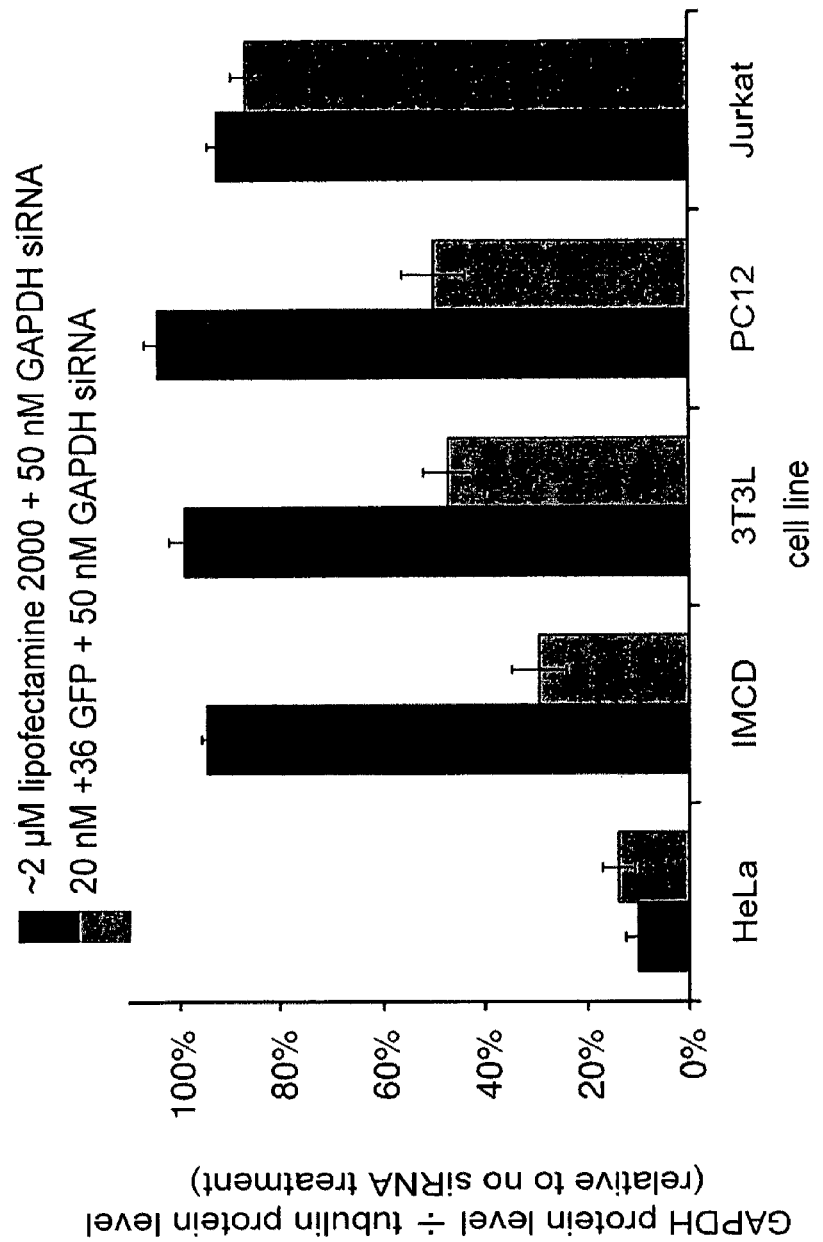
FIG. 13. siRNA Delivered with +36 GFP Can Induce Gene Knockdown. 50 nM GAPDH siRNA was transfected into five different cell types (HeLa, IMCD, 3T3L, PC12, and Jurkat cell lines) using either ~2 µM lipofectamine 2000 or 20 nM+36. The Y-axis represents GAPDH protein levels as a fraction of tubulin protein levels.

FIG. 13 presents flow cytometry analysis of siRNA transfection experiments. Each column corresponds to experiments performed with different transfection methods: Lipofectamine (blue); and 20 nM+36 GFP (red). Each chart corresponds to experiments performed with different cell types: IMCD cells, PC12 cells, HeLa cells, 3T3L cells, and Jurkat cells. The X-axis represents measurements obtained from the Cy3 channel, which is a readout of siRNA fluorescence. The Y-axis represents cell count in flow cytometry experiments. Flow cytometry data indicate that cells were more efficiently transfected with siRNA using +36 GFP than Lipofectamine.

In order to demonstrate the effectiveness of +36 GFP-delivered siRNA to suppress gene expression, cellular levels of GAPDH were examined by western blot. As shown in FIG. 13, +36 GFP effectively delivered siRNA to cells and suppressed GAPDH at levels comparable to that of lipofectamine. 50 nM GAPDH siRNA was transfected into five different cell types (HeLa, IMCD, 3T3L, PC12, and Jurkat cell lines) using either ~2 µM lipofectamine 2000 (black bars) or 20 nM+36 GFP (green bars). The Y-axis represents GAPDH protein levels as a fraction of tubulin protein levels.

Figure 14A:
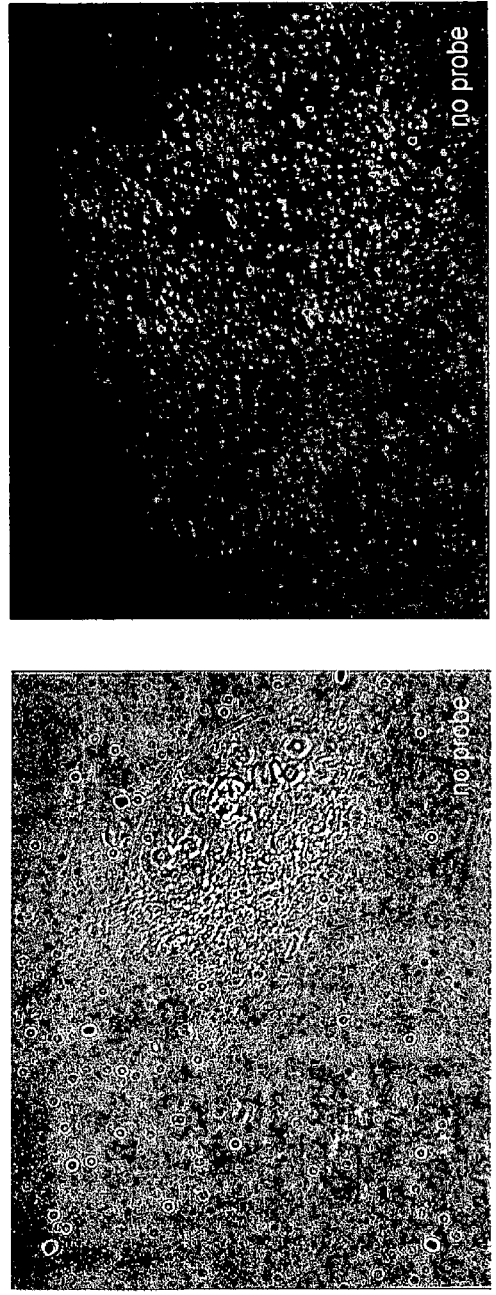
FIG. 14. Mechanistic Probes of Cell Penetration. HeLa cells were treated with one of a variety of probes for 30 minutes and were then treated with 5 nM+36 GFP. Samples included: (A) no probe; (B) 4° C. preincubation (inhibits energy-dependent processes); (C) 100 mM sucrose (inhibits clathrin-mediated endocytosis), left, and 25 µg/ml nystatin (disrupts caveolar function), right; (D) 25 µM cytochalisin B (inhibits macropinocytosis), left, and 5 µM monensin (inhibits endosome receptor recycling), right.
Figure 14C:
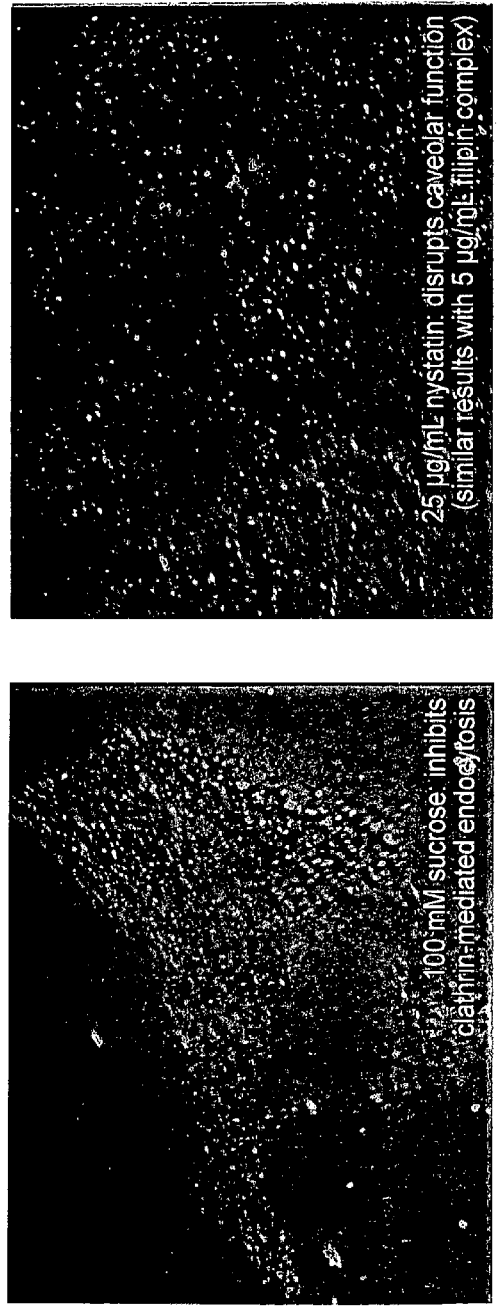
Figure 14D:
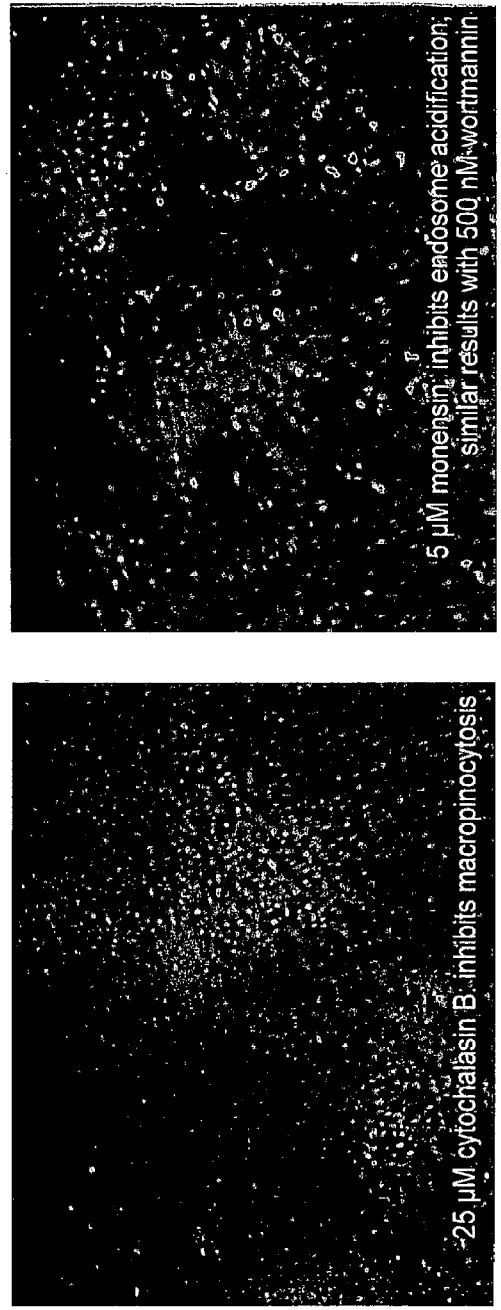

FIG. 14 demonstrates the effects of a variety of mechanistic probes of cell penetration on superpositively charged GFP-mediated siRNA transfection. HeLa cells were treated with one of a variety of probes for 30 minutes and were then treated with 5 nM+36 GFP. Cells were then washed with heparin+probe and imaged in PBS+probe. Samples included: no probe; 4° C. preincubation (inhibits energy-dependent processes); 100 mM sucrose (inhibits clathrin-mediated endocytosis); 25 µg/ml nystatin (disrupts caveolar function); 25 µM cytochalasin B (inhibits macropinocytosis); and 5 µM monensin (inhibits endosome receptor recycling). Experiments at 4° C. demonstrated that cell penetration of +36 GFP involves energy consumption. Experiments with sucrose and nystatin demonstrate that cellular uptake of +36 GFP does not involve clathrin-mediated endocytosis or caveolar endocytosis. Experiments with cytochalasin B and monensin demonstrate that cellular uptake of +36 GFP does not involve macropinocytosis, but is likely to involve early endosomes.

Figure 15:
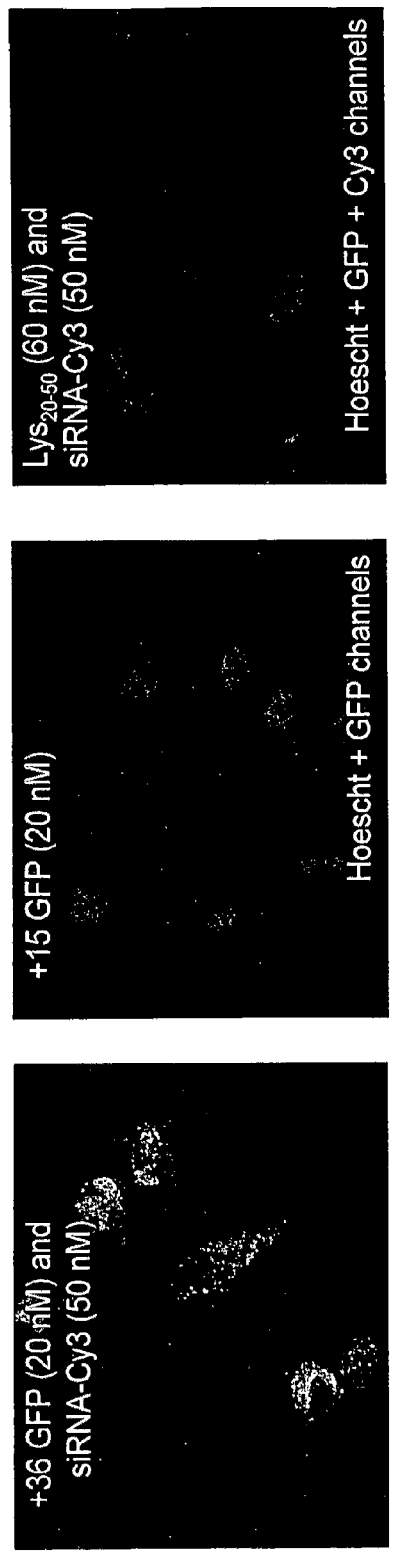
FIG. 15. Factors Contributing to Cell-Penetrating Activity. Charge magnitude was shown to contribute to cell-penetrating activity. In particular, +15 GFP or Lys$_{20-50}$ was shown not to penetrate cells. Left: 20 mM+15 GFP and 50 nM siRNA-Cy3. Middle: 20 nM+36 GFP. Right: 60 nM Lys$_{20-50}$ and 50 nM siRNA-Cy3. Hoechst channel was used to visualize DNA, thereby marking the position of cells; GFP channel was used to visualize GFP.

FIG. 15 demonstrates various factors contributing to cell-penetrating activity. Charge density was shown to contribute to cell-penetrating activity. For example, 60 nM $Arg_6$ was shown not to transfect siRNA. Charge magnitude was shown to contribute to cell-penetrating activity. For example, +15 GFP was shown not to penetrate cells or transfect siRNA. "Protein-like" character was also shown to contribute to cell-penetrating activity. For example, 60 nM $Lys_{20-50}$ was shown not to transfect siRNA. The present invention demonstrates that, in some embodiments, charge density is not sufficient to allow a protein to penetrate into cells. The present invention demonstrates that, in some situations, charge magnitude may necessary but not sufficient to allow a protein to penetrate into cells. The present invention further shows that some protein-like features may contribute to cell penetration.

Example 3

Mammalian Cell Penetration, siRNA Transfection, and DNA Transfection by Supercharged Green Fluorescent Proteins Resurfacing proteins without abolishing their structure or function through the extensive mutagenesis of non-conserved, solvent-exposed residues were previously described (Lawrence M S, Phillips K J, Liu D R (2007). Supercharging proteins can impart unusual resilience. *J. Am. Chem. Soc.* 129:10110-10112; International PCT patent application, PCT/US07/70254, filed Jun. 1, 2007, published as WO 2007/143574 on Dec. 13, 2007; U.S. provisional patent applications, U.S. Ser. No. 60/810,364, filed Jun. 2, 2006, and U.S. Ser. No. 60/836,607, filed Aug. 9, 2006; each of which is incorporated herein by reference). When the replacement residues are all positively or all negatively charged, the resulting "supercharged" proteins can retain their activity while gaining unusual properties such as robust resistance to aggregation and the ability to bind oppositely charged macromolecules. For example, a green fluorescent protein with a +36 net theoretical charge (+36 GFP) was highly aggregation-resistant, could retain fluorescence even after being boiled and cooled, and reversibly complexed DNA and RNA through electrostatic interactions.

A variety of cationic peptides with the ability to penetrate mammalian cells including peptides derived from HIV Tat (Frankel A D, Pabo C O (1988) Cellular uptake of the tat protein from human immunodeficiency virus. *Cell* 55: 1189-1193; Green M, Loewenstein P M (1988) Autonomous functional domains of chemically synthesized human immunodeficiency virus tat trans-activator protein. *Cell* 55: 1179-1188; each of which is incorporated herein by reference) and penetratin from the Antennapedia homeodomain (Thoren P E, Persson D, Karlsson M, Norden B (2000) The antennapedia peptide penetratin translocates across lipid bilayers—the first direct observation. *FEBS Lett* 482: 265-268; incorporated herein by reference) have been previously described. Schepartz and coworkers have recently shown that small, folded proteins containing a minimal cationic motif embedded within a type II polyproline helix efficiently penetrate eukaryotic cells (Daniels D S, Schepartz A (2007) Intrinsically cell-permeable miniature proteins based on a minimal cationic PPII motif. *J Am Chem Soc* 129: 14578-14579; Smith B A, Daniels D S, Coplin A E, Jordan G E, McGregor L M, et al. (2008) Minimally cationic cell-permeable miniature proteins via alpha-helical arginine display. *J Am Chem Soc* 130: 2948-2949; each of which is incorporated herein by reference). Raines and coworkers recently engineered proteins with a surface-exposed poly-arginine patch that confers the ability to penetrate cells (Fuchs S M, Raines R T (2007) Arginine grafting to endow cell permeability. *ACS Chem Biol* 2: 167-170; Fuchs S M, Rutkoski T J, Kung V M, Groeschl R T, Raines R T (2007) Increasing the potency of a cytotoxin with an arginine graft. *Protein Eng Des Sel* 20: 505-509; each of which is incorporated herein by reference). In light of these studies, it was suggested that superpositively charged proteins such as +36 GFP might associate with negatively charged components of the cell membrane in a manner that results in cell penetration.

The present Example describes, inter alia, the cell-penetrating characteristics of superpositively charged GFP variants with net charges of +15, +25, and +36. It was found that +36 GFP potently enters cells through sulfated peptidoglycan-mediated, actin-dependent endocytosis. When pre-mixed with siRNA, +36 GFP delivers siRNA effectively and without cytotoxicity into a variety of cell lines, including several known to be resistant to cationic lipid-mediated transfection. The siRNA delivered into cells using +36 GFP was able to effect gene silencing in four out of five mammalian cell lines tested. Comparison of the siRNA transfection ability of +36 GFP with that of several synthetic peptides of comparable or greater charge magnitude and charge density suggests that the observed mode of siRNA delivery may require protein-like features of +36 GFP that are not present among cationic peptides. When fused to an endosomolytic peptide derived from hemagglutinin, +36 GFP is also able to transfect plasmid DNA into several cell lines that resist cationic lipid-mediated transfection in a manner that enables plasmid-based gene expression.

Results

Mammalian Cell Penetration by Supercharged GFPs.

Figure 22:
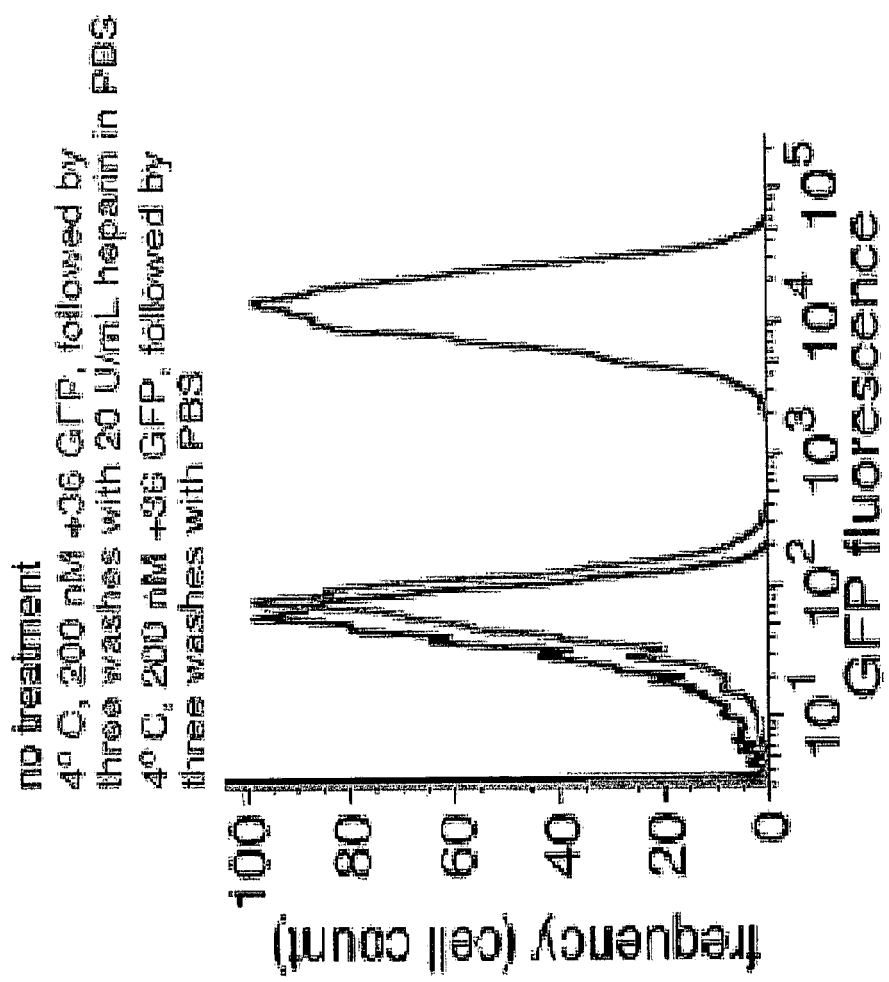
FIG. 22. The effectiveness of the washing protocol used to remove cell surface-bound supercharged GFP. HeLa cells were treated with 200 nM+36 GFP at 4° C. (to block cell uptake of GFP, see the main text) for 1 hour. Cells were then washed three times (1 minute for each wash) with 4° C. PBS or with 4° C. 20 U/mL heparin sulfate in PBS, then analyzed by flow cytometry. Cells washed with PBS show significant GFP fluorescence presumably arising from cell-surface bound GFP. In contrast, cells washed with 20 U/mL heparin in PBS exhibit GFP fluorescence levels equivalent to untreated cells.

A series of resurfaced variants of "superfolder GFP" (sf-GFP) was previously generated and characterized (Pedelacq J D, Cabantous S, Tran T, Terwilliger T C, Waldo G S (2006) Engineering and characterization of a superfolder green fluorescent protein. *Nat Biotechnol* 24: 79-88; incorporated herein by reference) with theoretical net charges ranging from −30 to +48 that retain fluorescence (Lawrence M S, Phillips K J, Liu D R (2007) Supercharging proteins can impart unusual resilience. *J Am Chem Soc* 129: 10110-10112; incorporated herein by reference). The evaluation of the ability of these supercharged GFPs to penetrate mammalian cells requires a method to remove surface-bound, non-internalized GFP. Wit was, therefore, confirmed that washing conditions known to remove surface-bound cationic proteins from cells (Pedelacq J D, Cabantous S, Tran T, Terwilliger T C, Waldo G S (2006) Engineering and characterization of a superfolder green fluorescent protein. *Nat Biotechnol* 24: 79-88) also effectively remove cell surface-bound superpositively charged GFP. HeLa cells were treated with +36 GFP at 4° C., a temperature that allows +36 GFP to bind to the outside of cells but blocks internalization (vide infra). Cells were washed three times at 4° C. with either PBS or with PBS containing heparin and analyzed by flow cytometry for GFP fluorescence. Cells washed with PBS were found to have significant levels of GFP (presumably surface-bound), while cells washed with PBS containing heparin exhibited GFP fluorescence intensity very similar to that of untreated cells (FIG. 22). These observations confirmed the effectiveness of three washes with heparin at removing surface-bound superpositively charged GFP.

Figure 16:
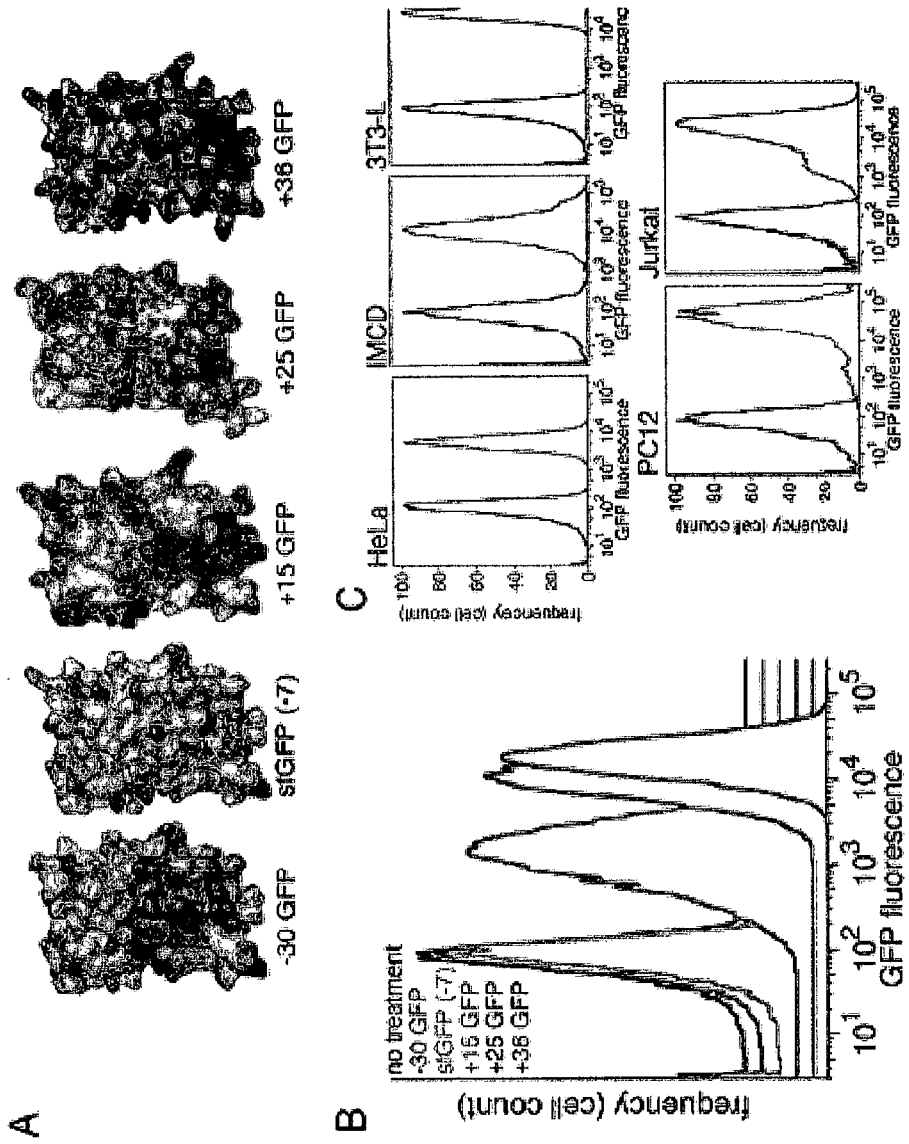
FIG. 16. Supercharged GFP variants and their ability to penetrate cells. (A) Calculated electrostatic surface potential of GFP variants, colored from −25 kT/e to +25 kT/e. (B) Flow cytometry analysis showing amounts of internalized GFP in HeLa cells independently treated with 200 nM of each GFP variant and washed three times with PBS containing heparin to remove cell surface-bound GFP. (C) Flow cytometry analysis showing amounts of internalized +36 GFP (green) in HeLa, IMCD, 3T3-L, PC12, and Jurkat cells compared to background fluorescence in untreated cells (black).
Figure 23:
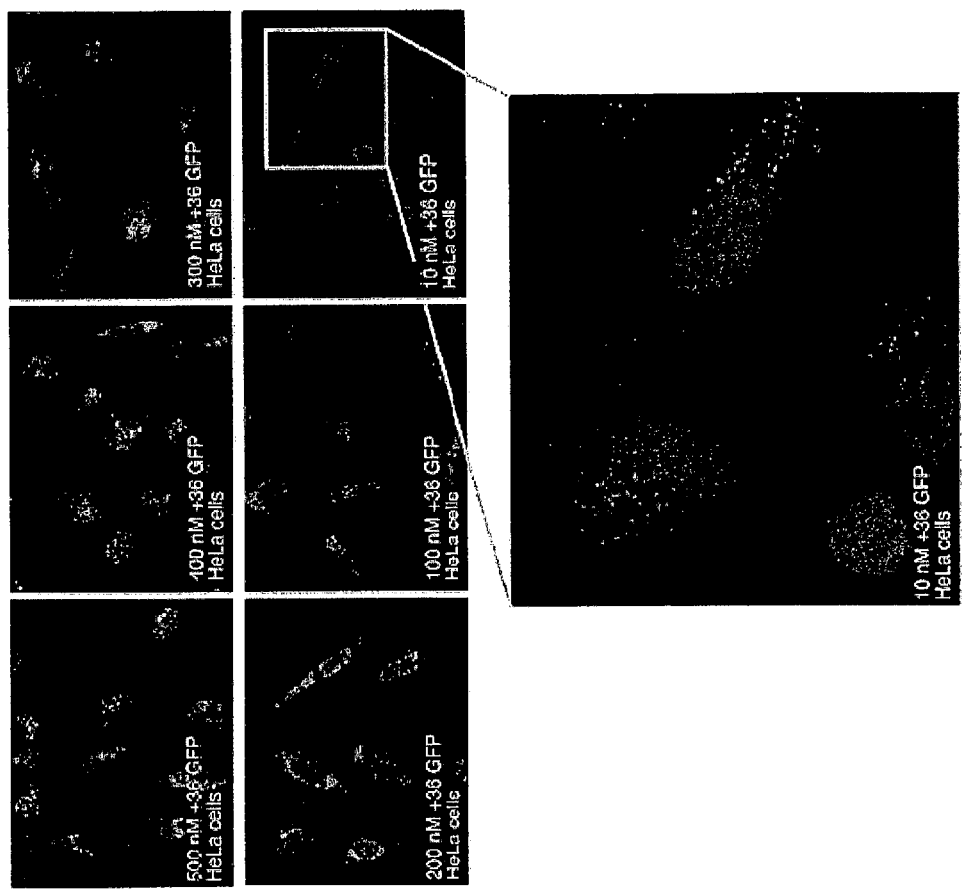
FIG. 23. Concentration dependence of +36 GFP cell penetration in HeLa cells. HeLa cells were treated with +36 GFP in serum-free media for 4 hours. Cells were trypsinized and replated in 10% FBS in DMEM on glass slides coated with Matrigel (BD Biosciences). After 24 hours at 37° C., cells were fixed with 4% formaldehyde in PBS, stained with DAPI, and imaged using a Leica DMRB inverted microscope. Magnification for all images is 20×.

Next, HeLa cells were incubated with 10-500 nM sfGFP (theoretical net charge of −7), −30 GFP, +15 GFP, +25 GFP, or +36 GFP for 4 hours at 37° C. (FIG. 16A). After incubation, cells were washed three times with PBS containing heparin and analyzed by flow cytometry. No detectable internalized protein was observed in cells treated with sfGFP or −30 GFP. HeLa cells treated with +25 GFP or +36 GFP, however, were found to contain high levels of internalized GFP. In contrast, cells treated with +15 GFP contained 10-fold less internalized GFP, indicating that positive charge magnitude is an important determinant of effective cell penetration (FIG. 16B). It was found that +36 GFP readily penetrates HeLa cells even at concentrations as low as 10 nM (FIG. 23).

In order to test the generality of cell penetration by +36 GFP, these experiments were repeated using four additional mammalian cell types: inner medullary collecting duct (IMCD) cells, 3T3-L pre-adipocytes, rat pheochromocytoma PC12 cells, and Jurkat T-cells. Flow cytometry analysis revealed that 200 nM+36 GFP effectively penetrates all five types of cells tested (FIG. 16C). Internalization of +36 GFP in stably adherent HeLa, IMCD, and 3T3-L cell lines was confirmed by fluorescence microscopy (vide infra). Real-time imaging showed +36 GFP bound rapidly to the cell membrane of HeLa cells and was internalized within minutes as punctate foci that migrated towards the interior of the cell and consolidated into larger foci, consistent with uptake via endocytosis.

Determinants of Cell-Penetration Potency.

Figure 47:
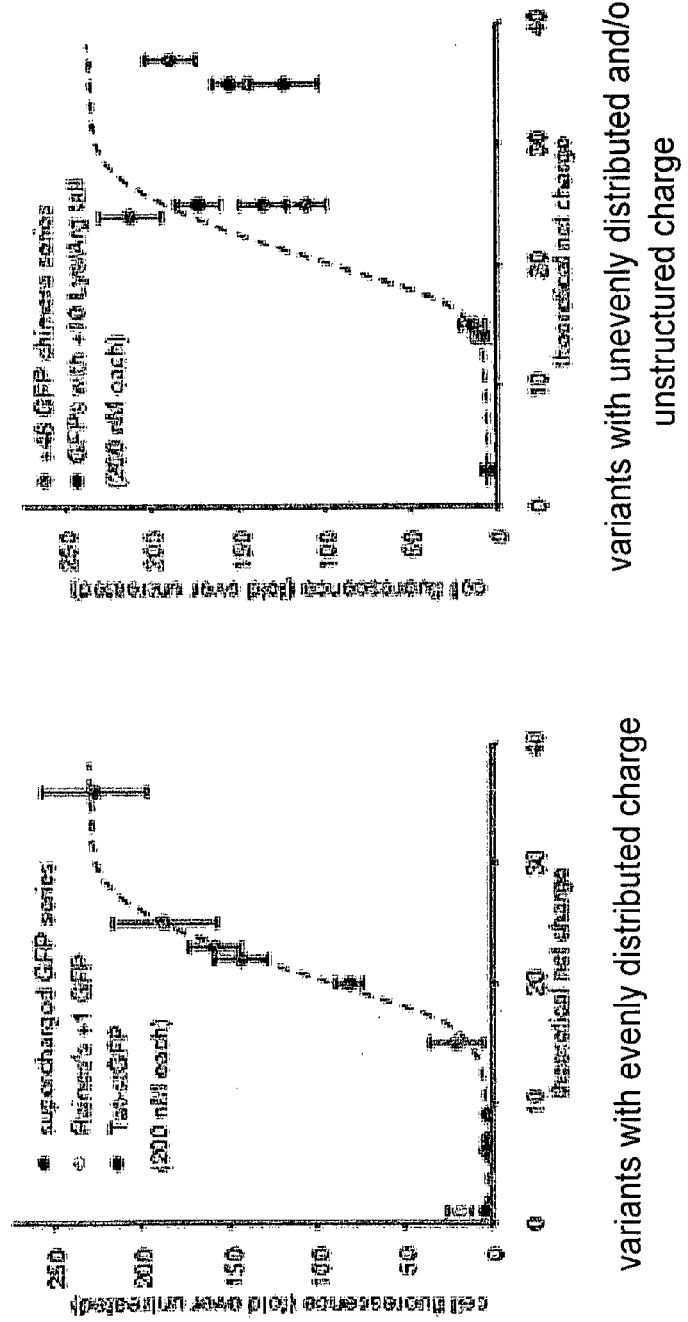
FIG. 47. Net charge magnitude, distribution, and structure as determinants of cell-penetration potency.

To determine the effect of net charge, charge distribution, and charge structure on cell-penetration potency of supercharged proteins, cells were treated with supercharged GFP protein variants with various, evenly distributed net charges (supercharged GFP series), unevenly distributed and/or unstructured charges (+48 GFP chimera series and GFP with +10 Lys/Arg tail) (FIG. 47). A large potency increase at ~+22 (~0.8 charge units per kD) was observed in the supercharged GFP series. Charge distribution and charge structure also had a marked effect on cell penetration potency, suggesting that not just charge magnitude, but also charge distribution and protein structure determine cell-penetration characteristics in the high-potency regime.

Mechanistic Probes of +36 GFP Cell Penetration

Figure 17:
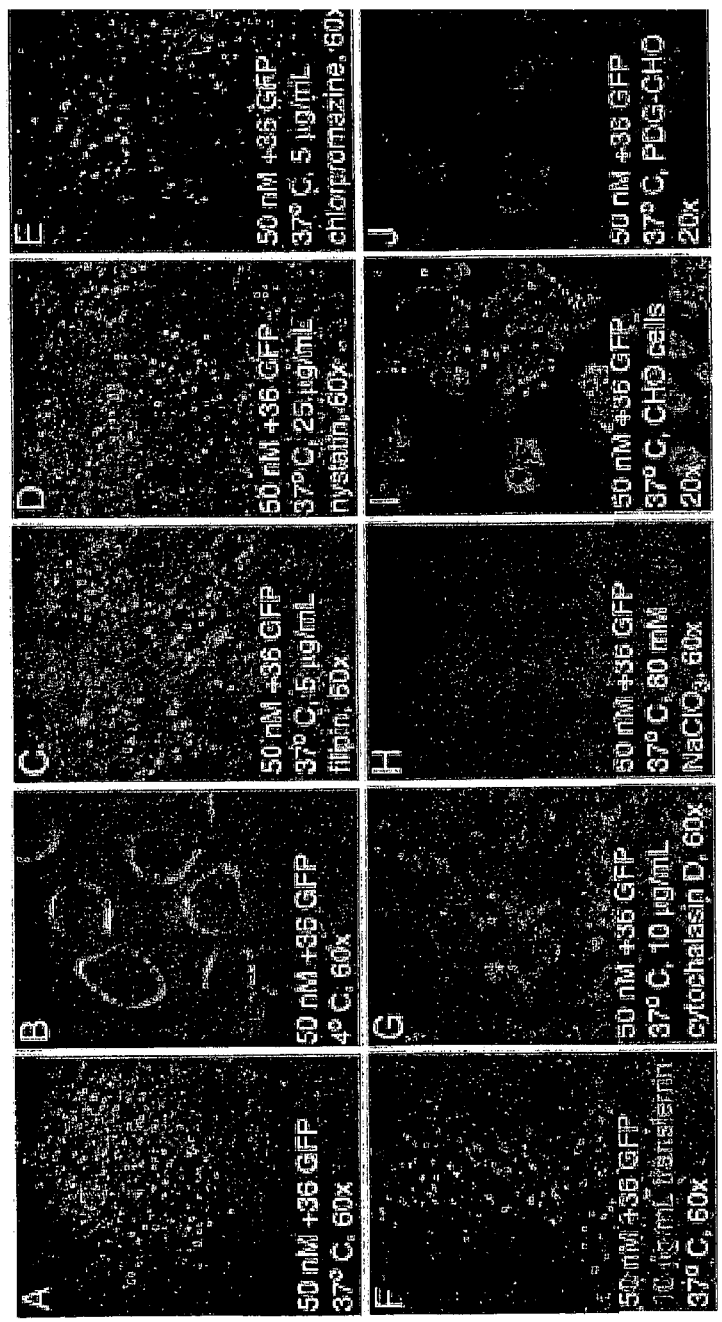
FIG. 17. (A) Internalization of +36 GFP in HeLa cells after co-incubation for 1 hour at 37_C. (B) Inhibition of +36 GFP cell penetration in HeLa cells incubated at 4° C. for 1 hour. Cells were only partially washed to enable +36 GFP to remain partially bound to the cell surface. (C) and (D) +36 GFP internalization under the conditions in (A) but in the presence of caveolin-dependent endocytosis inhibitors filipin and nystatin, respectively. (E) +36 GFP internalization under the conditions in (A) but in the presence of the clathrin-dependent endocytosis inhibitor chlorpromazine. (F) Cellular localization of Alexa Fluor 647-labeled transferrin and +36 GFP 20 minutes after endocytosis. (G) Inhibition of +36 GFP internalization in HeLa cells in the presence of the actin polymerization inhibitor cytochalasin D. (H) Inhibition of +36 GFP internalization in HeLa cells treated with 80 mM sodium chlorate. (I) Internalization of +36 GFP in CHO cells incubated at 37° C. for 1 hour. (J) Lack of +36 GFP internalization in PDG-CHO cells. In (I) and (J) cell nuclei were stained with DAPI.

To illuminate the mechanism by which +36 GFP enters cells, the cell penetration experiments were repeated in HeLa cells under a variety of conditions that each blocks a different component of an endocytosis pathway (Payne C K, Jones S A, Chen C, Zhuang X (2007) Internalization and trafficking of cell surface proteoglycans and proteoglycan-binding ligands. *Traffic* 8: 389-401; Veldhoen S, Laufer S D, Trampe A, Restle T (2006) Cellular delivery of small interfering RNA by a non-covalently attached cell-penetrating peptide: quantitative analysis of uptake and biological effect. *Nucleic Acids Res* 34: 6561-6573; each of which is incorporated herein by reference). Cell penetration of +36 GFP was not observed when HeLa cells were cooled to 4° C. prior to and during +36 GFP treatment (FIG. 17B). This result suggests that uptake of +36 GFP requires an energy-dependent process, consistent with endocytosis (Deshayes S, Morris M C, Divita G, Heitz F (2005) Cell-penetrating peptides: tools for intracellular delivery of therapeutics. *Cell Mol Life Sci* 62: 1839-1849; incorporated herein by reference). The effects of 5 µg/mL filipin or 25 µg/mL nystatin, small molecules known to inhibit caveolin-dependent endocytosis, were evaluated. Neither inhibitor significantly altered +36 GFP internalization (FIGS. 17C and 17D, respectively). Treatment with chlorpromazine, a known inhibitor of clathrin-mediated endocytosis, similarly had little effect on +36 GFP cell penetration (FIG. 17E). In addition, simultaneous treatment of HeLa cells with 50 nM+36 GFP and 10 µg/mL of fluorescently labeled transferrin, a protein known to be internalized in a clathrin-dependent manner (Hopkins C R, Trowbridge I S (1983) Internalization and processing of transferrin and the transferrin receptor in human carcinoma A431 cells. *J Cell Biol* 97: 508-521; incorporated herein by reference), resulted in little GFP/transferrin co-localization (FIG. 17F). Treatment with cytochalasin D, an actin polymerization inhibitor, however, significantly decreased +36 GFP cell penetration (FIG. 17G). Taken together, these results are consistent with a model in which +36 GFP uptake proceeds through an endocytotic pathway that is energy-dependent, requires actin polymerization, and does not require clathrin or caveolin.

Based on previous studies on the mechanism of cellular uptake of cationic peptides (Payne C K, Jones S A, Chen C, Zhuang X (2007) Internalization and trafficking of cell surface proteoglycans and proteoglycan-binding ligands. *Traffic* 8: 389-401; Fuchs S M, Raines R T (2004) Pathway for polyarginine entry into mammalian cells. *Biochemistry* 43: 2438-2444; each of which is incorporated herein by reference), it was suggested that anionic cell-surface proteoglycans might serve as receptors to mediate +36 GFP internalization. To probe this hypothesis HeLa cells were pre-treated with 80 mM sodium chlorate, an inhibitor of ATP sulphurylase, an enzyme required for the biosynthesis of sulfated proteoglycans (Baeuerle P A, Huttner W B (1986) Chlorate—a potent inhibitor of protein sulfation in intact cells. *Biochem Biophys Res Commun* 141: 870-877; incorporated herein by reference). These conditions completely blocked +36 GFP penetration (FIG. 17H). As a further probe of the role proteoglycans play in +36 GFP uptake, internalization was compared in wild-type Chinese hamster ovary (CHO) cells with proteoglycan-deficient CHO cells (PGD-CHO) that lack xylosyltransferase, an enzyme required for glycosaminoglycan synthesis. Wild-type CHO cells (FIG. 17I), but not PGD-CHO cells (FIG. 17J), efficiently internalized +36 GFP. These findings suggest that +36 GFP penetration of mammalian cells requires binding to sulfated cell-surface peptidoglycans.

+36 GFP Binds siRNA and Delivers siRNA into a Variety of Mammalian Cell Lines

Figure 18:
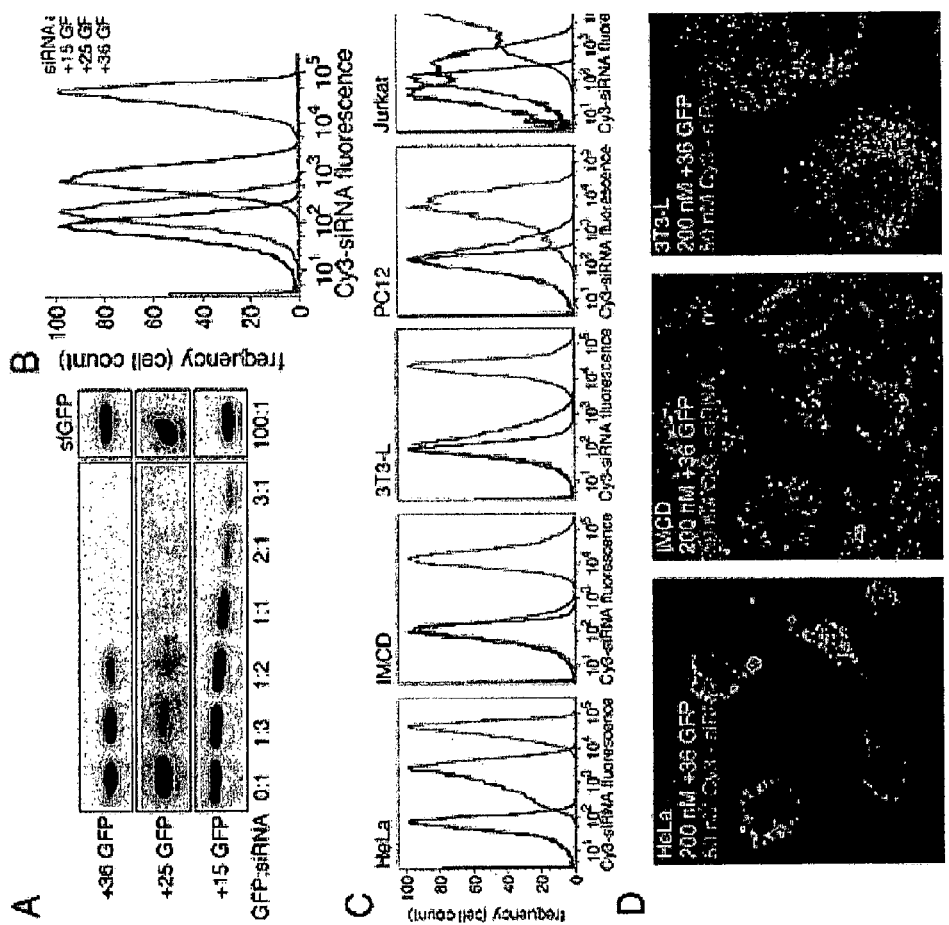
FIG. 18. (A) Gel-shift assay showing unbound siRNA (33) stained by ethidium bromide to determine superpositive GFP: siRNA binding stoichiometry. 10 pmoles of siRNA was mixed with various molar ratios of each GFP for 10 minutes at 25° C., then analyzed by non-denaturing PAGE. The rightmost lane in each row shows a 100:1 mixture of sfGFP and siRNA. (B) Flow cytometry analysis showing levels of internalized siRNA in HeLa cells treated with a mixture of 50 nM Cy3-siRNA and 200 nM of +15, +25, or +36 GFP, followed by three heparin washes to remove non-internalized protein (see FIG. 22). Data from HeLa cells treated with siRNA but no transfection reagent is shown in black. (C) Flow cytometry analysis showing levels of Cy3-labeled siRNA delivered into HeLa, IMCD, 3T3-L, PC12, and Jurkat cells after incubation with a mixture of 50 nM Cy3-siRNA and either 200 nM+36 GFP or ~2 μM Lipofectamine 2000 in comparison to cells treated with siRNA without transfection reagent (black). Cells were washed before flow cytometry as described above. (D) Fluorescence microscopy images of stably adherent cell lines (HeLa, IMCD, and 3T3-L) 24 hours after a 4-hour treatment with 200 nM +36 GFP and 50 nM Cy3-siRNA. Each image is an overlay of three channels: DAPI stain, Cy3-siRNA, and 36 GFP; -Cy3/GFP channel overlap yellow indicates the colocalization of siRNA and GFP. Magnification for all three images was 40×.

The ability of superpositively charged proteins to form complexes with DNA and tRNA was previously reported (Lawrence et al. (2007) Supercharging proteins can impart unusual resilience. *J Am Chem Soc* 129: 10110-10112; incorporated herein by reference). In light of these results, the ability of +15, +25, and +36 GFP to bind siRNA in vitro in a variety of stoichiometric ratios was evaluated. Using a gel-shift assay (Kumar P, Wu H, McBride J L, Jung K E, Kim M H, et al. (2007) Transvascular delivery of small interfering RNA to the central nervous system. *Nature* 448: 39-43; incorporated herein by reference), binding of +25 and +36 GFP to siRNA with a stoichiometry of ~2:1 was observed, while greater than five +15 GFP proteins on average were required to complex a single siRNA molecule (FIG. 18A). In contrast, 100 equivalents of sfGFP did not detectably bind siRNA under the assay conditions.

Next the ability of +15, +25, and +36 GFP to deliver bound siRNA into HeLa cells was examined. A Cy3-conjugated GAPDH siRNA (Ambion) was briefly mixed with 200 nM+36 GFP and the resulting mixture was added to cells in serum-free media for 4 hours. The cells were washed three times with PBS containing heparin and analyzed by flow cytometry for Cy3-siRNA uptake. It was observed that +25 and +36 GFP delivered 100- and 1000-fold more siRNA into HeLa cells, respectively, than treatment with siRNA alone (FIG. 3B), and ~20-fold more siRNA than was delivered with the common cationic lipid transfection reagent Lipofectamine 2000 (FIG. 18C). In contrast, +15 GFP did not efficiently transfect siRNA into HeLa cells (FIG. 18B).

Figure 24:
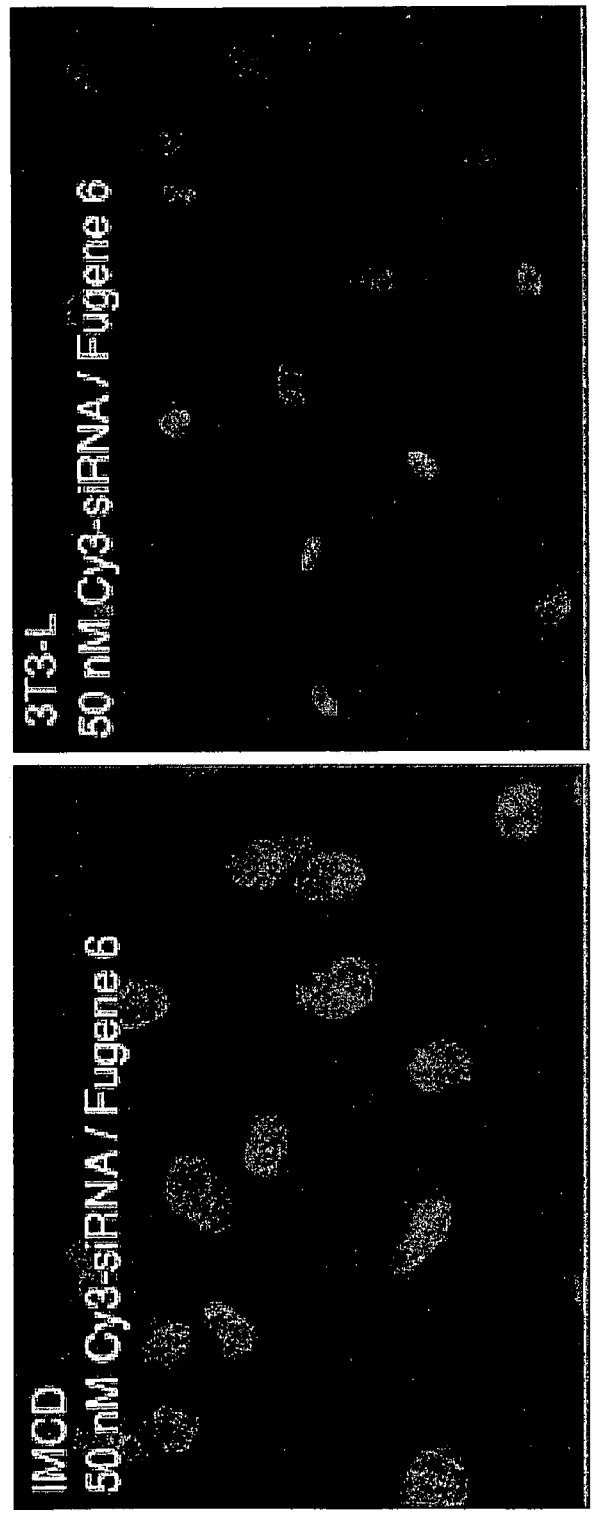
FIG. 24. Fluorescence microscopy reveals no internalized Cy3-siRNA in IMCD and 3T3-L cells using Fugene 6 (Roche) transfection agent. Cells were treated with Fugene 6 in serum-free media for 4 hours following the manufacturer's protocol. Cells were trypsinized and pelleted. The trypsin-containing media was removed by aspiration and the cells were resuspended in 10% FBS in DMEM then plated on glass slides precoated with Matrigel™. Cells were allowed to adhere for 24 hours, fixed with 4% formaldehyde in PBS, stained with DAPI, and imaged using a Leica DMRB inverted microscope. Magnification for all images is 20×. No Cy3 fluorescence was observed (compare with FIG. 18D).

In addition to HeLa cells, +36 GFP was able to efficiently deliver siRNA in IMCD cells, 3T3-L preadipocytes, rat pheochromocytoma PC12 cells, and Jurkat T-cells, four cell lines that are resistant to siRNA transfection using Lipofectamine 2000 (Carlotti F, Bazuine M, Kekarainen T, Seppen J, Pognonec et al. (2004) Lentiviral vectors efficiently transduce quiescent mature 3TL-L1 adipocytes. *Mol Ther* 9: 209-217; Ma H, Zhu J, Maronski M, Kotzbauer P T, Lee V M, Dichter M A, et al. (2002) Non-classical nuclear localization signal peptides for high efficiency lipofection of primary neurons and neuronal cell lines. *Neuroscience* 112: 1-5; McManus M T, Haines B B, Dillon C P, Whitehurst C E, van Parijs L, et al. (2002) Small interfering RNA-mediated gene silencing in T lymphocytes. *J Immunol* 169: 5754-5760; Strait K A, Stricklett P K, Kohan J L, Miller M B, Kohan D E (2007) Calcium regulation of endothelin-1 synthesis in rat inner medullary collecting duct. *Am J Physiol Renal Physiol* 293: F601-606; each of which is incorporated herein by reference). Treatment with Lipofectamine 2000 and Cy3-siRNA resulted in efficient siRNA delivery in HeLa cells, but no significant delivery of siRNA into IMCD, 3T3-L, PC12, or Jurkat cells (FIG. 18C). Treatment of IMCD or 3T3-L cells with Fugene 6 (Roche), a different cationic lipid transfection agent, and Cy3-siRNA also did not result in significant siRNA delivery these cells (FIG. 24). In contrast, treatment with +36 GFP and Cy3-siRNA resulted in significant siRNA levels in all five cell lines tested (FIG. 18C). Compared with Lipofectamine 2000, +36 GFP resulted in 20- to 200-fold higher levels of Cy3 signal in all cases. Based on the effectiveness of three heparin washes at removing non-internalized +36 GFP, (FIG. 22) these higher Cy3 levels can be attributed to higher levels of internalized Cy3-siRNA rather than to cell surface-bound +36 GFP/Cy3-siRNA complexes. Consistent with this interpretation, fluorescence microscopy of the adherent cell lines used in this study (HeLa, IMCD, and 3T3-L) reveal internalized Cy3-siRNA and +36 GFP in punctate foci that presumed to be endosomes (FIG. 18D). These results collectively indicate that +36 GFP can effectively deliver siRNA into a variety of mammalian cell lines, including several that are poorly transfected by commonly used cationic lipid transfection reagents.

Figure 30:
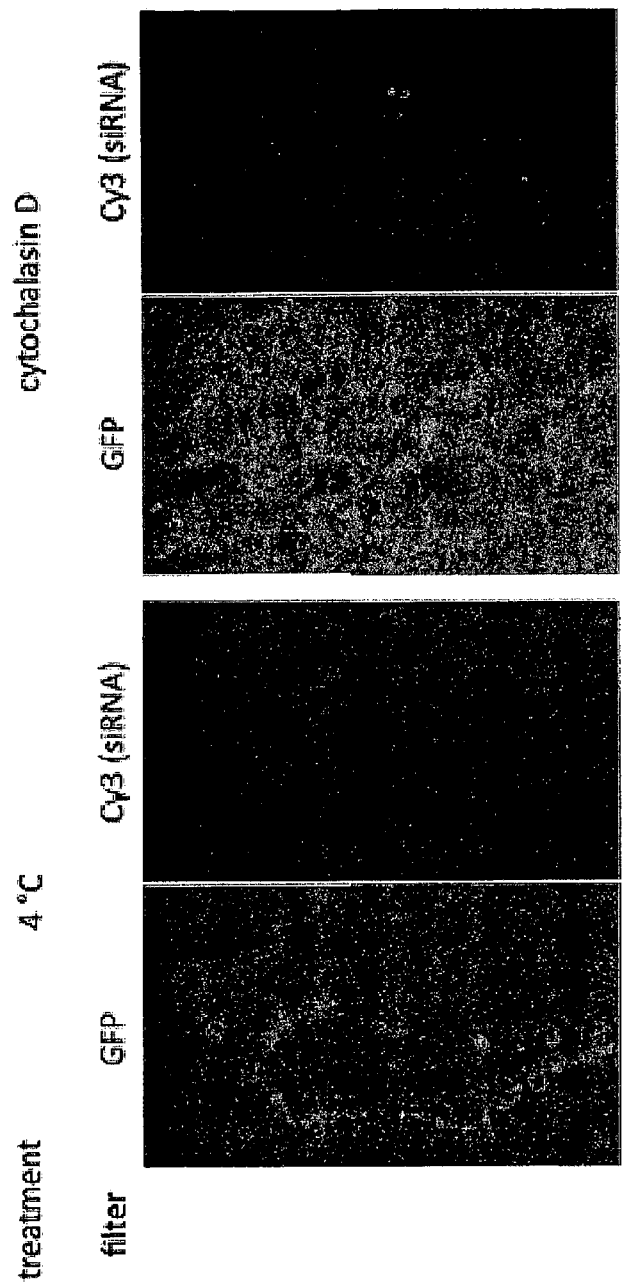
FIG. 30. Fluorescence microscopy reveals no internalized Cy3-siRNA or GFP in HeLa cells treated at either 4° C., or in HeLa cells pretreated with cytochalisin D (10 µg/mL). Image is of cells 1 hour after treatment with a solution containing 200 nM+36 GFP and 50 nM siRNA. Images were taken on an inverted spinning disk confocal microscope equipped with a filter to detect GFP emission. To facilitate visualization, cells were washed twice (one minute each) with 20 U/mL heparin in PBS to remove most (but not all) surface bound GFP-siRNA.

When HeLa cells were treated with the a premixed solution containing 200 nM+36 GFP and 50 nM Cy3-siRNA in the presence of cytochalasin D or at 4° C., no internalized GFP or Cy3 siRNA was observed (FIG. 30). These data support a mechanism of siRNA delivery that is dependent on endocytosis and actin polymerization, consistent with the present inventors' mechanistic studies of +36 GFP in the absence of siRNA.

Size and Cytotoxicity of +36 GFP-siRNA Complexes.

Figure 31:
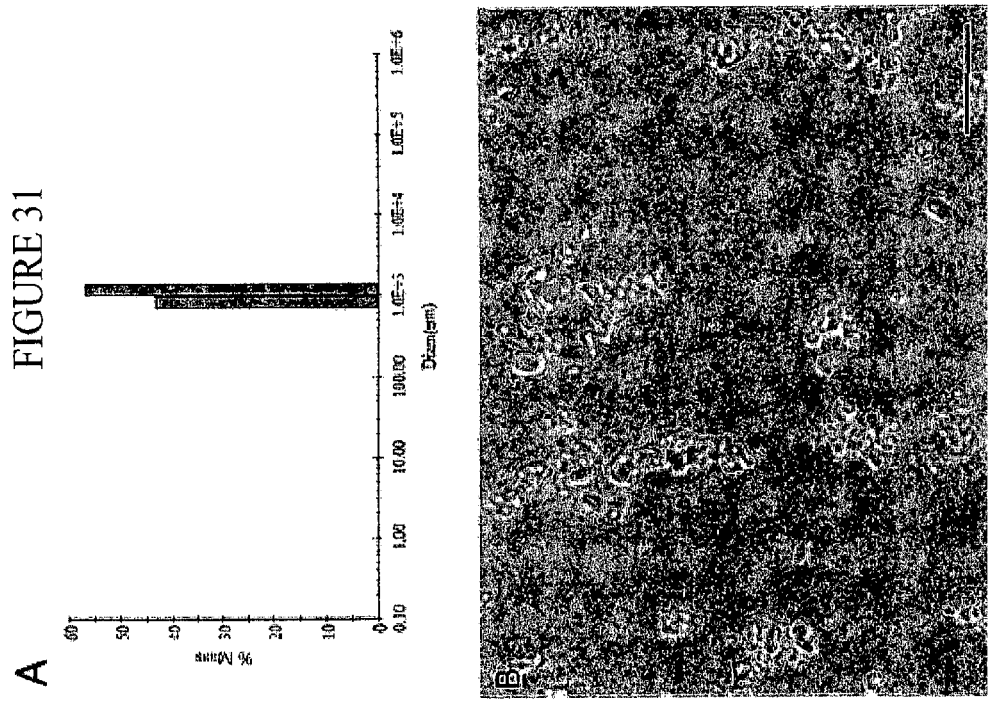
FIG. 31. (A) Dynamic Light Scattering (DLS) data showing the hydrodynamic radius (Hr) of particles formed from mixing 20 µM+36 GFP and 5 µM of a double-stranded RNA 20-mer. (B) Fluorescence microscopy image of the above sample. The image shown is an overlay of brightfield and GFP channel images; note that the larger features are actually smaller particles associated together as the sample dried. Scale bar=10 µm.

+36 GFP-siRNA complexes were analyzed by dynamic light scattering (DLS) using stoichiometric ratios identical to those used for transfection. From a mixture containing 20 µM+36 GFP and 5 µM siRNA, a fairly monodisperse population of particles with a hydrodynamic radius (Hr) of 880.6±62.2 nm was observed (FIG. 31A), consistent with microscopy data (FIG. 31B). These observations demonstrate the potential for +36 GFP to form large particles when mixed with siRNA, a phenomena observed by previous researchers using cationic delivery reagents (Deshayes et al., 2005, *Cell Mol. Life Sci.*, 62:1839-49; and Meade and Dowdy, 2008, *Adv. Drug Deliv. Rev.*, 60:530-36; both of which are incorporated herein by reference).

Figure 25A:
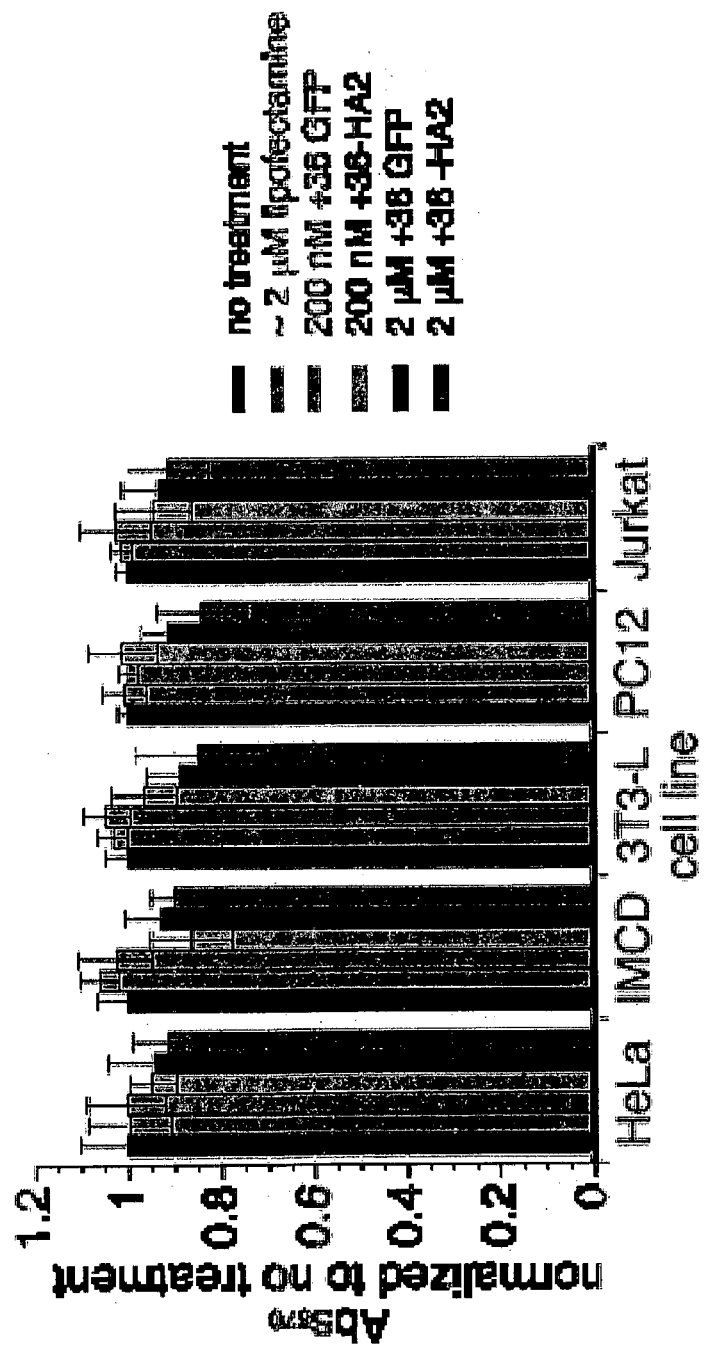
FIG. 25. (A) MTT cytotoxicity assay for five mammalian cell lines treated with 50 nM siRNA and ~2 μM Lipofectamine 2000, +36 GFP, or +36 GFP-HA2. Data were taken 24 hours after treatment. Values and error bars reflect the mean and the standard deviation of three independent experiments. Cells treated with +36 GFP or +36 GFP-HA2 but without the MTT reagent did not exhibit significant absorbance under these conditions. (B) MTT cytotoxicity assay of HeLa cells treated with 50 nM siRNA and either 200 nM or 2 μM cationic polymer. Treatment with chloroquine or pyrene butyric acid proved cytotoxic (lanes 9 and 10, respectively).

To assess the cytotoxicity of +36 GFP-siRNA complexes, MTT assays were performed on all five cell lines 24 hours after treatment with 0.2 to 2 µM+36 GFP and 50 nM siRNA. These assays revealed no significant apparent cytotoxicity to HeLa, IMCD, 3T3-L, PC12, or Jurkat cells (FIG. 25A).

Gene Silencing with +36 GFP-Delivered siRNA

While the above results demonstrate the ability of +36 GFP to deliver siRNA into a variety of mammalian cells, they do not establish the availability of this siRNA for gene silencing. Based on the punctate localization of intracellular +36 GFP (FIG. 18D), it was suggested that gene silencing would require at least partial escape of +36 GFP-transfected siRNA from endosomes. To evaluate the gene suppression activity of siRNA delivered with +36 GFP, HeLa, IMCD, 3T3-L, PC12, and Jurkat cells were treated with a solution containing 50 nM of GAPDH-targeting siRNA and either ~2 µM Lipofectamine 2000 or 200 nM+36 GFP. Cells were exposed to the siRNA transfection solution for 4 hours, then grown for up to 4 days.

In HeLa cells, observed decreases in GAPDH mRNA and protein levels indicate that both Lipofectamine 2000 and +36 GFP mediate efficient siRNA-induced suppression of GAPDH expression with similar kinetics. GAPDH-targeting siRNA delivered with Lipofectamine 2000 or +36 GFP resulted in a ~85% decrease in GAPDH mRNA level after 72 hours (FIG. 19A). Similarly, a decrease in GAPDH protein levels of ~75% was observed in HeLa cells 96 hours after delivery of siRNA with Lipofectamine 2000 or with +36 GFP (FIG. 19B). Similarly, delivery of β-actin targeting siRNA with either ~2 µM Lipofectamine 2000 or 200 nM+36 GFP resulted in a decrease in β-actin protein levels in HeLa cells of 70-78% for both transfection agents (FIG. 19B).

In contrast to the efficiency of gene suppression in HeLa cells, treatment with Lipofectamine 2000 and 50 nM siRNA in IMCD, 3T3-L, PC12, and Jurkat cells effected no significant decrease in GAPDH protein levels (FIG. 19C), consistent with the resistance of these cell lines to cationic lipid-mediated transfection (FIG. 18C). However, treatment with 200 nM+36 GFP and 50 nM siRNA resulted in 44-60% suppression of GAPDH protein levels in IMCD, 3T3-L, and PC12 cells (FIG. 19C). Despite efficient siRNA delivery by +36 GFP (FIG. 18C), no significant siRNA-mediated suppression of GAPDH expression in Jurkat cells was observed (FIG. 19C).

We speculated that enhancing the escape of +36 GFP-delivered siRNA from endosomes may increase the effectiveness of gene silencing. In an attempt to chemically disrupt endocytotic vesicles, cells were treated with 200 nM+36 GFP and 50 nM siRNA together with either chloroquine, a small molecule known to have endosomolytic activity (Erbacher P, Roche A C, Monsigny M, Midoux P (1996) Putative role of chloroquine in gene transfer into a human hepatoma cell line by DNA/lactosylated polylysine complexes. *Exp Cell Res* 225, 186-194; incorporated herein by reference), or pyrene butyric acid, which has been shown to increase cytosolic distribution of internalized poly-arginine (Takeuchi T, Kosuge M, Tadokoro A, Sugiura Y, Nishi M, et al. (2006) Direct and rapid cytosolic delivery using cell-penetrating peptides mediated by pyrenebutyrate. *ACS Chem Biol* 1: 299-303; incorporated herein by reference). Addition of these reagents to mixtures containing +36 GFP and siRNA proved cytotoxic in the cell lines tested. In addition, we generated and purified a C-terminal fusion of +36 GFP and the hemagglutinin 2 (HA2) peptide, which has been reported to enhance endosome degradation (Lundberg P, El-Andaloussi S, Sutlu T, Johansson H, Langel U (2007) Delivery of short interfering RNA using endosomolytic cell-penetrating peptides. *FASEB J* 21: 2664-2671; incorporated herein by reference). As was the case with +36 GFP, the HA2-fused variant exhibited low cytotoxicity in the five cell lines tested (FIG. 25A). While the delivery of siRNA with +36 GFP-HA2 fusion resulted in decreased GAPDH protein levels in HeLa, IMCD, 3T3-L, and PC12 cells, the degree of suppression was comparable to that arising from the use of +36 GFP (FIG. 19C).

Together, these results indicate that +36 GFP and +36 GFP-HA2 are capable of delivering siRNA and effecting gene silencing in a variety of mammalian cells, including some cell lines that do not exhibit gene silencing when treated with siRNA and cationic lipid-based transfection agents.

Stability of +36 GFP and Stability of RNA and DNA Complexed with +36 GFP

Figure 32:
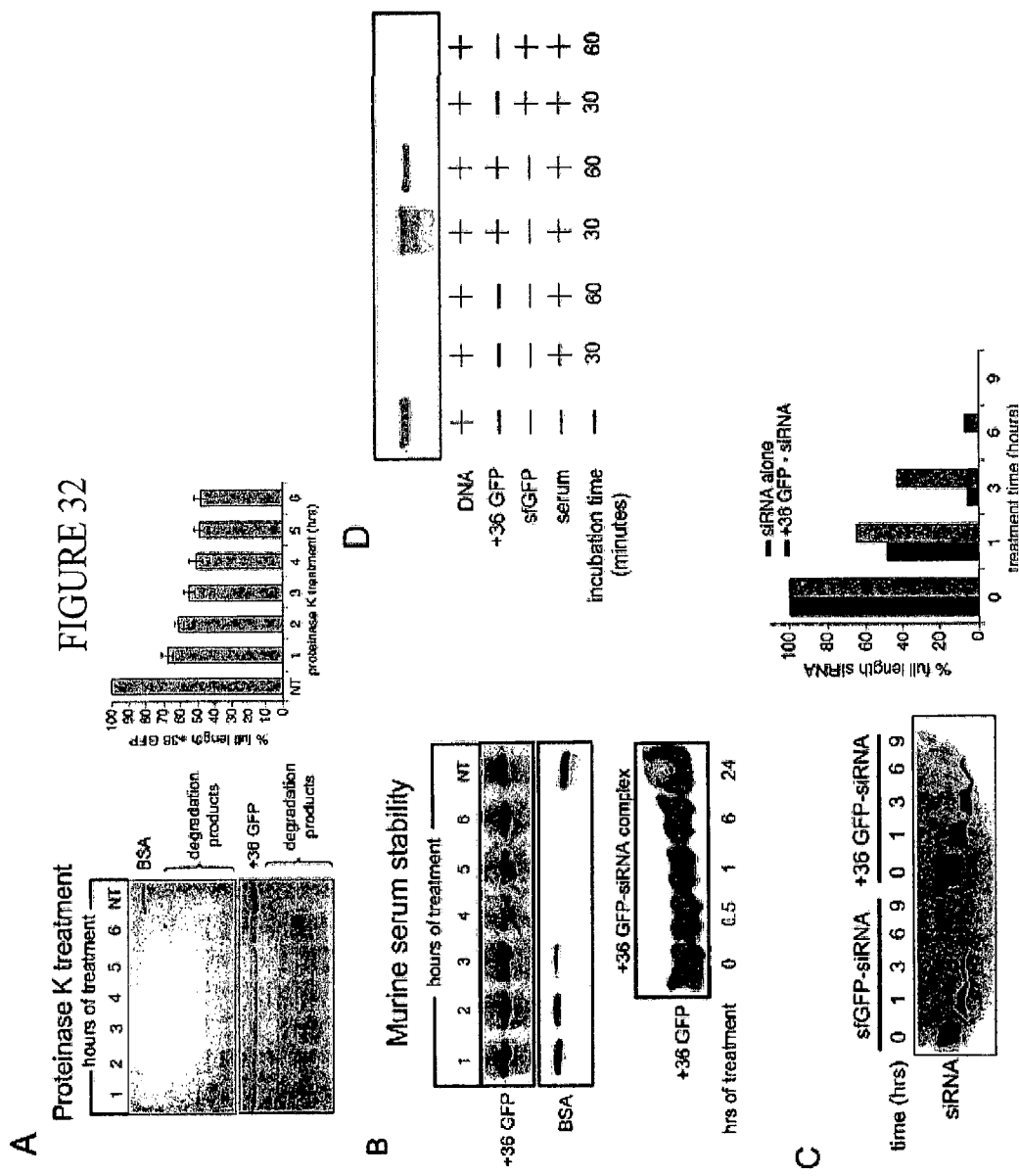
FIG. 32. (A) Digestion of +36 GFP and bovine serum albumin by proteinase K. 100 pmol of +36 GFP or bovine serum albumin (BSA) was treated with 0.6 units of proteinase K at 37° C. Samples were mixed with SDS protein loading buffer, heated to 90° C. for 10 minutes, and analyzed by SDS-PAGE on a 4-12% acrylamide gel staining with Coomassie Blue. (B) Stability of +36 GFP and BSA in murine serum. 100 µmol of each protein in PBS was mixed with 5 µL of murine serum to a total volume of 10 µL and incubated at 37° C. Samples were mixed with SDS protein loading buffer and heated to 90° C. for 10 minutes. The resulting mixture was analyzed by SDS-PAGE on a 4-12% acrylamide gel and the +36 GFP and BSA protein bands were revealed by Western blot. The bottom image is 5 µL of sample of +36 GFP-siRNA complexes (discussed in C) and analyzed for GFP by Western blot. (C) Stability of siRNA complexed with +36 GFP in murine serum. siRNA (10 pmol) was mixed with sfGFP (40 pmol) or +36 GFP (40 pmol), and incubated in 4 µL of PBS for 10 minutes at 25° C. The resulting solution was added to four volumes of mouse serum (20 µL total) and incubated at 37° C. for the indicated times, precipitated with ethanol, and analyzed by gel electrophoresis on a 15% acrylamide gel. (D) Stability of plasmid DNA complexed with +36 GFP or sfGFP in murine serum. Plasmid DNA (0.026 pmol) was mixed with 12.8 pmol of either +36 GFP or sfGFP in 4 µL of PBS for 10 minutes. To this solution was added 16 µL of mouse serum (20 µL total). Samples were incubated at 37° C. for the indicated times. DNA was isolated by extraction with phenol-chloroform and precipitation with ethanol, then analyzed by gel electrophoresis on a 1% agarose gel.

In addition to generality across different mammalian cell types and low cytotoxicity, siRNA delivery agents may be resistant to rapid degradation. Treatment of +36 GFP with proteinase K (a robust, broad-spectrum protease) revealed that +36 GFP exhibits significant protease resistance compared with bovine serum albumin. While no uncleaved BSA remained one hour after proteinase K digestion, 68% of +36 GFP remained uncleaved after one hour, and 48% remained uncleaved after six hours (FIG. 32A). We also treated +36 GFP with murine serum at 37° C. (FIG. 32B). After six hours, no significant degradation was observed, suggesting its potential in vivo serum stability. In comparison, when bovine serum albumin was incubated in mouse serum for the same period of time, 71% degradation was observed after three hours, and complete degradation by four hours.

The ability of +36 GFP to protect siRNA and plasmid DNA from degradation was assessed. siRNA or siRNA pre-complexed with +36 GFP was treated with murine serum at 37° C. After three hours, only 5.9% of the siRNA remained intact in the sample lacking +36 GFP, while 34% of the siRNA remained intact in the sample pre-complexed with +36 GFP (FIG. 32C). Similarly, while plasmid DNA was nearly completely degraded by murine serum after 30 minutes at 37° C., virtually all plasmid DNA pre-complexed with +36 GFP remained intact after 30 minutes, and 84% of plasmid DNA was intact after one hour (FIG. 32D). These results together indicate that +36 GFP is capable of significantly inhibiting serum-mediated siRNA and plasmid DNA degradation.

Comparison of +36 GFP with Synthetic Cationic Peptides

Figure 20:
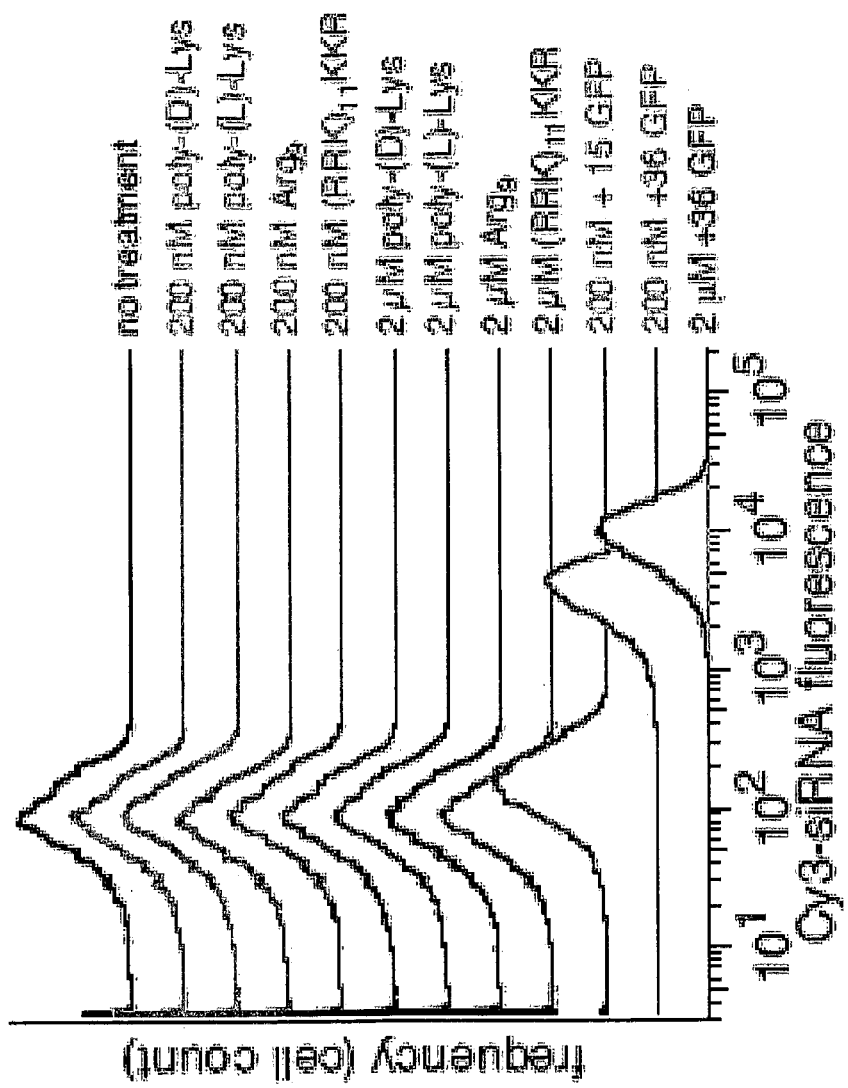
FIG. 20. The siRNA transfection activities of a variety of cationic synthetic peptides compared with that of +15 and +36 GFP. Flow cytometry was used to measure the levels of internalized Cy3-siRNA in HeLa cells treated for 4 hours with a mixture of 50 nM Cy3-siRNA and either 200 nM or 2 μM of the peptide or protein shown.
Figure 25B:
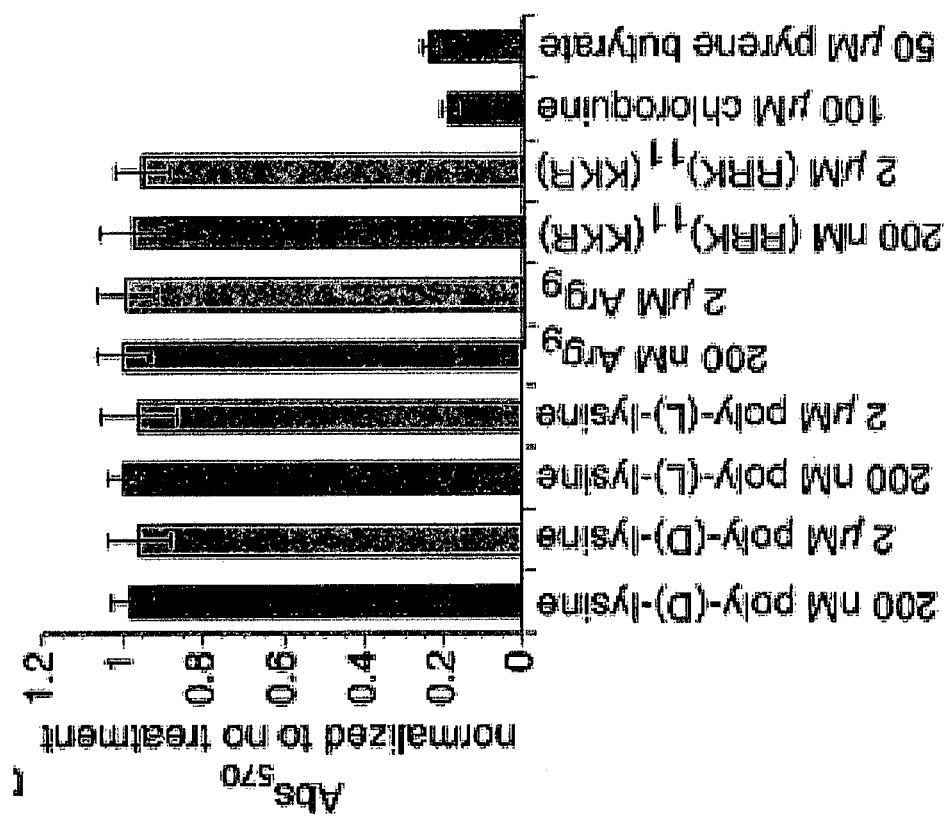

To probe the features of superpositively charged GFPs that impart their ability to deliver siRNA into cells, we compared the siRNA transfection ability of +36 GFP at 200 nM with that of a panel of synthetic cationic peptides at 200 nM or 2 μM. This panel consisted of poly-(L)-Lys (a mixture containing an average of ~30 Lys residues per polypeptide), poly-(D)-Lys, Arg$_9$, and a synthetic +36 peptide ((KKR)$_{11}$RRK) that contains the same theoretical net charge and Lys:Arg ratio as +36 GFP. MTT assays on HeLa cells treated with these synthetic polycations indicated low cytoxicity at the concentrations used, consistent with that of superpositively charged GFPs (FIG. 25B). None of the four synthetic peptides tested delivered a detectable amount of Cy3-siRNA into HeLa cells as assayed by flow cytometry, even when used at concentrations 10-fold higher than those needed for +36 GFP to effect efficient siRNA delivery or for +15 GFP to effect detectable siRNA delivery (FIG. 20).

Coupled with our observation that +15 GFP exhibits low cell penetration and siRNA binding activity in comparison to +25 and +36 GFP (FIGS. 18A and 18B), these results indicate that while GFP must be sufficiently positively charged to acquire the ability to enter cells and transfect siRNA efficiently, positive charge magnitude and charge density are not sufficient to confer transfection activity. Instead, our findings suggest that protein-like features of +36 GFP such as size, globular shape, or stability may be required to achieve the full set of cell penetration and siRNA transfection activities that we observed.

+36 GFP-Mediated Transfection of Plasmid DNA

Figure 26:
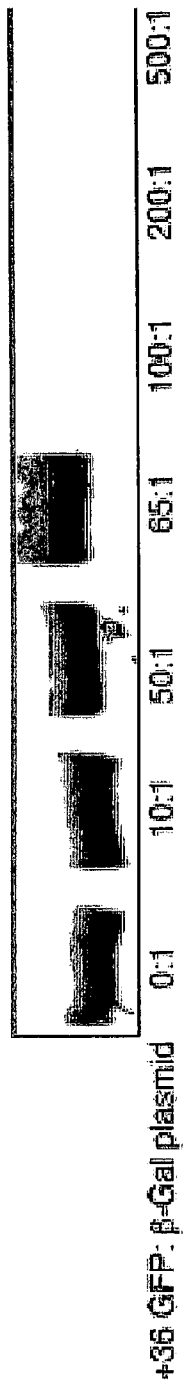
FIG. 26. Gel-shift assay showing unbound linearized pSV-β-galactosidase plasmid DNA (Promega) to determine +36 GFP:plasmid DNA binding stoichiometry. In each lane 22 fmol of pSV-β-galactosidase linearized by EcoRI digestion was combined with various molar ratios of +36 GFP and incubated at 25° C. for 10 minutes. Samples were analyzed by electrophoresis at 140 V for 50 minutes on a 1% agarose gel containing ethidium bromide.

Similar to the case with siRNA, we observed by gel-shift assay that +36 GFP forms a complex with plasmid DNA (FIG. 26). To test if +36 GFP can deliver plasmid DNA to cells in a manner that supports plasmid-based gene expression, we treated HeLa, IMCD, 3T3-L, PC12, and Jurkat cells with a β-galactosidase expression plasmid premixed with Lipofectamine 2000, +36 GFP, or a C-terminal fusion of +36 GFP and the hemagglutinin 2 (HA2) peptide, which has been reported to enhance endosome degradation (Lundberg et al., 2007, *Faseb J.,* 21:2664-71; incorporated herein by reference). After 24 hours, cells were analyzed for β-galactosidase activity using a fluorogenic substrate-based assay.

Figure 19:
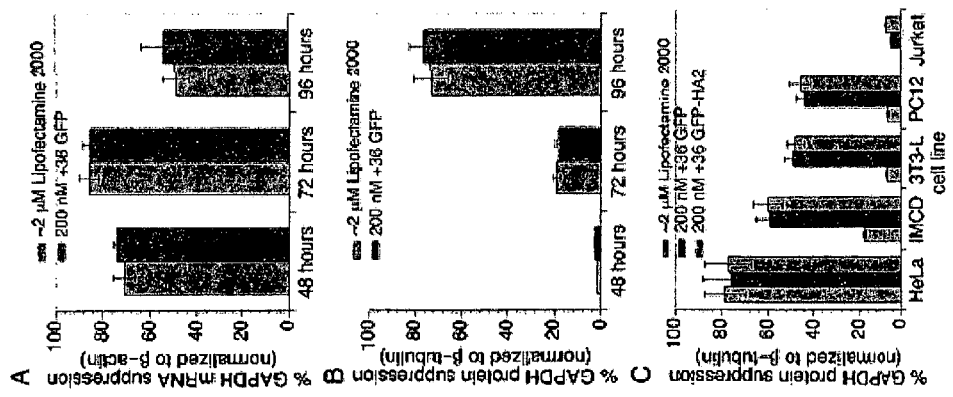
FIG. 19. Suppression of GAPDH mRNA and protein levels resulting from siRNA delivery. (A) GAPDH mRNA level suppression in HeLa cells 48, 72, or 96 hours after treatment with 50 nM siRNA and ~2 μM Lipofectamine 2000, or with 50 nM siRNA and 200 nM+36 GFP, as measured by RT-QPCR. Suppression levels shown are normalized to β-actin mRNA levels; 0% suppression is defined as the mRNA level in cells treated with ~2 μM Lipofectamine 2000 and 50 nM scrambled negative control siRNA. (B) GAPDH protein level suppression in HeLa cells 48, 72, and 96 hours after treatment with siRNA and ~2 μM Lipofectamine 2000, or with siRNA and 200 nM+36 GFP. (C) GAPDH protein level suppression in HeLa, IMCD, 3T3-L, PC12, and Jurkat cells 96 hours after treatment with 50 nM siRNA and ~2 μM Lipofectamine 2000, 200 nM+36 GFP, or 200 nM+36 GFP-HA2. For (B) and (C), suppression levels shown are measured by Western blot and are normalized to β-tubulin protein levels; 0% suppression is defined as the protein level in cells treated with ~2 μM Lipofectamine 2000 and a scrambled negative control siRNA. Values and error bars represent the mean and the standard deviation of three independent experiments in (A) and (B) and five independent experiments in (C).
Figure 21:
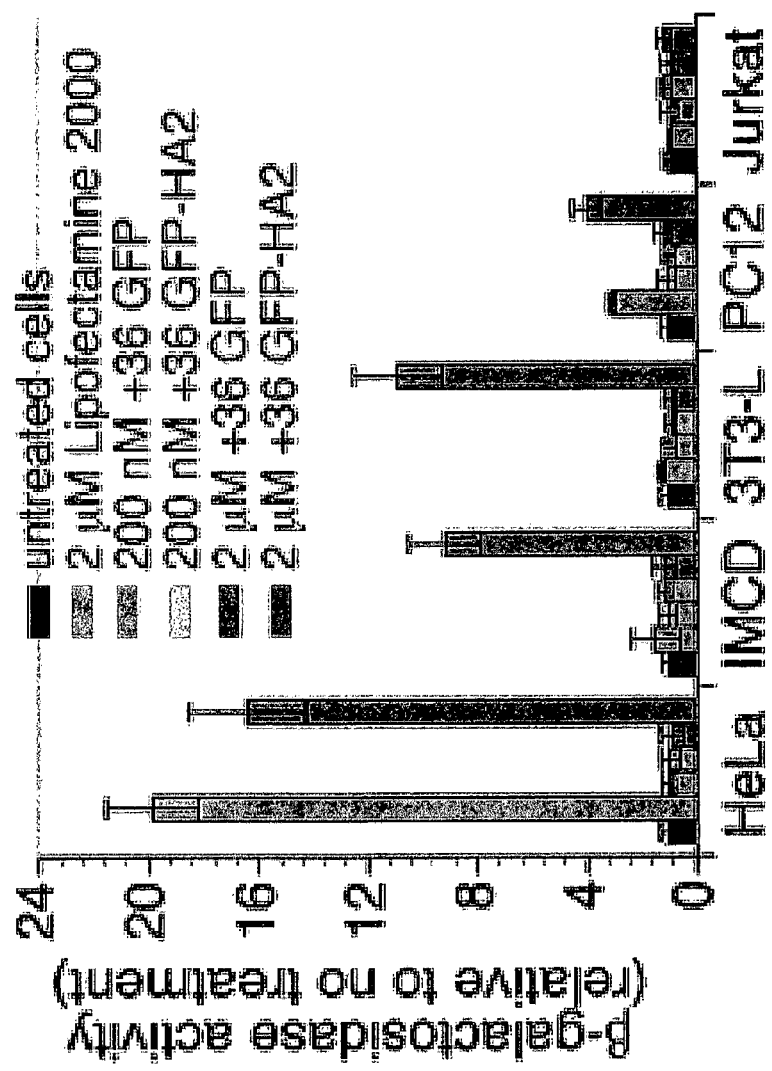
FIG. 21. Plasmid DNA transfection into HeLa, IMCD, 3T3-L, PC 12, and Jurkat cells by Lipofectamine 2000, +36 GFP, or +36 GFP-HA2. Cells were treated with 800 ng pSV-β-galactosidase plasmid and 200 nM or 2 μM of +36 GFP or +36 GFP-HA2 for 4 hours. After 24 hours, β-galactosidase activity was measured using the β-Fluor kit (Novagen). Values and error bars represent the mean and standard deviation of three independent experiments.

Consistent with our previous results (FIGS. 18 and 19), Lipofectamine 2000 treatment resulted in significant β-galactosidase activity in HeLa cells, but only modest β-galactosidase activity in PC12 cells, and no detectable activity in any of the other three cell lines tested (FIG. 21). In contrast, plasmid transfection mediated by 2 μM+36 GFP-HA2 resulted in significant β-galactosidase activity in HeLa, IMCD, and 3T3-L cells, and modest activity in PC12 cells (FIG. 21). Interestingly, treatment with plasmid DNA and 2 μM+36 GFP did not result in detectable β-galactosidase activity (FIG. 21), suggesting that the hemagglutinin-derived peptide enhances DNA transfection or plasmid-based expression efficiency despite its lack of effect on siRNA-mediated gene silencing (FIG. 19C).

These results collectively indicate that +36 GFP-HA2 is able to deliver plasmid DNA into mammalian cells, including several cell lines resistant to cationic lipid-mediated transfection, in a manner that enables plasmid-based gene expression. Higher concentrations of +36 GFP-HA2 are required to mediate plasmid DNA transfection than the amount of +36 GFP or +36 GFP-HA2 needed to induce efficient siRNA transfection.

Conclusion

The present inventors have characterized the cell penetration, siRNA delivery, siRNA-mediated gene silencing, and plasmid DNA transfection properties of three superpositively charged GFP variants with net charges of +15, +25, and +36. The present inventors discovered that +36 GFP is highly cell permeable and capable of efficiently delivering siRNA into a variety of mammalian cell lines, including those resistant to cationic lipid-based transfection, with low cytotoxicity.

Mechanistic studies revealed that +36 GFP enters cells through a clathrin- and caveolin-independent endocytosis pathway that requires sulfated cell-surface proteoglycans and actin polymerization. This delivery pathway differs from previously described strategies for nucleic acid delivery to eukaryotic cells that rely on cell-specific targeting to localize their nucleic acid cargo (Song et al., 2005, Nat. Biotechnol., 23:709-17; Kumar et al., 2007, Nature, 448:39-43; and Cardoso et al., 2007, J. Gene Med., 9:170-83; all of which are incorporated herein by reference). For use in cell culture and even in certain in vivo applications, a general, noncell type-specific approach to nucleic acid delivery may be desirable.

In four of the five cell lines tested, +36 GFP-mediated siRNA delivery induces significant suppression of gene expression. Moreover, a +36 GFP-hemagglutinin peptide fusion can mediate plasmid DNA transfection in a manner that enables plasmid-based gene expression in the same four cell lines. The presently demonstrated ability to transfect RNA 21 base pairs in length as well as plasmid DNA over 5,000 bp in length suggests that +36 GFP and its derivatives may serve as general nucleic acid delivery vectors.

Many traditional delivery methods rely on the synthesis of covalently linked transfection agent-nucleic acid conjugates such as, carbon nanotube-siRNA (Liu et al., 2007, Agnew Chem. Int. Ed. Engl., 46:2023-27; incorporated herein by reference), nanoparticle-siRNA (Rosi et al., 2006, Science, 312:1027-30; incorporated herein by reference), TAT peptide-siRNA (Fisher et al., 2002, J. Biol. Chem., 277:22980-84; incorporated herein by reference), cholesterol-siRNA (Soutschek et al., 2004, Nature, 432:173-78; incorporated herein by reference), and dynamic polyconjugate-siRNA (Rozema et al., 2007, Proc. Natl. Acad. Sci., USA, 104:12982-87; incorporated herein by reference). Use of +36 GFP simply requires mixing the protein and nucleic acid together. Moreover, the reagent described here is purified directly from bacterial cells and used without chemical co-transfectants such as exogenous calcium or chloroquine.

The present inventors previously reported that +36 GFP is thermodynamically almost as stable as sfGFP but unlike the latter is able to refold after boiling and cooling (Lawrence et al., 2007, J. Am. Chem. Soc., 129:10110-12; incorporated herein by reference). The present inventors have now demonstrated that +36 GFP exhibits resistance to proteolysis, stability in murine serum, and significant protection of complexed siRNA in murine serum. Thus, the present invention encompasses the recognition that these systems may be useful for in vivo nucleic acid delivery (e.g., to human, mammalian, non-human, or non-mammalian cells).

Thus, the present invention describes for the first time use of protein resurfacing methods for the potent delivery of nucleic acids into mammalian cells. This surprising and significant potency (Deshayes et al., 2007, Meth. Mol. Biol., 386:299-308; and Lundberg et al., 2007, Faseb J., 21:2664-71; both of which are incorporated herein by reference) is complemented by low cytotoxicity, stability in mammalian serum, generality across various mammalian cell types including several that resist traditional transfection methods, the ability to transfect both small RNAs and large DNA plasmids, straightforward preparation from E. coli cells, and simple use by mixing with an unmodified nucleic acid of interest. Thus the present invention encompasses the recognition that supercharged proteins represent a new class of solutions to general nucleic acid delivery problems in mammalian cells.

Materials and Methods

Cell Culture

HeLa, IMCD, PC12, and 3T3-L cells were cultured in Dulbecco's modification of Eagle's medium (DMEM, purchased from Sigma) with 10% fetal bovine serum (FBS, purchased from Sigma), 2 mM glutamine, 5 I.U. penicillin, and 5 µg/mL streptamycin. Jurkat cells were cultured in RPMI 1640 medium (Sigma) with 10% FBS, 2 mM glutamine, 5 I.U. penicillin, and 5 streptamycin. All cells were cultured at 37° C. with 5% $CO_2$. PC12 cells were purchased from ATCC.

Expression and Purification of Supercharged GFP Proteins

Figure 27:
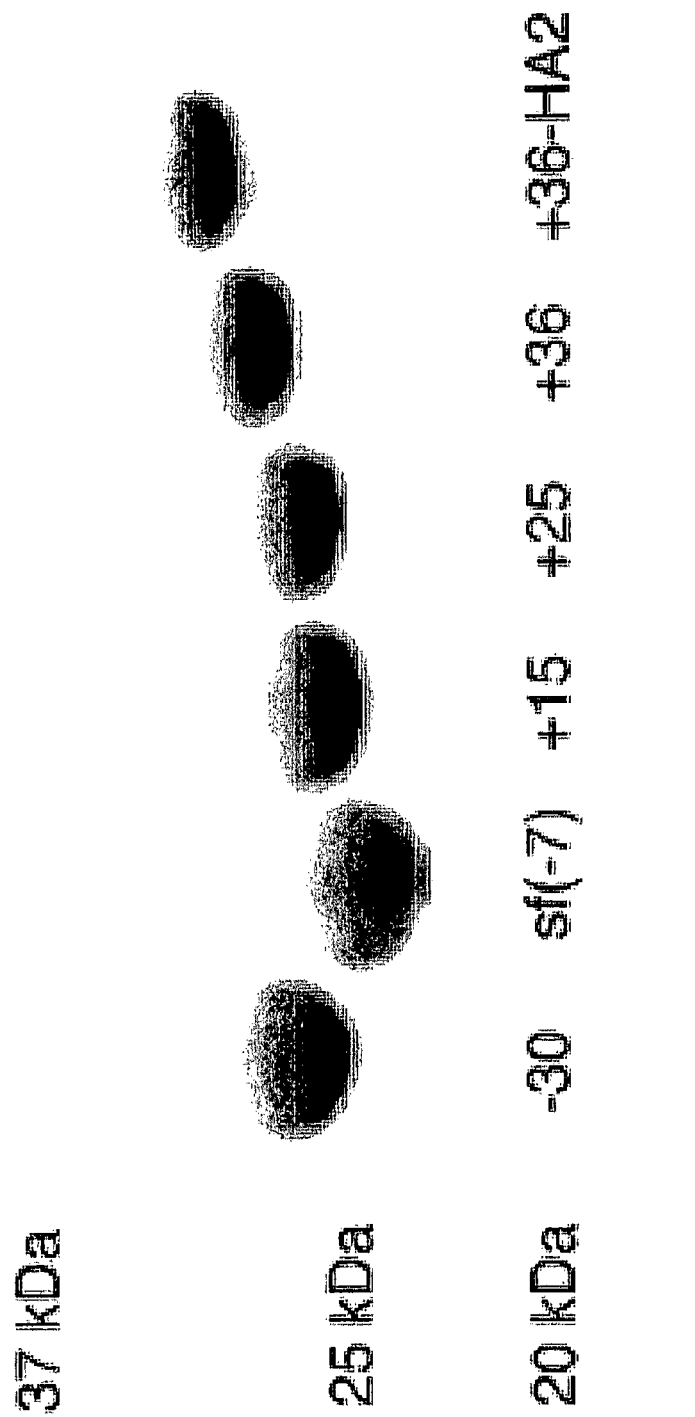
FIG. 27. SDS-PAGE analysis of purified GFP variants used in this work. The proteins were visualized by staining with Coomassie Blue. The migration points of molecular weight markers are listed on the left. Note that supercharged GFP migrates during SDS-PAGE in a manner that is partially dependent on theoretical net charge magnitude, rather than solely on actual molecular weight.
Figure 28:
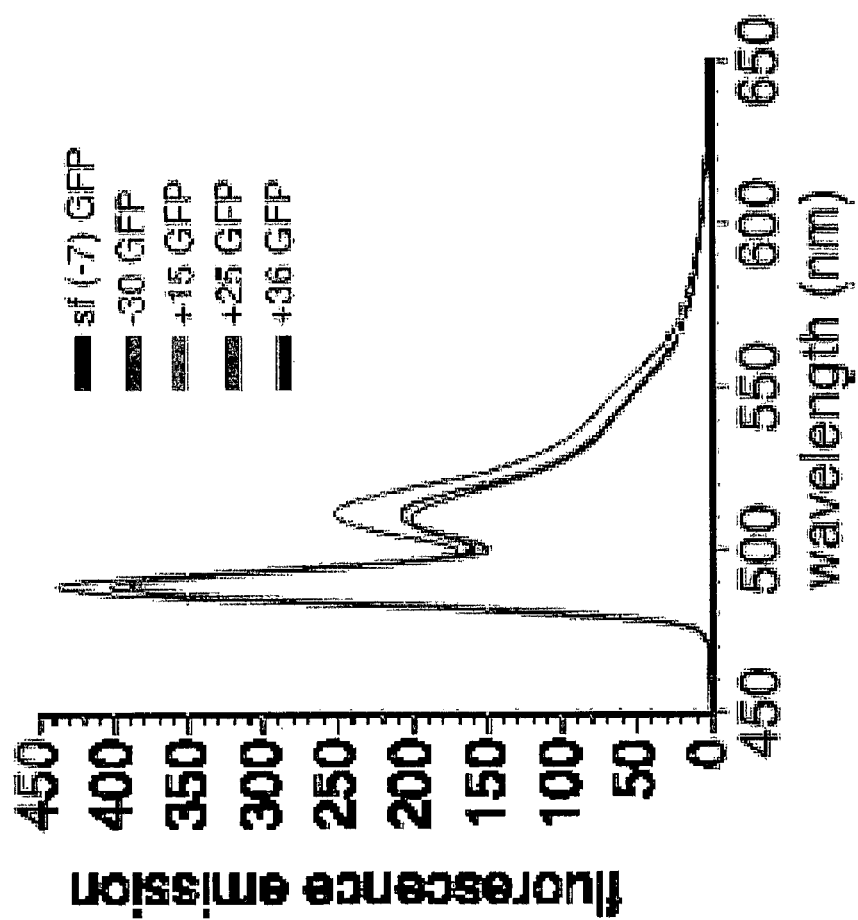
FIG. 28. Fluorescence spectra of all GFP analogs used in this study (10 nM each protein, excitation at 488 nm).

Supercharged GFP variants (protein sequences are listed below) were purified using a variation on our previously reported method. Overexpression plasmids were constructed on a pETDuet-1 backbone. Genes encoding mCherry and Cre were subcloned with a C-terminal His6 tag installed using a PCR primer. Genes encoding Tat, Arg10, penetratin, or +36 GFP and a (GGS)9 linker were inserted N-terminal of mCherry and Cre by USER cloning. The genes encoding the (GGS)9 linker, Tat, Arg10 and penetratin were designed by Gene Designer (DNA 2.0) and ordered as separate complementary DNA strands, phosphorylated using T4 PNK, and hybridized prior to cloning. Sequences encoding N-terminal His6-tagged ubiquitin, and the corresponding G76V mutant, were assembled from a set of overlapping oligonucleotides) and ligated into NcoI and NheI restriction enzyme cleavage sites upstream of pET-+36 GFP2 to create a fusion directly to the N-terminus of +36 GFP. Plasmids created in this work will be accessible through Addgene. Briefly, GFP was overexpressed in BL21(DE3) E. coli. Cells were lysed by sonication in 2 M NaCl in PBS which was found to increase overall yield of isolated GFP, and purified as previously described (Lawrence M S, Phillips K J, Liu D R (2007) Supercharging proteins can impart unusual resilience. J Am Chem Soc 129: 10110-10112; incorporated herein by reference). Purified GFPs were quantitated by absorbance at 488 nm assuming an extinction coefficient of $8.33 \times 10^4$ $M^{-1}cm^{-1}$ (Pedelacq J D, Cabantous S, Tran T, Terwilliger T C, Waldo G S (2006) Engineering and characterization of a superfolder green fluorescent protein. Nat Biotechnol 24: 79-88; incorporated herein by reference). Protein purity was evaluated by SDS PAGE and Coomassie Blue staining (FIG. 27). Fluorescence emission spectra of the GFP variants used in this work are similar (FIG. 28).

Protein Sequences of Supercharged GFP Variants

-30 GFP:

(SEQ ID NO: 97)

MGHHHHHHGGASKGEELFDGVVPILVELDGDVNGHEFSVR

GEGEGDATEGELTLKFICTTGELPVPWPTLVTTLTYGVQCFSDYPDHMDQ

HDFFKSAMPEGYVQERTISFKDDGTYKTRAEVKFEGDTLVNRIELKGIDF

-continued

KEDGNILGHKLEYNFNSHDVYITADKQENGIKAEFEIRHNVEDGSVQLAD

HYQQNTPIGDGPVLLPDDHYLSTESALSKDPNEDRDHMVLLEFVTAAGID

HGMDELYK

+15 GFP:

(SEQ ID NO: 98)

MGHHHHHHGGASKGERLFTGVVPILVELDGDVNGHKFSVR

GEGEGDATRGKLTLKFICTTGKLPVPWPTLVTTLTYGVQCFSRYPKHMKR

HDFFKSAMPEGYVQERTISFKKDGTYKTRAEVKFEGRTLVNRIELKGRDF

KEKGNILGHKLEYNFNSHNVYITADKRKNGIKANFKIRHNVKDGSVQLAD

HYQQNTPIGRGPVLLPRNHYLSTRSALSKDPKEKRDHMVLLEFVTAAGIT

HGMDELYK

+25 GFP:

(SEQ ID NO: 99)

MGHHHHHHGGASKGERLFTGVVPILVELDGDVNGHKFSVR

GKGKGDATRGKLTLKFICTTGKLPVPWPTLVTTLTYGVQCFSRYPKHMKR

HDFFKSAMPKGYVQERTISFKKDGTYKTRAEVKFEGRTLVNRIKLKGRDF

KEKGNILGHKLRYNFNSHNVYITADKRKNGIKANFKIRHNVKDGSVQLAD

HYQQNTPIGRGPVLLPRNHYLSTRSALSKDPKEKRDHMVLLEFVTAAGIT

HGMDELYK

+36 GFP:

(SEQ ID NO: 100)

MGHHHHHHGGASKGERLFRGKVPILVELKGDVNGHKFSVR

GKGKGDATRGKLTLKFICTTGKLPVPWPTLVTTLTYGVQCFSRYPKHMKR

HDFFKSAMPKGYVQERTISFKKDGKYKTRAEVKFEGRTLVNRIKLKGRDF

KEKGNILGHKLRYNFNSHKVYITADKRKNGIKAKFKIRHNVKDGSVQLAD

HYQQNTPIGRGPVLLPRNHYLSTRSKLSKDPKEKRDHMVLLEFVTAAGIK

HGRDERYK

+36 GFP-HA2:

(SEQ ID NO: 101)

MGHHHHHHGGASKGERLFRGKVPILVELKGDVNGHKFSVR

GKGKGDATRGKLTLKFICTTGKLPVPWPTLVTTLTYGVQCFSRYPKHMKR

HDFFKSAMPKGYVQERTISFKKDGKYKTRAEVKFEGRTLVNRIKLKGRDF

KEKGNILGHKLRYNFNSHKVYITADKRKNGIKAKFKIRHNVKDGSVQLAD

HYQQNTPIGRGPVLLPRNHYLSTRSKLSKDPKEKRDHMVLLEFVTAAGIK

HGRDERYKGSAGSAAGSGEFGLFGAIAGFIENGWEGMIDG

Gel-Shift Assay

Gel-shift assays were based on the method of Kumar et al. (Kumar P, Wu H, McBride J L, Jung K E, Kim M H, et al. (2007) Transvascular delivery of small interfering RNA to the central nervous system. Nature 448: 39-43; incorporated herein by reference). siRNA (10 pmol) or plasmid DNA (22 fmol) was mixed with the specified quantity of a GFP variant in phosphate buffered saline (PBS) for 10 minutes at 25° C. The resulting solution was analyzed by non-denaturing electrophoresis using a 15% acrylamide gel for siRNA or a 1% agarose gel for plasmid DNA, stained with ethidium bromide, and visualized with UV light.

Cationic Lipid-Based and GFP-Based Transfection

Transfections using Lipofectamine 2000 (Invitrogen) and Fugene 6 (Roche) were performed following the manufacturer's protocol. Although the molecular weight of these reagents are not provided by the manufacturer, the working concentration of Lipofectamine 2000 during transfection is 2 µg/mL and based on an assumption that the molecular weight of this cationic lipid is ≤1,000 Da it was estimated that this concentration corresponds to ≥~2 µM.

Cells were plated in a 12-well tissue culture plate at a density of 80,000 cells per well. After 12 hours at 37° C., the cells were washed with 4° C. (PBS) and for HeLa, IMCD, 3T3-L, and PC12 cells the media were replaced with 500 µL of serum-free DMEM at 4° C.

Jurkat cells were transferred from the culture plate wells into individual 1.5 mL tubes, pelleted by centrifugation, and resuspended in 500 µL of serum-free RPMI 1640 at 4° C.

A solution of GFP and either siRNA or plasmid DNA was mixed in 500 µL of either 4° C. DMEM (for HeLa, IMCD, 3T3-L, and PC12 cells) or 4° C. RPMI 1640 (for Jurkat cells). After 5 min at 25° C., this solution was added to the cells and slightly agitated to mix. After 4 hours at 37° C., the solution was removed from the cells and replaced with 37° C. media containing 10% FBS. GAPDH-targeting Cy3-labeled siRNA and unlabeled siRNA were purchased from Ambion. Plasmid transfections were performed using pSV-β-galactosidase (Promega). β-galactosidase activity was measured using the β-fluor assay kit (Novagen) following the manufacturer's protocol.

Fixed-Cell Imaging

Four hours after treatment with GFP and Cy3-siRNA, cells were trypsinized and replated in medium containing 10% FBS on glass slides coated with Matrigel (BD Biosciences). After 24 hours at 37° C., cells were fixed with 4% formaldehyde in PBS, stained with DAPI where indicated, and imaged with a Leica DMRB inverted microscope equipped with filters for GFP and Cy3 emission. Images were prepared using OpenLab software (Improvision). Exposure times for GFP and Cy3 were fixed at 350 msec and 500 msec, respectively.

Live-Cell Imaging

For experiments using small-molecule inhibitors, cells were plated on a glass-bottomed tissue culture plate (MatTek, 50 mm uncoated plastic dishes with #1.5 glass thickness and a 14 mm glass diameter) and incubated with inhibitor for 1 hour at 37° C., followed by treatment with 50 nM+36 GFP and inhibitor for an additional 1 hour at 37° C. The resulting cells were washed three times with PBS containing the inhibitor and 20 U/mL heparin to remove surface-associated GFP, with the exception that cells treated with 50 nM+36 GFP at 4° C. were washed only one time with PBS containing 20 U/mL heparin to remove GFP bound to the glass slide but to still allow a perimeter of some cell surface-bound GFP to be visible.

Cells were imaged using an inverted microscope (Olympus IX70) in an epi-fluorescent configuration with an oil-immersion objective (numerical aperture 1.45, 60×, Olympus). GFP was excited with the 488 nm line an argon ion laser (Melles-Griot), and Alexa Fluor 647 was excited with a 633 nm helium-neon laser (Melles-Griot). Long- and short-wavelength emissions were spectrally separated by a 650 nm long-pass dichroic mirror (Chroma) and imaged onto a CCD camera (CoolSnap HQ). A 665 nm long-pass filter was used for Alexa Fluor 647 detection, and a 535/20 nm bandpass filter for GFP. Imaging was conducted at 37° C.

RT-QPCR

Cells were washed with PBS 48, 72, or 96 hours after transfection and total RNA was extracted using the Ribopure kit (Ambion) following the manufacturer's protocol. Samples were treated with 1 uL DNase I (Ambion) and incubated for 30 minutes at 37° C. DNase I was inactivated with DNase I Inactivation Reagent (Ambion) following the manufacturer's protocol. Complementary DNA was generated from 800 ng of RNA using the Retroscript kit (Ambion) following the manufacturer's protocol. QPCR reactions contained 1×IQ SYBR green Master Mix (BioRad), 3 nM ROX reference dye (Stratagene), 2.5 μL of reverse transcription reaction mixture, and 200 nM of both forward and reverse primers:

```
Forward GAPDH      5'-CAACTCACTCAAGATTGTCAGCAA-3'
                                    (SEQ ID NO: 102)

Reverse GAPDH      5'-GGGATGGACTGTGGTCATGA-3'
                                    (SEQ ID NO: 103)

Forward β-actin    5'-ATAGCACAGCCTGGATAGCAACGTAC-3'
                                    (SEQ ID NO: 104)

Reverse β-actin    5'-CACCTTCTACAATGAGCTGCGTGTG-3'
                                    (SEQ ID NO: 105)
```

QPCR reactions were subjected to the following program on a Stratagene MX3000p QPCR system: 15 minutes at 95° C., then 40 cycles of (30 seconds at 95° C., 1 minute at 55° C., and 30 seconds at 72° C.). Amplification was quantified during the 72° C. step. Dissociation curves were obtained by subjecting samples to 1 minute at 95° C., 30 seconds at 55° C., and 30 seconds at 95° C. and monitoring fluorescence during heating from 55° C. to 95° C. Threshold cycle values were determined using MxPro v3.0 software (Stratagene) and analyzed by the ΔΔCt method.

Western Blotting

Cells were washed once with 4° C. PBS 96 hours after transfection. Cells were lysed with 200 μL RIPA buffer (Boston Bioproducts) containing a protease inhibitor cocktail (Roche) for 5 minutes. The resulting cell lysate was analyzed by SDS-PAGE on a 4-12% acrylamide gel (Invitrogen).

Figure 29:
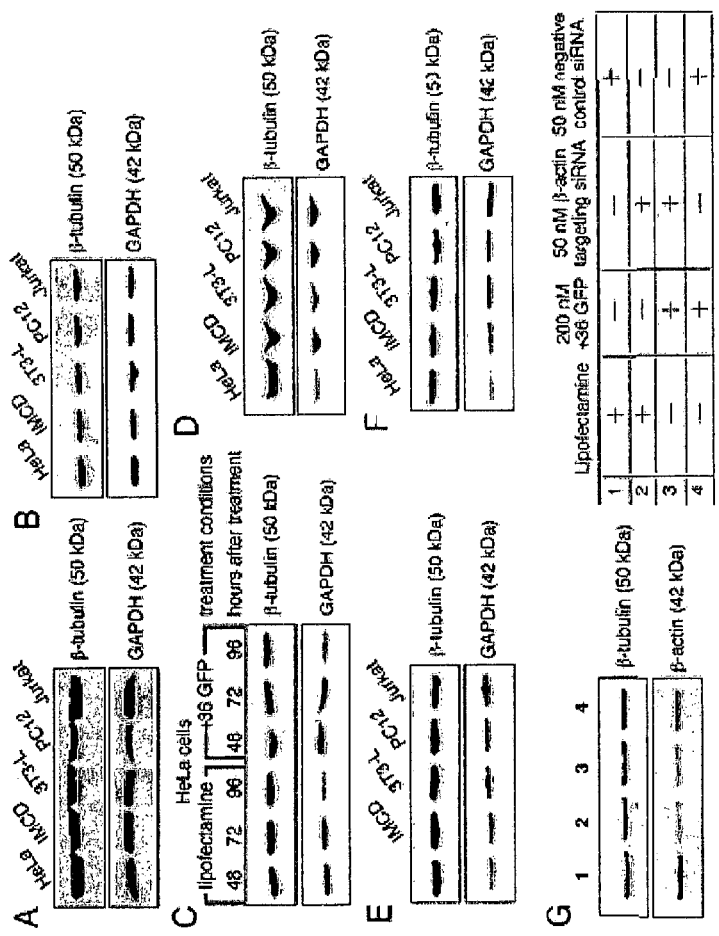
FIG. 29. (A) Representative Western blot data 4 days after treatment with ~2 µM Lipofectamine 2000 and 50 nM negative control siRNA. (B) Representative Western blot data 4 days after treatment with 200 nM+36 GFP and 50 nM negative control siRNA. (C) Representative Western blot data showing GAPDH and β-tubulin levels 48, 72, and 96 hours after treatment with 50 nM GAPDH siRNA and either ~2 µM Lipofectamine 2000 or 200 nM+36 GFP. (D) Representative Western blot data 4 days after treatment with ~2 µM Lipofectamine 2000 and 50 nM GAPDH siRNA. (E) Representative Western blot data 4 days after treatment with 200 nM+36 GFP and 50 nM GAPDH siRNA. (F) Representative Western blot data 4 days after treatment with 200 nM+36 GFP-HA2 and 50 nM GAPDH siRNA. (G) Representative western blot data from HeLa cells four days after treatment with ~2 µM Lipofectamine 2000 and 50 nM negative control siRNA, Lipofectamine 2000 and 50 nM β-actin targeting siRNA, 200 nM+36 GFP and 50 nM β-actin targeting siRNA, or 200 nM+36 GFP and 50 nM negative control siRNA.

The proteins on the gel were transferred by electroblotting onto a PVDF membrane (Millipore) pre-soaked in methanol. Membranes were blocked in 5% milk for 1 hour, and incubated in primary antibody in 5% milk overnight at 4° C. All antibodies were purchased from Abcam. The membrane was washed three times with PBS and treated with secondary antibody (Alexa Fluor 680 goat anti-rabbit IgG (Invitrogen) or Alexa Fluor 800 rabbit anti-mouse IgG (Rockland)) in blocking buffer (Li-COR Biosciences) for 30 minutes. The membrane was washed three times with 50 mM Tris, pH 7.4 containing 150 mM NaCl and 0.05% Tween-20 and imaged using an Odyssey infrared imaging system (Li-COR Biosciences). Images were analyzed using Odyssey imaging software version 2.0. Representative data are shown in FIG. 29. GAPDH suppression levels shown are normalized to β-tubulin protein levels; 0% suppression is defined as the protein level in cells treated with ~2 μM Lipofectamine 2000 and 50 nM negative control siRNA.

Flow Cytometry

Cells were washed three times with 20 U/mL heparin (Sigma) in PBS to remove non-internalized GFP. Adherent cells were trypsinized, resuspended in 1 mL PBS with 1% FBS and 75 U/mL DNase (New England Biolabs). Flow cytometry was performed on a BD LSRII instrument at 25° C. Cells were analyzed in PBS using filters for GFP (FITC) and Cy3 emission. At least $10^4$ cells were analyzed for each sample.

Synthetic Cationic Peptides $(Arg)_9$ and $(KKR)_{11}(RRK)$ (SEQ ID NO: 156) were purchased from Chi Scientific and used at a purity of ≥95%. Poly-(L)-Lys and poly-(D)-Lys were purchased from Sigma. Poly-(L)-Lys is a mixture with a molecular weight window of 1,000-5,000 Da, and a median molecular weight of 3,000 Da. Poly-(D)-Lys is a mixture with a molecular weight window of 1,000-5,000 Da, and a median molecular weight of 2,500 Da. Stock solutions of all synthetic peptides were prepared at a concentration of 20 μM in PBS.

+36 GFP-siRNA Particle Size Characterization

Dynamic light scattering was performed using a Protein Solution DynaPro instrument at 25° C. using 20 μM+36 GFP and 5 μM siRNA in PBS. A purified 20-bp RNA duplex (5' GCAUGCCAUUACCUGGCCAU 3', from IDT; SEQ ID NO: 106) was used in these experiments. Data were modeled to fit an isotrophic sphere. 5 μL of solution analyzed by DLS (20 μM+36 GFP and 5 μM siRNA in PBS) was imaged using a Leica DMRB inverted microscope.

Deubiquitination Assay Western Blot

Cells were plated in a 48-well plate at a density of $1\times10^5$ cells per well. After 18 h, cells were washed with cold PBS and incubated with 100 nM ubiquitin-+36 GFP or 100 nM mutant G76V ubiquitin-+36GFP in serum-free media for 1 h. Cells were washed three times with 20 U/mL heparin in PBS, and lysed directly in LDS sample buffer and sonicated.

Crude HeLa cytosolic extract was prepared by harvesting $5\times10^6$ HeLa cells using a plate scraper into ice-cold PBS. Cells were pelleted at 200 G for 5 min and resuspended in 1 mL of 50 mM Tris-HCl pH 7.5, 150 nM NaCl, 2 mM EDTA, 2 mM DTT, 1.7 μg/mL aprotinin, 10 μg/mL leupeptin, 10 mM PMSF, and 0.5% NP-40. Homogenized cells were incubated on ice for 10 min before centrifugation at 13,000 G for 15 min to remove nuclei and cell debris. Either wt or mutant ubiquitin-+36 GFP (5 pmol) was added to the lysate. The mixture was incubated with or without either 10 mM N-ethylmaleimide or 20 μg/mL ubiquitin-aldehyde for 1 hour at 37° C.

Samples were analyzed on a 12% SDS-PAGE gel and transferred by electroblot onto a PVDF membrane (Millipore) pre-soaked in methanol. Membranes were blocked in 5% milk for 1 h and incubated in primary antibody in 3% BSA for 30 min at room temperature. Anti-GFP antibody (1/10,000 dilution, ab290) was purchased from Abcam. The membrane was washed three times with PBS and treated with the secondary antibody IRDye 800CW Goat Anti-Mouse IgG (1/10,000 dilution, Li-COR Biosciences) in blocking buffer (Li-COR Biosciences) for 30 min. The membrane was washed three times with 50 mM Tris, pH 7.4, containing 150 mM NaCl and 0.05% Tween-20 and visualized using an Odyssey infrared imaging system (Li-COR Biosciences). Images were analyzed using Odyssey imaging software version 2.0.

Cre Reporter Cell Lines

Hela cells were plated at $3\times10^4$ cells/well in 48-well plates. After 16 hours, cells were transfected with pCALNL-DsRed26 using Effectene transfection reagent (Qiagen). After incubation with 100-1000 nM of each Cre fusion protein for 4 hours in serum-free DMEM, cells were washed three times with 20 U/mL heparin in PBS and incubated in full media for 48 hours. Delivery of Cre was assayed by following DsRed2 expression using flow cytometry and fluorescence microscopy. Cre reporter 3T3 cells were plated at $1\times10^5$ cells/well in 48-well plates. After 16 hours, cells were incubated with various concentrations of protein for 4 hours in serum-free media. Cells were washed with three times with 20 U/mL heparin in PBS and incubated in full media for 48 hours. Recombined cells were quantified by X-gal staining and manual counting. BSR cells were obtained from Matthias Schnell (Thomas Jefferson University). A pQCXIX MMLV retrovirus (Clontech) containing the tdTomato cre reporter construct was generated by subcloning the tdTomato gene (Clontech) into a pCALNL backbone6 and packaged using Plat-E cells7. BSR cells were infected with retrovirus and integrants were selected for one week in the presence of 1 mg/ml G418 (Sigma). BSR.LNL.tdTomato cells were plated at 1×105 cells/well in 48 well plates. After 16 hours, cells were incubated with various concentrations of protein for 4 hours in serum-free media. Cells were washed with three times with 20 U/mL heparin in PBS and incubated in full media for 48 hours. For chloroquine treatment of BSR cells, cells were incubated with Cre fusion proteins for 4 hours in serum-free media containing 100 µM chloroquine, washed three times with 20 U/mL heparin in PBS, and incubated 12 hours in full media containing 100 µM chloroquine. Following this incubation, cells were washed once with PBS and incubated a further 36 hours in full media without chloroquine. Delivery of Cre was assayed by following tdTomato expression using flow cytometry and fluorescence microscopy.

For fluorescent Cre reporters, recombinants were identified by flow cytometry as those cells of the live-cell population that exhibited significantly higher fluorescence than that of non-treated reporter cells. Typically, the recombined population exhibited fluorescence at least 10-fold higher than the non-recombined cells and were readily detected as a distinct subpopulation. Fluorescence gates were drawn accordingly to quantitate recombined and non-recombined cells.

In Vivo Retinal Injections

Adult CD1 mice were subretinally injected with 0.5 µL of 100 µM+36 GFP. After 6 hours, the retinas were harvested and analyzed by fluorescence microscopy. p0 pups were subretinally injected with 0.5 µL of 40 µM wtCre, Tat-Cre, or +36 GFP-Cre. After 72 hours, retinae were harvested and fixed with 0.5% glutaraldehyde. Fixed retinae were stained with X-gal overnight and embedded in 50% OCT, 50% of 30% sucrose and stored at −80° C. Retinae were cut into 30 µm sections and imaged for X-gal staining on a Zeiss Axiophot brightfield microscope with a Nikon CXM-1200F camera. Delivery of Cre was assayed by manually counting LacZ+ cells.

Stability Assays

To assess siRNA stability in murine serum, siRNA (10 pmol) was mixed with sfGFP (40 pmol), mixed with +36 GFP (40 pmol), or incubated alone in PBS for 10 minutes at 25° C. The resulting solution was added to four volumes of mouse serum (20 µL total) and incubated at 37° C. for the indicated times. 15 µL of the resulting solution was diluted in water to a total volume of 100 µL. 100 µL of TRI reagent (Ambion) and 30 µL of chloroform was added. After vigorous mixing and centrifugation at 1,000 G for 15 minutes, the aqueous layer was recovered. siRNA was precipitated by the addition of 15 µL of 3 M sodium acetate, pH 5.5, and two volumes of 95% ethanol. siRNA was resuspended in 10 mM Tris pH 7.5 and analyzed by gel electrophoresis on a 15% acrylamide gel. Serum stability of +36 GFP when complexed with siRNA was simultaneously measured by anti-GFP Western blot with 5 µL of the incubation.

To assess the stability of plasmid DNA complexed with +36 GFP in murine serum, plasmid DNA (0.0257 pmol) was mixed with either 2.57 pmol, 100 eq. or 12.84 pmol, 500 eq. of either sfGFP or +36 GFP in 4 µL of PBS for 10 minutes. To this solution was added 16 µL of mouse serum (20 µL total) and incubated at 37° C. for the indicated times. DNA was isolated by phenol chloroform extraction and analyzed by gel electrophoresis on a 1% agarose gel, stained with ethidium bromide, and visualized with UV light.

To assess the stability of proteins in murine serum, 100 pmol of each protein in 2 µL of PBS was mixed with 8 µL of murine serum (Sigma) and incubated at 37° C. The samples were mixed with SDS protein loading buffer and heated to 90° C. for 10 minutes. The resulting mixture was analyzed by SDS-PAGE on a 4-12% acrylamide gel (Invitrogen) and imaged by Western blot.

To assess stability in the presence of proteinase K, 100 pmol of +36 GFP or BSA was treated with 0.6 units of proteinase K (New England Biosciences) at 37° C. The samples were mixed with SDS protein loading buffer, heated to 90° C. for 10 minutes, and analyzed by SDS-PAGE on a 4-12% acrylamide gel (Invitrogen).

Example 4

Supercharged Proteins are Effective Protein Delivery Reagents mCherry, a fluorescent protein, was fused to each of +36 GFP (via a cleavable linker having amino acid sequence ALAL, SEQ ID NO: 107), TAT, and $Arg_9$ to generate three mCherry fusion proteins. These fusions were tested for their ability to deliver mCherry to HeLa, IMCD, and PC12 cells.

Figure 33A:
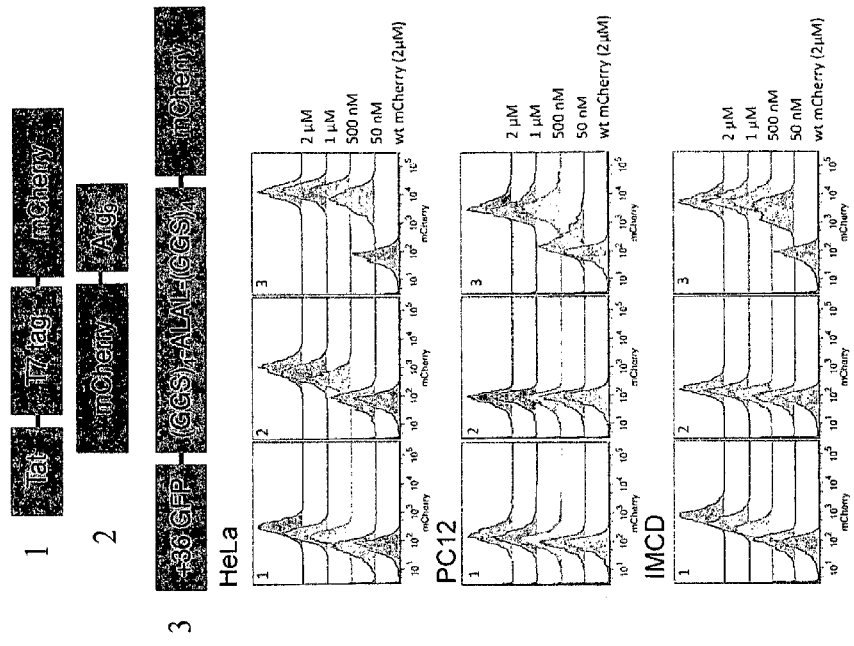
FIG. 33. A: Internalization of mCherry using (1) mCherry-TAT; (2) mCherry-Arg$_9$; and (3) mCherry-ALAL-+36 GFP in HeLa, PC12, and IMCD cell lines. Flow cytometry of HeLa, P12 and IMCD (inner medullary collecting duct) cells incubated in the presence of the specified concentrations of Tat-mCherry, Arg9-mCherry, +36 GFP-mCherry, or wild-type mCherry alone for 4 hours at 37° C. Cells were washed three times with 20 U/mL heparin in PBS to remove membrane-bound protein before analysis. (GGS)$_4$-ALAL-(GGS)$_4$ corresponds to SEQ ID NO: 154. B: Membrane-bound protein is removed by heparin washing conditions. (a) Live-cell fluorescence microscopy indicates that at 4° C. +36 GFP-mCherry is membrane-bound but not internalized. After washing with heparin (but not after washing with PBS), this +36 GFP-mCherry signal is largely removed. At 37° C., most of +36 GFP-mCherry signal remains even after heparin washing, consistent with internalization of +36 GFP-mCherry. (b) HeLa and PC12 cells subjected to the conditions described in (a) were trypsinized (which destroys surface-bound mCherry) then analyzed by flow cytometry. Cells incubated with +36 GFP-mCherry at 4° C. do not show significant mCherry fluorescence compared to cells incubated at 37° C., further suggesting that the signal at 37° C. represents internalized protein signal, and that internalization at 4° C. is inefficient.
Figure 33B:
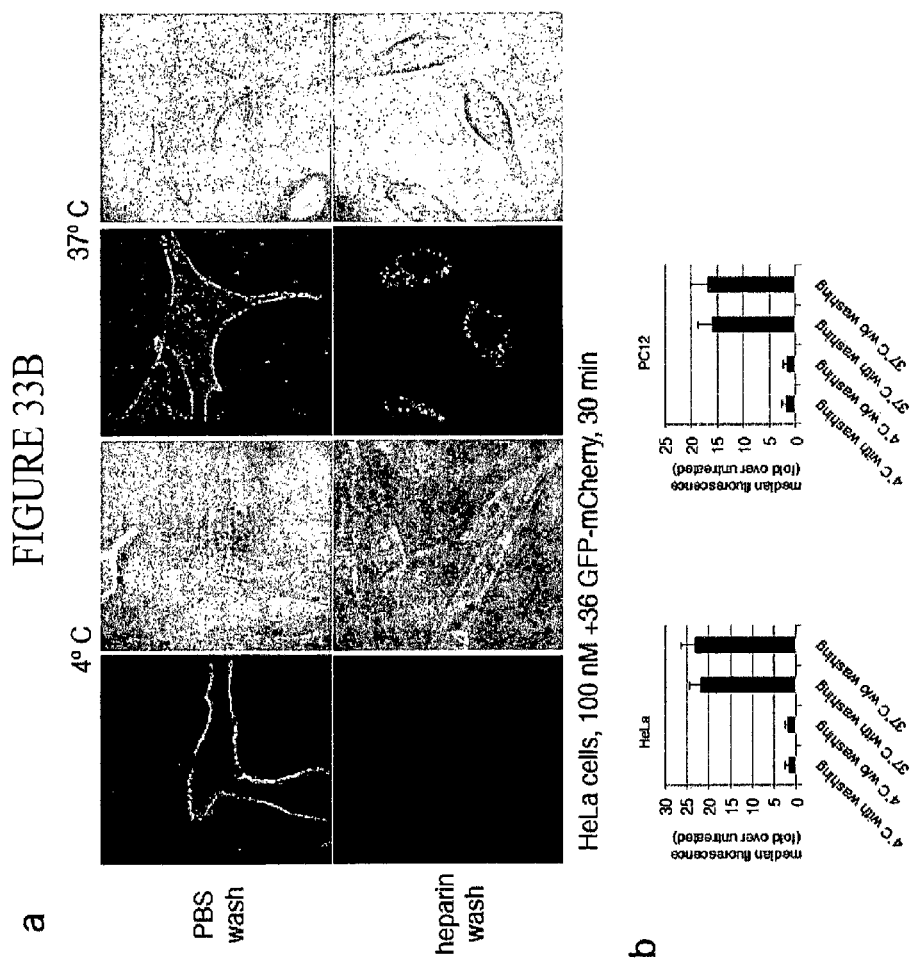
Figure 34:
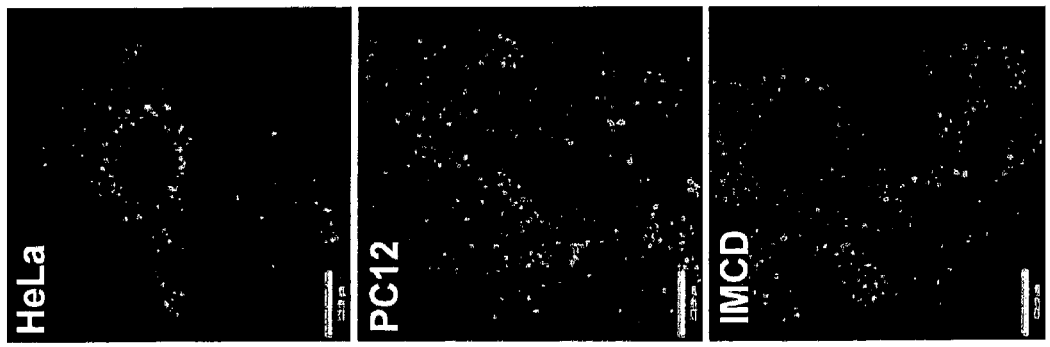
FIG. 34. Fluorescence microscopy images of HeLa, PC12, and IMCD cells four hours after treatment with 50 nM mCherry-ALAL-+36 GFP. Each image is an overlay of three channels: DAPI stain for DNA, mCherry, and +36 GFP.

In order to assess how well +36 GFP delivers proteins to cells HeLa, PC12 and 3T3-L cells were treated with either (1) mCherry-TAT, (2) mCherry-$R_9$, or (3) mCherry-+36 GFP. Cells were treated with 50 nM, 500 nM, 1 or 2 µM material for 4 hours in DMEM, followed by heparin wash and FACS.

mCherry-ALAL-+36 GFP penetrated cells much more potently than mCherry-TAT or mCherry $Arg_9$ (FIG. 33). FIG. 34 shows internalization of these three fusions via fluorescence microscopy. Data show that +36 GFP is a highly potent and general protein delivery reagent (FIG. 34).

Example 5

Mining Genomes for Natural Supercharged Proteins

The present invention encompasses the recognition that genomes (e.g., the human genome) can be mined to identify natural supercharged proteins that might be useful for delivery of agents (e.g., nucleic acids, proteins, etc.). Ten human proteins were expressed and purified (i.e., C-Jun (Protein Accession No.: P05412); TERF 1 (P54274); Defensin 3 (P81534); Eotaxin (Q9Y258); N-DEK (P35659); PIAS 1 (O75925); Ku70 (P12956); Midkine (P21741); HBEGF (Q99075); HGF (P14210); SFRS12-IP1 (Q8N9Q2); Cyclon (Q9H6F5)), and four of these (i.e., HBEGF, N-DEK, C-jun, and 2HGF) displayed the ability to bind to siRNA and deliver siRNA to cells (i.e., cultured HeLa cells).

Human proteins were assayed for binding to siRNA by gel shift assay. Gel-shift assays were based on the method of Kumar et al. (Kumar P, Wu H, McBride J L, Jung K E, Kim M H, et al. (2007) Transvascular delivery of small interfering RNA to the central nervous system. *Nature* 448: 39-43; incorporated herein by reference). Ambion negative control siRNA (~150 ng) was mixed with the specified quantity of human protein in phosphate buffered saline (PBS) for 10 minutes at 25° C. The resulting solution was analyzed for unbound siRNA by non-denaturing electrophoresis using a 15% acrylamide gel for siRNA, stained with ethidium bromide, and visualized with UV light (FIG. 35A).

Human proteins were assayed for delivery of siRNA to HeLa cells. Cells were plated in a 12-well tissue culture plate at a density of 80,000 cells per well. After 12 hours at 37° C., the cells were washed with 4° C. (PBS) and replaced with 500 µL of serum-free DMEM at 4° C. A solution of human protein and Ambion negative control Cy3-labeled siRNA was mixed in 500 µL of 4° C. DMEM. After 5 min at 25° C., this solution was added to the cells and slightly agitated to mix. Final concentration of human proteins was 1 micromolar and siRNA was 50 micromolar. After 4 hours at 37° C., the solution was removed from the cells and replaced with 37° C. media containing 10% FBS. Cells were then analyzed for siRNA delivery by fixed cell imaging and flow cytometry. Internalization of protein-siRNA complexes is shown in FIG. 35B.

Figure 35:
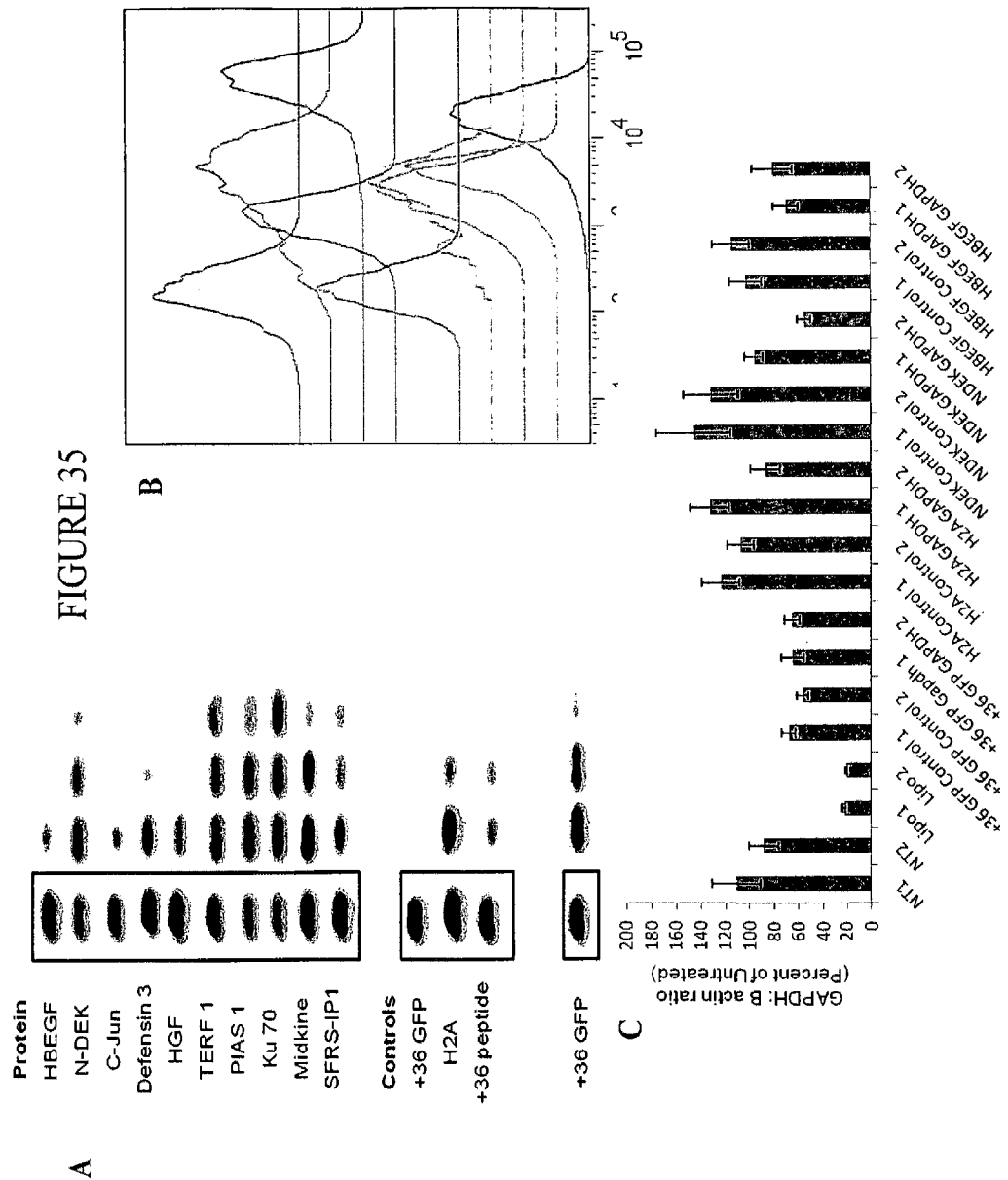
FIG. 35. Human proteins deliver siRNA to HeLa cells. (A) Human proteins were mixed at increasing mass ratios with siRNA and assayed for unbound siRNA by PAGE and ethidium bromide staining. Decreasing band intensities demonstrate siRNA binding by human proteins. (B) Human proteins were mixed with Cy3-labelled siRNA and applied to HeLa cells for four hours. Cells were then washed and assayed for Cy3 fluorescence by flow cytometry. A shift of the peak to the right demonstrates siRNA internalization. (C) HeLa cells were transfected with siRNA using human proteins, incubated for three days, and assayed for degradation of a targeted mRNA. Targeted GAPDH mRNA levels were compared relative to β-actin mRNA levels. "Control" indicates use of a non-targeting siRNA. Lipofectamine 2000 was used as positive control.
Figure 48:
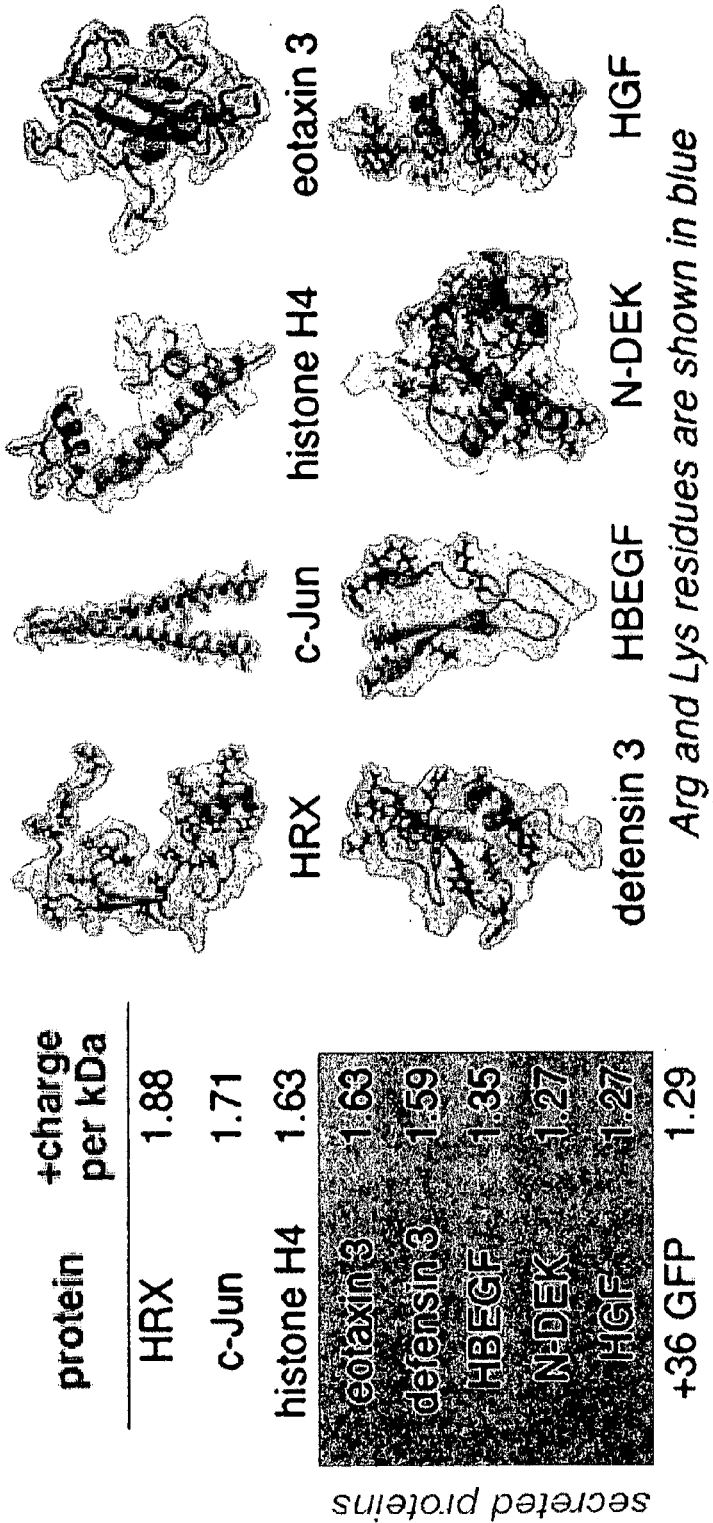
FIG. 48. Supercharged proteins encoded in the human genome.
Figure 49:
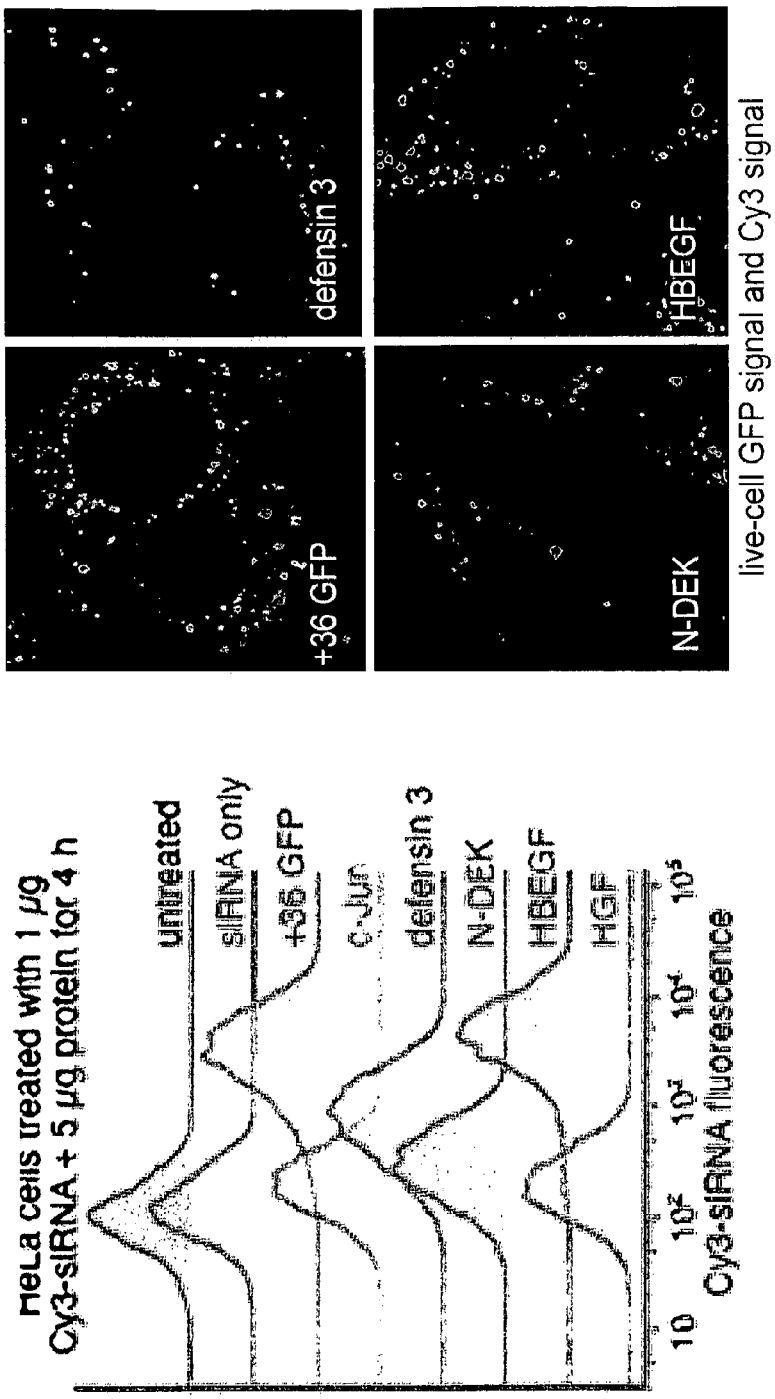
FIG. 49. Naturally occurring human supercharged proteins can deliver siRNA into cells.
Figure 50:
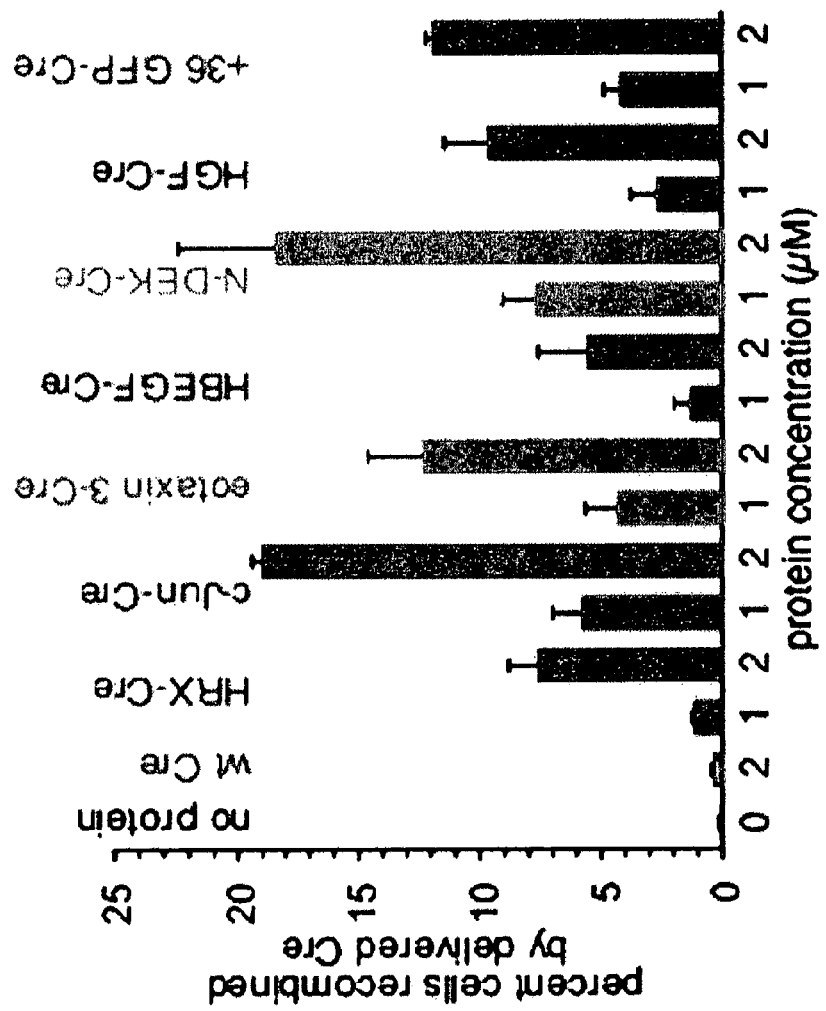
FIG. 50. Naturally occurring human proteins can deliver functional Cre recombinase.

HeLa cells were transfected with Ambion Cy3-labeled siRNA using human proteins, incubated for three days, and then assayed for degradation of a targeted mRNA (FIG. 35C). Targeted GAPDH mRNA levels were compared to β-actin mRNA levels. "Control" indicates use of a non-targeting siRNA. Lipofectamine 2000 was used as a positive control. Delivery of siRNA and Functional Protein into Cells by Supercharged Human Proteins To test whether naturally occurring supercharged human proteins, which may offer may offer less immunogenic alternatives to +36 GFP, can be employed to deliver a nucleic acid or a functional protein to cells, we investigated the delivery characteristics of seven naturally occurring supercharged proteins: HRX, c-Jun, Eotaxin, defensin3, HBEGF, N-DEK, and HGF (see FIG. 48 for net chare per kDa and distribution of Arg/Lys residues. HeLa cells were assayed for Cy3 fluorescence after treatment with 1 μg Cy3-labelled siRNA+5 μg or the respective protein for 4 h by flow cytometry and fluorescence microscopy (FIG. 49). Efficient delivery of siRNA was observed with some of the tested proteins, for example, with HBEGF, defensin-3, and N-DEK. Similarly, Cre recombinase was efficiently delivered to BSR cells by various naturally occurring supercharged proteins, for example, c-Jun, N-DEK, and Eotaxin (FIG. 50). The previously uncharacterized ability of superpositive human proteins to penetrate cells suggests potential new biological roles.

Example 6

Pyrene Butyric Acid Improves Consistency of Gene Silencing

The present inventors have discovered that pyrene butyrate, an endosomolytic agent (Futaki et al., 2006, *ACS Chem. Biol.*, 1:299; incorporated herein by reference), can increase gene silencing effects and decrease batch-to-batch variability. Without wishing to be bound by any one particular theory, such variability may be caused by variable ion endosome escape efficiency). Thus, the present inventors have developed a method for improving the efficiency, consistency, and reproducibility of gene silencing.

The protocol below utilizes +36 GFP and pyrene butyric acid (PBA), but can readily be generalized to any supercharged protein and any endosomolytic agent (e.g., chloroquine, HA2, melittin).

HeLa cells were grown to ~80% confluency in a 12-well plate. DMEM/10% FBS was removed and the cells were washed 3 times with PBS. To each well was added 1 mL of a solution containing 50 μM PBA in PBS. Cells were incubated in this solution for 5 minutes at 37° C. In a small plastic tube, 200 fmol of GAPDH-suppressing siRNA (2 μL of a 100 μM siRNA solution) and 800 fmol+36 GFP were pre-mixed and allowed to incubate for 5 minutes at 25° C. One quarter (¼) of the total volume of the siRNA/+36 GFP complex was added to each well containing 1 mL 50 μM PBA in PBS. The tissue culture tray was agitated slightly to homogenize the solution in each well, resulting in a solution containing 50 μM siRNA and 200 μM+36 GFP. Cells were incubated under these conditions for 3 hours at 37° C. The 50 μM PBA/PBS solution was removed and cells were washed three times with PBS, followed by the addition of 1 mL DMEM in 10% FBS. Cells were incubated under these conditions for 4 days, and knockdown of GAPDH expression was quantitated by Western blot.

About 20% cytotoxicity was observed after 3 hour incubation in 50 μM PBA/PBS. Much higher cytotoxicity (~80%) was observed when HeLa cells were incubated in 50 μM PBA/PBS for ≥4 hours. Cytotoxicity of PBA may vary by cell type.

Example 7

Potent Delivery of Functional Proteins into Mammalian Cells by Supercharged Green Fluorescent Protein "Supercharged" GFP variants that have been extensively mutated at their surface-exposed residues to impart extremely high theoretical net charge magnitudes ranging from −30 to +48 that can enter a variety of mammalian cells by binding to anionic cell-surface proteoglycans and undergo endocytosis in an energy-dependent and clathrin-independent fashion and can deliver siRNA and plasmid DNA into a variety of mammalian cell lines without detectable cytotoxicity were previously described. (Lawrence et al., *JACS* 129, 10110-10112, 2007, McNaughton et al., *Proc. Natl. Acad. Sci. U.S.A.* 106, 6111-6116, 2009).

This Example describes that +36 GFP can be fused to a variety of proteins while maintaining its ability to rapidly and potently penetrate a variety of mammalian cell types. When delivered as fusions with +36 GFP, mCherry, ubiquitin, and Cre recombinase all retain their native functions, suggesting that fusions with +36 GFP can escape endosomes and travel in functional form to the cytosol or the nucleus. When +36 GFP is fused to a protein of interest through a protease-sensitive linker, the internalized protein of interest is readily cleaved from the +36 GFP moiety both in vitro and in cells. Side-by-side comparisons of +36 GFP, Tat, and Arg$_9$ fused to mCherry or Cre recombinase revealed that fusions with +36 GFP result in significantly higher levels of internalized protein (~10- to 100-fold) and in greater efficiencies of Cre-induced recombination (~2 to 15-fold). Collectively, these results suggest that superpositively charged proteins may serve as a promising new tool for the delivery of proteins into mammalian cells.

Mammalian Cell Penetration of +36 GFP and Tat Protein Fusions

Figure 39:
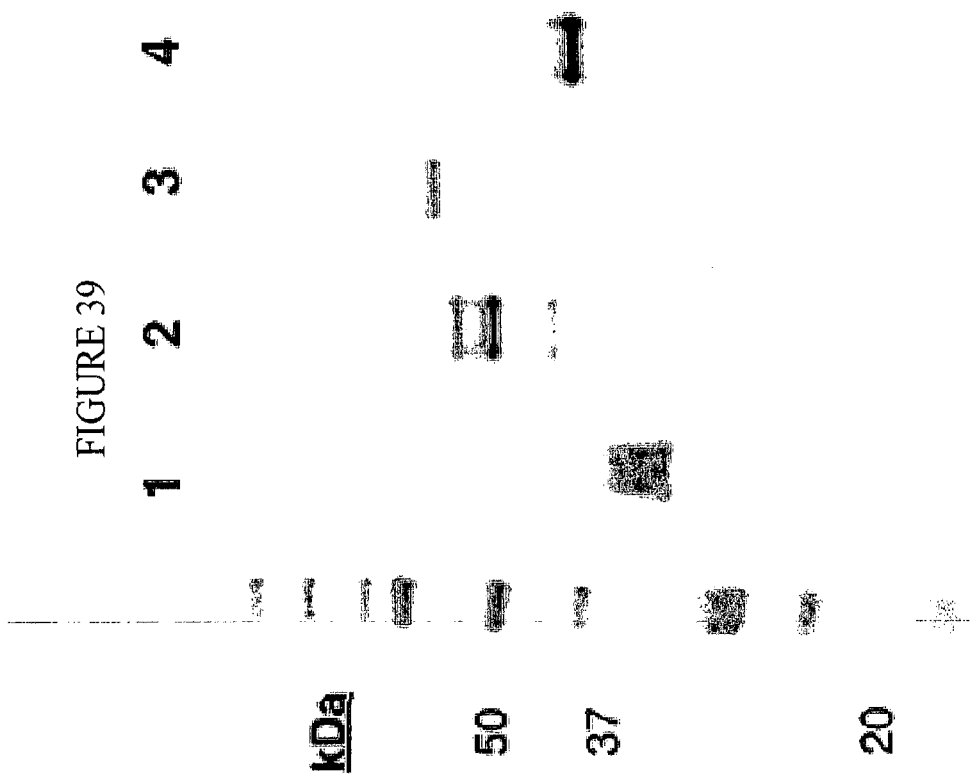
FIG. 39. SDS-PAGE analysis of +36 GFP fusion proteins after purification. Lane 1: +36 GFP; lane 2: +36 GFP-mCherry; lane 3: +36 GFP-Cre; lane 4: Ubiquitin-+36 GFP. The proteins on the gel were stained with Coomassie Blue.
Figure 40:
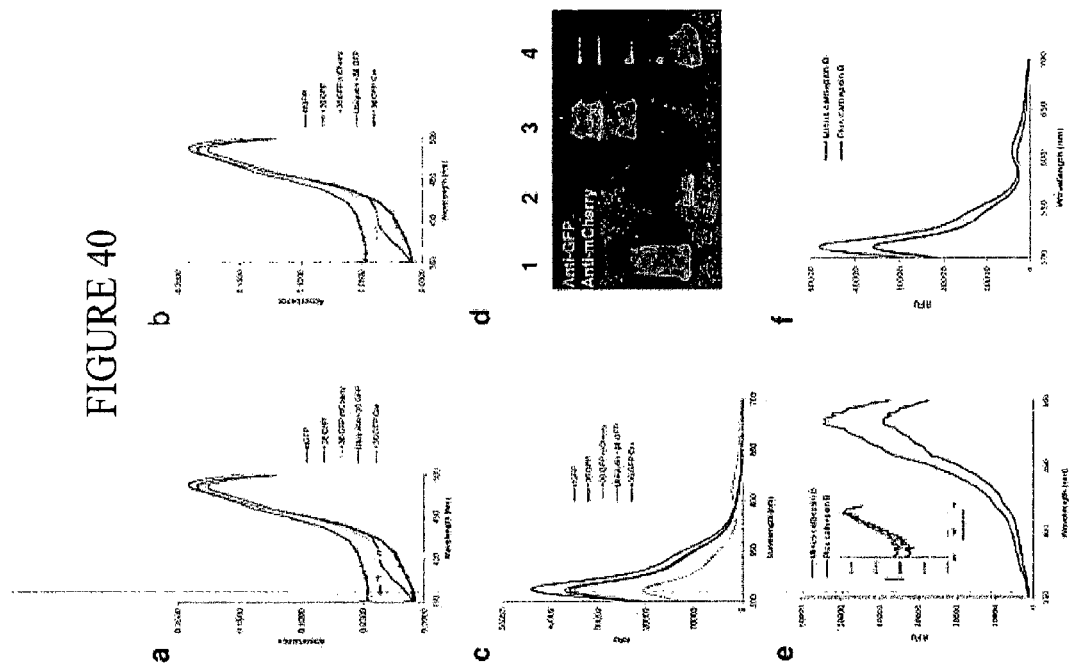
FIG. 40. Fluorescence spectra of +36 GFP fusion proteins. (a) Absorbance spectra of +36 GFP fusions. (b) Excitation spectra of +36 GFP fusions; emission wavelength=515 nm. (c) Emission spectra of +36 GFP fusions; excitation wavelength=488 nm. (d) Cleavage of +36 GFP-mCherry fusion. Lane 1: +36 GFP; lane 2: mCherry; lane 3: +36 GFP-mCherry fusion; lane 4: +36 GFP-mCherry fusion after treatment with 500 ng cathepsin B for 45 min at 37° C. (e) Excitation spectrum of +36 GFP-mCherry after incubation with or without cathepsin B; emission wavelength=515 nm. The inset absorbance spectrum shows that the absorbance level of the GFP fluorophore in both samples is equivalent. (f) Emission spectrum of +36 GFP-mCherry incubated with or without cathepsin B; excitation wavelength=488 nm. Spectra were obtained on a Tecan Safire II with 5 nm bandwidth filters in a 96-well glass-bottom white wall Costar plate.

The ability of +36 GFP to enter cells when genetically fused with a variety of other proteins was tested. Fusions of +36 GFP to mCherry (Shaner et al., *Nat. Biotechnol.* 22, 1567-1572, 2004), Cre recombinase (Abremski et al., *Cell* 32, 1301-1311, 1983), and ubiquitin (Schlesinger et al., *Nature* 255, 42304-42304, 1975) in various orientations and with different linkers were generated. For mCherry and Cre, optimal yield of purified, full-length protein was obtained from +36 GFP-(GGS)$_4$-ALAL-(GGS)$_4$-(protein of interest)-His$_6$. Full-length ubiquitin-+36 GFP was optimally expressed and purified with an amino-terminal His$_6$ tag. Fusion architectures are shown schematically in FIG. 36 *a* and SDS-PAGE analyses of purified proteins are shown in FIG. 39. The fluorescent properties of +36 GFP were not significantly altered by fusion with Cre or ubiquitin (FIG. 40). The +36 GFP-mCherry fusion protein exhibited a lower fluorescence emission at 515 nm and an additional weaker fluorescence emission peak at 620 nm when excited at 488 nm, consistent with Förster resonance energy transfer (FRET) from the +36 GFP fluorophore to the tethered mCherry fluorophore. These effects were diminished upon proteolytic separation of mCherry and +36 GFP (FIG. 40*d, e, f*).

Figure 36:
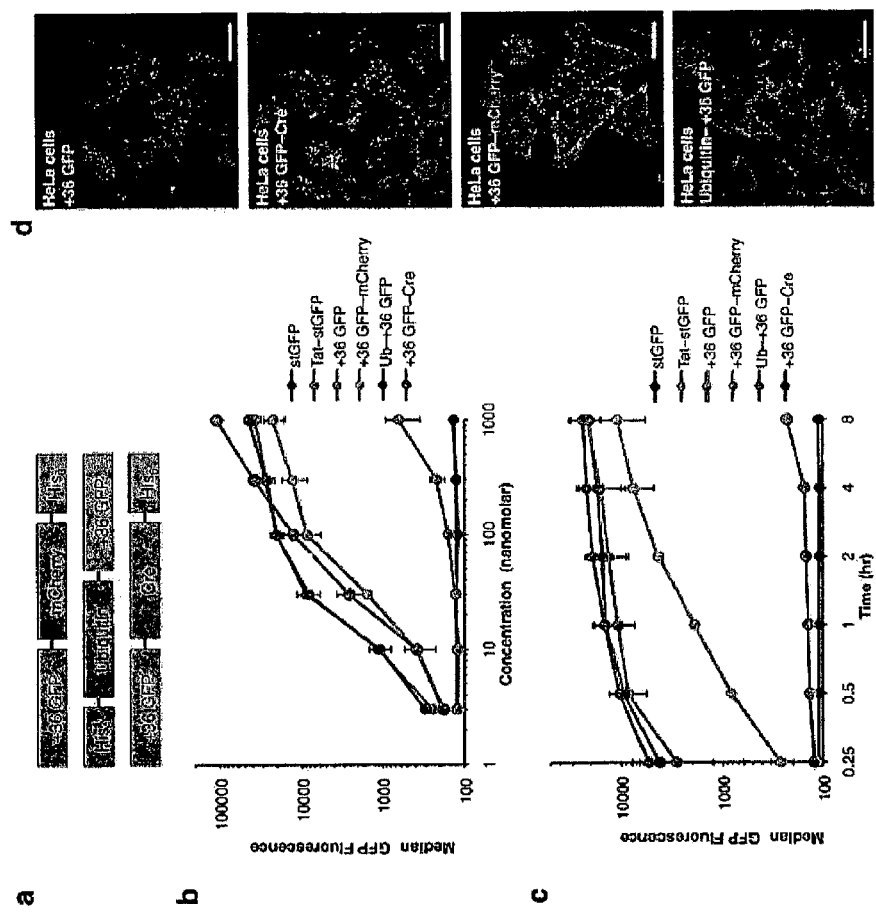
FIG. 36. Mammalian cell penetration of +36 GFP protein fusions. (a) +36 GFP fusion architectures. (b) Flow cytometry of HeLa cells incubated at the concentrations shown in the presence of +36 GFP fusions for 4 hours at 37° C. Cells were washed three times with 20 U/mL heparin in PBS to remove membrane-bound protein prior to analysis. Untreated cells resulted in median GFP fluorescence values of $10^7 \pm 5$. Error bars represent the range of values of two independent biological replicates. (c) Flow cytometry of HeLa cells incubated in the presence of 100 nM of each +36 GFP fusion at 37° C. for the specified time. Untreated cells resulted in median GFP fluorescence values of 100±6. Error bars represent the range of values of two independent biological replicates. (d) Fluorescence microscopy of HeLa cells incubated in the presence of +36 GFP fusions at 100 nM for 30 min at 37° C. Cell nuclei were stained with DAPI. The scale bar represents 15 µm.

To test whether the ability of +36 GFP to penetrate mammalian cells was retained in these fusions, HeLa cells were incubated with various concentrations of the three protein fusions in serum-free DMEM for 4 hours at 37° C. After incubation, cells were washed three times with heparin under conditions that have been shown to remove protein bound to the cell membrane (McNaughton et al., Proc. Natl. Acad. Sci. U.S.A. 106, 6111-6116, 2009; Veldhoen et al., Nucleic Acids Res. 34, 6561-6573, 2006). The degree of internalized GFP was measured by flow cytometry. For comparison, +36 GFP, non-supercharged starting GFP (stGFP (Lawrence et al., JACS 129, 10110-10112, 2007), a single-mutant variant of superfolder GFP (Pedelacq et al., Nat. Biotechnol. 24, 79-88, 2006)), and Tat-fused stGFP were also incubated with HeLa cells under the same conditions. At concentrations up to 100 nM, both stGFP and Tat-stGFP exhibited little or no detectable cell penetration. Tat-stGFP penetrated HeLa cells modestly at 300 nM and significantly at 1 µM, while, as expected, stGFP did not penetrate cells to a detectable extent even at 1 µM (FIG. 36 *b*). In contrast, +36 GFP alone, +36 GFP-mCherry, +36 GFP-Cre, and ubiquitin-+36 GFP all penetrated cells potently at low nanomolar concentrations. HeLa cells treated with 10 nM+36 GFP alone, +36 GFP-mCherry, +36 GFP-Cre, or ubiquitin-+36 GFP resulted in cellular levels of GFP comparable to treatment with 1 µM Tat-stGFP. HeLa cells treated with 1 µM+36 GFP, +36 GFP-mCherry, +36 GFP-Cre, or ubiquitin-+36 GFP resulted in cellular levels of GFP ~50- to 100-fold greater than HeLa cells treated with 1 µM Tat-stGFP (FIG. 36 *b*).

Similarly, when the concentration of protein was fixed at 100 nM and the amount of internalized GFP was measured over time by flow cytometry, +36 GFP and its protein fusions exhibited significant levels of internalized protein within 15 minutes (the earliest measurement). In contrast, significant levels of internalized protein were not observed by flow cytometry in HeLa cells treated with 100 nM Tat-stGFP until ~8 hours (FIG. 36 *c*). The +36 GFP fusions penetrated cells after 2 hours of incubation at 100 nM to an extent ~20- to 100-fold greater than that of Tat-stGFP after 8 hours of incubation (FIG. 36 *c*). These results were supported by fluorescence microscopy of HeLa cells fixed after a 30-minute incubation with +36 GFP protein fusions at 100 nM (FIG. 36 *d*).

Figure 41A:
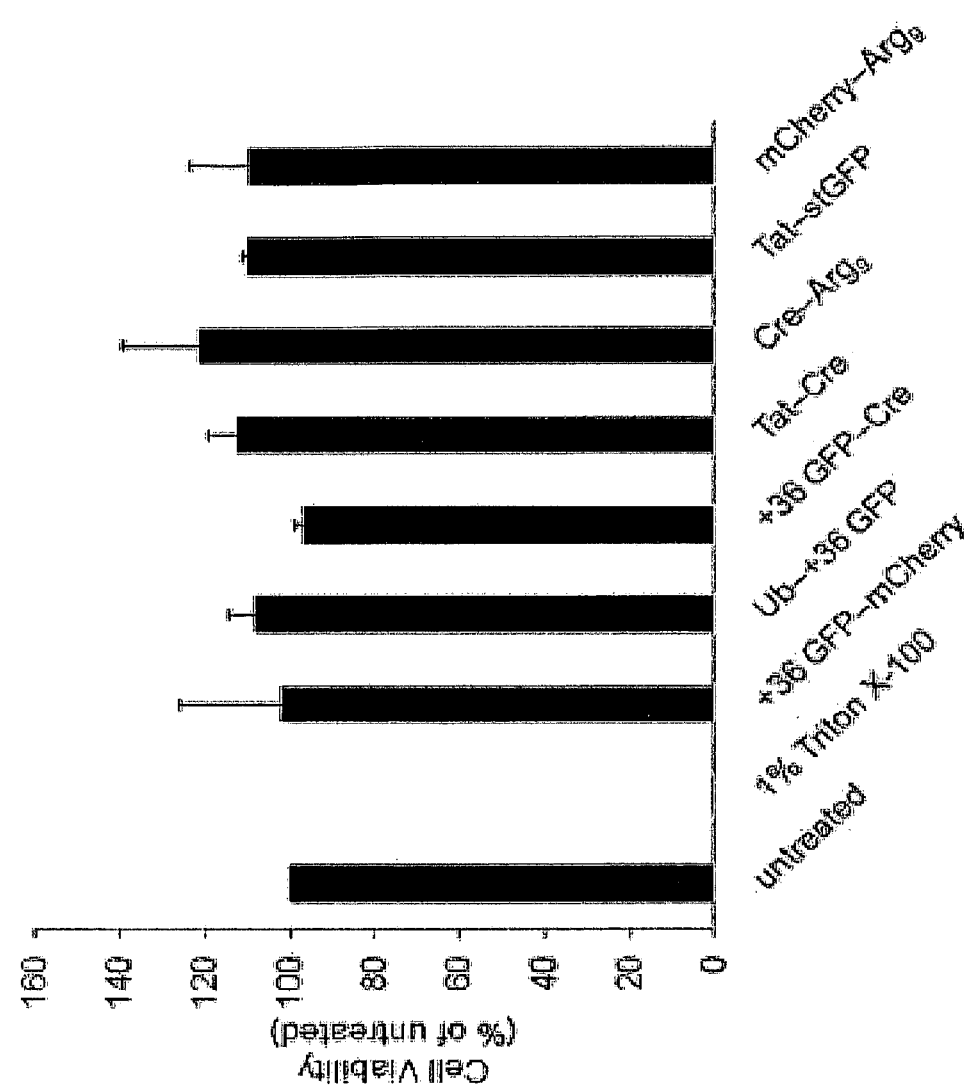
FIG. 41. Protein fusions with +36 GFP exhibit no significant cell toxicity. A: HeLa cells were plated at 50,000 cells per well in a 24-well plate. After 12 hours, cells were incubated with 2 µM of the indicated protein for four hours in serum-free DMEM. Cells were washed three times with heparin and incubated in complete DMEM for 24 hours, then subjected to an MTT assay (Sigma). Values represent the average of two independent experiments each performed in duplicate normalized to untreated cells. Error bars indicate the range in values. B: +36 GFP and +36 GFP fusions are not toxic at concentrations effective for protein delivery. At concentrations ≥~10 to 100 times the effective concentration for protein delivery in this work, +36 GFP-Cre (but not other +36 GFP fusion proteins or +36 GFP itself) reduced the viability of some cell lines and possibly stimulated IMCD cells. Values and error bars represent the average of and standard deviation, respectively, of three independent biological replicates.
Figure 41B:
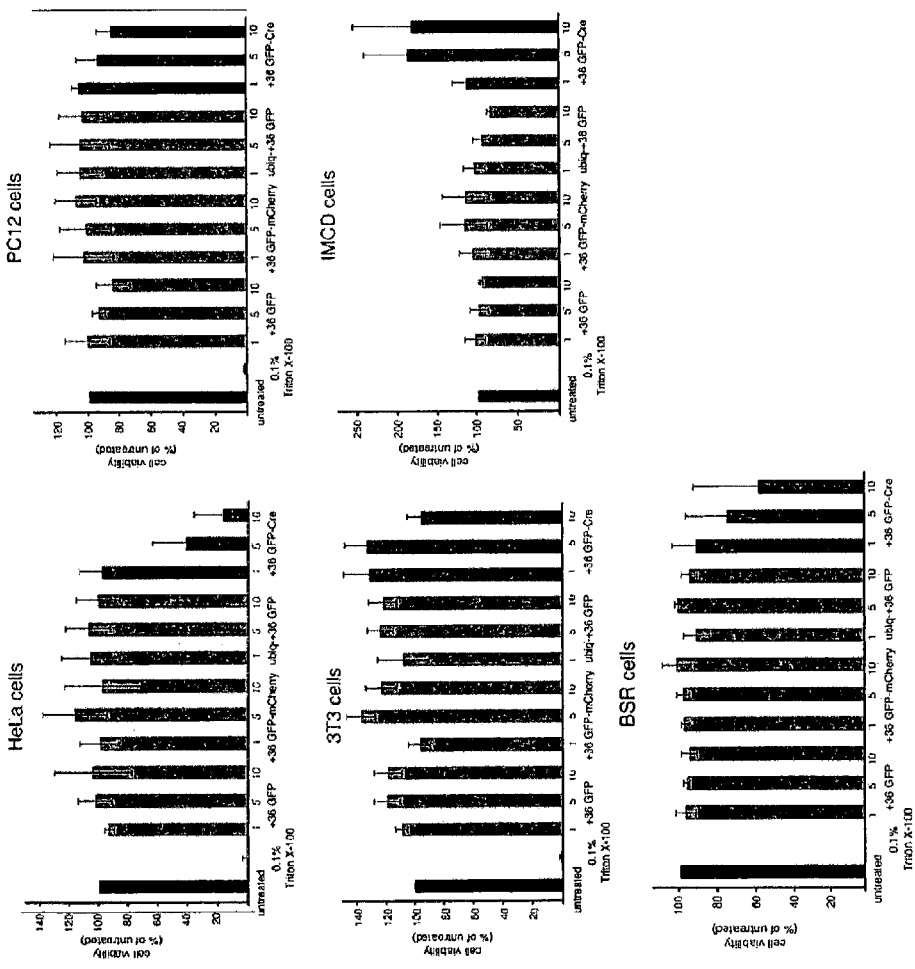

HeLa cells treated for 4 h with 2 µM+36 GFP mCherry, +36 GFP Cre, and ubiquitin +36 GFP did not exhibit significant cytotoxicity by MTT assay (FIG. 41). Taken together, these results indicate that all three proteins tested as fusions with +36 GFP retain the dose-dependent ability of +36 GFP to penetrate HeLa cells potently (at nanomolar concentrations), quickly (in minutes), and without apparent cytotoxicity. In addition, +36 GFP and all +36 GFP protein fusions tested exhibited significantly greater potency and speed of cell penetration than that of Tat-stGFP, which behaved in a manner consistent with previous descriptions of Tat-GFP fusions (Ryu et al., Mol. Cells. 16, 385-391, 2003).

Comparison of mCherry Delivery by +36 GFP, Tat, and Arg$_9$

+36-GFP, Tat, and Arg$_9$-mediated protein delivery were compared in a variety of mammalian cells. HeLa cells, inner medullary collecting duct (IMCD) cells, and rat pheochromocytoma PC12 cells were incubated with various concentrations of +36 GFP-mCherry, Tat-mCherry, or Arg$_9$-mCherry fusion proteins for 4 hours at 37° C. After incubation, cells were washed with heparin to remove membrane-bound proteins and assayed for internalized mCherry by flow cytometry (FIG. 33). Depending on the cell line, +36 GFP delivered ~10- to 100-fold more mCherry than either Tat or Arg$_9$. Effective delivery of mCherry by 100 nM+36 GFP across cell lines was further confirmed by fluorescence microscopy (FIG. 34). In all cell lines, +36 GFP and mCherry were observed primarily as distinct green and red puncti (presumably endosomes based on our previous studies (McNaughton et al., Proc. Natl. Acad. Sci. U.S.A. 106, 6111-6116, 2009)) dispersed throughout the cellular cytoplasm. The lack of colocalization of the GFP and mCherry chromophores suggests significant proteolytic separation of the two proteins and reshuffling of the endosomal vacuoles and their cargo. These results suggest that +36 GFP may be a significantly more potent protein transduction domain than the widely used Tat and Arg$_9$ peptides.

Figure 44A:
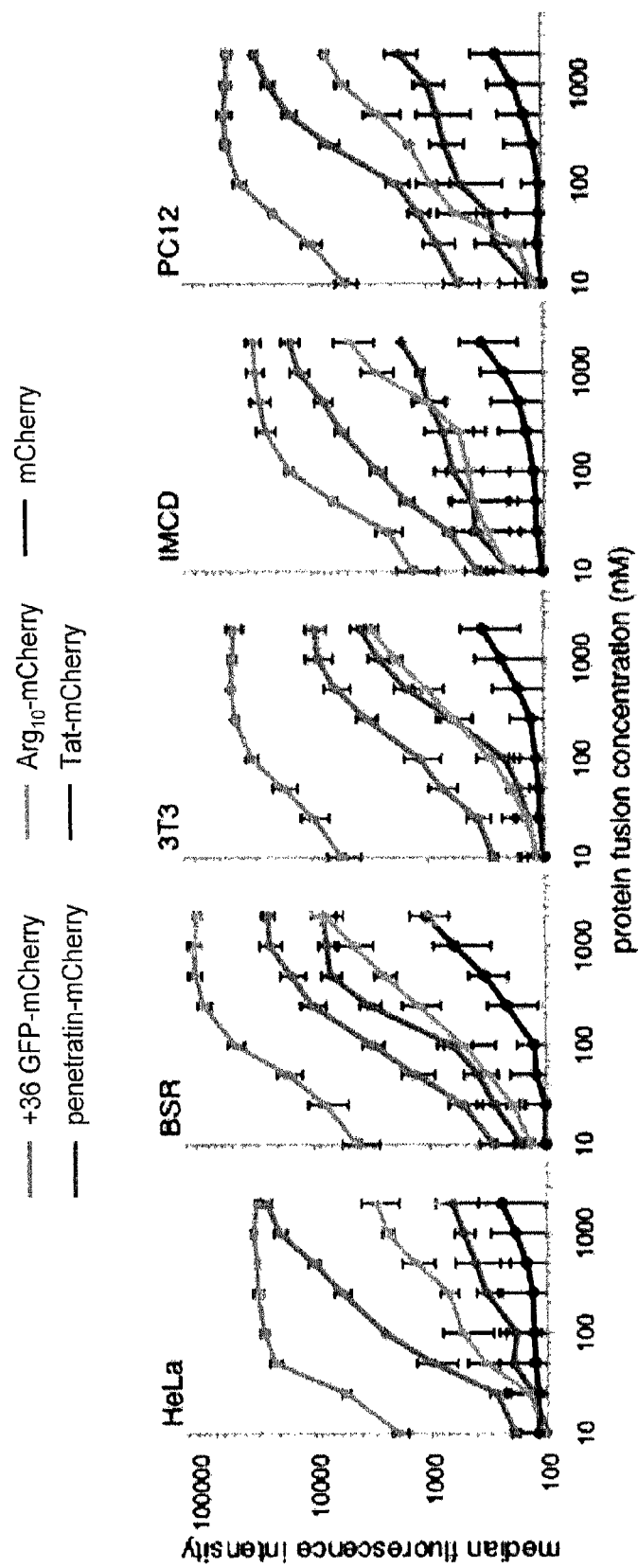
FIG. 44. A: +36 GFP potently delivers fused proteins into mammalian cells. Cell-penetration potency of +36 GFP exceeds that of known cell-penetrating peptides and proteins, especially at low concentrations. B: Comparison of mCherry delivery by +36 GFP, Tat, Arg10, and penetratin. (a) Flow cytometry of HeLa, BSR, 3T3, PC12 and IMCD cells incubated in the presence of the specified concentrations of +36 GFP-mCherry, Tat-mCherry, Arg10-mCherry, penetratin-mCherry or wild-type mCherry alone for 4 hours at 37° C. Cells were washed three times with 20 U/mL heparin in PBS to remove membrane-bound protein before analysis. Error bars represent the standard error of three independent biological replicates. (b) Confocal fluorescence microscopy of live cells incubated with 100 nM+36 GFP-mCherry for 4 hours at 37° C. mCherry signal and +36 GFP signal are represented. The scale bar is 15 µm.
Figure 44B:
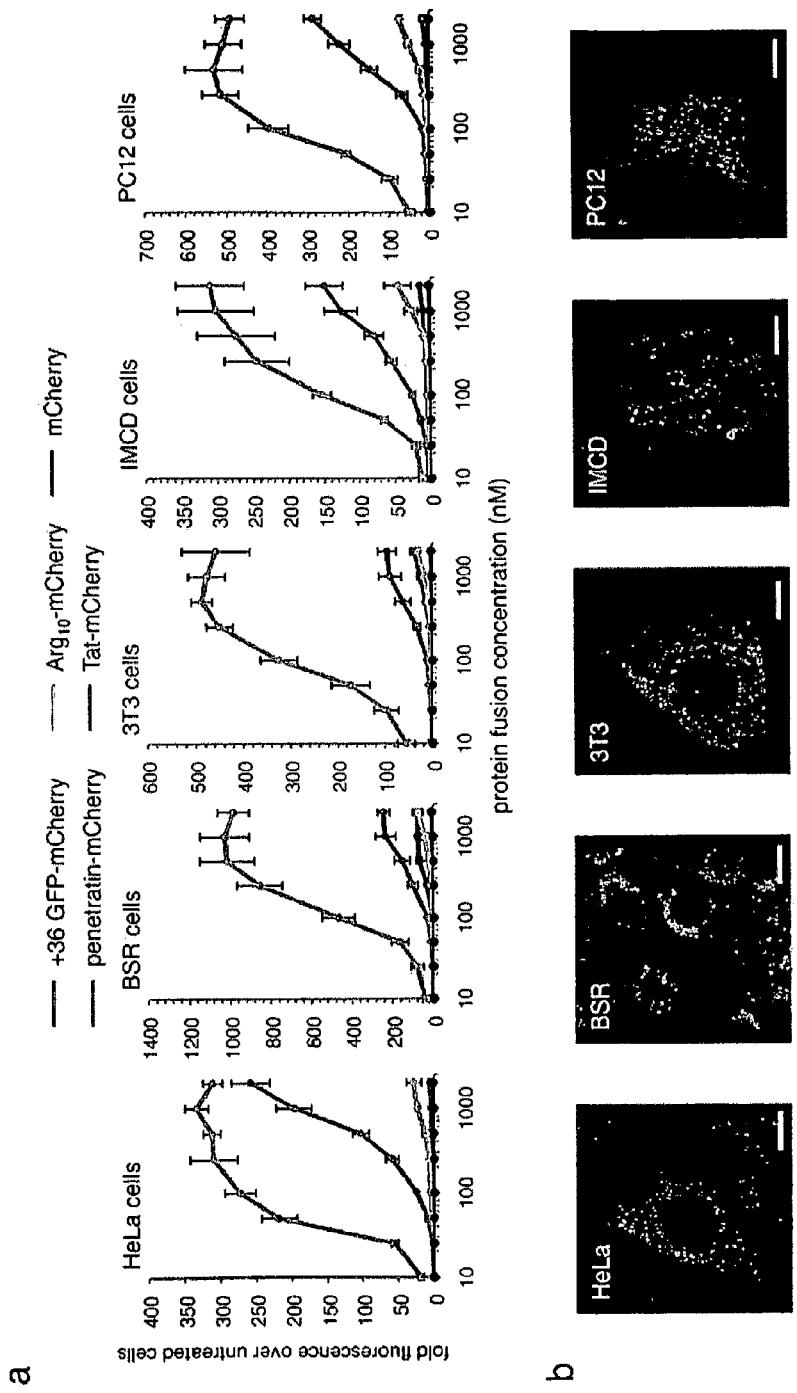

Comparison of mCherry Delivery by +36 GFP, Tat, Arg10, and Penetratin at Different Concentrations +36-GFP, Tat, Arg$_{10}$, and penetratin-mediated delivery of mCherry were compared in a variety of mammalian cells using a variety of protein fusion concentrations (FIG. 44). In HeLa cells, BSR cells (a baby hamster kidney (BHK) cell derivative), inner medullary collecting duct (IMCD) cells, 3T3 murine fibroblast cells, and rat pheochromocytoma PC12 cells, increased median mCherry fluorescence intensity was observed with +36GFP as compared to the other delivery vehicles at all concentrations. The cell-penetration potency of +36 GFP exceeded that of known cell-penetrating peptides and proteins, especially at low concentrations.

Ability of +36 GFP Protein Fusions to Access the Cytosol

Figure 42:
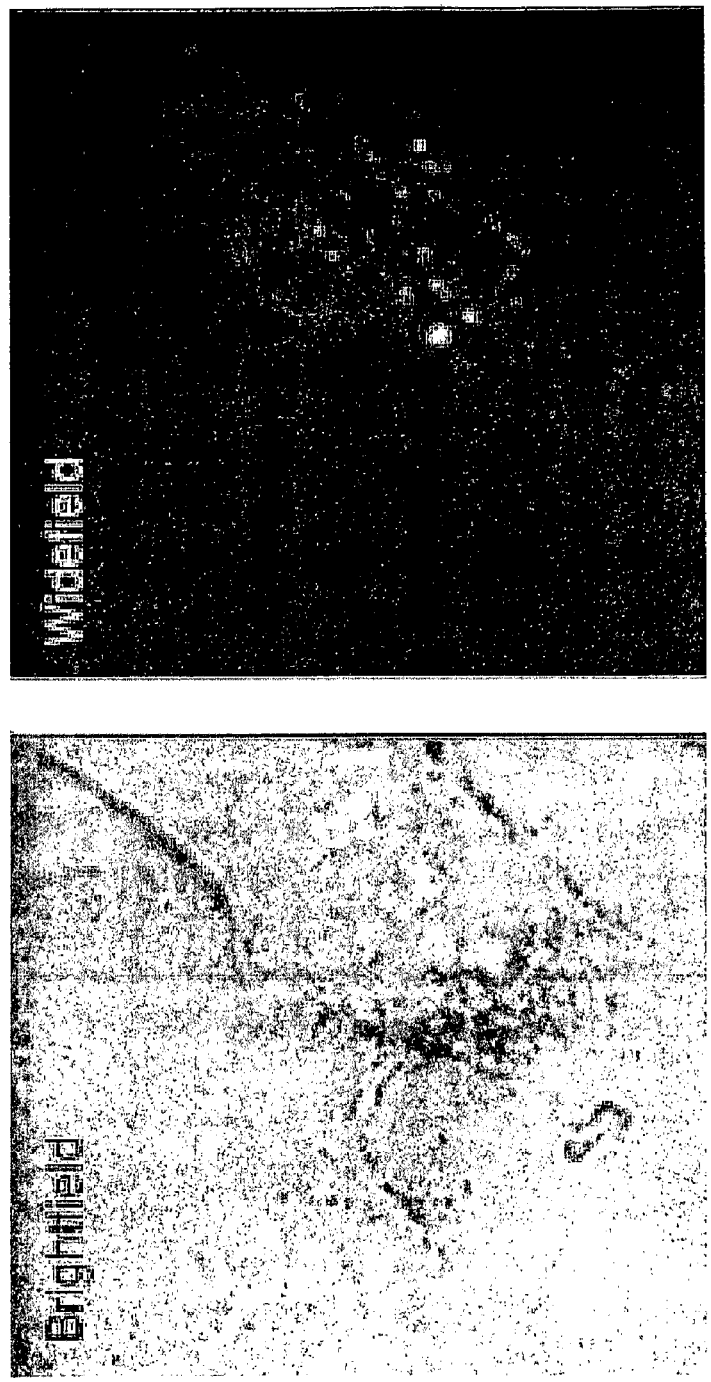
FIG. 42. Localization of internalized mCherry. HeLa cells incubated with 100 nM+36 GFP mCherry for four hours were trypsinized and plated together with untreated HeLa cells. As imaged by live-cell widefield fluorescence, a diffuse red signal (mCherry) was observed in the cytoplasm of the GFP-containing cells, while adjacent GFP negative cells did not have a diffuse red signal. +36 GFP (green signal) appears to remain as puncti.

To probe localization of mCherry after delivery as a fusion with +36 GFP, HeLa cells were incubated with 100 nM+36 GFP-mCherry for 4 h and plated the resulting cells together with untreated HeLa cells. As imaged by live-cell widefield fluorescence microscopy, a diffuse red fluorescence was observed from the cytoplasm of cells containing GFP puncti, while cells lacking GFP puncti did not contain a diffuse red signal (FIG. 42). This observation suggests that some of the internalized mCherry protein was separated from GFP, escaped from endosomes, and was distributed throughout the cytosol. In contrast, the absence of a significant green fluorescent signal outside puncti suggests that +36 GFP may remain associated with endosomes or with anionic components of former endosomes.

A deubiquitination assay was used to more rigorously evaluate the ability of +36 GFP fusions to escape endosomes and access the cytosol. Deubiquitinase (DUB)-dependent removal of a ubiquitin moiety from a translationally fused protein domain has been previously used as an indicator of exposure to the cytosolic environment in mammalian cells (Loison et al., Mol. Ther. 11, 205-214, 2005). A ubiquitin-+36 GFP fusion in which the C-terminus of ubiquitin was directly followed by the N-terminus of +36 GFP was expressed and purified. A direct fusion of this type is known to be recognized and processed by endogenous DUBs, resulting in a ~9 kDa reduction in molecular weight. A mutant form of ubiquitin (G76V) that is not a substrate for DUBs (Loison et al., Mol. Ther. 11, 205-214, 2005) was similarly fused to +36 GFP to distinguish the effect of cytosolic DUBs from non-specific proteolysis.

Figure 37A:
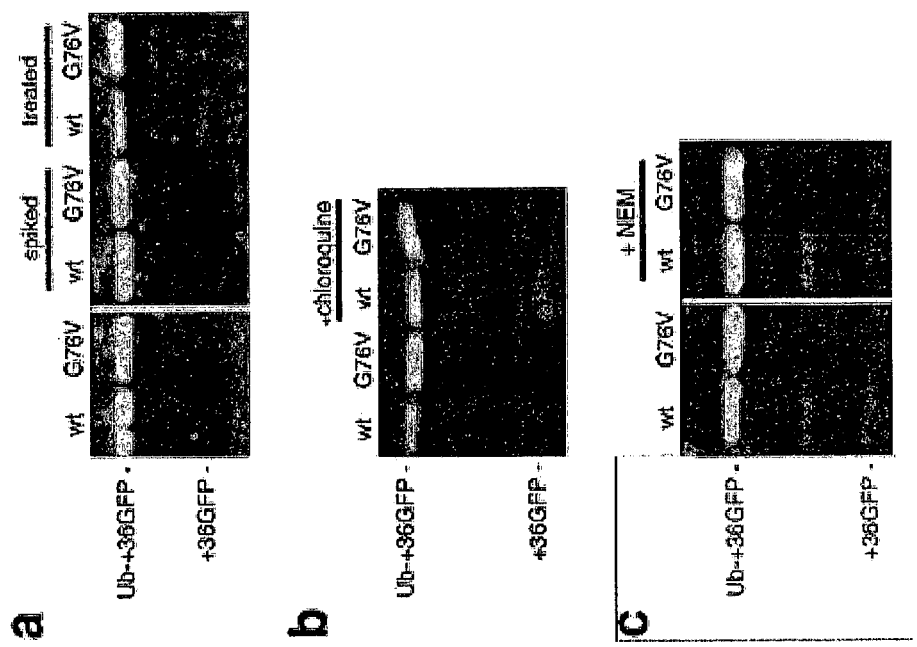
FIG. 37. A: Deubiquitination suggests cytosolic exposure of a ubiquitin-+36 GFP fusion protein. Shown are Western blots using anti-His and anti-GFP antibodies. All proteins carry an N-terminal 6×His tag on the ubiquitin moiety. (a) Lanes 1 and 2: purified protein samples of wild-type ubiquitin-+36 GFP (wt) or G76V mutant ubiquitin-+36 GFP (G76V). Lanes 3 and 4: purified protein spiked into HeLa cell lysate to check the possible effect of lysis conditions on fusion protein integrity. Lanes 5 and 6: HeLa cell lysates treated with 200 nM of either the wt or G76V ubiquitin-+36 GFP for 1 hour. (b) Effect of chloroquine on ubiquitin-+36 GFP deubiquitination. Cells were treated with 200 nM of wt or G76V ubiquitin-+36 GFP, either in the presence or absence of 200 µM chloroquine for 1 hour. (c) In vitro deubiquitination assay. Ubiquitin-+36 GFP fusion proteins were incubated either in HeLa cytosolic extract or in HeLa cytosolic extract containing 10 mM of the DUB inhibitor N-ethylmaleimide (NEM) for 30 minutes at 37° C. B: (a) Western blots using anti-GFP antibodies. Lanes 1-3: purified protein samples of +36 GFP, wild-type ubiquitin-+36 GFP fusion (wt) or G76V mutant ubiquitin-+36 GFP fusion (mut). Lanes 4 and 5: purified protein spiked into HeLa cell lysate to confirm that lysis conditions do not affect fusion protein integrity. Lanes 6-11: the indicated cells were treated with 100 nM of either the wt or mutant ubiquitin-+36 GFP for 1 hour, then lysed. (b) Mean extent of deubiquitination of wt ubiquitin-+36 GFP fusion protein in HeLa, 3T3, and BSR cells. Error bars reflect the standard deviation of three independent biological replicates. (c) In vitro deubiquitination control experiment. Ubiquitin-+36 GFP fusion proteins were incubated in either HeLa cytosolic extract or in HeLa cytosolic extract containing one of two DUB inhibitors, 10 mM N-ethylmaleimide (NEM) or 20 µg/mL ubiquitinaldehyde (Ub-A1) for 1 hour at 37° C.
Figure 37B:
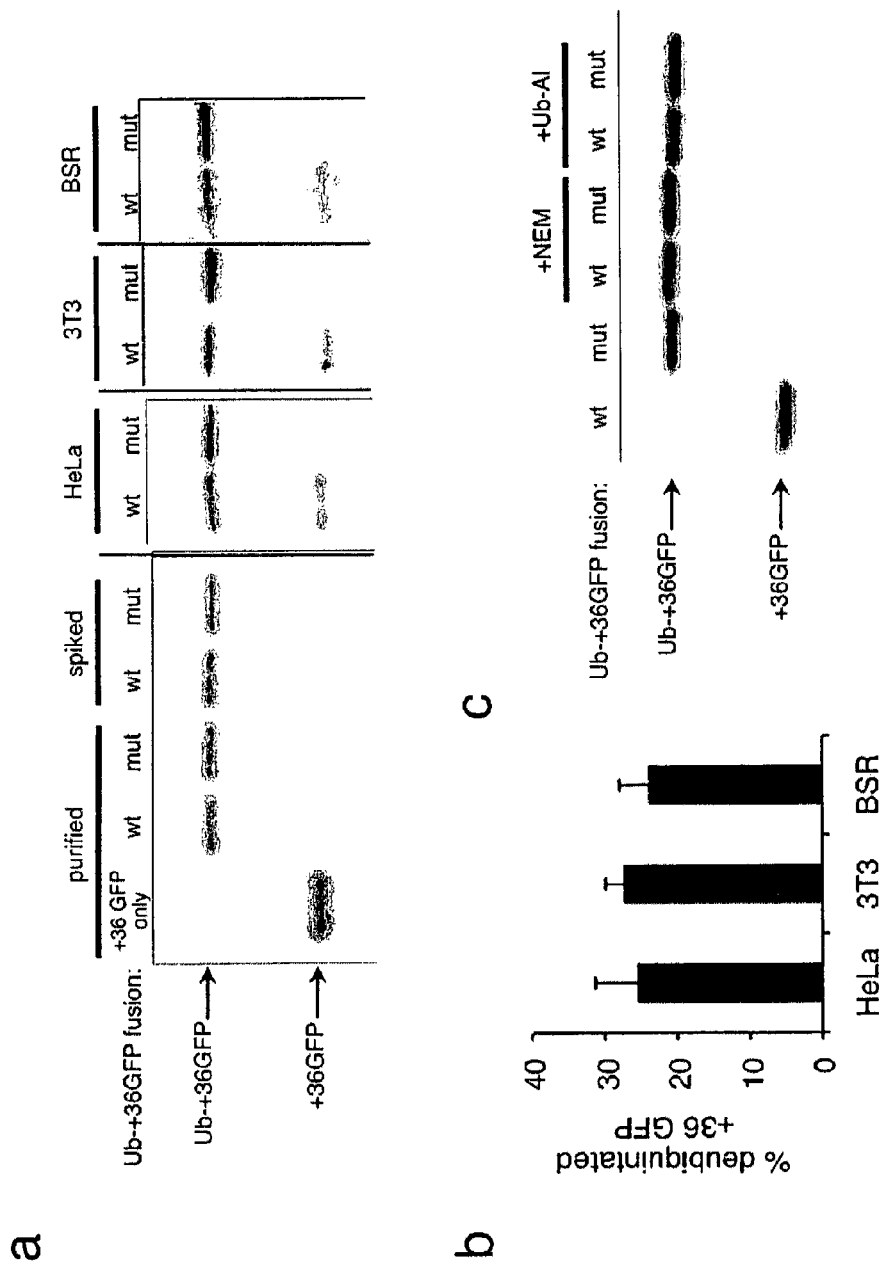

HeLa cells were incubated with either 200 nM ubiquitin-+36 GFP or 200 nM ubiquitin G76V+36 GFP, washed with heparin to remove surface-bound proteins, and analyzed by western blot. After a 1-hour incubation, 22% of ubiquitin-+36GFP was deubiquitinated, producing a protein equal in size to +36 GFP (FIG. 41 *a*). In contrast, the G76V mutant-+36 GFP fusion was not cleaved, indicating that this reduction in size does not arise from non-specific endosomal proteases but instead from the action of cytosolic DUBs. In the presence of chloroquine, a small molecule known to disrupt endosomal acidification and enhance release of endocytosed molecules (Wadia et al., Nat. Med. 10, 310-315, 2004), cleavage of ubiquitin-+36 GFP increased from 22% to 36% (FIG. 37 b). The enhanced cleavage upon addition of chloroquine further supports the assumption that cleavage of the ubiquitin-+36 GFP fusion protein reflects its cytosolic exposure. Additionally, ubiquitin-+36 GFP spiked into the cell lysis buffer prior to harvesting untreated cells was not cleaved (FIG. 37 a), indicating that the observed deubiquitination is a result of exposure to cytosolic DUBs resulting from cell penetration of +36 GFP, and not due to contact with DUBs during the cell harvesting procedure.

Finally, an in vitro deubiquitination assay was performed using HeLa cytosolic extract. Incubation of ubiquitin-+36 GFP, but not G76V mutant ubiquitin-+36 GFP, in the cytosolic extract resulted in deubiquitination; in contrast, incubation of either protein in cytosolic extract in the presence of the DUB inhibitor N-ethylmaleimide (Borodovsky et al., EMBO J. 20, 5187-5196, 2001) did not result in cleavage, further suggesting that the cleavage of ubiquitin-+36 GFP is a result of DUB activity (FIG. 37 c). These results demonstrate that a significant fraction of the ubiquitin-+36 GFP protein fusion can rapidly enter cells and access the cytosol, rather than remaining entirely localized within endosomes.

Comparison of Active Cre Recombinase Delivery by +36 GFP, Tat, and Arg$_9$

Figure 38:
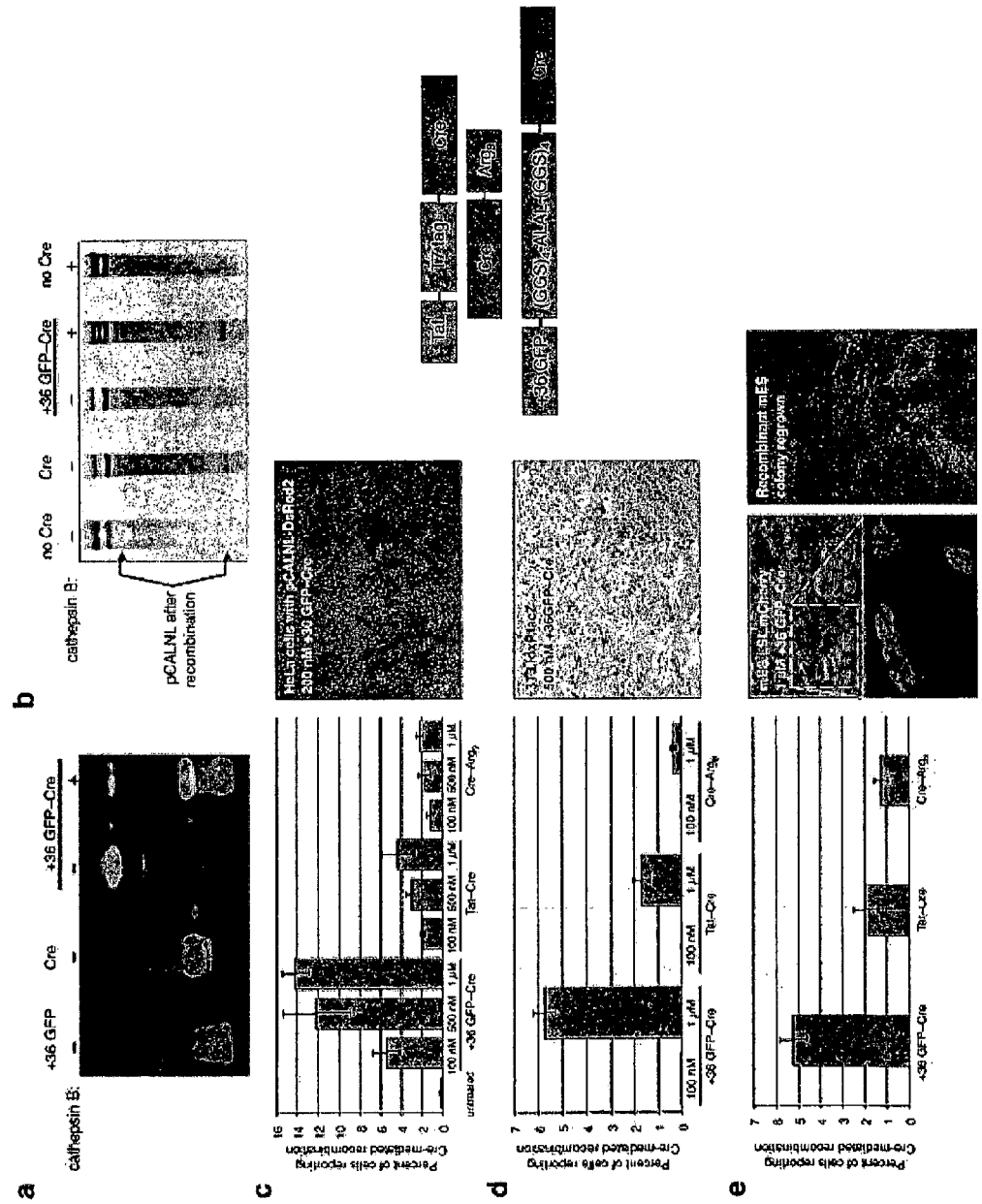
FIG. 38. Comparison of delivery of Cre recombinase to mammalian cells using Tat, Arg$_9$, or +36 GFP fusions. (a) Cathepsin B-mediated cleavage of +36 GFP-Cre. Lane 1: +36 GFP; lane 2: Cre; lane 3: +36 GFP Cre fusion; lane 4: +36 GFP-Cre after incubation with cathepsin B. (b) In vitro Cre activity assay. Lane 1: pCALNL alone; lane 2: pCALNL after incubation with 100 nM Cre for 30 minutes at 37° C.; lane 3: identical to lane 2, but with +36 GFP-Cre; lane 4: identical to lane 2 but with +36 GFP-Cre pre-treated with cathepsin B; lane 5: identical to lane 2 but with cathepsin B. (c) Cre-mediated recombination frequency in HeLa cells transiently transfected with pCALNL and treated with +36 GFP-Cre, Tat-Cre, or Arg$_9$-Cre. The picture is an overlay of DsRed2 signal and brightfield images of HeLa cells transfected with pCALNL-DsRed2 and treated with 100 nM+36 GFP-Cre. (d) Cre-mediated recombination frequency in 3T3.1oxP.lacZ cells treated with +36 GFP-Cre, Tat-Cre, or Arg$_9$-Cre. The picture is of 3T3.1oxP.lacZ cells treated with 500 nM+36 GFP-Cre and stained with X-Gal. (e) Cre mediated recombination frequency in mES.LSL.mCherry cells treated with 1 µM+36 GFP-Cre, Tat-Cre, or Arg$_9$-Cre. The pictures are of cells 24 hours after treatment (left) and of replated recombinant mES cells allowed to regrow into colonies (right). Error bars reflect the standard error of either five (c and d) or three (e) independent biological replicates. (GGS)$_4$-ALAL-(GGS)$_4$ corresponds to SEQ ID NO: 154.

To further explore the ability of +36 GFP to deliver fused proteins in functional form to specific subcellular locations, the ability of +36 GFP, Tat, and Arg$_9$ to deliver Cre recombinase into a variety of mammalian cells was compared. Cre has been used as a reporter of functional protein delivery in a wide range of cell lines (Wadia et al., Nat. Med. 10, 310-315, 2004). In mammalian cells, Cre must localize to the nucleus and eventually tetramerize in order to mediate DNA recombination (Quo et al., Nature 389, 40-46, 1997). To assess the possibility that localization or oligomerization of Cre is impeded by an attached protein transduction domain, susceptibility of the linker bridging +36 GFP and Cre to cleavage by endogenous proteases was determined. Cathepsin B is a ubiquitous mammalian endosomal protease that exhibits broad substrate specificity and efficiently cleaves the peptide Ala-Leu-Ala-Leu (Trouet et al., Proc. Natl. Acad. Sci. U.S.A. 79, 626-629, 1982). This motif was included in the linker joining +36 GFP and Cre (FIG. 36 a). When incubated with purified cathepsin B in vitro, the +36 GFP-Cre fusion was indeed cleaved into two protein fragments with lengths consistent with separated +36 GFP and Cre (FIG. 38 a).

Figure 43:
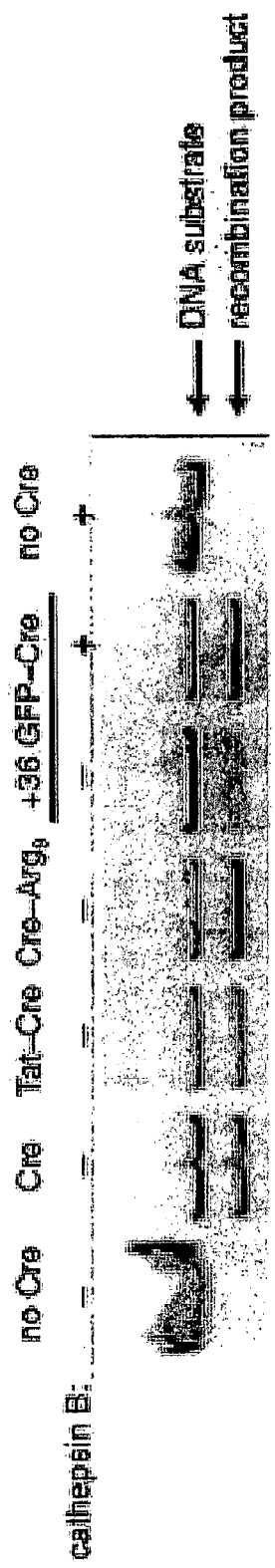
FIG. 43. Tat-Cre and Cre-Arg fusions retain Cre recombinase activity in vitro. pCALNL-DsRed2 (Addgene: 13769) contains a 1.2 kB region flanked by parallel loxP recognition sites. 500 ng of pCALNL-DsRed2 linearized by PvuI was incubated with 1 picomole of the listed protein in 50 µL of 50 mM Tris pH 7.5, 33 mM NaCl, 10 mM MgCl at 37° C. for 30 min, then at 70° C. for 10 min. DNA was isolated from the reaction by QIAquick spin column (Qiagen) and analyzed by electrophoresis on a 1% agarose gel. The gel was stained with ethidium bromide for 30 minutes and recombination products were visualized by ultraviolet light.

To evaluate the ability of the +36 GFP-Cre fusion to catalyze DNA recombination before and after proteolytic cleavage of the linker, an in vitro recombination assay was performed. Incubation of pCALNL (Matsuda et al., Proc. Natl. Acad. Sci. U.S.A. 104, 1027-1032, 2007), a 6.8 kB circular plasmid containing a 1.2 kB region flanked by loxP sites, with Cre recombinase in vitro leads to excision of the 1.2 kB region (FIG. 38 a). Excision of the 1.2 kB region was not observed when pCALNL was incubated with the intact +36 GFP-Cre fusion. After the fusion protein was incubated with cathepsin B, recombinase activity was restored (FIG. 38 b). These results indicate that cleavage of the +36 GFP-Cre linker is required for efficient Cre recombinase activity. When fused to Tat and to Arg$_9$, Cre was found to retain recombinase activity (FIG. 43).

The abilities of +36 GFP, Tat, and Arg$_9$ to deliver functional (nuclearly localized and active) Cre to HeLa, NIH-3T3, and murine embryonic stem cells was compared. Following transfection with pCALNL, which also serves as a DsRed2-based Cre activity reporter plasmid (Matsuda et al., Proc. Natl. Acad. Sci. U.S.A. 104, 1027-1032, 2007), HeLa cells were incubated with 100 nM, 500 nM, or 1 µM of each fusion protein for 1 hour in serum-free media. After incubation, cells were washed with heparin and incubated in full media for 24 hours. Cre recombinase activity was assayed by expression of DsRed2 via flow cytometry and fluorescence microscopy (FIG. 38 c). At all protein concentrations tested, +36 GFP-Cre was ~3- to 7-fold more effective at producing recombinants than the corresponding fusions with Tat or Arg$_9$.

The delivery of active Cre was further evaluated in a NIH-3T3 cell line harboring an integrated lacZ-based Cre-reporter (Wadia et al., Nat. Med. 10, 310-315, 2004). 3T3 cells were incubated with either 100 nM or 1 µM of each fusion protein for 18 hours and then stained with X-Gal to identify recombinants. Consistent with the HeLa cell results, +36 GFP-Cre resulted in 2- to 10-fold more efficient generation of recombinants than either Tat or Arg$_9$ (FIG. 38 d).

Finally, the ability of +36 GFP-Cre, Tat-Cre, and Arg$_9$-Cre were also compared for their ability to enter and catalyze recombination in a murine embryonic stem (mES) cell line containing an integrated mCherry-based Cre activity reporter. Colonies of mES cells were treated with 1 µM of each fusion protein in serum-free media for 4 hours, washed three times with heparin and incubated for 18 hours. Recombination and expression of mCherry was assayed by flow cytometry and fluorescence microscopy (FIG. 38 e). Similar to the results in HeLa and NIH-3T3 cells, +36 GFP-Cre generated 2- to 5-fold more recombinants than Tat-Cre or Arg$_9$-Cre (FIG. 38 e). Fluorescence microscopy confirmed that +36 GFP was able to produce recombinants in intact mES colonies, with multiple recombinant cells within a given colony. Furthermore, treated mES cells were able to form recombinant colonies when harvested and replated (FIG. 38 e). These data suggest that +36 GFP is a highly potent protein transduction domain, capable of mediating significantly higher levels of functional Cre recombinase delivery compared to the widely used Tat and Arg$_9$ peptides.

Comparison of Active Cre Recombinase Delivery by +36 GFP, Tat, and Arg$_9$

Figure 45:
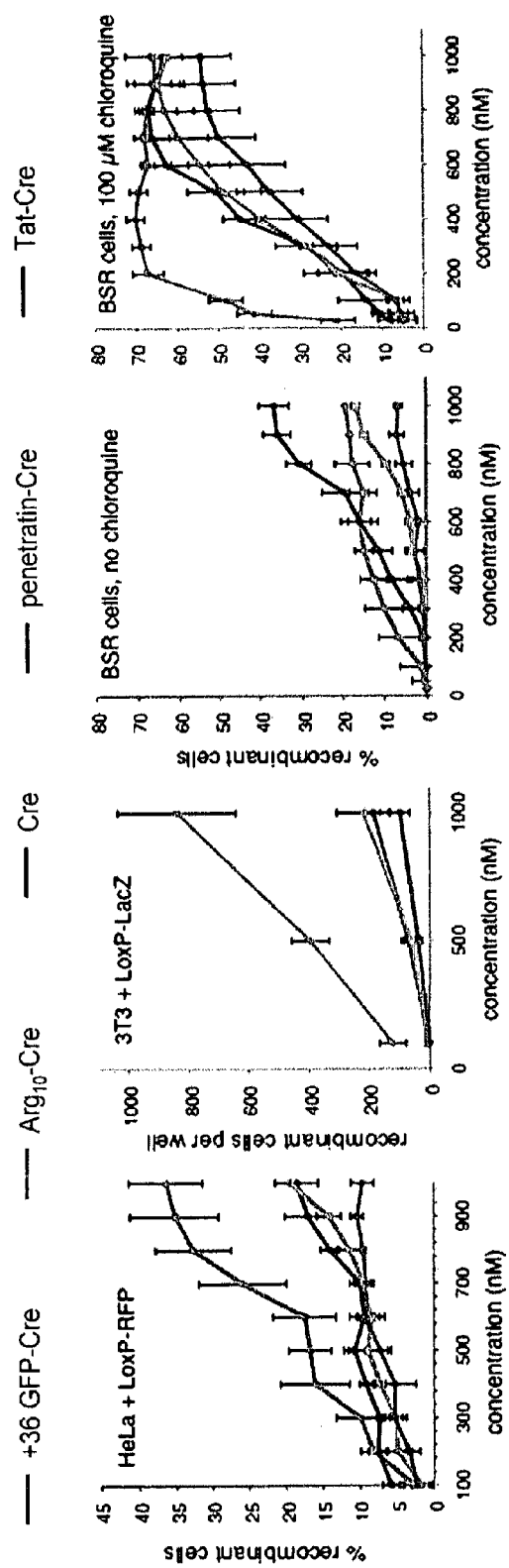
FIG. 45. Functional, nuclearly localized protein delivered by +36 GFP. In HeLa and NIH-3T3 cells, Cre delivery is more effective with +36 GFP than with known cell-penetrating peptides and proteins.

HeLa cells, 3T3 cells, and BSR cells harboring a loxP reporter construct were treated with +36 GFP-Cre, Arg$_{10}$-Cre, penetratin-Cre, and Tat-Cre at different concentrations (FIG. 45). In HeLa and 3T3 cells, Cre delivery was more effective with +36 GFP than with other cell-penetrating peptides and proteins. In BSR cells, +36 GFP-Cre yielded more recombinant cells at lower concentrations than other known cell-penetrating peptides and proteins. Chloroquine greatly enhanced functional +36 GFP-mediated Cre delivery in BSR cells, suggesting an endosomal escape bottleneck.

Figure 54:
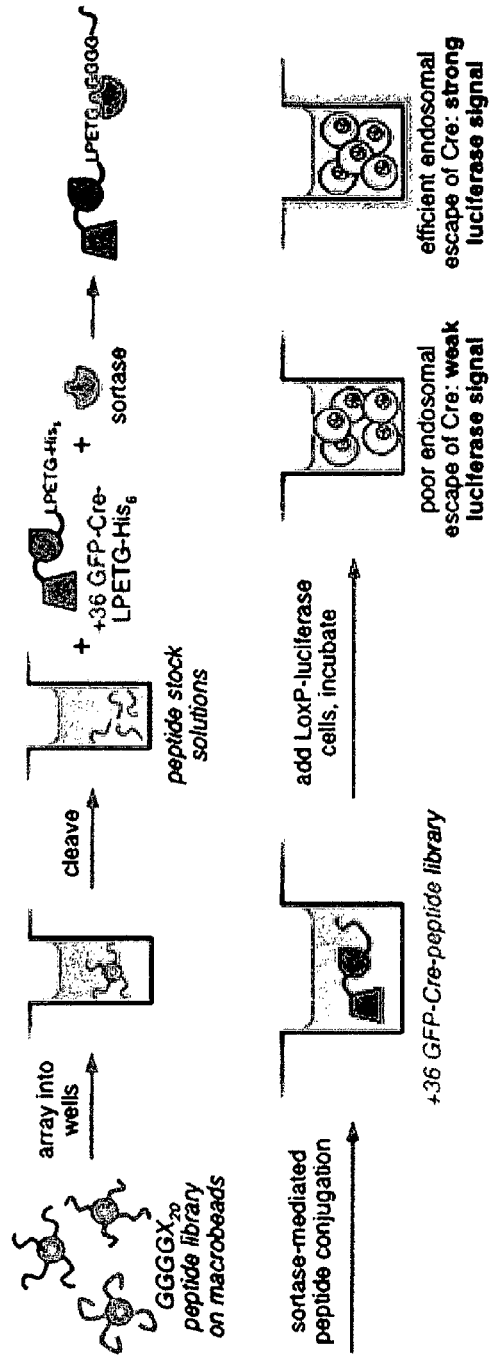
FIG. 54. Peptide fusion strategies for improvement of endosomal escape. LEPTG and GGGG correspond to SEQ ID NO: 108 and SEQ ID NO: 109, respectively.

While supercharged protein-mediated cell-penetration potency can be much greater (>100-fold) than that of other methods, delivery of functional siRNA, DNA, or protein delivery was observed to be only ~3- to 20-fold more efficient than with conventional methods. The endosomal escape bottleneck, as indicated by the results described elsewhere herein, is likely limiting the delivery of functional nucleic acids and proteins. One exemplary approach to address the endosomal bottleneck is to combine a supercharged protein or agent to be delivered with an agent that disrupts endosomolytic vesicles or enhances the degradation of endosomes (e.g., chloroquine, pyrene butyric acid, fusogenic peptides, polyethyleneimine, hemagglutinin 2 (HA2) peptide, melittin peptide). Peptides and proteins can be fused post-translational, for example, by a sortase, if the original peptide/protein contains the respective sortase recognition sequences. FIG. 54 shows a schematic of a screening assay to identify peptides that effect efficient endosomal escape of an agent (e.g., Cre recombinase) after delivery to a cell by a supercharged protein (e.g. +36 GFP). In the example shown, the Cre recombinase carries a sortase recognition sequence (LPETG, SEQ ID NO: 108). When combined with a library of candidate peptides, carrying a second sortase recognition sequence (GGGG, SEQ ID NO: 109), the sortase-mediated peptide-conjugation reaction yields peptide-conjugated supercharged protein/agent complexes. Peptides effecting efficient endosomal escape can be identified by incubating these complexes with cells harboring a suitable reporter construct (e.g., loxP-luciferase). Weak reporter signal indicates poor endosomal escape of the respective complex, while strong reporter signal indicates efficient endosomal escape.

Sortase enzymes, recognition sequences, and sortase-mediated protein ligation strategies and methods are well known to those of skill in the art (see, e.g., Proft, "Sortase-mediated protein ligation: an emerging biotechnology tool for protein modification and immobilization" Biotechnol Lett. 2010 January; 32(1):1-10, incorporated herein by reference for disclosure of methods and reagents for sortase-mediated protein ligation).

Delivery of Proteins Non-Covalently Associated with Supercharged Protein

Figure 46:
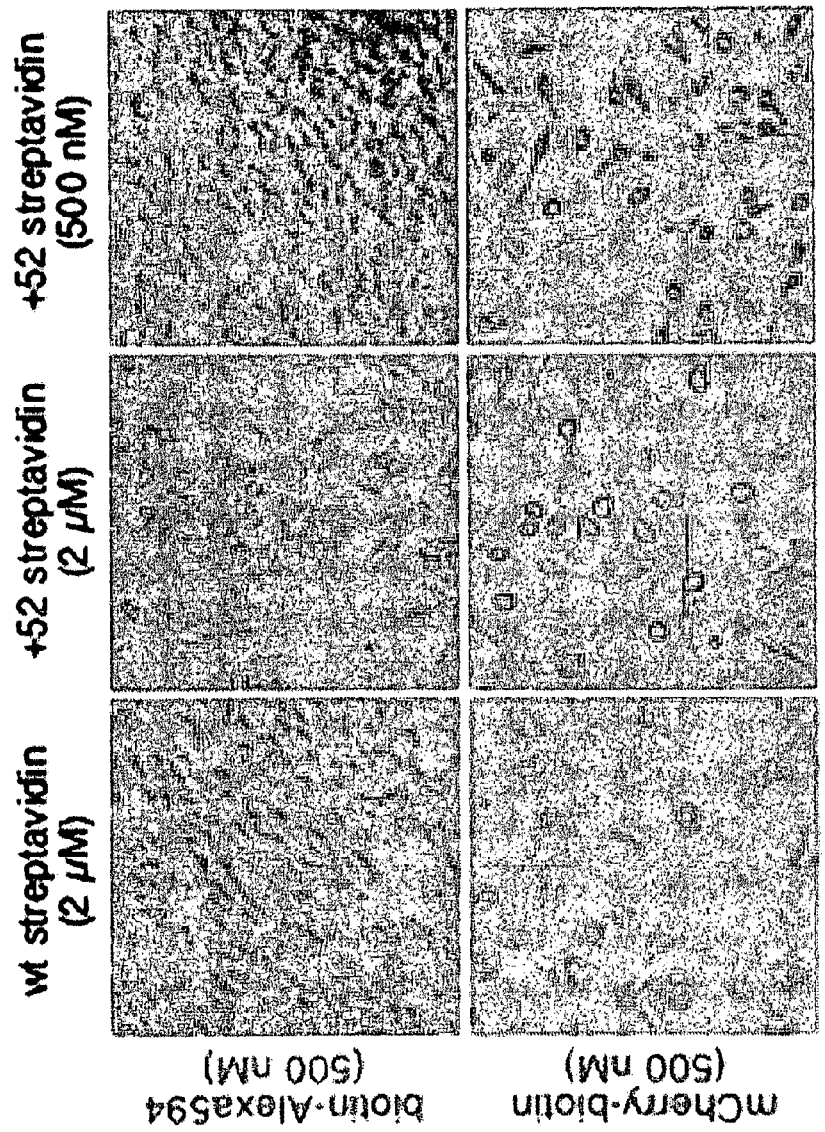
FIG. 46. Delivery of proteins non-covalently associated with supercharged protein. +52 streptavidin delivers biotinylated small molecules and biotinylated protein into cells.

To determine, whether supercharged proteins can deliver non-covalently bound agents, for example, a non-covalently bound small molecule or a non-covalently bound protein; cells were treated with +52 streptavidin non-covalently bound to biotinylated Alexa594 or biotinylated mCherry at a concentration of 2 µM and 500 nM (FIG. 46). Wild type streptavidin was used as a control. +52 streptavidin delivered biotinylated small molecules and biotinylated protein into cells. These results expand the scope of deliverable molecules to agents, like small molecules and proteins, that cannot covalently bound to or expressed as a fusion with a supercharged protein. As evidenced above, such agents can efficiently be delivered when bound non-covalently to a supercharged protein.

Discussion

The development of more effective protein delivery methods would expand and enhance opportunities for studying and manipulating biological pathways. Our findings establish that superpositively charged GFP, when fused to a variety of proteins, can deliver proteins quickly and efficiently into a variety of mammalian cells. The cell-penetrating ability of +36 GFP tolerates translational fusion to mCherry, ubiquitin, and Cre recombinase. Supercharged GFP can deliver these proteins into mammalian cells at low nanomolar concentrations and in minutes. In a side-by-side comparison across three mammalian cell types, supercharged GFP delivered ~10- to 100-fold more fused mCherry than either Tat or $Arg_9$, two widely used cell-penetrating peptides. Likewise, products of Cre recombinase activity were observed with greater frequency in HeLa cells, mouse 3T3 cells, and mES cells treated with +36 GFP-Cre fusions than in the same cells treated with the same concentrations of Tat-Cre or $Arg_9$-Cre fusions.

The delivery of ubiquitin-+36 GFP fusions in a manner that resulted in deubiquitination by cytosolic DUBs indicates that fusion proteins delivered in this manner are capable of accessing the cytosol and are not limited to endosomal localization. Likewise, the ability of +36 GFP-Cre fusions to effect recombination in the nucleus further establishes that these fusions can access non-endosomal regions of mammalian cells when proteolytically labile linkers are used to connect +36 GFP and the protein of interest.

It was previously reported that the capacity of scGFPs to penetrate mammalian cells increases as a function of theoretical net charge even at charges as high as +25 and +36. U.S. Provisional Application Nos. 61/173,430 and 61/105,287, and PCT Application PCT/US2009/041984, incorporated herein by reference. This property contrasts with peptidic PTDs such as arginine oligomers, which have been observed to lose mammalian cell penetration ability when their net theoretical charge exceeds +15 (Mitchell et al., J. Pept. Res. 56, 318-325, 2000). The cell penetration potency of +36 GFP may therefore be due in part to charge distribution over a comparatively large area, which may provide a more stable and extended cationic surface that interacts more effectively with mammalian cells. The significantly greater potency of +36 GFP mediated protein delivery compared with that of Tat and $Arg_9$ may also be a consequence of its structure. Unlike the globular β-barrel of GFP, the nine-residue Tat peptide and $Arg_9$ peptides are unlikely to be well-folded, although the former has been observed to adopt a structure similar to a poly(proline) II helix (Ruzza et al., J. Pept. Sci. 10, 423-426, 2004).

The detailed mechanism by which +36 GFP protein fusions can escape endosomes before or after proteolytic cleavage from +36 GFP remains to be determined. One possibility is that the high concentration of ionizable groups in +36 GFP (including 72 basic amino acids, predominantly at surface-exposed positions) buffers endosomes during acidification, promoting endosome swelling and endosomal leakage. This mechanism has been previously implicated in the release of macromolecules delivered by synthetic polyamines (Boussif et al., Proc. Natl. Acad. Sci. U.S.A. 92, 7297-7301, 1995; Sonawane et al., J. Biol. Chem. 278, 44826-44831, 2003). Protein escape may also result from the stochastic leakage of proteins from endosomes packed with large amounts of the +36 GFP fusion protein. Endosomal integrity may vary according to cell type and may explain differences in functional protein delivery efficiency. As enhanced endosomal escape has been reported in the presence of the anionic lipid-like small molecule pyrene butyrate (Takeuchi et al., ACS Chem. Bio. 1, 299-303, 2006), it is also possible that anionic lipids from E. coli may co-purify with a +36 GFP fusion and enhance endosomal escape.

Although +36 GFP is considerably larger than Tat or $Arg_9$ (29 kDa vs~1 kDa), +36 GFP can be fused to proteins of interest via a proteolytically labile linker so that the proteins can exist intracellularly in a relatively unmodified form. Cleavage of such a linker decreased GFP fluorescence quenching and FRET in the case of the +36 GFP-mCherry fusion, and restored Cre recombinase activity in vitro Methods Design, Expression, and Purification of Protein Fusions.

Protein fusions involving +36 GFP were constructed as: +36 GFP-$(GGS)_4$-ALAL-$(GGS)_4$-mCherry-$His_6$ (SEQ ID NO: 112); +36 GFP-$(GGS)_4$-ALAL$(GGS)_4$-Cre-$His_6$ (SEQ ID NO: 147); and $His_6$-Ubiquitin-+36 GFP (SEQ ID NO: 113). Tat fusions were constructed as Tat-T7 tag-(protein of interest)-$His_6$ (Wadia et al., Nat. Med. 10, 310-315, 2004). $Arg_9$ fusions were constructed similar to previously used polyarginine-tagged proteins[7], in the form $His_6$-(protein of interest)-$(GGGS)_2$-$Arg_9$ (SEQ ID NO: 157). Complete protein sequences are listed elsewhere herein. Genes encoding each fusion were cloned into a pET vector and transformed into BL21(DE3) E. coli. Cells were grown in 1 L LB cultures at 37° C. to $OD_{600}$=~0.6 and induced with 1 mM IPTG at 30° C. for 4 h. Cells were harvested by centrifugation, resuspended in 40 mL PBS+2M NaCl, and lysed by sonication.

The lysate was cleared by centrifugation (10,000 G, 8 min) and the supernatant was mixed with 1 mL of Ni-NTA agarose resin (Qiagen) for 30 minutes at 4° C. on a rotating drum. The resin was recovered by centrifugation (10,000 G, 8 min), resuspended in 20 mL PBS+2 M NaCl, and packed into a 5 mL syringe containing a glass wool plug. The resin was washed with 15 mL of PBS containing 2 M NaCl and 20 mM imidazole. The protein fusion was eluted with 3 mL PBS containing 2 M NaCl and 500 mM imidazole. The eluate was immediately dialyzed against PBS+1 M NaCl at 4° C. for one hour. All fusions except for the +36 GFP-Cre protein were dialyzed against PBS at 4° C. overnight; the +36 GFP-Cre fusion was dialyzed against PBS+500 mM NaCl to minimize precipitation. Tat Cre and $Arg_9$ Cre fusions were stored at −20° C. in 20% glycerol. Purified GFPs were centrifuged after dialysis to remove any precipitated protein or contaminants and quantitated by absorbance at 488 nm assuming an extinction coefficient of $8.33\times10^4 M^{-1} cm^{-1}$ (Pedelacq et al., Nat. Biotechnol. 24, 79-88, 2006). Purified mCherry fusions were quantified by absorbance at 587 nm assuming an extinction coefficient of $7.2\times10^4 M^{-1} cm^{-1}$ (Shaner et al., Nat. Biotechnol. 22, 1567-1572, 2004). Tat-Cre and Arg_ Cre were quantified using a Modified Lowry Protein Assay Kit (Pierce). Proteins were evaluated by SDS-PAGE analysis (FIG. 39).

Cell Culture

HeLa, IMCD and PC12 cells were cultured in Dulbecco's modification of Eagle's medium (DMEM, Sigma) with 10% fetal bovine serum (FBS, Sigma), 2 mM glutamine, 5 I.U. penicillin, and 5 µg/mL streptamycin. All cells were cultured at 37° C. with 5% $CO_2$. PC12 cells were purchased from ATCC.

Fixed-Cell Imaging

Cells were plated directly onto glass cover slips in a six-well tissue culture plate at a density of $10^6$ cells per well. After 12 h, cells were washed once with cold PBS and incubated with protein in serum-free DMEM. Cells were washed three times with 20 U/mL heparin PBS to remove membrane-bound protein, fixed in 4% formaldehyde in PBS, stained with DAPI, and imaged with an Olympus IX71 spinning disk confocal microscope. GFP and mCherry were visualized by confocal laser microscopy with a 491 nm and 561 nm excitation laser, respectively. DAPI stain was imaged by widefield fluorescence. Images were prepared using OpenLab software (Improvision).

Cathepsin B-Mediated Linker Cleavage.

The +36 GFP mCherry and +36 GFP Cre fusion was cleaved by incubating 30 pmol of protein in 10 µL of 20 mM MES, pH 6.5 with 500 ng of cathepsin B from human liver (Sigma) at 37° C. for 45 mm. A µL aliquot of the +36 GFP Cre fusion cleavage reaction was used for the Cre recombinase in vitro assay; the remaining 9 µL were used for Western blot analysis. Anti-GFP (1/10,000 dilution, ab290) and anti Cre (1/2,000 dilution, ab24607) primary antibodies were purchased from Abcam. Anti-mCherry primary antibody (1/2,000 dilution, 632393) was purchased from Clontech. Western blots were performed as described above.

Deubiquitination Assay.

HeLa cells were seeded in a 24-well tissue culture plate at a density of 100,000 cells per well. After 12 h, cells were washed once with PBS and incubated either with ubiquitin-+36 GFP or with ubiquitin(G76V)-+36 GFP at 500 nM in serum free DMEM for 1 hour at 37° C. Cells were washed three times with 20 U/mL heparin PBS to remove cell surface-bound protein. Cells were incubated with 250 µL of ice-cold PBS, allowed to detach from the plate, lysed by adding 250 µL of denaturing LDS Sample Buffer (Invitrogen) to the well, transferred to a microcentrifuge tube, heated at 95° C. for 10 minutes, and loaded on a 12% SDSPAGE gel. Alternatively, untreated cells were washed and lysed as described with 100 pmoles of ubiquitin-+36 GFP or ubiquitin (G76V)-+36 GFP spiked into the denaturing LDS Sample Buffer. Crude HeLa cytosolic extract was prepared by harvesting cells with a cell scraper and lysing in non-denaturing 0.5% Triton X-100 containing 1.7 µg/mL aprotinin, 10 µg/mL leupeptin, and 1 mM PMSF. The lysate was cleared by centrifugation (13,000 G, 10 minutes) to yield the cytosolic fraction. 50 fmol of either ubiquitin-+36 GFP or ubiquitin (G76V)-+36 GFP was added to 250 µL of lysate and incubated at 37° C. for 30 minutes either with or without the addition of 10 mM N-ethylmaleimide.

Cre Recombinase Cellular Assay.

Cre fusions were assayed for activity in HeLa cells using pCALNL-DsRed2. HeLa cells were transiently transfected with pCALNL-DsRed2 using Effectene (Qiagen) using the manufacturer's protocol. 24 h after transfection, purified Cre fusion proteins were added into serum-free DMEM, incubated at room temperature for 5 minutes and applied to cells. Cells were incubated for 4 h at 37° C. and washed three times with 20 U/mL heparin PBS to remove membrane-bound protein. 24 h after protein treatment, cells were assayed for recombination by flow cytometry and live-cell microscopy.

Cre fusions were assayed for in vivo activity in 3T3 cells containing an integrated β-galactosidase-based Cre reporter (S. Dowdy, UCSD). 3T3.loxP.lacZ cells were treated with Cre protein fusions in complete medium. 24 h after treatment, cells were fixed in 4% formaldehyde in PBS and stained for β-galactosidase activity using the Promega In Situ β-Galactosidase Staining Kit. The number of recombinants was quantitated by counting X-gal-stained cells. Cre fusions were assayed for activity in mouse embryonic stem (mES) cells using an integrated foxed mCherry reporter (D. Melton, Harvard University). mES cells were harvested by trypsinization and MEF depletion over gelatinized plates. The MEF-depleted mES cells were seeded in gelatinized 12-well plates at 200,000 cells per well. 24 h after seeding, mES colonies were treated with purified Cre fusion proteins for 4 h in serum-free medium. Cells were washed in heparin PBS, and incubated in full mES culture media for and additional 24 h, harvested by trypsinization, and analyzed by flow cytometry.

Deubiquitination Assay Western Blot

Samples were analyzed on a 12% SDS PAGE (Invitrogen) gel and transferred by electroblotting onto a PVDF membrane (Millipore) pre-soaked in methanol. Membranes were blocked in 5% milk for 1 h, and incubated in primary antibody in 3% BSA for 30 minutes at room temperature. Anti-GFP (1/10,000 dilution, ab290) and anti-$His_6$ (1/2,500 dilution, ab18184) primary antibodies were purchased from Abeam. The membrane was washed three times with PBS and treated with the secondary antibodies, IRDye 800CW Goat Anti-Mouse IgG (1/10,000 dilution, Li-COR Biosciences) and IRDye 680 Goat Anti-Rabbit IgG (1/10,000 dilution, Li-COR Biosciences), in blocking buffer (Li-COR Biosciences) for 30 minutes. The membrane was washed three times with 50 mM Tris, pH 7.4 containing 150 mM NaCl and 0.05% Tween-20 and visualized using an Odyssey infrared imaging system (Li-COR Biosciences). Images were analyzed using Odyssey imaging software version 2.0.

Cathepsin B-Mediated Linker Cleavage

The +36 GFP mCherry and +36 GFP Cre fusion was cleaved by incubating 30 µmol of protein in 10 µL of 20 mM MES, pH 6.5 with 500 ng of cathepsin B from human liver (Sigma) at 37° C. for 45 min. A 1 µL aliquot of the +36 GFP Cre fusion cleavage reaction was used for the Cre recombinase in vitro assay; the remaining 9 µL were used for Western blot analysis.

Anti-GFP (1/10,000 dilution, ab290) and anti Cre (1/2,000 dilution, ab24607) primary antibodies were purchased from Abcam. Anti-mCherry primary antibody (1/2,000 dilution, 632393) was purchased from Clontech. Western blots were performed as described above.

Protein Sequences stGFP:
(SEQ ID NO: 110)
MGHHHHHHGGASKGEELFTGVVPILVELDGDVNGHKFSVRGEGEGDATNG
KLTLKFICTTGKLPVPWPTLVTTLTYGVQCFSRYPDHMKQHDFFKSAMPE
GYVQERTISFKDDGTYKTRAEVKFEGDTLVNRIELKGIDFKEDGNILGHK
LEYNFNSHNVYITADKQKNGIKANFKIRHNVEDGSVQLADHYQQNTPIGD
GPVLLPDNHYLSTQSALSKDPNEKRDHMVLLEFVTAAGITHGMDELYK Examples of Supercharged GFPs and Fusion Proteins:

+36 GFP:
(SEQ ID NO: 111)
MGHHHHHHGGASKGERLFRGKVPILVELKGDVNGHKFSVRGKGKGDATRG
KLTLKFICTTGKLPVPWPTLVTTLTYGVQCFSRYPKHMKRHDFFKSAMPK
GYVQERTISFKKDGKYKTRAEVKFEGRTLVNRIKLKGRDFKEKGNILGHK
LRYNFNSHKVYITADKRKNGIKAKFKIRHNVKDGSVQLADHYQQNTPIGR
GPVLLPRNHYLSTRSKLSKDPKEKRDHMVLLEFVTAAGIKHGRDERYK

+36 GFP-mCherry:
(SEQ ID NO: 112)
MASKGERLFRGKVPILVELKGDVNGHKFSVRGKGKGDATRGKLTLKFICT
TGKLPVPWPTLVTTLTYGVQCFSRYPKHMKRHDFFKSAMPKGYVQERTIS
FKKDGKYKTRAEVKFEGRTLVNRIKLKGRDFKEKGNILGHKLRYNFNSHK
VYITADKRKNGIKAKFKIRHNVKDGSVQLADHYQQNTPIGRGPVLLPRNH
YLSTRSKLSKDPKEKRDHMVLLEFVTAAGIKHGRDERYKGGSGGSGGSGG
SALALGGSGGSGGSGGSVSKGEEDNMAIIKEFMRFKVHMEGSVNGHEFEI
EGEGEGRPYEGTQTAKLKVTKGGPLPFAWDILSPQFMYGSKAYVKHPADI
PDYLKLSFPEGFKWERVMNFEDGGVVTVTQDSSLQDGEFIYKVKLRGTNF
PSDGPVMQKKTMGWEASSERMYPEDGALKGEIKQRLKLKDGGHYDAEVKT
TYKAKKPVQLPGAYNVNIKLDITSHNEDYTIVEQYERAEGRHSTGGMDEL
YKLEHHHHHH H39 GFP (His39 GFP):
(SEQ ID NO: 133)
MGASKGEHLFHGHVPILVELHGDVNGHKFSVRGHGHGDATHGKLTLKFIC
TTGKLPVPWPTLVTTLTYGVQCFSRYPHHMKHHDFFKSAMPHGYVQERTI
SFKHDGHYKTRAEVKFEGHTLVNRIHLKGHDFKEHGNILGHKLHYNFNSH
HVYITADKHKNGIKAHFKIRHNVHDGSVQLADHYQQNTPIGHGPVLLPHN
HYLSTHSHLSKDPHEKRDHMVLLEFVTAAGIHHGHDEHYK Ubiquitin- +36 GFP:
(SEQ ID NO: 113)
MGHHHHHHGGMQIFVKTLTGKTITLEVEPSDTIENVKAKIQDKEGIPPDQ
QRLIFAGKQLEDGRTLSDYNIQKESTLHLVLRLRGGASKGERLFRGKVPI
LVELKGDVNGHKFSVRGKGKGDATRGKLTLKFICTTGKLPVPWPTLVTTL
TYGVQCFSRYPKHMKRHDFFKSAMPKGYVQERTISFKKDGKYKTRAEVKF
EGRTLVNRIKLKGRDFKEKGNILGHKLRYNFNSHKVYITADKRKNGIKAK
FKIRHNVKDGSVQLADHYQQNTPIGRGPVLLPRNHYLSTRSKLSKDPKEK
RDHMVLLEFVTAAGIKHGRDERYK Ubiquitin G76V- +36 GFP:
(SEQ ID NO: 114)
MGHHHHHHGGMQIFVKTLIGKTITLEVEPSDTIENVKAKIQDKEGIPPDQ
QRLIFAGKQLEDGRTLSDYNIQKESTLHLVLRLRGVASKGERLFRGKVPI
LVELKGDVNGHKFSVRGKGKGDATRGKLTLKFICTTGKLPVPWPTLVTTL
TYGVQCFSRYPKHMKRHDFFKSAMPKGYVQERTISFKKDGKYKTRAEVKF
EGRTLVNRIKLKGRDFKEKGNILGHKLRYNFNSHKVYITADKRKNGIKAK
FKIRHNVKDGSVQLADHYQQNTPIGRGPVLLPRNHYLSTRSKLSKDPKEK
RDHMVLLEFVTAAGIKHGRDERYK +36 GFP-Cre:
(SEQ ID NO: 115)
MASKGERLFRGKVPILVELKGDVNGHKFSVRGKGKGDATRGKLTLKFICT
TGKLPVPWPTLVTTLTYGVQCFSRYPKHMKRHDFFKSAMPKGYVQERTIS
FKKDGKYKTRAEVKFEGRTLVNRIKLKGRDFKEKGNILGHKLRYNFNSHK
VYITADKRKNGIKAKFKIRHNVKDGSVQLADHYQQNTPIGRGPVLLPRNH
YLSTRSKLSKDPKEKRDHMVLLEFVTAAGIKHGRDERYKGGSGGSGGSGG
SALALGGSGGSGGSGGSMASNLLTVHQNLPALPVDATSDEVRKNLMDMFR
DRQAFSEHTWKMLLSVCRSWAAWCKLNNRKWFPAEPEDVRDYLLYLQARG
LAVKTIQQHLGQLNMLHRRSGLPRPSDSNAVSLVMRRIRKENVDAGERAK
QALAFERTDFDQVRSLMENSDRCQDIRNLAFLGIAYNTLLRIAEIARIRV
KDISRTDGGRMLIHIGRTKTLVSTAGVEKALSLGVTKLVERWISVSGVAD
DPNNYLFCRVRKNGVAAPSATSQLSTRALEGIFEATHRLIYGAKDDSGQR
YLAWSGHSARVGAARDMARAGVSIPEIMQAGGWTNVNIVMNYIRNLDSET
GAMVRLLEDGDHHHHHH +36 GFP-(GGS)4-ALAL-(GGS)4-Cre:
(SEQ ID NO: 147)
MASKGERLFRGKVPILVELKGDVNGHKFSVRGKGKGDATRGKLTLKFICT
TGKLPVPWPTLVTTLTYGVQCFSRYPKHMKRHDFFKSAMPKGYVQERTIS
FKKDGKYKTRAEVKFEGRTLVNRIKLKGRDFKEKGNILGHKLRYNFNSHK
VYITADKRKNGIKAKFKIRHNVKDGSVQLADHYQQNTPIGRGPVLLPRNH
YLSTRSKLSKDPKEKRDHMVLLEFVTAAGIKHGRDERYKGGSGGSGGSGG
SALALGGSGGSGGSGGSMASNLLTVHQNLPALPVDATSDEVRKNLMDMFR
DRQAFSEHTWKMLLSVCRSWAAWCKLNNRKWFPAEPEDVRDYLLYLQARG
LAVKTIQQHLGQLNMLHRRSGLPRPSDSNAVSLVMRRIRKENVDAGERAK
QALAFERTDFDQVRSLMENSDRCQDIRNLAFLGIAYNTLLRIAEIARIRV
KDISRTDGGRMLIHIGRTKTLVSTAGVEKALSLGVTKLVERWISVSGVAD
DPNNYLFCRVRKNGVAAPSATSQLSTRALEGIFEATHRLIYGAKDDSGQR
YLAWSGHSARVGAARDMARAGVSIPEIMQAGGWTNVNIVMNYIRNLDSET
GAMVRLLEDGDHHHHHH PTD Fusion Proteins:

Tat-stGFP:
(SEQ ID NO: 116)
MGRKKRRQRRRGHMASMTGGQQMGRDPASKGEELFTGVVPILVELDGDVN
GHKFSVRGEGEGDATNGKLTLKFICTTGKLPVPWPTLVTTLTYGVQCFSR
YPDHMKQHDFFKSAMPEGYVQERTISFKDDGTYKTRAEVKFEGDTLVNRI
ELKGIDFKEDGNILGHKLEYNFNSHNVYITADKQKNGIKANFKIRHNVED
GSVQLADHYQQNTPIGDGPVLLPDNHYLSTQSALSKDPNEKRDHMVLLEF
VTAAGITHGMDELYKAAALEHHHHHH

Tat-mCherry:
(SEQ ID NO: 117)
MGRKKRRQRRRGHMASMTGGQQMGRDPNSVSKGEEDNMAIIKEFMRFKVH
MEGSVNGHEFEIEGEGEGRPYEGTQTAKLKVTKGGPLPFAWDILSPQFMY
GSKAYVKHPADIPDYLKLSFPEGFKWERVMNFEDGGVVTVTQDSSLQDGE
FIYKVKLRGTNFPSDGPVMQKKTMGWEASSERMYPEDGALKGEIKQRLKL
KDGGHYDAEVKITYKAKKPVQLPGAYNVNIKLDITSHNEDYTIVEQYERA
EGRHSTGGMDELYKARGAAALEHHHHHH mCherry-Arg9:
(SEQ ID NO: 118)
MGHHHHHHGGASKGEEDNMAIIKEFMRFKVHMEGSVNGHEFEIEGEGEGR
PYEGTQTAKLKVTKGGPLPFAWDILSPQFMYGSKAYVKHPADIPDYLKLS
FPEGFKWERVMNFEDGGVVTVTQDSSLQDGEFIYKVKLRGTNFPSDGPVM
QKKTMGWEASSERMYPEDGALKGEIKQRLKLKDGGHYDAEVKTTYKAKKP
VQLPGAYNVNIKLDITSHNEDYTIVEQYERAEGRHSTGGMDELYKARGGG
SGGGSRRRRRRRRR Arg10-mCherry:
(SEQ ID NO: 142)
MRRRRRRRRRGGSGGSGGSGGSGGSGGSGGSGGSGGSVSKGEEDNMAII
KEFMRFKVHMEGSVNGHEFEIEGEGEGRPYEGTQTAKLKVTKGGPLPFAW
DILSPQFMYGSKAYVKHPADIPDYLKLSFPEGFKWERVMNFEDGGVVTVT
QDSSLQDGEFIYKVKLRGTNFPSDGPVMQKKTMGWEASSERMYPEDGALK
GEIKQRLKLKDGGHYDAEVKTTYKAKKPVQLPGAYNVNIKLDITSHNEDY
TIVEQYERAEGRHSTGGMDELYKLEHHHHHH penetratin-mCherry:
(SEQ ID NO: 143)
MRQIKIWFQNRRMKWKKGGSGGSGGSGGSGGSGGSGGSGGSGGSVSKGEE
DNMAIIKEFMRFKVHMEGSVNGHEFEIEGEGEGRPYEGTQTAKLKVTKGG
PLPFAWDILSPQFMYGSKAYVKHPADIPDYLKLSFPEGFKWERVMNFEDG
GVVTVTQDSSLQDGEFIYKVKLRGTNFPSDGPVMQKKTMGWEASSERMYP
EDGALKGEIKQRLKLKDGGHYDAEVKTTYKAKKPVQLPGAYNVNIKLDIT
SHNEDYTIVEQYERAEGRHSTGGMDELYKLEHHHHHH Tat-Cre:
(SEQ ID NO: 119)
MGRKKRRQRRRGHMASMTGGQQMGRDPNSMSNLLTVHQNLPALPVDATSD
EVRKNLMDMFRDRQAFSEHTWKMLLSVCRSWAAWCKLNNRKWFPAEPEDV
RDYLLYLQARGLAVKTIQQHLGQLNMLHRRSGLPRPSDSNAVSLVMRRIR
KENVDAGERAKQALAFERTDFDQVRSLMENSDRCQDIRNLAFLGIAYNTL
LRIAEIARIRVKDISRTDGGRMLIHIGRTKTLVSTAGVEKALSLGVTKLV
ERWISVSGVADDPNNYLFCRVRKNGVAAPSATSQLSTRALEGIFEATHRL
IYGAKDDSGQRYLAWSGHSARVGAARDMARAGVSIPEIMQAGGWTNVNIV
MNYIRNLDSETGAMVRLLEDGDAAALEHHHHHH Cre-Arg9:
(SEQ ID NO: 120)
MGHHHHHHGGASMSNLLTVHQNLPALPVDATSDEVRKNLMDMFRDRQAFS
EHTWKMLLSVCRSWAAWCKLNNRKWFPAEPEDVRDYLLYLQARGLAVKTI
QQHLGQLNMLHRRSGLPRPSDSNAVSLVMRRIRKENVDAGERAKQALAFE
RTDFDQVRSLMENSDRCQDIRNLAFLGIAYNTLLRIAEIARIRVKDISRT
DGGRMLIHIGRTKTLVSTAGVEKALSLGVTKLVERWISVSGVADDPNNYL
FCRVRKNGVAAPSATSQLSTRALEGIFEATHRLIYGAKDDSGQRYLAWSG
HSARVGAARDMARAGVSIPEIMQAGGWTNVNIVMNYIRNLDSETGAMVRL
LEDGDRGGSGGGSRRRRRRRRR Tat-Cre (FIG. 52 and 53):
(SEQ ID NO: 144)
MGRKKRRQRRRGGSGGSGGSGGSGGSGGSGGSGGSMASNLLTVHQNL
PALPVDATSDEVRKNLMDMFRDRQAFSEHTWKMLLSVCRSWAAWCKLNNR
KWFPAEPEDVRDYLLYLQARGLAVKTIQQHLGQLNMLHRRSGLPRPSDSN
AVSLVMRRIRKENVDAGERAKQALAFERTDFDQVRSLMENSDRCQDIRNL
AFLGIAYNTLLRIAEIARIRVKDISRTDGGRMLIHIGRTKTLVSTAGVEK
ALSLGVTKLVERWISVSGVADDPNNYLFCRVRKNGVAAPSATSQLSTRAL
EGIFEATHRLIYGAKDDSGQRYLAWSGHSARVGAARDMARAGVSIPEIMQ
AGGWTNVNIVMNYIRNLDSETGAMVRLLEDGDHHHHHH Arg10-Cre:
(SEQ ID NO: 145)
MRRRRRRRRRGGSGGSGGSGGSGGSGGSGGSGGSGGSMASNLLTVHQNL
PALPVDATSDEVRKNLMDMFRDRQAFSEHTWKMLLSVCRSWAAWCKLNNR
KWFPAEPEDVRDYLLYLQARGLAVKTIQQHLGQLNMLHRRSGLPRPSDSN
AVSLVMRRIRKENVDAGERAKQALAFERTDFDQVRSLMENSDRCQDIRNL
AFLGIAYNTLLRIAEIARIRVKDISRTDGGRMLIHIGRTKTLVSTAGVEK
ALSLGVTKLVERWISVSGVADDPNNYLFCRVRKNGVAAPSATSQLSTRAL
EGIFEATHRLIYGAKDDSGQRYLAWSGHSARVGAARDMARAGVSIPEIMQ
AGGWTNVNIVMNYIRNLDSETGAMVRLLEDGDHHHHHH penetratin-Cre:
(SEQ ID NO: 146)
MRQIKIWFQNRRMKWKKGGSGGSGGSGGSGGSGGSGGSGGSGGSMASNLL
TVHQNLPALPVDATSDEVRKNLMDMFRDRQAFSEHTWKMLLSVCRSWAAW
CKLNNRKWFPAEPEDVRDYLLYLQARGLAVKTIQQHLGQLNMLHRRSGLP
RPSDSNAVSLVMRRIRKENVDAGERAKQALAFERTDFDQVRSLMENSDRC
QDIRNLAFLGIAYNTLLRIAEIARIRVKDISRTDGGRMLIHIGRTKTLVS
TAGVEKALSLGVTKLVERWISVSGVADDPNNYLFCRVRKNGVAAPSATSQ
LSTRALEGIFEATHRLIYGAKDDSGQRYLAWSGHSARVGAARDMARAGVS
IPEIMQAGGWTNVNIVMNYIRNLDSETGAMVRLLEDGDHHHHHH Tat-T7 tag-mCherry:
(SEQ ID NO: 148)
MGRKKRRQRRRGHMASMTGGQQMGRDPNSVSKGEEDNMAIIKEFMRFKVH
MEGSVNGHEFEIEGEGEGRPYEGTQTAKLKVTKGGPLPFAWDILSPQFMY
GSKAYVKHPADIPDYLKLSFPEGFKWERVMNFEDGGVVTVTQDSSLQDGE
FIYKVKLRGTNFPSDGPVMQKKTMGWEASSERMYPEDGALKGEIKQRLKL
KDGGHYDAEVKITYKAKKPVQLPGAYNVNIKLDITSHNEDYTIVEYERAE
GRHSTGGMDELYKARGAAALEHHHHHH Tat-T7 tag-Cre:
(SEQ ID NO: 149)
MGRKKRRQRRRGHMASMTGGQQMGRDPNSMSNLLTVHQNLPALPVDATSD
EVRKNLMDMFRDRQAFSEHTWKMLLSVCRSWAAWCKLNNRKWFPAEPEDV
RDYLLYLQARGLAVKTIQQHLGQLNMLHRRSGLPRPSDSNAVSLVMRRIR
KENVDAGERAKQALAFERTDFDQVRSLMENSDRCQDIRNLAFLGIAYNTL
LRIAEIARIRVKDISRTDGGRMLIHIGRTKTLVSTAGVEKALSLGVTKLV
ERWISVSGVADDPNNYLFCRVRKNGVAAPSATSQLSTRALEGIFEATHRL
IYGAKDDSGQRYLAWSGHSARVGAARDMARAGVSIPEIMQAGGWTNVNIV
MNYIRNLDSETGAMVRLLEDGDAAALEHHHHHH

Examples of Naturally Occurring Superpositively Charged Human Proteins and Fusion Proteins:

HRX (UNIPROT: Q03164 PDB: 2J2S)
HRX-(GGS)$_9$-mCherry-His$_6$
(SEQ ID NO: 121)
MVKKGRRSRRCGQCPGCQVPEDCGVCTNCLDKPKFGGRNIKKQCCKMRKC
QNLQWMPSKAYLQKQAKAVKGGSGGSGGSGGSGGSGGSGGSGGSGGSVSK
GEEDNMAIIKEFMRFKVHMEGSVNGHEFEIEGEGEGRPYEGTQTAKLKVT
KGGPLPFAWDILSPQFMYGSKAYVKHPADIPDYLKLSFPEGFKWERVMNF
EDGGVVTVTQDSSLQDGEFIYKVKLRGTNFPSDGPVMQKKTMGWEASSER
MYPEDGALKGEIKQRLKLKDGGHYDAEVKTTYKAKKPVQLPGAYNVNIKL
DITSHNEDYTIVEQYERAEGRHSTGGMDELYKLEHHHHHH HRX-(GGS)$_9$-Cre-His$_6$
(SEQ ID NO: 122)
MVKKGRRSRRCGQCPGCQVPEDCGVCINCLDKPKFGGRNIKKQCCKMRKC
QNLQWMPSKAYLQKQAKAVKGGSGGSGGSGGSGGSGGSGGSGGSGGSMAS
NLLTVHQNLPALPVDATSDEVRKNLMDMFRDRQAFSEHTWKMLLSVCRSW
AAWCKLNNRKWFPAEPEDVRDYLLYLQARGLAVKTIQQHLGQLNMLHRRS
GLPRPSDSNAVSLVMRRIRKENVDAGERAKQALAFERTDFDQVRSLMENS
DRCQDIRNLAFLGIAYNTLLRIAEIARIRVKDISRTDGGRMLIHIGRTKT
LVSTAGVEKALSLGVTKLVERWISVSGVADDPNNYLFCRVRKNGVAAPSA
TSQLSTRALEGIFEATHRLIYGAKDDSGQRYLAWSGHSARVGAARDMARA
GVSIPEIMQAGGWTNVNIVMNYIRNLDSETGAMVRLLEDGDHHHHHH C-JUN (UNIPROT: P05412 PDB: 1JNM)
C-JUN -(GGS)$_9$-mCherry-His$_6$
(SEQ ID NO: 123)
MKAERKRMRNRIAASKSRKRKLERIARLEEKVKTLKAQNSELASTANMLR
EQVAQLKQKVMNHGGSGGSGGSGGSGGSGGSGGSGGSGGSVSKGEEDNMA
IIKEFMRFKVHMEGSVNGHEFEIEGEGEGRPYEGTQTAKLKVTKGGPLPF
AWDILSPQFMYGSKAYVKHPADIPDYLKLSFPEGFKWERVMNFEDGGVVT
VTQDSSLQDGEFIYKVKLRGTNFPSDGPVMQKKTMGWEASSERMYPEDGA
LKGEIKQRLKLKDGGHYDAEVKTTYKAKKPVQLPGAYNVNIKLDITSHNE
DYTIVEQYERAEGRHSTGGMDELYKLEHHHHHH C-JUN -(GGS)$_9$-Cre-His$_6$
(SEQ ID NO: 124)
MKAERKRMRNRIAASKSRKRKLERIARLEEKVKTLKAQNSELASTANMLR
EQVAQLKQKVMNHGGSGGSGGSGGSGGSGGSGGSGGSGGSMASNLLTVHQ
NLPALPVDATSDEVRKNLMDMFRDRQAFSEHTWKMLLSVCRSWAAWCKLN
NRKWFPAEPEDVRDYLLYLQARGLAVKTIQQHLGQLNMLHRRSGLPRPSD
SNAVSLVMRRIRKENVDAGERAKQALAFERTDFDQVRSLMENSDRCQDIR
NLAFLGIAYNTLLRIAEIARIRVKDISRTDGGRMLIHIGRTKTLVSTAGV
EKALSLGVTKLVERWISVSGVADDPNNYLFCRVRKNGVAAPSATSQLSTR
ALEGIFEATHRLIYGAKDDSGQRYLAWSGHSARVGAARDMARAGVSIPEI
MQAGGWTNVNIVMNYIRNLDSETGAMVRLLEDGDHHHHHH DEFENSIN 3 (UNIPROT: P81534 PDB: 1KJ6)
DEFENSIN 3 -(GGS)$_9$-mCherry-His$_6$
(SEQ ID NO: 125)
MGIINTLQKYYCRVRGGRCAVLSCLPKEEQIGKCSTRGRKCCRRKKGGSG
GSGGSGGSGGSGGSGGSGGSGGSVSKGEEDNMAIIKEFMRFKVHMEGSVN
GHEFEIEGEGEGRPYEGTQTAKLKVTKGGPLPFAWDILSPQFMYGSKAYV
KHPADIPDYLKLSFPEGFKWERVMNFEDGGVVTVTQDSSLQDGEFIYKVK
LRGTNFPSDGPVMQKKTMGWEASSERMYPEDGALKGEIKQRLKLKDGGHY
DAEVKTTYKAKKPVQLPGAYNVNIKLDITSHNEDYTIVEQYERAEGRHST
GGMDELYKLEHHHHHH DEFENSIN 3 -(GGS)$_9$-Cre-His$_6$
(SEQ ID NO: 126)
MGIINTLQKYYCRVRGGRCAVLSCLPKEEQIGKCSTRGRKCCRRKKGGSG
GSGGSGGSGGSGGSGGSGGSGGSMASNLLTVHQNLPALPVDATSDEVRKN
LMDMFRDRQAFSEHTWKMLLSVCRSWAAWCKLNNRKWFPAEPEDVRDYLL
YLQARGLAVKTIQQHLGQLNMLHRRSGLPRPSDSNAVSLVMRRIRKENVD
AGERAKQALAFERTDFDQVRSLMENSDRCQDIRNLAFLGIAYNTLLRIAE
IARIRVKDISRTDGGRMLIHIGRTKTLVSTAGVEKALSLGVTKLVERWIS
VSGVADDPNNYLFCRVRKNGVAAPSATSQLSTRALEGIFEATHRLIYGAK
DDSGQRYLAWSGHSARVGAARDMARAGVSIPEIMQAGGWTNVNIVMNYIR
NLDSETGAMVRLLEDGDHHHHHH HBEGF (UNIPROT: Q99075 PDB: 1XDT)
HBEGF-(GGS)$_9$-mCherry-His$_6$
(SEQ ID NO: 127)
MRVTLSSKPQALATPNKEEHGKRKKKGKGLGKKRDPCLRKYKDFCIHGEC
KYVKELRAPSCICHPGYHGERCHGLSGGSGGSGGSGGSGGSGGSGGSGGS
GGSVSKGEEDNMAIIKEFMRFKVHMEGSVNGHEFEIEGEGEGRPYEGTQT
AKLKVTKGGPLPFAWDILSPQFMYGSKAYVKHPADIPDYLKLSFPEGFKW
ERVMNFEDGGVVTVTQDSSLQDGEFIYKVKLRGTNFPSDGPVMQKKTMGW EASSERMYPEDGALKGEIKQRLKLKDGGHYDAEVKTTYKAKKPVQLPGAY
NVNIKLDITSHNEDYTIVEQYERAEGRHSTGGMDELYKLEHHHHHH HBEGF -(GGS)$_9$-Cre-His$_6$
(SEQ ID NO: 128)
MRVTLSSKPQALATPNKEEHGKRKKKGKGLGKKRDPCLRKYKDFCIHGEC
KYVKELRAPSCICHPGYHGERCHGLSGGSGGSGGSGGSGGSGGSGGSGGS
GGSMASNLLTVHQNLPALPVDATSDEVRKNLMDMFRDRQAFSEHTWKMLL
SVCRSWAAWCKLNNRKWFPAEPEDVRDYLLYLQARGLAVKTIQQHLGQLN
MLHRRSGLPRPSDSNAVSLVMRRIRKENVDAGERAKQALAFERTDFDQVR
SLMENSDRCQDIRNLAFLGIAYNTLLRIAEIARIRVKDISRTDGGRMLIH
IGRTKTLVSTAGVEKALSLGVTKLVERWISVSGVADDPNNYLFCRVRKNG
VAAPSATSQLSTRALEGIFEATHRLIYGAKDDSGQRYLAWSGHSARVGAA
RDMARAGVSIPEIMQAGGWTNVNIVMNYIRNLDSETGAMVRLLEDGDHH
HHHH N-DEK (UNIPROT: P35659 PDB: 2JX3)
N-DEK-(GGS)$_9$-mCherry-His$_6$
(SEQ ID NO: 129)
MFTIAQGKGQKLCEIERIHFFLSKKKTDELRNLHKLLYNRPGTVSSLKKN
VGQFSGFPPFEKGSVQYKKKEEMLKKFRNAMLKSICEVLDLERSGVNSELV
KRILNFLMHPKPSGKPLPKSKKTCSKGSKKERGGSGGSGGSGGSGGSGGS
GGSGGSGGSVSKGEEDNMAIIKEFMRFKVHMEGSVNGHEFEIEGEGEGRP
YEGTQTAKLKVTKGGPLPFAWDILSPQFMYGSKAYVKHPADIPDYKLSF
PEGFKWERVMNFEDGGVVTVTQDSSLQDGEFIYKVKLRGTNFPSDGPVMQ
KKTMGWEASSERMYPEDGALKGEIKQRLKLKDGGHYDAEVKTTYKAKKPV
QLPGAYNVNIKLDITSHNEDYTIVEQYERAEGRHSTGGMDELYKLEHHHH
HH N-DEK -(GGS)$_9$-Cre-His$_6$
(SEQ ID NO: 130)
MFTIAQGKGQKLCEIERIHFFLSKKKTDELRNLHKLLYNRPGTVSSLKKN
VGQFSGFPPFEKGSVQYKKKEEMLKKFRNAMLKSICEVLDLERSGVNSELV
KRILNFLMHPKPSGKPLPKSKKTCSKGSKKERGGSGGSGGSGGSGGSGGS
GGSGGSGGSMASNLLTVHQNLPALPVDATSDEVRKNLMDMFRDRQAFSEH
TWKMLLSVCRSWAAWCKLNNRKWFPAEPEDVRDYLLYLQARGLAVKTIQQ
HLGQLNMLHRRSGLPRPSDSNAVSLVMRRIRKENVDAGERAKQALAFERT
DFDQVRSLMENSDRCQDIRNLAFLGIAYNTLLRIAEIARIRVKDISRTDG
GRMLIHIGRTKTLVSTAGVEKALSLGVTKLVERWISVSGVADDPNNYLFC
RVRKNGVAAPSATSQLSTRALEGIFEATHRLIYGAKDDSGQRYLAWSGHS
ARVGAARDMARAGVSIPEIMQAGGWTNVNIVMNYIRNLDSETGAMVRLLE
DGDHHHHHH HGF (UNIPROT: P14210 PDB: 2HGF)
HGF-(GGS)$_9$-mCherry-His$_6$
(SEQ ID NO: 131)
MGQRKRRNTIHEFICKSAKTTLIKIDPALKIKTKKVNTADQCANRCTRNK
GLPFTCKAFVFDKARKQCLWFPFNSMSSGVKKEFGHEFDLYENKDYIRNG
GSGGSGGSGGSGGSGGSGGSGGSVSKGEEDNMAIIKEFMRFKVHMEG
SVNGHEFEIEGEGEGRPYEGTQTAKLKVTKGGPLPFAWDILSPQFMYGSK AYVKHPADIPDYLKLSFPEGFKWERVMNFEDGGVVTVTQDSSLQDGEFIY
KVKLRGTNFPSDGPVMQKKTMGWEASSERMYPEDGALKGEIKQRLKLKDG
GHYDAEVKTTYKAKKPVQLPGAYNVNIKLDITSHNEDYTIVEQYERAEGR
HSTGGMDELYKLEHHHHHH HGF -(GGS)$_9$-Cre-His$_6$
(SEQ ID NO: 132)
MGQRKRRNTIHEFKKSAKTTLIKIDPALKIKTKKVNTADQCANRCTRNKG
LPFTCKAFVFDKARKQCLWFPFNSMSSGVKKEFGHEFDLYENKDYIRNGG
SGGSGGSGGSGGSGGSGGSGGSMASNLLTVHQNLPALPVDATSDEVR
KNLMDMFRDRQAFSEHTWKMLLSVCRSWAAWCKLNNRKWFPAEPEDVRDY
LLYLQARGLAVKTIQQHLGQLNMLHRRSGLPRPSDSNAVSLVMRRIRKEN
VDAGERAKQALAFERTDFDQVRSLMENSDRCQDIRNLAFLGIAYNTLLRI
AEIARIRVKDISRTDGGRMLIHIGRTKTLVSTAGVEKALSLGVTKLVERW
ISVSGVADDPNNYLFCRVRKNGVAAPSATSQLSTRALEGIFEATHRLIYG
AKDDSGQRYLAWSGHSARVGAARDMARAGVSIPEIMQAGGWTNVNIVMNY
IRNLDSETGAMVRLLEDGDHHHHHH HIST4 (UNIPROT: P62805 PDB: 2CV5)
HIST4 -(GGS)$_9$-mCherry-His$_6$
(SEQ ID NO: 150)
MSGRGKGGKGLGKGGAKRHRKVLRDNIQGITKPAIRRLARRGGVKRISGL
IYEETRGVLKVFLENVIRDAVTYTEHAKRKTVTAMDVVYALKRQGRTLYG
FGGGGSGGSGGSGGSGGSGGSGGSGGSGGSVSKGEEDNMAIIKEFMRFKV
HMEGSVNGHEFEIEGEGEGRPYEGTQTAKLKVTKGGPLPFAWDILSPQFM
YGSKAYVKHPADIPDYLKLSFPEGFKWERVMNFEDGGVVTVTQDSSLQDG
EFIYKVKLRGTNFPSDGPVMQKKTMGWEASSERMYPEDGALKGEIKQRLK
LKDGGHYDAEVKTTYKAKKPVQLPGAYNVNIKLDITSHNEDYTIVEQYER
AEGRHSTGGMDELYKLEHHHHHH HIST4 -(GGS)$_9$-Cre-His$_6$
(SEQ ID NO: 151)
MSGRGKGGKGLGKGGAKRHRKVLRDNIQGITKPAIRRLARRGGVKRISGL
IYEETRGVLKVFLENVIRDAVTYTEHAKRKTVTAMDVVYALKRQGRTLYG
FGGGGSGGSGGSGGSGGSGGSGGSGGSGGSMASNLLTVHQNLPALPVDAT
SDEVRKNLMDMFRDRQAFSEHTWKMLLSVCRSWAAWCKLNNRKWFPAEPE
DVRDYLLYLQARGLAVKTIQQHLGQLNMLHRRSGLPRPSDSNAVSLVMRR
IRKENVDAGERAKQALAFERTDFDQVRSLMENSDRCQDIRNLAFLGIAYN
TLLRIAEIARIRVKDISRTDGGRMLIHIGRTKTLVSTAGVEKALSLGVTK
LVERWISVSGVADDPNNYLFCRVRKNGVAAPSATSQLSTRALEGIFEATH
RLIYGAKDDSGQRYLAWSGHSARVGAARDMARAGVSIPEIMQAGGWTNVN
IVMNYIRNLDSETGAMVRLLEDGDHHHHHH EOTAXIN 3 (UNIPROT: Q9Y258 PDE: 1G2S)
EOTAXIN 3-(GGS)$_9$-mCherry-His$_6$
(SEQ ID NO: 155)
MTRGSDISKTCCFQYSHKPLPWTWVRSYEFTSNSCSQRAVIFTTKRGKKV
CTHPRKKWVQKYISLLKTPKQLGGSGGSGGSGGSGGSGGSGGSGGSGGSV
SKGEEDNMAIIKEFMRFKVHMEGSVNGHEFEIEGEGEGRPYEGTQTAKLK -continued
VTKGGPLPFAWDILSPQFMYGSKAYVKHPADIPDYLKLSFPEGFKWERVM

NFEDGGVVTVTQDSSLQDGEFIYKVKLRGTNFPSDGPVMQKKTMGWEASS

ERMYPEDGALKGEIKQRLKLKDGGHYDAEVKTTYKAKKPVQLPGAYNVNI

KIDITSHNEDYTIVEQYERAEGRHSTGGMDELYKLEHHHHHH

EOTAXIN 3-(GGS)$_9$-Cre-His$_6$ (SEQ ID NO: 152)
MTRGSDISKTCCFQYSHKPLPWTWVRSYEFTSNSCSQRAVIFTTKRGKKV

CTHPRKKWVQKYISLLKTPKQLGGSGGSGGSGGSGGSGGSGGSGGSGGSM

ASNLLTVHQNLPALPVDATSDEVRKNLMDMFRDRQAFSEHTWKMLLSVCR

SWAAWCKLNNRKWFPAEPEDVRDYLLYLQARGLAVKTIQQHLGQLNMLHR

RSGLPRPSDSNAVSLVMRRIRKENVDAGERAKQALAFERTDFDQVRSLME

NSDRCQDIRNLAFLGIAYNTLLRIAEIARIRVKDISRTDGGRMLIHIGRT

KTLVSTAGVEKALSLGVTKLVERWISVSGVADDPNNYLFCRVRKNGVAAP

SATSQLSTRALEGIFEATHRLIYGAKDDSGQRYLAWSGHSARVGAARDMA

RAGVSIPEIMQAGGWTNVNIVMNYIRNLDSETGAMVRLLEDGDHHHHHH

Example 8

Supercharged Protein-Mediated In Vivo Delivery

Figure 51:
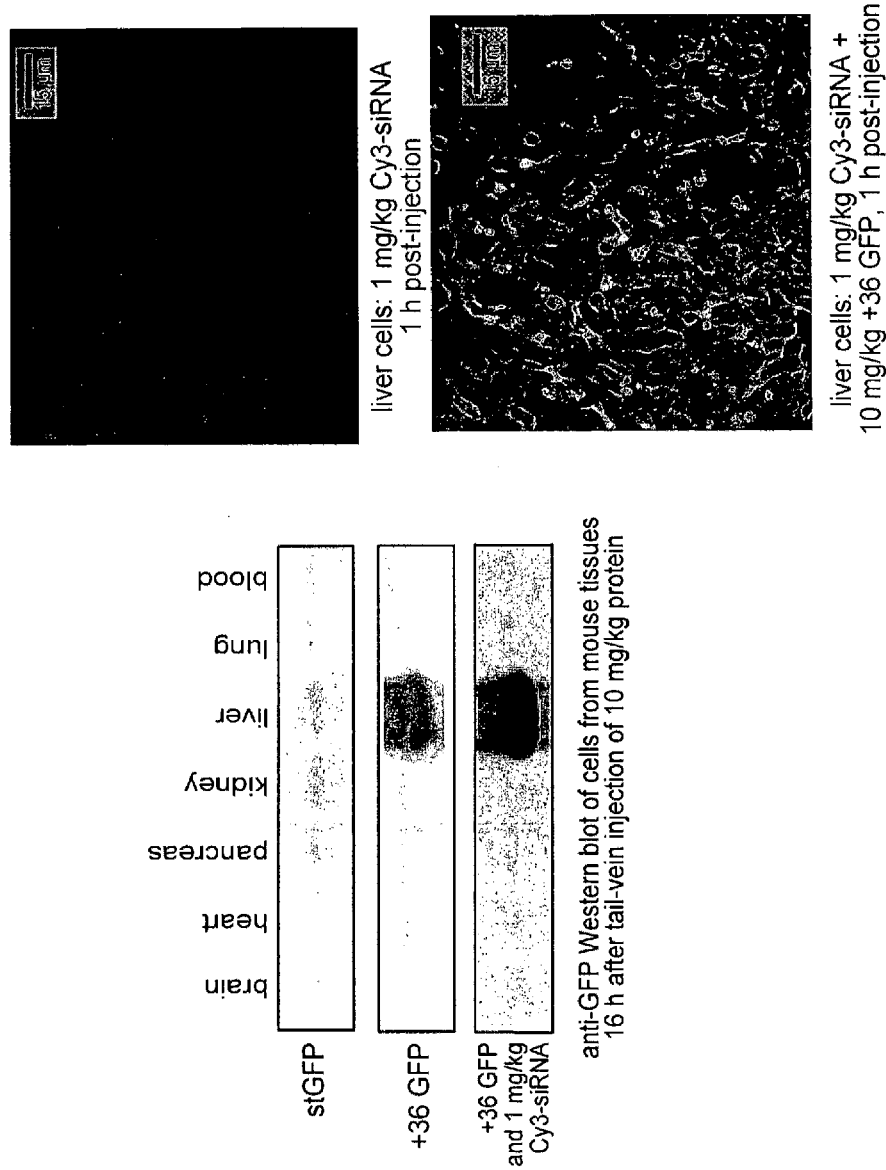
FIG. 51. In vivo siRNA delivery by +36 GFP.

+36 GFP and +36 GFP:Cy3-siRNA was introduced into mice by tail-vein injection. Both +36 GFP and +36 GFP:Cy3-siRNA were localized to liver cells 1 h post-injection and detectable by western blot in liver tissue 16 h post-injection (FIG. 51).

Figure 52:
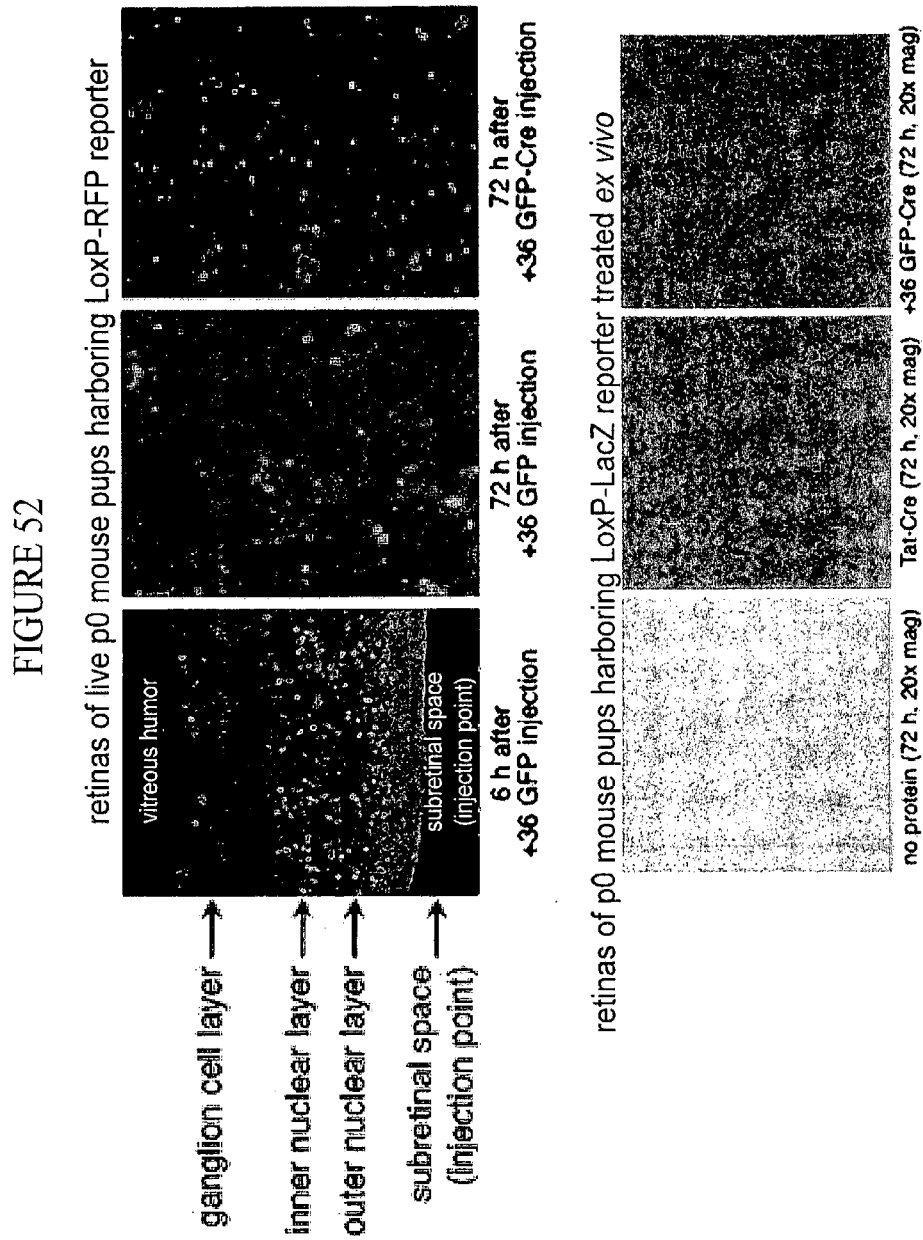
FIG. 52. In vivo: delivery of functional Cre recombinase by +36 GFP. Upper panel: fluorescence microscopy of a retinal section of a CD1 adult mouse injected with 0.5 µL of 100 µM+36 GFP. The retina was harvested and analyzed six hours after injection. GFP fluorescence is shown and DAPI nuclear stain is shown. Bright fluorescence on the right image indicated recombination of a RFP-loxP reporter construct by Cre. Lower panel: X-gal staining of p0 mouse pup retinas harboring a loxP-LacZ reporter treated ex vivo.

The ability of +36 GFP to act as a protein delivery agent in vivo was tested. First, the tissue penetration of +36 GFP in the adult mouse retina was examined. 0.5 µL of 100 µM+36 GFP were injected into the subretinal space of CD1 adult mice. After 6 hours, the retinas were harvested and analyzed by fluorescence microscopy (FIG. 52). Most of +36 GFP was observed by the photoreceptor outer segments, but significant signal was observed throughout the retina, including all three nuclear layers (the outer, inner, and ganglion cell layers) as well as in the cell processes.

Figure 53:
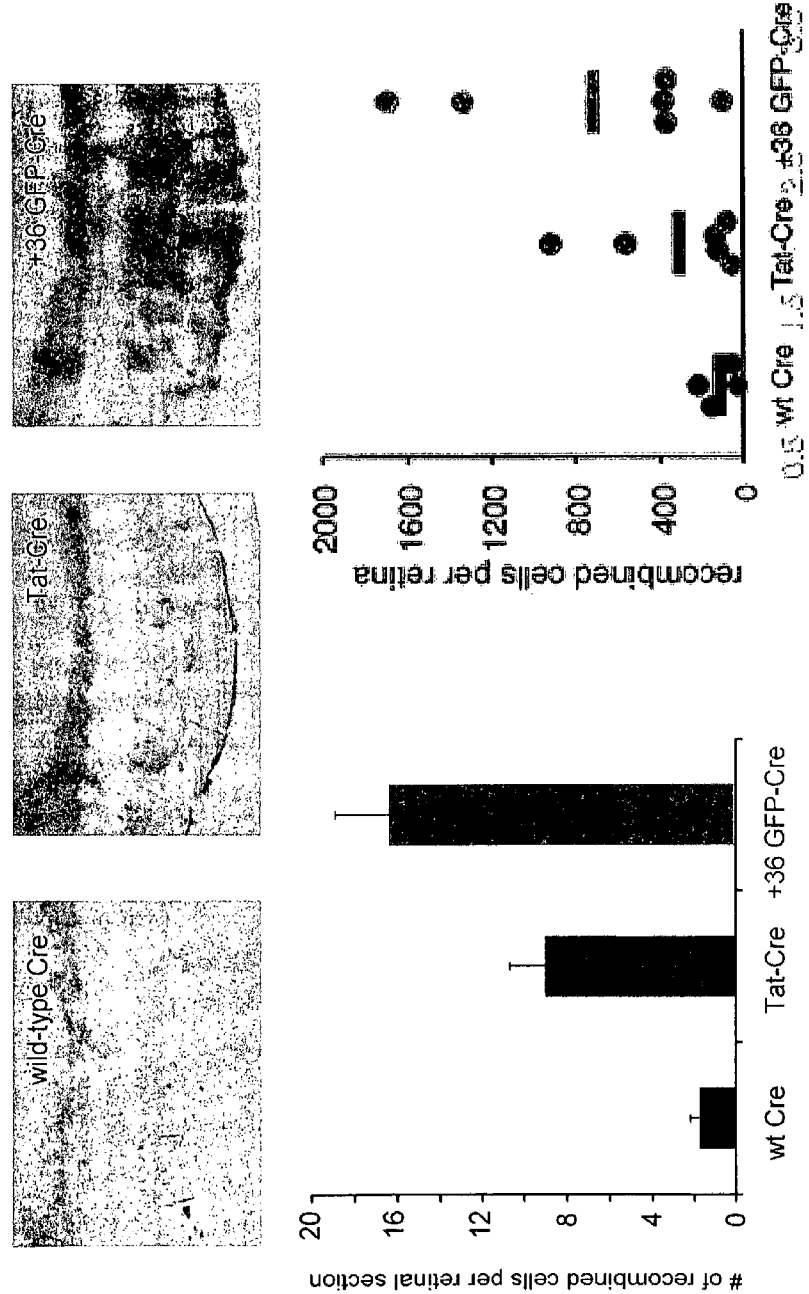
FIG. 53. In vivo delivery of functional Cre recombinase by +36 GFP. Retinal sections of neonatal RC::PFwe mouse pups harboring a nuclear LacZ reporter of Cre activity. Three days after injection of 0.5 µL of 40 µM wild-type Cre, Tat-Cre, or +36 GFP-Cre, retinae were harvested, fixed, and stained with X-gal. Dots on the lower right graph represent the total number of recombined cells counted in each retina. The horizontal bar represents the average number of recombined cells per retina for each protein injected (n=4 for wild-type Cre, n=6 for Tat-Cre, n=6 for +36 GFP-Cre).

To test ability of +36 GFP to deliver functional protein in vivo, +36 GFP-Cre was injected into the subretinal space of RC::PFwe mouse p0 pups containing a LoxP-flanked transcriptional terminator upstream of a nuclear lacZ reporter gene. 20 Three days after injection of 0.5 µL of 40 µM wild-type Cre, Tat-Cre, or +36 GFPCre, retinae were harvested, fixed, and stained with X-gal (FIG. 52). A comparison of loopout efficiencies of wild type Cre, Tat-Cre and +36 GFP-Cre by ex vivo X-gal staining of p0 pup retinas harboring a nuclear LacZ reporter 72 h post-treatment showed more efficient recombination after +36 GFP-Cre treatment, suggesting more efficient Cre-delivery to the retina by +36 GFP than by Tat. Similarly, +36 GFP-Cre effects recombination in vivo in murine p0 pups harboring a nuclear LacZ Cre reporter (FIG. 53). Consistent with the findings ex vivo, the in vivo recombination potency in this setting is higher for +36 GFP-Cre than that of Tat-Cre. Injection of +36 GFP-Cre generated an average of 715 recombined cells per injected retina (n=6), Tat-Cre generated an average of 318 recombined cells (n=6) while wild-type Cre generated an average of 117 recombined cells per retina (n=4) (FIG. 53). To the inventors knowledge, this is the first report of functional delivery of an enzyme into retinal cells in vivo.

EQUIVALENTS AND SCOPE

Those skilled in the art will recognize, or be able to ascertain using no more than routine experimentation, many equivalents to the specific embodiments, described herein. The scope of the present invention is not intended to be limited to the above Description, but rather is as set forth in the appended claims.

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It should it be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not been specifically set forth in haec verba herein. It is also noted that the term "comprising" is intended to be open and permits the inclusion of additional elements or steps.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any supercharged protein; any nucleic acid; any method of production; any method of use; etc.) can be excluded from any one or more claims, for any reason, whether or not related to the existence of prior art.

All cited sources, for example, references, publications, databases, database entries, and art cited herein, are incorporated into this application by reference, even if not expressly stated in the citation. In case of conflicting statements of a cited source and the instant application, the statement in the instant application shall control.

What is claimed is:

1. A supercharged protein associated with a functional peptide or protein, comprising a supercharged protein having a molecular weight of 4-100 kDa, a theoretical net charge of at least +10 at physiological pH, and a charge to molecular weight ratio of at least 0.8, wherein the supercharged protein is a supercharged protein variant of a wild-type protein and comprises a modified primary amino acid sequence as compared to the wild-type sequence, wherein the modified primary amino acid sequence comprises replacement of a plurality of charged or polar, solvent-exposed residues with a natural amino acid residue that is positively charged at physiological pH; and a functional peptide or protein selected from the group consisting of enzymes, DNA-binding proteins, histones, cytoskeletal proteins, receptor proteins, chaperone proteins, transcription factors, tumor suppressors, developmental regulators, growth factors, metastasis suppressors, pro-apoptotic proteins, and reprogramming factors, wherein the supercharged protein is covalently bound to the functional peptide or protein, and wherein the supercharged protein associated with the functional peptide or protein is able to penetrate a cell and deliver the functional peptide or protein to the cell.

2. The supercharged protein associated with a functional peptide or protein of claim 1, wherein the supercharged protein is bound to the functional protein or peptide via a peptide bond, thus forming a fusion protein.

3. The supercharged protein associated with a functional peptide or protein of claim 1, wherein the supercharged protein and the functional protein or peptide are bound to a linker connecting the supercharged protein and the functional peptide or protein.

4. The supercharged protein associated with a functional peptide or protein of claim 1, wherein the supercharged protein or the linker can be cleaved by a cellular enzyme.

5. The supercharged protein associated with a functional peptide or protein of claim 1, wherein the supercharged protein is a globular protein.

6. The supercharged protein associated with a functional peptide or protein of claim 1, wherein the supercharged protein is a protein comprising a β-barrel.

7. The supercharged protein associated with a functional peptide or protein of claim 1, wherein the supercharged protein is a supercharged green fluorescent protein (GFP).

8. The supercharged protein associated with a functional peptide or protein of claim 1, wherein the functional protein is a protein chosen from the group consisting of histone acetyltransferases, histone deacetylases, DNA methyltransferases, kinases, phosphatases, proteases, oxidoreductases, transferases, hydrolases, lyases, isomerases, ligases, nucleases, zinc finger nucleases, and recombinases.

9. The supercharged protein associated with a functional peptide or protein of claim 8, wherein the functional protein is a protein selected from the group consisting of BCL-2 family proteins, caspases, TIMP-family proteins, BMP-family growth factors, GDF-family growth factors, and zinc finger nucleases targeting a site within the human CCR5 gene.

10. A method of delivering a functional peptide or protein to a cell, comprising:
   contacting the cell with a supercharged protein covalently bound to the functional peptide or protein of claim 1, under conditions sufficient for the functional peptide or protein to enter the cell.

11. The method of claim 10, wherein the functional peptide or protein is a nuclear peptide or protein, and the step of contacting results in delivery of the functional protein or peptide to the nucleus of the cell.

12. The method of claim 10, wherein the functional protein or peptide delivered to the cell is a transcription factor or a reprogramming factor.

13. The method of claim 12, wherein the cell is a somatic cell from a subject diagnosed with a disease and is contacted with a supercharged protein covalently bound to a reprogramming factor in an amount, for a time, and under conditions sufficient to induce reprogramming of the somatic cell to a pluripotent state.

14. The method of claim 13, further comprising:
   isolating a pluripotent cell generated from the somatic cell;
   differentiating the isolated pluripotent cell, or progeny thereof, into a differentiated cell type; and/or
   using the pluripotent cell, or differentiated progeny thereof, in a cell replacement therapeutic approach.

15. The method of claim 10, wherein the cell is a cell carrying a genomic allele associated with a disease and the supercharged protein is associated with a nuclease specifically targeting the allele.

16. The method of claim 15, wherein the nuclease targets the human CCR5 gene in a T-lymphocyte of a subject diagnosed with HIV/AIDS.

17. The method of claim 10, wherein the functional protein is a recombinase, and the cell comprises a recombination site recognized by the recombinase in its genome.

18. The method of claim 17, wherein the cell comprises a plurality of recombination sites recognized by the recombinase, and recombinase-mediated recombination of the plurality of recombination sites results in deletion of a genomic region.

19. The method of claim 10, wherein the cell is a tumor cell, and the functional protein is a tumor suppressor protein, a metastasis suppressor protein, a cytostatic protein, or a cytotoxic protein.

20. The supercharged protein covalently bound to a functional peptide or protein of claim 1, wherein the supercharged protein has a molecular weight of 10-100 kDa, a theoretical net charge of at least +10 at physiological pH, and a charge to molecular weight ratio of at least 0.8.

21. The supercharged protein associated with a functional peptide or protein of claim 1, wherein the supercharged protein is covalently bound to the functional peptide or protein using a linker comprising an amide, ester, or disulfide bond.

22. The supercharged protein associated with a functional peptide or protein of claim 7, wherein the supercharged protein is +25 GFP, +36 GFP, +42 GFP, +48 GFP, or +49 GFP.

23. The supercharged protein associated with a functional peptide or protein of claim 3, wherein the linker comprises an amino acid sequence chosen from the group consisting of: X-AGVF-X (SEQ ID NO: 136), X-GFLG-X (SEQ ID NO: 137), X-FK-X (SEQ ID NO: 138), X-AL-X (SEQ ID NO: 139), X-ALAL-X (SEQ ID NO: 140), and X-ALALA-X (SEQ ID NO: 141), wherein X denotes the supercharged protein or the functional peptide or protein.

24. The supercharged protein associated with a functional peptide or protein of claim 8, wherein the functional protein is a protein selected from the group consisting of: p53, Rb (retinoblastoma protein), BRCA1, BRCA2, PTEN, APC, CD95, ST7, ST14, BRMS1, CRSP3, DRG1, KAI1, KISS1, NM23, EGF, EPO, FGF, G-CSF, GM-CSF, HGF, HDGF, IGF, PDGF, TPO, TGF-α, TGF-β, VEGF, Cre recombinase, Dre recombinase, and FLP recombinase.

25. The supercharged protein associated with a functional peptide or protein of claim 1, wherein the modified primary amino acid sequence comprises replacement of a plurality of charged or highly polar, solvent-exposed residues with a natural amino acid residue that is positively charged at physiological pH.

* * * * *

SEQUENCE LISTING

```
<160> NUMBER OF SEQ ID NOS: 157

<210> SEQ ID NO 1
<211> LENGTH: 238
<212> TYPE: PRT
<213> ORGANISM: Artificial Sequence
<220> FEATURE:
<223> OTHER INFORMATION: synthetic polypeptide

<400> SEQUENCE: 1

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Ser Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235

<210> SEQ ID NO 2
<211> LENGTH: 248
<212> TYPE: PRT
<213> ORGANISM: Artificial Sequence
<220> FEATURE:
<223> OTHER INFORMATION: synthetic polypeptide

<400> SEQUENCE: 2

Met Gly His His His His His His Gly Gly Ala Ser Lys Gly Glu Glu
1               5                   10                  15

Leu Phe Thr Gly Val Val Pro Ile Leu Val Glu Leu Asp Gly Asp Val
```

```
            20                  25                  30
Asn Gly His Lys Phe Ser Val Arg Gly Glu Gly Glu Gly Asp Ala Thr
             35                  40                  45
Asn Gly Lys Leu Thr Leu Lys Phe Ile Cys Thr Thr Gly Lys Leu Pro
 50                  55                  60
Val Pro Trp Pro Thr Leu Val Thr Thr Leu Thr Tyr Gly Val Gln Cys
 65                  70                  75                  80
Phe Ser Arg Tyr Pro Asp His Met Lys Gln His Asp Phe Phe Lys Ser
                 85                  90                  95
Ala Met Pro Glu Gly Tyr Val Gln Glu Arg Thr Ile Ser Phe Lys Asp
            100                 105                 110
Asp Gly Thr Tyr Lys Thr Arg Ala Glu Val Lys Phe Glu Gly Asp Thr
            115                 120                 125
Leu Val Asn Arg Ile Glu Leu Lys Gly Ile Asp Phe Lys Glu Asp Gly
            130                 135                 140
Asn Ile Leu Gly His Lys Leu Glu Tyr Asn Phe Asn Ser His Asn Val
145                 150                 155                 160
Tyr Ile Thr Ala Asp Lys Gln Lys Asn Gly Ile Lys Ala Asn Phe Lys
                165                 170                 175
Ile Arg His Asn Val Glu Asp Gly Ser Val Gln Leu Ala Asp His Tyr
                180                 185                 190
Gln Gln Asn Thr Pro Ile Gly Asp Gly Pro Val Leu Leu Pro Asp Asn
            195                 200                 205
His Tyr Leu Ser Thr Gln Ser Ala Leu Ser Lys Asp Pro Asn Glu Lys
            210                 215                 220
Arg Asp His Met Val Leu Leu Glu Phe Val Thr Ala Ala Gly Ile Thr
225                 230                 235                 240
His Gly Met Asp Glu Leu Tyr Lys
                245

<210> SEQ ID NO 3
<211> LENGTH: 248
<212> TYPE: PRT
<213> ORGANISM: Artificial Sequence
<220> FEATURE:
<223> OTHER INFORMATION: synthetic polypeptide

<400> SEQUENCE: 3

Met Gly His His His His His His Gly Gly Ala Ser Lys Gly Glu Glu
 1               5                  10                  15
Leu Phe Thr Gly Val Val Pro Ile Leu Val Glu Leu Asp Gly Asp Val
            20                  25                  30
Asn Gly His Glu Phe Ser Val Arg Gly Glu Gly Glu Gly Asp Ala Thr
             35                  40                  45
Glu Gly Glu Leu Thr Leu Lys Phe Ile Cys Thr Thr Gly Glu Leu Pro
 50                  55                  60
Val Pro Trp Pro Thr Leu Val Thr Thr Leu Thr Tyr Gly Val Gln Cys
 65                  70                  75                  80
Phe Ser Arg Tyr Pro Asp His Met Lys Gln His Asp Phe Phe Lys Ser
                 85                  90                  95
Ala Met Pro Glu Gly Tyr Val Gln Glu Arg Thr Ile Ser Phe Lys Asp
            100                 105                 110
Asp Gly Thr Tyr Lys Thr Arg Ala Glu Val Lys Phe Glu Gly Asp Thr
            115                 120                 125
Leu Val Asn Arg Ile Glu Leu Lys Gly Ile Asp Phe Lys Glu Asp Gly
```

```
                130                 135                 140
Asn Ile Leu Gly His Lys Leu Glu Tyr Asn Phe Asn Ser His Asp Val
145                 150                 155                 160

Tyr Ile Thr Ala Asp Lys Gln Glu Asn Gly Ile Lys Ala Glu Phe Glu
                165                 170                 175

Ile Arg His Asn Val Glu Asp Gly Ser Val Gln Leu Ala Asp His Tyr
                180                 185                 190

Gln Gln Asn Thr Pro Ile Gly Asp Gly Pro Val Leu Leu Pro Asp Asp
                195                 200                 205

His Tyr Leu Ser Thr Glu Ser Ala Leu Ser Lys Asp Pro Asn Glu Asp
                210                 215                 220

Arg Asp His Met Val Leu Leu Glu Phe Val Thr Ala Ala Gly Ile Asp
225                 230                 235                 240

His Gly Met Asp Glu Leu Tyr Lys
                245

<210> SEQ ID NO 4
<211> LENGTH: 248
<212> TYPE: PRT
<213> ORGANISM: Artificial Sequence
<220> FEATURE:
<223> OTHER INFORMATION: synthetic polypeptide

<400> SEQUENCE: 4

Met Gly His His His His His His Gly Gly Ala Ser Lys Gly Glu Glu
1               5                   10                  15

Leu Phe Asp Gly Glu Val Pro Ile Leu Val Glu Leu Asp Gly Asp Val
                20                  25                  30

Asn Gly His Glu Phe Ser Val Arg Gly Glu Gly Glu Gly Asp Ala Thr
                35                  40                  45

Glu Gly Glu Leu Thr Leu Lys Phe Ile Cys Thr Thr Gly Glu Leu Pro
    50                  55                  60

Val Pro Trp Pro Thr Leu Val Thr Thr Leu Thr Tyr Gly Val Gln Cys
65                  70                  75                  80

Phe Ser Arg Tyr Pro Asp His Met Asp Gln His Asp Phe Phe Lys Ser
                85                  90                  95

Ala Met Pro Glu Gly Tyr Val Gln Glu Arg Thr Ile Ser Phe Lys Asp
                100                 105                 110

Asp Gly Thr Tyr Lys Thr Arg Ala Glu Val Lys Phe Glu Gly Asp Thr
                115                 120                 125

Leu Val Asn Arg Ile Glu Leu Lys Gly Ile Asp Phe Lys Glu Asp Gly
                130                 135                 140

Asn Ile Leu Gly His Lys Leu Glu Tyr Asn Phe Asn Ser His Asp Val
145                 150                 155                 160

Tyr Ile Thr Ala Asp Lys Gln Glu Asn Gly Ile Lys Ala Glu Phe Glu
                165                 170                 175

Ile Arg His Asn Val Glu Asp Gly Ser Val Gln Leu Ala Asp His Tyr
                180                 185                 190

Gln Gln Asn Thr Pro Ile Gly Asp Gly Pro Val Leu Leu Pro Asp Asp
                195                 200                 205

His Tyr Leu Ser Thr Glu Ser Ala Leu Ser Lys Asp Pro Asn Glu Asp
                210                 215                 220

Arg Asp His Met Val Leu Leu Glu Phe Val Thr Ala Ala Gly Ile Asp
225                 230                 235                 240

His Gly Met Asp Glu Leu Tyr Lys
```

<210> SEQ ID NO 5
<211> LENGTH: 248
<212> TYPE: PRT
<213> ORGANISM: Artificial Sequence
<220> FEATURE:
<223> OTHER INFORMATION: synthetic polypeptide

<400> SEQUENCE: 5

```
Met Gly His His His His His Gly Gly Ala Ser Lys Gly Glu Glu
1               5                   10                  15

Leu Phe Asp Gly Val Val Pro Ile Leu Val Glu Leu Asp Gly Asp Val
            20                  25                  30

Asn Gly His Glu Phe Ser Val Arg Gly Glu Gly Glu Gly Asp Ala Thr
            35                  40                  45

Glu Gly Glu Leu Thr Leu Lys Phe Ile Cys Thr Thr Gly Glu Leu Pro
    50                  55                  60

Val Pro Trp Pro Thr Leu Val Thr Thr Leu Thr Tyr Gly Val Gln Cys
65                  70                  75                  80

Phe Ser Asp Tyr Pro Asp His Met Asp Gln His Asp Phe Phe Lys Ser
                85                  90                  95

Ala Met Pro Glu Gly Tyr Val Gln Glu Arg Thr Ile Ser Phe Lys Asp
            100                 105                 110

Asp Gly Thr Tyr Lys Thr Arg Ala Glu Val Lys Phe Glu Gly Asp Thr
        115                 120                 125

Leu Val Asn Arg Ile Glu Leu Lys Gly Ile Asp Phe Lys Glu Asp Gly
    130                 135                 140

Asn Ile Leu Gly His Lys Leu Glu Tyr Asn Phe Asn Ser His Asp Val
145                 150                 155                 160

Tyr Ile Thr Ala Asp Lys Gln Glu Asn Gly Ile Lys Ala Glu Phe Glu
                165                 170                 175

Ile Arg His Asn Val Glu Asp Gly Ser Val Gln Leu Ala Asp His Tyr
            180                 185                 190

Gln Gln Asn Thr Pro Ile Gly Asp Gly Pro Val Leu Leu Pro Asp Asp
        195                 200                 205

His Tyr Leu Ser Thr Glu Ser Ala Leu Ser Lys Asp Pro Asn Glu Asp
    210                 215                 220

Arg Asp His Met Val Leu Leu Glu Phe Val Thr Ala Ala Gly Ile Asp
225                 230                 235                 240

His Gly Met Asp Glu Leu Tyr Lys
                245
```

<210> SEQ ID NO 6
<211> LENGTH: 248
<212> TYPE: PRT
<213> ORGANISM: Artificial Sequence
<220> FEATURE:
<223> OTHER INFORMATION: synthetic polypeptide

<400> SEQUENCE: 6

```
Met Gly His His His His His Gly Gly Ala Ser Lys Gly Glu Arg
1               5                   10                  15

Leu Phe Thr Gly Val Val Pro Ile Leu Val Glu Leu Asp Gly Asp Val
            20                  25                  30

Asn Gly His Lys Phe Ser Val Arg Gly Glu Gly Glu Gly Asp Ala Thr
            35                  40                  45
```

```
Arg Gly Lys Leu Thr Leu Lys Phe Ile Cys Thr Thr Gly Lys Leu Pro
    50                  55                  60

Val Pro Trp Pro Thr Leu Val Thr Thr Leu Thr Tyr Gly Val Gln Cys
65                  70                  75                  80

Phe Ser Arg Tyr Pro Lys His Met Lys Arg His Asp Phe Phe Lys Ser
                85                  90                  95

Ala Met Pro Glu Gly Tyr Val Gln Glu Arg Thr Ile Ser Phe Lys Lys
            100                 105                 110

Asp Gly Thr Tyr Lys Thr Arg Ala Glu Val Lys Phe Glu Gly Arg Thr
            115                 120                 125

Leu Val Asn Arg Ile Glu Leu Lys Gly Arg Asp Phe Lys Glu Lys Gly
    130                 135                 140

Asn Ile Leu Gly His Lys Leu Glu Tyr Asn Phe Asn Ser His Asn Val
145                 150                 155                 160

Tyr Ile Thr Ala Asp Lys Arg Lys Asn Gly Ile Lys Ala Asn Phe Lys
                165                 170                 175

Ile Arg His Asn Val Lys Asp Gly Ser Val Gln Leu Ala Asp His Tyr
            180                 185                 190

Gln Gln Asn Thr Pro Ile Gly Arg Gly Pro Val Leu Leu Pro Arg Asn
    195                 200                 205

His Tyr Leu Ser Thr Arg Ser Ala Leu Ser Lys Asp Pro Lys Glu Lys
    210                 215                 220

Arg Asp His Met Val Leu Leu Glu Phe Val Thr Ala Ala Gly Ile Thr
225                 230                 235                 240

His Gly Met Asp Glu Leu Tyr Lys
                245

<210> SEQ ID NO 7
<211> LENGTH: 248
<212> TYPE: PRT
<213> ORGANISM: Artificial Sequence
<220> FEATURE:
<223> OTHER INFORMATION: synthetic polypeptide

<400> SEQUENCE: 7

Met Gly His His His His His His Gly Gly Ala Ser Lys Gly Glu Arg
1               5                   10                  15

Leu Phe Arg Gly Lys Val Pro Ile Leu Val Glu Leu Lys Gly Asp Val
            20                  25                  30

Asn Gly His Lys Phe Ser Val Arg Gly Lys Gly Lys Gly Asp Ala Thr
        35                  40                  45

Arg Gly Lys Leu Thr Leu Lys Phe Ile Cys Thr Thr Gly Lys Leu Pro
    50                  55                  60

Val Pro Trp Pro Thr Leu Val Thr Thr Leu Thr Tyr Gly Val Gln Cys
65                  70                  75                  80

Phe Ser Arg Tyr Pro Lys His Met Lys Arg His Asp Phe Phe Lys Ser
                85                  90                  95

Ala Met Pro Lys Gly Tyr Val Gln Glu Arg Thr Ile Ser Phe Lys Lys
            100                 105                 110

Asp Gly Lys Tyr Lys Thr Arg Ala Glu Val Lys Phe Glu Gly Arg Thr
            115                 120                 125

Leu Val Asn Arg Ile Lys Leu Lys Gly Arg Asp Phe Lys Glu Lys Gly
    130                 135                 140

Asn Ile Leu Gly His Lys Leu Arg Tyr Asn Phe Asn Ser His Lys Val
145                 150                 155                 160
```

```
Tyr Ile Thr Ala Asp Lys Arg Lys Asn Gly Ile Lys Ala Lys Phe Lys
                165                 170                 175

Ile Arg His Asn Val Lys Asp Gly Ser Val Gln Leu Ala Asp His Tyr
            180                 185                 190

Gln Gln Asn Thr Pro Ile Gly Arg Gly Pro Val Leu Leu Pro Arg Asn
        195                 200                 205

His Tyr Leu Ser Thr Arg Ser Lys Leu Ser Asp Pro Lys Glu Lys
    210                 215                 220

Arg Asp His Met Val Leu Leu Glu Phe Val Thr Ala Ala Gly Ile Lys
225                 230                 235                 240

His Gly Arg Asp Glu Arg Tyr Lys
                245

<210> SEQ ID NO 8
<211> LENGTH: 248
<212> TYPE: PRT
<213> ORGANISM: Artificial Sequence
<220> FEATURE:
<223> OTHER INFORMATION: synthetic polypeptide

<400> SEQUENCE: 8

Met Gly His His His His His Gly Gly Arg Ser Lys Gly Lys Arg
1               5                   10                  15

Leu Phe Arg Gly Lys Val Pro Ile Leu Val Glu Leu Lys Gly Asp Val
            20                  25                  30

Asn Gly His Lys Phe Ser Val Arg Gly Lys Gly Lys Gly Asp Ala Thr
        35                  40                  45

Arg Gly Lys Leu Thr Leu Lys Phe Ile Cys Thr Thr Gly Lys Leu Pro
50                  55                  60

Val Pro Trp Pro Thr Leu Val Thr Thr Leu Thr Tyr Gly Val Gln Cys
65                  70                  75                  80

Phe Ser Arg Tyr Pro Lys His Met Lys Arg His Asp Phe Phe Lys Ser
                85                  90                  95

Ala Met Pro Lys Gly Tyr Val Gln Glu Arg Thr Ile Ser Phe Lys Lys
            100                 105                 110

Asp Gly Lys Tyr Lys Thr Arg Ala Glu Val Lys Phe Glu Gly Arg Thr
        115                 120                 125

Leu Val Asn Arg Ile Lys Leu Lys Gly Arg Asp Phe Lys Glu Lys Gly
    130                 135                 140

Asn Ile Leu Gly His Lys Leu Arg Tyr Asn Phe Asn Ser His Lys Val
145                 150                 155                 160

Tyr Ile Thr Ala Asp Lys Arg Lys Asn Gly Ile Lys Ala Lys Phe Lys
                165                 170                 175

Ile Arg His Asn Val Lys Asp Gly Ser Val Gln Leu Ala Asp His Tyr
            180                 185                 190

Gln Gln Asn Thr Pro Ile Gly Arg Gly Pro Val Leu Leu Pro Arg Lys
        195                 200                 205

His Tyr Leu Ser Thr Arg Ser Lys Leu Ser Lys Asp Pro Lys Glu Lys
    210                 215                 220

Arg Asp His Met Val Leu Leu Glu Phe Val Thr Ala Ala Gly Ile Lys
225                 230                 235                 240

His Gly Arg Lys Glu Arg Tyr Lys
                245

<210> SEQ ID NO 9
<211> LENGTH: 248
```

```
<212> TYPE: PRT
<213> ORGANISM: Artificial Sequence
<220> FEATURE:
<223> OTHER INFORMATION: synthetic polypeptide

<400> SEQUENCE: 9

Met Gly His His His His His Gly Gly Arg Ser Lys Gly Lys Arg
1               5                   10                  15

Leu Phe Arg Gly Lys Val Pro Ile Leu Val Lys Leu Lys Gly Asp Val
                20                  25                  30

Asn Gly His Lys Phe Ser Val Arg Gly Lys Gly Lys Gly Asp Ala Thr
            35                  40                  45

Arg Gly Lys Leu Thr Leu Lys Phe Ile Cys Thr Thr Gly Lys Leu Pro
50                  55                  60

Val Pro Trp Pro Thr Leu Val Thr Thr Leu Thr Tyr Gly Val Gln Cys
65                  70                  75                  80

Phe Ser Arg Tyr Pro Lys His Met Lys Arg His Asp Phe Phe Lys Ser
                85                  90                  95

Ala Met Pro Lys Gly Tyr Val Gln Glu Arg Thr Ile Ser Phe Lys Lys
            100                 105                 110

Asp Gly Lys Tyr Lys Thr Arg Ala Glu Val Lys Phe Lys Gly Arg Thr
        115                 120                 125

Leu Val Asn Arg Ile Lys Leu Lys Gly Arg Asp Phe Lys Glu Lys Gly
130                 135                 140

Asn Ile Leu Gly His Lys Leu Arg Tyr Asn Phe Asn Ser His Lys Val
145                 150                 155                 160

Tyr Ile Thr Ala Asp Lys Arg Lys Asn Gly Ile Lys Ala Lys Phe Lys
                165                 170                 175

Ile Arg His Asn Val Lys Asp Gly Ser Val Gln Leu Ala Lys His Tyr
            180                 185                 190

Gln Gln Asn Thr Pro Ile Gly Arg Gly Pro Val Leu Leu Pro Arg Lys
        195                 200                 205

His Tyr Leu Ser Thr Arg Ser Lys Leu Ser Lys Asp Pro Lys Glu Lys
210                 215                 220

Arg Asp His Met Val Leu Leu Glu Phe Val Thr Ala Ala Gly Ile Lys
225                 230                 235                 240

His Gly Arg Lys Glu Arg Tyr Lys
                245

<210> SEQ ID NO 10
<211> LENGTH: 248
<212> TYPE: PRT
<213> ORGANISM: Artificial Sequence
<220> FEATURE:
<223> OTHER INFORMATION: synthetic polypeptide

<400> SEQUENCE: 10

Met Gly His His His His His Gly Gly Arg Ser Lys Gly Lys Arg
1               5                   10                  15

Leu Phe Arg Gly Lys Val Pro Ile Leu Val Lys Leu Lys Gly Asp Val
                20                  25                  30

Asn Gly His Lys Phe Ser Val Arg Gly Lys Gly Lys Gly Asp Ala Thr
            35                  40                  45

Arg Gly Lys Leu Thr Leu Lys Phe Ile Cys Thr Thr Gly Lys Leu Pro
50                  55                  60

Val Pro Trp Pro Thr Leu Val Thr Thr Leu Thr Tyr Gly Val Gln Cys
65                  70                  75                  80
```

```
Phe Ser Arg Tyr Pro Lys His Met Lys Arg His Asp Phe Phe Lys Ser
                85                  90                  95

Ala Met Pro Lys Gly Tyr Val Gln Glu Arg Thr Ile Ser Phe Lys Lys
            100                 105                 110

Asp Gly Lys Tyr Lys Thr Arg Ala Glu Val Lys Phe Lys Gly Arg Thr
            115                 120                 125

Leu Val Asn Arg Ile Lys Leu Lys Gly Arg Asp Phe Lys Glu Lys Gly
            130                 135                 140

Asn Ile Leu Gly His Lys Leu Arg Tyr Asn Phe Asn Ser His Lys Val
145                 150                 155                 160

Tyr Ile Thr Ala Asp Lys Arg Lys Asn Gly Ile Lys Ala Lys Phe Lys
                165                 170                 175

Ile Arg His Asn Val Lys Asp Gly Ser Val Gln Leu Ala Lys His Tyr
            180                 185                 190

Gln Gln Asn Thr Pro Ile Gly Arg Gly Pro Val Leu Leu Pro Arg Lys
            195                 200                 205

His Tyr Leu Ser Thr Arg Ser Lys Leu Ser Lys Asp Pro Lys Glu Lys
            210                 215                 220

Arg Asp His Met Val Leu Lys Glu Phe Val Thr Ala Ala Gly Ile Lys
225                 230                 235                 240

His Gly Arg Lys Glu Arg Tyr Lys
                245

<210> SEQ ID NO 11
<211> LENGTH: 4
<212> TYPE: PRT
<213> ORGANISM: Artificial Sequence
<220> FEATURE:
<223> OTHER INFORMATION: synthetic polypeptide

<400> SEQUENCE: 11

Ala Gly Val Phe
1

<210> SEQ ID NO 12
<211> LENGTH: 4
<212> TYPE: PRT
<213> ORGANISM: Artificial Sequence
<220> FEATURE:
<223> OTHER INFORMATION: synthetic polypeptide

<400> SEQUENCE: 12

Gly Phe Leu Gly
1

<210> SEQ ID NO 13
<211> LENGTH: 2
<212> TYPE: PRT
<213> ORGANISM: Artificial Sequence
<220> FEATURE:
<223> OTHER INFORMATION: synthetic polypeptide

<400> SEQUENCE: 13

Phe Lys
1

<210> SEQ ID NO 14
<211> LENGTH: 2
<212> TYPE: PRT
<213> ORGANISM: Artificial Sequence
<220> FEATURE:
```

<223> OTHER INFORMATION: synthetic polypeptide

<400> SEQUENCE: 14

Ala Leu
1

<210> SEQ ID NO 15
<211> LENGTH: 4
<212> TYPE: PRT
<213> ORGANISM: Artificial Sequence
<220> FEATURE:
<223> OTHER INFORMATION: synthetic polypeptide

<400> SEQUENCE: 15

Ala Leu Ala Leu
1

<210> SEQ ID NO 16
<211> LENGTH: 5
<212> TYPE: PRT
<213> ORGANISM: Artificial Sequence
<220> FEATURE:
<223> OTHER INFORMATION: synthetic polypeptide

<400> SEQUENCE: 16

Ala Leu Ala Leu Ala
1               5

<210> SEQ ID NO 17
<211> LENGTH: 238
<212> TYPE: PRT
<213> ORGANISM: Artificial Sequence
<220> FEATURE:
<223> OTHER INFORMATION: synthetic polypeptide

<400> SEQUENCE: 17

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Ser Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

```
Val Leu Leu Pro Asp Asn His Tyr Leu Ser Thr Gln Ser Ala Leu Ser
            195                 200                 205

Lys Asp Pro Asn Glu Lys Arg Asp His Met Val Leu Leu Glu Phe Val
            210                 215                 220

Thr Ala Ala Gly Ile Thr His Gly Met Asp Glu Leu Tyr Lys
225                 230                 235

<210> SEQ ID NO 18
<211> LENGTH: 248
<212> TYPE: PRT
<213> ORGANISM: Artificial Sequence
<220> FEATURE:
<223> OTHER INFORMATION: synthetic polypeptide

<400> SEQUENCE: 18

Met Gly His His His His His Gly Gly Ala Ser Lys Gly Glu Arg
1               5                   10                  15

Leu Phe Thr Gly Val Val Pro Ile Leu Val Glu Leu Asp Gly Asp Val
            20                  25                  30

Asn Gly His Lys Phe Ser Val Arg Gly Lys Gly Lys Gly Asp Ala Thr
        35                  40                  45

Arg Gly Lys Leu Thr Leu Lys Phe Ile Cys Thr Thr Gly Lys Leu Pro
50                  55                  60

Val Pro Trp Pro Thr Leu Val Thr Thr Leu Thr Tyr Gly Val Gln Cys
65                  70                  75                  80

Phe Ser Arg Tyr Pro Lys His Met Lys Arg His Asp Phe Phe Lys Ser
                85                  90                  95

Ala Met Pro Lys Gly Tyr Val Gln Glu Arg Thr Ile Ser Phe Lys Lys
            100                 105                 110

Asp Gly Thr Tyr Lys Thr Arg Ala Glu Val Lys Phe Glu Gly Arg Thr
        115                 120                 125

Leu Val Asn Arg Ile Lys Leu Lys Gly Arg Asp Phe Lys Glu Lys Gly
    130                 135                 140

Asn Ile Leu Gly His Lys Leu Arg Tyr Asn Phe Asn Ser His Asn Val
145                 150                 155                 160

Tyr Ile Thr Ala Asp Lys Arg Lys Asn Gly Ile Lys Ala Asn Phe Lys
                165                 170                 175

Ile Arg His Asn Val Lys Asp Gly Ser Val Gln Leu Ala Asp His Tyr
            180                 185                 190

Gln Gln Asn Thr Pro Ile Gly Arg Gly Pro Val Leu Leu Pro Arg Asn
        195                 200                 205

His Tyr Leu Ser Thr Arg Ser Ala Leu Ser Lys Asp Pro Lys Glu Lys
    210                 215                 220

Arg Asp His Met Val Leu Leu Glu Phe Val Thr Ala Ala Gly Ile Thr
225                 230                 235                 240

His Gly Met Asp Glu Leu Tyr Lys
                245

<210> SEQ ID NO 19
<211> LENGTH: 280
<212> TYPE: PRT
<213> ORGANISM: Artificial Sequence
<220> FEATURE:
<223> OTHER INFORMATION: synthetic polypeptide

<400> SEQUENCE: 19

Met Gly His His His His His Gly Gly Ala Ser Lys Gly Glu Arg
1               5                   10                  15
```

```
Leu Phe Arg Gly Lys Val Pro Ile Leu Val Glu Leu Lys Gly Asp Val
         20                  25                  30

Asn Gly His Lys Phe Ser Val Arg Gly Lys Gly Lys Gly Asp Ala Thr
             35                  40                  45

Arg Gly Lys Leu Thr Leu Lys Phe Ile Cys Thr Thr Gly Lys Leu Pro
 50                  55                  60

Val Pro Trp Pro Thr Leu Val Thr Thr Leu Thr Tyr Gly Val Gln Cys
 65                  70                  75                  80

Phe Ser Arg Tyr Pro Lys His Met Lys Arg His Asp Phe Phe Lys Ser
                 85                  90                  95

Ala Met Pro Lys Gly Tyr Val Gln Glu Arg Thr Ile Ser Phe Lys Lys
                100                 105                 110

Asp Gly Lys Tyr Lys Thr Arg Ala Glu Val Lys Phe Glu Gly Arg Thr
            115                 120                 125

Leu Val Asn Arg Ile Lys Leu Lys Gly Arg Asp Phe Lys Glu Lys Gly
130                 135                 140

Asn Ile Leu Gly His Lys Leu Arg Tyr Asn Phe Asn Ser His Lys Val
145                 150                 155                 160

Tyr Ile Thr Ala Asp Lys Arg Lys Asn Gly Ile Lys Ala Lys Phe Lys
                165                 170                 175

Ile Arg His Asn Val Lys Asp Gly Ser Val Gln Leu Ala Asp His Tyr
                180                 185                 190

Gln Gln Asn Thr Pro Ile Gly Arg Gly Pro Val Leu Leu Pro Arg Asn
            195                 200                 205

His Tyr Leu Ser Thr Arg Ser Lys Leu Ser Lys Asp Pro Lys Glu Lys
            210                 215                 220

Arg Asp His Met Val Leu Leu Glu Phe Val Thr Ala Ala Gly Ile Lys
225                 230                 235                 240

His Gly Arg Asp Glu Arg Tyr Lys Gly Ser Ala Gly Ser Ala Ala Gly
                245                 250                 255

Ser Gly Glu Phe Gly Leu Phe Gly Ala Ile Ala Gly Phe Ile Glu Asn
                260                 265                 270

Gly Trp Glu Gly Met Ile Asp Gly
            275                 280

<210> SEQ ID NO 20
<211> LENGTH: 26
<212> TYPE: PRT
<213> ORGANISM: Artificial Sequence
<220> FEATURE:
<223> OTHER INFORMATION: synthetic polypeptide

<400> SEQUENCE: 20

Gly Ile Gly Ala Val Leu Lys Val Leu Thr Thr Gly Leu Pro Ala Leu
 1               5                  10                  15

Ile Ser Trp Ile Lys Arg Lys Arg Gln Gln
             20                  25

<210> SEQ ID NO 21
<211> LENGTH: 26
<212> TYPE: PRT
<213> ORGANISM: Artificial Sequence
<220> FEATURE:
<223> OTHER INFORMATION: synthetic polypeptide

<400> SEQUENCE: 21

Cys Ile Gly Ala Val Leu Lys Val Leu Thr Thr Gly Leu Pro Ala Leu
```

```
1               5                   10                  15
Ile Ser Trp Ile Lys Arg Lys Arg Gln Gln
            20                  25

<210> SEQ ID NO 22
<211> LENGTH: 16
<212> TYPE: PRT
<213> ORGANISM: Artificial Sequence
<220> FEATURE:
<223> OTHER INFORMATION: synthetic polypeptide

<400> SEQUENCE: 22

Arg Gln Ile Lys Ile Trp Phe Gln Asn Arg Arg Met Lys Trp Lys Lys
1               5                   10                  15

<210> SEQ ID NO 23
<211> LENGTH: 30
<212> TYPE: PRT
<213> ORGANISM: Artificial Sequence
<220> FEATURE:
<223> OTHER INFORMATION: synthetic polypeptide

<400> SEQUENCE: 23

Met Val Lys Ser Lys Ile Gly Ser Trp Ile Leu Val Leu Phe Val Ala
1               5                   10                  15

Met Trp Ser Asp Val Gly Leu Cys Lys Lys Arg Pro Lys Pro
            20                  25                  30

<210> SEQ ID NO 24
<211> LENGTH: 24
<212> TYPE: PRT
<213> ORGANISM: Artificial Sequence
<220> FEATURE:
<223> OTHER INFORMATION: synthetic polypeptide

<400> SEQUENCE: 24

Gly Ala Leu Phe Leu Gly Trp Leu Gly Ala Ala Gly Ser Thr Met Gly
1               5                   10                  15

Ala Pro Lys Ser Lys Arg Lys Val
            20

<210> SEQ ID NO 25
<211> LENGTH: 21
<212> TYPE: PRT
<213> ORGANISM: Artificial Sequence
<220> FEATURE:
<223> OTHER INFORMATION: synthetic polypeptide

<400> SEQUENCE: 25

Ala Gly Tyr Leu Leu Gly Lys Ile Asn Leu Lys Ala Leu Ala Ala Leu
1               5                   10                  15

Ala Lys Lys Ile Leu
            20

<210> SEQ ID NO 26
<211> LENGTH: 23
<212> TYPE: PRT
<213> ORGANISM: Artificial Sequence
<220> FEATURE:
<223> OTHER INFORMATION: synthetic polypeptide

<400> SEQUENCE: 26

Leu Ile Arg Leu Trp Ser His Leu Ile His Ile Trp Phe Gln Asn Arg
1               5                   10                  15
```

Arg Leu Lys Trp Lys Lys Lys
            20

<210> SEQ ID NO 27
<211> LENGTH: 253
<212> TYPE: PRT
<213> ORGANISM: Artificial Sequence
<220> FEATURE:
<223> OTHER INFORMATION: synthetic polypeptide

<400> SEQUENCE: 27

Ser Thr Thr Glu Val Val Met Glu Asn Val Thr Ala Phe Trp Glu Glu
1               5                   10                  15

Gly Phe Gly Glu Leu Phe Glu Lys Ala Lys Gly Thr Pro Val Leu Lys
            20                  25                  30

Asp Ile Asn Phe Lys Ile Glu Arg Gly Gln Leu Leu Ala Val Ala Gly
        35                  40                  45

Ser Thr Gly Ala Gly Lys Thr Ser Leu Leu Met Met Ile Met Gly Glu
    50                  55                  60

Leu Glu Pro Ser Glu Gly Lys Ile Lys His Ser Gly Arg Ile Ser Phe
65                  70                  75                  80

Cys Ser Gln Asn Ser Trp Ile Met Pro Gly Thr Ile Lys Glu Asn Ile
                85                  90                  95

Ile Gly Val Ser Tyr Asp Glu Tyr Arg Tyr Arg Ser Val Ile Lys Ala
            100                 105                 110

Cys Gln Leu Glu Glu Asp Ile Ser Lys Phe Ala Glu Lys Asp Asn Ile
        115                 120                 125

Val Leu Ile Thr Leu Ser Gly Gly Gln Arg Ala Arg Ile Ser Leu Ala
    130                 135                 140

Arg Ala Val Tyr Lys Asp Ala Asp Leu Tyr Leu Leu Asp Ser Pro Phe
145                 150                 155                 160

Gly Tyr Leu Asp Val Leu Thr Glu Lys Glu Ile Phe Glu Ser Cys Val
                165                 170                 175

Cys Lys Leu Met Ala Asn Lys Thr Arg Ile Leu Val Thr Ser Lys Met
            180                 185                 190

Glu His Leu Lys Lys Ala Asp Lys Ile Leu Ile Leu His Glu Gly Ser
        195                 200                 205

Ser Tyr Phe Tyr Gly Thr Phe Ser Glu Leu Gln Asn Leu Arg Pro Asp
    210                 215                 220

Phe Ser Ser Lys Leu Met Ser Phe Asp Gln Phe Ser Ala Glu Arg Arg
225                 230                 235                 240

Asn Ser Ile Leu Thr Glu Thr Leu His Arg Phe Ser Leu
                245                 250

<210> SEQ ID NO 28
<211> LENGTH: 213
<212> TYPE: PRT
<213> ORGANISM: Artificial Sequence
<220> FEATURE:
<223> OTHER INFORMATION: synthetic polypeptide

<400> SEQUENCE: 28

Asp Pro Lys Phe Glu Ser Lys Ala Ala Leu Leu Ala Ala Arg Gly Pro
1               5                   10                  15

Glu Glu Leu Leu Cys Phe Thr Glu Arg Leu Glu Asp Leu Val Cys Phe
            20                  25                  30

Trp Glu Ala Ala Ser Ala Gly Val Gly Pro Gly Asn Tyr Ser Phe
            35                  40                  45

```
Ser Tyr Gln Leu Glu Asp Glu Pro Trp Lys Leu Cys Arg Leu His Gln
 50                  55                  60

Ala Pro Thr Ala Arg Gly Ala Val Arg Phe Trp Cys Ser Leu Pro Thr
 65                  70                  75                  80

Ala Asp Thr Ser Ser Phe Val Pro Leu Glu Leu Arg Val Thr Ala Ala
                 85                  90                  95

Ser Gly Ala Pro Arg Tyr His Arg Val Ile His Ile Asn Glu Val Val
                100                 105                 110

Leu Leu Asp Ala Pro Val Gly Leu Val Ala Arg Leu Ala Asp Glu Ser
            115                 120                 125

Gly His Val Val Leu Arg Trp Leu Pro Pro Glu Thr Pro Met Thr
        130                 135                 140

Ser His Ile Arg Tyr Glu Val Asp Val Ser Ala Gly Gln Gly Ala Gly
145                 150                 155                 160

Ser Val Gln Arg Val Glu Ile Leu Glu Gly Arg Thr Glu Cys Val Leu
                165                 170                 175

Ser Asn Leu Arg Gly Arg Thr Arg Tyr Thr Phe Ala Val Arg Ala Arg
                180                 185                 190

Met Ala Glu Pro Ser Phe Gly Gly Phe Trp Ser Glu Trp Ser Glu Pro
                195                 200                 205

Val Ser Leu Leu Thr
                210

<210> SEQ ID NO 29
<211> LENGTH: 299
<212> TYPE: PRT
<213> ORGANISM: Artificial Sequence
<220> FEATURE:
<223> OTHER INFORMATION: synthetic polypeptide

<400> SEQUENCE: 29

Cys Gly His Ile Ser Val Ser Ala Pro Ile Val His Leu Gly Asp Pro
 1               5                  10                  15

Ile Thr Ala Ser Cys Ile Ile Lys Gln Asn Cys Ser His Leu Asp Pro
                 20                  25                  30

Glu Pro Gln Ile Leu Trp Arg Leu Gly Ala Glu Leu Gln Pro Gly Gly
                 35                  40                  45

Arg Gln Gln Arg Leu Ser Asp Gly Thr Gln Glu Ser Ile Ile Thr Leu
 50                  55                  60

Pro His Leu Asn His Thr Gln Ala Phe Leu Ser Cys Ser Leu Asn Trp
 65                  70                  75                  80

Gly Asn Ser Leu Gln Ile Leu Asp Gln Val Glu Leu Arg Ala Gly Tyr
                 85                  90                  95

Pro Pro Ala Ile Pro His Asn Leu Ser Cys Leu Met Asn Leu Thr Thr
                100                 105                 110

Ser Ser Leu Ile Cys Gln Trp Glu Pro Gly Pro Glu Thr His Leu Pro
            115                 120                 125

Thr Ser Phe Thr Leu Lys Ser Phe Lys Ser Arg Gly Asn Cys Gln Thr
130                 135                 140

Gln Gly Asp Ser Ile Leu Asp Cys Val Pro Lys Asp Gly Gln Ser His
145                 150                 155                 160

Cys Ser Ile Pro Arg Lys His Leu Leu Leu Tyr Gln Asn Met Gly Ile
                165                 170                 175

Trp Val Gln Ala Glu Asn Ala Leu Gly Thr Ser Met Ser Pro Gln Leu
                180                 185                 190
```

```
Cys Leu Asp Pro Met Asp Val Lys Leu Glu Pro Pro Met Leu Arg
        195                 200                 205

Thr Met Asp Pro Gln Ala Gly Cys Leu Gln Leu Ser Trp Glu Pro Trp
    210                 215                 220

Gln Pro Gly Leu His Ile Asn Gln Lys Cys Glu Leu Arg His Lys Pro
225                 230                 235                 240

Gln Arg Gly Glu Ala Ser Trp Ala Leu Val Gly Pro Leu Pro Leu Glu
                245                 250                 255

Ala Leu Gln Tyr Glu Leu Cys Gly Leu Leu Pro Ala Thr Ala Tyr Thr
                260                 265                 270

Leu Gln Ile Arg Cys Ile Arg Trp Pro Leu Pro Gly His Trp Ser Asp
        275                 280                 285

Trp Ser Pro Ser Leu Glu Leu Arg Thr Thr Glu
        290                 295

<210> SEQ ID NO 30
<211> LENGTH: 191
<212> TYPE: PRT
<213> ORGANISM: Artificial Sequence
<220> FEATURE:
<223> OTHER INFORMATION: synthetic polypeptide

<400> SEQUENCE: 30

Glu Pro Lys Phe Thr Lys Cys Arg Ser Pro Glu Arg Glu Thr Phe Ser
1               5                   10                  15

Cys His Trp Thr Asp Glu Gly Pro Ile Gln Leu Phe Tyr Thr Arg Arg
            20                  25                  30

Asn Glu Trp Lys Glu Cys Pro Asp Tyr Val Ser Ala Gly Glu Asn Ser
        35                  40                  45

Cys Tyr Phe Asn Ser Ser Phe Thr Ser Ile Ala Ile Pro Tyr Cys Ile
    50                  55                  60

Lys Leu Thr Ser Asn Gly Gly Thr Val Asp Glu Lys Cys Phe Ser Val
65                  70                  75                  80

Asp Glu Ile Val Gln Pro Asp Pro Pro Ile Ala Leu Asn Trp Thr Leu
                85                  90                  95

Leu Asn Val Ser Leu Thr Gly Ile His Ala Asp Ile Gln Val Arg Trp
            100                 105                 110

Glu Ala Pro Arg Asn Ala Asp Ile Gln Lys Gly Trp Met Val Leu Glu
        115                 120                 125

Tyr Glu Leu Gln Tyr Lys Glu Val Asn Glu Thr Lys Trp Lys Met Met
    130                 135                 140

Asp Pro Ile Leu Thr Thr Ser Val Pro Val Tyr Ser Leu Lys Val Asp
145                 150                 155                 160

Lys Glu Tyr Glu Val Arg Val Arg Ser Lys Gln Arg Asn Ser Gly Asn
                165                 170                 175

Tyr Gly Glu Phe Ser Glu Val Leu Tyr Val Thr Leu Pro Gln Met
            180                 185                 190

<210> SEQ ID NO 31
<211> LENGTH: 310
<212> TYPE: PRT
<213> ORGANISM: Artificial Sequence
<220> FEATURE:
<223> OTHER INFORMATION: synthetic polypeptide

<400> SEQUENCE: 31

Cys Lys Glu Arg Glu Glu Lys Ile Ile Leu Val Ser Ser Ala Asn Glu
```

```
  1               5                   10                  15
Ile Asp Val Arg Pro Cys Pro Leu Asn Pro Asn Glu His Lys Gly Thr
                20                  25                  30

Ile Thr Trp Tyr Lys Asp Asp Ser Lys Thr Pro Val Ser Thr Glu Gln
                35                  40                  45

Ala Ser Arg Ile His Gln His Lys Glu Lys Leu Trp Phe Val Pro Ala
        50                  55                  60

Lys Val Glu Asp Ser Gly His Tyr Tyr Cys Val Val Arg Asn Ser Ser
65                  70                  75                  80

Tyr Cys Leu Arg Ile Lys Ile Ser Ala Lys Phe Val Glu Asn Glu Pro
                85                  90                  95

Asn Leu Cys Tyr Asn Ala Gln Ala Ile Phe Lys Gln Lys Leu Pro Val
                100                 105                 110

Ala Gly Asp Gly Gly Leu Val Cys Pro Tyr Met Glu Phe Phe Lys Asn
                115                 120                 125

Glu Asn Asn Glu Leu Pro Lys Leu Gln Trp Tyr Lys Asp Cys Lys Pro
                130                 135                 140

Leu Leu Leu Asp Asn Ile His Phe Ser Gly Val Lys Asp Arg Leu Ile
145                 150                 155                 160

Val Met Asn Val Ala Glu Lys His Arg Gly Asn Tyr Thr Cys His Ala
                165                 170                 175

Ser Tyr Thr Tyr Leu Gly Lys Gln Tyr Pro Ile Thr Arg Val Ile Glu
                180                 185                 190

Phe Ile Thr Leu Glu Glu Asn Lys Pro Thr Arg Pro Val Ile Val Ser
                195                 200                 205

Pro Ala Asn Glu Thr Met Glu Val Asp Leu Gly Ser Gln Ile Gln Leu
        210                 215                 220

Ile Cys Asn Val Thr Gly Gln Leu Ser Asp Ile Ala Tyr Trp Lys Trp
225                 230                 235                 240

Asn Gly Ser Val Ile Asp Glu Asp Pro Val Leu Gly Glu Asp Tyr
                245                 250                 255

Tyr Ser Val Glu Asn Pro Ala Asn Lys Arg Arg Ser Thr Leu Ile Thr
                260                 265                 270

Val Leu Asn Ile Ser Glu Ile Glu Ser Arg Phe Tyr Lys His Pro Phe
                275                 280                 285

Thr Cys Phe Ala Lys Asn Thr His Gly Ile Asp Ala Ala Tyr Ile Gln
                290                 295                 300

Leu Ile Tyr Pro Val Thr
305                 310

<210> SEQ ID NO 32
<211> LENGTH: 158
<212> TYPE: PRT
<213> ORGANISM: Artificial Sequence
<220> FEATURE:
<223> OTHER INFORMATION: synthetic polypeptide

<400> SEQUENCE: 32

Met Asp Ser Val Cys Pro Gln Gly Lys Tyr Ile His Pro Gln Asn Asn
1               5                   10                  15

Ser Ile Cys Cys Thr Lys Cys His Lys Gly Thr Tyr Leu Tyr Asn Asp
                20                  25                  30

Cys Pro Gly Pro Gly Gln Asp Thr Asp Cys Arg Glu Cys Glu Ser Gly
                35                  40                  45

Ser Phe Thr Ala Ser Glu Asn His Leu Arg His Cys Leu Ser Cys Ser
```

```
                    50                  55                  60
Lys Cys Arg Lys Glu Met Gly Gln Val Glu Ile Ser Ser Cys Thr Val
 65                  70                  75                  80

Asp Arg Asp Thr Val Cys Gly Cys Arg Lys Asn Gln Tyr Arg His Tyr
                     85                  90                  95

Trp Ser Glu Asn Leu Phe Gln Cys Phe Asn Cys Ser Leu Cys Leu Asn
                100                 105                 110

Gly Thr Val His Leu Ser Cys Gln Glu Lys Gln Asn Thr Val Cys Thr
                115                 120                 125

Cys His Ala Gly Phe Phe Leu Arg Glu Asn Glu Cys Val Ser Cys Ser
                130                 135                 140

Asn Cys Lys Lys Ser Leu Glu Cys Thr Lys Leu Cys Leu Pro
145                 150                 155
```

<210> SEQ ID NO 33
<211> LENGTH: 192
<212> TYPE: PRT
<213> ORGANISM: Artificial Sequence
<220> FEATURE:
<223> OTHER INFORMATION: synthetic polypeptide

<400> SEQUENCE: 33

```
Asn Thr Gly Leu Leu Glu Ser Gln Leu Ser Arg His Asp Gln Met Leu
 1               5                  10                  15

Ser Val His Asp Ile Arg Leu Ala Asp Met Asp Leu Arg Phe Gln Val
                 20                  25                  30

Leu Glu Thr Ala Ser Tyr Asn Gly Val Leu Ile Trp Lys Ile Arg Asp
                 35                  40                  45

Tyr Lys Arg Arg Lys Gln Glu Ala Val Met Gly Lys Thr Leu Ser Leu
 50                  55                  60

Tyr Ser Gln Pro Phe Tyr Thr Gly Tyr Phe Gly Tyr Lys Met Cys Ala
 65                  70                  75                  80

Arg Val Tyr Leu Asn Gly Asp Gly Met Gly Lys Gly Thr His Leu Ser
                 85                  90                  95

Leu Phe Phe Val Ile Met Arg Gly Glu Tyr Asp Ala Leu Leu Pro Trp
                100                 105                 110

Pro Phe Lys Gln Lys Val Thr Leu Met Leu Met Asp Gln Gly Ser Ser
                115                 120                 125

Arg Arg His Leu Gly Asp Ala Phe Lys Pro Asp Pro Asn Ser Ser Ser
                130                 135                 140

Phe Lys Lys Pro Thr Gly Glu Met Asn Ile Ala Ser Gly Cys Pro Val
145                 150                 155                 160

Phe Val Ala Gln Thr Val Leu Glu Asn Gly Thr Tyr Ile Lys Asp Asp
                165                 170                 175

Thr Ile Phe Ile Lys Val Ile Val Asp Thr Ser Asp Leu Pro Asp Pro
                180                 185                 190
```

<210> SEQ ID NO 34
<211> LENGTH: 146
<212> TYPE: PRT
<213> ORGANISM: Artificial Sequence
<220> FEATURE:
<223> OTHER INFORMATION: synthetic polypeptide

<400> SEQUENCE: 34

```
Gly Asp Gln Asn Pro Gln Ile Ala Ala His Val Ile Ser Glu Ala Ser
 1               5                  10                  15
```

```
Ser Lys Thr Thr Ser Val Leu Gln Trp Ala Glu Lys Gly Tyr Tyr Thr
            20                  25                  30

Met Ser Asn Asn Leu Val Thr Leu Glu Asn Gly Lys Gln Leu Thr Val
        35                  40                  45

Lys Arg Gln Gly Leu Tyr Tyr Ile Tyr Ala Gln Val Thr Phe Cys Ser
    50                  55                  60

Asn Arg Glu Ala Ser Ser Gln Ala Pro Phe Ile Ala Ser Leu Cys Leu
65                  70                  75                  80

Lys Ser Pro Gly Arg Phe Glu Arg Ile Leu Leu Arg Ala Ala Asn Thr
                85                  90                  95

His Ser Ser Ala Lys Pro Cys Gly Gln Gln Ser Ile His Leu Gly Gly
            100                 105                 110

Val Phe Glu Leu Gln Pro Gly Ala Ser Val Phe Val Asn Val Thr Asp
        115                 120                 125

Pro Ser Gln Val Ser His Gly Thr Gly Phe Thr Ser Phe Gly Leu Leu
    130                 135                 140

Lys Leu
145

<210> SEQ ID NO 35
<211> LENGTH: 299
<212> TYPE: PRT
<213> ORGANISM: Artificial Sequence
<220> FEATURE:
<223> OTHER INFORMATION: synthetic polypeptide

<400> SEQUENCE: 35

Ile Ala Arg Thr Ile Val Leu Gln Glu Ser Ile Gly Lys Gly Arg Phe
1               5                   10                  15

Gly Glu Val Trp Arg Gly Lys Trp Arg Gly Glu Glu Val Ala Val Lys
            20                  25                  30

Ile Phe Ser Ser Arg Glu Glu Arg Ser Trp Phe Arg Glu Ala Glu Ile
        35                  40                  45

Tyr Gln Thr Val Met Leu Arg His Glu Asn Ile Leu Gly Phe Ile Ala
    50                  55                  60

Ala Asp Asn Lys Asp Asn Gly Thr Trp Thr Gln Leu Trp Leu Val Ser
65                  70                  75                  80

Asp Tyr His Glu His Gly Ser Leu Phe Asp Tyr Leu Asn Arg Tyr Thr
                85                  90                  95

Val Thr Val Glu Gly Met Ile Lys Leu Ala Leu Ser Thr Ala Ser Gly
            100                 105                 110

Leu Ala His Leu His Met Glu Ile Val Gly Thr Gln Gly Lys Pro Ala
        115                 120                 125

Ile Ala His Arg Asp Leu Lys Ser Lys Asn Ile Leu Val Lys Lys Asn
    130                 135                 140

Gly Thr Cys Cys Ile Ala Asp Leu Gly Leu Ala Val Arg His Asp Ser
145                 150                 155                 160

Ala Thr Asp Thr Ile Asp Ile Arg Val Gly Thr Lys Arg Tyr Met Ala
                165                 170                 175

Pro Glu Val Leu Asp Asp Ser Ile Asn Met Lys His Phe Glu Ser Phe
            180                 185                 190

Lys Arg Ala Asp Ile Tyr Ala Met Gly Leu Val Phe Trp Glu Ile Ala
        195                 200                 205

Arg Arg Cys Ser Ile Gly Gly Ile His Glu Asp Tyr Gln Leu Pro Tyr
    210                 215                 220
```

```
Tyr Asp Leu Val Pro Ser Asp Pro Ser Val Glu Met Arg Lys Val
225                 230                 235                 240

Val Cys Glu Gln Lys Leu Arg Pro Asn Ile Pro Asn Arg Trp Gln Ser
                245                 250                 255

Cys Glu Ala Leu Arg Val Met Ala Lys Ile Met Arg Glu Cys Trp Tyr
            260                 265                 270

Ala Asn Gly Ala Ala Arg Leu Thr Ala Leu Arg Ile Lys Lys Thr Leu
        275                 280                 285

Ser Gln Leu Ser Gln Gln Glu Gly Ile Lys Met
    290                 295
```

<210> SEQ ID NO 36
<211> LENGTH: 195
<212> TYPE: PRT
<213> ORGANISM: Artificial Sequence
<220> FEATURE:
<223> OTHER INFORMATION: synthetic polypeptide

<400> SEQUENCE: 36

```
Ser Val Pro Ser Gln Lys Thr Tyr Gln Gly Ser Tyr Gly Phe Arg Leu
1               5                   10                  15

Gly Phe Leu His Ser Gly Thr Ala Lys Ser Val Thr Cys Thr Tyr Ser
            20                  25                  30

Pro Ala Leu Asn Lys Leu Phe Cys Gln Leu Ala Lys Thr Cys Pro Val
        35                  40                  45

Gln Leu Trp Val Asp Ser Thr Pro Pro Gly Thr Arg Val Arg Ala
    50                  55                  60

Met Ala Ile Tyr Lys Gln Ser Gln His Met Thr Glu Val Val Arg Arg
65                  70                  75                  80

Cys Pro His His Glu Arg Cys Ser Asp Ser Asp Gly Leu Ala Pro Pro
                85                  90                  95

Gln His Leu Ile Arg Val Glu Gly Asn Leu Arg Ala Glu Tyr Leu Asp
            100                 105                 110

Asp Arg Asn Thr Phe Arg His Ser Val Val Val Pro Cys Glu Pro Pro
        115                 120                 125

Glu Val Gly Ser Asp Cys Thr Thr Ile His Tyr Asn Tyr Met Cys Tyr
    130                 135                 140

Ser Ser Cys Met Gly Gly Met Asn Arg Arg Pro Ile Leu Thr Ile Ile
145                 150                 155                 160

Thr Leu Glu Asp Ser Ser Gly Asn Leu Leu Gly Arg Asp Ser Phe Glu
                165                 170                 175

Val Arg Val Cys Ala Cys Pro Gly Arg Asp Arg Arg Thr Glu Glu Glu
            180                 185                 190

Asn Leu Arg
    195
```

<210> SEQ ID NO 37
<211> LENGTH: 196
<212> TYPE: PRT
<213> ORGANISM: Artificial Sequence
<220> FEATURE:
<223> OTHER INFORMATION: synthetic polypeptide

<400> SEQUENCE: 37

```
Ser Ser Val Pro Ser Gln Lys Thr Tyr Gln Gly Ser Tyr Gly Phe Arg
1               5                   10                  15

Leu Gly Phe Leu His Ser Gly Thr Ala Lys Ser Val Thr Cys Thr Tyr
            20                  25                  30
```

```
Ser Pro Ala Leu Asn Lys Leu Phe Cys Gln Leu Ala Lys Thr Cys Pro
        35                  40                  45

Val Gln Leu Trp Val Asp Ser Thr Pro Pro Gly Thr Arg Val Arg
 50                  55                  60

Ala Met Ala Ile Tyr Lys Gln Ser Gln His Met Thr Glu Val Val Arg
 65                  70                  75                  80

Arg Cys Pro His His Glu Arg Cys Ser Asp Ser Asp Gly Leu Ala Pro
                 85                  90                  95

Pro Gln His Leu Ile Arg Val Glu Gly Asn Leu Arg Ala Glu Tyr Leu
            100                 105                 110

Asp Asp Arg Asn Thr Phe Arg His Ser Val Val Val Pro Cys Glu Pro
            115                 120                 125

Pro Glu Val Gly Ser Asp Cys Thr Thr Ile His Tyr Asn Tyr Met Cys
            130                 135                 140

Tyr Ser Ser Cys Met Gly Gly Met Asn Arg Arg Pro Ile Leu Thr Ile
145                 150                 155                 160

Ile Thr Leu Glu Asp Ser Ser Gly Asn Leu Leu Gly Arg Asp Ser Phe
                165                 170                 175

Glu Val Arg Val Cys Ala Cys Pro Gly Arg Asp Arg Arg Thr Glu Glu
            180                 185                 190

Glu Asn Leu Arg
        195

<210> SEQ ID NO 38
<211> LENGTH: 314
<212> TYPE: PRT
<213> ORGANISM: Artificial Sequence
<220> FEATURE:
<223> OTHER INFORMATION: synthetic polypeptide

<400> SEQUENCE: 38

Met Asp Gly Pro Tyr Leu Gln Ile Leu Glu Gln Pro Lys Gln Arg Gly
1               5                   10                  15

Phe Arg Phe Arg Tyr Val Cys Glu Gly Pro Ser His Gly Gly Leu Pro
            20                  25                  30

Gly Ala Ser Ser Glu Lys Asn Lys Lys Ser Tyr Pro Gln Val Lys Ile
        35                  40                  45

Cys Asn Tyr Val Gly Pro Ala Lys Val Ile Val Gln Leu Val Thr Asn
 50                  55                  60

Gly Lys Asn Ile His Leu His Ala His Ser Leu Val Gly Lys His Cys
 65                  70                  75                  80

Glu Asp Gly Ile Cys Thr Val Thr Ala Gly Pro Lys Asp Met Val Val
                 85                  90                  95

Gly Phe Ala Asn Leu Gly Ile Leu His Val Thr Lys Lys Lys Val Phe
            100                 105                 110

Glu Thr Leu Glu Ala Arg Met Thr Glu Ala Cys Ile Arg Gly Tyr Asn
            115                 120                 125

Pro Gly Leu Leu Val His Pro Asp Leu Ala Tyr Leu Gln Ala Glu Gly
            130                 135                 140

Gly Gly Asp Arg Gln Leu Gly Asp Arg Glu Lys Glu Leu Ile Arg Gln
145                 150                 155                 160

Ala Ala Leu Gln Gln Thr Lys Glu Met Asp Leu Ser Val Val Arg Leu
                165                 170                 175

Met Phe Thr Ala Phe Leu Pro Asp Ser Thr Gly Ser Phe Thr Arg Arg
            180                 185                 190
```

```
Leu Glu Pro Val Val Ser Asp Ala Ile Tyr Asp Ser Lys Ala Pro Asn
            195                 200                 205

Ala Ser Asn Leu Lys Ile Val Arg Met Asp Arg Thr Ala Gly Cys Val
    210                 215                 220

Thr Gly Glu Glu Ile Tyr Leu Leu Cys Asp Lys Val Gln Lys Asp
225                 230                 235                 240

Asp Ile Gln Ile Arg Phe Tyr Glu Glu Glu Asn Gly Gly Val Trp
                245                 250                 255

Glu Gly Phe Gly Asp Phe Ser Pro Thr Asp Val His Arg Gln Phe Ala
            260                 265                 270

Ile Val Phe Lys Thr Pro Lys Tyr Lys Asp Ile Asn Ile Thr Lys Pro
            275                 280                 285

Ala Ser Val Phe Val Gln Leu Arg Arg Lys Ser Asp Leu Glu Thr Ser
            290                 295                 300

Glu Pro Lys Pro Phe Leu Tyr Tyr Pro Glu
305                 310

<210> SEQ ID NO 39
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 39

Thr Thr Cys Cys Gly Leu Arg Gln Tyr
1               5

<210> SEQ ID NO 40
<211> LENGTH: 303
<212> TYPE: PRT
<213> ORGANISM: Artificial Sequence
<220> FEATURE:
<223> OTHER INFORMATION: synthetic polypeptide

<400> SEQUENCE: 40

Ile Lys Gly Gly Leu Phe Ala Asp Ile Ala Ser His Pro Trp Gln Ala
1               5                   10                  15

Ala Ile Phe Ala Lys His His Arg Arg Gly Gly Glu Arg Phe Leu Cys
            20                  25                  30

Gly Gly Ile Leu Ile Ser Ser Cys Trp Ile Leu Ser Ala Ala His Cys
            35                  40                  45

Phe Gln Gln Gln Gln Glu Glu Glu Glu Arg Arg Arg Arg
    50                  55                  60

Phe Phe Phe Phe Phe Pro Pro Pro Pro Pro His His Leu Thr Val
65                  70                  75                  80

Ile Leu Gly Arg Thr Tyr Arg Val Pro Gly Glu Glu Gln Lys
            85                  90                  95

Phe Glu Val Glu Lys Tyr Ile Val His Lys Glu Phe Asp Asp Thr
                100                 105                 110

Tyr Asp Asn Asp Ile Ala Leu Leu Gln Leu Lys Ser Ser Ser Ser
            115                 120                 125

Asp Asp Asp Asp Ser Ser Ser Ser Ser Ser Ser Ser Arg
    130                 135                 140

Arg Arg Arg Arg Cys Ala Gln Glu Ser Ser Val Val Arg Thr Val Cys
145                 150                 155                 160

Leu Pro Pro Ala Asp Leu Gln Leu Pro Asp Trp Thr Glu Cys Glu Leu
```

```
                165                 170                 175
Ser Gly Tyr Gly Lys His Glu Ala Leu Ser Pro Phe Tyr Ser Glu Arg
            180                 185                 190

Leu Lys Glu Ala His Val Arg Leu Tyr Pro Ser Ser Arg Cys Thr Thr
        195                 200                 205

Thr Ser Ser Ser Gln Gln His Leu Leu Asn Arg Thr Val Thr Asp
    210                 215                 220

Asn Met Leu Cys Ala Gly Asp Thr Thr Thr Arg Arg Arg Ser Ser
225                 230                 235                 240

Asn Asn Asn Leu His Asp Ala Cys Gln Gly Asp Ser Gly Pro Leu
                245                 250                 255

Val Cys Leu Asn Asp Gly Arg Met Thr Leu Val Gly Ile Ile Ser Trp
                260                 265                 270

Gly Leu Gly Cys Gly Gln Gln Lys Asp Val Pro Gly Val Tyr Thr
            275                 280                 285

Lys Val Thr Asn Tyr Leu Asp Trp Ile Arg Asp Asn Met Arg Pro
        290                 295                 300

<210> SEQ ID NO 41
<211> LENGTH: 255
<212> TYPE: PRT
<213> ORGANISM: Artificial Sequence
<220> FEATURE:
<223> OTHER INFORMATION: synthetic polypeptide

<400> SEQUENCE: 41

Val Val Gly Gly Glu Asp Ala Lys Pro Gly Gln Phe Pro Trp Gln Val
1               5                   10                  15

Val Leu Asn Gly Lys Val Asp Ala Phe Cys Gly Gly Ser Ile Val Asn
            20                  25                  30

Glu Lys Trp Ile Val Thr Ala Ala His Cys Val Glu Thr Thr Gly
        35                  40                  45

Val Lys Ile Thr Val Val Ala Gly Glu His Asn Ile Glu Glu Thr Glu
    50                  55                  60

His Thr Glu Gln Lys Arg Asn Val Ile Arg Ile Ile Pro His His Asn
65                  70                  75                  80

Tyr Asn Asn Asn Ala Ala Ala Ala Ala Ile Asn Lys Tyr Asn His
                85                  90                  95

Asp Ile Ala Leu Leu Glu Leu Asp Glu Pro Leu Val Leu Asn Ser Tyr
            100                 105                 110

Val Thr Pro Ile Cys Ile Ala Asp Lys Glu Tyr Thr Thr Thr Asn Asn
        115                 120                 125

Asn Ile Ile Ile Phe Leu Lys Phe Gly Ser Gly Tyr Val Ser Gly Trp
    130                 135                 140

Gly Arg Val Phe His Lys Gly Arg Ser Ala Leu Val Leu Gln Tyr Leu
145                 150                 155                 160

Arg Val Pro Leu Val Asp Arg Ala Thr Cys Leu Arg Ser Thr Lys Phe
                165                 170                 175

Thr Ile Tyr Asn Asn Met Phe Cys Ala Gly Phe His Glu Gly
            180                 185                 190

Gly Gly Arg Arg Asp Ser Cys Gln Gly Asp Ser Gly Pro His Val
        195                 200                 205

Thr Glu Val Glu Gly Thr Ser Phe Leu Thr Gly Ile Ile Ser Trp Gly
    210                 215                 220

Glu Glu Cys Ala Ala Met Met Lys Gly Lys Tyr Gly Ile Tyr Thr Lys
```

```
                225                 230                 235                 240
Val Ser Arg Tyr Val Asn Trp Ile Lys Glu Lys Thr Lys Leu Thr
                245                 250                 255
```

<210> SEQ ID NO 42
<211> LENGTH: 57
<212> TYPE: PRT
<213> ORGANISM: Artificial Sequence
<220> FEATURE:
<223> OTHER INFORMATION: synthetic polypeptide

<400> SEQUENCE: 42

```
Met Thr Cys Asn Ile Lys Asn Gly Arg Cys Glu Gln Phe Cys Lys Asn
1               5                   10                  15
Ser Ala Asp Asn Lys Val Val Cys Ser Cys Thr Glu Gly Tyr Arg Leu
                20                  25                  30
Ala Glu Asn Gln Lys Ser Cys Glu Pro Ala Val Pro Phe Pro Cys Gly
                35                  40                  45
Arg Val Ser Val Ser Gln Thr Ser Lys
                50                  55
```

<210> SEQ ID NO 43
<211> LENGTH: 496
<212> TYPE: PRT
<213> ORGANISM: Artificial Sequence
<220> FEATURE:
<223> OTHER INFORMATION: synthetic polypeptide

<400> SEQUENCE: 43

```
Glu Phe Ala Arg Pro Cys Ile Pro Lys Ser Phe Gly Tyr Ser Ser Val
1               5                   10                  15
Val Cys Val Cys Asn Ala Thr Tyr Cys Asp Ser Phe Asp Pro Pro Ala
                20                  25                  30
Leu Gly Thr Phe Ser Arg Tyr Glu Ser Thr Arg Ser Gly Arg Arg Met
                35                  40                  45
Glu Leu Ser Met Gly Pro Ile Gln Ala Asn His Thr Gly Thr Gly Leu
            50                  55                  60
Leu Leu Thr Leu Gln Pro Glu Gln Lys Phe Gln Lys Val Lys Gly Phe
65                  70                  75                  80
Gly Gly Ala Met Thr Asp Ala Ala Ala Leu Asn Ile Leu Ala Leu Ser
                85                  90                  95
Pro Pro Ala Gln Asn Leu Leu Leu Lys Ser Tyr Phe Ser Glu Glu Gly
                100                 105                 110
Ile Gly Tyr Asn Ile Ile Arg Val Pro Met Ala Ser Cys Asp Phe Ser
                115                 120                 125
Ile Arg Thr Tyr Thr Tyr Ala Asp Thr Pro Asp Asp Phe Gln Leu His
                130                 135                 140
Asn Phe Ser Leu Pro Glu Glu Asp Thr Lys Leu Lys Ile Pro Leu Ile
145                 150                 155                 160
His Arg Ala Leu Gln Leu Ala Gln Arg Pro Val Ser Leu Leu Ala Ser
                165                 170                 175
Pro Trp Thr Ser Pro Thr Trp Leu Lys Thr Asn Gly Ala Val Asn Gly
                180                 185                 190
Lys Gly Ser Leu Lys Gly Gln Pro Gly Asp Ile Tyr His Gln Thr Trp
                195                 200                 205
Ala Arg Tyr Phe Val Lys Phe Leu Asp Ala Tyr Ala Glu His Lys Leu
                210                 215                 220
```

Gln Phe Trp Ala Val Thr Ala Glu Asn Glu Pro Ser Ala Gly Leu Leu
225                 230                 235                 240

Ser Gly Tyr Pro Phe Gln Cys Leu Gly Phe Thr Pro Glu His Gln Arg
            245                 250                 255

Asp Phe Ile Ala Arg Asp Leu Gly Pro Thr Leu Ala Asn Ser Thr His
        260                 265                 270

His Asn Val Arg Leu Leu Met Leu Asp Asp Gln Arg Leu Leu Leu Pro
    275                 280                 285

His Trp Ala Lys Val Val Leu Thr Asp Pro Glu Ala Ala Lys Tyr Val
290                 295                 300

His Gly Ile Ala Val His Trp Tyr Leu Asp Phe Leu Ala Pro Ala Lys
305                 310                 315                 320

Ala Thr Leu Gly Glu Thr His Arg Leu Phe Pro Asn Thr Met Leu Phe
            325                 330                 335

Ala Ser Glu Ala Cys Val Gly Ser Lys Phe Trp Glu Gln Ser Val Arg
        340                 345                 350

Leu Gly Ser Trp Asp Arg Gly Met Gln Tyr Ser His Ser Ile Ile Thr
    355                 360                 365

Asn Leu Leu Tyr His Val Gly Trp Thr Asp Trp Asn Leu Ala Leu
370                 375                 380

Asn Pro Glu Gly Gly Pro Asn Trp Val Arg Asn Phe Val Asp Ser Pro
385                 390                 395                 400

Ile Ile Val Asp Ile Thr Lys Asp Thr Phe Tyr Lys Gln Pro Met Phe
            405                 410                 415

Tyr His Leu Gly His Phe Ser Lys Phe Ile Pro Glu Gly Ser Gln Arg
        420                 425                 430

Val Gly Leu Val Ala Ser Gln Lys Asn Asp Leu Asp Ala Val Ala Leu
    435                 440                 445

Met His Pro Asp Gly Ser Ala Val Val Val Leu Asn Arg Ser Ser
450                 455                 460

Lys Asp Val Pro Leu Thr Ile Lys Asp Pro Ala Val Gly Phe Leu Glu
465                 470                 475                 480

Thr Ile Ser Pro Gly Tyr Ser Ile His Thr Tyr Leu Trp His Arg Gln
            485                 490                 495

<210> SEQ ID NO 44
<211> LENGTH: 390
<212> TYPE: PRT
<213> ORGANISM: Artificial Sequence
<220> FEATURE:
<223> OTHER INFORMATION: synthetic polypeptide

<400> SEQUENCE: 44

Leu Asp Asn Gly Leu Ala Arg Thr Pro Thr Met Gly Trp Leu His Trp
1               5                   10                  15

Glu Arg Phe Met Cys Asn Leu Asp Cys Gln Glu Glu Pro Asp Ser Cys
            20                  25                  30

Ile Ser Glu Lys Leu Phe Met Glu Met Ala Glu Leu Met Val Ser Glu
        35                  40                  45

Gly Trp Lys Asp Ala Gly Tyr Glu Tyr Leu Cys Ile Asp Asp Cys Trp
    50                  55                  60

Met Ala Pro Gln Arg Asp Ser Glu Gly Arg Leu Gln Ala Asp Pro Gln
65                  70                  75                  80

Arg Phe Pro His Gly Ile Arg Gln Leu Ala Asn Tyr Val His Ser Lys
                85                  90                  95

```
Gly Leu Lys Leu Gly Ile Tyr Ala Asp Val Gly Asn Lys Thr Cys Ala
                100                 105                 110

Gly Phe Pro Gly Ser Phe Gly Tyr Tyr Asp Ile Asp Ala Gln Thr Phe
            115                 120                 125

Ala Asp Trp Gly Val Asp Leu Leu Lys Phe Asp Gly Cys Tyr Cys Asp
        130                 135                 140

Ser Leu Glu Asn Leu Ala Asp Gly Tyr Lys His Met Ser Leu Ala Leu
145                 150                 155                 160

Asn Arg Thr Gly Arg Ser Ile Val Tyr Ser Cys Glu Trp Pro Leu Tyr
                165                 170                 175

Met Trp Pro Phe Gln Lys Pro Asn Tyr Thr Glu Ile Arg Gln Tyr Cys
            180                 185                 190

Asn His Trp Arg Asn Phe Ala Asp Ile Asp Asp Ser Trp Lys Ser Ile
        195                 200                 205

Lys Ser Ile Leu Asp Trp Thr Ser Phe Asn Gln Glu Arg Ile Val Asp
210                 215                 220

Val Ala Gly Pro Gly Gly Trp Asn Asp Pro Asp Met Leu Val Ile Gly
225                 230                 235                 240

Asn Phe Gly Leu Ser Trp Asn Gln Gln Val Thr Gln Met Ala Leu Trp
                245                 250                 255

Ala Ile Met Ala Ala Pro Leu Phe Met Ser Asn Asp Leu Arg His Ile
            260                 265                 270

Ser Pro Gln Ala Lys Ala Leu Leu Gln Asp Lys Asp Val Ile Ala Ile
        275                 280                 285

Asn Gln Asp Pro Leu Gly Lys Gln Gly Tyr Gln Leu Arg Gln Gly Asp
290                 295                 300

Asn Phe Glu Val Trp Glu Arg Pro Leu Ser Gly Leu Ala Trp Ala Val
305                 310                 315                 320

Ala Met Ile Asn Arg Gln Glu Ile Gly Pro Arg Ser Tyr Thr Ile
                325                 330                 335

Ala Val Ala Ser Leu Gly Lys Gly Val Ala Cys Asn Pro Ala Cys Phe
            340                 345                 350

Ile Thr Gln Leu Leu Pro Val Lys Arg Lys Leu Gly Phe Tyr Glu Trp
        355                 360                 365

Thr Ser Arg Leu Arg Ser His Ile Asn Pro Thr Gly Thr Val Leu Leu
370                 375                 380

Gln Leu Glu Asn Thr Met
385                 390

<210> SEQ ID NO 45
<211> LENGTH: 479
<212> TYPE: PRT
<213> ORGANISM: Artificial Sequence
<220> FEATURE:
<223> OTHER INFORMATION: synthetic polypeptide

<400> SEQUENCE: 45

Arg Pro Pro Asn Ile Val Leu Ile Phe Ala Asp Asp Leu Gly Tyr Gly
1               5                   10                  15

Asp Leu Gly Cys Tyr Gly His Pro Ser Ser Thr Thr Pro Asn Leu Asp
            20                  25                  30

Gln Leu Ala Ala Gly Gly Leu Arg Phe Thr Asp Phe Tyr Val Pro Val
        35                  40                  45

Ser Leu Pro Ser Arg Ala Ala Leu Leu Thr Gly Arg Leu Pro Val Arg
50                  55                  60
```

```
Met Gly Met Tyr Pro Gly Val Leu Val Pro Ser Ser Arg Gly Gly Leu
 65                  70                  75                  80

Pro Leu Glu Glu Val Thr Val Ala Glu Val Leu Ala Ala Arg Gly Tyr
                 85                  90                  95

Leu Thr Gly Met Ala Gly Lys Trp His Leu Gly Val Gly Pro Glu Gly
             100                 105                 110

Ala Phe Leu Pro Pro His Gln Gly Phe His Arg Phe Leu Gly Ile Pro
         115                 120                 125

Tyr Ser His Asp Gln Gly Pro Cys Gln Asn Leu Thr Cys Phe Pro Pro
     130                 135                 140

Ala Thr Pro Cys Asp Gly Gly Cys Asp Gln Gly Leu Val Pro Ile Pro
145                 150                 155                 160

Leu Leu Ala Asn Leu Ser Val Glu Ala Gln Pro Pro Trp Leu Pro Gly
                 165                 170                 175

Leu Glu Ala Arg Tyr Met Ala Phe Ala His Asp Leu Met Ala Asp Ala
             180                 185                 190

Gln Arg Gln Asp Arg Pro Phe Phe Leu Tyr Tyr Ala Ser His His Thr
         195                 200                 205

His Tyr Pro Gln Phe Ser Gly Gln Ser Phe Ala Glu Arg Ser Gly Arg
     210                 215                 220

Gly Pro Phe Gly Asp Ser Leu Met Glu Leu Asp Ala Ala Val Gly Thr
225                 230                 235                 240

Leu Met Thr Ala Ile Gly Asp Leu Gly Leu Leu Glu Glu Thr Leu Val
                 245                 250                 255

Ile Phe Thr Ala Asp Asn Gly Pro Glu Thr Met Arg Met Ser Arg Gly
             260                 265                 270

Gly Cys Ser Gly Leu Leu Arg Cys Gly Lys Gly Thr Thr Tyr Glu Gly
         275                 280                 285

Gly Val Arg Glu Pro Ala Leu Ala Phe Trp Pro Gly His Ile Ala Pro
     290                 295                 300

Gly Val Thr His Glu Leu Ala Ser Ser Leu Asp Leu Leu Pro Thr Leu
305                 310                 315                 320

Ala Ala Leu Ala Gly Ala Pro Leu Pro Asn Val Thr Leu Asp Gly Phe
                 325                 330                 335

Asp Leu Ser Pro Leu Leu Leu Gly Thr Gly Lys Ser Pro Arg Gln Ser
             340                 345                 350

Leu Phe Phe Tyr Pro Ser Tyr Pro Asp Glu Val Arg Gly Val Phe Ala
         355                 360                 365

Val Arg Thr Gly Lys Tyr Lys Ala His Phe Phe Thr Gln Gly Ser Ala
     370                 375                 380

His Ser Asp Thr Thr Ala Asp Pro Ala Cys His Ala Ser Ser Ser Leu
385                 390                 395                 400

Thr Ala His Glu Pro Pro Leu Leu Tyr Asp Leu Ser Lys Asp Pro Gly
                 405                 410                 415

Glu Asn Tyr Asn Leu Leu Gly Ala Thr Pro Glu Val Leu Gln Ala Leu
             420                 425                 430

Lys Gln Leu Gln Leu Leu Lys Ala Gln Leu Asp Ala Ala Val Thr Phe
         435                 440                 445

Gly Pro Ser Gln Val Ala Arg Gly Glu Asp Pro Ala Leu Gln Ile Cys
     450                 455                 460

Cys His Pro Gly Cys Thr Pro Arg Pro Ala Cys Cys His Cys Pro
465                 470                 475
```

<210> SEQ ID NO 46
<211> LENGTH: 474
<212> TYPE: PRT
<213> ORGANISM: Artificial Sequence
<220> FEATURE:
<223> OTHER INFORMATION: synthetic polypeptide

<400> SEQUENCE: 46

```
Ser Arg Pro Pro His Leu Val Phe Leu Leu Ala Asp Leu Gly Trp
1               5                   10                  15

Asn Asp Val Gly Phe His Gly Ser Arg Ile Arg Thr Pro His Leu Asp
            20                  25                  30

Ala Leu Ala Ala Gly Gly Val Leu Leu Asp Asn Tyr Tyr Thr Gln Pro
        35                  40                  45

Leu Thr Pro Ser Arg Ser Gln Leu Leu Thr Gly Arg Tyr Gln Ile Arg
    50                  55                  60

Thr Gly Leu Gln His Gln Ile Ile Trp Pro Cys Gln Pro Ser Cys Val
65                  70                  75                  80

Pro Leu Asp Glu Lys Leu Leu Pro Gln Leu Leu Lys Glu Ala Gly Tyr
                85                  90                  95

Thr Thr His Met Val Gly Lys Trp His Leu Gly Met Tyr Arg Lys Glu
            100                 105                 110

Cys Leu Pro Thr Arg Arg Gly Phe Asp Thr Tyr Phe Gly Tyr Leu Leu
        115                 120                 125

Gly Ser Glu Asp Tyr Tyr Ser His Glu Arg Cys Thr Leu Ile Asp Ala
    130                 135                 140

Leu Asn Val Thr Arg Cys Ala Leu Asp Phe Arg Asp Gly Glu Glu Val
145                 150                 155                 160

Ala Thr Gly Tyr Lys Asn Met Tyr Ser Thr Asn Ile Phe Thr Lys Arg
                165                 170                 175

Ala Ile Ala Leu Ile Thr Asn His Pro Pro Glu Lys Pro Leu Phe Leu
            180                 185                 190

Tyr Leu Ala Leu Gln Ser Val His Glu Pro Leu Gln Val Pro Glu Glu
        195                 200                 205

Tyr Leu Lys Pro Tyr Asp Phe Ile Gln Asp Lys Asn Arg His His Tyr
    210                 215                 220

Ala Gly Met Val Ser Leu Met Asp Glu Ala Val Gly Asn Val Thr Ala
225                 230                 235                 240

Ala Leu Lys Ser Ser Gly Leu Trp Asn Asn Thr Val Phe Ile Phe Ser
                245                 250                 255

Thr Asp Asn Gly Gly Gln Thr Leu Ala Gly Gly Asn Asn Trp Pro Leu
            260                 265                 270

Arg Gly Arg Lys Trp Ser Leu Trp Glu Gly Gly Val Arg Gly Val Gly
        275                 280                 285

Phe Val Ala Ser Pro Leu Leu Lys Gln Lys Gly Val Lys Asn Arg Glu
    290                 295                 300

Leu Ile His Ile Ser Asp Trp Leu Pro Thr Leu Val Lys Leu Ala Arg
305                 310                 315                 320

Gly His Thr Asn Gly Thr Lys Pro Leu Asp Gly Phe Asp Val Trp Lys
                325                 330                 335

Thr Ile Ser Glu Gly Ser Pro Ser Pro Arg Ile Glu Leu Leu His Asn
            340                 345                 350

Ile Asp Pro Asn Phe Val Asp Ser Ser Pro Cys Ser Ala Phe Asn Thr
        355                 360                 365

Ser Val His Ala Ala Ile Arg His Gly Asn Trp Lys Leu Leu Thr Gly
```

```
                370                 375                 380
Tyr Pro Gly Cys Gly Tyr Trp Phe Pro Pro Ser Gln Tyr Asn Val
385                 390                 395                 400

Ser Glu Ile Pro Ser Ser Asp Pro Pro Thr Lys Thr Leu Trp Leu Phe
                405                 410                 415

Asp Ile Asp Arg Asp Pro Glu Glu Arg His Asp Leu Ser Arg Glu Tyr
                420                 425                 430

Pro His Ile Val Thr Lys Leu Leu Ser Arg Leu Gln Phe Tyr His Lys
                435                 440                 445

His Ser Val Pro Val Tyr Phe Pro Ala Gln Asp Pro Arg Cys Asp Pro
            450                 455                 460

Lys Ala Thr Gly Val Trp Gly Pro Trp Met
465                 470
```

<210> SEQ ID NO 47
<211> LENGTH: 492
<212> TYPE: PRT
<213> ORGANISM: Artificial Sequence
<220> FEATURE:
<223> OTHER INFORMATION: synthetic polypeptide

<400> SEQUENCE: 47

```
Leu Trp Pro Trp Pro Gln Asn Phe Gln Thr Ser Asp Gln Arg Tyr Val
1               5                   10                  15

Leu Tyr Pro Asn Asn Phe Gln Phe Gln Tyr Asp Val Ser Ser Ala Ala
                20                  25                  30

Gln Pro Gly Cys Ser Val Leu Asp Glu Ala Phe Gln Arg Tyr Arg Asp
            35                  40                  45

Leu Leu Phe Gly Thr Leu Glu Lys Asn Val Leu Val Ser Val Val
50                  55                  60

Thr Pro Gly Cys Asn Gln Leu Pro Thr Leu Glu Ser Val Glu Asn Tyr
65                  70                  75                  80

Thr Leu Thr Ile Asn Asp Asp Gln Cys Leu Leu Leu Ser Glu Thr Val
                85                  90                  95

Trp Gly Ala Leu Arg Gly Leu Glu Thr Phe Ser Gln Leu Val Trp Lys
            100                 105                 110

Ser Ala Glu Gly Thr Phe Phe Ile Asn Lys Thr Glu Ile Glu Asp Phe
        115                 120                 125

Pro Arg Phe Pro His Arg Gly Leu Leu Leu Asp Thr Ser Arg His Tyr
130                 135                 140

Leu Pro Leu Ser Ser Ile Leu Asp Thr Leu Asp Val Met Ala Tyr Asn
145                 150                 155                 160

Lys Leu Asn Val Phe His Trp His Leu Val Asp Asp Pro Ser Phe Pro
                165                 170                 175

Tyr Glu Ser Phe Thr Phe Pro Glu Leu Met Arg Lys Gly Ser Tyr Asn
            180                 185                 190

Pro Val Thr His Ile Tyr Thr Ala Gln Asp Val Lys Glu Val Ile Glu
        195                 200                 205

Tyr Ala Arg Leu Arg Gly Ile Arg Val Leu Ala Glu Phe Asp Thr Pro
    210                 215                 220

Gly His Thr Leu Ser Trp Gly Pro Gly Ile Pro Gly Leu Leu Thr Pro
225                 230                 235                 240

Cys Tyr Ser Gly Ser Glu Pro Ser Gly Thr Phe Gly Pro Val Asn Pro
                245                 250                 255

Ser Leu Asn Asn Thr Tyr Glu Phe Met Ser Thr Phe Phe Leu Glu Val
```

Ser Ser Val Phe Pro Asp Phe Tyr Leu His Leu Gly Gly Asp Glu Val
                260                 265                 270

Asp Phe Thr Cys Trp Lys Ser Asn Pro Glu Ile Gln Asp Phe Met Arg
        275                 280                 285

Lys Lys Gly Phe Gly Glu Asp Phe Lys Gln Leu Glu Ser Phe Tyr Ile
290                 295                 300

Gln Thr Leu Leu Asp Ile Val Ser Ser Tyr Gly Lys Gly Tyr Val Val
305                 310                 315                 320

Trp Gln Glu Val Phe Asp Asn Lys Val Lys Ile Gln Pro Asp Thr Ile
            325                 330                 335

Ile Gln Val Trp Arg Glu Asp Ile Pro Val Asn Tyr Met Lys Glu Leu
                340                 345                 350

Glu Leu Val Thr Lys Ala Gly Phe Arg Ala Leu Leu Ser Ala Pro Trp
        355                 360                 365

Tyr Leu Asn Arg Ile Ser Tyr Gly Pro Asp Trp Lys Asp Phe Tyr Val
370                 375                 380

Val Glu Pro Leu Ala Phe Glu Gly Thr Pro Glu Gln Lys Ala Leu Val
385                 390                 395                 400

Ile Gly Gly Glu Ala Cys Met Trp Gly Glu Tyr Val Asp Asn Thr Asn
            405                 410                 415

Leu Val Pro Arg Leu Trp Pro Arg Ala Gly Ala Val Ala Glu Arg Leu
                420                 425                 430

Trp Ser Asn Lys Leu Thr Ser Asp Leu Thr Phe Ala Tyr Glu Arg Leu
        435                 440                 445

Ser His Phe Arg Cys Glu Leu Leu Arg Arg Gly Val Gln Ala Gln Pro
465                 470                 475                 480

Leu Asn Val Gly Phe Cys Glu Gln Glu Phe Glu Gln
            485                 490

<210> SEQ ID NO 48
<211> LENGTH: 492
<212> TYPE: PRT
<213> ORGANISM: Artificial Sequence
<220> FEATURE:
<223> OTHER INFORMATION: synthetic polypeptide

<400> SEQUENCE: 48

Leu Trp Pro Trp Pro Gln Asn Phe Gln Thr Ser Asp Gln Arg Tyr Val
1               5                   10                  15

Leu Tyr Pro Asn Asn Phe Gln Phe Gln Tyr Asp Val Ser Ser Ala Ala
            20                  25                  30

Gln Pro Gly Cys Ser Val Leu Asp Glu Ala Phe Gln Arg Tyr Arg Asp
        35                  40                  45

Leu Leu Phe Gly Thr Leu Glu Lys Asn Val Leu Val Val Ser Val Val
50                  55                  60

Thr Pro Gly Cys Asn Gln Leu Pro Thr Leu Glu Ser Val Glu Asn Tyr
65                  70                  75                  80

Thr Leu Thr Ile Asn Asp Asp Gln Cys Leu Leu Leu Ser Glu Thr Val
                85                  90                  95

Trp Gly Ala Leu Arg Gly Leu Glu Thr Phe Ser Gln Leu Val Trp Lys
            100                 105                 110

Ser Ala Glu Gly Thr Phe Phe Ile Asn Lys Thr Glu Ile Glu Asp Phe
        115                 120                 125

Pro Arg Phe Pro His Arg Gly Leu Leu Leu Asp Thr Ser Arg His Tyr 130                 135                 140
Leu Pro Leu Ser Ser Ile Leu Asp Thr Leu Asp Val Met Ala Tyr Asn
145                 150                 155                 160

Lys Leu Asn Val Phe His Trp His Leu Val Asp Asp Pro Ser Phe Pro
                165                 170                 175

Tyr Glu Ser Phe Thr Phe Pro Glu Leu Met Arg Lys Gly Ser Tyr Asn
            180                 185                 190

Pro Val Thr His Ile Tyr Thr Ala Gln Asp Val Lys Glu Val Ile Glu
        195                 200                 205

Tyr Ala Arg Leu Arg Gly Ile Arg Val Leu Ala Glu Phe Asp Thr Pro
210                 215                 220

Gly His Thr Leu Ser Trp Gly Pro Gly Ile Pro Gly Leu Leu Thr Pro
225                 230                 235                 240

Cys Tyr Ser Gly Ser Glu Pro Ser Gly Thr Phe Gly Pro Val Asn Pro
                245                 250                 255

Ser Leu Asn Asn Thr Tyr Glu Phe Met Ser Thr Phe Phe Leu Glu Val
            260                 265                 270

Ser Ser Val Phe Pro Asp Phe Tyr Leu His Leu Gly Gly Asp Glu Val
        275                 280                 285

Asp Phe Thr Cys Trp Lys Ser Asn Pro Glu Ile Gln Asp Phe Met Arg
290                 295                 300

Lys Lys Gly Phe Gly Glu Asp Phe Lys Gln Leu Glu Ser Phe Tyr Ile
305                 310                 315                 320

Gln Thr Leu Leu Asp Ile Val Ser Ser Tyr Gly Lys Gly Tyr Val Val
                325                 330                 335

Trp Gln Glu Val Phe Asp Asn Lys Val Lys Ile Gln Pro Asp Thr Ile
            340                 345                 350

Ile Gln Val Trp Arg Glu Asp Ile Pro Val Asn Tyr Met Lys Glu Leu
        355                 360                 365

Glu Leu Val Thr Lys Ala Gly Phe Arg Ala Leu Leu Ser Ala Pro Trp
370                 375                 380

Tyr Leu Asn Arg Ile Ser Tyr Gly Pro Asp Trp Lys Asp Phe Tyr Val
385                 390                 395                 400

Val Glu Pro Leu Ala Phe Glu Gly Thr Pro Glu Gln Lys Ala Leu Val
                405                 410                 415

Ile Gly Gly Glu Ala Cys Met Trp Gly Glu Tyr Val Asp Asn Thr Asn
            420                 425                 430

Leu Val Pro Arg Leu Trp Pro Arg Ala Gly Ala Val Ala Glu Arg Leu
        435                 440                 445

Trp Ser Asn Lys Leu Thr Ser Asp Leu Thr Phe Ala Tyr Glu Arg Leu
450                 455                 460

Ser His Phe Arg Cys Glu Leu Leu Arg Arg Gly Val Gln Ala Gln Pro
465                 470                 475                 480

Leu Asn Val Gly Phe Cys Glu Gln Glu Phe Glu Gln
                485                 490

<210> SEQ ID NO 49
<211> LENGTH: 480
<212> TYPE: PRT
<213> ORGANISM: Artificial Sequence
<220> FEATURE:
<223> OTHER INFORMATION: synthetic polypeptide

<400> SEQUENCE: 49

Pro Ala Leu Trp Pro Leu Pro Leu Ser Val Lys Met Thr Pro Asn Leu

-continued

```
1               5                   10                  15
Leu His Leu Ala Pro Glu Asn Phe Tyr Ile Ser His Ser Pro Asn Ser
            20                  25                  30

Thr Ala Gly Pro Ser Cys Thr Leu Glu Glu Ala Phe Arg Arg Tyr
            35                  40                  45

His Gly Tyr Ile Phe Gly Thr Gln Val Gln Gln Leu Leu Val Ser Ile
    50                  55                      60

Thr Leu Gln Ser Glu Cys Asp Ala Phe Pro Asn Ile Ser Ser Asp Glu
65                  70                      75                  80

Ser Tyr Thr Leu Leu Val Lys Glu Pro Val Ala Val Leu Lys Ala Asn
                85                  90                  95

Arg Val Trp Gly Ala Leu Arg Gly Leu Glu Thr Phe Ser Gln Leu Val
                100                 105                 110

Tyr Gln Asp Ser Tyr Gly Thr Phe Thr Ile Asn Glu Ser Thr Ile Ile
                115                 120                 125

Asp Ser Pro Arg Phe Ser His Arg Gly Ile Leu Ile Asp Thr Ser Arg
            130                 135                 140

His Tyr Leu Pro Val Lys Ile Ile Leu Lys Thr Leu Asp Ala Met Ala
145                 150                 155                 160

Phe Asn Lys Phe Asn Val Leu His Trp His Ile Val Asp Asp Gln Ser
                165                 170                 175

Phe Pro Tyr Gln Ser Ile Thr Phe Pro Glu Leu Ser Asn Lys Gly Ser
                180                 185                 190

Tyr Ser Leu Ser His Val Tyr Thr Pro Asn Asp Val Arg Met Val Ile
                195                 200                 205

Glu Tyr Ala Arg Leu Arg Gly Ile Arg Val Leu Pro Glu Phe Asp Thr
    210                 215                 220

Pro Gly His Thr Leu Ser Trp Gly Lys Gly Gln Lys Asp Leu Leu Thr
225                 230                 235                 240

Pro Cys Tyr Ser Asp Ser Phe Gly Pro Ile Asn Pro Thr Leu Asn Thr
                245                 250                 255

Thr Tyr Ser Phe Leu Thr Thr Phe Phe Lys Glu Ile Ser Glu Val Phe
                260                 265                 270

Pro Asp Gln Phe Ile His Leu Gly Gly Asp Glu Val Glu Phe Lys Cys
                275                 280                 285

Trp Glu Ser Asn Pro Lys Ile Gln Asp Phe Met Arg Gln Lys Gly Phe
                290                 295                 300

Gly Thr Asp Phe Lys Lys Leu Glu Ser Phe Tyr Ile Gln Lys Val Leu
305                 310                 315                 320

Asp Ile Ile Ala Thr Ile Asn Lys Gly Ser Ile Val Trp Gln Glu Val
                325                 330                 335

Phe Asp Asp Lys Ala Lys Leu Ala Pro Gly Thr Ile Val Glu Val Trp
                340                 345                 350

Lys Asp Ser Ala Tyr Pro Glu Glu Leu Ser Arg Val Thr Ala Ser Gly
                355                 360                 365

Phe Pro Val Ile Leu Ser Ala Pro Trp Tyr Leu Asp Leu Ile Ser Tyr
    370                 375                 380

Gly Gln Asp Trp Arg Lys Tyr Tyr Lys Val Glu Pro Leu Asp Phe Gly
385                 390                 395                 400

Gly Thr Gln Lys Gln Lys Gln Leu Phe Ile Gly Gly Glu Ala Cys Leu
                405                 410                 415

Trp Gly Glu Tyr Val Asp Ala Thr Asn Leu Thr Pro Arg Leu Trp Pro
                420                 425                 430
```

Arg Ala Ser Ala Val Gly Glu Arg Leu Trp Ser Ser Lys Asp Val Arg
        435                 440                 445

Asp Met Asp Asp Ala Tyr Asp Arg Leu Thr Arg His Arg Cys Arg Met
        450                 455                 460

Val Glu Arg Gly Ile Ala Ala Gln Pro Leu Tyr Ala Gly Tyr Cys Asn
465                 470                 475                 480

<210> SEQ ID NO 50
<211> LENGTH: 481
<212> TYPE: PRT
<213> ORGANISM: Artificial Sequence
<220> FEATURE:
<223> OTHER INFORMATION: synthetic polypeptide

<400> SEQUENCE: 50

Pro Ala Leu Trp Pro Leu Pro Leu Ser Val Lys Met Thr Pro Asn Leu
1               5                   10                  15

Leu His Leu Ala Pro Glu Asn Phe Tyr Ile Ser His Ser Pro Asn Ser
            20                  25                  30

Thr Ala Gly Pro Ser Cys Thr Leu Leu Glu Glu Ala Phe Arg Arg Tyr
        35                  40                  45

His Gly Tyr Ile Phe Gly Thr Gln Val Gln Gln Leu Leu Val Ser Ile
    50                  55                  60

Thr Leu Gln Ser Glu Cys Asp Ala Phe Pro Asn Ile Ser Ser Asp Glu
65                  70                  75                  80

Ser Tyr Thr Leu Leu Val Lys Glu Pro Val Ala Val Leu Lys Ala Asn
                85                  90                  95

Arg Val Trp Gly Ala Leu Arg Gly Leu Glu Thr Phe Ser Gln Leu Val
            100                 105                 110

Tyr Gln Asp Ser Tyr Gly Thr Phe Thr Ile Asn Glu Ser Thr Ile Ile
        115                 120                 125

Asp Ser Pro Arg Phe Ser His Arg Gly Ile Leu Ile Asp Thr Ser Arg
    130                 135                 140

His Tyr Leu Pro Val Lys Ile Ile Leu Lys Thr Leu Asp Ala Met Ala
145                 150                 155                 160

Phe Asn Lys Phe Asn Val Leu His Trp His Ile Val Asp Asp Gln Ser
                165                 170                 175

Phe Pro Tyr Gln Ser Ile Thr Phe Pro Glu Leu Ser Asn Lys Gly Ser
            180                 185                 190

Tyr Ser Leu Ser His Val Tyr Thr Pro Asn Asp Val Arg Met Val Ile
        195                 200                 205

Glu Tyr Ala Arg Leu Arg Gly Ile Arg Val Leu Pro Glu Phe Asp Thr
    210                 215                 220

Pro Gly His Thr Leu Ser Trp Gly Lys Gly Gln Lys Asp Leu Leu Thr
225                 230                 235                 240

Pro Cys Tyr Ser Leu Asp Ser Phe Gly Pro Ile Asn Pro Thr Leu Asn
                245                 250                 255

Thr Thr Tyr Ser Phe Leu Thr Thr Phe Phe Lys Glu Ile Ser Glu Val
            260                 265                 270

Phe Pro Asp Gln Phe Ile His Leu Gly Gly Asp Glu Val Glu Phe Lys
        275                 280                 285

Cys Trp Glu Ser Asn Pro Lys Ile Gln Asp Phe Met Arg Gln Lys Gly
    290                 295                 300

Phe Gly Thr Asp Phe Lys Lys Leu Glu Ser Phe Tyr Ile Gln Lys Val
305                 310                 315                 320

```
Leu Asp Ile Ile Ala Thr Ile Asn Lys Gly Ser Ile Val Trp Gln Glu
                325                 330                 335

Val Phe Asp Asp Lys Ala Lys Leu Ala Pro Gly Thr Ile Val Glu Val
            340                 345                 350

Trp Lys Asp Ser Ala Tyr Pro Glu Glu Leu Ser Arg Val Thr Ala Ser
        355                 360                 365

Gly Phe Pro Val Ile Leu Ser Ala Pro Trp Tyr Leu Asp Leu Ile Ser
    370                 375                 380

Tyr Gly Gln Asp Trp Arg Lys Tyr Lys Val Glu Pro Leu Asp Phe
385                 390                 395                 400

Gly Gly Thr Gln Lys Gln Lys Gln Leu Phe Ile Gly Glu Ala Cys
                405                 410                 415

Leu Trp Gly Glu Tyr Val Asp Ala Thr Asn Leu Thr Pro Arg Leu Trp
            420                 425                 430

Pro Arg Ala Ser Ala Val Gly Glu Arg Leu Trp Ser Ser Lys Asp Val
        435                 440                 445

Arg Asp Met Asp Asp Ala Tyr Asp Arg Leu Thr Arg His Arg Cys Arg
    450                 455                 460

Met Val Glu Arg Gly Ile Ala Ala Gln Pro Leu Tyr Ala Gly Tyr Cys
465                 470                 475                 480

Asn

<210> SEQ ID NO 51
<211> LENGTH: 492
<212> TYPE: PRT
<213> ORGANISM: Artificial Sequence
<220> FEATURE:
<223> OTHER INFORMATION: synthetic polypeptide

<400> SEQUENCE: 51

Leu Trp Pro Trp Pro Gln Asn Phe Gln Thr Ser Asp Gln Arg Tyr Val
1               5                   10                  15

Leu Tyr Pro Asn Asn Phe Gln Phe Gln Tyr Asp Val Ser Ser Ala Ala
            20                  25                  30

Gln Pro Gly Cys Ser Val Leu Asp Glu Ala Phe Gln Arg Tyr Arg Asp
        35                  40                  45

Leu Leu Phe Gly Thr Leu Glu Lys Asn Val Leu Val Val Ser Val Val
    50                  55                  60

Thr Pro Gly Cys Asn Gln Leu Pro Thr Leu Glu Ser Val Glu Asn Tyr
65                  70                  75                  80

Thr Leu Thr Ile Asn Asp Asp Gln Cys Leu Leu Leu Ser Glu Thr Val
                85                  90                  95

Trp Gly Ala Leu Arg Gly Leu Glu Thr Phe Ser Gln Leu Val Trp Lys
            100                 105                 110

Ser Ala Glu Gly Thr Phe Phe Ile Asn Lys Thr Glu Ile Glu Asp Phe
        115                 120                 125

Pro Arg Phe Pro His Arg Gly Leu Leu Leu Asp Thr Ser Arg His Tyr
    130                 135                 140

Leu Pro Leu Ser Ser Ile Leu Asp Thr Leu Asp Val Met Ala Tyr Asn
145                 150                 155                 160

Lys Leu Asn Val Phe His Trp His Leu Val Asp Asp Pro Ser Phe Pro
                165                 170                 175

Tyr Glu Ser Phe Thr Phe Pro Glu Leu Met Arg Lys Gly Ser Tyr Asn
            180                 185                 190
```

Pro Val Thr His Ile Tyr Thr Ala Gln Asp Val Lys Glu Val Ile Glu
            195                 200                 205

Tyr Ala Arg Leu Arg Gly Ile Arg Val Leu Ala Glu Phe Asp Thr Pro
    210                 215                 220

Gly His Thr Leu Ser Trp Gly Pro Gly Ile Pro Gly Leu Leu Thr Pro
225                 230                 235                 240

Cys Tyr Ser Gly Ser Glu Pro Ser Gly Thr Phe Gly Pro Val Asn Pro
                245                 250                 255

Ser Leu Asn Asn Thr Tyr Glu Phe Met Ser Thr Phe Phe Leu Glu Val
            260                 265                 270

Ser Ser Val Phe Pro Asp Phe Tyr Leu His Leu Gly Gly Asp Glu Val
        275                 280                 285

Asp Phe Thr Cys Trp Lys Ser Asn Pro Glu Ile Gln Asp Phe Met Arg
    290                 295                 300

Lys Lys Gly Phe Gly Glu Asp Phe Lys Gln Leu Glu Ser Phe Tyr Ile
305                 310                 315                 320

Gln Thr Leu Leu Asp Ile Val Ser Ser Tyr Gly Lys Gly Tyr Val Val
                325                 330                 335

Trp Gln Glu Val Phe Asp Asn Lys Val Lys Ile Gln Pro Asp Thr Ile
            340                 345                 350

Ile Gln Val Trp Arg Glu Asp Ile Pro Val Asn Tyr Met Lys Glu Leu
        355                 360                 365

Glu Leu Val Thr Lys Ala Gly Phe Arg Ala Leu Leu Ser Ala Pro Trp
    370                 375                 380

Tyr Leu Asn Arg Ile Ser Tyr Gly Pro Asp Trp Lys Asp Phe Tyr Val
385                 390                 395                 400

Val Glu Pro Leu Ala Phe Glu Gly Thr Pro Glu Gln Lys Ala Leu Val
                405                 410                 415

Ile Gly Gly Glu Ala Cys Met Trp Gly Glu Tyr Val Asp Asn Thr Asn
            420                 425                 430

Leu Val Pro Arg Leu Trp Pro Arg Ala Gly Ala Val Ala Glu Arg Leu
        435                 440                 445

Trp Ser Asn Lys Leu Thr Ser Asp Leu Thr Phe Ala Tyr Glu Arg Leu
    450                 455                 460

Ser His Phe Arg Cys Glu Leu Leu Arg Arg Gly Val Gln Ala Gln Pro
465                 470                 475                 480

Leu Asn Val Gly Phe Cys Glu Gln Glu Phe Glu Gln
                485                 490

<210> SEQ ID NO 52
<211> LENGTH: 307
<212> TYPE: PRT
<213> ORGANISM: Artificial Sequence
<220> FEATURE:
<223> OTHER INFORMATION: synthetic polypeptide

<400> SEQUENCE: 52

Val Pro Trp Phe Pro Arg Thr Ile Gln Glu Leu Asp Arg Phe Ala Asn
1               5                   10                  15

Gln Ile Leu Ser Tyr Gly Ala Glu Leu Asp Ala Asp His Pro Gly Phe
            20                  25                  30

Lys Asp Pro Val Tyr Arg Ala Arg Arg Lys Gln Phe Ala Asp Ile Ala
        35                  40                  45

Tyr Asn Tyr Arg His Gly Gln Pro Ile Pro Arg Val Glu Tyr Met Glu
    50                  55                  60

```
Glu Glu Lys Lys Thr Trp Gly Thr Val Phe Lys Thr Leu Lys Ser Leu
 65                  70                  75                  80

Tyr Lys Thr His Ala Cys Tyr Glu Tyr Asn His Ile Phe Pro Leu Leu
                 85                  90                  95

Glu Lys Tyr Cys Gly Phe His Glu Asp Asn Ile Pro Gln Leu Glu Asp
            100                 105                 110

Val Ser Gln Phe Leu Gln Thr Cys Thr Gly Phe Arg Leu Arg Pro Val
        115                 120                 125

Ala Gly Leu Leu Ser Ser Arg Asp Phe Leu Gly Leu Ala Phe Arg
    130                 135                 140

Val Phe His Cys Thr Gln Tyr Ile Arg His Gly Ser Lys Pro Met Tyr
145                 150                 155                 160

Thr Pro Glu Pro Asp Ile Cys His Glu Leu Leu Gly His Val Pro Leu
                165                 170                 175

Phe Ser Asp Arg Ser Phe Ala Gln Phe Ser Gln Glu Ile Gly Leu Ala
            180                 185                 190

Ser Leu Gly Ala Pro Asp Glu Tyr Ile Glu Lys Leu Ala Thr Ile Tyr
        195                 200                 205

Trp Phe Thr Val Glu Phe Gly Leu Cys Lys Gln Gly Asp Ser Ile Lys
    210                 215                 220

Ala Tyr Gly Ala Gly Leu Leu Ser Ser Phe Gly Glu Leu Gln Tyr Cys
225                 230                 235                 240

Leu Ser Glu Lys Pro Lys Leu Leu Pro Leu Glu Leu Glu Lys Thr Ala
                245                 250                 255

Ile Gln Asn Tyr Thr Val Thr Glu Phe Gln Pro Leu Tyr Tyr Val Ala
            260                 265                 270

Glu Ser Phe Asn Asp Ala Lys Glu Lys Val Arg Asn Phe Ala Ala Thr
        275                 280                 285

Ile Pro Arg Pro Phe Ser Val Arg Tyr Asp Pro Tyr Thr Gln Arg Ile
    290                 295                 300

Glu Val Leu
305

<210> SEQ ID NO 53
<211> LENGTH: 452
<212> TYPE: PRT
<213> ORGANISM: Artificial Sequence
<220> FEATURE:
<223> OTHER INFORMATION: synthetic polypeptide

<400> SEQUENCE: 53

Ala Pro Asp Gln Asp Glu Ile Gln Arg Leu Pro Gly Leu Ala Lys Gln
 1               5                  10                  15

Pro Ser Phe Arg Gln Tyr Ser Gly Tyr Leu Lys Ser Ser Gly Ser Lys
                 20                  25                  30

His Leu His Tyr Trp Phe Val Glu Ser Gln Lys Asp Pro Glu Asn Ser
            35                  40                  45

Pro Val Val Leu Trp Leu Asn Gly Gly Pro Gly Cys Ser Ser Leu Asp
        50                  55                  60

Gly Leu Leu Thr Glu His Gly Pro Phe Leu Val Gln Pro Asp Gly Val
 65                  70                  75                  80

Thr Leu Glu Tyr Asn Pro Tyr Ser Trp Asn Leu Ile Ala Asn Val Leu
                 85                  90                  95

Tyr Leu Glu Ser Pro Ala Gly Val Gly Phe Ser Tyr Ser Asp Asp Lys
            100                 105                 110
```

```
Phe Tyr Ala Thr Asn Asp Thr Glu Val Ala Gln Ser Asn Phe Glu Ala
            115                 120                 125

Leu Gln Asp Phe Phe Arg Leu Phe Pro Glu Tyr Lys Asn Asn Lys Leu
        130                 135                 140

Phe Leu Thr Gly Glu Ser Tyr Ala Gly Ile Tyr Ile Pro Thr Leu Ala
145                 150                 155                 160

Val Leu Val Met Gln Asp Pro Ser Met Asn Leu Gln Gly Leu Ala Val
                165                 170                 175

Gly Asn Gly Leu Ser Ser Tyr Glu Gln Asn Asp Asn Ser Leu Val Tyr
                180                 185                 190

Phe Ala Tyr Tyr His Gly Leu Leu Gly Asn Arg Leu Trp Ser Ser Leu
                195                 200                 205

Gln Thr His Cys Cys Ser Gln Asn Lys Cys Asn Phe Tyr Asp Asn Lys
        210                 215                 220

Asp Leu Glu Cys Val Thr Asn Leu Gln Glu Val Ala Arg Ile Val Gly
225                 230                 235                 240

Asn Ser Gly Leu Asn Ile Tyr Asn Leu Tyr Ala Pro Cys Ala Gly Gly
                245                 250                 255

Val Pro Ser His Phe Arg Tyr Glu Lys Asp Thr Val Val Gln Asp
                260                 265                 270

Leu Gly Asn Ile Phe Thr Arg Leu Pro Leu Lys Arg Met Trp His Gln
        275                 280                 285

Ala Leu Leu Arg Ser Gly Asp Lys Val Arg Met Asp Pro Pro Cys Thr
        290                 295                 300

Asn Thr Thr Ala Ala Ser Thr Tyr Leu Asn Asn Pro Tyr Val Arg Lys
305                 310                 315                 320

Ala Leu Asn Ile Pro Glu Gln Leu Pro Gln Trp Asp Met Cys Asn Phe
                325                 330                 335

Leu Val Asn Leu Gln Tyr Arg Arg Leu Tyr Arg Ser Met Asn Ser Gln
                340                 345                 350

Tyr Leu Lys Leu Leu Ser Ser Gln Lys Tyr Gln Ile Leu Leu Tyr Asn
                355                 360                 365

Gly Asp Val Asp Met Ala Cys Asn Phe Met Gly Asp Glu Trp Phe Val
370                 375                 380

Asp Ser Leu Asn Gln Lys Met Glu Val Gln Arg Arg Pro Trp Leu Val
385                 390                 395                 400

Lys Tyr Gly Asp Ser Gly Glu Gln Ile Ala Gly Phe Val Lys Glu Phe
                405                 410                 415

Ser His Ile Ala Phe Leu Thr Ile Lys Gly Ala Gly His Met Val Pro
                420                 425                 430

Thr Asp Lys Pro Leu Ala Ala Phe Thr Met Phe Ser Arg Phe Leu Asn
                435                 440                 445

Lys Gln Pro Tyr
450

<210> SEQ ID NO 54
<211> LENGTH: 359
<212> TYPE: PRT
<213> ORGANISM: Artificial Sequence
<220> FEATURE:
<223> OTHER INFORMATION: synthetic polypeptide

<400> SEQUENCE: 54

Asp Glu Thr Thr Ala Leu Val Cys Asp Asn Gly Ser Gly Leu Val Lys
1               5                   10                  15
```

```
Ala Gly Phe Ala Gly Asp Asp Ala Pro Arg Ala Val Phe Pro Ser Ile
            20                  25                  30

Val Gly Arg Pro Arg Asp Ser Tyr Val Gly Asp Glu Ala Gln Ser Lys
        35                  40                  45

Arg Gly Ile Leu Thr Leu Lys Tyr Pro Ile Glu Gly Ile Ile Thr Asn
    50                  55                  60

Trp Asp Asp Met Glu Lys Ile Trp His His Thr Phe Tyr Asn Glu Leu
65                  70                  75                  80

Arg Val Ala Pro Glu Glu His Pro Thr Leu Thr Glu Ala Pro Leu
                85                  90                  95

Asn Pro Lys Ala Asn Arg Glu Lys Met Thr Gln Ile Met Phe Glu Thr
            100                 105                 110

Phe Asn Val Pro Ala Met Tyr Val Ala Ile Gln Ala Val Leu Ser Leu
        115                 120                 125

Tyr Ala Ser Gly Arg Thr Thr Gly Ile Val Leu Asp Ser Gly Asp Gly
    130                 135                 140

Val Thr His Asn Val Pro Ile Tyr Glu Gly Tyr Ala Leu Pro His Ala
145                 150                 155                 160

Ile Met Arg Leu Asp Leu Ala Gly Arg Asp Leu Thr Asp Tyr Leu Met
                165                 170                 175

Lys Ile Leu Thr Glu Arg Gly Tyr Ser Phe Val Thr Thr Ala Glu Arg
            180                 185                 190

Glu Ile Val Arg Asp Ile Lys Glu Lys Leu Cys Tyr Val Ala Leu Asp
        195                 200                 205

Phe Glu Asn Glu Met Ala Thr Ala Ala Ser Ser Ser Leu Glu Lys
    210                 215                 220

Ser Tyr Glu Leu Pro Asp Gly Gln Val Ile Thr Ile Gly Asn Glu Arg
225                 230                 235                 240

Phe Arg Cys Pro Glu Thr Leu Phe Gln Pro Ser Phe Ile Gly Met Glu
                245                 250                 255

Ser Ala Gly Ile His Glu Thr Thr Tyr Asn Ser Ile Met Lys Cys Asp
            260                 265                 270

Ile Asp Ile Arg Lys Asp Leu Tyr Ala Asn Asn Val Met Ser Gly Gly
        275                 280                 285

Thr Thr Met Tyr Pro Gly Ile Ala Asp Arg Met Gln Lys Glu Ile Thr
    290                 295                 300

Ala Leu Ala Pro Ser Thr Met Lys Ile Lys Ile Ala Pro Pro Glu
305                 310                 315                 320

Arg Lys Tyr Ser Val Trp Ile Gly Gly Ser Ile Leu Ala Ser Leu Ser
                325                 330                 335

Thr Phe Gln Gln Met Trp Ile Thr Lys Gln Glu Tyr Asp Glu Ala Gly
            340                 345                 350

Pro Ser Ile Val His Arg Lys
            355

<210> SEQ ID NO 55
<211> LENGTH: 432
<212> TYPE: PRT
<213> ORGANISM: Artificial Sequence
<220> FEATURE:
<223> OTHER INFORMATION: synthetic polypeptide

<400> SEQUENCE: 55

Pro Arg Glu Ile Ile Thr Leu Gln Leu Gly Gln Cys Gly Asn Gln Ile
1               5                   10                  15
```

```
Gly Phe Glu Phe Trp Lys Gln Leu Cys Ala His Gly Ile Ser Pro
            20                  25                  30

Glu Ala Ile Val Glu Glu Phe Ala Thr Glu Gly Thr Asp Arg Lys Asp
        35                  40                  45

Val Phe Phe Tyr Gln Ala Asp Asp Glu His Tyr Ile Pro Arg Ala Val
50                  55                  60

Leu Leu Asp Leu Glu Pro Arg Val Ile His Ser Ile Leu Asn Ser Pro
65                  70                  75                  80

Tyr Ala Lys Leu Tyr Asn Pro Glu Asn Ile Tyr Leu Ser Glu His Gly
                85                  90                  95

Gly Gly Ala Gly Asn Asn Trp Ala Ser Gly Phe Ser Gln Gly Glu Lys
            100                 105                 110

Ile His Glu Asp Ile Phe Asp Ile Ile Asp Arg Glu Ala Asp Gly Ser
        115                 120                 125

Asp Ser Leu Glu Gly Phe Val Leu Cys His Ser Ile Ala Gly Gly Thr
130                 135                 140

Gly Ser Gly Leu Gly Ser Tyr Leu Leu Glu Arg Leu Asn Asp Arg Tyr
145                 150                 155                 160

Pro Lys Lys Leu Val Gln Thr Tyr Ser Val Phe Pro Asn Gln Asp Glu
                165                 170                 175

Met Ser Asp Val Val Val Gln Pro Tyr Asn Ser Leu Leu Thr Leu Lys
            180                 185                 190

Arg Leu Thr Gln Asn Ala Asp Cys Leu Val Val Leu Asp Asn Thr Ala
        195                 200                 205

Leu Asn Arg Ile Ala Thr Asp Arg Leu His Ile Gln Asn Pro Ser Phe
210                 215                 220

Ser Gln Ile Asn Gln Leu Val Ser Thr Ile Met Ser Ala Ser Thr Thr
225                 230                 235                 240

Thr Leu Arg Tyr Pro Gly Tyr Met Asn Asn Asp Leu Ile Gly Leu Ile
                245                 250                 255

Ala Ser Leu Ile Pro Thr Pro Arg Leu His Phe Leu Met Thr Gly Tyr
            260                 265                 270

Thr Pro Leu Thr Ser Val Arg Lys Thr Thr Val Leu Asp Val Met Arg
        275                 280                 285

Arg Leu Leu Gln Pro Lys Asn Val Met Val Ser Thr Gly Arg Asp Thr
290                 295                 300

Asn His Cys Tyr Ile Ala Ile Leu Asn Ile Ile Gln Gly Glu Val Asp
305                 310                 315                 320

Pro Thr Gln Val His Lys Ser Leu Gln Arg Ile Arg Glu Arg Lys Leu
                325                 330                 335

Ala Asn Phe Ile Pro Trp Gly Pro Ala Ser Ile Gln Val Ala Leu Ser
            340                 345                 350

Arg Lys Ser Pro Tyr Arg Val Ser Gly Leu Met Met Ala Asn His Thr
        355                 360                 365

Ser Ile Ser Ser Leu Phe Glu Arg Thr Cys Arg Gln Tyr Asp Lys Leu
370                 375                 380

Arg Lys Arg Glu Ala Phe Leu Glu Gln Phe Arg Lys Glu Asp Met Phe
385                 390                 395                 400

Lys Asp Asn Phe Asp Glu Met Asp Thr Ser Arg Glu Ile Val Gln Gln
                405                 410                 415

Leu Ile Asp Glu Tyr His Ala Ala Thr Arg Pro Asp Tyr Ile Ser Trp
            420                 425                 430
```

<210> SEQ ID NO 56
<211> LENGTH: 424
<212> TYPE: PRT
<213> ORGANISM: Artificial Sequence
<220> FEATURE:
<223> OTHER INFORMATION: synthetic polypeptide

<400> SEQUENCE: 56

```
Arg Glu Ile Ile Thr Leu Gln Leu Gly Gln Cys Gly Asn Gln Ile Gly
1               5                   10                  15

Phe Glu Phe Trp Lys Gln Leu Cys Ala Glu His Gly Ile Ser Pro Glu
            20                  25                  30

Ala Ile Val Glu Glu Phe Ala Thr Glu Gly Thr Asp Arg Lys Asp Val
        35                  40                  45

Phe Phe Tyr Gln Ala Asp Asp Glu His Tyr Ile Pro Arg Ala Val Leu
    50                  55                  60

Leu Asp Leu Glu Pro Arg Val Ile His Ser Ile Leu Asn Ser Pro Tyr
65                  70                  75                  80

Ala Lys Leu Tyr Asn Pro Glu Asn Ile Tyr Leu Ser Glu His Gly Ala
                85                  90                  95

Gly Asn Asn Trp Ala Ser Gly Phe Ser Gln Gly Glu Lys Ile His Glu
            100                 105                 110

Asp Ile Phe Asp Ile Ile Asp Arg Glu Ala Asp Gly Ser Asp Ser Leu
        115                 120                 125

Glu Gly Phe Val Leu Cys His Ser Ile Ala Gly Gly Thr Gly Ser Gly
    130                 135                 140

Leu Gly Ser Tyr Leu Leu Glu Arg Leu Asn Asp Arg Tyr Pro Lys Lys
145                 150                 155                 160

Leu Val Gln Thr Tyr Ser Val Phe Pro Asn Gln Asp Glu Met Ser Asp
                165                 170                 175

Val Val Val Gln Pro Tyr Asn Ser Leu Leu Thr Leu Lys Arg Leu Thr
            180                 185                 190

Gln Asn Ala Asp Cys Leu Val Val Leu Asp Asn Thr Ala Leu Asn Arg
        195                 200                 205

Ile Ala Thr Asp Arg Leu His Ile Gln Asn Pro Ser Phe Ser Gln Ile
    210                 215                 220

Asn Gln Leu Val Ser Thr Ile Met Ser Ala Ser Thr Thr Thr Leu Arg
225                 230                 235                 240

Tyr Pro Gly Tyr Met Asn Asn Asp Leu Ile Gly Leu Ile Ala Ser Leu
                245                 250                 255

Ile Pro Thr Pro Arg Leu His Phe Leu Met Thr Gly Tyr Thr Pro Leu
            260                 265                 270

Thr Lys Thr Thr Val Leu Asp Val Met Arg Arg Leu Leu Gln Pro Lys
        275                 280                 285

Asn Val Met Val Ser Thr Thr Asn His Cys Tyr Ile Ala Ile Leu Asn
    290                 295                 300

Ile Ile Gln Gly Glu Val Asp Pro Thr Gln Val His Lys Ser Leu Gln
305                 310                 315                 320

Arg Ile Arg Glu Arg Leu Ala Asn Phe Ile Pro Trp Gly Pro Ala Ser
                325                 330                 335

Ile Gln Val Ala Leu Ser Arg Lys Ser Pro Tyr Leu Pro Arg Val Ser
            340                 345                 350

Gly Leu Met Met Ala Asn His Thr Ser Ile Ser Ser Leu Phe Glu Arg
        355                 360                 365

Thr Cys Arg Gln Tyr Asp Lys Leu Arg Lys Arg Glu Ala Phe Leu Glu
```

```
                370                 375                 380
Gln Phe Arg Lys Glu Asp Met Phe Lys Asp Asn Phe Asp Glu Met Asp
385                 390                 395                 400

Thr Ser Arg Glu Ile Val Gln Gln Leu Ile Asp Glu Tyr His Ala Ala
                405                 410                 415

Thr Arg Pro Asp Tyr Ile Ser Trp
            420

<210> SEQ ID NO 57
<211> LENGTH: 129
<212> TYPE: PRT
<213> ORGANISM: Artificial Sequence
<220> FEATURE:
<223> OTHER INFORMATION: synthetic polypeptide

<400> SEQUENCE: 57

Gly Ser Ser Pro Leu Leu Lys Ser Ala Glu Arg Glu Lys Glu Met Ala
1               5                   10                  15

Ser Met Lys Glu Glu Phe Thr Arg Leu Lys Glu Ala Leu Glu Lys Ser
            20                  25                  30

Glu Ala Arg Arg Lys Glu Leu Glu Glu Lys Met Val Ser Leu Leu Gln
        35                  40                  45

Glu Lys Asn Asp Leu Gln Leu Gln Val Gln Ala Glu Gln Asp Asn Leu
    50                  55                  60

Ala Asp Ala Glu Glu Arg Cys Asp Gln Leu Ile Lys Asn Lys Ile Gln
65                  70                  75                  80

Leu Glu Ala Lys Val Lys Glu Met Asn Lys Arg Leu Glu Asp Glu Glu
                85                  90                  95

Glu Met Asn Ala Glu Leu Thr Ala Lys Lys Arg Lys Leu Glu Asp Glu
            100                 105                 110

Cys Ser Glu Leu Lys Arg Asp Ile Asp Asp Leu Glu Leu Thr Leu Ala
        115                 120                 125

Lys

<210> SEQ ID NO 58
<211> LENGTH: 125
<212> TYPE: PRT
<213> ORGANISM: Artificial Sequence
<220> FEATURE:
<223> OTHER INFORMATION: synthetic polypeptide

<400> SEQUENCE: 58

Ser Pro Leu Leu Lys Ser Ala Glu Arg Glu Lys Glu Met Ala Ser Met
1               5                   10                  15

Lys Glu Glu Phe Thr Arg Leu Lys Glu Ala Leu Glu Lys Ser Glu Ala
            20                  25                  30

Arg Arg Lys Glu Leu Glu Glu Lys Met Val Ser Leu Leu Gln Glu Lys
        35                  40                  45

Asn Asp Leu Gln Leu Gln Val Gln Ala Glu Gln Asp Asn Leu Ala Asp
    50                  55                  60

Ala Glu Glu Arg Cys Asp Gln Leu Ile Lys Asn Lys Ile Gln Leu Glu
65                  70                  75                  80

Ala Lys Val Lys Glu Met Asn Lys Arg Leu Glu Asp Glu Glu Met
                85                  90                  95

Asn Ala Glu Leu Thr Ala Lys Lys Arg Lys Leu Glu Asp Glu Cys Ser
            100                 105                 110

Glu Leu Lys Arg Asp Ile Asp Asp Leu Glu Leu Thr Leu
```

-continued

```
                115                 120                 125
```

<210> SEQ ID NO 59
<211> LENGTH: 127
<212> TYPE: PRT
<213> ORGANISM: Artificial Sequence
<220> FEATURE:
<223> OTHER INFORMATION: synthetic polypeptide

<400> SEQUENCE: 59

```
Ser Ser Pro Leu Leu Lys Ser Ala Glu Arg Glu Lys Glu Met Ala Ser
1               5                   10                  15

Met Lys Glu Glu Phe Thr Arg Leu Lys Glu Ala Leu Glu Lys Ser Glu
            20                  25                  30

Ala Arg Arg Lys Glu Leu Glu Glu Lys Met Val Ser Leu Leu Gln Glu
        35                  40                  45

Lys Asn Asp Leu Gln Leu Gln Val Gln Ala Glu Gln Asp Asn Leu Ala
    50                  55                  60

Asp Ala Glu Glu Arg Cys Asp Gln Leu Ile Lys Asn Lys Ile Gln Leu
65                  70                  75                  80

Glu Ala Lys Val Lys Glu Met Asn Lys Arg Leu Glu Asp Glu Glu Glu
                85                  90                  95

Met Asn Ala Glu Leu Thr Ala Lys Lys Arg Lys Leu Glu Asp Glu Cys
            100                 105                 110

Ser Glu Leu Lys Arg Asp Ile Asp Asp Leu Glu Leu Thr Leu Ala
        115                 120                 125
```

<210> SEQ ID NO 60
<211> LENGTH: 127
<212> TYPE: PRT
<213> ORGANISM: Artificial Sequence
<220> FEATURE:
<223> OTHER INFORMATION: synthetic polypeptide

<400> SEQUENCE: 60

```
Ser Pro Leu Leu Lys Ser Ala Glu Arg Glu Lys Glu Met Ala Ser Met
1               5                   10                  15

Lys Glu Glu Phe Thr Arg Leu Lys Glu Ala Leu Glu Lys Ser Glu Ala
            20                  25                  30

Arg Arg Lys Glu Leu Glu Glu Lys Met Val Ser Leu Leu Gln Glu Lys
        35                  40                  45

Asn Asp Leu Gln Leu Gln Val Gln Ala Glu Gln Asp Asn Leu Ala Asp
    50                  55                  60

Ala Glu Glu Arg Cys Asp Gln Leu Ile Lys Asn Lys Ile Gln Leu Glu
65                  70                  75                  80

Ala Lys Val Lys Glu Met Asn Lys Arg Leu Glu Asp Glu Glu Glu Met
                85                  90                  95

Asn Ala Glu Leu Thr Ala Lys Lys Arg Lys Leu Glu Asp Glu Cys Ser
            100                 105                 110

Glu Leu Lys Arg Asp Ile Asp Asp Leu Glu Leu Thr Leu Ala Lys
        115                 120                 125
```

<210> SEQ ID NO 61
<211> LENGTH: 145
<212> TYPE: PRT
<213> ORGANISM: Artificial Sequence
<220> FEATURE:
<223> OTHER INFORMATION: synthetic polypeptide

<400> SEQUENCE: 61

```
Leu Pro Gln Ser Phe Leu Leu Lys Cys Leu Glu Gln Val Arg Lys Ile
1               5                   10                  15

Gln Gly Asp Gly Ala Ala Leu Gln Glu Lys Leu Cys Ala Thr Tyr Lys
                20                  25                  30

Leu Cys His Pro Glu Glu Leu Val Leu Leu Gly His Ser Leu Gly Ile
            35                  40                  45

Pro Trp Ala Pro Leu Leu Ala Gly Cys Leu Ser Gln Leu His Ser Gly
        50                  55                  60

Leu Phe Leu Tyr Gln Gly Leu Leu Gln Ala Leu Glu Gly Ile Ser Pro
65                  70                  75                  80

Glu Leu Gly Pro Thr Leu Asp Thr Leu Gln Leu Asp Val Ala Asp Phe
                85                  90                  95

Ala Thr Thr Ile Trp Gln Gln Met Glu Glu Leu Gly Met Met Pro Ala
            100                 105                 110

Phe Ala Ser Ala Phe Gln Arg Arg Ala Gly Gly Val Leu Val Ala Ser
        115                 120                 125

His Leu Gln Ser Phe Leu Glu Val Ser Tyr Arg Val Leu Arg His Leu
    130                 135                 140

Ala
145

<210> SEQ ID NO 62
<211> LENGTH: 105
<212> TYPE: PRT
<213> ORGANISM: Artificial Sequence
<220> FEATURE:
<223> OTHER INFORMATION: synthetic polypeptide

<400> SEQUENCE: 62

Glu His Val Asn Ala Ile Gln Glu Ala Arg Arg Leu Leu Asn Leu Ser
1               5                   10                  15

Arg Asp Thr Ala Ala Glu Met Asn Glu Thr Val Glu Val Ile Ser Glu
                20                  25                  30

Met Phe Asp Leu Gln Glu Pro Thr Cys Leu Gln Thr Arg Leu Glu Leu
            35                  40                  45

Tyr Lys Gln Gly Leu Arg Gly Ser Leu Thr Lys Leu Lys Gly Pro Leu
        50                  55                  60

Thr Met Met Ala Ser His Tyr Lys Gln His Cys Pro Pro Thr Pro Glu
65                  70                  75                  80

Thr Ser Cys Ala Thr Gln Ile Ile Thr Phe Glu Ser Phe Lys Glu Asn
                85                  90                  95

Leu Lys Asp Phe Leu Leu Val Ile Pro
            100                 105

<210> SEQ ID NO 63
<211> LENGTH: 165
<212> TYPE: PRT
<213> ORGANISM: Artificial Sequence
<220> FEATURE:
<223> OTHER INFORMATION: synthetic polypeptide

<400> SEQUENCE: 63

Cys Asp Leu Pro Gln Thr His Ser Leu Gly Ser Arg Arg Thr Leu Met
1               5                   10                  15

Leu Leu Ala Gln Met Arg Lys Ile Ser Leu Phe Ser Cys Leu Lys Asp
                20                  25                  30

Arg His Asp Phe Gly Phe Pro Gln Glu Glu Phe Gly Asn Gln Phe Gln
```

```
            35                  40                  45
Lys Ala Glu Thr Ile Pro Val Leu His Glu Met Ile Gln Gln Ile Phe
 50                  55                  60
Asn Leu Phe Ser Thr Lys Asp Ser Ala Ala Trp Asp Glu Thr Leu
 65                  70                  75                  80
Leu Asp Lys Phe Tyr Thr Glu Leu Tyr Gln Gln Leu Asn Asp Leu Glu
                 85                  90                  95
Ala Cys Val Ile Gln Gly Val Gly Val Thr Glu Thr Pro Leu Met Lys
                100                 105                 110
Glu Asp Ser Ile Leu Ala Val Arg Lys Tyr Phe Gln Arg Ile Thr Leu
            115                 120                 125
Tyr Leu Lys Glu Lys Lys Tyr Ser Pro Cys Ala Trp Glu Val Val Arg
130                 135                 140
Ala Glu Ile Met Arg Ser Phe Ser Leu Ser Thr Asn Leu Gln Glu Ser
145                 150                 155                 160
Leu Arg Ser Lys Glu
                165

<210> SEQ ID NO 64
<211> LENGTH: 166
<212> TYPE: PRT
<213> ORGANISM: Artificial Sequence
<220> FEATURE:
<223> OTHER INFORMATION: synthetic polypeptide

<400> SEQUENCE: 64

Met Ser Tyr Asn Leu Leu Gly Phe Leu Gln Arg Ser Ser Asn Phe Gln
 1               5                  10                  15
Cys Gln Lys Leu Leu Trp Gln Leu Asn Gly Arg Leu Glu Tyr Cys Leu
                20                  25                  30
Lys Asp Arg Met Asn Phe Asp Ile Pro Glu Glu Ile Lys Gln Leu Gln
            35                  40                  45
Gln Phe Gln Lys Glu Asp Ala Ala Leu Thr Ile Tyr Glu Met Leu Gln
 50                  55                  60
Asn Ile Phe Ala Ile Phe Arg Gln Asp Ser Ser Ser Thr Gly Trp Asn
 65                  70                  75                  80
Glu Thr Ile Val Glu Asn Leu Leu Ala Asn Val Tyr His Gln Ile Asn
                 85                  90                  95
His Leu Lys Thr Val Leu Glu Glu Lys Leu Glu Lys Glu Asp Phe Thr
                100                 105                 110
Arg Gly Lys Leu Met Ser Ser Leu His Leu Lys Arg Tyr Tyr Gly Arg
            115                 120                 125
Ile Leu His Tyr Leu Lys Ala Lys Glu Tyr Ser His Cys Ala Trp Thr
130                 135                 140
Ile Val Arg Val Glu Ile Leu Arg Asn Phe Tyr Phe Ile Asn Arg Leu
145                 150                 155                 160
Thr Gly Tyr Leu Arg Asn
                165

<210> SEQ ID NO 65
<211> LENGTH: 242
<212> TYPE: PRT
<213> ORGANISM: Artificial Sequence
<220> FEATURE:
<223> OTHER INFORMATION: synthetic polypeptide

<400> SEQUENCE: 65
```

```
Met Gln Asp Pro Tyr Val Lys Glu Ala Glu Asn Leu Lys Lys Tyr Phe
1               5                   10                  15

Asn Ala Gly His Ser Asp Val Ala Asp Asn Gly Thr Leu Phe Leu Gly
                20                  25                  30

Ile Leu Lys Asn Trp Lys Glu Glu Ser Asp Arg Lys Ile Met Gln Ser
            35                  40                  45

Gln Ile Val Ser Phe Tyr Phe Lys Leu Phe Lys Asn Phe Lys Asp Asp
50                  55                  60

Gln Ser Ile Gln Lys Ser Val Glu Thr Ile Lys Glu Asp Met Asn Val
65                  70                  75                  80

Lys Phe Phe Asn Ser Asn Lys Lys Arg Asp Asp Phe Glu Lys Leu
                85                  90                  95

Thr Asn Tyr Ser Val Thr Asp Leu Asn Val Gln Arg Lys Ala Ile Asp
                100                 105                 110

Glu Leu Ile Gln Val Met Ala Glu Leu Gly Ala Asn Val Ser Gly Glu
            115                 120                 125

Phe Val Lys Glu Ala Glu Asn Leu Lys Lys Tyr Phe Asn Asp Asn Gly
    130                 135                 140

Thr Leu Phe Leu Gly Ile Leu Lys Asn Trp Lys Glu Glu Ser Asp Arg
145                 150                 155                 160

Lys Ile Met Gln Ser Gln Ile Val Ser Phe Tyr Phe Lys Leu Phe Lys
                165                 170                 175

Asn Phe Lys Asp Asp Gln Ser Ile Gln Lys Ser Val Glu Thr Ile Lys
            180                 185                 190

Glu Asp Met Asn Val Lys Phe Phe Asn Ser Lys Lys Lys Arg Asp
                195                 200                 205

Asp Phe Glu Lys Leu Thr Asn Tyr Ser Val Thr Asp Leu Asn Val Gln
    210                 215                 220

Arg Lys Ala Ile His Glu Leu Ile Gln Val Met Ala Glu Leu Ser Pro
225                 230                 235                 240

Ala Ala

<210> SEQ ID NO 66
<211> LENGTH: 122
<212> TYPE: PRT
<213> ORGANISM: Artificial Sequence
<220> FEATURE:
<223> OTHER INFORMATION: synthetic polypeptide

<400> SEQUENCE: 66

Ser Thr Lys Lys Thr Gln Leu Gln Leu Glu His Leu Leu Leu Asp Leu
1               5                   10                  15

Gln Met Ile Leu Asn Gly Ile Asn Asn Tyr Lys Asn Pro Lys Leu Thr
                20                  25                  30

Arg Met Leu Thr Phe Lys Phe Tyr Met Pro Lys Lys Ala Thr Glu Leu
            35                  40                  45

Lys His Leu Gln Cys Leu Glu Glu Glu Leu Lys Pro Leu Glu Glu Val
50                  55                  60

Leu Asn Leu Ala Gln Asn Phe His Leu Arg Pro Arg Asp Leu Ile Ser
65                  70                  75                  80

Asn Ile Asn Val Ile Val Leu Glu Leu Lys Gly Phe Met Cys Glu Tyr
                85                  90                  95

Ala Asp Glu Thr Ala Thr Ile Val Glu Phe Leu Asn Arg Trp Ile Thr
            100                 105                 110

Phe Cys Gln Ser Ile Ile Ser Thr Leu Thr
```

```
              115                 120

<210> SEQ ID NO 67
<211> LENGTH: 123
<212> TYPE: PRT
<213> ORGANISM: Artificial Sequence
<220> FEATURE:
<223> OTHER INFORMATION: synthetic polypeptide

<400> SEQUENCE: 67

Ala Leu Trp Gln Phe Asn Gly Met Ile Lys Cys Lys Ile Pro Ser Ser
1               5                   10                  15

Glu Pro Leu Leu Asp Phe Asn Asn Tyr Gly Cys Tyr Cys Gly Leu Gly
            20                  25                  30

Gly Ser Gly Thr Pro Val Asp Asp Leu Asp Arg Cys Cys Gln Thr His
        35                  40                  45

Asp Asn Cys Tyr Lys Gln Ala Lys Lys Leu Asp Ser Cys Lys Val Leu
    50                  55                  60

Val Asp Asn Pro Tyr Thr Asn Asn Tyr Ser Tyr Ser Cys Ser Asn Asn
65                  70                  75                  80

Glu Ile Thr Cys Ser Ser Glu Asn Asn Ala Cys Glu Ala Phe Ile Cys
                85                  90                  95

Asn Cys Asp Arg Asn Ala Ala Ile Cys Phe Ser Lys Val Pro Tyr Asn
            100                 105                 110

Lys Glu His Lys Asn Leu Asp Ala Ala Asn Cys
            115                 120

<210> SEQ ID NO 68
<211> LENGTH: 152
<212> TYPE: PRT
<213> ORGANISM: Artificial Sequence
<220> FEATURE:
<223> OTHER INFORMATION: synthetic polypeptide

<400> SEQUENCE: 68

Ala Pro Val Arg Ser Leu Asn Cys Thr Leu Arg Asp Ser Gln Gln Lys
1               5                   10                  15

Ser Leu Val Met Ser Gly Pro Tyr Glu Leu Lys Ala Leu His Leu Gln
            20                  25                  30

Gly Gln Asp Met Glu Gln Gln Val Val Phe Ser Met Ser Phe Val Gln
        35                  40                  45

Gly Glu Glu Ser Asn Asp Lys Ile Pro Val Ala Leu Gly Leu Lys Glu
    50                  55                  60

Lys Asn Leu Tyr Leu Ser Cys Val Leu Lys Asp Asp Lys Pro Thr Leu
65                  70                  75                  80

Gln Leu Glu Ser Val Asp Pro Lys Asn Tyr Pro Lys Lys Lys Met Glu
                85                  90                  95

Lys Arg Phe Val Phe Asn Lys Ile Glu Ile Asn Asn Lys Leu Glu Phe
            100                 105                 110

Glu Ser Ala Gln Phe Pro Asn Trp Tyr Ile Ser Thr Ser Gln Ala Glu
            115                 120                 125

Asn Met Pro Val Phe Leu Gly Gly Thr Lys Gly Gly Gln Asp Ile Thr
        130                 135                 140

Asp Phe Thr Met Gln Phe Val Ser
145                 150

<210> SEQ ID NO 69
<211> LENGTH: 150
```

```
<212> TYPE: PRT
<213> ORGANISM: Artificial Sequence
<220> FEATURE:
<223> OTHER INFORMATION: synthetic polypeptide

<400> SEQUENCE: 69

Pro His Arg Arg Asp Leu Cys Ser Arg Ser Ile Trp Leu Ala Arg Lys
1               5                   10                  15

Ile Arg Ser Asp Leu Thr Ala Leu Thr Glu Ser Tyr Val Lys His Gln
            20                  25                  30

Gly Leu Trp Ser Glu Leu Thr Glu Ala Glu Arg Leu Gln Glu Asn Leu
        35                  40                  45

Gln Ala Tyr Arg Thr Phe His Val Leu Leu Ala Arg Leu Leu Glu Asp
50                  55                  60

Gln Gln Val His Phe Thr Pro Thr Glu Gly Asp Phe His Gln Ala Ile
65                  70                  75                  80

His Thr Leu Leu Leu Gln Val Ala Ala Phe Ala Tyr Gln Ile Glu Glu
                85                  90                  95

Leu Met Ile Leu Leu Glu Tyr Lys Ile Pro Arg Asn Glu Ala Asp Gly
            100                 105                 110

Met Leu Phe Glu Lys Lys Leu Trp Gly Leu Lys Val Leu Gln Glu Leu
        115                 120                 125

Ser Gln Trp Thr Val Arg Ser Ile His Asp Leu Arg Phe Ile Ser Ser
130                 135                 140

His Gln Thr Gly Ile Pro
145                 150

<210> SEQ ID NO 70
<211> LENGTH: 126
<212> TYPE: PRT
<213> ORGANISM: Artificial Sequence
<220> FEATURE:
<223> OTHER INFORMATION: synthetic polypeptide

<400> SEQUENCE: 70

His Arg Arg Asp Leu Cys Ser Arg Ser Ile Trp Leu Ala Arg Lys Ile
1               5                   10                  15

Arg Ser Asp Leu Thr Ala Leu Thr Glu Ser Tyr Val Lys His Gln Gly
            20                  25                  30

Leu Glu Leu Thr Glu Ala Glu Arg Leu Gln Glu Asn Leu Gln Ala Tyr
        35                  40                  45

Arg Thr Phe His Val Leu Leu Ala Arg Leu Leu Glu Asp Gln Gln Glu
    50                  55                  60

Gly Asp Phe His Gln Ala Ile His Thr Leu Leu Leu Gln Val Ala Ala
65                  70                  75                  80

Phe Ala Tyr Gln Ile Glu Glu Leu Met Ile Leu Leu Glu Tyr Lys Ile
                85                  90                  95

Pro Arg Asn Lys Lys Leu Trp Gly Leu Lys Val Leu Gln Glu Leu Ser
            100                 105                 110

Gln Trp Thr Val Arg Ser Ile His Asp Leu Arg Phe Ile Ser
        115                 120                 125

<210> SEQ ID NO 71
<211> LENGTH: 148
<212> TYPE: PRT
<213> ORGANISM: Artificial Sequence
<220> FEATURE:
<223> OTHER INFORMATION: synthetic polypeptide
```

<400> SEQUENCE: 71

Asp Lys Pro Val Ala His Val Ala Asn Pro Gln Ala Glu Gly Gln
1               5                   10                  15

Leu Gln Trp Ser Asn Arg Arg Ala Asn Ala Leu Leu Ala Asn Gly Val
            20                  25                  30

Glu Leu Arg Asp Asn Gln Leu Val Pro Ile Glu Gly Leu Phe Leu
        35                  40                  45

Ile Tyr Ser Gln Val Leu Phe Lys Gly Gln Gly Cys Pro Ser Thr His
    50                  55                  60

Val Leu Leu Thr His Thr Ile Ser Arg Ile Ala Val Ser Tyr Gln Thr
65                  70                  75                  80

Lys Val Asn Leu Leu Ser Ala Ile Lys Ser Pro Cys Gln Arg Glu Thr
                85                  90                  95

Pro Glu Gly Ala Glu Ala Lys Pro Trp Tyr Gln Pro Ile Tyr Leu Gly
            100                 105                 110

Gly Val Phe Gln Leu Glu Lys Gly Asp Arg Leu Ser Ala Glu Ile Asn
        115                 120                 125

Arg Pro Asp Tyr Leu Asp Phe Ala Glu Ser Gly Gln Val Tyr Phe Gly
    130                 135                 140

Ile Ile Ala Leu
145

<210> SEQ ID NO 72
<211> LENGTH: 144
<212> TYPE: PRT
<213> ORGANISM: Artificial Sequence
<220> FEATURE:
<223> OTHER INFORMATION: synthetic polypeptide

<400> SEQUENCE: 72

Lys Pro Ala Ala His Leu Ile Gly Asp Pro Ser Lys Gln Asn Ser Leu
1               5                   10                  15

Leu Trp Arg Ala Asn Thr Asp Arg Ala Phe Leu Gln Asp Gly Phe Ser
            20                  25                  30

Leu Ser Asn Asn Ser Leu Leu Val Pro Thr Ser Gly Ile Tyr Phe Val
        35                  40                  45

Tyr Ser Gln Val Val Phe Ser Gly Lys Ala Tyr Ser Pro Lys Ala Thr
    50                  55                  60

Ser Ser Pro Leu Tyr Leu Ala His Glu Val Gln Leu Phe Ser Ser Gln
65                  70                  75                  80

Tyr Pro Phe His Val Pro Leu Leu Ser Ser Gln Lys Met Val Tyr Pro
                85                  90                  95

Gly Leu Gln Glu Pro Trp Leu His Ser Met Tyr His Gly Ala Ala Phe
            100                 105                 110

Gln Leu Thr Gln Gly Asp Gln Leu Ser Thr His Thr Asp Gly Ile Pro
        115                 120                 125

His Leu Val Leu Ser Pro Ser Thr Val Phe Phe Gly Ala Phe Ala Leu
    130                 135                 140

<210> SEQ ID NO 73
<211> LENGTH: 166
<212> TYPE: PRT
<213> ORGANISM: Artificial Sequence
<220> FEATURE:
<223> OTHER INFORMATION: synthetic polypeptide

<400> SEQUENCE: 73

```
Ala Pro Pro Arg Leu Ile Cys Asp Ser Arg Val Leu Glu Arg Tyr Leu
1               5                   10                  15

Leu Glu Ala Lys Glu Ala Glu Lys Ile Thr Thr Gly Cys Ala Glu His
            20                  25                  30

Cys Ser Leu Asn Glu Lys Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Lys Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Asn Ser Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 74
<211> LENGTH: 21
<212> TYPE: PRT
<213> ORGANISM: Artificial Sequence
<220> FEATURE:
<223> OTHER INFORMATION: synthetic polypeptide

<400> SEQUENCE: 74

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 75
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 75

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys
            20                  25

<210> SEQ ID NO 76
<211> LENGTH: 166
<212> TYPE: PRT
<213> ORGANISM: Artificial Sequence
<220> FEATURE:
<223> OTHER INFORMATION: synthetic polypeptide

<400> SEQUENCE: 76

Phe Pro Thr Ile Pro Leu Ser Arg Leu Ala Asp Asn Ala Trp Leu Arg
1               5                   10                  15

Ala Asp Arg Leu Asn Gln Leu Ala Phe Asp Thr Tyr Gln Glu Phe Glu
```

```
                    20                  25                  30
Glu Ala Tyr Ile Pro Lys Glu Gln Ile His Ser Phe Trp Trp Asn Pro
             35                  40                  45

Gln Thr Ser Leu Cys Pro Ser Glu Ser Ile Pro Thr Pro Ser Asn Lys
 50                  55                  60

Glu Glu Thr Gln Gln Lys Ser Asn Leu Glu Leu Arg Ile Ser Leu
 65                  70                  75                  80

Leu Leu Ile Gln Ser Trp Leu Glu Pro Val Gln Phe Leu Arg Ser Val
                 85                  90                  95

Phe Ala Asn Ser Leu Val Tyr Gly Ala Ser Asp Ser Asn Val Tyr Asp
            100                 105                 110

Leu Leu Lys Asp Leu Glu Glu Gly Ile Gln Thr Leu Met Gly Arg Leu
            115                 120                 125

Glu Ala Leu Leu Lys Asn Tyr Gly Leu Leu Tyr Cys Phe Asn Lys Asp
            130                 135                 140

Met Ser Lys Val Ser Thr Tyr Leu Arg Thr Val Gln Cys Arg Ser Val
145                 150                 155                 160

Glu Gly Ser Cys Gly Phe
                165

<210> SEQ ID NO 77
<211> LENGTH: 242
<212> TYPE: PRT
<213> ORGANISM: Artificial Sequence
<220> FEATURE:
<223> OTHER INFORMATION: synthetic polypeptide

<400> SEQUENCE: 77

Cys His His Arg Ile Cys His Cys Ser Asn Arg Val Phe Leu Cys Gln
1               5                  10                  15

Glu Ser Lys Val Thr Glu Ile Pro Ser Asp Leu Pro Arg Asn Ala Ile
             20                  25                  30

Glu Leu Arg Phe Val Leu Thr Lys Leu Arg Val Ile Gln Lys Gly Ala
             35                  40                  45

Phe Ser Gly Phe Gly Asp Leu Glu Lys Ile Glu Ile Ser Gln Asn Asp
 50                  55                  60

Val Leu Glu Val Ile Glu Ala Asp Val Phe Ser Asn Leu Pro Lys Leu
 65                  70                  75                  80

His Glu Ile Arg Ile Glu Lys Ala Asn Asn Leu Leu Tyr Ile Asn Pro
                 85                  90                  95

Glu Ala Phe Gln Asn Leu Pro Asn Leu Gln Tyr Leu Leu Ile Ser Asn
            100                 105                 110

Thr Gly Ile Lys His Leu Pro Asp Val His Lys Ile His Ser Leu Gln
            115                 120                 125

Lys Val Leu Leu Asp Ile Gln Asp Asn Ile Asn Ile His Thr Ile Glu
            130                 135                 140

Arg Asn Ser Phe Val Gly Leu Ser Phe Glu Ser Val Ile Leu Trp Leu
145                 150                 155                 160

Asn Lys Asn Gly Ile Gln Glu Ile His Asn Cys Ala Phe Asn Gly Thr
                165                 170                 175

Gln Leu Asp Glu Leu Asn Leu Ser Asp Asn Asn Leu Glu Glu Leu
            180                 185                 190

Pro Asn Asp Val Phe His Gly Ala Ser Gly Pro Val Ile Leu Asp Ile
            195                 200                 205

Ser Arg Thr Arg Ile His Ser Leu Pro Ser Tyr Gly Leu Glu Asn Leu
```

```
                 210                 215                 220
Lys Lys Leu Arg Ala Arg Ser Thr Tyr Asn Leu Lys Lys Leu Pro Thr
225                 230                 235                 240

Leu Glu

<210> SEQ ID NO 78
<211> LENGTH: 130
<212> TYPE: PRT
<213> ORGANISM: Artificial Sequence
<220> FEATURE:
<223> OTHER INFORMATION: synthetic polypeptide

<400> SEQUENCE: 78

Ile Gln Lys Val Gln Asp Asp Thr Lys Thr Leu Ile Lys Thr Ile Val
1               5                   10                  15

Thr Arg Ile Asn Asp Ile Leu Asp Phe Ile Pro Gly Leu His Pro Ile
                20                  25                  30

Leu Thr Leu Ser Lys Met Asp Gln Thr Leu Ala Val Tyr Gln Gln Ile
            35                  40                  45

Leu Thr Ser Met Pro Ser Arg Asn Val Ile Gln Ile Ser Asn Asp Leu
        50                  55                  60

Glu Asn Leu Arg Asp Leu Leu His Val Leu Ala Phe Ser Lys Ser Cys
65                  70                  75                  80

His Leu Pro Glu Ala Ser Gly Leu Glu Thr Leu Asp Ser Leu Gly Gly
                85                  90                  95

Val Leu Glu Ala Ser Gly Tyr Ser Thr Glu Val Val Ala Leu Ser Arg
                100                 105                 110

Leu Gln Gly Ser Leu Gln Asp Met Leu Trp Gln Leu Asp Leu Ser Pro
        115                 120                 125

Gly Cys
    130

<210> SEQ ID NO 79
<211> LENGTH: 62
<212> TYPE: PRT
<213> ORGANISM: Artificial Sequence
<220> FEATURE:
<223> OTHER INFORMATION: synthetic polypeptide

<400> SEQUENCE: 79

Pro Glu Thr Leu Cys Gly Ala Glu Leu Val Asp Ala Leu Gln Phe Val
1               5                   10                  15

Cys Gly Asp Arg Gly Phe Tyr Phe Asn Lys Pro Thr Gly Tyr Gly Ser
                20                  25                  30

Ser Ser Arg Arg Ala Pro Gln Thr Gly Ile Val Asp Glu Cys Cys Phe
            35                  40                  45

Arg Ser Cys Asp Leu Arg Arg Leu Glu Met Tyr Cys Ala Pro
        50                  55                  60

<210> SEQ ID NO 80
<211> LENGTH: 125
<212> TYPE: PRT
<213> ORGANISM: Artificial Sequence
<220> FEATURE:
<223> OTHER INFORMATION: synthetic polypeptide

<400> SEQUENCE: 80

Met Tyr Arg Ser Ala Phe Ser Val Gly Leu Glu Thr Arg Val Thr Val
1               5                   10                  15
```

```
Pro Asn Val Pro Ile Arg Phe Thr Lys Ile Phe Tyr Asn Gln Gln Asn
            20                  25                  30

His Tyr Asp Gly Ser Thr Gly Lys Phe Tyr Cys Asn Ile Pro Gly Leu
        35                  40                  45

Tyr Tyr Phe Ser Tyr His Ile Thr Val Tyr Met Lys Asp Val Lys Val
    50                  55                  60

Ser Leu Phe Lys Lys Asp Lys Ala Val Leu Phe Thr Tyr Asp Gln Tyr
65                  70                  75                  80

Gln Glu Asn Val Asp Gln Ala Ser Gly Ser Val Leu Leu His Leu Glu
                85                  90                  95

Val Gly Asp Gln Val Trp Leu Gln Val Tyr Tyr Ala Asp Asn Val Asn
            100                 105                 110

Asp Ser Thr Phe Thr Gly Phe Leu Leu Tyr His Asp Thr
        115                 120                 125

<210> SEQ ID NO 81
<211> LENGTH: 111
<212> TYPE: PRT
<213> ORGANISM: Artificial Sequence
<220> FEATURE:
<223> OTHER INFORMATION: synthetic polypeptide

<400> SEQUENCE: 81

Met Tyr Arg Ser Ala Phe Ser Val Gly Leu Pro Asn Val Pro Ile Arg
1               5                   10                  15

Phe Thr Lys Ile Phe Tyr Asn Gln Gln Asn His Tyr Asp Gly Ser Thr
            20                  25                  30

Gly Lys Phe Tyr Cys Asn Ile Pro Gly Leu Tyr Tyr Phe Ser Tyr His
        35                  40                  45

Ile Thr Val Tyr Met Lys Asp Val Lys Val Ser Leu Phe Lys Lys Asp
    50                  55                  60

Lys Val Leu Phe Thr Tyr Asp Gln Tyr Gln Glu Lys Val Asp Gln Ala
65                  70                  75                  80

Ser Gly Ser Val Leu Leu His Leu Glu Val Gly Asp Gln Val Trp Leu
                85                  90                  95

Gln Val Tyr Asp Ser Thr Phe Thr Gly Phe Leu Leu Tyr His Asp
            100                 105                 110

<210> SEQ ID NO 82
<211> LENGTH: 102
<212> TYPE: PRT
<213> ORGANISM: Artificial Sequence
<220> FEATURE:
<223> OTHER INFORMATION: synthetic polypeptide

<400> SEQUENCE: 82

Met Tyr Arg Ser Ala Phe Ser Val Gly Leu Glu Thr Arg Val Thr Val
1               5                   10                  15

Pro Ile Arg Phe Thr Lys Ile Phe Tyr Asn Gln Gln Asn His Tyr Asp
            20                  25                  30

Gly Ser Thr Gly Lys Phe Tyr Cys Asn Ile Pro Gly Leu Tyr Tyr Phe
        35                  40                  45

Ser Tyr His Ile Thr Val Asp Val Lys Val Ser Leu Phe Lys Lys Asp
    50                  55                  60

Lys Ala Val Leu Phe Thr Gln Ala Ser Gly Ser Val Leu Leu His Leu
65                  70                  75                  80

Glu Val Gly Asp Gln Val Trp Leu Gln Asn Asp Ser Thr Phe Thr Gly
                85                  90                  95
```

```
Phe Leu Leu Tyr His Asp
            100

<210> SEQ ID NO 83
<211> LENGTH: 693
<212> TYPE: PRT
<213> ORGANISM: Artificial Sequence
<220> FEATURE:
<223> OTHER INFORMATION: synthetic polypeptide

<400> SEQUENCE: 83

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ala Ala Ser Ala Arg Ala Trp Pro Lys Met
    210                 215                 220

His Thr Val Asn Gly Tyr Val Asn Arg Ser Leu Pro Gly Leu Ile Gly
225                 230                 235                 240

Cys His Arg Lys Ser Val Tyr Trp His Val Ile Gly Met Gly Thr Thr
                245                 250                 255

Pro Glu Val His Ser Ile Phe Leu Glu Gly His Thr Phe Leu Val Arg
            260                 265                 270

Asn His Arg Gln Ala Ser Leu Glu Ile Ser Pro Ile Thr Phe Leu Thr
        275                 280                 285

Ala Gln Thr Leu Leu Met Asp Leu Gly Gln Phe Leu Leu Phe Cys His
    290                 295                 300

Ile Ser Ser His Gln His Asp Gly Met Glu Ala Tyr Val Lys Val Asp
305                 310                 315                 320

Ser Cys Pro Glu Glu Pro Gln Phe Asp Asp Asn Ser Pro Ser Phe
                325                 330                 335

Ile Gln Ile Arg Ser Val Ala Lys Lys His Pro Lys Thr Trp Val His
            340                 345                 350
```

Tyr Ile Ala Ala Glu Glu Asp Trp Asp Tyr Ala Pro Leu Val Leu
            355                 360                 365

Ala Pro Asp Asp Arg Ser Tyr Lys Ser Gln Tyr Leu Asn Asn Gly Pro
        370                 375                 380

Gln Arg Ile Gly Arg Lys Tyr Lys Lys Val Arg Phe Met Ala Tyr Thr
385                 390                 395                 400

Asp Glu Thr Phe Lys Thr Arg Glu Ala Ile Gln His Glu Ser Gly Ile
                405                 410                 415

Leu Gly Pro Leu Leu Tyr Gly Glu Val Gly Asp Thr Leu Leu Ile Ile
            420                 425                 430

Phe Lys Asn Gln Ala Ser Arg Pro Tyr Asn Ile Tyr Pro His Gly Ile
        435                 440                 445

Thr Asp Val Arg Pro Leu Tyr Ser Arg Arg Leu Pro Lys Gly Val Lys
450                 455                 460

His Leu Lys Asp Phe Pro Ile Leu Pro Gly Glu Ile Phe Lys Tyr Lys
465                 470                 475                 480

Trp Thr Val Thr Val Glu Asp Gly Pro Thr Lys Ser Asp Pro Arg Cys
                485                 490                 495

Leu Thr Arg Tyr Tyr Ser Ser Phe Val Asn Met Glu Arg Asp Leu Ala
            500                 505                 510

Ser Gly Leu Ile Gly Pro Leu Leu Ile Cys Tyr Lys Glu Ser Val Asp
        515                 520                 525

Gln Arg Gly Asn Gln Ile Met Ser Asp Lys Arg Asn Val Ile Leu Phe
530                 535                 540

Ser Val Phe Asp Glu Asn Arg Ser Trp Tyr Leu Thr Glu Asn Ile Gln
545                 550                 555                 560

Arg Phe Leu Pro Asn Pro Ala Gly Val Gln Leu Glu Asp Pro Glu Phe
                565                 570                 575

Gln Ala Ser Asn Ile Met His Ser Ile Asn Gly Tyr Val Phe Asp Ser
            580                 585                 590

Leu Gln Leu Ser Val Cys Leu His Glu Val Ala Tyr Trp Tyr Ile Leu
        595                 600                 605

Ser Ile Gly Ala Gln Thr Asp Phe Leu Ser Val Phe Phe Ser Gly Tyr
610                 615                 620

Thr Phe Lys His Lys Met Val Tyr Glu Asp Thr Leu Thr Leu Phe Pro
625                 630                 635                 640

Phe Ser Gly Glu Thr Val Phe Met Ser Met Glu Asn Pro Gly Leu Trp
                645                 650                 655

Ile Leu Gly Cys His Asn Ser Asp Phe Arg Asn Arg Gly Met Thr Ala
            660                 665                 670

Leu Leu Lys Val Ser Ser Cys Asp Lys Asn Thr Gly Asp Tyr Tyr Glu
        675                 680                 685

Asp Ser Tyr Glu Asp
    690

<210> SEQ ID NO 84
<211> LENGTH: 644
<212> TYPE: PRT
<213> ORGANISM: Artificial Sequence
<220> FEATURE:
<223> OTHER INFORMATION: synthetic polypeptide

<400> SEQUENCE: 84

Arg Ser Phe Gln Lys Lys Thr Arg His Tyr Phe Ile Ala Ala Val Glu
1               5                   10                  15

-continued

```
Arg Leu Trp Asp Tyr Gly Met Ser Ser Pro His Val Leu Arg Asn
             20                  25                  30

Arg Ala Gln Ser Gly Ser Val Pro Gln Phe Lys Lys Val Phe Gln
         35                  40                  45

Glu Phe Thr Asp Gly Ser Phe Thr Gln Pro Leu Tyr Arg Gly Glu Leu
 50                  55                  60

Asn Glu His Leu Gly Leu Leu Gly Pro Tyr Ile Arg Ala Glu Val Glu
 65                  70                  75                  80

Asp Asn Ile Met Val Thr Phe Arg Asn Gln Ala Ser Arg Pro Tyr Ser
             85                  90                  95

Phe Tyr Ser Ser Leu Ile Ser Tyr Glu Glu Asp Gln Arg Gln Gly Ala
            100                 105                 110

Glu Pro Arg Lys Asn Phe Val Lys Pro Asn Glu Thr Lys Thr Tyr Phe
            115                 120                 125

Trp Lys Val Gln His His Met Ala Pro Thr Lys Asp Glu Phe Asp Cys
130                 135                 140

Lys Ala Trp Ala Tyr Ser Ser Asp Val Asp Leu Glu Lys Asp Val His
145                 150                 155                 160

Ser Gly Leu Ile Gly Pro Leu Leu Val Cys His Thr Asn Thr Leu Asn
                165                 170                 175

Pro Ala His Gly Arg Gln Val Thr Val Gln Glu Phe Ala Leu Phe Phe
            180                 185                 190

Thr Ile Phe Asp Glu Thr Lys Ser Trp Tyr Phe Thr Glu Asn Met Glu
        195                 200                 205

Arg Asn Cys Arg Ala Pro Cys Asn Ile Gln Met Glu Asp Pro Thr Phe
210                 215                 220

Lys Glu Asn Tyr Arg Phe His Ala Ile Asn Gly Tyr Ile Met Asp Thr
225                 230                 235                 240

Leu Pro Gly Leu Val Met Ala Gln Asp Gln Arg Ile Arg Trp Tyr Leu
                245                 250                 255

Leu Ser Met Gly Ser Asn Glu Asn Ile His Ser Ile His Phe Ser Gly
            260                 265                 270

His Val Phe Thr Val Arg Lys Lys Glu Glu Tyr Lys Met Ala Leu Tyr
        275                 280                 285

Asn Leu Tyr Pro Gly Val Phe Glu Thr Val Glu Met Leu Pro Ser Lys
290                 295                 300

Ala Gly Ile Trp Arg Val Glu Cys Leu Ile Gly Glu His Leu His Ala
305                 310                 315                 320

Gly Met Ser Thr Leu Phe Leu Val Tyr Ser Asn Lys Cys Gln Thr Pro
                325                 330                 335

Leu Gly Met Ala Ser Gly His Ile Arg Asp Phe Gln Ile Thr Ala Ser
            340                 345                 350

Gly Gln Tyr Gly Gln Trp Ala Pro Lys Leu Ala Arg Leu His Tyr Ser
        355                 360                 365

Gly Ser Ile Asn Ala Trp Ser Thr Lys Glu Pro Phe Ser Trp Ile Lys
370                 375                 380

Val Asp Leu Leu Ala Pro Met Ile Ile His Gly Ile Lys Thr Gln Gly
385                 390                 395                 400

Ala Arg Gln Lys Phe Ser Ser Leu Tyr Ile Ser Gln Phe Ile Ile Met
                405                 410                 415

Tyr Ser Leu Asp Gly Lys Lys Trp Gln Thr Tyr Arg Gly Asn Ser Thr
            420                 425                 430
```

```
Gly Thr Leu Met Val Phe Phe Gly Asn Val Asp Ser Ser Gly Ile Lys
            435                 440                 445

His Asn Ile Phe Asn Pro Pro Ile Ile Ala Arg Tyr Ile Arg Leu His
450                 455                 460

Pro Thr His Tyr Ser Ile Arg Ser Thr Leu Arg Met Glu Leu Met Gly
465                 470                 475                 480

Cys Asp Leu Asn Ser Cys Ser Met Pro Leu Gly Met Glu Ser Lys Ala
                485                 490                 495

Ile Ser Asp Ala Gln Ile Thr Ala Ser Ser Tyr Phe Thr Asn Met Phe
            500                 505                 510

Ala Thr Trp Ser Pro Ser Lys Ala Arg Leu His Leu Gln Gly Arg Ser
        515                 520                 525

Asn Ala Trp Arg Pro Gln Val Asn Asn Pro Lys Glu Trp Leu Gln Val
530                 535                 540

Asp Phe Gln Lys Thr Met Lys Val Thr Gly Val Thr Thr Gln Gly Val
545                 550                 555                 560

Lys Ser Leu Leu Thr Ser Met Tyr Val Lys Glu Phe Leu Ile Ser Ser
                565                 570                 575

Ser Gln Asp Gly His Gln Trp Thr Leu Phe Phe Gln Asn Gly Lys Val
            580                 585                 590

Lys Val Phe Gln Gly Asn Gln Asp Ser Phe Thr Pro Val Val Asn Ser
        595                 600                 605

Leu Asp Pro Pro Leu Leu Thr Arg Tyr Leu Arg Ile His Pro Gln Ser
610                 615                 620

Trp Val His Gln Ile Ala Leu Arg Met Glu Val Leu Gly Cys Glu Ala
625                 630                 635                 640

Gln Asp Leu Tyr

<210> SEQ ID NO 85
<211> LENGTH: 578
<212> TYPE: PRT
<213> ORGANISM: Artificial Sequence
<220> FEATURE:
<223> OTHER INFORMATION: synthetic polypeptide

<400> SEQUENCE: 85

Ser Glu Val Ala His Arg Phe Lys Asp Leu Gly Glu Glu Asn Phe Lys
1               5                   10                  15

Ala Leu Val Leu Ile Ala Phe Ala Gln Tyr Leu Gln Gln Cys Pro Phe
            20                  25                  30

Glu Asp His Val Lys Leu Val Asn Glu Val Thr Glu Phe Ala Lys Thr
        35                  40                  45

Cys Val Ala Asp Glu Ser Ala Glu Asn Cys Asp Lys Ser Leu His Thr
    50                  55                  60

Leu Phe Gly Asp Lys Leu Cys Thr Val Ala Thr Leu Arg Glu Thr Tyr
65                  70                  75                  80

Gly Glu Met Ala Asp Cys Cys Ala Lys Gln Glu Pro Glu Arg Asn Glu
                85                  90                  95

Cys Phe Leu Gln His Lys Asp Asp Asn Pro Asn Leu Pro Arg Leu Val
            100                 105                 110

Arg Pro Glu Val Asp Val Met Cys Thr Ala Phe His Asp Asn Glu Glu
        115                 120                 125

Thr Phe Leu Lys Lys Tyr Leu Tyr Glu Ile Ala Arg Arg His Pro Tyr
    130                 135                 140

Phe Tyr Ala Pro Glu Leu Leu Phe Phe Ala Lys Arg Tyr Lys Ala Ala
```

-continued

```
            145                 150                 155                 160
        Phe Thr Glu Cys Cys Gln Ala Ala Asp Lys Ala Ala Cys Leu Leu Pro
                        165                 170                 175
        Lys Leu Asp Glu Leu Arg Asp Glu Gly Lys Ala Ser Ser Ala Lys Gln
                        180                 185                 190
        Arg Leu Lys Cys Ala Ser Leu Gln Lys Phe Gly Glu Arg Ala Phe Lys
                        195                 200                 205
        Ala Trp Ala Val Ala Arg Leu Ser Gln Arg Phe Pro Lys Ala Glu Phe
                        210                 215                 220
        Ala Glu Val Ser Lys Leu Val Thr Asp Leu Thr Lys Val His Thr Glu
        225                 230                 235                 240
        Cys Cys His Gly Asp Leu Leu Glu Cys Ala Asp Asp Arg Ala Asp Leu
                        245                 250                 255
        Ala Lys Tyr Ile Cys Glu Asn Gln Asp Ser Ile Ser Ser Lys Leu Lys
                        260                 265                 270
        Glu Cys Cys Glu Lys Pro Leu Leu Glu Lys Ser His Cys Ile Ala Glu
                        275                 280                 285
        Val Glu Asn Asp Glu Met Pro Ala Asp Leu Pro Ser Leu Ala Ala Asp
                        290                 295                 300
        Phe Val Glu Ser Lys Asp Val Cys Lys Asn Tyr Ala Glu Ala Lys Asp
        305                 310                 315                 320
        Val Phe Leu Gly Met Phe Leu Tyr Glu Tyr Ala Arg Arg His Pro Asp
                        325                 330                 335
        Tyr Ser Val Val Leu Leu Leu Arg Leu Ala Lys Thr Tyr Glu Thr Thr
                        340                 345                 350
        Leu Glu Lys Cys Cys Ala Ala Ala Asp Pro His Glu Cys Tyr Ala Lys
                        355                 360                 365
        Val Phe Asp Glu Phe Lys Pro Leu Val Glu Glu Pro Gln Asn Leu Ile
                        370                 375                 380
        Lys Gln Asn Cys Glu Leu Phe Glu Gln Leu Gly Glu Tyr Lys Phe Gln
        385                 390                 395                 400
        Asn Ala Leu Leu Val Arg Tyr Thr Lys Lys Val Pro Gln Val Ser Thr
                        405                 410                 415
        Pro Thr Leu Val Glu Val Ser Arg Asn Leu Gly Lys Val Gly Ser Lys
                        420                 425                 430
        Cys Cys Lys His Pro Glu Ala Lys Arg Met Pro Cys Ala Glu Asp Tyr
                        435                 440                 445
        Leu Ser Val Val Leu Asn Gln Leu Cys Val Leu His Glu Lys Thr Pro
        450                 455                 460
        Val Ser Asp Arg Val Thr Lys Cys Cys Thr Glu Ser Leu Val Asn Arg
        465                 470                 475                 480
        Arg Pro Cys Phe Ser Ala Leu Glu Val Asp Glu Thr Tyr Val Pro Lys
                        485                 490                 495
        Glu Phe Asn Ala Glu Thr Phe Thr Phe His Ala Asp Ile Cys Thr Leu
                        500                 505                 510
        Ser Glu Lys Glu Arg Gln Ile Lys Lys Gln Thr Ala Leu Val Glu Leu
                        515                 520                 525
        Val Lys His Lys Pro Lys Ala Thr Lys Glu Gln Leu Lys Ala Val Met
                        530                 535                 540
        Asp Asp Phe Ala Ala Phe Val Glu Lys Cys Cys Lys Ala Asp Asp Lys
        545                 550                 555                 560
        Glu Thr Cys Phe Ala Glu Glu Gly Lys Lys Leu Val Ala Ala Ser Gln
                        565                 570                 575
```

Ala Ala

<210> SEQ ID NO 86
<211> LENGTH: 578
<212> TYPE: PRT
<213> ORGANISM: Artificial Sequence
<220> FEATURE:
<223> OTHER INFORMATION: synthetic polypeptide

<400> SEQUENCE: 86

Ser Glu Val Ala His Arg Phe Lys Asp Leu Gly Glu Glu Asn Phe Lys
1               5                   10                  15

Ala Leu Val Leu Ile Ala Phe Ala Gln Tyr Leu Gln Gln Cys Pro Phe
            20                  25                  30

Glu Asp His Val Lys Leu Val Asn Glu Val Thr Glu Phe Ala Lys Thr
        35                  40                  45

Cys Val Ala Asp Glu Ser Ala Glu Asn Cys Asp Lys Ser Leu His Thr
    50                  55                  60

Leu Phe Gly Asp Lys Leu Cys Thr Val Ala Thr Leu Arg Glu Thr Tyr
65                  70                  75                  80

Gly Glu Met Ala Asp Cys Cys Ala Lys Gln Glu Pro Glu Arg Asn Glu
                85                  90                  95

Cys Phe Leu Gln His Lys Asp Asp Asn Pro Asn Leu Pro Arg Leu Val
            100                 105                 110

Arg Pro Glu Val Asp Val Met Cys Thr Ala Phe His Asp Asn Glu Glu
        115                 120                 125

Thr Phe Leu Lys Lys Tyr Leu Tyr Glu Ile Ala Arg Arg His Pro Tyr
    130                 135                 140

Phe Tyr Ala Pro Glu Leu Leu Phe Phe Ala Lys Arg Tyr Lys Ala Ala
145                 150                 155                 160

Phe Thr Glu Cys Cys Gln Ala Ala Asp Lys Ala Ala Cys Leu Leu Pro
                165                 170                 175

Lys Leu Asp Glu Leu Arg Asp Glu Gly Lys Ala Ser Ser Ala Lys Gln
            180                 185                 190

Arg Leu Lys Cys Ala Ser Leu Gln Lys Phe Gly Glu Arg Ala Phe Lys
        195                 200                 205

Ala Trp Ala Val Ala Arg Leu Ser Gln Arg Phe Pro Lys Ala Glu Phe
    210                 215                 220

Ala Glu Val Ser Lys Leu Val Thr Asp Leu Thr Lys Val His Thr Glu
225                 230                 235                 240

Cys Cys His Gly Asp Leu Leu Glu Cys Ala Asp Asp Arg Ala Asp Leu
                245                 250                 255

Ala Lys Tyr Ile Cys Glu Asn Gln Asp Ser Ile Ser Ser Lys Leu Lys
            260                 265                 270

Glu Cys Cys Glu Lys Pro Leu Leu Glu Lys Ser His Cys Ile Ala Glu
        275                 280                 285

Val Glu Asn Asp Glu Met Pro Ala Asp Leu Pro Ser Leu Ala Ala Asp
    290                 295                 300

Phe Val Glu Ser Lys Asp Val Cys Lys Asn Tyr Ala Glu Ala Lys Asp
305                 310                 315                 320

Val Phe Leu Gly Met Phe Leu Tyr Glu Tyr Ala Arg Arg His Pro Asp
                325                 330                 335

Tyr Ser Val Val Leu Leu Leu Arg Leu Ala Lys Thr Tyr Glu Thr Thr
            340                 345                 350

Leu Glu Lys Cys Cys Ala Ala Asp Pro His Glu Cys Tyr Ala Lys
              355                 360                 365

Val Phe Asp Glu Phe Lys Pro Leu Val Glu Pro Gln Asn Leu Ile
      370                 375                 380

Lys Gln Asn Cys Glu Leu Phe Glu Gln Leu Gly Glu Tyr Lys Phe Gln
385                 390                 395                 400

Asn Ala Leu Leu Val Arg Tyr Thr Lys Lys Val Pro Gln Val Ser Thr
                405                 410                 415

Pro Thr Leu Val Glu Val Ser Arg Asn Leu Gly Lys Val Gly Ser Lys
                420                 425                 430

Cys Cys Lys His Pro Glu Ala Lys Arg Met Pro Cys Ala Glu Asp Tyr
            435                 440                 445

Leu Ser Val Val Leu Asn Gln Leu Cys Val Leu His Glu Lys Thr Pro
            450                 455                 460

Val Ser Asp Arg Val Thr Lys Cys Cys Thr Glu Ser Leu Val Asn Arg
465                 470                 475                 480

Arg Pro Cys Phe Ser Ala Leu Glu Val Asp Glu Thr Tyr Val Pro Lys
                485                 490                 495

Glu Phe Asn Ala Glu Thr Phe Thr Phe His Ala Asp Ile Cys Thr Leu
                500                 505                 510

Ser Glu Lys Glu Arg Gln Ile Lys Lys Gln Thr Ala Leu Val Glu Leu
            515                 520                 525

Val Lys His Lys Pro Lys Ala Thr Lys Glu Gln Leu Lys Ala Val Met
            530                 535                 540

Asp Asp Phe Ala Ala Phe Val Glu Lys Cys Cys Lys Ala Asp Asp Lys
545                 550                 555                 560

Glu Thr Cys Phe Ala Glu Glu Gly Lys Lys Leu Val Ala Ala Ser Gln
                565                 570                 575

Ala Ala

<210> SEQ ID NO 87
<211> LENGTH: 375
<212> TYPE: PRT
<213> ORGANISM: Artificial Sequence
<220> FEATURE:
<223> OTHER INFORMATION: synthetic polypeptide

<400> SEQUENCE: 87

His Pro Thr Phe Asn Lys Ile Thr Pro Asn Leu Ala Glu Phe Ala Phe
1               5                   10                  15

Ser Leu Tyr Arg Gln Leu Ala His Gln Ser Asn Ser Thr Asn Ile Phe
                20                  25                  30

Phe Ser Pro Val Ser Ile Ala Ala Ala Phe Ala Met Leu Ser Leu Gly
            35                  40                  45

Ala Lys Gly Asp Thr His Asp Glu Ile Leu Glu Gly Leu Asn Phe Asn
    50                  55                  60

Leu Thr Glu Ile Pro Glu Ala Gln Ile His Glu Gly Phe Gln Glu Leu
65                  70                  75                  80

Leu Arg Thr Leu Asn Gln Pro Asp Ser Gln Leu Gln Leu Thr Thr Gly
                85                  90                  95

Asn Gly Leu Phe Leu Ser Glu Gly Leu Lys Leu Val Asp Lys Phe Leu
            100                 105                 110

Glu Asp Val Lys Lys Leu Tyr His Ser Glu Ala Phe Thr Val Asn Phe
        115                 120                 125

Gly Asp Thr Glu Glu Ala Lys Lys Gln Ile Asn Asp Tyr Val Glu Lys

```
                130                 135                 140
Gly Thr Gln Gly Lys Ile Val Asp Leu Val Lys Glu Leu Asp Arg Asp
145                 150                 155                 160

Thr Val Phe Ala Leu Val Asn Tyr Ile Phe Phe Lys Gly Lys Trp Glu
                165                 170                 175

Arg Pro Phe Glu Val Lys Asp Thr Glu Glu Asp Phe His Val Asp
                180                 185                 190

Gln Val Thr Thr Val Lys Val Pro Met Met Lys Arg Leu Gly Met Phe
                195                 200                 205

Asn Ile Gln His Cys Lys Lys Leu Ser Ser Trp Val Leu Leu Met Lys
                210                 215                 220

Tyr Leu Gly Asn Ala Thr Ala Ile Phe Phe Leu Pro Asp Glu Gly Lys
225                 230                 235                 240

Leu Gln His Leu Glu Asn Glu Leu Thr His Asp Ile Ile Thr Lys Phe
                245                 250                 255

Leu Glu Asn Glu Asp Arg Arg Ser Ala Ser Leu His Leu Pro Lys Leu
                260                 265                 270

Ser Ile Thr Gly Thr Tyr Asp Leu Lys Ser Val Leu Gly Gln Leu Gly
                275                 280                 285

Ile Thr Lys Val Phe Ser Asn Gly Ala Asp Leu Ser Gly Val Thr Glu
                290                 295                 300

Glu Ala Pro Leu Lys Leu Ser Lys Ala Val His Lys Ala Val Leu Thr
305                 310                 315                 320

Ile Asp Glu Lys Gly Thr Glu Ala Ala Gly Ala Met Phe Leu Glu Ala
                325                 330                 335

Ile Pro Met Ser Ile Pro Pro Glu Val Lys Phe Asn Lys Pro Phe Val
                340                 345                 350

Phe Leu Met Ile Glu Gln Asn Thr Lys Ser Pro Leu Phe Met Gly Lys
                355                 360                 365

Val Val Asn Pro Thr Gln Lys
                370                 375

<210> SEQ ID NO 88
<211> LENGTH: 141
<212> TYPE: PRT
<213> ORGANISM: Artificial Sequence
<220> FEATURE:
<223> OTHER INFORMATION: synthetic polypeptide

<400> SEQUENCE: 88

Val Leu Ser Pro Ala Asp Lys Thr Asn Val Lys Ala Ala Trp Gly Lys
1               5                   10                  15

Val Gly Ala His Ala Gly Glu Tyr Gly Ala Glu Ala Leu Glu Arg Met
                20                  25                  30

Phe Leu Ser Phe Pro Thr Thr Lys Thr Tyr Phe Pro His Phe Asp Leu
                35                  40                  45

Ser His Gly Ser Ala Gln Val Lys Gly His Gly Lys Lys Val Ala Asp
                50                  55                  60

Ala Leu Thr Asn Ala Val Ala His Val Asp Asp Met Pro Asn Ala Leu
65                  70                  75                  80

Ser Ala Leu Ser Asp Leu His Ala His Lys Leu Arg Val Asp Pro Val
                85                  90                  95

Asn Phe Lys Leu Leu Ser His Cys Leu Leu Val Thr Leu Ala Ala His
                100                 105                 110

Leu Pro Ala Glu Phe Thr Pro Ala Val His Ala Ser Leu Asp Lys Phe
```

```
            115                 120                 125
Leu Ala Ser Val Ser Thr Val Leu Thr Ser Lys Tyr Arg
    130                 135                 140

<210> SEQ ID NO 89
<211> LENGTH: 146
<212> TYPE: PRT
<213> ORGANISM: Artificial Sequence
<220> FEATURE:
<223> OTHER INFORMATION: synthetic polypeptide

<400> SEQUENCE: 89

Val His Leu Thr Pro Glu Glu Lys Ser Ala Val Thr Ala Leu Trp Gly
1               5                   10                  15

Lys Val Asn Val Asp Glu Val Gly Gly Glu Ala Leu Gly Arg Leu Leu
            20                  25                  30

Val Val Tyr Pro Trp Thr Gln Arg Phe Phe Glu Ser Phe Gly Asp Leu
        35                  40                  45

Ser Thr Pro Asp Ala Val Met Gly Asn Pro Lys Val Lys Ala His Gly
    50                  55                  60

Lys Lys Val Leu Gly Ala Phe Ser Asp Gly Leu Ala His Leu Asp Asn
65                  70                  75                  80

Leu Lys Gly Thr Phe Ala Thr Leu Ser Glu Leu His Cys Asp Lys Leu
                85                  90                  95

His Val Asp Pro Glu Asn Phe Arg Leu Leu Gly Asn Val Leu Val Cys
            100                 105                 110

Val Leu Ala His His Phe Gly Lys Glu Phe Thr Pro Pro Val Gln Ala
        115                 120                 125

Ala Tyr Gln Lys Val Val Ala Gly Val Ala Asn Ala Leu Ala His Lys
    130                 135                 140

Tyr His
145

<210> SEQ ID NO 90
<211> LENGTH: 4
<212> TYPE: PRT
<213> ORGANISM: Artificial Sequence
<220> FEATURE:
<223> OTHER INFORMATION: synthetic polypeptide

<400> SEQUENCE: 90

Ala Gly Val Phe
1

<210> SEQ ID NO 91
<211> LENGTH: 4
<212> TYPE: PRT
<213> ORGANISM: Artificial Sequence
<220> FEATURE:
<223> OTHER INFORMATION: synthetic polypeptide

<400> SEQUENCE: 91

Gly Phe Leu Gly
1

<210> SEQ ID NO 92
<211> LENGTH: 2
<212> TYPE: PRT
<213> ORGANISM: Artificial Sequence
<220> FEATURE:
<223> OTHER INFORMATION: synthetic polypeptide
```

<400> SEQUENCE: 92

Phe Lys
1

<210> SEQ ID NO 93
<211> LENGTH: 2
<212> TYPE: PRT
<213> ORGANISM: Artificial Sequence
<220> FEATURE:
<223> OTHER INFORMATION: synthetic polypeptide

<400> SEQUENCE: 93

Ala Leu
1

<210> SEQ ID NO 94
<211> LENGTH: 4
<212> TYPE: PRT
<213> ORGANISM: Artificial Sequence
<220> FEATURE:
<223> OTHER INFORMATION: synthetic polypeptide

<400> SEQUENCE: 94

Ala Leu Ala Leu
1

<210> SEQ ID NO 95
<211> LENGTH: 5
<212> TYPE: PRT
<213> ORGANISM: Artificial Sequence
<220> FEATURE:
<223> OTHER INFORMATION: synthetic polypeptide

<400> SEQUENCE: 95

Ala Leu Ala Leu Ala
1               5

<210> SEQ ID NO 96
<211> LENGTH: 4
<212> TYPE: PRT
<213> ORGANISM: Artificial Sequence
<220> FEATURE:
<223> OTHER INFORMATION: synthetic polypeptide

<400> SEQUENCE: 96

Ala Leu Ala Leu
1

<210> SEQ ID NO 97
<211> LENGTH: 248
<212> TYPE: PRT
<213> ORGANISM: Artificial Sequence
<220> FEATURE:
<223> OTHER INFORMATION: synthetic polypeptide

<400> SEQUENCE: 97

Met Gly His His His His His His Gly Gly Ala Ser Lys Gly Glu Glu
1               5                   10                  15

Leu Phe Asp Gly Val Val Pro Ile Leu Val Glu Leu Asp Gly Asp Val
                20                  25                  30

Asn Gly His Glu Phe Ser Val Arg Gly Glu Gly Glu Gly Asp Ala Thr
            35                  40                  45

Glu Gly Glu Leu Thr Leu Lys Phe Ile Cys Thr Thr Gly Glu Leu Pro
        50                  55                  60

```
Val Pro Trp Pro Thr Leu Val Thr Thr Leu Thr Tyr Gly Val Gln Cys
 65                  70                  75                  80

Phe Ser Asp Tyr Pro Asp His Met Asp Gln His Asp Phe Phe Lys Ser
                 85                  90                  95

Ala Met Pro Glu Gly Tyr Val Gln Glu Arg Thr Ile Ser Phe Lys Asp
            100                 105                 110

Asp Gly Thr Tyr Lys Thr Arg Ala Glu Val Lys Phe Glu Gly Asp Thr
        115                 120                 125

Leu Val Asn Arg Ile Glu Leu Lys Gly Ile Asp Phe Lys Glu Asp Gly
130                 135                 140

Asn Ile Leu Gly His Lys Leu Glu Tyr Asn Phe Asn Ser His Asp Val
145                 150                 155                 160

Tyr Ile Thr Ala Asp Lys Gln Glu Asn Gly Ile Lys Ala Glu Phe Glu
                165                 170                 175

Ile Arg His Asn Val Glu Asp Gly Ser Val Gln Leu Ala Asp His Tyr
            180                 185                 190

Gln Gln Asn Thr Pro Ile Gly Asp Gly Pro Val Leu Leu Pro Asp Asp
        195                 200                 205

His Tyr Leu Ser Thr Glu Ser Ala Leu Ser Lys Asp Pro Asn Glu Asp
210                 215                 220

Arg Asp His Met Val Leu Leu Glu Phe Val Thr Ala Ala Gly Ile Asp
225                 230                 235                 240

His Gly Met Asp Glu Leu Tyr Lys
                245

<210> SEQ ID NO 98
<211> LENGTH: 248
<212> TYPE: PRT
<213> ORGANISM: Artificial Sequence
<220> FEATURE:
<223> OTHER INFORMATION: synthetic polypeptide

<400> SEQUENCE: 98

Met Gly His His His His His Gly Gly Ala Ser Lys Gly Glu Arg
 1               5                  10                  15

Leu Phe Thr Gly Val Val Pro Ile Leu Val Glu Leu Asp Gly Asp Val
                 20                  25                  30

Asn Gly His Lys Phe Ser Val Arg Gly Glu Gly Glu Gly Asp Ala Thr
             35                  40                  45

Arg Gly Lys Leu Thr Leu Lys Phe Ile Cys Thr Thr Gly Lys Leu Pro
 50                  55                  60

Val Pro Trp Pro Thr Leu Val Thr Thr Leu Thr Tyr Gly Val Gln Cys
 65                  70                  75                  80

Phe Ser Arg Tyr Pro Lys His Met Lys Arg His Asp Phe Phe Lys Ser
                 85                  90                  95

Ala Met Pro Glu Gly Tyr Val Gln Glu Arg Thr Ile Ser Phe Lys Lys
            100                 105                 110

Asp Gly Thr Tyr Lys Thr Arg Ala Glu Val Lys Phe Glu Gly Arg Thr
        115                 120                 125

Leu Val Asn Arg Ile Glu Leu Lys Gly Arg Asp Phe Lys Glu Lys Gly
130                 135                 140

Asn Ile Leu Gly His Lys Leu Glu Tyr Asn Phe Asn Ser His Asn Val
145                 150                 155                 160

Tyr Ile Thr Ala Asp Lys Arg Lys Asn Gly Ile Lys Ala Asn Phe Lys
                165                 170                 175
```

```
Ile Arg His Asn Val Lys Asp Gly Ser Val Gln Leu Ala Asp His Tyr
            180                 185                 190

Gln Gln Asn Thr Pro Ile Gly Arg Gly Pro Val Leu Leu Pro Arg Asn
        195                 200                 205

His Tyr Leu Ser Thr Arg Ser Ala Leu Ser Lys Asp Pro Lys Glu Lys
    210                 215                 220

Arg Asp His Met Val Leu Leu Glu Phe Val Thr Ala Ala Gly Ile Thr
225                 230                 235                 240

His Gly Met Asp Glu Leu Tyr Lys
                245

<210> SEQ ID NO 99
<211> LENGTH: 248
<212> TYPE: PRT
<213> ORGANISM: Artificial Sequence
<220> FEATURE:
<223> OTHER INFORMATION: synthetic polypeptide

<400> SEQUENCE: 99

Met Gly His His His His His Gly Gly Ala Ser Lys Gly Glu Arg
1               5                   10                  15

Leu Phe Thr Gly Val Val Pro Ile Leu Val Glu Leu Asp Gly Asp Val
            20                  25                  30

Asn Gly His Lys Phe Ser Val Arg Gly Lys Gly Lys Gly Asp Ala Thr
        35                  40                  45

Arg Gly Lys Leu Thr Leu Lys Phe Ile Cys Thr Thr Gly Lys Leu Pro
    50                  55                  60

Val Pro Trp Pro Thr Leu Val Thr Thr Leu Thr Tyr Gly Val Gln Cys
65                  70                  75                  80

Phe Ser Arg Tyr Pro Lys His Met Lys Arg His Asp Phe Phe Lys Ser
                85                  90                  95

Ala Met Pro Lys Gly Tyr Val Gln Glu Arg Thr Ile Ser Phe Lys Lys
            100                 105                 110

Asp Gly Thr Tyr Lys Thr Arg Ala Glu Val Lys Phe Glu Gly Arg Thr
        115                 120                 125

Leu Val Asn Arg Ile Lys Leu Lys Gly Arg Asp Phe Lys Glu Lys Gly
    130                 135                 140

Asn Ile Leu Gly His Lys Leu Arg Tyr Asn Phe Asn Ser His Asn Val
145                 150                 155                 160

Tyr Ile Thr Ala Asp Lys Arg Lys Asn Gly Ile Lys Ala Asn Phe Lys
                165                 170                 175

Ile Arg His Asn Val Lys Asp Gly Ser Val Gln Leu Ala Asp His Tyr
            180                 185                 190

Gln Gln Asn Thr Pro Ile Gly Arg Gly Pro Val Leu Leu Pro Arg Asn
        195                 200                 205

His Tyr Leu Ser Thr Arg Ser Ala Leu Ser Lys Asp Pro Lys Glu Lys
    210                 215                 220

Arg Asp His Met Val Leu Leu Glu Phe Val Thr Ala Ala Gly Ile Thr
225                 230                 235                 240

His Gly Met Asp Glu Leu Tyr Lys
                245

<210> SEQ ID NO 100
<211> LENGTH: 248
<212> TYPE: PRT
<213> ORGANISM: Artificial Sequence
<220> FEATURE:
```

<223> OTHER INFORMATION: synthetic polypeptide

<400> SEQUENCE: 100

Met Gly His His His His His Gly Gly Ala Ser Lys Gly Glu Arg
1               5                   10                  15

Leu Phe Arg Gly Lys Val Pro Ile Leu Val Glu Leu Lys Gly Asp Val
            20                  25                  30

Asn Gly His Lys Phe Ser Val Arg Gly Lys Gly Lys Gly Asp Ala Thr
        35                  40                  45

Arg Gly Lys Leu Thr Leu Lys Phe Ile Cys Thr Thr Gly Lys Leu Pro
    50                  55                  60

Val Pro Trp Pro Thr Leu Val Thr Thr Leu Thr Tyr Gly Val Gln Cys
65                  70                  75                  80

Phe Ser Arg Tyr Pro Lys His Met Lys Arg His Asp Phe Phe Lys Ser
                85                  90                  95

Ala Met Pro Lys Gly Tyr Val Gln Glu Arg Thr Ile Ser Phe Lys Lys
            100                 105                 110

Asp Gly Lys Tyr Lys Thr Arg Ala Glu Val Lys Phe Glu Gly Arg Thr
        115                 120                 125

Leu Val Asn Arg Ile Lys Leu Lys Gly Arg Asp Phe Lys Glu Lys Gly
    130                 135                 140

Asn Ile Leu Gly His Lys Leu Arg Tyr Asn Phe Asn Ser His Lys Val
145                 150                 155                 160

Tyr Ile Thr Ala Asp Lys Arg Lys Asn Gly Ile Lys Ala Lys Phe Lys
                165                 170                 175

Ile Arg His Asn Val Lys Asp Gly Ser Val Gln Leu Ala Asp His Tyr
            180                 185                 190

Gln Gln Asn Thr Pro Ile Gly Arg Gly Pro Val Leu Leu Pro Arg Asn
        195                 200                 205

His Tyr Leu Ser Thr Arg Ser Lys Leu Ser Lys Asp Pro Lys Glu Lys
    210                 215                 220

Arg Asp His Met Val Leu Leu Glu Phe Val Thr Ala Ala Gly Ile Lys
225                 230                 235                 240

His Gly Arg Asp Glu Arg Tyr Lys
                245

<210> SEQ ID NO 101
<211> LENGTH: 280
<212> TYPE: PRT
<213> ORGANISM: Artificial Sequence
<220> FEATURE:
<223> OTHER INFORMATION: synthetic polypeptide

<400> SEQUENCE: 101

Met Gly His His His His His Gly Gly Ala Ser Lys Gly Glu Arg
1               5                   10                  15

Leu Phe Arg Gly Lys Val Pro Ile Leu Val Glu Leu Lys Gly Asp Val
            20                  25                  30

Asn Gly His Lys Phe Ser Val Arg Gly Lys Gly Lys Gly Asp Ala Thr
        35                  40                  45

Arg Gly Lys Leu Thr Leu Lys Phe Ile Cys Thr Thr Gly Lys Leu Pro
    50                  55                  60

Val Pro Trp Pro Thr Leu Val Thr Thr Leu Thr Tyr Gly Val Gln Cys
65                  70                  75                  80

Phe Ser Arg Tyr Pro Lys His Met Lys Arg His Asp Phe Phe Lys Ser
                85                  90                  95

```
Ala Met Pro Lys Gly Tyr Val Gln Glu Arg Thr Ile Ser Phe Lys Lys
            100                 105                 110

Asp Gly Lys Tyr Lys Thr Arg Ala Glu Val Lys Phe Glu Gly Arg Thr
            115                 120                 125

Leu Val Asn Arg Ile Lys Leu Lys Gly Arg Asp Phe Lys Glu Lys Gly
            130                 135                 140

Asn Ile Leu Gly His Lys Leu Arg Tyr Asn Phe Asn Ser His Lys Val
145                 150                 155                 160

Tyr Ile Thr Ala Asp Lys Arg Lys Asn Gly Ile Lys Ala Lys Phe Lys
                165                 170                 175

Ile Arg His Asn Val Lys Asp Gly Ser Val Gln Leu Ala Asp His Tyr
                180                 185                 190

Gln Gln Asn Thr Pro Ile Gly Arg Gly Pro Val Leu Leu Pro Arg Asn
                195                 200                 205

His Tyr Leu Ser Thr Arg Ser Lys Leu Ser Lys Asp Pro Lys Glu Lys
            210                 215                 220

Arg Asp His Met Val Leu Leu Glu Phe Val Thr Ala Ala Gly Ile Lys
225                 230                 235                 240

His Gly Arg Asp Glu Arg Tyr Lys Gly Ser Ala Gly Ser Ala Ala Gly
                245                 250                 255

Ser Gly Glu Phe Gly Leu Phe Gly Ala Ile Ala Gly Phe Ile Glu Asn
            260                 265                 270

Gly Trp Glu Gly Met Ile Asp Gly
            275                 280

<210> SEQ ID NO 102
<211> LENGTH: 24
<212> TYPE: DNA
<213> ORGANISM: Artificial Sequence
<220> FEATURE:
<223> OTHER INFORMATION: synthetic polynucleotide

<400> SEQUENCE: 102
caactcactc aagattgtca gcaa                                          24

<210> SEQ ID NO 103
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 103
gggatggact gtggtcatga                                               20

<210> SEQ ID NO 104
<211> LENGTH: 26
<212> TYPE: DNA
<213> ORGANISM: Artificial Sequence
<220> FEATURE:
<223> OTHER INFORMATION: synthetic polynucleotide

<400> SEQUENCE: 104
atagcacagc ctggatagca acgtac                                        26

<210> SEQ ID NO 105
<211> LENGTH: 25
<212> TYPE: DNA
<213> ORGANISM: Artificial Sequence
<220> FEATURE:
```

-continued

<223> OTHER INFORMATION: synthetic polynucleotide

<400> SEQUENCE: 105
caccttctac aatgagctgc gtgtg                                          25

<210> SEQ ID NO 106
<211> LENGTH: 20
<212> TYPE: RNA
<213> ORGANISM: Artificial Sequence
<220> FEATURE:
<223> OTHER INFORMATION: synthetic polynucleotide

<400> SEQUENCE: 106
gcaugccauu accuggccau                                                20

<210> SEQ ID NO 107
<211> LENGTH: 4
<212> TYPE: PRT
<213> ORGANISM: Artificial Sequence
<220> FEATURE:
<223> OTHER INFORMATION: synthetic polypeptide

<400> SEQUENCE: 107

Ala Leu Ala Leu
1

<210> SEQ ID NO 108
<211> LENGTH: 5
<212> TYPE: PRT
<213> ORGANISM: Artificial Sequence
<220> FEATURE:
<223> OTHER INFORMATION: synthetic polypeptide

<400> SEQUENCE: 108

Leu Pro Glu Thr Gly
1               5

<210> SEQ ID NO 109
<211> LENGTH: 4
<212> TYPE: PRT
<213> ORGANISM: Artificial Sequence
<220> FEATURE:
<223> OTHER INFORMATION: synthetic polypeptide

<400> SEQUENCE: 109

Gly Gly Gly Gly
1

<210> SEQ ID NO 110
<211> LENGTH: 248
<212> TYPE: PRT
<213> ORGANISM: Artificial Sequence
<220> FEATURE:
<223> OTHER INFORMATION: synthetic polypeptide

<400> SEQUENCE: 110

Met Gly His His His His His His Gly Gly Ala Ser Lys Gly Glu Glu
1               5                   10                  15

Leu Phe Thr Gly Val Val Pro Ile Leu Val Glu Leu Asp Gly Asp Val
                20                  25                  30

Asn Gly His Lys Phe Ser Val Arg Gly Glu Gly Glu Gly Asp Ala Thr
            35                  40                  45

Asn Gly Lys Leu Thr Leu Lys Phe Ile Cys Thr Thr Gly Lys Leu Pro
        50                  55                  60

Val Pro Trp Pro Thr Leu Val Thr Thr Leu Thr Tyr Gly Val Gln Cys
65                  70                  75                  80

Phe Ser Arg Tyr Pro Asp His Met Lys Gln His Asp Phe Phe Lys Ser
                85                  90                  95

Ala Met Pro Glu Gly Tyr Val Gln Glu Arg Thr Ile Ser Phe Lys Asp
            100                 105                 110

Asp Gly Thr Tyr Lys Thr Arg Ala Glu Val Lys Phe Glu Gly Asp Thr
        115                 120                 125

Leu Val Asn Arg Ile Glu Leu Lys Gly Ile Asp Phe Lys Glu Asp Gly
    130                 135                 140

Asn Ile Leu Gly His Lys Leu Glu Tyr Asn Phe Asn Ser His Asn Val
145                 150                 155                 160

Tyr Ile Thr Ala Asp Lys Gln Lys Asn Gly Ile Lys Ala Asn Phe Lys
                165                 170                 175

Ile Arg His Asn Val Glu Asp Gly Ser Val Gln Leu Ala Asp His Tyr
            180                 185                 190

Gln Gln Asn Thr Pro Ile Gly Asp Gly Pro Val Leu Leu Pro Asp Asn
        195                 200                 205

His Tyr Leu Ser Thr Gln Ser Ala Leu Ser Lys Asp Pro Asn Glu Lys
    210                 215                 220

Arg Asp His Met Val Leu Leu Glu Phe Val Thr Ala Ala Gly Ile Thr
225                 230                 235                 240

His Gly Met Asp Glu Leu Tyr Lys
                245

<210> SEQ ID NO 111
<211> LENGTH: 248
<212> TYPE: PRT
<213> ORGANISM: Artificial Sequence
<220> FEATURE:
<223> OTHER INFORMATION: synthetic polypeptide

<400> SEQUENCE: 111

Met Gly His His His His His Gly Gly Ala Ser Lys Gly Glu Arg
1               5                   10                  15

Leu Phe Arg Gly Lys Val Pro Ile Leu Val Glu Leu Lys Gly Asp Val
                20                  25                  30

Asn Gly His Lys Phe Ser Val Arg Gly Lys Gly Lys Gly Asp Ala Thr
            35                  40                  45

Arg Gly Lys Leu Thr Leu Lys Phe Ile Cys Thr Thr Gly Lys Leu Pro
        50                  55                  60

Val Pro Trp Pro Thr Leu Val Thr Thr Leu Thr Tyr Gly Val Gln Cys
65                  70                  75                  80

Phe Ser Arg Tyr Pro Lys His Met Lys Arg His Asp Phe Phe Lys Ser
                85                  90                  95

Ala Met Pro Lys Gly Tyr Val Gln Glu Arg Thr Ile Ser Phe Lys Lys
            100                 105                 110

Asp Gly Lys Tyr Lys Thr Arg Ala Glu Val Lys Phe Glu Gly Arg Thr
        115                 120                 125

Leu Val Asn Arg Ile Lys Leu Lys Gly Arg Asp Phe Lys Glu Lys Gly
    130                 135                 140

Asn Ile Leu Gly His Lys Leu Arg Tyr Asn Phe Asn Ser His Lys Val
145                 150                 155                 160

Tyr Ile Thr Ala Asp Lys Arg Lys Asn Gly Ile Lys Ala Lys Phe Lys
                165                 170                 175

```
Ile Arg His Asn Val Lys Asp Gly Ser Val Gln Leu Ala Asp His Tyr
            180                 185                 190

Gln Gln Asn Thr Pro Ile Gly Arg Gly Pro Val Leu Leu Pro Arg Asn
            195                 200                 205

His Tyr Leu Ser Thr Arg Ser Lys Leu Ser Lys Asp Pro Lys Glu Lys
            210                 215                 220

Arg Asp His Met Val Leu Leu Glu Phe Val Thr Ala Ala Gly Ile Lys
225                 230                 235                 240

His Gly Arg Asp Glu Arg Tyr Lys
                245

<210> SEQ ID NO 112
<211> LENGTH: 510
<212> TYPE: PRT
<213> ORGANISM: Artificial Sequence
<220> FEATURE:
<223> OTHER INFORMATION: synthetic polypeptide

<400> SEQUENCE: 112

Met Ala Ser Lys Gly Glu Arg Leu Phe Arg Gly Lys Val Pro Ile Leu
1               5                   10                  15

Val Glu Leu Lys Gly Asp Val Asn Gly His Lys Phe Ser Val Arg Gly
            20                  25                  30

Lys Gly Lys Gly Asp Ala Thr Arg Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Lys His Met Lys
65                  70                  75                  80

Arg His Asp Phe Phe Lys Ser Ala Met Pro Lys Gly Tyr Val Gln Glu
                85                  90                  95

Arg Thr Ile Ser Phe Lys Lys Asp Gly Lys Tyr Lys Thr Arg Ala Glu
            100                 105                 110

Val Lys Phe Glu Gly Arg Thr Leu Val Asn Arg Ile Lys Leu Lys Gly
        115                 120                 125

Arg Asp Phe Lys Glu Lys Gly Asn Ile Leu Gly His Lys Leu Arg Tyr
    130                 135                 140

Asn Phe Asn Ser His Lys Val Tyr Ile Thr Ala Asp Lys Arg Lys Asn
145                 150                 155                 160

Gly Ile Lys Ala Lys Phe Lys Ile Arg His Asn Val Lys Asp Gly Ser
                165                 170                 175

Val Gln Leu Ala Asp His Tyr Gln Gln Asn Thr Pro Ile Gly Arg Gly
            180                 185                 190

Pro Val Leu Leu Pro Arg Asn His Tyr Leu Ser Thr Arg Ser Lys Leu
        195                 200                 205

Ser Lys Asp Pro Lys Glu Lys Arg Asp His Met Val Leu Leu Glu Phe
    210                 215                 220

Val Thr Ala Ala Gly Ile Lys His Gly Arg Asp Glu Arg Tyr Lys Gly
225                 230                 235                 240

Gly Ser Gly Gly Ser Gly Gly Ser Gly Gly Ser Ala Leu Ala Leu Gly
                245                 250                 255

Gly Ser Gly Gly Ser Gly Gly Ser Gly Gly Ser Val Ser Lys Gly Glu
            260                 265                 270

Glu Asp Asn Met Ala Ile Ile Lys Glu Phe Met Arg Phe Lys Val His
        275                 280                 285
```

Met Glu Gly Ser Val Asn Gly His Glu Phe Glu Ile Glu Gly Glu Gly
    290                 295                 300

Glu Gly Arg Pro Tyr Glu Gly Thr Gln Thr Ala Lys Leu Lys Val Thr
305                 310                 315                 320

Lys Gly Gly Pro Leu Pro Phe Ala Trp Asp Ile Leu Ser Pro Gln Phe
                325                 330                 335

Met Tyr Gly Ser Lys Ala Tyr Val Lys His Pro Ala Asp Ile Pro Asp
            340                 345                 350

Tyr Leu Lys Leu Ser Phe Pro Glu Gly Phe Lys Trp Glu Arg Val Met
        355                 360                 365

Asn Phe Glu Asp Gly Gly Val Val Thr Val Thr Gln Asp Ser Ser Leu
370                 375                 380

Gln Asp Gly Glu Phe Ile Tyr Lys Val Lys Leu Arg Gly Thr Asn Phe
385                 390                 395                 400

Pro Ser Asp Gly Pro Val Met Gln Lys Lys Thr Met Gly Trp Glu Ala
                405                 410                 415

Ser Ser Glu Arg Met Tyr Pro Glu Asp Gly Ala Leu Lys Gly Glu Ile
            420                 425                 430

Lys Gln Arg Leu Lys Leu Lys Asp Gly Gly His Tyr Asp Ala Glu Val
        435                 440                 445

Lys Thr Thr Tyr Lys Ala Lys Lys Pro Val Gln Leu Pro Gly Ala Tyr
    450                 455                 460

Asn Val Asn Ile Lys Leu Asp Ile Thr Ser His Asn Glu Asp Tyr Thr
465                 470                 475                 480

Ile Val Glu Gln Tyr Glu Arg Ala Glu Gly Arg His Ser Thr Gly Gly
                485                 490                 495

Met Asp Glu Leu Tyr Lys Leu Glu His His His His His His
            500                 505                 510

<210> SEQ ID NO 113
<211> LENGTH: 324
<212> TYPE: PRT
<213> ORGANISM: Artificial Sequence
<220> FEATURE:
<223> OTHER INFORMATION: synthetic polypeptide

<400> SEQUENCE: 113

Met Gly His His His His His His Gly Gly Met Gln Ile Phe Val Lys
1               5                   10                  15

Thr Leu Thr Gly Lys Thr Ile Thr Leu Glu Val Glu Pro Ser Asp Thr
            20                  25                  30

Ile Glu Asn Val Lys Ala Lys Ile Gln Asp Lys Glu Gly Ile Pro Pro
        35                  40                  45

Asp Gln Gln Arg Leu Ile Phe Ala Gly Lys Gln Leu Glu Asp Gly Arg
    50                  55                  60

Thr Leu Ser Asp Tyr Asn Ile Gln Lys Glu Ser Thr Leu His Leu Val
65                  70                  75                  80

Leu Arg Leu Arg Gly Gly Ala Ser Lys Gly Glu Arg Leu Phe Arg Gly
                85                  90                  95

Lys Val Pro Ile Leu Val Glu Leu Lys Gly Asp Val Asn Gly His Lys
            100                 105                 110

Phe Ser Val Arg Gly Lys Gly Lys Gly Asp Ala Thr Arg Gly Lys Leu
        115                 120                 125

Thr Leu Lys Phe Ile Cys Thr Thr Gly Lys Leu Pro Val Pro Trp Pro
    130                 135                 140

Thr Leu Val Thr Thr Leu Thr Tyr Gly Val Gln Cys Phe Ser Arg Tyr
145                 150                 155                 160

Pro Lys His Met Lys Arg His Asp Phe Phe Lys Ser Ala Met Pro Lys
            165                 170                 175

Gly Tyr Val Gln Glu Arg Thr Ile Ser Phe Lys Lys Asp Gly Lys Tyr
            180                 185                 190

Lys Thr Arg Ala Glu Val Lys Phe Glu Gly Arg Thr Leu Val Asn Arg
            195                 200                 205

Ile Lys Leu Lys Gly Arg Asp Phe Lys Glu Lys Gly Asn Ile Leu Gly
        210                 215                 220

His Lys Leu Arg Tyr Asn Phe Asn Ser His Lys Val Tyr Ile Thr Ala
225                 230                 235                 240

Asp Lys Arg Lys Asn Gly Ile Lys Ala Lys Phe Lys Ile Arg His Asn
            245                 250                 255

Val Lys Asp Gly Ser Val Gln Leu Ala Asp His Tyr Gln Gln Asn Thr
            260                 265                 270

Pro Ile Gly Arg Gly Pro Val Leu Leu Pro Arg Asn His Tyr Leu Ser
        275                 280                 285

Thr Arg Ser Lys Leu Ser Lys Asp Pro Lys Glu Lys Arg Asp His Met
290                 295                 300

Val Leu Leu Glu Phe Val Thr Ala Ala Gly Ile Lys His Gly Arg Asp
305                 310                 315                 320

Glu Arg Tyr Lys

<210> SEQ ID NO 114
<211> LENGTH: 324
<212> TYPE: PRT
<213> ORGANISM: Artificial Sequence
<220> FEATURE:
<223> OTHER INFORMATION: synthetic polypeptide

<400> SEQUENCE: 114

Met Gly His His His His His His Gly Gly Met Gln Ile Phe Val Lys
1               5                   10                  15

Thr Leu Thr Gly Lys Thr Ile Thr Leu Glu Val Glu Pro Ser Asp Thr
            20                  25                  30

Ile Glu Asn Val Lys Ala Lys Ile Gln Asp Lys Glu Gly Ile Pro Pro
        35                  40                  45

Asp Gln Gln Arg Leu Ile Phe Ala Gly Lys Gln Leu Glu Asp Gly Arg
    50                  55                  60

Thr Leu Ser Asp Tyr Asn Ile Gln Lys Glu Ser Thr Leu His Leu Val
65                  70                  75                  80

Leu Arg Leu Arg Gly Val Ala Ser Lys Gly Glu Arg Leu Phe Arg Gly
            85                  90                  95

Lys Val Pro Ile Leu Val Glu Leu Lys Gly Asp Val Asn Gly His Lys
            100                 105                 110

Phe Ser Val Arg Gly Lys Gly Lys Gly Asp Ala Thr Arg Gly Lys Leu
        115                 120                 125

Thr Leu Lys Phe Ile Cys Thr Thr Gly Lys Leu Pro Val Pro Trp Pro
130                 135                 140

Thr Leu Val Thr Thr Leu Thr Tyr Gly Val Gln Cys Phe Ser Arg Tyr
145                 150                 155                 160

Pro Lys His Met Lys Arg His Asp Phe Phe Lys Ser Ala Met Pro Lys
            165                 170                 175

Gly Tyr Val Gln Glu Arg Thr Ile Ser Phe Lys Lys Asp Gly Lys Tyr

```
                180                 185                 190
Lys Thr Arg Ala Glu Val Lys Phe Glu Gly Arg Thr Leu Val Asn Arg
            195                 200                 205
Ile Lys Leu Lys Gly Arg Asp Phe Lys Glu Lys Gly Asn Ile Leu Gly
        210                 215                 220
His Lys Leu Arg Tyr Asn Phe Asn Ser His Lys Val Tyr Ile Thr Ala
225                 230                 235                 240
Asp Lys Arg Lys Asn Gly Ile Lys Ala Lys Phe Lys Ile Arg His Asn
                245                 250                 255
Val Lys Asp Gly Ser Val Gln Leu Ala Asp His Tyr Gln Gln Asn Thr
            260                 265                 270
Pro Ile Gly Arg Gly Pro Val Leu Leu Pro Arg Asn His Tyr Leu Ser
        275                 280                 285
Thr Arg Ser Lys Leu Ser Lys Asp Pro Lys Glu Lys Arg Asp His Met
    290                 295                 300
Val Leu Leu Glu Phe Val Thr Ala Ala Gly Ile Lys His Gly Arg Asp
305                 310                 315                 320
Glu Arg Tyr Lys

<210> SEQ ID NO 115
<211> LENGTH: 617
<212> TYPE: PRT
<213> ORGANISM: Artificial Sequence
<220> FEATURE:
<223> OTHER INFORMATION: synthetic polypeptide

<400> SEQUENCE: 115

Met Ala Ser Lys Gly Glu Arg Leu Phe Arg Gly Lys Val Pro Ile Leu
1               5                   10                  15
Val Glu Leu Lys Gly Asp Val Asn Gly His Lys Phe Ser Val Arg Gly
                20                  25                  30
Lys Gly Lys Gly Asp Ala Thr Arg Gly Lys Leu Thr Leu Lys Phe Ile
            35                  40                  45
Cys Thr Thr Gly Lys Leu Pro Val Pro Trp Pro Thr Leu Val Thr Thr
        50                  55                  60
Leu Thr Tyr Gly Val Gln Cys Phe Ser Arg Tyr Pro Lys His Met Lys
65                  70                  75                  80
Arg His Asp Phe Phe Lys Ser Ala Met Pro Lys Gly Tyr Val Gln Glu
                85                  90                  95
Arg Thr Ile Ser Phe Lys Lys Asp Gly Lys Tyr Lys Thr Arg Ala Glu
            100                 105                 110
Val Lys Phe Glu Gly Arg Thr Leu Val Asn Arg Ile Lys Leu Lys Gly
        115                 120                 125
Arg Asp Phe Lys Glu Lys Gly Asn Ile Leu Gly His Lys Leu Arg Tyr
    130                 135                 140
Asn Phe Asn Ser His Lys Val Tyr Ile Thr Ala Asp Lys Arg Lys Asn
145                 150                 155                 160
Gly Ile Lys Ala Lys Phe Lys Ile Arg His Asn Val Lys Asp Gly Ser
                165                 170                 175
Val Gln Leu Ala Asp His Tyr Gln Gln Asn Thr Pro Ile Gly Arg Gly
            180                 185                 190
Pro Val Leu Leu Pro Arg Asn His Tyr Leu Ser Thr Arg Ser Lys Leu
        195                 200                 205
Ser Lys Asp Pro Lys Glu Lys Arg Asp His Met Val Leu Leu Glu Phe
    210                 215                 220
```

Val Thr Ala Ala Gly Ile Lys His Gly Arg Asp Glu Arg Tyr Lys Gly
225                 230                 235                 240

Gly Ser Gly Gly Ser Gly Ser Gly Gly Ser Ala Leu Ala Leu Gly
            245                 250                 255

Gly Ser Gly Gly Ser Gly Gly Ser Gly Gly Ser Met Ala Ser Asn Leu
            260                 265                 270

Leu Thr Val His Gln Asn Leu Pro Ala Leu Pro Val Asp Ala Thr Ser
        275                 280                 285

Asp Glu Val Arg Lys Asn Leu Met Asp Met Phe Arg Asp Arg Gln Ala
        290                 295                 300

Phe Ser Glu His Thr Trp Lys Met Leu Leu Ser Val Cys Arg Ser Trp
305                 310                 315                 320

Ala Ala Trp Cys Lys Leu Asn Asn Arg Lys Trp Phe Pro Ala Glu Pro
                325                 330                 335

Glu Asp Val Arg Asp Tyr Leu Leu Tyr Leu Gln Ala Arg Gly Leu Ala
            340                 345                 350

Val Lys Thr Ile Gln Gln His Leu Gly Gln Leu Asn Met Leu His Arg
        355                 360                 365

Arg Ser Gly Leu Pro Arg Pro Ser Asp Ser Asn Ala Val Ser Leu Val
370                 375                 380

Met Arg Arg Ile Arg Lys Glu Asn Val Asp Ala Gly Glu Arg Ala Lys
385                 390                 395                 400

Gln Ala Leu Ala Phe Glu Arg Thr Asp Phe Asp Gln Val Arg Ser Leu
                405                 410                 415

Met Glu Asn Ser Asp Arg Cys Gln Asp Ile Arg Asn Leu Ala Phe Leu
            420                 425                 430

Gly Ile Ala Tyr Asn Thr Leu Leu Arg Ile Ala Glu Ile Ala Arg Ile
        435                 440                 445

Arg Val Lys Asp Ile Ser Arg Thr Asp Gly Gly Arg Met Leu Ile His
        450                 455                 460

Ile Gly Arg Thr Lys Thr Leu Val Ser Thr Ala Gly Val Glu Lys Ala
465                 470                 475                 480

Leu Ser Leu Gly Val Thr Lys Leu Val Glu Arg Trp Ile Ser Val Ser
            485                 490                 495

Gly Val Ala Asp Asp Pro Asn Asn Tyr Leu Phe Cys Arg Val Arg Lys
            500                 505                 510

Asn Gly Val Ala Ala Pro Ser Ala Thr Ser Gln Leu Ser Thr Arg Ala
        515                 520                 525

Leu Glu Gly Ile Phe Glu Ala Thr His Arg Leu Ile Tyr Gly Ala Lys
        530                 535                 540

Asp Asp Ser Gly Gln Arg Tyr Leu Ala Trp Ser Gly His Ser Ala Arg
545                 550                 555                 560

Val Gly Ala Ala Arg Asp Met Ala Arg Ala Gly Val Ser Ile Pro Glu
            565                 570                 575

Ile Met Gln Ala Gly Gly Trp Thr Asn Val Asn Ile Val Met Asn Tyr
            580                 585                 590

Ile Arg Asn Leu Asp Ser Glu Thr Gly Ala Met Val Arg Leu Leu Glu
        595                 600                 605

Asp Gly Asp His His His His His His
610                 615

<210> SEQ ID NO 116
<211> LENGTH: 276

```
<212> TYPE: PRT
<213> ORGANISM: Artificial Sequence
<220> FEATURE:
<223> OTHER INFORMATION: synthetic polypeptide

<400> SEQUENCE: 116

Met Gly Arg Lys Lys Arg Arg Gln Arg Arg Gly His Met Ala Ser
1               5                   10                  15

Met Thr Gly Gly Gln Gln Met Gly Arg Asp Pro Ala Ser Lys Gly Glu
            20                  25                  30

Glu Leu Phe Thr Gly Val Val Pro Ile Leu Val Glu Leu Asp Gly Asp
            35                  40                  45

Val Asn Gly His Lys Phe Ser Val Arg Gly Glu Gly Glu Gly Asp Ala
        50                  55                  60

Thr Asn Gly Lys Leu Thr Leu Lys Phe Ile Cys Thr Thr Gly Lys Leu
65                  70                  75                  80

Pro Val Pro Trp Pro Thr Leu Val Thr Thr Leu Thr Tyr Gly Val Gln
                85                  90                  95

Cys Phe Ser Arg Tyr Pro Asp His Met Lys Gln His Asp Phe Phe Lys
                100                 105                 110

Ser Ala Met Pro Glu Gly Tyr Val Gln Glu Arg Thr Ile Ser Phe Lys
            115                 120                 125

Asp Asp Gly Thr Tyr Lys Thr Arg Ala Glu Val Lys Phe Glu Gly Asp
            130                 135                 140

Thr Leu Val Asn Arg Ile Glu Leu Lys Gly Ile Asp Phe Lys Glu Asp
145                 150                 155                 160

Gly Asn Ile Leu Gly His Lys Leu Glu Tyr Asn Phe Asn Ser His Asn
                165                 170                 175

Val Tyr Ile Thr Ala Asp Lys Gln Lys Asn Gly Ile Lys Ala Asn Phe
            180                 185                 190

Lys Ile Arg His Asn Val Glu Asp Gly Ser Val Gln Leu Ala Asp His
            195                 200                 205

Tyr Gln Gln Asn Thr Pro Ile Gly Asp Gly Pro Val Leu Leu Pro Asp
            210                 215                 220

Asn His Tyr Leu Ser Thr Gln Ser Ala Leu Ser Lys Asp Pro Asn Glu
225                 230                 235                 240

Lys Arg Asp His Met Val Leu Leu Glu Phe Val Thr Ala Ala Gly Ile
                245                 250                 255

Thr His Gly Met Asp Glu Leu Tyr Lys Ala Ala Ala Leu Glu His His
                260                 265                 270

His His His His
        275

<210> SEQ ID NO 117
<211> LENGTH: 278
<212> TYPE: PRT
<213> ORGANISM: Artificial Sequence
<220> FEATURE:
<223> OTHER INFORMATION: synthetic polypeptide

<400> SEQUENCE: 117

Met Gly Arg Lys Lys Arg Arg Gln Arg Arg Gly His Met Ala Ser
1               5                   10                  15

Met Thr Gly Gly Gln Gln Met Gly Arg Asp Pro Asn Ser Val Ser Lys
            20                  25                  30

Gly Glu Glu Asp Asn Met Ala Ile Ile Lys Glu Phe Met Arg Phe Lys
            35                  40                  45
```

```
Val His Met Glu Gly Ser Val Asn Gly His Glu Phe Glu Ile Glu Gly
    50                  55                  60

Glu Gly Glu Gly Arg Pro Tyr Glu Gly Thr Gln Thr Ala Lys Leu Lys
65                  70                  75                  80

Val Thr Lys Gly Gly Pro Leu Pro Phe Ala Trp Asp Ile Leu Ser Pro
                85                  90                  95

Gln Phe Met Tyr Gly Ser Lys Ala Tyr Val Lys His Pro Ala Asp Ile
            100                 105                 110

Pro Asp Tyr Leu Lys Leu Ser Phe Pro Glu Gly Phe Lys Trp Glu Arg
        115                 120                 125

Val Met Asn Phe Glu Asp Gly Gly Val Val Thr Val Thr Gln Asp Ser
    130                 135                 140

Ser Leu Gln Asp Gly Glu Phe Ile Tyr Lys Val Lys Leu Arg Gly Thr
145                 150                 155                 160

Asn Phe Pro Ser Asp Gly Pro Val Met Gln Lys Lys Thr Met Gly Trp
                165                 170                 175

Glu Ala Ser Ser Glu Arg Met Tyr Pro Glu Asp Gly Ala Leu Lys Gly
            180                 185                 190

Glu Ile Lys Gln Arg Leu Lys Leu Lys Asp Gly Gly His Tyr Asp Ala
        195                 200                 205

Glu Val Lys Thr Thr Tyr Lys Ala Lys Lys Pro Val Gln Leu Pro Gly
    210                 215                 220

Ala Tyr Asn Val Asn Ile Lys Leu Asp Ile Thr Ser His Asn Glu Asp
225                 230                 235                 240

Tyr Thr Ile Val Glu Gln Tyr Glu Arg Ala Glu Gly Arg His Ser Thr
                245                 250                 255

Gly Gly Met Asp Glu Leu Tyr Lys Ala Arg Gly Ala Ala Ala Leu Glu
            260                 265                 270

His His His His His His
        275

<210> SEQ ID NO 118
<211> LENGTH: 264
<212> TYPE: PRT
<213> ORGANISM: Artificial Sequence
<220> FEATURE:
<223> OTHER INFORMATION: synthetic polypeptide

<400> SEQUENCE: 118

Met Gly His His His His His His Gly Gly Ala Ser Lys Gly Glu Glu
1               5                   10                  15

Asp Asn Met Ala Ile Ile Lys Glu Phe Met Arg Phe Lys Val His Met
            20                  25                  30

Glu Gly Ser Val Asn Gly His Glu Phe Glu Ile Glu Gly Glu Gly Glu
        35                  40                  45

Gly Arg Pro Tyr Glu Gly Thr Gln Thr Ala Lys Leu Lys Val Thr Lys
    50                  55                  60

Gly Gly Pro Leu Pro Phe Ala Trp Asp Ile Leu Ser Pro Gln Phe Met
65                  70                  75                  80

Tyr Gly Ser Lys Ala Tyr Val Lys His Pro Ala Asp Ile Pro Asp Tyr
                85                  90                  95

Leu Lys Leu Ser Phe Pro Glu Gly Phe Lys Trp Glu Arg Val Met Asn
            100                 105                 110

Phe Glu Asp Gly Gly Val Val Thr Val Thr Gln Asp Ser Ser Leu Gln
        115                 120                 125
```

```
Asp Gly Glu Phe Ile Tyr Lys Val Lys Leu Arg Gly Thr Asn Phe Pro
            130                 135                 140

Ser Asp Gly Pro Val Met Gln Lys Lys Thr Met Gly Trp Glu Ala Ser
145                 150                 155                 160

Ser Glu Arg Met Tyr Pro Glu Asp Gly Ala Leu Lys Gly Glu Ile Lys
                165                 170                 175

Gln Arg Leu Lys Leu Lys Asp Gly Gly His Tyr Asp Ala Glu Val Lys
            180                 185                 190

Thr Thr Tyr Lys Ala Lys Lys Pro Val Gln Leu Pro Gly Ala Tyr Asn
        195                 200                 205

Val Asn Ile Lys Leu Asp Ile Thr Ser His Asn Glu Asp Tyr Thr Ile
        210                 215                 220

Val Glu Gln Tyr Glu Arg Ala Glu Gly Arg His Ser Thr Gly Gly Met
225                 230                 235                 240

Asp Glu Leu Tyr Lys Ala Arg Gly Gly Ser Gly Gly Gly Ser Arg
                245                 250                 255

Arg Arg Arg Arg Arg Arg Arg
            260

<210> SEQ ID NO 119
<211> LENGTH: 383
<212> TYPE: PRT
<213> ORGANISM: Artificial Sequence
<220> FEATURE:
<223> OTHER INFORMATION: synthetic polypeptide

<400> SEQUENCE: 119

Met Gly Arg Lys Lys Arg Arg Gln Arg Arg Gly His Met Ala Ser
1               5                   10                  15

Met Thr Gly Gly Gln Gln Met Gly Arg Asp Pro Asn Ser Met Ser Asn
            20                  25                  30

Leu Leu Thr Val His Gln Asn Leu Pro Ala Leu Pro Val Asp Ala Thr
        35                  40                  45

Ser Asp Glu Val Arg Lys Asn Leu Met Asp Met Phe Arg Asp Arg Gln
50                  55                  60

Ala Phe Ser Glu His Thr Trp Lys Met Leu Leu Ser Val Cys Arg Ser
65                  70                  75                  80

Trp Ala Ala Trp Cys Lys Leu Asn Asn Arg Lys Trp Phe Pro Ala Glu
                85                  90                  95

Pro Glu Asp Val Arg Asp Tyr Leu Leu Tyr Leu Gln Ala Arg Gly Leu
            100                 105                 110

Ala Val Lys Thr Ile Gln Gln His Leu Gly Gln Leu Asn Met Leu His
        115                 120                 125

Arg Arg Ser Gly Leu Pro Arg Pro Ser Asp Ser Asn Ala Val Ser Leu
    130                 135                 140

Val Met Arg Arg Ile Arg Lys Glu Asn Val Asp Ala Gly Glu Arg Ala
145                 150                 155                 160

Lys Gln Ala Leu Ala Phe Glu Arg Thr Asp Phe Asp Gln Val Arg Ser
                165                 170                 175

Leu Met Glu Asn Ser Asp Arg Cys Gln Asp Ile Arg Asn Leu Ala Phe
            180                 185                 190

Leu Gly Ile Ala Tyr Asn Thr Leu Leu Arg Ile Ala Glu Ile Ala Arg
        195                 200                 205

Ile Arg Val Lys Asp Ile Ser Arg Thr Asp Gly Gly Arg Met Leu Ile
    210                 215                 220
```

His Ile Gly Arg Thr Lys Thr Leu Val Ser Thr Ala Gly Val Glu Lys
225                 230                 235                 240

Ala Leu Ser Leu Gly Val Thr Lys Leu Val Glu Arg Trp Ile Ser Val
            245                 250                 255

Ser Gly Val Ala Asp Pro Asn Asn Tyr Leu Phe Cys Arg Val Arg
        260                 265                 270

Lys Asn Gly Val Ala Ala Pro Ser Ala Thr Ser Gln Leu Ser Thr Arg
            275                 280                 285

Ala Leu Glu Gly Ile Phe Glu Ala Thr His Arg Leu Ile Tyr Gly Ala
        290                 295                 300

Lys Asp Asp Ser Gly Gln Arg Tyr Leu Ala Trp Ser Gly His Ser Ala
305                 310                 315                 320

Arg Val Gly Ala Ala Arg Asp Met Ala Arg Ala Gly Val Ser Ile Pro
                325                 330                 335

Glu Ile Met Gln Ala Gly Gly Trp Thr Asn Val Asn Ile Val Met Asn
            340                 345                 350

Tyr Ile Arg Asn Leu Asp Ser Glu Thr Gly Ala Met Val Arg Leu Leu
        355                 360                 365

Glu Asp Gly Asp Ala Ala Ala Leu Glu His His His His His His
    370                 375                 380

<210> SEQ ID NO 120
<211> LENGTH: 373
<212> TYPE: PRT
<213> ORGANISM: Artificial Sequence
<220> FEATURE:
<223> OTHER INFORMATION: synthetic polypeptide

<400> SEQUENCE: 120

Met Gly His His His His His Gly Gly Ala Ser Met Ser Asn Leu
1               5                   10                  15

Leu Thr Val His Gln Asn Leu Pro Ala Leu Pro Val Asp Ala Thr Ser
            20                  25                  30

Asp Glu Val Arg Lys Asn Leu Met Asp Met Phe Arg Asp Arg Gln Ala
        35                  40                  45

Phe Ser Glu His Thr Trp Lys Met Leu Leu Ser Val Cys Arg Ser Trp
    50                  55                  60

Ala Ala Trp Cys Lys Leu Asn Asn Arg Lys Trp Phe Pro Ala Glu Pro
65                  70                  75                  80

Glu Asp Val Arg Asp Tyr Leu Leu Tyr Leu Gln Ala Arg Gly Leu Ala
                85                  90                  95

Val Lys Thr Ile Gln Gln His Leu Gly Gln Leu Asn Met Leu His Arg
            100                 105                 110

Arg Ser Gly Leu Pro Arg Pro Ser Asp Ser Asn Ala Val Ser Leu Val
        115                 120                 125

Met Arg Arg Ile Arg Lys Glu Asn Val Asp Ala Gly Glu Arg Ala Lys
130                 135                 140

Gln Ala Leu Ala Phe Glu Arg Thr Asp Phe Asp Gln Val Arg Ser Leu
145                 150                 155                 160

Met Glu Asn Ser Asp Arg Cys Gln Asp Ile Arg Asn Leu Ala Phe Leu
                165                 170                 175

Gly Ile Ala Tyr Asn Thr Leu Leu Arg Ile Ala Glu Ile Ala Arg Ile
            180                 185                 190

Arg Val Lys Asp Ile Ser Arg Thr Asp Gly Gly Arg Met Leu Ile His
        195                 200                 205

```
Ile Gly Arg Thr Lys Thr Leu Val Ser Thr Ala Gly Val Glu Lys Ala
210                 215                 220

Leu Ser Leu Gly Val Thr Lys Leu Val Glu Arg Trp Ile Ser Val Ser
225                 230                 235                 240

Gly Val Ala Asp Asp Pro Asn Asn Tyr Leu Phe Cys Arg Val Arg Lys
            245                 250                 255

Asn Gly Val Ala Ala Pro Ser Ala Thr Ser Gln Leu Ser Thr Arg Ala
            260                 265                 270

Leu Glu Gly Ile Phe Glu Ala Thr His Arg Leu Ile Tyr Gly Ala Lys
        275                 280                 285

Asp Asp Ser Gly Gln Arg Tyr Leu Ala Trp Ser His Ser Ala Arg
290                 295                 300

Val Gly Ala Ala Arg Asp Met Ala Arg Ala Gly Val Ser Ile Pro Glu
305                 310                 315                 320

Ile Met Gln Ala Gly Gly Trp Thr Asn Val Asn Ile Val Met Asn Tyr
                325                 330                 335

Ile Arg Asn Leu Asp Ser Glu Thr Gly Ala Met Val Arg Leu Leu Glu
                340                 345                 350

Asp Gly Asp Arg Gly Gly Ser Gly Gly Ser Arg Arg Arg
                355                 360                 365

Arg Arg Arg Arg Arg
        370
```

<210> SEQ ID NO 121
<211> LENGTH: 340
<212> TYPE: PRT
<213> ORGANISM: Artificial Sequence
<220> FEATURE:
<223> OTHER INFORMATION: synthetic polypeptide

<400> SEQUENCE: 121

```
Met Val Lys Lys Gly Arg Arg Ser Arg Arg Cys Gly Gln Cys Pro Gly
1               5                   10                  15

Cys Gln Val Pro Glu Asp Cys Gly Val Cys Thr Asn Cys Leu Asp Lys
                20                  25                  30

Pro Lys Phe Gly Gly Arg Asn Ile Lys Lys Gln Cys Cys Lys Met Arg
            35                  40                  45

Lys Cys Gln Asn Leu Gln Trp Met Pro Ser Lys Ala Tyr Leu Gln Lys
50                  55                  60

Gln Ala Lys Ala Val Lys Gly Gly Ser Gly Gly Ser Gly Gly Ser Gly
65                  70                  75                  80

Gly Ser Gly Gly Ser Gly Gly Ser Gly Gly Ser Gly Gly Ser Gly Gly
                85                  90                  95

Ser Val Ser Lys Gly Glu Glu Asp Asn Met Ala Ile Ile Lys Glu Phe
                100                 105                 110

Met Arg Phe Lys Val His Met Glu Gly Ser Val Asn Gly His Glu Phe
            115                 120                 125

Glu Ile Glu Gly Glu Gly Glu Gly Arg Pro Tyr Glu Gly Thr Gln Thr
        130                 135                 140

Ala Lys Leu Lys Val Thr Lys Gly Gly Pro Leu Pro Phe Ala Trp Asp
145                 150                 155                 160

Ile Leu Ser Pro Gln Phe Met Tyr Gly Ser Lys Ala Tyr Val Lys His
                165                 170                 175

Pro Ala Asp Ile Pro Asp Tyr Leu Lys Leu Ser Phe Pro Glu Gly Phe
            180                 185                 190
```

```
Lys Trp Glu Arg Val Met Asn Phe Glu Asp Gly Gly Val Thr Val
            195                 200                 205

Thr Gln Asp Ser Ser Leu Gln Asp Gly Glu Phe Ile Tyr Lys Val Lys
210                 215                 220

Leu Arg Gly Thr Asn Phe Pro Ser Asp Gly Pro Val Met Gln Lys Lys
225                 230                 235                 240

Thr Met Gly Trp Glu Ala Ser Ser Glu Arg Met Tyr Pro Glu Asp Gly
                245                 250                 255

Ala Leu Lys Gly Glu Ile Lys Gln Arg Leu Lys Leu Lys Asp Gly Gly
                260                 265                 270

His Tyr Asp Ala Glu Val Lys Thr Thr Tyr Lys Ala Lys Lys Pro Val
            275                 280                 285

Gln Leu Pro Gly Ala Tyr Asn Val Asn Ile Lys Leu Asp Ile Thr Ser
290                 295                 300

His Asn Glu Asp Tyr Thr Ile Val Glu Gln Tyr Glu Arg Ala Glu Gly
305                 310                 315                 320

Arg His Ser Thr Gly Gly Met Asp Glu Leu Tyr Lys Leu Glu His His
                325                 330                 335

His His His His
            340

<210> SEQ ID NO 122
<211> LENGTH: 447
<212> TYPE: PRT
<213> ORGANISM: Artificial Sequence
<220> FEATURE:
<223> OTHER INFORMATION: synthetic polypeptide

<400> SEQUENCE: 122

Met Val Lys Lys Gly Arg Arg Ser Arg Arg Cys Gly Gln Cys Pro Gly
1               5                   10                  15

Cys Gln Val Pro Glu Asp Cys Gly Val Cys Thr Asn Cys Leu Asp Lys
                20                  25                  30

Pro Lys Phe Gly Gly Arg Asn Ile Lys Lys Gln Cys Cys Lys Met Arg
            35                  40                  45

Lys Cys Gln Asn Leu Gln Trp Met Pro Ser Lys Ala Tyr Leu Gln Lys
50                  55                  60

Gln Ala Lys Ala Val Lys Gly Ser Gly Ser Gly Gly Ser Gly Gly Gly
65                  70                  75                  80

Gly Ser Gly Gly Ser Gly Ser Gly Gly Ser Gly Gly Ser Gly Gly Gly
                85                  90                  95

Ser Met Ala Ser Asn Leu Leu Thr Val His Gln Asn Leu Pro Ala Leu
                100                 105                 110

Pro Val Asp Ala Thr Ser Asp Glu Val Arg Lys Asn Leu Met Asp Met
            115                 120                 125

Phe Arg Asp Arg Gln Ala Phe Ser Glu His Thr Trp Lys Met Leu Leu
130                 135                 140

Ser Val Cys Arg Ser Trp Ala Ala Trp Cys Lys Leu Asn Asn Arg Lys
145                 150                 155                 160

Trp Phe Pro Ala Glu Pro Glu Asp Val Arg Asp Tyr Leu Leu Tyr Leu
                165                 170                 175

Gln Ala Arg Gly Leu Ala Val Lys Thr Ile Gln Gln His Leu Gly Gln
            180                 185                 190

Leu Asn Met Leu His Arg Arg Ser Gly Leu Pro Arg Pro Ser Asp Ser
            195                 200                 205
```

```
Asn Ala Val Ser Leu Val Met Arg Arg Ile Arg Lys Glu Asn Val Asp
            210                 215                 220

Ala Gly Glu Arg Ala Lys Gln Ala Leu Ala Phe Arg Thr Asp Phe
225                 230                 235                 240

Asp Gln Val Arg Ser Leu Met Glu Asn Ser Asp Arg Cys Gln Asp Ile
                245                 250                 255

Arg Asn Leu Ala Phe Leu Gly Ile Ala Tyr Asn Thr Leu Leu Arg Ile
            260                 265                 270

Ala Glu Ile Ala Arg Ile Arg Val Lys Asp Ile Ser Arg Thr Asp Gly
        275                 280                 285

Gly Arg Met Leu Ile His Ile Gly Arg Thr Lys Thr Leu Val Ser Thr
        290                 295                 300

Ala Gly Val Glu Lys Ala Leu Ser Leu Gly Val Thr Lys Leu Val Glu
305                 310                 315                 320

Arg Trp Ile Ser Val Ser Gly Val Ala Asp Asp Pro Asn Asn Tyr Leu
                325                 330                 335

Phe Cys Arg Val Arg Lys Asn Gly Val Ala Ala Pro Ser Ala Thr Ser
            340                 345                 350

Gln Leu Ser Thr Arg Ala Leu Glu Gly Ile Phe Glu Ala Thr His Arg
        355                 360                 365

Leu Ile Tyr Gly Ala Lys Asp Asp Ser Gly Gln Arg Tyr Leu Ala Trp
    370                 375                 380

Ser Gly His Ser Ala Arg Val Gly Ala Ala Arg Asp Met Ala Arg Ala
385                 390                 395                 400

Gly Val Ser Ile Pro Glu Ile Met Gln Ala Gly Trp Thr Asn Val
                405                 410                 415

Asn Ile Val Met Asn Tyr Ile Arg Asn Leu Asp Ser Glu Thr Gly Ala
            420                 425                 430

Met Val Arg Leu Leu Glu Asp Gly Asp His His His His His His
        435                 440                 445

<210> SEQ ID NO 123
<211> LENGTH: 333
<212> TYPE: PRT
<213> ORGANISM: Artificial Sequence
<220> FEATURE:
<223> OTHER INFORMATION: synthetic polypeptide

<400> SEQUENCE: 123

Met Lys Ala Glu Arg Lys Arg Met Arg Asn Arg Ile Ala Ala Ser Lys
1               5                   10                  15

Ser Arg Lys Arg Lys Leu Glu Arg Ile Ala Arg Leu Glu Glu Lys Val
            20                  25                  30

Lys Thr Leu Lys Ala Gln Asn Ser Glu Leu Ala Ser Thr Ala Asn Met
        35                  40                  45

Leu Arg Glu Gln Val Ala Gln Leu Lys Gln Lys Val Met Asn His Gly
    50                  55                  60

Gly Ser Gly Gly Ser Gly Gly Ser Gly Gly Ser Gly Gly Ser Gly Gly
65                  70                  75                  80

Ser Gly Gly Ser Gly Gly Ser Gly Gly Ser Val Ser Lys Gly Glu Glu
                85                  90                  95

Asp Asn Met Ala Ile Ile Lys Glu Phe Met Arg Phe Lys Val His Met
            100                 105                 110

Glu Gly Ser Val Asn Gly His Glu Phe Glu Ile Glu Gly Glu Gly Glu
        115                 120                 125
```

Gly Arg Pro Tyr Glu Gly Thr Gln Thr Ala Lys Leu Lys Val Thr Lys
            130                 135                 140

Gly Gly Pro Leu Pro Phe Ala Trp Asp Ile Leu Ser Pro Gln Phe Met
145                 150                 155                 160

Tyr Gly Ser Lys Ala Tyr Val Lys His Pro Ala Asp Ile Pro Asp Tyr
                165                 170                 175

Leu Lys Leu Ser Phe Pro Glu Gly Phe Lys Trp Glu Arg Val Met Asn
            180                 185                 190

Phe Glu Asp Gly Gly Val Val Thr Val Thr Gln Asp Ser Ser Leu Gln
        195                 200                 205

Asp Gly Glu Phe Ile Tyr Lys Val Lys Leu Arg Gly Thr Asn Phe Pro
    210                 215                 220

Ser Asp Gly Pro Val Met Gln Lys Lys Thr Met Gly Trp Glu Ala Ser
225                 230                 235                 240

Ser Glu Arg Met Tyr Pro Glu Asp Gly Ala Leu Lys Gly Glu Ile Lys
                245                 250                 255

Gln Arg Leu Lys Leu Lys Asp Gly Gly His Tyr Asp Ala Glu Val Lys
            260                 265                 270

Thr Thr Tyr Lys Ala Lys Lys Pro Val Gln Leu Pro Gly Ala Tyr Asn
        275                 280                 285

Val Asn Ile Lys Leu Asp Ile Thr Ser His Asn Glu Asp Tyr Thr Ile
    290                 295                 300

Val Glu Gln Tyr Glu Arg Ala Glu Gly Arg His Ser Thr Gly Gly Met
305                 310                 315                 320

Asp Glu Leu Tyr Lys Leu Glu His His His His His
                325                 330

<210> SEQ ID NO 124
<211> LENGTH: 440
<212> TYPE: PRT
<213> ORGANISM: Artificial Sequence
<220> FEATURE:
<223> OTHER INFORMATION: synthetic polypeptide

<400> SEQUENCE: 124

Met Lys Ala Glu Arg Lys Arg Met Arg Asn Arg Ile Ala Ala Ser Lys
1               5                   10                  15

Ser Arg Lys Arg Lys Leu Glu Arg Ile Ala Arg Leu Glu Glu Lys Val
            20                  25                  30

Lys Thr Leu Lys Ala Gln Asn Ser Glu Leu Ala Ser Thr Ala Asn Met
        35                  40                  45

Leu Arg Glu Gln Val Ala Gln Leu Lys Gln Lys Val Met Asn His Gly
    50                  55                  60

Gly Ser Gly Gly Ser Gly Ser Gly Gly Ser Gly Ser Gly Gly Ser Gly
65                  70                  75                  80

Ser Gly Gly Ser Gly Gly Ser Gly Gly Ser Met Ala Ser Asn Leu Leu
                85                  90                  95

Thr Val His Gln Asn Leu Pro Ala Leu Pro Val Asp Ala Thr Ser Asp
            100                 105                 110

Glu Val Arg Lys Asn Leu Met Asp Met Phe Arg Asp Arg Gln Ala Phe
        115                 120                 125

Ser Glu His Thr Trp Lys Met Leu Leu Ser Val Cys Arg Ser Trp Ala
    130                 135                 140

Ala Trp Cys Lys Leu Asn Asn Arg Lys Trp Phe Pro Ala Glu Pro Glu
145                 150                 155                 160

```
Asp Val Arg Asp Tyr Leu Leu Tyr Leu Gln Ala Arg Gly Leu Ala Val
            165                 170                 175

Lys Thr Ile Gln Gln His Leu Gly Gln Leu Asn Met Leu His Arg Arg
            180                 185                 190

Ser Gly Leu Pro Arg Pro Ser Asp Ser Asn Ala Val Ser Leu Val Met
            195                 200                 205

Arg Arg Ile Arg Lys Glu Asn Val Asp Ala Gly Glu Arg Ala Lys Gln
            210                 215                 220

Ala Leu Ala Phe Glu Arg Thr Asp Phe Asp Gln Val Arg Ser Leu Met
225                 230                 235                 240

Glu Asn Ser Asp Arg Cys Gln Asp Ile Arg Asn Leu Ala Phe Leu Gly
            245                 250                 255

Ile Ala Tyr Asn Thr Leu Leu Arg Ile Ala Glu Ile Ala Arg Ile Arg
            260                 265                 270

Val Lys Asp Ile Ser Arg Thr Asp Gly Gly Arg Met Leu Ile His Ile
            275                 280                 285

Gly Arg Thr Lys Thr Leu Val Ser Thr Ala Gly Val Glu Lys Ala Leu
            290                 295                 300

Ser Leu Gly Val Thr Lys Leu Val Glu Arg Trp Ile Ser Val Ser Gly
305                 310                 315                 320

Val Ala Asp Asp Pro Asn Asn Tyr Leu Phe Cys Arg Val Arg Lys Asn
            325                 330                 335

Gly Val Ala Ala Pro Ser Ala Thr Ser Gln Leu Ser Thr Arg Ala Leu
            340                 345                 350

Glu Gly Ile Phe Glu Ala Thr His Arg Leu Ile Tyr Gly Ala Lys Asp
            355                 360                 365

Asp Ser Gly Gln Arg Tyr Leu Ala Trp Ser Gly His Ser Ala Arg Val
            370                 375                 380

Gly Ala Ala Arg Asp Met Ala Arg Ala Gly Val Ser Ile Pro Glu Ile
385                 390                 395                 400

Met Gln Ala Gly Gly Trp Thr Asn Val Asn Ile Val Met Asn Tyr Ile
            405                 410                 415

Arg Asn Leu Asp Ser Glu Thr Gly Ala Met Val Arg Leu Leu Glu Asp
            420                 425                 430

Gly Asp His His His His His His
            435                 440

<210> SEQ ID NO 125
<211> LENGTH: 316
<212> TYPE: PRT
<213> ORGANISM: Artificial Sequence
<220> FEATURE:
<223> OTHER INFORMATION: synthetic polypeptide

<400> SEQUENCE: 125

Met Gly Ile Ile Asn Thr Leu Gln Lys Tyr Tyr Cys Arg Val Arg Gly
1               5                   10                  15

Gly Arg Cys Ala Val Leu Ser Cys Leu Pro Lys Glu Glu Gln Ile Gly
            20                  25                  30

Lys Cys Ser Thr Arg Gly Arg Lys Cys Cys Arg Arg Lys Lys Gly Gly
            35                  40                  45

Ser Gly Gly Ser Gly Gly Ser Gly Gly Ser Gly Gly Ser Gly Gly Ser
        50                  55                  60

Gly Gly Ser Gly Gly Ser Gly Ser Val Ser Lys Gly Glu Glu Asp
65                  70                  75                  80
```

```
Asn Met Ala Ile Ile Lys Glu Phe Met Arg Phe Lys Val His Met Glu
                85                  90                  95

Gly Ser Val Asn Gly His Glu Phe Glu Ile Glu Gly Glu Gly Glu Gly
            100                 105                 110

Arg Pro Tyr Glu Gly Thr Gln Thr Ala Lys Leu Lys Val Thr Lys Gly
        115                 120                 125

Gly Pro Leu Pro Phe Ala Trp Asp Ile Leu Ser Pro Gln Phe Met Tyr
    130                 135                 140

Gly Ser Lys Ala Tyr Val Lys His Pro Ala Asp Ile Pro Asp Tyr Leu
145                 150                 155                 160

Lys Leu Ser Phe Pro Glu Gly Phe Lys Trp Glu Arg Val Met Asn Phe
                165                 170                 175

Glu Asp Gly Gly Val Val Thr Val Thr Gln Asp Ser Ser Leu Gln Asp
            180                 185                 190

Gly Glu Phe Ile Tyr Lys Val Lys Leu Arg Gly Thr Asn Phe Pro Ser
        195                 200                 205

Asp Gly Pro Val Met Gln Lys Lys Thr Met Gly Trp Glu Ala Ser Ser
    210                 215                 220

Glu Arg Met Tyr Pro Glu Asp Gly Ala Leu Lys Gly Glu Ile Lys Gln
225                 230                 235                 240

Arg Leu Lys Leu Lys Asp Gly Gly His Tyr Asp Ala Glu Val Lys Thr
                245                 250                 255

Thr Tyr Lys Ala Lys Lys Pro Val Gln Leu Pro Gly Ala Tyr Asn Val
            260                 265                 270

Asn Ile Lys Leu Asp Ile Thr Ser His Asn Glu Asp Tyr Thr Ile Val
        275                 280                 285

Glu Gln Tyr Glu Arg Ala Glu Gly Arg His Ser Thr Gly Gly Met Asp
    290                 295                 300

Glu Leu Tyr Lys Leu Glu His His His His His
305                 310                 315

<210> SEQ ID NO 126
<211> LENGTH: 423
<212> TYPE: PRT
<213> ORGANISM: Artificial Sequence
<220> FEATURE:
<223> OTHER INFORMATION: synthetic polypeptide

<400> SEQUENCE: 126

Met Gly Ile Ile Asn Thr Leu Gln Lys Tyr Tyr Cys Arg Val Arg Gly
1               5                   10                  15

Gly Arg Cys Ala Val Leu Ser Cys Leu Pro Lys Glu Glu Gln Ile Gly
            20                  25                  30

Lys Cys Ser Thr Arg Gly Arg Lys Cys Cys Arg Arg Lys Lys Gly Gly
        35                  40                  45

Ser Gly Gly Ser Gly Gly Ser Gly Gly Ser Gly Gly Ser Gly Gly Ser
    50                  55                  60

Gly Gly Ser Gly Gly Ser Gly Gly Ser Met Ala Ser Asn Leu Leu Thr
65                  70                  75                  80

Val His Gln Asn Leu Pro Ala Leu Pro Val Asp Ala Thr Ser Asp Glu
                85                  90                  95

Val Arg Lys Asn Leu Met Asp Met Phe Arg Asp Arg Gln Ala Phe Ser
            100                 105                 110

Glu His Thr Trp Lys Met Leu Leu Ser Val Cys Arg Ser Trp Ala Ala
        115                 120                 125
```

-continued

Trp Cys Lys Leu Asn Asn Arg Lys Trp Phe Pro Ala Glu Pro Glu Asp
            130                 135                 140

Val Arg Asp Tyr Leu Leu Tyr Leu Gln Ala Arg Gly Leu Ala Val Lys
145                 150                 155                 160

Thr Ile Gln Gln His Leu Gly Gln Leu Asn Met Leu His Arg Arg Ser
                165                 170                 175

Gly Leu Pro Arg Pro Ser Asp Ser Asn Ala Val Ser Leu Val Met Arg
            180                 185                 190

Arg Ile Arg Lys Glu Asn Val Asp Ala Gly Glu Arg Ala Lys Gln Ala
        195                 200                 205

Leu Ala Phe Glu Arg Thr Asp Phe Asp Gln Val Arg Ser Leu Met Glu
    210                 215                 220

Asn Ser Asp Arg Cys Gln Asp Ile Arg Asn Leu Ala Phe Leu Gly Ile
225                 230                 235                 240

Ala Tyr Asn Thr Leu Leu Arg Ile Ala Glu Ile Ala Arg Ile Arg Val
                245                 250                 255

Lys Asp Ile Ser Arg Thr Asp Gly Gly Arg Met Leu Ile His Ile Gly
            260                 265                 270

Arg Thr Lys Thr Leu Val Ser Thr Ala Gly Val Glu Lys Ala Leu Ser
        275                 280                 285

Leu Gly Val Thr Lys Leu Val Glu Arg Trp Ile Ser Val Ser Gly Val
    290                 295                 300

Ala Asp Asp Pro Asn Asn Tyr Leu Phe Cys Arg Val Arg Lys Asn Gly
305                 310                 315                 320

Val Ala Ala Pro Ser Ala Thr Ser Gln Leu Ser Thr Arg Ala Leu Glu
                325                 330                 335

Gly Ile Phe Glu Ala Thr His Arg Leu Ile Tyr Gly Ala Lys Asp Asp
            340                 345                 350

Ser Gly Gln Arg Tyr Leu Ala Trp Ser Gly His Ser Ala Arg Val Gly
        355                 360                 365

Ala Ala Arg Asp Met Ala Arg Ala Gly Val Ser Ile Pro Glu Ile Met
    370                 375                 380

Gln Ala Gly Gly Trp Thr Asn Val Asn Ile Val Met Asn Tyr Ile Arg
385                 390                 395                 400

Asn Leu Asp Ser Glu Thr Gly Ala Met Val Arg Leu Leu Glu Asp Gly
                405                 410                 415

Asp His His His His His
            420

<210> SEQ ID NO 127
<211> LENGTH: 346
<212> TYPE: PRT
<213> ORGANISM: Artificial Sequence
<220> FEATURE:
<223> OTHER INFORMATION: synthetic polypeptide

<400> SEQUENCE: 127

Met Arg Val Thr Leu Ser Ser Lys Pro Gln Ala Leu Ala Thr Pro Asn
1               5                   10                  15

Lys Glu Glu His Gly Lys Arg Lys Lys Gly Lys Gly Leu Gly Lys
            20                  25                  30

Lys Arg Asp Pro Cys Leu Arg Lys Tyr Lys Asp Phe Cys Ile His Gly
        35                  40                  45

Glu Cys Lys Tyr Val Lys Glu Leu Arg Ala Pro Ser Cys Ile Cys His
    50                  55                  60

Pro Gly Tyr His Gly Glu Arg Cys His Gly Leu Ser Gly Gly Ser Gly
65                  70                  75                  80

Gly Ser Gly Gly Ser Gly Gly Ser Gly Gly Ser Gly Ser Gly Gly
                85                  90                  95

Ser Gly Ser Gly Gly Ser Val Ser Lys Gly Glu Glu Asp Asn Met
            100                 105                 110

Ala Ile Ile Lys Glu Phe Met Arg Phe Lys Val His Met Glu Gly Ser
            115                 120                 125

Val Asn Gly His Glu Phe Glu Ile Glu Gly Glu Gly Glu Gly Arg Pro
130                 135                 140

Tyr Glu Gly Thr Gln Thr Ala Lys Leu Lys Val Thr Lys Gly Gly Pro
145                 150                 155                 160

Leu Pro Phe Ala Trp Asp Ile Leu Ser Pro Gln Phe Met Tyr Gly Ser
                165                 170                 175

Lys Ala Tyr Val Lys His Pro Ala Asp Ile Pro Asp Tyr Leu Lys Leu
            180                 185                 190

Ser Phe Pro Glu Gly Phe Lys Trp Glu Arg Val Met Asn Phe Glu Asp
        195                 200                 205

Gly Gly Val Val Thr Val Thr Gln Asp Ser Ser Leu Gln Asp Gly Glu
210                 215                 220

Phe Ile Tyr Lys Val Lys Leu Arg Gly Thr Asn Phe Pro Ser Asp Gly
225                 230                 235                 240

Pro Val Met Gln Lys Lys Thr Met Gly Trp Glu Ala Ser Ser Glu Arg
                245                 250                 255

Met Tyr Pro Glu Asp Gly Ala Leu Lys Gly Glu Ile Lys Gln Arg Leu
            260                 265                 270

Lys Leu Lys Asp Gly Gly His Tyr Asp Ala Glu Val Lys Thr Thr Tyr
        275                 280                 285

Lys Ala Lys Lys Pro Val Gln Leu Pro Gly Ala Tyr Asn Val Asn Ile
290                 295                 300

Lys Leu Asp Ile Thr Ser His Asn Glu Asp Tyr Thr Ile Val Glu Gln
305                 310                 315                 320

Tyr Glu Arg Ala Glu Gly Arg His Ser Thr Gly Gly Met Asp Glu Leu
                325                 330                 335

Tyr Lys Leu Glu His His His His His His
            340                 345

<210> SEQ ID NO 128
<211> LENGTH: 453
<212> TYPE: PRT
<213> ORGANISM: Artificial Sequence
<220> FEATURE:
<223> OTHER INFORMATION: synthetic polypeptide

<400> SEQUENCE: 128

Met Arg Val Thr Leu Ser Ser Lys Pro Gln Ala Leu Ala Thr Pro Asn
1               5                   10                  15

Lys Glu Glu His Gly Lys Arg Lys Lys Gly Lys Gly Leu Gly Lys
            20                  25                  30

Lys Arg Asp Pro Cys Leu Arg Lys Tyr Lys Asp Phe Cys Ile His Gly
        35                  40                  45

Glu Cys Lys Tyr Val Lys Glu Leu Arg Ala Pro Ser Cys Ile Cys His
    50                  55                  60

Pro Gly Tyr His Gly Glu Arg Cys His Gly Leu Ser Gly Gly Ser Gly
65                  70                  75                  80

```
Gly Ser Gly Gly Ser Gly Gly Ser Gly Gly Ser Gly Gly
            85                  90                  95
Ser Gly Gly Ser Gly Gly Ser Met Ala Ser Asn Leu Leu Thr Val His
            100                 105                 110
Gln Asn Leu Pro Ala Leu Pro Val Asp Ala Thr Ser Asp Glu Val Arg
        115                 120                 125
Lys Asn Leu Met Asp Met Phe Arg Asp Arg Gln Ala Phe Ser Glu His
    130                 135                 140
Thr Trp Lys Met Leu Leu Ser Val Cys Arg Ser Trp Ala Ala Trp Cys
145                 150                 155                 160
Lys Leu Asn Asn Arg Lys Trp Phe Pro Ala Glu Pro Glu Asp Val Arg
                165                 170                 175
Asp Tyr Leu Leu Tyr Leu Gln Ala Arg Gly Leu Ala Val Lys Thr Ile
            180                 185                 190
Gln Gln His Leu Gly Gln Leu Asn Met Leu His Arg Arg Ser Gly Leu
        195                 200                 205
Pro Arg Pro Ser Asp Ser Asn Ala Val Ser Leu Val Met Arg Arg Ile
    210                 215                 220
Arg Lys Glu Asn Val Asp Ala Gly Glu Arg Ala Lys Gln Ala Leu Ala
225                 230                 235                 240
Phe Glu Arg Thr Asp Phe Asp Gln Val Arg Ser Leu Met Glu Asn Ser
                245                 250                 255
Asp Arg Cys Gln Asp Ile Arg Asn Leu Ala Phe Leu Gly Ile Ala Tyr
            260                 265                 270
Asn Thr Leu Leu Arg Ile Ala Glu Ile Ala Arg Ile Arg Val Lys Asp
        275                 280                 285
Ile Ser Arg Thr Asp Gly Gly Arg Met Leu Ile His Ile Gly Arg Thr
    290                 295                 300
Lys Thr Leu Val Ser Thr Ala Gly Val Glu Lys Ala Leu Ser Leu Gly
305                 310                 315                 320
Val Thr Lys Leu Val Glu Arg Trp Ile Ser Val Ser Gly Val Ala Asp
                325                 330                 335
Asp Pro Asn Asn Tyr Leu Phe Cys Arg Val Arg Lys Asn Gly Val Ala
            340                 345                 350
Ala Pro Ser Ala Thr Ser Gln Leu Ser Thr Arg Ala Leu Glu Gly Ile
        355                 360                 365
Phe Glu Ala Thr His Arg Leu Ile Tyr Gly Ala Lys Asp Asp Ser Gly
    370                 375                 380
Gln Arg Tyr Leu Ala Trp Ser Gly His Ser Ala Arg Val Gly Ala Ala
385                 390                 395                 400
Arg Asp Met Ala Arg Ala Gly Val Ser Ile Pro Glu Ile Met Gln Ala
                405                 410                 415
Gly Gly Trp Thr Asn Val Asn Ile Val Met Asn Tyr Ile Arg Asn Leu
            420                 425                 430
Asp Ser Glu Thr Gly Ala Met Val Arg Leu Leu Glu Asp Gly Asp His
        435                 440                 445
His His His His His
    450

<210> SEQ ID NO 129
<211> LENGTH: 402
<212> TYPE: PRT
<213> ORGANISM: Artificial Sequence
<220> FEATURE:
```

<223> OTHER INFORMATION: synthetic polypeptide

<400> SEQUENCE: 129

```
Met Phe Thr Ile Ala Gln Gly Lys Gly Gln Lys Leu Cys Glu Ile Glu
1               5                   10                  15

Arg Ile His Phe Phe Leu Ser Lys Lys Thr Asp Glu Leu Arg Asn
            20                  25                  30

Leu His Lys Leu Leu Tyr Asn Arg Pro Gly Thr Val Ser Ser Leu Lys
            35                  40                  45

Lys Asn Val Gly Gln Phe Ser Gly Phe Pro Phe Glu Lys Gly Ser Val
        50                  55                  60

Gln Tyr Lys Lys Lys Glu Glu Met Leu Lys Lys Phe Arg Asn Ala Met
65                  70                  75                  80

Leu Lys Ser Ile Cys Glu Val Leu Asp Leu Glu Arg Ser Gly Val Asn
                85                  90                  95

Ser Glu Leu Val Lys Arg Ile Leu Asn Phe Leu Met His Pro Lys Pro
                100                 105                 110

Ser Gly Lys Pro Leu Pro Lys Ser Lys Thr Cys Ser Lys Gly Ser
            115                 120                 125

Lys Lys Glu Arg Gly Gly Ser Gly Gly Ser Gly Gly Ser
130                 135                 140

Gly Gly Ser Gly Gly Ser Gly Gly Ser Gly Gly Ser Val
145                 150                 155                 160

Ser Lys Gly Glu Glu Asp Asn Met Ala Ile Ile Lys Glu Phe Met Arg
                165                 170                 175

Phe Lys Val His Met Glu Gly Ser Val Asn Gly His Glu Phe Glu Ile
            180                 185                 190

Glu Gly Glu Gly Glu Gly Arg Pro Tyr Glu Gly Thr Gln Thr Ala Lys
        195                 200                 205

Leu Lys Val Thr Lys Gly Gly Pro Leu Pro Phe Ala Trp Asp Ile Leu
210                 215                 220

Ser Pro Gln Phe Met Tyr Gly Ser Lys Ala Tyr Val Lys His Pro Ala
225                 230                 235                 240

Asp Ile Pro Asp Tyr Leu Lys Leu Ser Phe Pro Glu Gly Phe Lys Trp
                245                 250                 255

Glu Arg Val Met Asn Phe Glu Asp Gly Gly Val Val Thr Val Thr Gln
            260                 265                 270

Asp Ser Ser Leu Gln Asp Gly Glu Phe Ile Tyr Lys Val Lys Leu Arg
        275                 280                 285

Gly Thr Asn Phe Pro Ser Asp Gly Pro Val Met Gln Lys Lys Thr Met
290                 295                 300

Gly Trp Glu Ala Ser Ser Glu Arg Met Tyr Pro Glu Asp Gly Ala Leu
305                 310                 315                 320

Lys Gly Glu Ile Lys Gln Arg Leu Lys Leu Lys Asp Gly Gly His Tyr
                325                 330                 335

Asp Ala Glu Val Lys Thr Thr Tyr Lys Ala Lys Lys Pro Val Gln Leu
            340                 345                 350

Pro Gly Ala Tyr Asn Val Asn Ile Lys Leu Asp Ile Thr Ser His Asn
        355                 360                 365

Glu Asp Tyr Thr Ile Val Glu Gln Tyr Glu Arg Ala Glu Gly Arg His
370                 375                 380

Ser Thr Gly Gly Met Asp Glu Leu Tyr Lys Leu Glu His His His
385                 390                 395                 400
```

His His

<210> SEQ ID NO 130
<211> LENGTH: 509
<212> TYPE: PRT
<213> ORGANISM: Artificial Sequence
<220> FEATURE:
<223> OTHER INFORMATION: synthetic polypeptide

<400> SEQUENCE: 130

```
Met Phe Thr Ile Ala Gln Gly Lys Gly Gln Lys Leu Cys Glu Ile Glu
1               5                   10                  15

Arg Ile His Phe Phe Leu Ser Lys Lys Thr Asp Glu Leu Arg Asn
            20                  25                  30

Leu His Lys Leu Leu Tyr Asn Arg Pro Gly Thr Val Ser Ser Leu Lys
        35                  40                  45

Lys Asn Val Gly Gln Phe Ser Gly Phe Pro Phe Glu Lys Gly Ser Val
    50                  55                  60

Gln Tyr Lys Lys Lys Glu Glu Met Leu Lys Lys Phe Arg Asn Ala Met
65                  70                  75                  80

Leu Lys Ser Ile Cys Glu Val Leu Asp Leu Glu Arg Ser Gly Val Asn
                85                  90                  95

Ser Glu Leu Val Lys Arg Ile Leu Asn Phe Leu Met His Pro Lys Pro
            100                 105                 110

Ser Gly Lys Pro Leu Pro Lys Ser Lys Lys Thr Cys Ser Lys Gly Ser
        115                 120                 125

Lys Lys Glu Arg Gly Gly Ser Gly Gly Ser Gly Gly Ser Gly Gly Ser
130                 135                 140

Gly Gly Ser Gly Gly Ser Gly Gly Ser Gly Gly Ser Gly Gly Ser Met
145                 150                 155                 160

Ala Ser Asn Leu Leu Thr Val His Gln Asn Leu Pro Ala Leu Pro Val
                165                 170                 175

Asp Ala Thr Ser Asp Glu Val Arg Lys Asn Leu Met Asp Met Phe Arg
            180                 185                 190

Asp Arg Gln Ala Phe Ser Glu His Thr Trp Lys Met Leu Leu Ser Val
        195                 200                 205

Cys Arg Ser Trp Ala Ala Trp Cys Lys Leu Asn Asn Arg Lys Trp Phe
    210                 215                 220

Pro Ala Glu Pro Glu Asp Val Arg Asp Tyr Leu Leu Tyr Leu Gln Ala
225                 230                 235                 240

Arg Gly Leu Ala Val Lys Thr Ile Gln Gln His Leu Gly Gln Leu Asn
                245                 250                 255

Met Leu His Arg Arg Ser Gly Leu Pro Arg Pro Ser Asp Ser Asn Ala
            260                 265                 270

Val Ser Leu Val Met Arg Arg Ile Arg Lys Glu Asn Val Asp Ala Gly
        275                 280                 285

Glu Arg Ala Lys Gln Ala Leu Ala Phe Glu Arg Thr Asp Phe Asp Gln
    290                 295                 300

Val Arg Ser Leu Met Glu Asn Ser Asp Arg Cys Gln Asp Ile Arg Asn
305                 310                 315                 320

Leu Ala Phe Leu Gly Ile Ala Tyr Asn Thr Leu Leu Arg Ile Ala Glu
                325                 330                 335

Ile Ala Arg Ile Arg Val Lys Asp Ile Ser Arg Thr Asp Gly Gly Arg
            340                 345                 350

Met Leu Ile His Ile Gly Arg Thr Lys Thr Leu Val Ser Thr Ala Gly
```

```
                355                 360                 365
Val Glu Lys Ala Leu Ser Leu Gly Val Thr Lys Leu Val Glu Arg Trp
    370                 375                 380

Ile Ser Val Ser Gly Val Ala Asp Asp Pro Asn Asn Tyr Leu Phe Cys
385                 390                 395                 400

Arg Val Arg Lys Asn Gly Val Ala Ala Pro Ser Ala Thr Ser Gln Leu
                405                 410                 415

Ser Thr Arg Ala Leu Glu Gly Ile Phe Glu Ala Thr His Arg Leu Ile
            420                 425                 430

Tyr Gly Ala Lys Asp Asp Ser Gly Gln Arg Tyr Leu Ala Trp Ser Gly
            435                 440                 445

His Ser Ala Arg Val Gly Ala Ala Arg Asp Met Ala Arg Ala Gly Val
        450                 455                 460

Ser Ile Pro Glu Ile Met Gln Ala Gly Gly Trp Thr Asn Val Asn Ile
465                 470                 475                 480

Val Met Asn Tyr Ile Arg Asn Leu Asp Ser Glu Thr Gly Ala Met Val
                485                 490                 495

Arg Leu Leu Glu Asp Gly Asp His His His His His His
            500                 505

<210> SEQ ID NO 131
<211> LENGTH: 368
<212> TYPE: PRT
<213> ORGANISM: Artificial Sequence
<220> FEATURE:
<223> OTHER INFORMATION: synthetic polypeptide

<400> SEQUENCE: 131

Met Gly Gln Arg Lys Arg Asn Thr Ile His Glu Phe Lys Lys Ser
1               5                   10                  15

Ala Lys Thr Thr Leu Ile Lys Ile Asp Pro Ala Leu Lys Ile Lys Thr
                20                  25                  30

Lys Lys Val Asn Thr Ala Asp Gln Cys Ala Asn Arg Cys Thr Arg Asn
            35                  40                  45

Lys Gly Leu Pro Phe Thr Cys Lys Ala Phe Val Phe Asp Lys Ala Arg
        50                  55                  60

Lys Gln Cys Leu Trp Phe Pro Phe Asn Ser Met Ser Ser Gly Val Lys
65                  70                  75                  80

Lys Glu Phe Gly His Glu Phe Asp Leu Tyr Glu Asn Lys Asp Tyr Ile
                85                  90                  95

Arg Asn Gly Gly Ser Gly Gly Ser Gly Gly Ser Gly Gly Ser Gly Gly
                100                 105                 110

Ser Gly Gly Ser Gly Gly Ser Gly Gly Ser Gly Gly Ser Val Ser Lys
            115                 120                 125

Gly Glu Glu Asp Asn Met Ala Ile Ile Lys Glu Phe Met Arg Phe Lys
        130                 135                 140

Val His Met Glu Gly Ser Val Asn Gly His Glu Phe Glu Ile Glu Gly
145                 150                 155                 160

Glu Gly Glu Gly Arg Pro Tyr Glu Gly Thr Gln Thr Ala Lys Leu Lys
                165                 170                 175

Val Thr Lys Gly Gly Pro Leu Pro Phe Ala Trp Asp Ile Leu Ser Pro
            180                 185                 190

Gln Phe Met Tyr Gly Ser Lys Ala Tyr Val Lys His Pro Ala Asp Ile
        195                 200                 205

Pro Asp Tyr Leu Lys Leu Ser Phe Pro Glu Gly Phe Lys Trp Glu Arg
```

```
            210                 215                 220
Val Met Asn Phe Glu Asp Gly Val Val Thr Val Thr Gln Asp Ser
225                 230                 235                 240

Ser Leu Gln Asp Gly Glu Phe Ile Tyr Lys Val Lys Leu Arg Gly Thr
                245                 250                 255

Asn Phe Pro Ser Asp Gly Pro Val Met Gln Lys Lys Thr Met Gly Trp
            260                 265                 270

Glu Ala Ser Ser Glu Arg Met Tyr Pro Glu Asp Gly Ala Leu Lys Gly
        275                 280                 285

Glu Ile Lys Gln Arg Leu Lys Leu Lys Asp Gly Gly His Tyr Asp Ala
        290                 295                 300

Glu Val Lys Thr Thr Tyr Lys Ala Lys Lys Pro Val Gln Leu Pro Gly
305                 310                 315                 320

Ala Tyr Asn Val Asn Ile Lys Leu Asp Ile Thr Ser His Asn Glu Asp
                325                 330                 335

Tyr Thr Ile Val Glu Gln Tyr Glu Arg Ala Glu Gly Arg His Ser Thr
            340                 345                 350

Gly Gly Met Asp Glu Leu Tyr Lys Leu Glu His His His His His His
        355                 360                 365

<210> SEQ ID NO 132
<211> LENGTH: 475
<212> TYPE: PRT
<213> ORGANISM: Artificial Sequence
<220> FEATURE:
<223> OTHER INFORMATION: synthetic polypeptide

<400> SEQUENCE: 132

Met Gly Gln Arg Lys Arg Asn Thr Ile His Glu Phe Lys Lys Ser
1               5                   10                  15

Ala Lys Thr Thr Leu Ile Lys Ile Asp Pro Ala Leu Lys Ile Lys Thr
                20                  25                  30

Lys Lys Val Asn Thr Ala Asp Gln Cys Ala Asn Arg Cys Thr Arg Asn
                35                  40                  45

Lys Gly Leu Pro Phe Thr Cys Lys Ala Phe Val Phe Asp Lys Ala Arg
            50                  55                  60

Lys Gln Cys Leu Trp Phe Pro Phe Asn Ser Met Ser Ser Gly Val Lys
65                  70                  75                  80

Lys Glu Phe Gly His Glu Phe Asp Leu Tyr Glu Asn Lys Asp Tyr Ile
                85                  90                  95

Arg Asn Gly Gly Ser Gly Gly Ser Gly Gly Ser Gly Gly Ser Gly Gly
            100                 105                 110

Ser Gly Gly Ser Gly Gly Ser Gly Gly Ser Gly Gly Ser Met Ala Ser
        115                 120                 125

Asn Leu Leu Thr Val His Gln Asn Leu Pro Ala Leu Pro Val Asp Ala
        130                 135                 140

Thr Ser Asp Glu Val Arg Lys Asn Leu Met Asp Met Phe Arg Asp Arg
145                 150                 155                 160

Gln Ala Phe Ser Glu His Thr Trp Lys Met Leu Leu Ser Val Cys Arg
                165                 170                 175

Ser Trp Ala Ala Trp Cys Lys Leu Asn Asn Arg Lys Trp Phe Pro Ala
            180                 185                 190

Glu Pro Glu Asp Val Arg Asp Tyr Leu Leu Tyr Leu Gln Ala Arg Gly
        195                 200                 205

Leu Ala Val Lys Thr Ile Gln Gln His Leu Gly Gln Leu Asn Met Leu
```

```
                210                 215                 220
His Arg Arg Ser Gly Leu Pro Arg Pro Ser Asp Ser Asn Ala Val Ser
225                 230                 235                 240

Leu Val Met Arg Arg Ile Arg Lys Glu Asn Val Asp Ala Gly Glu Arg
                245                 250                 255

Ala Lys Gln Ala Leu Ala Phe Glu Arg Thr Asp Phe Asp Gln Val Arg
                260                 265                 270

Ser Leu Met Glu Asn Ser Asp Arg Cys Gln Asp Ile Arg Asn Leu Ala
                275                 280                 285

Phe Leu Gly Ile Ala Tyr Asn Thr Leu Leu Arg Ile Ala Glu Ile Ala
                290                 295                 300

Arg Ile Arg Val Lys Asp Ile Ser Arg Thr Asp Gly Gly Arg Met Leu
305                 310                 315                 320

Ile His Ile Gly Arg Thr Lys Thr Leu Val Ser Thr Ala Gly Val Glu
                325                 330                 335

Lys Ala Leu Ser Leu Gly Val Thr Lys Leu Val Glu Arg Trp Ile Ser
                340                 345                 350

Val Ser Gly Val Ala Asp Asp Pro Asn Asn Tyr Leu Phe Cys Arg Val
                355                 360                 365

Arg Lys Asn Gly Val Ala Ala Pro Ser Ala Thr Ser Gln Leu Ser Thr
                370                 375                 380

Arg Ala Leu Glu Gly Ile Phe Glu Ala Thr His Arg Leu Ile Tyr Gly
385                 390                 395                 400

Ala Lys Asp Asp Ser Gly Gln Arg Tyr Leu Ala Trp Ser Gly His Ser
                405                 410                 415

Ala Arg Val Gly Ala Ala Arg Asp Met Ala Arg Ala Gly Val Ser Ile
                420                 425                 430

Pro Glu Ile Met Gln Ala Gly Gly Trp Thr Asn Val Asn Ile Val Met
                435                 440                 445

Asn Tyr Ile Arg Asn Leu Asp Ser Glu Thr Gly Ala Met Val Arg Leu
                450                 455                 460

Leu Glu Asp Gly Asp His His His His His
465                 470                 475

<210> SEQ ID NO 133
<211> LENGTH: 240
<212> TYPE: PRT
<213> ORGANISM: Artificial Sequence
<220> FEATURE:
<223> OTHER INFORMATION: synthetic polypeptide

<400> SEQUENCE: 133

Met Gly Ala Ser Lys Gly Glu His Leu Phe His Gly His Val Pro Ile
1               5                   10                  15

Leu Val Glu Leu His Gly Asp Val Asn Gly His Lys Phe Ser Val Arg
                20                  25                  30

Gly His Gly His Gly Asp Ala Thr His Gly Lys Leu Thr Leu Lys Phe
            35                  40                  45

Ile Cys Thr Thr Gly Lys Leu Pro Val Pro Trp Pro Thr Leu Val Thr
        50                  55                  60

Thr Leu Thr Tyr Gly Val Gln Cys Phe Ser Arg Tyr Pro His His Met
65                  70                  75                  80

Lys His His Asp Phe Phe Lys Ser Ala Met Pro His Gly Tyr Val Gln
                85                  90                  95

Glu Arg Thr Ile Ser Phe Lys His Asp Gly His Tyr Lys Thr Arg Ala
```

```
              100                 105                 110
Glu Val Lys Phe Glu Gly His Thr Leu Val Asn Arg Ile His Leu Lys
            115                 120                 125
Gly His Asp Phe Lys Glu His Gly Asn Ile Leu Gly His Lys Leu His
            130                 135                 140
Tyr Asn Phe Asn Ser His His Val Tyr Ile Thr Ala Asp Lys His Lys
145                 150                 155                 160
Asn Gly Ile Lys Ala His Phe Lys Ile Arg His Asn Val His Asp Gly
                165                 170                 175
Ser Val Gln Leu Ala Asp His Tyr Gln Gln Asn Thr Pro Ile Gly His
            180                 185                 190
Gly Pro Val Leu Leu Pro His Asn His Tyr Leu Ser Thr His Ser His
            195                 200                 205
Leu Ser Lys Asp Pro His Glu Lys Arg Asp His Met Val Leu Leu Glu
            210                 215                 220
Phe Val Thr Ala Ala Gly Ile His His Gly His Asp Glu His Tyr Lys
225                 230                 235                 240
```

<210> SEQ ID NO 134
<211> LENGTH: 248
<212> TYPE: PRT
<213> ORGANISM: Artificial Sequence
<220> FEATURE:
<223> OTHER INFORMATION: synthetic polypeptide

<400> SEQUENCE: 134

```
Met Gly His His His His His His Gly Gly Ala Ser Lys Gly Glu Arg
1               5                  10                  15
Leu Phe Arg Gly Lys Val Pro Ile Leu Val Glu Leu Lys Gly Asp Val
            20                  25                  30
Asn Gly His Lys Phe Ser Val Arg Gly Lys Gly Lys Gly Asp Ala Thr
        35                  40                  45
Arg Gly Lys Leu Thr Leu Lys Phe Ile Cys Thr Thr Gly Lys Leu Pro
50                  55                  60
Val Pro Trp Pro Thr Leu Val Thr Thr Leu Thr Tyr Gly Val Gln Cys
65                  70                  75                  80
Phe Ser Arg Tyr Pro Lys His Met Lys Arg His Asp Phe Phe Lys Ser
                85                  90                  95
Ala Met Pro Lys Gly Tyr Val Gln Glu Arg Thr Ile Ser Phe Lys Lys
            100                 105                 110
Asp Gly Lys Tyr Lys Thr Arg Ala Glu Val Lys Phe Glu Gly Arg Thr
            115                 120                 125
Leu Val Asn Arg Ile Lys Leu Lys Gly Arg Asp Phe Lys Glu Lys Gly
            130                 135                 140
Asn Ile Leu Gly His Lys Leu Arg Tyr Asn Phe Asn Ser His Lys Val
145                 150                 155                 160
Tyr Ile Thr Ala Asp Lys Arg Lys Asn Gly Ile Lys Ala Lys Phe Lys
                165                 170                 175
Ile Arg His Asn Val Lys Asp Gly Ser Val Gln Leu Ala Asp His Tyr
            180                 185                 190
Gln Gln Asn Thr Pro Ile Gly Arg Gly Pro Val Leu Leu Pro Arg Asn
            195                 200                 205
His Tyr Leu Ser Thr Arg Ser Lys Leu Ser Lys Asp Pro Lys Glu Lys
            210                 215                 220
Arg Asp His Met Val Leu Leu Glu Phe Val Thr Ala Ala Gly Ile Lys
```

His Gly Arg Asp Glu Arg Tyr Lys
            245

<210> SEQ ID NO 135
<211> LENGTH: 280
<212> TYPE: PRT
<213> ORGANISM: Artificial Sequence
<220> FEATURE:
<223> OTHER INFORMATION: synthetic polypeptide

<400> SEQUENCE: 135

Met Gly His His His His His Gly Gly Ala Ser Lys Gly Glu Arg
1               5                   10                  15

Leu Phe Arg Gly Lys Val Pro Ile Leu Val Glu Leu Lys Gly Asp Val
            20                  25                  30

Asn Gly His Lys Phe Ser Val Arg Gly Lys Gly Lys Gly Asp Ala Thr
        35                  40                  45

Arg Gly Lys Leu Thr Leu Lys Phe Ile Cys Thr Thr Gly Lys Leu Pro
    50                  55                  60

Val Pro Trp Pro Thr Leu Val Thr Thr Leu Thr Tyr Gly Val Gln Cys
65                  70                  75                  80

Phe Ser Arg Tyr Pro Lys His Met Lys Arg His Asp Phe Phe Lys Ser
                85                  90                  95

Ala Met Pro Lys Gly Tyr Val Gln Glu Arg Thr Ile Ser Phe Lys Lys
            100                 105                 110

Asp Gly Lys Tyr Lys Thr Arg Ala Glu Val Lys Phe Glu Gly Arg Thr
        115                 120                 125

Leu Val Asn Arg Ile Lys Leu Lys Gly Arg Asp Phe Lys Glu Lys Gly
    130                 135                 140

Asn Ile Leu Gly His Lys Leu Arg Tyr Asn Phe Asn Ser His Lys Val
145                 150                 155                 160

Tyr Ile Thr Ala Asp Lys Arg Lys Asn Gly Ile Lys Ala Lys Phe Lys
                165                 170                 175

Ile Arg His Asn Val Lys Asp Gly Ser Val Gln Leu Ala Asp His Tyr
            180                 185                 190

Gln Gln Asn Thr Pro Ile Gly Arg Gly Pro Val Leu Leu Pro Arg Asn
        195                 200                 205

His Tyr Leu Ser Thr Arg Ser Lys Leu Ser Lys Asp Pro Lys Glu Lys
    210                 215                 220

Arg Asp His Met Val Leu Leu Glu Phe Val Thr Ala Ala Gly Ile Lys
225                 230                 235                 240

His Gly Arg Asp Glu Arg Tyr Lys Gly Ser Ala Gly Ser Ala Ala Gly
                245                 250                 255

Ser Gly Glu Phe Gly Leu Phe Gly Ala Ile Ala Gly Phe Ile Glu Asn
            260                 265                 270

Gly Trp Glu Gly Met Ile Asp Gly
        275                 280

<210> SEQ ID NO 136
<211> LENGTH: 4
<212> TYPE: PRT
<213> ORGANISM: Artificial Sequence
<220> FEATURE:
<223> OTHER INFORMATION: synthetic polypeptide

<400> SEQUENCE: 136

Ala Gly Val Phe
1

<210> SEQ ID NO 137
<211> LENGTH: 4
<212> TYPE: PRT
<213> ORGANISM: Artificial Sequence
<220> FEATURE:
<223> OTHER INFORMATION: synthetic polypeptide

<400> SEQUENCE: 137

Gly Phe Leu Gly
1

<210> SEQ ID NO 138
<211> LENGTH: 2
<212> TYPE: PRT
<213> ORGANISM: Artificial Sequence
<220> FEATURE:
<223> OTHER INFORMATION: synthetic polypeptide

<400> SEQUENCE: 138

Phe Lys
1

<210> SEQ ID NO 139
<211> LENGTH: 2
<212> TYPE: PRT
<213> ORGANISM: Artificial Sequence
<220> FEATURE:
<223> OTHER INFORMATION: synthetic polypeptide

<400> SEQUENCE: 139

Ala Leu
1

<210> SEQ ID NO 140
<211> LENGTH: 4
<212> TYPE: PRT
<213> ORGANISM: Artificial Sequence
<220> FEATURE:
<223> OTHER INFORMATION: synthetic polypeptide

<400> SEQUENCE: 140

Ala Leu Ala Leu
1

<210> SEQ ID NO 141
<211> LENGTH: 5
<212> TYPE: PRT
<213> ORGANISM: Artificial Sequence
<220> FEATURE:
<223> OTHER INFORMATION: synthetic polypeptide

<400> SEQUENCE: 141

Ala Leu Ala Leu Ala
1               5

<210> SEQ ID NO 142
<211> LENGTH: 281
<212> TYPE: PRT
<213> ORGANISM: Artificial Sequence
<220> FEATURE:
<223> OTHER INFORMATION: synthetic polypeptide

<400> SEQUENCE: 142

Met Arg Arg Arg Arg Arg Arg Arg Arg Arg Gly Gly Ser Gly Gly

```
  1               5                  10                 15
Ser Gly Gly Ser Gly Gly Ser Gly Gly Ser Gly Gly Ser Gly Gly Ser
             20                 25                 30

Gly Gly Ser Gly Gly Ser Val Ser Lys Gly Glu Glu Asp Asn Met Ala
             35                 40                 45

Ile Ile Lys Glu Phe Met Arg Phe Lys Val His Met Glu Gly Ser Val
 50                 55                 60

Asn Gly His Glu Phe Glu Ile Glu Gly Glu Gly Arg Pro Tyr
 65                 70                 75                 80

Glu Gly Thr Gln Thr Ala Lys Leu Lys Val Thr Lys Gly Gly Pro Leu
             85                 90                 95

Pro Phe Ala Trp Asp Ile Leu Ser Pro Gln Phe Met Tyr Gly Ser Lys
             100                105                110

Ala Tyr Val Lys His Pro Ala Asp Ile Pro Asp Tyr Leu Lys Leu Ser
             115                120                125

Phe Pro Glu Gly Phe Lys Trp Glu Arg Val Met Asn Phe Glu Asp Gly
 130                135                140

Gly Val Val Thr Val Thr Gln Asp Ser Ser Leu Gln Asp Gly Glu Phe
145                 150                155                160

Ile Tyr Lys Val Lys Leu Arg Gly Thr Asn Phe Pro Ser Asp Gly Pro
             165                170                175

Val Met Gln Lys Lys Thr Met Gly Trp Glu Ala Ser Ser Glu Arg Met
             180                185                190

Tyr Pro Glu Asp Gly Ala Leu Lys Gly Glu Ile Lys Gln Arg Leu Lys
             195                200                205

Leu Lys Asp Gly Gly His Tyr Asp Ala Glu Val Lys Thr Thr Tyr Lys
             210                215                220

Ala Lys Lys Pro Val Gln Leu Pro Gly Ala Tyr Asn Val Asn Ile Lys
225                 230                235                240

Leu Asp Ile Thr Ser His Asn Glu Asp Tyr Thr Ile Val Glu Gln Tyr
             245                250                255

Glu Arg Ala Glu Gly Arg His Ser Thr Gly Gly Met Asp Glu Leu Tyr
             260                265                270

Lys Leu Glu His His His His His His
             275                280
```

<210> SEQ ID NO 143
<211> LENGTH: 287
<212> TYPE: PRT
<213> ORGANISM: Artificial Sequence
<220> FEATURE:
<223> OTHER INFORMATION: synthetic polypeptide

<400> SEQUENCE: 143

```
Met Arg Gln Ile Lys Ile Trp Phe Gln Asn Arg Arg Met Lys Trp Lys
 1                  5                 10                 15

Lys Gly Gly Ser Gly Gly Ser Gly Gly Ser Gly Gly Ser Gly Gly Ser
             20                 25                 30

Gly Gly Ser Gly Gly Ser Gly Gly Ser Val Ser Lys Gly
             35                 40                 45

Glu Glu Asp Asn Met Ala Ile Ile Lys Glu Phe Met Arg Phe Lys Val
             50                 55                 60

His Met Glu Gly Ser Val Asn Gly His Glu Phe Glu Ile Glu Gly Glu
 65                 70                 75                 80

Gly Glu Gly Arg Pro Tyr Glu Gly Thr Gln Thr Ala Lys Leu Lys Val
```

```
                85                  90                  95
Thr Lys Gly Gly Pro Leu Pro Phe Ala Trp Asp Ile Leu Ser Pro Gln
            100                 105                 110

Phe Met Tyr Gly Ser Lys Ala Tyr Val Lys His Pro Ala Asp Ile Pro
            115                 120                 125

Asp Tyr Leu Lys Leu Ser Phe Pro Glu Gly Phe Lys Trp Glu Arg Val
    130                 135                 140

Met Asn Phe Glu Asp Gly Gly Val Val Thr Val Thr Gln Asp Ser Ser
145                 150                 155                 160

Leu Gln Asp Gly Glu Phe Ile Tyr Lys Val Lys Leu Arg Gly Thr Asn
                165                 170                 175

Phe Pro Ser Asp Gly Pro Val Met Gln Lys Lys Thr Met Gly Trp Glu
            180                 185                 190

Ala Ser Ser Glu Arg Met Tyr Pro Glu Asp Gly Ala Leu Lys Gly Glu
        195                 200                 205

Ile Lys Gln Arg Leu Lys Leu Lys Asp Gly Gly His Tyr Asp Ala Glu
    210                 215                 220

Val Lys Thr Thr Tyr Lys Ala Lys Lys Pro Val Gln Leu Pro Gly Ala
225                 230                 235                 240

Tyr Asn Val Asn Ile Lys Leu Asp Ile Thr Ser His Asn Glu Asp Tyr
                245                 250                 255

Thr Ile Val Glu Gln Tyr Glu Arg Ala Glu Gly Arg His Ser Thr Gly
            260                 265                 270

Gly Met Asp Glu Leu Tyr Lys Leu Glu His His His His His His
        275                 280                 285

<210> SEQ ID NO 144
<211> LENGTH: 388
<212> TYPE: PRT
<213> ORGANISM: Artificial Sequence
<220> FEATURE:
<223> OTHER INFORMATION: synthetic polypeptide

<400> SEQUENCE: 144

Met Gly Arg Lys Lys Arg Arg Gln Arg Arg Gly Gly Ser Gly Gly
1               5                   10                  15

Ser Gly Gly Ser Gly Gly Ser Gly Gly Ser Gly Gly Ser Gly Gly Ser
            20                  25                  30

Gly Gly Ser Gly Gly Ser Met Ala Ser Asn Leu Leu Thr Val His Gln
        35                  40                  45

Asn Leu Pro Ala Leu Pro Val Asp Ala Thr Ser Asp Glu Val Arg Lys
    50                  55                  60

Asn Leu Met Asp Met Phe Arg Asp Arg Gln Ala Phe Ser Glu His Thr
65                  70                  75                  80

Trp Lys Met Leu Leu Ser Val Cys Arg Ser Trp Ala Ala Trp Cys Lys
                85                  90                  95

Leu Asn Asn Arg Lys Trp Phe Pro Ala Glu Pro Glu Asp Val Arg Asp
            100                 105                 110

Tyr Leu Leu Tyr Leu Gln Ala Arg Gly Leu Ala Val Lys Thr Ile Gln
        115                 120                 125

Gln His Leu Gly Gln Leu Asn Met Leu His Arg Arg Ser Gly Leu Pro
    130                 135                 140

Arg Pro Ser Asp Ser Asn Ala Val Ser Leu Val Met Arg Arg Ile Arg
145                 150                 155                 160

Lys Glu Asn Val Asp Ala Gly Glu Arg Ala Lys Gln Ala Leu Ala Phe
```

```
                      165                 170                 175

Glu Arg Thr Asp Phe Asp Gln Val Arg Ser Leu Met Glu Asn Ser Asp
                180                 185                 190

Arg Cys Gln Asp Ile Arg Asn Leu Ala Phe Leu Gly Ile Ala Tyr Asn
            195                 200                 205

Thr Leu Leu Arg Ile Ala Glu Ile Ala Arg Ile Arg Val Lys Asp Ile
        210                 215                 220

Ser Arg Thr Asp Gly Gly Arg Met Leu Ile His Ile Gly Arg Thr Lys
225                 230                 235                 240

Thr Leu Val Ser Thr Ala Gly Val Glu Lys Ala Leu Ser Leu Gly Val
                245                 250                 255

Thr Lys Leu Val Glu Arg Trp Ile Ser Val Ser Gly Val Ala Asp Asp
                260                 265                 270

Pro Asn Asn Tyr Leu Phe Cys Arg Val Arg Lys Asn Gly Val Ala Ala
            275                 280                 285

Pro Ser Ala Thr Ser Gln Leu Ser Thr Arg Ala Leu Glu Gly Ile Phe
        290                 295                 300

Glu Ala Thr His Arg Leu Ile Tyr Gly Ala Lys Asp Asp Ser Gly Gln
305                 310                 315                 320

Arg Tyr Leu Ala Trp Ser Gly His Ser Ala Arg Val Gly Ala Ala Arg
                325                 330                 335

Asp Met Ala Arg Ala Gly Val Ser Ile Pro Glu Ile Met Gln Ala Gly
                340                 345                 350

Gly Trp Thr Asn Val Asn Ile Val Met Asn Tyr Ile Arg Asn Leu Asp
            355                 360                 365

Ser Glu Thr Gly Ala Met Val Arg Leu Leu Glu Asp Gly Asp His His
        370                 375                 380

His His His His
385

<210> SEQ ID NO 145
<211> LENGTH: 388
<212> TYPE: PRT
<213> ORGANISM: Artificial Sequence
<220> FEATURE:
<223> OTHER INFORMATION: synthetic polypeptide

<400> SEQUENCE: 145

Met Arg Arg Arg Arg Arg Arg Arg Arg Gly Gly Ser Gly Gly
1               5                   10                  15

Ser Gly Gly Ser Gly Gly Ser Gly Gly Ser Gly Gly Ser Gly Gly Ser
            20                  25                  30

Gly Gly Ser Gly Gly Ser Met Ala Ser Asn Leu Leu Thr Val His Gln
        35                  40                  45

Asn Leu Pro Ala Leu Pro Val Asp Ala Thr Ser Asp Glu Val Arg Lys
    50                  55                  60

Asn Leu Met Asp Met Phe Arg Asp Arg Gln Ala Phe Ser Glu His Thr
65                  70                  75                  80

Trp Lys Met Leu Leu Ser Val Cys Arg Ser Trp Ala Ala Trp Cys Lys
                85                  90                  95

Leu Asn Asn Arg Lys Trp Phe Pro Ala Glu Pro Glu Asp Val Arg Asp
            100                 105                 110

Tyr Leu Leu Tyr Leu Gln Ala Arg Gly Leu Ala Val Lys Thr Ile Gln
        115                 120                 125

Gln His Leu Gly Gln Leu Asn Met Leu His Arg Arg Ser Gly Leu Pro
```

```
                130             135             140
Arg Pro Ser Asp Ser Asn Ala Val Ser Leu Val Met Arg Arg Ile Arg
145                 150                 155                 160

Lys Glu Asn Val Asp Ala Gly Glu Arg Ala Lys Gln Ala Leu Ala Phe
                165                 170                 175

Glu Arg Thr Asp Phe Asp Gln Val Arg Ser Leu Met Glu Asn Ser Asp
            180                 185                 190

Arg Cys Gln Asp Ile Arg Asn Leu Ala Phe Leu Gly Ile Ala Tyr Asn
        195                 200                 205

Thr Leu Leu Arg Ile Ala Glu Ile Ala Arg Ile Arg Val Lys Asp Ile
    210                 215                 220

Ser Arg Thr Asp Gly Gly Arg Met Leu Ile His Ile Gly Arg Thr Lys
225                 230                 235                 240

Thr Leu Val Ser Thr Ala Gly Val Glu Lys Ala Leu Ser Leu Gly Val
                245                 250                 255

Thr Lys Leu Val Glu Arg Trp Ile Ser Val Ser Gly Val Ala Asp Asp
                260                 265                 270

Pro Asn Asn Tyr Leu Phe Cys Arg Val Arg Lys Asn Gly Val Ala Ala
            275                 280                 285

Pro Ser Ala Thr Ser Gln Leu Ser Thr Arg Ala Leu Glu Gly Ile Phe
        290                 295                 300

Glu Ala Thr His Arg Leu Ile Tyr Gly Ala Lys Asp Asp Ser Gly Gln
305                 310                 315                 320

Arg Tyr Leu Ala Trp Ser Gly His Ser Ala Arg Val Gly Ala Ala Arg
                325                 330                 335

Asp Met Ala Arg Ala Gly Val Ser Ile Pro Glu Ile Met Gln Ala Gly
                340                 345                 350

Gly Trp Thr Asn Val Asn Ile Val Met Asn Tyr Ile Arg Asn Leu Asp
            355                 360                 365

Ser Glu Thr Gly Ala Met Val Arg Leu Leu Glu Asp Gly Asp His His
        370                 375                 380

His His His His
385

<210> SEQ ID NO 146
<211> LENGTH: 394
<212> TYPE: PRT
<213> ORGANISM: Artificial Sequence
<220> FEATURE:
<223> OTHER INFORMATION: synthetic polypeptide

<400> SEQUENCE: 146

Met Arg Gln Ile Lys Ile Trp Phe Gln Asn Arg Arg Met Lys Trp Lys
1               5                   10                  15

Lys Gly Gly Ser Gly Gly Ser Gly Gly Ser Gly Gly Ser Gly Gly Ser
                20                  25                  30

Gly Gly Ser Gly Gly Ser Gly Gly Ser Gly Gly Ser Met Ala Ser Asn
            35                  40                  45

Leu Leu Thr Val His Gln Asn Leu Pro Ala Leu Pro Val Asp Ala Thr
    50                  55                  60

Ser Asp Glu Val Arg Lys Asn Leu Met Asp Met Phe Arg Asp Arg Gln
65                  70                  75                  80

Ala Phe Ser Glu His Thr Trp Lys Met Leu Leu Ser Val Cys Arg Ser
                85                  90                  95

Trp Ala Ala Trp Cys Lys Leu Asn Asn Arg Lys Trp Phe Pro Ala Glu
```

```
                100             105             110
Pro Glu Asp Val Arg Asp Tyr Leu Leu Tyr Leu Gln Ala Arg Gly Leu
            115                 120                 125

Ala Val Lys Thr Ile Gln Gln His Leu Gly Gln Leu Asn Met Leu His
130                 135                 140

Arg Arg Ser Gly Leu Pro Arg Pro Ser Asp Ser Asn Ala Val Ser Leu
145                 150                 155                 160

Val Met Arg Arg Ile Arg Lys Glu Asn Val Asp Ala Gly Glu Arg Ala
            165                 170                 175

Lys Gln Ala Leu Ala Phe Glu Arg Thr Asp Phe Asp Gln Val Arg Ser
            180                 185                 190

Leu Met Glu Asn Ser Asp Arg Cys Gln Asp Ile Arg Asn Leu Ala Phe
            195                 200                 205

Leu Gly Ile Ala Tyr Asn Thr Leu Leu Arg Ile Ala Glu Ile Ala Arg
            210                 215                 220

Ile Arg Val Lys Asp Ile Ser Arg Thr Asp Gly Gly Arg Met Leu Ile
225                 230                 235                 240

His Ile Gly Arg Thr Lys Thr Leu Val Ser Thr Ala Gly Val Glu Lys
            245                 250                 255

Ala Leu Ser Leu Gly Val Thr Lys Leu Val Glu Arg Trp Ile Ser Val
            260                 265                 270

Ser Gly Val Ala Asp Asp Pro Asn Asn Tyr Leu Phe Cys Arg Val Arg
            275                 280                 285

Lys Asn Gly Val Ala Ala Pro Ser Ala Thr Ser Gln Leu Ser Thr Arg
290                 295                 300

Ala Leu Glu Gly Ile Phe Glu Ala Thr His Arg Leu Ile Tyr Gly Ala
305                 310                 315                 320

Lys Asp Asp Ser Gly Gln Arg Tyr Leu Ala Trp Ser Gly His Ser Ala
            325                 330                 335

Arg Val Gly Ala Ala Arg Asp Met Ala Arg Ala Gly Val Ser Ile Pro
            340                 345                 350

Glu Ile Met Gln Ala Gly Gly Trp Thr Asn Val Asn Ile Val Met Asn
            355                 360                 365

Tyr Ile Arg Asn Leu Asp Ser Glu Thr Gly Ala Met Val Arg Leu Leu
            370                 375                 380

Glu Asp Gly Asp His His His His His His
385                 390
```

`<210>` SEQ ID NO 147
`<211>` LENGTH: 617
`<212>` TYPE: PRT
`<213>` ORGANISM: Artificial Sequence
`<220>` FEATURE:
`<223>` OTHER INFORMATION: synthetic polypeptide

`<400>` SEQUENCE: 147

```
Met Ala Ser Lys Gly Glu Arg Leu Phe Arg Gly Lys Val Pro Ile Leu
1               5                   10                  15

Val Glu Leu Lys Gly Asp Val Asn Gly His Lys Phe Ser Val Arg Gly
            20                  25                  30

Lys Gly Lys Gly Asp Ala Thr Arg Gly Lys Leu Thr Leu Lys Phe Ile
            35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Lys His Met Lys
```

```
            65                  70                  75                  80
Arg His Asp Phe Phe Lys Ser Ala Met Pro Lys Gly Tyr Val Gln Glu
                85                  90                  95

Arg Thr Ile Ser Phe Lys Lys Asp Gly Lys Tyr Lys Thr Arg Ala Glu
                100                 105                 110

Val Lys Phe Glu Gly Arg Thr Leu Val Asn Arg Ile Lys Leu Lys Gly
                115                 120                 125

Arg Asp Phe Lys Glu Lys Gly Asn Ile Leu Gly His Lys Leu Arg Tyr
            130                 135                 140

Asn Phe Asn Ser His Lys Val Tyr Ile Thr Ala Asp Lys Arg Lys Asn
145                 150                 155                 160

Gly Ile Lys Ala Lys Phe Lys Ile Arg His Asn Val Lys Asp Gly Ser
                165                 170                 175

Val Gln Leu Ala Asp His Tyr Gln Gln Asn Thr Pro Ile Gly Arg Gly
                180                 185                 190

Pro Val Leu Leu Pro Arg Asn His Tyr Leu Ser Thr Arg Ser Lys Leu
            195                 200                 205

Ser Lys Asp Pro Lys Glu Lys Arg Asp His Met Val Leu Leu Glu Phe
210                 215                 220

Val Thr Ala Ala Gly Ile Lys His Gly Arg Asp Glu Arg Tyr Lys Gly
225                 230                 235                 240

Gly Ser Gly Gly Ser Gly Gly Ser Gly Gly Ser Ala Leu Ala Leu Gly
                245                 250                 255

Gly Ser Gly Gly Ser Gly Gly Ser Gly Gly Ser Met Ala Ser Asn Leu
                260                 265                 270

Leu Thr Val His Gln Asn Leu Pro Ala Leu Pro Val Asp Ala Thr Ser
            275                 280                 285

Asp Glu Val Arg Lys Asn Leu Met Asp Met Phe Arg Asp Arg Gln Ala
            290                 295                 300

Phe Ser Glu His Thr Trp Lys Met Leu Leu Ser Val Cys Arg Ser Trp
305                 310                 315                 320

Ala Ala Trp Cys Lys Leu Asn Asn Arg Lys Trp Phe Pro Ala Glu Pro
                325                 330                 335

Glu Asp Val Arg Asp Tyr Leu Leu Tyr Leu Gln Ala Arg Gly Leu Ala
                340                 345                 350

Val Lys Thr Ile Gln Gln His Leu Gly Gln Leu Asn Met Leu His Arg
            355                 360                 365

Arg Ser Gly Leu Pro Arg Pro Ser Asp Ser Asn Ala Val Ser Leu Val
            370                 375                 380

Met Arg Arg Ile Arg Lys Glu Asn Val Asp Ala Gly Glu Arg Ala Lys
385                 390                 395                 400

Gln Ala Leu Ala Phe Glu Arg Thr Asp Phe Asp Gln Val Arg Ser Leu
                405                 410                 415

Met Glu Asn Ser Asp Arg Cys Gln Asp Ile Arg Asn Leu Ala Phe Leu
                420                 425                 430

Gly Ile Ala Tyr Asn Thr Leu Leu Arg Ile Ala Glu Ile Ala Arg Ile
            435                 440                 445

Arg Val Lys Asp Ile Ser Arg Thr Asp Gly Gly Arg Met Leu Ile His
            450                 455                 460

Ile Gly Arg Thr Lys Thr Leu Val Ser Thr Ala Gly Val Glu Lys Ala
465                 470                 475                 480

Leu Ser Leu Gly Val Thr Lys Leu Val Glu Arg Trp Ile Ser Val Ser
                485                 490                 495
```

Gly Val Ala Asp Asp Pro Asn Asn Tyr Leu Phe Cys Arg Val Arg Lys
              500                 505                 510

Asn Gly Val Ala Ala Pro Ser Ala Thr Ser Gln Leu Ser Thr Arg Ala
              515                 520                 525

Leu Glu Gly Ile Phe Glu Ala Thr His Arg Leu Ile Tyr Gly Ala Lys
          530                 535                 540

Asp Asp Ser Gly Gln Arg Tyr Leu Ala Trp Ser Gly His Ser Ala Arg
545                 550                 555                 560

Val Gly Ala Ala Arg Asp Met Ala Arg Ala Gly Val Ser Ile Pro Glu
              565                 570                 575

Ile Met Gln Ala Gly Gly Trp Thr Asn Val Asn Ile Val Met Asn Tyr
              580                 585                 590

Ile Arg Asn Leu Asp Ser Glu Thr Gly Ala Met Val Arg Leu Leu Glu
              595                 600                 605

Asp Gly Asp His His His His His His
              610                 615

<210> SEQ ID NO 148
<211> LENGTH: 277
<212> TYPE: PRT
<213> ORGANISM: Artificial Sequence
<220> FEATURE:
<223> OTHER INFORMATION: synthetic polypeptide

<400> SEQUENCE: 148

Met Gly Arg Lys Lys Arg Arg Gln Arg Arg Gly His Met Ala Ser
1               5                   10                  15

Met Thr Gly Gly Gln Gln Met Gly Arg Asp Pro Asn Ser Val Ser Lys
                20                  25                  30

Gly Glu Glu Asp Asn Met Ala Ile Ile Lys Glu Phe Met Arg Phe Lys
            35                  40                  45

Val His Met Glu Gly Ser Val Asn Gly His Glu Phe Glu Ile Glu Gly
        50                  55                  60

Glu Gly Glu Gly Arg Pro Tyr Glu Gly Thr Gln Thr Ala Lys Leu Lys
65                  70                  75                  80

Val Thr Lys Gly Gly Pro Leu Pro Phe Ala Trp Asp Ile Leu Ser Pro
                85                  90                  95

Gln Phe Met Tyr Gly Ser Lys Ala Tyr Val Lys His Pro Ala Asp Ile
                100                 105                 110

Pro Asp Tyr Leu Lys Leu Ser Phe Pro Glu Gly Phe Lys Trp Glu Arg
            115                 120                 125

Val Met Asn Phe Glu Asp Gly Gly Val Val Thr Val Thr Gln Asp Ser
        130                 135                 140

Ser Leu Gln Asp Gly Glu Phe Ile Tyr Lys Val Lys Leu Arg Gly Thr
145                 150                 155                 160

Asn Phe Pro Ser Asp Gly Pro Val Met Gln Lys Lys Thr Met Gly Trp
                165                 170                 175

Glu Ala Ser Ser Glu Arg Met Tyr Pro Glu Asp Gly Ala Leu Lys Gly
                180                 185                 190

Glu Ile Lys Gln Arg Leu Lys Leu Lys Asp Gly Gly His Tyr Asp Ala
            195                 200                 205

Glu Val Lys Thr Thr Tyr Lys Ala Lys Lys Pro Val Gln Leu Pro Gly
        210                 215                 220

Ala Tyr Asn Val Asn Ile Lys Leu Asp Ile Thr Ser His Asn Glu Asp
225                 230                 235                 240

Tyr Thr Ile Val Glu Tyr Glu Arg Ala Glu Gly Arg His Ser Thr Gly
                245                 250                 255

Gly Met Asp Glu Leu Tyr Lys Ala Arg Gly Ala Ala Ala Leu Glu His
                260                 265                 270

His His His His His
        275

<210> SEQ ID NO 149
<211> LENGTH: 383
<212> TYPE: PRT
<213> ORGANISM: Artificial Sequence
<220> FEATURE:
<223> OTHER INFORMATION: synthetic polypeptide

<400> SEQUENCE: 149

Met Gly Arg Lys Lys Arg Gln Arg Arg Gly His Met Ala Ser
1               5                   10                  15

Met Thr Gly Gly Gln Gln Met Gly Arg Asp Pro Asn Ser Met Ser Asn
                20                  25                  30

Leu Leu Thr Val His Gln Asn Leu Pro Ala Leu Pro Val Asp Ala Thr
            35                  40                  45

Ser Asp Glu Val Arg Lys Asn Leu Met Asp Met Phe Arg Asp Arg Gln
50                  55                  60

Ala Phe Ser Glu His Thr Trp Lys Met Leu Leu Ser Val Cys Arg Ser
65                  70                  75                  80

Trp Ala Ala Trp Cys Lys Leu Asn Asn Arg Lys Trp Phe Pro Ala Glu
                85                  90                  95

Pro Glu Asp Val Arg Asp Tyr Leu Leu Tyr Leu Gln Ala Arg Gly Leu
                100                 105                 110

Ala Val Lys Thr Ile Gln Gln His Leu Gly Gln Leu Asn Met Leu His
            115                 120                 125

Arg Arg Ser Gly Leu Pro Arg Pro Ser Asp Ser Asn Ala Val Ser Leu
130                 135                 140

Val Met Arg Arg Ile Arg Lys Glu Asn Val Asp Ala Gly Glu Arg Ala
145                 150                 155                 160

Lys Gln Ala Leu Ala Phe Glu Arg Thr Asp Phe Asp Gln Val Arg Ser
                165                 170                 175

Leu Met Glu Asn Ser Asp Arg Cys Gln Asp Ile Arg Asn Leu Ala Phe
                180                 185                 190

Leu Gly Ile Ala Tyr Asn Thr Leu Leu Arg Ile Ala Glu Ile Ala Arg
            195                 200                 205

Ile Arg Val Lys Asp Ile Ser Arg Thr Asp Gly Gly Arg Met Leu Ile
210                 215                 220

His Ile Gly Arg Thr Lys Thr Leu Val Ser Thr Ala Gly Val Glu Lys
225                 230                 235                 240

Ala Leu Ser Leu Gly Val Thr Lys Leu Val Glu Arg Trp Ile Ser Val
                245                 250                 255

Ser Gly Val Ala Asp Asp Pro Asn Asn Tyr Leu Phe Cys Arg Val Arg
                260                 265                 270

Lys Asn Gly Val Ala Ala Pro Ser Ala Thr Ser Gln Leu Ser Thr Arg
            275                 280                 285

Ala Leu Glu Gly Ile Phe Glu Ala Thr His Arg Leu Ile Tyr Gly Ala
            290                 295                 300

Lys Asp Asp Ser Gly Gln Arg Tyr Leu Ala Trp Ser Gly His Ser Ala
305                 310                 315                 320

```
Arg Val Gly Ala Ala Arg Asp Met Ala Arg Ala Gly Val Ser Ile Pro
            325                 330                 335

Glu Ile Met Gln Ala Gly Gly Trp Thr Asn Val Asn Ile Val Met Asn
            340                 345                 350

Tyr Ile Arg Asn Leu Asp Ser Glu Thr Gly Ala Met Val Arg Leu Leu
            355                 360                 365

Glu Asp Gly Asp Ala Ala Leu Glu His His His His His His
            370                 375                 380

<210> SEQ ID NO 150
<211> LENGTH: 373
<212> TYPE: PRT
<213> ORGANISM: Artificial Sequence
<220> FEATURE:
<223> OTHER INFORMATION: synthetic polypeptide

<400> SEQUENCE: 150

Met Ser Gly Arg Gly Lys Gly Lys Gly Leu Gly Lys Gly Gly Ala
1               5                   10                  15

Lys Arg His Arg Lys Val Leu Arg Asp Asn Ile Gln Gly Ile Thr Lys
            20                  25                  30

Pro Ala Ile Arg Arg Leu Ala Arg Gly Gly Val Lys Arg Ile Ser
            35                  40                  45

Gly Leu Ile Tyr Glu Glu Thr Arg Gly Val Leu Lys Val Phe Leu Glu
            50                  55                  60

Asn Val Ile Arg Asp Ala Val Thr Tyr Thr Glu His Ala Lys Arg Lys
65                  70                  75                  80

Thr Val Thr Ala Met Asp Val Val Tyr Ala Leu Lys Arg Gln Gly Arg
                85                  90                  95

Thr Leu Tyr Gly Phe Gly Gly Gly Ser Gly Ser Gly Gly Ser
            100                 105                 110

Gly Gly Ser Gly Gly Ser Gly Gly Ser Gly Gly Ser Gly Gly Ser Gly
            115                 120                 125

Gly Ser Val Ser Lys Gly Glu Glu Asp Asn Met Ala Ile Ile Lys Glu
            130                 135                 140

Phe Met Arg Phe Lys Val His Met Glu Gly Ser Val Asn Gly His Glu
145                 150                 155                 160

Phe Glu Ile Glu Gly Glu Gly Glu Gly Arg Pro Tyr Glu Gly Thr Gln
                165                 170                 175

Thr Ala Lys Leu Lys Val Thr Lys Gly Gly Pro Leu Pro Phe Ala Trp
            180                 185                 190

Asp Ile Leu Ser Pro Gln Phe Met Tyr Gly Ser Lys Ala Tyr Val Lys
            195                 200                 205

His Pro Ala Asp Ile Pro Asp Tyr Leu Lys Leu Ser Phe Pro Glu Gly
            210                 215                 220

Phe Lys Trp Glu Arg Val Met Asn Phe Glu Asp Gly Gly Val Val Thr
225                 230                 235                 240

Val Thr Gln Asp Ser Ser Leu Gln Asp Gly Glu Phe Ile Tyr Lys Val
                245                 250                 255

Lys Leu Arg Gly Thr Asn Phe Pro Ser Asp Gly Pro Val Met Gln Lys
            260                 265                 270

Lys Thr Met Gly Trp Glu Ala Ser Ser Glu Arg Met Tyr Pro Glu Asp
            275                 280                 285

Gly Ala Leu Lys Gly Glu Ile Lys Gln Arg Leu Lys Leu Lys Asp Gly
            290                 295                 300
```

```
Gly His Tyr Asp Ala Glu Val Lys Thr Thr Tyr Lys Ala Lys Lys Pro
305                 310                 315                 320

Val Gln Leu Pro Gly Ala Tyr Asn Val Asn Ile Lys Leu Asp Ile Thr
                325                 330                 335

Ser His Asn Glu Asp Tyr Thr Ile Val Glu Gln Tyr Glu Arg Ala Glu
            340                 345                 350

Gly Arg His Ser Thr Gly Gly Met Asp Glu Leu Tyr Lys Leu Glu His
        355                 360                 365

His His His His His
        370

<210> SEQ ID NO 151
<211> LENGTH: 480
<212> TYPE: PRT
<213> ORGANISM: Artificial Sequence
<220> FEATURE:
<223> OTHER INFORMATION: synthetic polypeptide

<400> SEQUENCE: 151

Met Ser Gly Arg Gly Lys Gly Gly Lys Gly Leu Gly Lys Gly Gly Ala
1               5                   10                  15

Lys Arg His Arg Lys Val Leu Arg Asp Asn Ile Gln Gly Ile Thr Lys
                20                  25                  30

Pro Ala Ile Arg Arg Leu Ala Arg Arg Gly Gly Val Lys Arg Ile Ser
            35                  40                  45

Gly Leu Ile Tyr Glu Glu Thr Arg Gly Val Leu Lys Val Phe Leu Glu
    50                  55                  60

Asn Val Ile Arg Asp Ala Val Thr Tyr Thr Glu His Ala Lys Arg Lys
65                  70                  75                  80

Thr Val Thr Ala Met Asp Val Val Tyr Ala Leu Lys Arg Gln Gly Arg
                85                  90                  95

Thr Leu Tyr Gly Phe Gly Gly Gly Ser Gly Gly Ser Gly Gly Ser
            100                 105                 110

Gly Gly Ser Gly Gly Ser Gly Gly Ser Gly Gly Ser Gly Gly Ser Gly
        115                 120                 125

Gly Ser Met Ala Ser Asn Leu Leu Thr Val His Gln Asn Leu Pro Ala
130                 135                 140

Leu Pro Val Asp Ala Thr Ser Asp Glu Val Arg Lys Asn Leu Met Asp
145                 150                 155                 160

Met Phe Arg Asp Arg Gln Ala Phe Ser Glu His Thr Trp Lys Met Leu
                165                 170                 175

Leu Ser Val Cys Arg Ser Trp Ala Ala Trp Cys Lys Leu Asn Asn Arg
            180                 185                 190

Lys Trp Phe Pro Ala Glu Pro Glu Asp Val Arg Asp Tyr Leu Leu Tyr
        195                 200                 205

Leu Gln Ala Arg Gly Leu Ala Val Lys Thr Ile Gln Gln His Leu Gly
    210                 215                 220

Gln Leu Asn Met Leu His Arg Arg Ser Gly Leu Pro Arg Pro Ser Asp
225                 230                 235                 240

Ser Asn Ala Val Ser Leu Val Met Arg Arg Ile Arg Lys Glu Asn Val
                245                 250                 255

Asp Ala Gly Glu Arg Ala Lys Gln Ala Leu Ala Phe Glu Arg Thr Asp
            260                 265                 270

Phe Asp Gln Val Arg Ser Leu Met Glu Asn Ser Asp Arg Cys Gln Asp
        275                 280                 285
```

```
Ile Arg Asn Leu Ala Phe Leu Gly Ile Ala Tyr Asn Thr Leu Leu Arg
    290                 295                 300

Ile Ala Glu Ile Ala Arg Ile Arg Val Lys Asp Ile Ser Arg Thr Asp
305                 310                 315                 320

Gly Gly Arg Met Leu Ile His Ile Gly Arg Thr Lys Thr Leu Val Ser
                325                 330                 335

Thr Ala Gly Val Glu Lys Ala Leu Ser Leu Gly Val Thr Lys Leu Val
            340                 345                 350

Glu Arg Trp Ile Ser Val Ser Gly Val Ala Asp Asp Pro Asn Asn Tyr
        355                 360                 365

Leu Phe Cys Arg Val Arg Lys Asn Gly Val Ala Ala Pro Ser Ala Thr
    370                 375                 380

Ser Gln Leu Ser Thr Arg Ala Leu Glu Gly Ile Phe Glu Ala Thr His
385                 390                 395                 400

Arg Leu Ile Tyr Gly Ala Lys Asp Asp Ser Gly Gln Arg Tyr Leu Ala
                405                 410                 415

Trp Ser Gly His Ser Ala Arg Val Gly Ala Ala Arg Asp Met Ala Arg
            420                 425                 430

Ala Gly Val Ser Ile Pro Glu Ile Met Gln Ala Gly Gly Trp Thr Asn
        435                 440                 445

Val Asn Ile Val Met Asn Tyr Ile Arg Asn Leu Asp Ser Glu Thr Gly
    450                 455                 460

Ala Met Val Arg Leu Leu Glu Asp Gly Asp His His His His His His
465                 470                 475                 480

<210> SEQ ID NO 152
<211> LENGTH: 449
<212> TYPE: PRT
<213> ORGANISM: Artificial Sequence
<220> FEATURE:
<223> OTHER INFORMATION: synthetic polypeptide

<400> SEQUENCE: 152

Met Thr Arg Gly Ser Asp Ile Ser Lys Thr Cys Cys Phe Gln Tyr Ser
1               5                   10                  15

His Lys Pro Leu Pro Trp Thr Trp Val Arg Ser Tyr Glu Phe Thr Ser
                20                  25                  30

Asn Ser Cys Ser Gln Arg Ala Val Ile Phe Thr Thr Lys Arg Gly Lys
            35                  40                  45

Lys Val Cys Thr His Pro Arg Lys Lys Trp Val Gln Lys Tyr Ile Ser
        50                  55                  60

Leu Leu Lys Thr Pro Lys Gln Leu Gly Gly Ser Gly Gly Ser Gly Gly
65                  70                  75                  80

Ser Gly Gly Ser Gly Gly Ser Gly Gly Ser Gly Gly Ser Gly Gly Ser
                85                  90                  95

Gly Gly Ser Met Ala Ser Asn Leu Leu Thr Val His Gln Asn Leu Pro
                100                 105                 110

Ala Leu Pro Val Asp Ala Thr Ser Asp Glu Val Arg Lys Asn Leu Met
            115                 120                 125

Asp Met Phe Arg Asp Arg Gln Ala Phe Ser Glu His Thr Trp Lys Met
        130                 135                 140

Leu Leu Ser Val Cys Arg Ser Trp Ala Ala Trp Cys Lys Leu Asn Asn
145                 150                 155                 160

Arg Lys Trp Phe Pro Ala Glu Pro Glu Asp Val Arg Asp Tyr Leu Leu
                165                 170                 175
```

```
Tyr Leu Gln Ala Arg Gly Leu Ala Val Lys Thr Ile Gln Gln His Leu
            180                 185                 190

Gly Gln Leu Asn Met Leu His Arg Arg Ser Gly Leu Pro Arg Pro Ser
        195                 200                 205

Asp Ser Asn Ala Val Ser Leu Val Met Arg Arg Ile Arg Lys Glu Asn
    210                 215                 220

Val Asp Ala Gly Glu Arg Ala Lys Gln Ala Leu Ala Phe Glu Arg Thr
225                 230                 235                 240

Asp Phe Asp Gln Val Arg Ser Leu Met Glu Asn Ser Asp Arg Cys Gln
                245                 250                 255

Asp Ile Arg Asn Leu Ala Phe Leu Gly Ile Ala Tyr Asn Thr Leu Leu
            260                 265                 270

Arg Ile Ala Glu Ile Ala Arg Ile Arg Val Lys Asp Ile Ser Arg Thr
        275                 280                 285

Asp Gly Gly Arg Met Leu Ile His Ile Gly Arg Thr Lys Thr Leu Val
    290                 295                 300

Ser Thr Ala Gly Val Glu Lys Ala Leu Ser Leu Gly Val Thr Lys Leu
305                 310                 315                 320

Val Glu Arg Trp Ile Ser Val Ser Gly Val Ala Asp Asp Pro Asn Asn
                325                 330                 335

Tyr Leu Phe Cys Arg Val Arg Lys Asn Gly Val Ala Ala Pro Ser Ala
            340                 345                 350

Thr Ser Gln Leu Ser Thr Arg Ala Leu Glu Gly Ile Phe Glu Ala Thr
        355                 360                 365

His Arg Leu Ile Tyr Gly Ala Lys Asp Asp Ser Gly Gln Arg Tyr Leu
    370                 375                 380

Ala Trp Ser Gly His Ser Ala Arg Val Gly Ala Ala Arg Asp Met Ala
385                 390                 395                 400

Arg Ala Gly Val Ser Ile Pro Glu Ile Met Gln Ala Gly Gly Trp Thr
                405                 410                 415

Asn Val Asn Ile Val Met Asn Tyr Ile Arg Asn Leu Asp Ser Glu Thr
            420                 425                 430

Gly Ala Met Val Arg Leu Leu Glu Asp Gly Asp His His His His His
        435                 440                 445

His

<210> SEQ ID NO 153
<211> LENGTH: 160
<212> TYPE: PRT
<213> ORGANISM: Artificial Sequence
<220> FEATURE:
<223> OTHER INFORMATION: synthetic polypeptide

<400> SEQUENCE: 153

Ser Val Cys Pro Gln Gly Lys Tyr Ile His Pro Gln Asn Asn Ser Ile
1               5                   10                  15

Cys Cys Thr Lys Cys His Lys Gly Thr Tyr Leu Tyr Asn Asp Cys Pro
            20                  25                  30

Gly Pro Gly Gln Asp Thr Asp Cys Arg Glu Cys Glu Ser Gly Ser Phe
        35                  40                  45

Thr Ala Ser Glu Asn His Leu Arg His Cys Leu Ser Cys Ser Lys Cys
    50                  55                  60

Arg Lys Glu Met Gly Gln Val Glu Ile Ser Ser Cys Thr Val Asp Arg
65                  70                  75                  80
```

```
Asp Thr Val Cys Gly Cys Arg Lys Asn Gln Tyr Arg His Tyr Trp Ser
                85                  90                  95

Glu Asn Leu Phe Gln Cys Phe Asn Cys Ser Leu Cys Leu Asn Gly Thr
            100                 105                 110

Val His Leu Ser Cys Gln Glu Lys Gln Asn Thr Val Cys Thr Cys His
        115                 120                 125

Ala Gly Phe Phe Leu Arg Glu Asn Glu Cys Val Ser Cys Ser Asn Cys
    130                 135                 140

Lys Lys Ser Leu Glu Cys Thr Lys Leu Cys Leu Pro Gln Ile Glu Asn
145                 150                 155                 160

<210> SEQ ID NO 154
<211> LENGTH: 28
<212> TYPE: PRT
<213> ORGANISM: Artificial Sequence
<220> FEATURE:
<223> OTHER INFORMATION: synthetic polypeptide

<400> SEQUENCE: 154

Gly Gly Ser Gly Gly Ser Gly Gly Ser Gly Gly Ser Ala Leu Ala Leu
1               5                   10                  15

Gly Gly Ser Gly Gly Ser Gly Gly Ser Gly Gly Ser
            20                  25

<210> SEQ ID NO 155
<211> LENGTH: 342
<212> TYPE: PRT
<213> ORGANISM: Artificial Sequence
<220> FEATURE:
<223> OTHER INFORMATION: synthetic polypeptide

<400> SEQUENCE: 155

Met Thr Arg Gly Ser Asp Ile Ser Lys Thr Cys Cys Phe Gln Tyr Ser
1               5                   10                  15

His Lys Pro Leu Pro Trp Thr Trp Val Arg Ser Tyr Glu Phe Thr Ser
            20                  25                  30

Asn Ser Cys Ser Gln Arg Ala Val Ile Phe Thr Thr Lys Arg Gly Lys
        35                  40                  45

Lys Val Cys Thr His Pro Arg Lys Lys Trp Val Gln Lys Tyr Ile Ser
    50                  55                  60

Leu Leu Lys Thr Pro Lys Gln Leu Gly Gly Ser Gly Gly Ser Gly Gly
65                  70                  75                  80

Ser Gly Gly Ser Gly Gly Ser Gly Gly Ser Gly Gly Ser Gly Gly Ser
                85                  90                  95

Gly Gly Ser Val Ser Lys Gly Glu Glu Asp Asn Met Ala Ile Ile Lys
            100                 105                 110

Glu Phe Met Arg Phe Lys Val His Met Glu Gly Ser Val Asn Gly His
        115                 120                 125

Glu Phe Glu Ile Glu Gly Glu Gly Glu Gly Arg Pro Tyr Glu Gly Thr
    130                 135                 140

Gln Thr Ala Lys Leu Lys Val Thr Lys Gly Gly Pro Leu Pro Phe Ala
145                 150                 155                 160

Trp Asp Ile Leu Ser Pro Gln Phe Met Tyr Gly Ser Lys Ala Tyr Val
                165                 170                 175

Lys His Pro Ala Asp Ile Pro Asp Tyr Leu Lys Leu Ser Phe Pro Glu
            180                 185                 190

Gly Phe Lys Trp Glu Arg Val Met Asn Phe Glu Asp Gly Gly Val Val
        195                 200                 205
```

```
Thr Val Thr Gln Asp Ser Ser Leu Gln Asp Gly Glu Phe Ile Tyr Lys
    210                 215                 220

Val Lys Leu Arg Gly Thr Asn Phe Pro Ser Asp Gly Pro Val Met Gln
225                 230                 235                 240

Lys Lys Thr Met Gly Trp Glu Ala Ser Ser Glu Arg Met Tyr Pro Glu
                245                 250                 255

Asp Gly Ala Leu Lys Gly Glu Ile Lys Gln Arg Leu Lys Leu Lys Asp
                260                 265                 270

Gly Gly His Tyr Asp Ala Glu Val Lys Thr Thr Tyr Lys Ala Lys Lys
            275                 280                 285

Pro Val Gln Leu Pro Gly Ala Tyr Asn Val Asn Ile Lys Leu Asp Ile
    290                 295                 300

Thr Ser His Asn Glu Asp Tyr Thr Ile Val Glu Gln Tyr Glu Arg Ala
305                 310                 315                 320

Glu Gly Arg His Ser Thr Gly Gly Met Asp Glu Leu Tyr Lys Leu Glu
                325                 330                 335

His His His His His His
            340

<210> SEQ ID NO 156
<211> LENGTH: 36
<212> TYPE: PRT
<213> ORGANISM: Artificial Sequence
<220> FEATURE:
<223> OTHER INFORMATION: synthetic polypeptide

<400> SEQUENCE: 156

Lys Lys Arg Lys Lys Arg Lys Lys Arg Lys Lys Arg Lys Lys Arg Lys
1               5                   10                  15

Lys Arg Lys Lys Arg Lys Lys Arg Lys Lys Arg Lys Lys Arg Lys Lys
                20                  25                  30

Arg Arg Arg Lys
        35

<210> SEQ ID NO 157
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 157

Gly Gly Gly Ser Gly Gly Gly Ser Arg Arg Arg Arg Arg Arg Arg Arg
1               5                   10                  15

Arg
```